US010995095B2

(12) United States Patent
Pangan et al.

(10) Patent No.: US 10,995,095 B2
(45) Date of Patent: *May 4, 2021

(54) PROCESSES FOR THE PREPARATION OF (3S,4R)-3-ETHYL-4-(3H-IMIDAZO[1,2-A]PYRROLO[2,3-E]-PYRAZIN-8-YL)-N-(2,2,2-TRIFLUOROETHYL)PYRROLIDINE-1-CARBOXAMIDE AND SOLID STATE FORMS THEREOF

(71) Applicant: AbbVie Inc., North Chicago, IL (US)

(72) Inventors: Aileen L. Pangan, La Grange, IL (US); Henrique D. Teixeira, Green Oaks, IL (US); Mohamed-Eslam F. Mohamed, Gurnee, IL (US); Ahmed A. Othman, Libertyville, IL (US); Ben Klünder, Ludwigshafen (DE)

(73) Assignee: AbbVie Inc., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/721,076

(22) Filed: Dec. 19, 2019

(65) Prior Publication Data

US 2020/0385393 A1 Dec. 10, 2020

Related U.S. Application Data

(63) Continuation of application No. 15/954,039, filed on Apr. 16, 2018, now Pat. No. 10,550,126, which is a continuation-in-part of application No. 15/891,012, filed on Feb. 7, 2018, now abandoned, which is a continuation of application No. 15/295,561, filed on Oct. 17, 2016, now abandoned.

(60) Provisional application No. 62/352,380, filed on Jun. 20, 2016, provisional application No. 62/301,537, filed on Feb. 29, 2016, provisional application No. 62/267,672, filed on Dec. 15, 2015, provisional application No. 62/242,797, filed on Oct. 16, 2015.

(51) Int. Cl.
| | | |
|---|---|---|
| C07D 487/14 | (2006.01) | |
| A61K 31/4985 | (2006.01) | |
| A61K 47/12 | (2006.01) | |
| A61K 47/38 | (2006.01) | |
| A61K 9/20 | (2006.01) | |
| A61K 9/00 | (2006.01) | |

(52) U.S. Cl.
CPC .......... *C07D 487/14* (2013.01); *A61K 9/0053* (2013.01); *A61K 9/2013* (2013.01); *A61K 9/2027* (2013.01); *A61K 9/2054* (2013.01); *A61K 31/4985* (2013.01); *A61K 47/12* (2013.01); *A61K 47/38* (2013.01); *C07B 2200/13* (2013.01)

(58) Field of Classification Search
CPC .. C07D 487/14; A61K 9/0053; A61K 9/2013; A61K 9/2027; A61K 9/2054; A61K 31/4985; A61K 47/12; A61K 47/38; C07B 2200/13
USPC ........................................................ 514/250
See application file for complete search history.

(56) References Cited

U.S. PATENT DOCUMENTS

| | | | |
|---|---|---|---|
| 3,663,559 | A | 5/1972 | Antoon et al. |
| 3,929,992 | A | 12/1975 | Sehgal et al. |
| 4,053,474 | A | 10/1977 | Treuner et al. |
| 5,212,310 | A | 5/1993 | Thurkauf et al. |
| 5,266,698 | A | 11/1993 | Shaw et al. |
| 5,521,173 | A | 5/1996 | Venkatesan et al. |
| 5,605,690 | A | 2/1997 | Jacobs et al. |
| 5,693,801 | A | 12/1997 | Shaw et al. |
| 5,703,244 | A | 12/1997 | Li et al. |
| 5,733,905 | A | 3/1998 | Albright et al. |
| 5,736,540 | A | 4/1998 | Albright et al. |
| 5,753,648 | A | 5/1998 | Albright et al. |
| 5,763,137 | A | 6/1998 | Deprez et al. |
| 5,840,888 | A | 11/1998 | Shaw et al. |
| 5,990,109 | A | 11/1999 | Chen et al. |
| 6,090,382 | A | 7/2000 | Salfeld et al. |
| 6,120,778 | A | 9/2000 | Simonnet |
| 6,245,801 | B1 | 6/2001 | Bryans et al. |
| 6,262,241 | B1 | 7/2001 | Cook et al. |
| 6,653,471 | B2 | 11/2003 | Yohannes et al. |
| 6,949,562 | B2 | 9/2005 | Yohannes et al. |
| 7,169,926 | B1 | 1/2007 | Burgess et al. |
| 7,452,981 | B2 | 11/2008 | Wijdenes et al. |
| 7,593,820 | B2 | 9/2009 | Wilks et al. |
| 7,772,231 | B2 | 8/2010 | Sheppard et al. |
| 7,902,197 | B2 | 3/2011 | Elworthy et al. |
| 8,039,009 | B2 | 10/2011 | Rastogi et al. |
| 8,168,624 | B2 | 5/2012 | Agarwal et al. |
| 8,361,962 | B2 | 1/2013 | Billedeau |
| 8,426,411 | B2 | 4/2013 | Wishart et al. |

(Continued)

FOREIGN PATENT DOCUMENTS

| | | |
|---|---|---|
| CA | 2675288 A1 | 7/2008 |
| CN | 1762333 A | 4/2006 |

(Continued)

OTHER PUBLICATIONS

U.S. Appl. No. 15/954,039, filed Apr. 16, 2018, Granted, US10550126B2, US76.

(Continued)

*Primary Examiner* — Kristin A Vajda
(74) *Attorney, Agent, or Firm* — Cristin H. Cowles; Danielle L. Herritt; Scott R. Breining

(57) ABSTRACT

The present disclosure relates to processes for preparing (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide, solid state forms thereof, and corresponding pharmaceutical compositions, methods of treatment (including treatment of rheumatoid arthritis and atopic dermatitis), kits, methods of synthesis, and products-by-process.

9 Claims, 81 Drawing Sheets

(56) References Cited

U.S. PATENT DOCUMENTS

| | | |
|---|---|---|
| 8,637,529 B2 | 1/2014 | Woller et al. |
| 8,785,639 B2 | 7/2014 | Wishart et al. |
| 8,962,629 B2 | 2/2015 | Wishart et al. |
| 9,365,579 B2 | 6/2016 | Wishart et al. |
| 9,879,018 B2 | 1/2018 | Mulhern et al. |
| 9,879,019 B2 | 1/2018 | Nordstroem et al. |
| 9,951,080 B2 | 4/2018 | Allian |
| 9,963,459 B1 | 5/2018 | Jayanth et al. |
| 10,017,517 B2 | 7/2018 | Borchardt et al. |
| RE47,221 E | 2/2019 | Wishart et al. |
| 10,202,393 B2 | 2/2019 | Jayanth et al. |
| 10,202,394 B2 | 2/2019 | Jayanth et al. |
| 10,344,036 B2 | 7/2019 | Jayanth et al. |
| 10,519,164 B2 | 12/2019 | Allian et al. |
| 10,550,126 B2 | 2/2020 | Pangan et al. |
| 10,597,400 B2 | 3/2020 | Othman et al. |
| 10,730,883 B2 | 8/2020 | Allian et al. |
| 2003/0078277 A1 | 4/2003 | Hibi et al. |
| 2004/0023992 A1 | 2/2004 | Das et al. |
| 2005/0176796 A1 | 8/2005 | D'Alessio et al. |
| 2006/0160806 A1 | 7/2006 | Haviv et al. |
| 2006/0183758 A1 | 8/2006 | Beard et al. |
| 2007/0232653 A1 | 10/2007 | Bachmann et al. |
| 2008/0070914 A1 | 3/2008 | Freyne et al. |
| 2009/0215724 A1 | 8/2009 | Dubois et al. |
| 2009/0215750 A1 | 8/2009 | Bamberg et al. |
| 2009/0215788 A1 | 8/2009 | Elworthy et al. |
| 2009/0264399 A1 | 10/2009 | Inoue et al. |
| 2009/0312338 A1 | 12/2009 | Wishart et al. |
| 2011/0021425 A1 | 1/2011 | Billedeau |
| 2011/0190489 A1 | 8/2011 | Wishart et al. |
| 2011/0311474 A1 | 12/2011 | Wishart et al. |
| 2012/0015963 A1 | 1/2012 | Woller et al. |
| 2012/0034250 A1 | 2/2012 | Shirakami et al. |
| 2012/0330012 A1 | 12/2012 | Frank et al. |
| 2013/0072470 A1 | 3/2013 | Wishart et al. |
| 2013/0216497 A1 | 8/2013 | Wishart et al. |
| 2014/0140944 A1 | 5/2014 | Duccini |
| 2014/0271842 A1 | 9/2014 | Herbig et al. |
| 2015/0118229 A1 | 4/2015 | Voss et al. |
| 2015/0210708 A1 | 7/2015 | Wishart et al. |
| 2016/0222020 A1 | 8/2016 | Wishart et al. |
| 2016/0326181 A1 | 11/2016 | Wishart et al. |
| 2017/0129902 A1 | 5/2017 | Allian et al. |
| 2017/0266289 A1 | 9/2017 | Lipari et al. |
| 2018/0057502 A1 | 3/2018 | Allian et al. |
| 2018/0162865 A1 | 6/2018 | Borchardt et al. |
| 2018/0186805 A1 | 7/2018 | Jayanth et al. |
| 2018/0222913 A1 | 8/2018 | Jayanth et al. |
| 2018/0222914 A1 | 8/2018 | Jayanth et al. |
| 2018/0291029 A1 | 10/2018 | Wishart et al. |
| 2018/0298016 A1 | 10/2018 | Pangan et al. |
| 2019/0023714 A1 | 1/2019 | Allian et al. |
| 2019/0046527 A1 | 2/2019 | Thakkar et al. |
| 2020/0317682 A1 | 10/2020 | Allian et al. |

FOREIGN PATENT DOCUMENTS

| | | |
|---|---|---|
| EA | 007415 B1 | 10/2006 |
| EP | 0423805 A2 | 4/1991 |
| EP | 0423805 B1 | 8/2000 |
| EP | 1097709 A2 | 5/2001 |
| EP | 1112253 B1 | 10/2004 |
| EP | 2123651 A1 | 11/2009 |
| EP | 2438909 A1 | 4/2012 |
| GB | 716327 A | 10/1954 |
| RU | 2158127 C2 | 10/2000 |
| RU | 2250904 C2 | 4/2005 |
| WO | WO-9110671 A1 | 7/1991 |
| WO | WO-9216553 A1 | 10/1992 |
| WO | WO-9222552 A1 | 12/1992 |
| WO | WO-9322314 A1 | 11/1993 |
| WO | WO-9405665 A1 | 3/1994 |
| WO | WO-9411026 A2 | 5/1994 |
| WO | WO-9419351 A1 | 9/1994 |
| WO | WO-9519970 A1 | 7/1995 |
| WO | WO-9609304 A1 | 3/1996 |
| WO | WO-9822437 A1 | 5/1998 |
| WO | WO 9833782 A1 | 8/1998 |
| WO | WO-9945009 A1 | 9/1999 |
| WO | WO-0015231 A1 | 3/2000 |
| WO | WO-0015611 A1 | 3/2000 |
| WO | WO-03000695 A1 | 1/2003 |
| WO | WO-03031606 A2 | 4/2003 |
| WO | WO-2004032874 A2 | 4/2004 |
| WO | WO-2004065378 A1 | 8/2004 |
| WO | WO-2004092126 A2 | 10/2004 |
| WO | WO-2004106293 A2 | 12/2004 |
| WO | WO-2005035524 A1 | 4/2005 |
| WO | WO-2005110410 A2 | 11/2005 |
| WO | WO-2006002051 A1 | 1/2006 |
| WO | WO-2006010567 A1 | 2/2006 |
| WO | WO-2006015124 A2 | 2/2006 |
| WO | WO-2006058120 A1 | 6/2006 |
| WO | WO-2006069363 A2 | 6/2006 |
| WO | WO-2006074984 A1 | 7/2006 |
| WO | WO-2006074985 A1 | 7/2006 |
| WO | WO-2006107771 A2 | 10/2006 |
| WO | WO-2006122137 A1 | 11/2006 |
| WO | WO-2007007919 A2 | 1/2007 |
| WO | WO-2007022268 A2 | 2/2007 |
| WO | WO-2007035935 A1 | 3/2007 |
| WO | WO-2007061764 A2 | 5/2007 |
| WO | WO-2007077949 A1 | 7/2007 |
| WO | WO-2007079164 A2 | 7/2007 |
| WO | WO-2007143434 A2 | 12/2007 |
| WO | WO-2008019996 A2 | 2/2008 |
| WO | WO-2008021369 A2 | 2/2008 |
| WO | WO-2008063287 A2 | 5/2008 |
| WO | WO-2008084861 A1 | 7/2008 |
| WO | WO-2008094602 A2 | 8/2008 |
| WO | WO-2008112695 A2 | 9/2008 |
| WO | WO-2008121748 A2 | 10/2008 |
| WO | WO-2008124850 A1 | 10/2008 |
| WO | WO-2008135090 A1 | 11/2008 |
| WO | WO-2008139293 A1 | 11/2008 |
| WO | WO-2009005675 A1 | 1/2009 |
| WO | WO-2009011705 A1 | 1/2009 |
| WO | WO-2009106443 A1 | 9/2009 |
| WO | WO-2009108827 A1 | 9/2009 |
| WO | WO-2009152133 A1 | 12/2009 |
| WO | WO-2010003133 A2 | 1/2010 |
| WO | WO-2010099039 A1 | 9/2010 |
| WO | WO-2010117796 A2 | 10/2010 |
| WO | WO-201113082 A1 | 2/2011 |
| WO | WO-2011012540 A1 | 2/2011 |
| WO | WO-2011068881 A1 | 6/2011 |
| WO | WO-2011068899 A1 | 6/2011 |
| WO | WO-2011141791 A2 | 11/2011 |
| WO | WO-2011156543 A2 | 12/2011 |
| WO | WO-2012041814 A1 | 4/2012 |
| WO | WO-2013043826 A1 | 3/2013 |
| WO | WO-2013178752 A1 | 12/2013 |
| WO | WO-2014004863 A2 | 1/2014 |
| WO | WO-2014150289 A1 | 9/2014 |
| WO | WO-2015061665 A1 | 4/2015 |
| WO | WO-2016033308 A1 | 3/2016 |
| WO | WO-2016198983 A1 | 12/2016 |
| WO | WO-2017025849 A1 | 2/2017 |
| WO | WO-2017033093 A1 | 3/2017 |
| WO | WO-2017066775 A1 | 4/2017 |
| WO | WO-2017093857 A1 | 6/2017 |
| WO | WO-2017126488 A1 | 7/2017 |
| WO | WO-2017143014 A1 | 8/2017 |
| WO | WO-2018009566 A1 | 1/2018 |

OTHER PUBLICATIONS

U.S. Appl. No. 15/945,231, filed Apr. 4, 2018, Granted, US10202394B2, US77.

U.S. Appl. No. 15/945,225, filed Apr. 4, 2018, Granted, US10202393B2, US78.

(56) References Cited

OTHER PUBLICATIONS

U.S. Appl. No. 15/891,012, filed Feb. 7, 2018, Published, US20190023714A1, US83.
U.S. Appl. No. 15/908,347, filed Feb. 28, 2018, Granted, US10344036B2, US79.
U.S. Appl. No. 15/857,892, filed Dec. 29, 2017, Granted, U.S. Pat. No. 9,963,459B1, US37.
U.S. Appl. No. 15/803,538, filed Nov. 3, 2017, Granted, U.S. Pat. No. 9,951,080B2, US36.
U.S. Appl. No. 15/682,457, filed Aug. 21, 2017, Granted, U.S. Pat. No. 9,879,019B2, US35.
U.S. Appl. No. 15/682,451, filed Aug. 21, 2017, Granted, U.S. Pat. No. 9,879,018B2, US34.
U.S. Appl. No. 15/891,306, filed Feb. 7, 2017, Granted, US10017517B2, US38.
U.S. Appl. No. 15/295,561, filed Oct. 17, 2016, Published, US20170129902A1, US64.
U.S. Appl. No. 15/453,684, filed Dec. 31, 2019, Granted, US10519164, US80.
U.S. Appl. No. 15/458,622, filed Jul. 1, 2019, Granted, US10597400, US81.
U.S. Appl. No. 15/787,251, filed Feb. 11, 2020, Granted, US10730883, US82.
U.S. Appl. No. 15/905,667, filed Jun. 18, 2020, Published, US20200317682A1, US84.
U.S. Appl. No. 16/787,251, filed Feb. 11, 2020, Granted, US10730883, US82.
U.S. Appl. No. 16/458,622, filed Jul. 1, 2019, Granted, US10597400B2, US81.
U.S. Appl. No. 16/453,684, filed Jun. 26, 2019, Granted, US10519164B2, US80.
U.S. Appl. No. 15/908,347, filed Feb. 28, 2018, Granted, US-10344036-B2, US81.
U.S. Appl. No. 15/891,012, filed Feb. 7, 2018, Published, US-20190023714-A1, US72.
U.S. Appl. No. 15/954,039, filed Apr. 16, 2018, Granted, US-10550126-B2, US85.
U.S. Appl. No. 15/857,892, filed Dec. 29, 2017, Granted, US-9963459-B1, US37.
U.S. Appl. No. 15/803,538, filed Nov. 3, 2017, Granted, US-9951080-B2, US36.
U.S. Appl. No. 15/682,457, filed Aug. 21, 2017, Granted, US-9879019-B2, US35.
U.S. Appl. No. 15/682,451, filed Aug. 21, 2017, Granted, US-9879018-B2, US34.
U.S. Appl. No. 15/917,013, filed Mar. 9, 2018, Published, US-20190046527-A1, US86.
U.S. Appl. No. 15/806,104, filed Nov. 7, 2017, Published, US-20180291029-A1, US74.
U.S. Appl. No. 15/152,823, filed May 12, 2016, Published, US-20160326181-A1, US63.
U.S. Appl. No. 15/017,802, filed Feb. 8, 2016, Published, US-20160222020-A1, US62.
U.S. Appl. No. 15/610,119, filed Jan. 30, 2015, Granted, US-9365579-B2, US33.
U.S. Appl. No. 15/761,501, filed Feb. 7, 2013, Published, US-20130216497-A1, US58.
U.S. Appl. No. 15/481,028, filed Jun. 9, 2009, Granted, US-8962629-B2, US32.
U.S. Appl. No. 15/446,102, filed Mar. 1, 2017, Granted, US-RE47221-E1, US75.
U.S. Appl. No. 12/958,115, filed Dec. 1, 2010, Granted, US-8426411-B2, US29.
U.S. Appl. No. 15/506,310, filed Feb. 24, 2017, Published, US-20170266289-A1, US68.
U.S. Appl. No. 14/523,052, filed Oct. 24, 2014, Published, US-20150118229-A1, US60.
PCT/US20161057372, Feb. 13, 2017, International Search Report and Written Opinion, NPL95.
PCT/US20181021800, May 23, 2018, International Search Report and Written Opinion, NPL179.
PCT/US2009/046714, Aug. 13, 2009, International Search Report and Written Opinion, NPL180.
PCT/US2010/058572, Feb. 2, 2011, International Search Report and Written Opinion, NPL181.
PCT/US2015/047152, Dec. 19, 2014, International Search Report and Written Opinion, NPL182.
PCT/US2014/062145, Jan. 22, 2015, International Search Report and Written Opinion, NPL183.
IL 248466, Mar. 26, 2018, Amended Pleadings, NPL184.
EP2506716, Feb. 16, 2018, Notice of Opposition, NPL127.
Adamczyk, M., et al., "Synthesis of 3,7-dihydroimidazo[1,2a]pyrazine-3-ones and their Chemiluminescent Properties," Tetrahedron 59(41):8129-8142, Elsevier, England (2003).
Aletaha, D., et al., "2010 Rheumatoid Arthritis Classification Criteria: an American College of Rheumatology/european League Against Rheumatism Collaborative Initiative," Arthritis & Rheumatism 62(9):2569-2581, Wiley-Blackwell, United States (2010).
Allen., et al., Editors, "Ansel's Pharmaceutical Dosage Forms and Drug Delivery Systems," 9th Edition, Lippincott Williams & Wilkins, 2005 (8 pages, Table of Contents).
Anderson, J., et al., "Rheumatoid Arthritis Disease Activity Measures: American College of Rheumatology Recommendations for Use in Clinical Practice," Arthritis Care & Research 64(5):640-647, American College of Rheumatology, United States (2012).
Arnett, F.C., et al., "The American Rheumatism Association 1987 Revised Criteria for the Classification of Rheumatoid Arthritis," Arthritis and Rheumatism 31(3):315-324, Wiley-Blackwell, United States (1988).
Banerjee, S., et al., "JAK-STAT Signaling as a Target for Inflammatory and Autoimmune Diseases: Current and Future Prospects," Drugs 77(5):521-546, Springer International, Switzerland (Mar. 2017).
Banker, G.S. and Rhodes, C.T., "Prodrugs," in Modern Pharmaceutics, Third edition, p. 596, Marcel Dekker, Inc., United States (1996).
Baslund, B., et al., "Targeting Interleukin-15 in Patients With Rheumatoid Arthritis, A Proof-of-Concept Study," Arthritis & Rheumatism 52(9):2686-2692, American College of Rheumatology, United States (2005).
Bathon, J.M., et al., "A Comparison of Etanercept and Methotrexate in Patients with Early Rheumatoid Arthritis," The New England Journal of Medicine 343(22):1586-1593, Massachusetts Medical Society, United States (2000).
Bunnage, M.E., et al., "Asymmetric Synthesis of the cis- and trans-stereoisomers of 4-arninopyrrolidine-3-Carboxylic Acid and 4-arninotetrahydrofuran-3-carboxylic Acid," Organic & Biomolecular Chemistry 2(19):2763-2776, Royal Society of Chemistry, England (2004).
Burmester, G.R., et al., "Tofacitinib (CP-690,550) in Combination with Methotrexate in Patients with Active Rheumatoid Arthritis with an Inadequate Response to Tumour Necrosis Factor Inhibitors: A Randomised Phase 3 Trial.," Lancet 381(9865):451-460, Elsevier, England (2013).
Chaudhari, K., et al., "Rheumatoid Arthritis: Current and Future Trends," Nature Reviews. Drug Discovery 15(5):305-306, Macmillan Publishers Limited, England (May 2016).
Croasdell, G., "American College of Rheumatology/Association of Rheumatology Health Professionals—2015 Annual Meeting," Drugs of the Future 40(12):857-862, Prous Science S.A.U., United States (2015).
Dupre, et al., "An Improved Synthesis of Ethyl N-(methoxycarbonyl)-2,5-dihydro-IH-pyrrole-3-carboxylate," Journal of Organic Chemistry 56(9):3197-3198, (1991).
Dutta, S. and Reed, R.C., "Functional Half-Life is a Meaningful Descriptor of Steady-State Pharmacokinetics of an Extended-Release Formulation of a Rapidly Cleared Drug," Clinical Drug Investigation 26(12):681-690, Springer International, New Zealand (2006).
El-Nabi, H.A.A., et al., "1-Aryl-2-chloro-5-methoxy-1H-3-pyrrolecarbaldehyde as synthons for fused heterocycles: synthesis

(56) References Cited

OTHER PUBLICATIONS of pyrazolo[3,4-d]pyrrolo[2,3-b]pyridine derivatives," Journal of Chemical Research 5:325-327, Science Reviews Ltd., England (2004).

Farnia, et al., "Stille Reaction," Organic Reactions, L. Paquette et al., Editors, John Wiley & Sons, vol. 50, 1997 5 pages, 1997 (Table of Contents).

FDA, "Clinical Pharmacology and Biopharmaceutics Review(s)—Tofacitinib," Application No. 203214Origls000, Center for Drug Evaluation and Research, 181 pages (2011).

FDA, "Guidance for Industry Toxicity Grading Scale for Healthy Adult and Adolescent Volunteers Enrolled in Preventive Vaccine Clinical Trials," Department of Health and Human Services, FDA, Center for Biologics Evaluation and Research, 10 pages (2007).

FDA, "Medical Review; Addendum to Primary Clinical Review—Tofacitinib," Application No. 203214Origls000, Center for Drug Evaluation and Research, 303 pages (2012).

Fleischmann, R.M., et al., "A Randomized, Double-blind, Placebo-controlled, Twelve-week, Dose-ranging Study of Decemotinib, an Oral Selective JAK-3 Inhibitor, as Monotherapy in Patients With Active Rheumatoid Arthritis," Arthritis and Rheumatology 67(2):334-343, Wiley, United States (2015).

Gennaro, A., Editor "Remington's Pharmaceutical Sciences", 18th Edition, Mack Publishing Co., 5 pages, 1990 (Table of Contents).

Genovese, M.C., et al., "Safety and Efficacy of ABT-494, a Novel Selective JAK1 Inhibitor, in Patients with Active Rheumatoid Arthritis with an Inadequate Response to Methotrexate," Annals of the Rheumatic Diseases 75(2):141-142, Abstract OP0223, BMJ Publishing Group, England (Jun. 2016).

Genovese, M.C., et al., "Efficacy and Safety of ABT-494, a Selective JAK-1 Inhibitor, in a Phase IIb Study in Patients With Rheumatoid Arthritis and an Inadequate Response to Methotrexate," Arthritis & Rheumatology 68(12):2857-2866, Wiley, United States (Dec. 2016).

Genovese, M.C., et al., "OP0029 Baricitinib, An Oral Janus Kinase (JAK)1/JAK2 Inhibitor, in Patients with Active Rheumatoid Arthritis (RA) and an Inadequate Response to TNF Inhibitors: Results of the Phase 3 RA-Beacon Study:," Annals of the Rheumatic Diseases 74(2):75.3-76, H.K. Lewis, England (2015).

Genovese, M.C., et al., "VX-509 (Decernotinib), an Oral Selective JAK-3 Inhibitor, in Combination with Methotrexate in Patients with Rheumatoid Arthritis," Arthritis & Rheumatology 68(1):46-55, Wiley, United States (2016).

Gilworth, G., et al., "Development of a Work Instability Scale for Rheumatoid Arthritis," Arthritis and Rheumatism 49(3):349-354, Wiley-Blackwell, United States (2003).

Graff, C., et al., "Characterization of ABT-494, a Second Generation JAK1 Selective Inhibitor," 2014 ACR/ARHP Annual Meeting, Abstract No. 1499, 3 pages.

Graul, A.I., et al., "The Year's New Drugs and Biologics 2015—Part II: Trends and highlights that Marked a Complicated Year," Drugs of Today 52(2):131-163, Prous Science S.A.U., United States (Feb. 2016).

Greene, et al., Editors, "Protective Groups in Organic Synthesis," 3rd Ed., John Wiley & Sons, NY, 52 pages, 1999 (Table of Contents, Abbreviations).

Hauser, M., et al., "Pyrazolono(3,4-d)pyrimidines. II. 6-Methylpyrazolono(3,4-d)pyrimidines and some reactions of pyrazolono(3,4-d)pyrimidines," The Journal of Organic Chemistry 26(2):451-455, American Chemical Society, United States (1960).

Hirahara, K., et al., "Targeting Cytokine Signaling in Autoimmunity: Back to the Future and Beyond," Current Opinion in Immunology 43:89-97, Elsevier Ltd., England (Dec. 2016).

Iwata, S. and Tanaka, Y., "Progress in Understanding the Safety and Efficacy of Janus Kinase Inhibitors for Treatment of Rheumatoid Arthritis," Expert Review of Clinical Immunology 12(10):1047-1057, Informa UK Limited, England (Jun. 2016).

Jacobson, K.A., "Comprehensive Organic Transformations: A Guide to Functional Group Preparations," 2nd ed. Richard C. Larock. Wiley New York, 1999, pp. 2583.

Jain, S., et al., "A Novel Synthesis of DI(1-Methlazacycloalkeno)[2,3-b:2',3'-d]Pyridines Through Annulation on Lactam Acetals," Tetrahedron Letters 31(1):131-134, Pergamon Press PLC, Great Britain (1990).

Jenkins, et al., Editors, "Introduction to X-Ray Powder Diffractometry," John Wiley & Sons, 13 pages, 1996 (Table of Contents).

Jordan, V.C., "Tamoxifen: a most unlikely pioneering medicine," Nat Rev Drug Discov. 2(3):205-213, Nature Publishing Group, England (2003).

Kempson, J., et al., "Synthesis, initial SAR and biological evaluation of 1,6-dihydroimidazo[4,5-d]pyrrolo[2,3-b]pyridin-4-amine derived inhibitors of IKB kinase," Bioorg Med Chem Lett. 19(10):2646-2649, Elsevier Ltd., England (2009).

Kettle, J.G., et al., "Inhibitors of JAK-family Kinases: An Update on the Patent Literature 2013-2015, part 1," Expert Opinion on Therapeutic Patents 27(2):127-143, Informa UK Limited, England (Feb. 2017).

Keystone, E.C., et al., "Safety and Efficacy of Baricitinib at 24 Weeks in Patients with Rheumatoid Arthritis Who Have Had an Inadequate Response to Methotrexate," Annals of the Rheumatic Diseases 74(2):333-340, H.K. Lewis, England (2015).

Keystone, E.C., et al., "Certolizumab Pegol Plus Methotrexate Is Significantly More Effective Than Placebo Plus Methotrexate in Active Rheumatoid Arthritis: Findings of a Fifty-two-week, Phase III, Multicenter, Randomized, Double-blind, Placebo-controlled, Parallel-group Study," Arthritis & Rheumatology 58(11):3319-3329, Wiley, United States (2008).

Keystone, E.C., et al., "Radiographic, Clinical, and Functional Outcomes of Treatment With Adalimumab (a Human Anti-tumor Necrosis Factor Monoclonal Antibody) in Patients With Active Rheumatoid Arthritis Receiving Concomitant Methotrexate Therapy: a Randomized, Placebo-controlled, 52-week Trial," Arthritis and Rheumatism 50(5):1400-1411, Wiley-Blackwell, United States (2004).

Ko, et al., "N-Protecting Group Dependent Aromatization of 3-Pyrroline Systems to Pyrroles," Bulletin of the Korean Chemical Society 11(1):83-84, (1990).

Kremer, J.M., et al., "A Phase IIb Study of ABT-494, a Selective JAK-1 Inhibitor, in Patients with Rheumatoid Arthritis and an Inadequate Response to Anti-Tumor Necrosis Factor Therapy," Arthritis & Rheumatology 68(12):2867-2877, Wiley, United States (Nov. 2016).

Kremer, J.M., et al., "Safety and Efficacy of ABT-494, a Novel Selective JAK1 Inhibitor, in Patients with Active Rheumatoid Arthritis and Inadequate Response or Intolerance to Anti-TNF Biologic Therapy," 2015 ACR/ARHP Annual Meeting, Abstract 14L, 4 pages.

Lam, S., "JAK Inhibitors: A Broadening Approach in Rheumatoid Arthritis," Drugs of Today 52(8):467-469, Prous Science S.A.U., United States (Aug. 2016).

Larock, R.C., Editor, "Comprehensive Organic Transformations, A Guide to Functional Group Preparations," 2nd edition, Wiley-VCH, 22 pages, 1999 (Table of Contents).

Larson, G.L., et al., "Ionic and Organometallic-Catalyzed Organosilane Reductions," Organic Reactions 71:1-737, (2008).

Ma, M.H., et al., "A Systematic Comparison of Combination DMARD Therapy and Tumour Necrosis Inhibitor Therapy With Methotrexate in Patients With Early Rheumatoid Arthritis," Rheumatology 49(1):91-98, Mercury International, England (2010).

Mangoni, A.A. And Jackson, S.H., "Age-related Changes in Pharmacokinetics and Pharmacodynamics: Basic Principles and Practical Applications," British Journal of Clinical Pharmacology 57(1):42900, Wiley-Blackwell, England (2004).

MedDRA, Medical Dictionary for Regulatory Activities (MedDRA, version 17.1), http://www.meddra.ond (2014).

Menet, C.J., et al., "Progress Toward JAK1-selective Inhibitors," Future Medicinal Chemistry 7(2):203-235, Future Science Ltd., England (2015).

Mikhaleva, M.A. and Mamaev, V.P., "XXXV. 6-Hydroxypyrazolo[3,4-d]Pyrimidines," Khimiya Geterotsiklicheskikh Soedinenii, No. 12, pp. 1696-1699, Latvian Institute of Organic Synthesis, Latvia (1972).

(56) References Cited

OTHER PUBLICATIONS

Mohamed, M-E., et al., "Assessment of the Effect of CYP3A Inhibition, CYP Induction, OATP1B Inhibition and Administration of High-Fat Meal on the Pharmacokinetics of the Potent and Selective JAK1 Inhibitor ABT-494," 2015 ACR/ARHP Annual Meeting, Abstract 2751, 2 pages.

Mohamed, M-E., et al., "Pharmacokinetics of ABT-494 with the Once-Daily Extended-Release Tablet Formulation Being Utilized in the Ongoing Rheumatoid Arthritis Phase 3 Trials," 2016 ACR/ARHP Annual Meeting, Abstract No. 1629, 2 pages.

Mohamed, M-E., et al., "Pharmacokinetics, Safety and Tolerability of the Selective JAK1 Inhibitor, ABT-494, in Healthy Volunteers and Subjects with Rheumatoid Arthritis," Annals of the Rheumatic Diseases 74(2):258, Abstract THU0176, BMJ Publishing Group Ltd., (2015).

Mohamed, M-E., et al., "Preferential Inhibition of IL-6 Relative to IL-7 Signaling Pathways by ABT-494: Exposure-Response Analysis of Ex-Vivo Data from Two Phase 1 Clinical Trials and Comparison to Tofacitinib," Annals of the Rheumatic Diseases 75(2):256, Abstract THU0195, BMJ Publishing Group Ltd., England (Jun. 2016).

Mohamed, M-E.F., et al., "Population Pharmacokinetics of ABT-494 in Healthy Subjects and in Subjects With Rheumatoid Arthritis: Combined Analysis of Phase I and II Trials," Clinical Pharmacology & Therapeutics 101(1):S79, Abstract PII-098, John Wiley & Sons, Inc., United States (Feb. 2017).

Mohamed-Eslam, F., et al., "Pharmacokinetics, Safety and Tolerability of ABT-494, a Novel Selective JAK 1 Inhibitor, in Healthy Volunteers and Subjects with Rheumatoid Arthritis," Clinical Pharmacokinetics 55(12):1547-1558, Springer International, Switzerland (Jun. 2016).

Nakayamada, S., et al., "Chemical JAK Inhibitors for the Treatment of Rheumatoid Arthritis," Expert Opinion on Pharmacotherapy 17(16):2215-2225, Informa UK Limited, England (Oct. 2016).

Nakayamada, S., et al., "Recent Progress in JAK Inhibitors for the Treatment of Rheumatoid Arthritis," BioDrugs 30(5):407-419, Springer International, Switzerland (Aug. 2016).

Namour, F., "Pharmacokinetics and Pharmacokinetic/Pharmacodynamic Modeling of Filgotinib (GLPG0634), a Selective JAK1 Inhibitor, in Support of Phase IIB Dose Selection," Clinical pharmacokinetics 54(8):859-874, Springer Science+Business Media, Switzerland (2015).

Nayana, M.R.S., et al., "CoMFA and Docking Studies on Triazolopyridine Oxazole Derivatives as p38 MAP Kinase Inhibitors," European Journal of Medicinal Chemistry 43(6):1261-1269, Elsevier Masson SAS, France (2008).

Noble, M.E.M., et al., "Protein Kinase Inhibitors: Insights Into Drug Design From Structure," Science 303(5665):1800-1805, American Association for the Advancement of Science, United States (2004).

Norman, P., "Selective JAK Inhibitors in Development for Rheumatoid Arthritis," Expert Opinion on Investigational Drugs 23(8):1067-1077, Informa UK, Ltd., England (2014).

Olivera, P., et al., "Next Generation of Small Molecules in Inflammatory Bowel Disease," Gut 66(2):199-209, British Medical Assn, England (Feb. 2017).

Paulus, E.F. and Rivo, E., "1-Phenyl-3-carbethoxy-4-hydroxypyrroline," Acta Crystallographica C44:1242-1244, (1988).

Rochais, C., et al., "Synthesis of new dipyrrolo- and furopyrrolopyrazinones related to tripentones and their biological evaluation as potential kinases (CDKs1-5, GSK-3) inhibitors," Eur J Med Chem. 44(2):708-716, Elsevier Masson SAS, France (2009).

Rowe, et al., Editors, "Handbook of Pharmaceutical Excipients," 7th Ed., Pharmaceutical Press, 7 pages, 2012 (Table of Contents).

Rowe, R.C., et al., "Handbook of Pharmaceutical Excipients—7th Edition," Pharmaceutical Development and Technology, 18(2):544, Informa Healthcare USA, Inc., United States (2013).

Sahin, S. and Benet, L.Z., "The Operational Multiple Dosing Half-life: A Key to Defining Drug Accumulation in Patients and to Designing Extended Release Dosage Forms," Pharmaceutical Research 25(12):2869-2877, Kluwer Academic/Plenum Publishers, United States (2008).

Sandborn, W.J., "The Present and Future of Inflammatory Bowel Disease Treatment," Gastroenterology & Hepatology 12(7):438-441, Gastro-Hep Communications, United States (Jul. 2016).

Schram, K.H., et al., "Tricyclic nucleosides I. Synthesis of the new tricyclic ring system tetrazolo[1,5-c]pyrrolo[2,3-d]pyrimidine and certain tetrazolo[], 5-c] pyrrolo[2,3-d] pyrimidine ribonucleosides," Journal of Heterocyclic Chemistry 12:1021-1023, Journal of Heterocyclic Chemistry, United States (1975).

Schwartz, D.M., et al., "Type I/II Cytokines, JAKs, and New Strategies for Treating Autoimmune Diseases," Nature Reviews. Rheumatology 12(1):25-36, Macmillan Publishers Limited, United States (Jan. 2016).

Scott, I.C and Scott, D., "Joint Counts in Inflammatory Arthritis," Clinical and Experimental Rheumatology 32(85):S7-S12, (2014).

Semerano, L., et al., "Developments with Investigational Janus Kinase Inhibitors for Rheumatoid Arthritis," Expert Opinion on Investigational Drugs 25(12):1355-1359, Informa UK Limited, England (Oct. 2016).

Semerano, L., et al., "Novel Immunotherapeutic Avenues for Rheumatoid Arthritis," Trends in Molecular Medicine 22(3):214-229, Elsevier Science Ltd., England (Mar. 2016).

Singh, J.A., et al., "2012 Update of the 2008 American College of Rheumatology Recommendations for the Use of Disease-Modifying Antirheumatic Drugs and Biologic Agents in the Treatment of Rheumatoid Arthritis," Arthritis Care & Research 64(5):625-639, John Wiley & Sons, United States (2012).

Sivaraman, P. and Cohen, S.B., "Malignancy and Janus Kinase Inhibition," Rheumatic Diseases Clinics of North America 43(1):79-93, Elsevier Inc., United States (Feb. 2017).

Smolen, J., et al., "EULAR recommendation for the management of rheumatoid arthritis with synthetic and biological disease-modifying antirheumatic drugs," Annals of the Rheumatic Diseases 69(6):964-975, BMJ, England (2010).

Smolen, J.S., et al., "Eular Recommendations for the Management of Rheumatoid Arthritis With Synthetic and Biological Disease-modifying Antirheumatic Drugs: 2013 Update," Annals of the Rheumatic Diseases 73(3):492-509, H.K. Lewis, England (2014).

Solomon, D.H. and Bucala, R.J., "The Enduring Value of Reporting Randomized Controlled Clinical Trials in *Arthritis & Rheumatology*: 2016 and Beyond," Arthritis & Rheumatology 68(12):2831-2833, American College of Rheumatology, United States (Aug. 2016).

Stahl, et al., Editors "IUPAC Handbook of Pharmaceutical Salts: Properties, Selection, and Use," Wiley-VCH, Weinheim, Geffilany, 5 pages (2002) (Table of Contents).

Stella, V.J., et al., "A Case for Prodrugs," in Prodrugs: Challenges and Rewards Part 1, p. 24, American Association of Pharmaceutical Sciences, United States (2007).

Strand, V., et al., "Sustained Benefit in Rheumatoid Arthritis Following One Course of Rituximab: Improvements in Physical Function Over 2 Years," Rheumatology 45(12):1505-1513, Mercury International, England (2006).

Trost, B.M., et al., "Palladium-catalyzed DYKAT of Vinyl Epoxides: Enantioselective Total Synthesis and Assignment of the Configuration of (+)-Broussonetine G," Angewandte Chemie 42(48):5987-5990, Wiley-VCH, Germany (2003).

Van Epps, S., et al., "Design and synthesis of tricyclic cores for kinase inhibition," Bioorg Med Chem Lett. 23(3):693-698, Elsevier Ltd., England (2013).

Van Vollenhoven, R.F., et al., "THU0178 Relationship Between NK Cell Count and Important Safety Events in Rheumatoid Arthritis Patients Treated with Tofacitinib," Annals of the Rheumatic Diseases 74(2):258-259, H.K. Lewis, England (2015).

Voss, J., et al., "THU0127 Pharmacodynamics of a Novel JAK1 Selective Inhibitor in Rat Arthritis and Anemia Models and in Healthy Human Subjects," Annals of the Rheumatic Diseases 73(2):222, H.K. Lewis, England (2014).

Wang, G.T., et al., "Design, Synthesis, and Structural Analysis of Influenza Neuraminidase Inhibitors Containing Pyrrolidine Cores," Journal of Medicinal Chemistry 44(8):1192-1201, American Chemical Society, United States (2001).

(56) References Cited

OTHER PUBLICATIONS

Winthrop, K.L., "The Emerging Safety Profile of JAK Inhibitors in Rheumatic Disease," Nature Reviews. Rheumatology 13(4):234-243, Macmillan Publishers Limited, United States (Apr. 2017).
Wolff, M.E., "Some Considerations for Prodrug Design," in Burger's Medicinal Chemistry and Drug Discovery, Fifth Edition, vol. 1: Principles and Practices, pp. 975-977, John Wiley and Sons, United States (1995).
Woodworth, T., et al., "Standardizing Assessment and Reporting of Adverse Effects in Rheumatology Clinical Trials II: the Rheumatology Common Toxicity Criteria V.2.0.," The Journal of Rheumatology 34(6):1401-1414, Journal of Rheumatology Publishing Co, Canada (2007).
Wormser, H. C., "Synthesis of Azabiotin Analogs as Potential Cofactors for Biotin-dependent Enzymes," Journal of Pharmaceutical Sciences 59(12):1732-1737, Elsevier, United States (1970).
International Search Report and Written Opinion for International Application No. PCT/US2016/057372, European Patent Office, Netherlands, dated Feb. 13, 2017, 13 pages.
Stahl, P.H., et al., Chapters 7, 8, and 10 in *Handbook of Pharmaceutical Salts*, Stahl, P.H., et al., eds., pp. 161-189, 191-220, 237-247, 330-350, Verlag Helvetica Chimica Acta, Switzerland (2002).
AbbVie., Press Release on Sep. 7, 2017, "AbbVie's Upadacitinib (ABT-494) Meets All Primary Endpoint in Phase 2b Study in Atopic Dermatitis," accessed at https://news.abbvie.com/article_print.cfm?article_id=11530, 3 pages.
AbbVie., Press Release on Jan. 8, 2018, "AbbVie's Upadacitinib Granted Breakthrough Therapy Designation from the U.S. Food and Drug Administration for Atopic Dermatitis," accessed at https://news.abbvie.com/article_print.cfm?article_id=11593, 2 pages.
AbbVie., Press Release on Feb. 17, 2018, "AbbVie Presents New Late-Breaking Phase 2b Data on Upadacitinib in Atopic Dermatitis at the 2018 American Academy of Dermatology Annual Meeting," accessed at https://news.abbvie.com/article_print.cfm?article_id=11608, 3 pages.
AbbVie., Press Release on Apr. 9, 2018, "Upadacitinib Meets All Primary and Ranked Secondary Endpoints Including Superiority Versus Adalimumab in Phase 3 Study in Rheumatoid Arthritis," accessed at https://news.abbvie.com/article_print.cfm?article_id=11629, 5 pages.
Fraser, K., "American Academy of Dermatology Annual Meeting: San Diego, CA, USA Feb. 16-20, 2018," Am J. Clin Dermatol. 19:287-290 (2018).
Cotter, D., et al., "Emerging therapies for atopic dermatitis: JAK inhibitors," J A. Acad Dermatol 78:S53-S62, Mosby Inc. (2018).
Nygaard, U., et al., "Emerging Treatment Options in Atopic Dermatitis: Systemic Therapies," Dermatology 233:344-357 (2017).
Schwartz, D., et al., "JAK inhibition as a therapeutic strategy for immune and inflammatory diseases," Drug Discovery 16:843-862, Nature (2017).
Torres, T., "Atopic Dermatitis: the New Therapeutic Revolution in Dermatology," Acta Med Port 10:669-670, (2017).
Williams, H., "Atopic Dermatitis," N Engl J. Med 352:2314-2324 (2005).
Williams, H., et al., "The natural history of atopic dermatitis," Natural History 41-59 (2018).
Chamlin, S., et al., "The Price of Pruritus-Sleep Disturbance and Cosleeping in Atopic Dermatitis," Arch Pediatr Adolesc Med 159:745-750 (2005).
Bannister, M., et al., "Adult-onset atopic dermatitis," Australasian Journal of Dermatology 41:225-228 (2000).
Hanifin, J., et al., "Diagnostic Features of Atopic Dermatitis," Acta Dermatovener Suppl. 92:44-47 (1980).
Ellis, Charles, et al., "Understanding and Managing Atopic Dermatitis in Adult Patients," Seminars in Cutaneous Medicine and Surgery S18-S22 (2012).
Hanifin, J., et al., "A Population- Based Survey of Eczema Prevalence in the United States," Dermatitis 82:82-91 (2007).

Silverberg, J., et al., "Association between severe eczema in children and multiple comorbid conditions and increased healthcare utilization," Pediatric Allergy and Immunology 24:476-486 (2013).
AbbVie Announces Positive Phase 2 Study Results for Upadacitinib (ABT-494), an Investigational JAK1-Selective Inhibitor, in Crohn's Disease (May 9, 2017), accessed at https://news.abbvie.com/news/press-releases/abbvie-announces-positive-phase-2-study-results-for-upadacitinib-abt-494-an-investigational-jak1-selective-inhibitor-in-crohns-disease.htm, accessed on Dec. 18, 2017, 3 pages.
AbbVie's Upadacitinib (ABT-494) Meets All Primary and Ranked Secondary Endpoint in Phase 3 Study in Rheumatoid Arthritis (Jun. 7, 2017), accessed at https://news.abbvie.com/news/abbvies-upadacitinib-abt-494-meets-all-primary-and-ranked-secondary-endpoints-in-phase-3-study-in-rheumatoid-arthritis.htm, accessed on Dec. 18, 2017, 4 pages.
AbbVie's Upadacitinib (ABT-494) Meets All Primary and Ranked Secondary Endpoint in Second Phase 3 Study in Rheumatoid Arthritis (Sep. 11, 2017), accessed at https://news.abbvie.com/alert-topics/immunology/abbvies-upadacitinib-abt-494-meets-all-primary-and-ranked-secondarY-endpoints-in-second-phase-3-study-in-rheumatoid-arthritis.htm, accessed on Dec. 18, 2017, 4 pages.
AbbVie's Upadacitinib Shows Positive Results as Monotherapy in Phase 3 Rheumatoid Arthritis Study, Meeting All Primary and Key Secondary Endpoints, Dec. 2017, [retrieved on May 8, 2018]. Retrieved from the Internet: [URL: http://www.prnewswire.com/news-releases/abbvies-upadacitinib-showspositive-results-as-monotherapy-in-phase-3-rheumatoid-arthritis-study-meeting-all-primary-and-keysecondary-endpoints-300573705.html], 5 pages.
Alabdulaali, M.K., et al., "The Role of JAK2 Abnormalities in Hematologic Neoplasms," Hematology Reviews 1(1):e10, PagePress, Italy (Mar. 2009).
Amended Pleadings on Behalf of the Opponent in Opposition to Israel Patent Application 248466, dated Mar. 26, 2018, 12 pages.
Annex A—Relative IC50 Values for Compounds of Formula I(c), submitted in European Application No. EP10835061.2-1462, dated Nov. 7, 2014, cited as Document TM3 in Opposition to European Patent EP2506716, dated Feb. 16, 2018, 10 pages.
Product Label: "SEPINEO P600", XP002744402, accessed at http://gyermedhu/pdf/3664_Leaflet_Sepineo_P600_gb.pdf, accessed on Apr. 2008, pp. 1-2.
Clinical Trials, "A Phase 3, Randomized, Double-Blind Study Comparing Upadacitinib (ABT-494) to Placebo and to Adalimumab in Subjects With Moderately to Severely Active Rheumatoid Arthritis Who Are on a Stable Background of Methotrexate (MTX) and Who Have an Inadequate Response to MTX (MTX-IR)," Identifier NCT02629159 accessed at https://clinicaltrials.gov/ct2/show/NCT02629159 accessed on Oct. 23, 2018, 10 pages.
Banker, G.S., Modern Pharmaceutics, 3rd edition, Revised and expanded, Marcel Dekker, New York, Inc. (1996).
Burmester, G.R., et al., "A Phase 3 Randomized, Placebo-Controlled, Double-Blind Study of Upadacitinib (ABT-494), a Selective JAK-1 Inhibitor, in Patients with Active Rheumatoid Arthritis with Inadequate Response to Conventional Synthetic Dmards," 2017 ACR/ARHP Annual Meeting, Abstract No. 1904, United States, 5 pages (2017).
Weiss, G. and Goodnough, L.T., "Anemia of Chronic Disease," The New England Journal of Medicine 352:1011-1023, Massachusetts Medical Society, United States (Mar. 2005).
Wermuth, C., et al., "Molecular Variations D Based on Isoteric Replacements," in the Practice of Medicinal Chemistry, Chapter 13, pp. 203-237, Academic Press, London (1996).
Notice of Opposition for European Patent Application No. EP2506716, dated Feb. 16, 2018, 5 pages.
Declaration of Michael Friedman, dated Sep. 7, 2018, submitted in Response to Notice of Opposition in European Patent EP2506716, 15 pages.
Dorwald, F.Z., "Side Reactions in Organic Synthesis: A Guide to Successful Synthesis Design," Weinheim: WILEY-VCH Verlag GmbH & Co. KGaA, 2005.
Genovese, M.C., "Long-Term Safety and Efficacy of Upadacitinib (ABT-494), an Oral JAK-1 Inhibitor in Patients with Rheumatoid Arthritis in an Open Label Extension Study," 2017 ACR/ARHP Annual Meeting, Abstract No. 509, 4 pages.

(56) References Cited

OTHER PUBLICATIONS

Goedken, E.R, et al., "Minimum Significant Ratio of Selectivity Ratios (MSRSR) and Confidence in Ratio of Selectivity Ratios (CRSR): Quantitative Measures for Selectivity Ratios Obtained by Screening Assays," Journal of Biomolecular Screening 17(7):857-867, Sage Publications, United States (Apr. 2012).
Grebien, F., et al., "Stat5 Activation Enables Erythropoiesis in the Absence of EpoR and Jak2," Blood 111(9):4511-4522, American Society of Hematology, United States (May 2008).
Guschin, D., et al., "A Major Role for the Protein Tyrosine Kinase JAL1 in the JAK/STAT Signal Transduction Pathway in Response to Interleukin-6," The EMBO Journal 14(7):1421- 1429, Wiley Blackwell, England (Apr. 1995).
Klunder, B., et al., "Exposure-Response Analyses of the Effect of Upadacitinib on ACR Responses in the Phase 2b Rheumatoid Arthritis Trials in Patients with Inadequate Response to Methotrexate or to Anti-Tumor Necrosis Factor Therapy," 2017 ACR/ARHP Annual Meeting, Abstract No. 505, 4 pages (2017).
Lin, T.H., et al., "Selective Functional Inhibition of JAK-3 Is Sufficient for Efficacy in Collagen-induced Arthritis in Mice," Arthritis and Rheumatism 62(8):2283-2293, Wiley-Blackwell, United States (Aug. 2010).
Malemud, C.J, "Suppression of Autoimmune Arthritis by Small Molecule Inhibitors of the JAK/STAT Pathway," Pharmaceuticals (Basel) 3(5):1446-1455, MDPI, Switzerland (May 2010).
Merriam-Webster: Metabolite, accessed at https://www.merriam-webster.com/dictionary/metabolite, accessed on Dec. 2013.
Milici, A.J., et al., "Cartilage Preservation by Inhibition of Janus Kinase 3 in Two Rodent Models of Rheumatoid Arthritis," Arthritis Research & Therapy 10(1):R14, BioMed Central, England (2008).
Mohamed, M.E.F., et al., "ABT-494 Has no Effect on the QT Interval at the Doses Being Evaluated in Rheumatoid Arthritis Phase 3 Trials," Annals of the Rheumatic Diseases, Abstract No. AB0432, 1 page (Jun. 2017).
Mohamed, M.E.F., et al., "ABT-494 Pharmacokinetics Following Administration of the Once-Daily Extended-Release Tablet Formulation Being Utilized in the Ongoing Rheumatoid Arthritis Phase 3 Trials," Annals of the Rheumatic Diseases, Abstract No. THU0177, 2 pages (Jun. 2017).
Mohamed, M.E.F., et al., "The Selective JAK1 Inhibitor Upadacitinib has no Effect on Pharmacokinetics of the Hormonal Contraceptives Levonorgesrel and Ethinylestradiol," 2017 ACR/ARHP Annual Meeting, Abstract No. 506, 4 pages (Sep. 2017).
Mohamed, M.E.F., et al., "Use of Early Clinical Trial Data to Support Thorough QT Study Waiver for Upadacitinib and Utility of Food Effect to Demonstrate ECG Assay Sensitivity," Clinical Pharmacology & Therapeutics, 7 pages, John Wiley & Sons, Inc., United States (Jul. 2017).
Mohamed, M.E.F., "Exposure-Response Analysis to Assess the Effect of ABT-494 on QT Interval and Utilization of a Non-Pharmacological Approach to Demonstrate ECG Assay Sensitivity," Clinical Pharmacology & Therapeutics 101(51):S39, Abstract PI-076, John Wiley & Sons, Inc., United States (Feb. 2017).
Mohamed, M.F., et al., "Assessment of Effect of CYP3A Inhibition, CYP Induction, OATP1B Inhibition, and High-fat Meal on Pharmacokinetics of the JAK1 Inhibitor Upadacitinib," British Journal of Clinical Pharmacology 83(10):2242-2248, Wiley-Blackwell, England (Oct. 2017).
Neubauer, H., et al., "JAK2 Deficiency Defines an Essential Developmental Checkpoint in Definitive Hematopoiesis," Cell 93(3):397-409, Cell Press, United States (May 1998).
Clinical Trials, "A Phase 3, Randomized, Double-Blind Study Comparing Upadacitinib (ABT-494) Monotherapy to Methotrexate (MTX) in Subjects With Moderately to Severely Active Rheumatoid Arthritis With Inadequate Response to MTX," Identifier NCT02706951 accessed at https://clinicaltrials.gov/ct2/show/NCT02706951 accessed on Oct. 23, 2018, 8 pages.
Opposition Brief for European Patent Application No. EP2506716, dated Feb. 16, 2018, 16 pages Ortmann, R.A., et al., "Janus Kinases and Signal Transducers and Activators of Transcription: Their Roles in Cytokine Signaling, Development and Immunoregulation," Arthritis Research 2(1):16-32, BioMed Central Ltd, England (Dec. 1999).
Parmentier, J.M., et al., "In Vitro and in Vivo Characterization of the JAKI Selectivity of upadacitinib (ABT-494)," BMC Rheumatology 2(23):16, BioMed Central, United Kingdom (2018).
Response to Communication pursuant to Art. 94(3) EPC dated Jul. 12, 2016, submitted in European Application No. EP10835061.2-1462, cited as Document TM4 in Opposition to European Patent EP2506716, dated Feb. 16, 2018, 3 pages.
Response to Notice of Opposition, dated Sep. 10, 2018, submitted in European Patent EP2506716, 31 pages.
"Rituximab," in The Merck Index. 14th Ed., John Wiley & Sons, 2006; p. 1422.
Roskoski, R Jr, "Janus Kinase (Jak) Inhibitors in the Treatment of Inflammatory and Neoplastic Diseases," Pharmacological Research 111:784-803, Elsevier, Netherlands (Sep. 2016).
SEPPIC: "How to use Sepineo P600 in a formulation", XP054976186, accessed at https://www.youtube.com/watch?v=SHiwvwnx1tA, accessed on Aug. 30, 2012, 1 page.
Statement of Case in Opposition for Israel Patent Application 248466, dated Nov. 23, 2017, 4 pages.
Strand, V., et al., "Changes in Hemoglobin levels upon Treatment with ABT-494, a Selective JAK-1 Inhibitor and relation to baseline levels of C-Reactive Protein," THU0210, p. 283 (Jun. 2017).
Strand, V., et al., "Early Patient-Reported Outcomes and Clinical Outcomes with ABT-494 in Patients with Active Rheumatoid Arthritis who are Inadequate Responses to Methotrexate or Tumor Necrosis Factor Inhibitors: Post-Hoc Analysis of Phase 2 Randomized Controlled Trials," Annals of the Rheumatic Diseases, Abstract No. SAT0217, Jun. 2017, 1 page.
Strand, V., et al., "Economic Burden of Non-Responders to Biologic DMARD Treatments in Rheumatoid Arthritis," 2016 ACR/ARHP Annual Meeting, Abstract No. 2617, 2 pages. (2016).
Strand, V., et al., "Patient-Reported Outcomes of Long-Term Upadacitinib Use in Patients with Rheumatoid Arthritis: Interim Analysis Results of a Phase 2, Open-Label Extension Study," 2017 ACR/ARHP Annual Meeting, Abstract No. 501, 3 pages (2017).
Third Declaration of Michael Friedman, dated Oct. 23, 2018, submitted in U.S. Appl. No. 15/446,102, 41 pages.
Upadacitinib Meets All Primary and Ranked Secondary Endpoints Including Superiority Versus Adalimumab in Phase 3 Study in Rheumatoid Arthritis, [retrieved on Apr. 9, 2018]. Retrieved from the Internet: [URL http://www.prnewswire.com/news-releases/upadacitinib-meets-all-primary-and-ranked-secondary-endpoints-including-superiority-versus-adalimumab-in-phase-3-study-in-rheumatoid-arthritis-300626157.html], accessed on Apr. 10, 2018, 5 pages.
Verstovsek, S, "Therapeutic Potential of JAK2 Inhibitors," Hematology American Society of Hematology Education Program 636-642, American Society of Hematology, United States (2009).
Voss, J., et al., "THU0127 Pharmacodynamics of a Novel JAK1 Selective Inhibitor in Rat Arthritis and Anemia Models and in Healthy Human Subjects," 2013 ACR/ARHP Annual Meeting, Abstract No. 2374, 4 pages.
Clinical Trials, "A Phase 2 Study, Multicenter, Open-Label Extension (OLE) Study in Rheumatoid Arthritis Subjects Who Have Completed a Preceding Phase 2 Randomized Controlled Trial (RCT) With Upadacitinib (ABT-494)," Identifier NCT02049138, accessed at https://clinicaltrials.gov/ct2/show/NCT02049138, accessed on Oct. 3, 2018, 10 pages.
Clinical Trials, "A Randomized, Double-Blind, Placebo-Controlled, Phase 2 Study to Investigate the Safety and Efficacy of ABT-494 With Background Methotrexate (MTX) in Subjects With Active Rheumatoid Arthritis (RA) Who Have Had an Inadequate Response to MTX Alone," Identifier NCT02066389, accessed at https://clinicaltrials.gov/ct2/show/NCT02066389, accessed on Oct. 11, 2018, 11 pages.
Clinical Trials, "A Study in Healthy Adult Volunteers and Adult Subjects With Rheumatoid Arthritis to Evaluate the Safety, Tolerability, and Pharmacokinetics After Multiple Dosing of ABT-494,"

(56) References Cited

OTHER PUBLICATIONS

Identifier NCT01741493, accessed at https://clinicaltrials.gov/ct2/show/NCT01741493, accessed on Sep. 27, 2018, 7 pages.

Clinical Trials, "A Randomized, Double-Blind, Placebo-Controlled, Phase 2 Study to Investigate the Safety and Efficacy of ABT-494 Given With Methotrexate (MTX) in Subjects With Moderately to Severely Active Rheumatoid Arthritis (RA) Who Have Had an Inadequate Response or Intolerance to Anti-TNF Biologic Therapy," Identifier NCT01960855, accessed at https://clinicaltrials.gov/ct2/show/NCT01960855, accessed on Sep. 13, 2018, 8 pages.

Clinical Trials, "A Multicenter, Randomized, Double-Blind, Placebo-Controlled Study of ABT-494 for the Induction of Symptomatic and Endoscopic Remission in Subjects With Moderately to Severely Active Crohn's Disease Who Have Inadequately Responded to or Are Intolerant to Immunomodulators or Anti-TNF Therapy," Identifier NCT02365649, accessed at https://clinicaltrials.gov/ct2/show/NCT02365649, accessed on Aug. 24, 2018, 7 pages.

Clinical Trials, "A Phase 3, Randomized, Double-Blind Study Comparing Upadacitinib (ABT-494) to Placebo in Subjects With Moderately to Severely Active Rheumatoid Arthritis Who Are on a Stable Dose of Conventional Synthetic Disease-Modifying Anti-Rheumatic Drugs (csDMARDs) and Have an Inadequate Response to csDMARDs" Identifier NCT02675426, accessed at https://clinicaltrials.gov/ct2/show/NCT02675426, accessed on Oct. 22, 2018, 9 pages.

Clinical Trials, "A Phase 3, Randomized, Double-Blind Study Comparing Upadacitinib (ABT-494) Once Daily Monotherapy to Methotrexate (MTX) Monotherapy in MTX-Naive Subjects With Moderately to Severely Active Rheumatoid Arthritis", accessed at https://clinicaltrials.gov/ct2/show/NCT02706873, accessed on Oct. 17, 2018, 9 pages.

Clinical Trials, "A Phase 3 Randomized, Placebo-Controlled, Double-Blind Study to Evaluate Upadacitinib in Adolescent and Adult Subjects With Moderate to Severe Atopic Dermatitis," Identifier NCT03607422, accessed at https://clinicaltrials.gov/ct2/show/NCT03607422, accessed on Sep. 25, 2018, 9 pages.

Clinical Trials, "A Phase 3, Randomized, Double-Blind Study Comparing Upadacitinib (ABT-494) to Placebo on Stable Conventional Synthetic Disease-Modifying Anti-Rheumatic Drugs (csDMARDs) in Subjects With Moderately to Severely Active Rheumatoid Arthritis With Inadequate Response or Intolerance to Biologic DMARDs (bDMARDs)," Identifier NCT02706847, accessed at https://clinicaltrials.gov/ct2/show/NCT02706847, accessed on Oct. 23, 2018, 8 pages.

Klunder, B., et al., "Population Pharmacokinetics of Upadacitinib in Healthy Subjects and Subjects with Rheumatoid Arthritis: Analyses of Phase I and II Clinical Trials," Clinical Pharmacokinetics, 57(8):977-988, Adis, part of Springer Science+Business Media, Switzerland (Aug. 2018).

Kremer, J.M., et al., "A Phase IIb Study of ABT-494, a Selective JAK-1 Inhibitor, in Patients with Rheumatoid Arthritis and an Inadequate Response to Anti-Tumor Necrosis Factor Therapy," Arthritis & Rheumatology 68(12):2867-2877, Wiley, United States (Dec. 2016).

Mohamed, M.F., et al., "Pharmacokinetics of Upadacitinib With the Clinical Regimens of the Extended-Release Formulation Utilized in Rheumatoid Arthritis Phase 3 Trials," Clinical Pharmacology in Drug Development, 0(0):1-9, Wiley Periodicals, Inc., United States (Apr. 2018).

Mohamed, M.F., et al., "Pharmacokinetics, Safety and Tolerability of ABT-494, a Novel Selective JAK 1 Inhibitor, in Healthy Volunteers and Subjects with Rheumatoid Arthritis," Clinical Pharmacokinetics 55(12):1547-1558, ADIS Press, Switzerland (2016).

International Search Report and Written Opinion for International Application No. PCT/US2018/021800, European Patent Office, Netherlands, dated May 23, 2018, 23 pages.

International Search Report and Written Opinion for International Application No. PCT/US2009/046714, European Patent Office, Netherlands, dated Aug. 13, 2009, 10 pages.

International Search Report and Written Opinion for International Application No. PCT/US2010/058572, European Patent Office, Netherlands, dated Feb. 2, 2011, 10 pages.

International Search Report and Written Opinion for International Application No. PCT/US2015/047152, International Search Authority, United States, dated Dec. 19, 2014, 7 pages.

International Search Report and Written Opinion for International Application No. PCT/US2014/062145, European Patent Office, Netherlands, dated Jan. 22, 2015, 13 pages.

Clinical Trials, "A Phase 3 Randomized, Multicenter, Double-Blind Study to Evaluate the Safety of Upadacitinib in Combination With Topical Corticosteroids in Adolescent and Adult Subjects in Japan With Moderate to Severe Atopic Dermatitis," Identifier NCT03661138, accessed at https://clinicaltrials.gov/ct2/show/NCT03661138, accessed on Oct. 23, 2018, 10 pages.

Clinical Trials, "A Phase 2b/3, Randomized, Double-Blind Study Comparing Upadacitinib (ABT-494) to Placebo in Japanese Subjects With Moderately to Severely Active Rheumatoid Arthritis Who Are on a Stable Dose of Conventional Synthetic Disease-Modifying Anti-Rheumatic Drugs (csDMARDs) and Have an Inadequate Response to csDMARDs," Identifier NCT02720523, accessed at https://clinicaltrials.gov/ct2/show/NCT02720523, accessed on Oct. 23, 2018, 9 pages.

Clinical Trials, "A Phase 2, Multicenter, Open-Label Extension (OLE) Study to Observe the Long-Term Efficacy, Safety, and Tolerability of Repeated Administration of Upadacitinib (ABT-494) in Subjects With Crohn's Disease," Identifier NCT02782663, accessed at https://clinicaltrials.gov/ct2/show/NCT02782663 accessed on Oct. 23, 2018, 7 pages.

Clinical Trials, "A Multicenter, Randomized, Double-Blind, Placebo-Controlled Study to Evaluate the Safety and Efficacy of Upadacitinib (ABT-494) for Induction and Maintenance Therapy in Subjects With Moderately to Severely Active Ulcerative Colitis," Identifier NCT02819635, accessed at https://clinicaltrials.gov/ct2/show/NCT02819635, accessed on Oct. 23, 2018, 8 pages.

Clinical Trials, "A Phase 2b Multicenter, Randomized, Placebo-Controlled, Double-Blind Dose-Ranging Study to Evaluate ABT-494 (Upadacitinib) in Adult Subjects With Moderate to Severe Atopic Dermatitis," Identifier NCT02925117, accessed at https://clinicaltrials.gov/ct2/show/NCT02925117 accessed on Oct. 23, 2018, 9 pages.

Clinical Trials, "A Phase 3, Randomized, Double-Blind, Placebo-Controlled Study With Upadacitinib (ABT-494) in Subjects From China and Selected Countries With Moderately to Severely Active Rheumatoid Arthritis Who Have Had an Inadequate Response to Conventional Synthetic Disease-Modifying Anti-Rheumatic Drugs (csDMARDs)," Identifier NCT02955212, accessed at https://clinicaltrials.gov/ct2/show/NCT02955212 accessed on Oct. 23, 2018, 9 pages.

Clinical Trials, "A Phase 3 Multicenter, Long-Term Extension Study to Evaluate the Safety and Efficacy of Upadacitinib (ABT-494) in Subjects With Ulcerative Colitis," Identifier NCT03006068, accessed at https://clinicaltrials.gov/ct2/show/NCT03006068, accessed on Oct. 23, 2018, 8 pages.

Clinical Trials, "A Phase 3, Randomized, Active-Controlled, Double Blind Study Comparing Upadacitinib (ABT-494) to Abatacept in Subjects With Moderately to Severely Active Rheumatoid Arthritis With Inadequate Response or Intolerance to Biologic DMARDs (bDMARDs) on Stable Conventional Synthetic Disease Modifying Anti-Rheumatic Drugs (csDMARDs)," Identifier NCT03086343, accessed at https://clinicaltrials.gov/ct2/show/NCT03086343, accessed on Oct. 23, 2018, 8 pages.

Clinical Trials, "A Phase 3, Randomized, Double-Blind, Study Comparing Upadacitinib (ABT-494) to Placebo in Subjects With Active Psoriatic Arthritis Who Have a History of Inadequate Response to at Least One Biologic Disease Modifying Anti-Rheumatic Drug (bDMARD)," Identifier NCT03104374, accessed at https://clinicaltrials.gov/ct2/show/NCT03104374, accessed on Oct. 23, 2018, 10 pages.

Clinical Trials, "A Phase 3, Randomized, Double-Blind, Study Comparing Upadacitinib (ABT-494) to Placebo and to Adalimumab in Subjects With Active Psoriatic Arthritis Who Have a History of Inadequate Response to at Least One Non-Biologic Disease Modifying Anti-Rheumatic Drug (DMARD)—SELECT—PsA 1," Iden-

(56) References Cited

OTHER PUBLICATIONS tifier NCT03104400, accessed at https://clinicaltrials.gov/ct2/show/NCT03104400, accessed on Oct. 23, 2018, 12 pages.
Clinical Trials, "A Multicenter, Randomized, Double-Blind, Placebo-Controlled Study Evaluating the Safety and Efficacy of Upadacitinib in Subjects With Active Ankylosing Spondylitis," Identifier NCT03178487, accessed at https://clinicaltrials.gov/ct2/show/NCT03178487, accessed on Oct. 23, 2018, 10 pages.
Clinical Trials, "A Multicenter, Randomized, Double-Blind, Placebo-Controlled Maintenance and Long-Term Extension Study of the Efficacy and Safety of Upadacitinib (ABT-494) in Subjects With Crohn's Disease Who Completed the Studies M14-431 or M14-433," Identifier NCT03345823, accessed at https://clinicaltrials.gov/ct2/show/NCT03345823, accessed on Oct. 23, 2018, 9 pages.
Clinical Trials, "A Multicenter, Randomized, Double-Blind, Placebo-Controlled Induction Study of the Efficacy and Safety of Upadacitinib (ABT-494) in Subjects With Moderately to Severely Active Crohn's Disease Who Have Inadequately Responded to or Are Intolerant to Biologic Therapy," Identifier NCT03345836, accessed at https://clinicaltrials.gov/ct2/show/NCT03345836, accessed on Oct. 23, 2018, 8 pages.
Clinical Trials, "A Multicenter, Randomized, Double-Blind, Placebo-Controlled Induction Study of the Efficacy and Safety of Upadacitinib (ABT-494) in Subjects With Moderately to Severely Active Crohn's Disease Who Have Inadequately Responded to or Are Intolerant to Conventional Therapies But Have Not Failed Biologic Therapy," Identifier NCT03345849, accessed at https://clinicaltrials.gov/ct2/show/NCT03345849, accessed on Oct. 23, 2018, 8 pages.
Clinical Trials, "A Phase 3 Randomized, Placebo-Controlled, Double-Blind Study to Evaluate Upadacitinib in Combination With Topical Corticosteroids in Adolescent and Adult Subjects With Moderate to Severe Atopic Dermatitis," Identifier NCT03568318, accessed at https://clinicaltrials.gov/ct2/show/NCT03568318, accessed on Oct. 23, 2018, 8 pages.
Clinical Trials, "A Phase 3 Randomized, Placebo-Controlled, Double-Blind Study to Evaluate Upadacitinib in Adolescent and Adult Subjects With Moderate to Severe Atopic Dermatitis," Identifier NCT03569293, accessed at https://clinicaltrials.gov/ct2/show/NCT03569293, accessed on Oct. 23, 2018, 9 pages.
Clinical Trials, "An Open-label Multiple Dose Study to Evaluate the Pharmacokinetics, Safety and Tolerability of Upadacitinib in Pediatric Subjects With Severe Atopic Dermatitis," Identifier NCT03646604, accessed at https://clinicaltrials.gov/ct2/show/NCT03646604, accessed on Oct. 23, 2018, 6 pages.
Clinical Trials, "A Multicenter, Randomized, Double-Blind, Placebo-Controlled Induction Study to Evaluate the Efficacy and Safety of Upadacitinib (ABT-494) in Subjects With Moderately to Severely Active Ulcerative Colitis," Identifier NCT03653026, accessed at https://clinicaltrials.gov/ct2/show/NCT03653026, accessed on Oct. 23, 2018, 8 pages.
Clinical Trials, "A Phase 2 Study to Investigate the Safety and Efficacy of ABBV-105 Given Alone or in Combination With Upadacitinib (ABBV-599 Combination) With a Background of Conventional Synthetic DMARDs in Subjects With Active Rheumatoid Arthritis With Inadequate Response or Intolerance to Biologic DMARDs," Identifier NCT03682705, accessed at https://clinicaltrials.gov/ct2/show/NCT03682705, accessed on Oct. 23, 2018, 10 pages.
Bissonnette, R., et al., "Topical tofacitinib for atopic dermatitis: a phase II a randomized trial," British Journal of Dermatology (2016) 175:902-911.
Guttman-Yassky, E., et al., "Baricitinib in adult patients with moderate-to-severe atopic dermatitis: A phase 2 parallel, double-blinded, randomized placebo-controlled multiple-dose study," J Am Acad Dermatol (2018) 80(4): 913-921.
Levy, L.L., et al., "Treatment of recalcitrant atopic dermatitis with the oral Janus kinase inhibitor tofacitinib citrate," J Am Acad Dematol (2015) 73(3):395-398.
Vu, M., et al., "Oral tofacitinib: a promising treatment in atopic dermatitis, alopecia areata and vitiligo," Clinical and Experimental Dermatology (2017) 42:942-944.
Guttman-Yassky et al., "Upadacitinib in adults with moderate to severe atopic dermatitis: 16-week results from a randomized, placebo-controlled trial" J Allergy Clin Immunol, 2020, pp. 877-884.
RINVOQ™ (upadacitinib) Monotherapy Shows Improvement in Skin Clearance and Itch in First Phase 3 Study for Atopic Dermatitis Retrieved on Jun. 18, 2020. Retrieved from the Internet: [URL: https://news.abbvie.com/news/press-releases/rinvoq-upadacitinib-monotherapy-shows-improvement-in-skin-clearance-and-itch-in-first-phase-3-study-for-atopic-dermatitis.htm], 5 pages.
RINVOQ™ (upadacitinib) Monotherapy Meets All Primary and Secondary Endpoints in Second Phase 3 Study for Atopic Dermatitis. Retrieved on Jul. 21, 2020. Retrieved from the Internet: [URL: https://news.abbvie.com/news/press-releases/rinvoq-upadacitinib-monotherapy-meets-all-primary-and-secondary-endpoints-in-second-phase-3-study-for-atopic-dermatitis.htm], 5 pages.
Third Pivotal Phase 3 Study Shows RINVOQ™ (upadacitinib) Plus Topical Corticosteroids Improves Skin and Itch Symptoms in Atopic Dermatitis Patients, Retrieved on Jul. 28, 2020. Retrieved from the Internet: [URL: https://news.abbvie.com/news/press-releases/third-pivotal-phase-3-study-shows-rinvoq-upadacitinib-plus-topical-corticosteroids-improves-skin-and-itch-symptoms-in-atopic-dermatitis-patients.html], 5 pages.

Comparison of dissolution profiles of ER1, ER2 and ER3

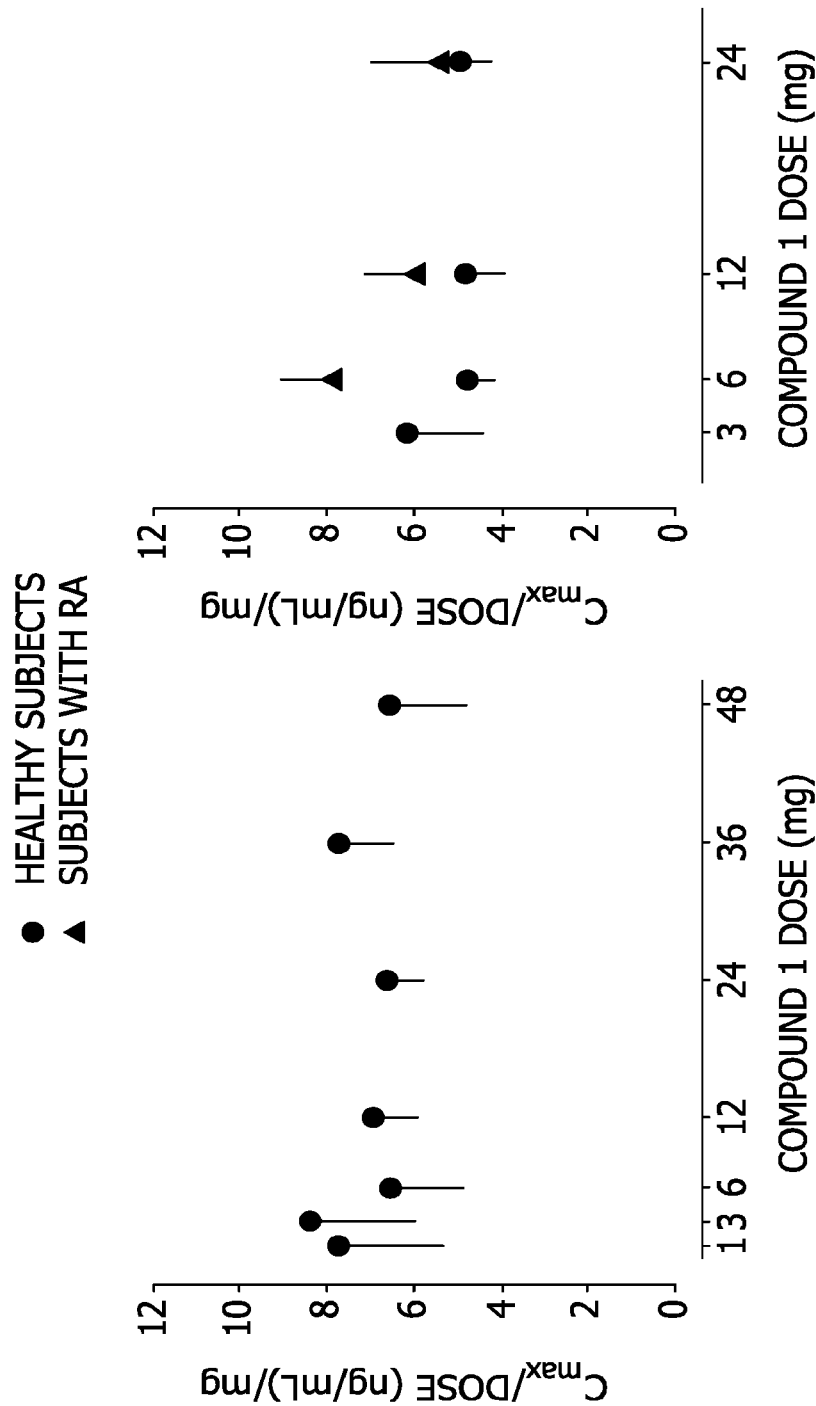

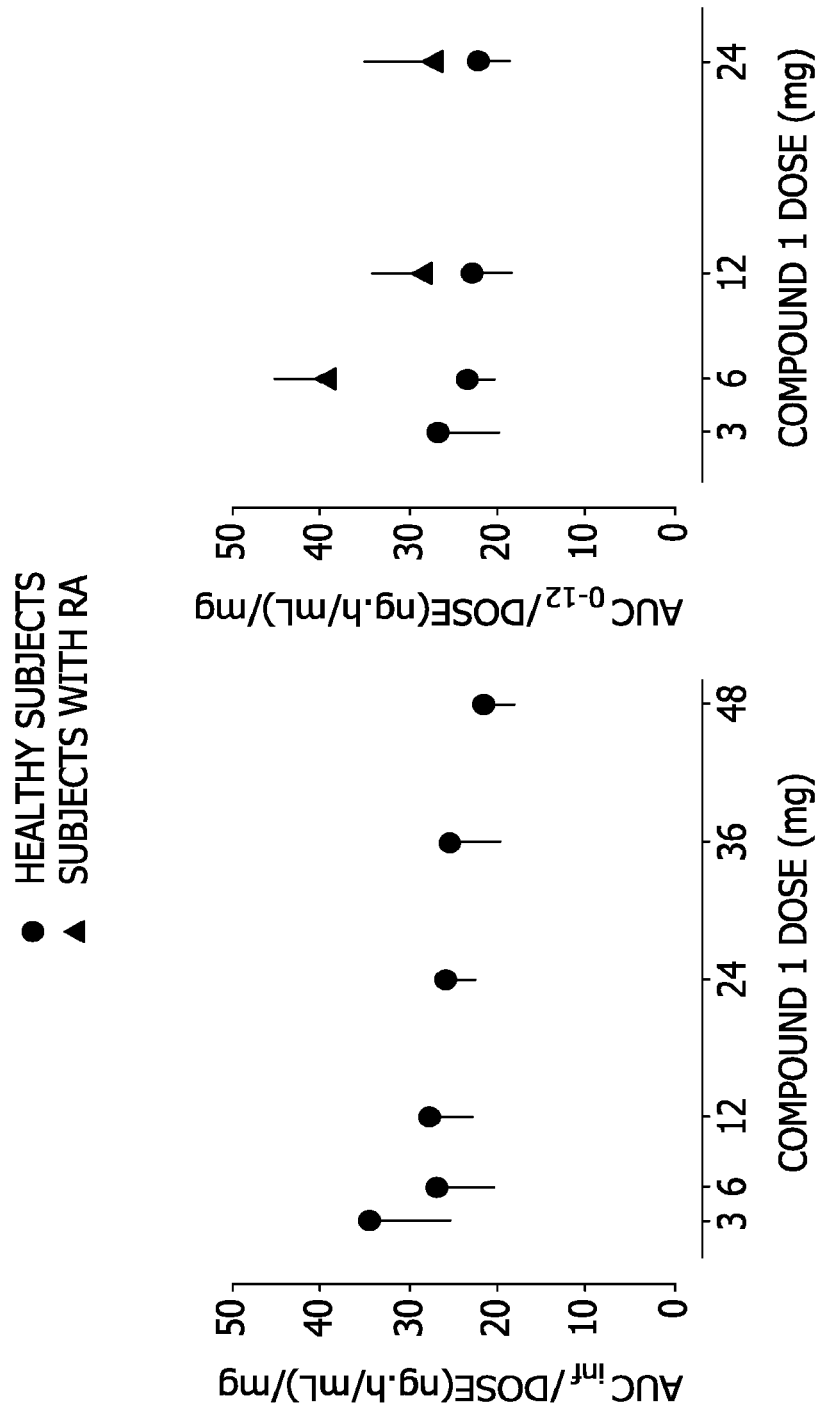

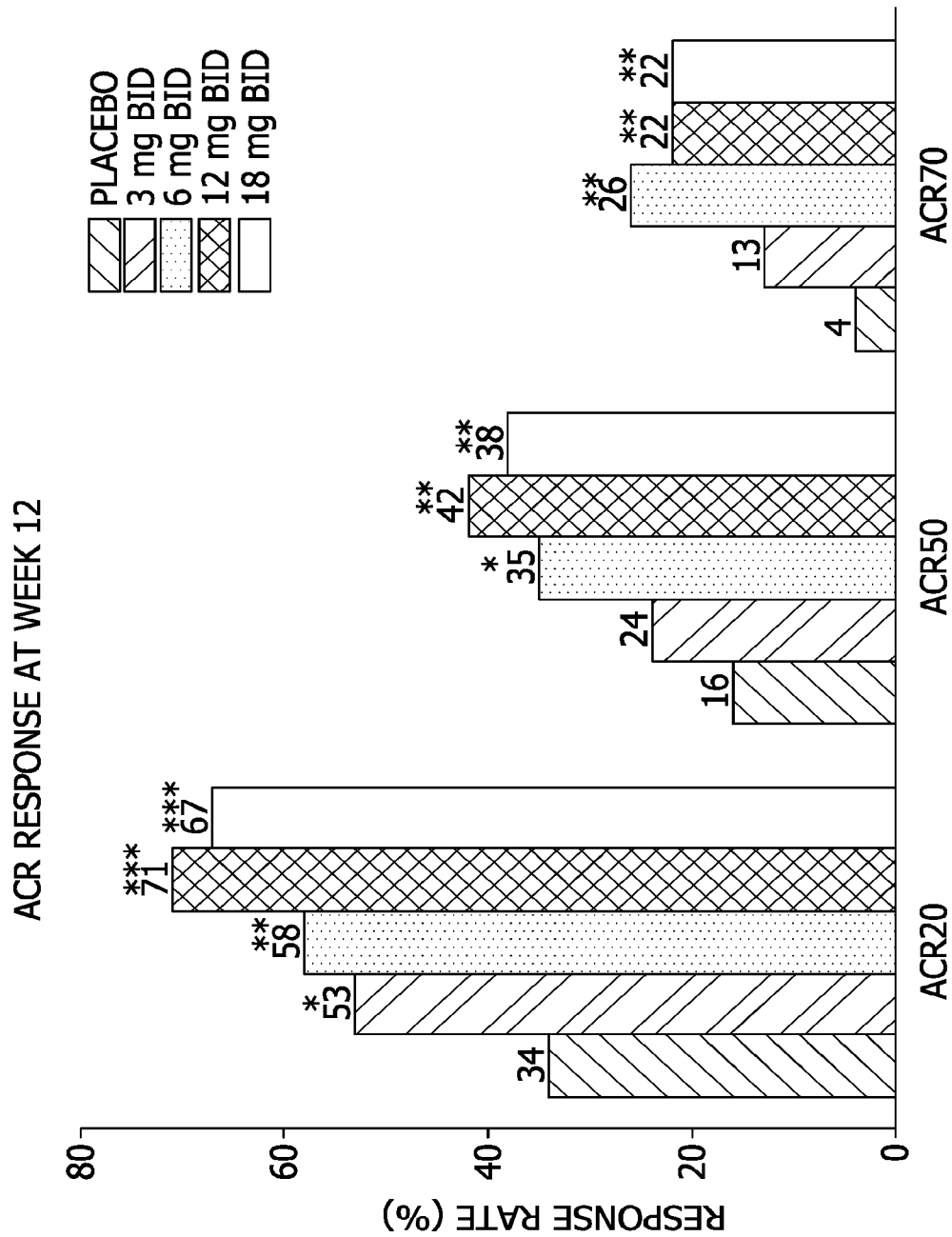

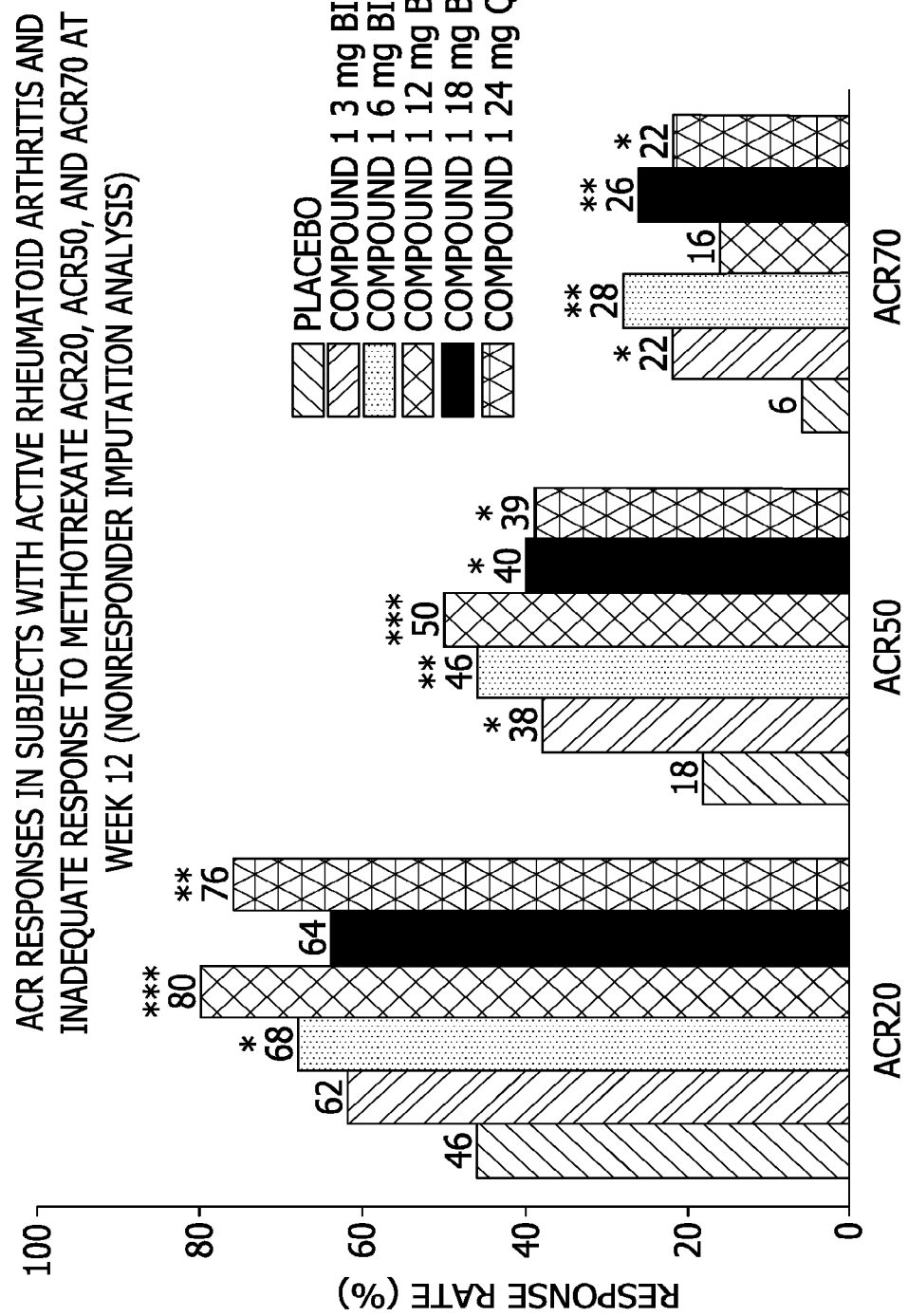

FIG. 47

Please circle one response for each of the seven questions below about your eczema.
Please leave blank any question you feel unable to answer.

1. Over the last week, on how many days has your skin been itchy because of your eczema?

No days    1-2 days    3-4 days    5-6 days    Every day

2. Over the last week, on how many nights has your sleep been disturbed because of your eczema?

No days    1-2 days    3-4 days    5-6 days    Every day

3. Over the last week, on how many days has your skin been bleeding because of your eczema?

No days    1-2 days    3-4 days    5-6 days    Every day

4. Over the last week, on how many days has your skin been weeping or oozing clear fluid because of your eczema?

No days    1-2 days    3-4 days    5-6 days    Every day

5. Over the last week, on how many days has your skin been cracked because of your eczema?

No days    1-2 days    3-4 days    5-6 days    Every day

6. Over the last week, on how many days has your skin been flaking off because of your eczema?

No days    1-2 days    3-4 days    5-6 days    Every day

7. Over the last week on how many days has your skin felt dry or rough because of your eczema?

No days    1-2 days    3-4 days    5-6 days    Every day

Each of the seven questions carries equal weight and is scored from 0 to 4 as follows:

No days    = 0
   1-2 days   = 1
   3-4 days   = 2
   5-6 days   = 3
   Every Day  = 4

If one question is left unanswered this is scored 0 and the scores are summed and expressed as usual out of a maximum of 28. If two or more questions are left unanswered the questionnaire is not scored. If two or more response options are selected, the response option with the highest score should be recorded.

FIG. 48

| Pruritus/Itch Numeric Rating Scale |
|---|
| On a scale of 0 to 10, with 0 being no itch and 10 being the worst imaginable itch, how would you rate your itch during the past 24 hours? |

| 0 | 1 | 2 | 3 | 4 | 5 | 6 | 7 | 8 | 9 | 10 |
|---|---|---|---|---|---|---|---|---|---|---|
| No Itch | | | | | | | | | | Worst Imaginable Itch |

PROCESSES FOR THE PREPARATION OF (3S,4R)-3-ETHYL-4-(3H-IMIDAZO[1,2-A]PYRROLO[2,3-E]-PYRAZIN-8-YL)-N-(2,2,2-TRIFLUOROETHYL)PYRROLIDINE-1-CARBOXAMIDE AND SOLID STATE FORMS THEREOF

CROSS-REFERENCE TO RELATED APPLICATIONS

This application is a continuation of U.S. application Ser. No. 15/954,039, filed Apr. 16, 2018, now U.S. Pat. No. 10,550,126, issued Feb. 4, 2020, which is a continuation-in-part of U.S. application Ser. No. 15/891,012, filed Feb. 7, 2018, which is a continuation of U.S. application Ser. No. 15/295,561, filed Oct. 17, 2016, which claims the benefit of U.S. Provisional Application No. 62/242,797, filed Oct. 16, 2015; and claims the benefit of U.S. Provisional Application No. 62/267,672, filed Dec. 15, 2015; and claims the benefit of U.S. Provisional Application No. 62/301,537, filed Feb. 29, 2016; and claims the benefit of U.S. Provisional Application No. 62/352,380, filed Jun. 20, 2016; all of which are herein incorporated by reference in their entirety.

FIELD OF THE INVENTION

The present disclosure relates to: (a) processes for the preparation of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide (referred to herein as "Compound 1"), (b) intermediates used in the preparation of Compound 1 and processes for preparing the intermediates; (c) solid state forms of Compound 1, (d) pharmaceutical compositions comprising one or more solid state forms of Compound 1, and, optionally, one or more additional therapeutic agents; (e) methods of treating Janus kinase-associated conditions (including rheumatoid arthritis and atopic dermatitis) by administering one or more solid state forms of Compound 1 to a subject in need thereof; (f) kits comprising a first pharmaceutical composition comprising a solid state form of Compound 1, and, optionally, a second pharmaceutical composition comprising one or more additional therapeutic agents; (g) methods for the preparation of solid state forms of Compound 1; and (h) solid state forms of Compound 1 prepared in accordance with such methods.

BACKGROUND OF THE INVENTION (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide ("Compound 1") was first disclosed in International Application WO2011/068881A1, which is herein incorporated by reference in its entirety. The compound has activity as a Janus kinase ("JAK") inhibitor, particularly as a JAK-1 inhibitor. Clinical trials are ongoing to evaluate the use of the compound to treat rheumatoid arthritis and atopic dermatitis.

The isolation and commercial-scale preparation of a solid state form of Compound 1 and corresponding pharmaceutical formulations having acceptable solid state properties (including chemical stability, thermal stability, solubility, hygroscopicity, and/or particle size), compound manufacturability (including yield, impurity rejection during crystallization, filtration properties, drying properties, and milling properties), and formulation feasibility (including stability with respect to pressure or compression forces during tableting) present a number of challenges that are discussed in greater detail below. Accordingly, there is a current need for one or more solid state forms of Compound 1 that have an acceptable balance of these properties and can be used in the preparation of pharmaceutically acceptable solid dosage forms.

Additionally, currently known processes for the preparation of Compound 1 involve the use of particularly hazardous reagents, such as trimethylsilyldiazomethane or diazomethane, and do not produce a crystalline product. There is thus also a need for a process for preparing Compound 1, and pharmaceutically acceptable salts thereof, that avoids the use of particularly hazardous reagents, and can produce a crystalline product and crystalline intermediates.

Additionally, sustained peak plasma concentrations can theoretically be achieved by means of sustained release matrix systems. However, when such systems are made of hydrophilic polymers, such as HPMC, they seldom provide pH independent drug release of pH-dependent soluble drugs, and they are normally incapable of attaining zero-order release except for practically insoluble drugs. Unexpectedly, is has been discovered that when tartaric acid is used as a pH-modifier in such a system, it allows Compound 1 to be released at a steady rate regardless of the pH of the environment.

In an unexpected finding, it was discovered that as a tablet containing the hydrophilic polymer matrix system erodes, Compound 1 reacts with the HPMC, creating a thicker gel layer which slows the release of Compound 1 from the tablet. The resulting gel layer provided an environment suitable for Compound 1 to dissolve.

Atopic Dermatitis (AD; also known as atopic eczema) is an inflammatory, pruritic, chronic or chronically relapsing skin disease. Common clinical characteristics include erythema, edema, xerosis, erosions/excoriations, oozing and crusting, and lichenification, but they vary by patient age and chronicity of lesions. Pruritus is a hallmark of the condition that is responsible for much of the disease burden borne by patients and their families (Williams H C. Clinical practice. Atopic dermatitis. *N. Engl. J. Med.* 352(22):2314-24, 2005). Sleep disturbance is commonly associated with AD and stems in large part from the significant itch associated with the disease (Chamlin S L, Mattson C L, Frieden I J, et al. The price of pruritus: sleep disturbance and cosleeping in atopic dermatitis. *Arch. Pediatr. Adolesc. Med.* 159(8):745-50, 2005; Hanifin J M, Reed M L; Eczema Prevalence and Impact Working Group. A population based survey of eczema prevalence in the United States. *Dermatitis* 18(2):82-91, 2007).

AD is also associated with multiple other comorbid conditions, including a higher prevalence of other atopic diseases such as rhinitis, food allergies and asthma with the severity of eczema directly related to the severity of these comorbidities (Silverger J I, Simpson E L. Association between severe eczema in children and multiple comorbid conditions and increased heathcare utilization. *Pediatr. Allergy Immunol.* 24(5):476-86, 2013).

The diagnosis of AD is made clinically and is based on historical features, morphology and distribution of skin lesions, and associated clinical signs. Several criteria have been developed by various groups to aid in classification. One of the earliest and most recognized sets of diagnostic criteria is the 1980 Hanifin and Rajka criteria which require that 3 of 4 major criteria and 3 of 23 minor criteria be met (Hanifin J M, Rajka G. Diagnostic features of atopic dermatitis. *Acta Der Venerol.* 92:44-7, 1980).

AD is one of the most common skin diseases which affects up to 20% of children and 1-3% of adults worldwide (Williams H C, ed. Atopic Dermatitis. The Epidemiology, Causes and Prevention of Atopic Eczema. Cambridge University press, Cambridge, UK, 2000). In approximately 70% of cases, the onset of AD starts in children under 5 years of age (Williams H C, Wüthrich B. The natural history of atopic dermatitis. In: Williams H C, ed. Atopic dermatitis: the epidemiology, causes, and prevention of atopic eczema. Cambridge, United Kingdom: Cambridge university Press, 2000:41-59) and while the majority of affected individuals have resolution of disease by adulthood, it persists in about 10% to 30% of cases (Ellis C N, Mancini A J, Paller A S, et al. Understanding and managing atopic dermatitis in adult patients. *Semin Cutan Med Surg.* 31 (3Suppl):S18-22, 2012). In addition, a smaller percentage of patients first develop symptoms of AD as adults (Bannister M J, Freeman S. Adult-onset atopic dermatitis. *Australas J Dermatol.* 41 (4):225-8, 2000).

SUMMARY OF THE INVENTION

In one aspect, the present disclosure relates to a process for preparing Compound 1, or a pharmaceutically acceptable salt thereof. The process comprises:

a) reacting a compound of formula (I)

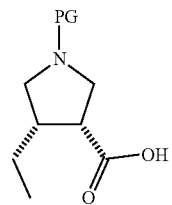

(I)

or a pharmaceutically acceptable salt thereof with trimethylsulfoxonium chloride to form a compound of formula (II)

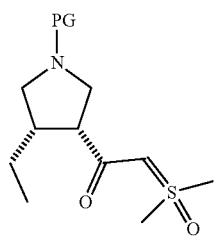

(II)

wherein PG is a protecting group;

b) contacting the compound of formula (II) with LiX and a sulfonic acid to form a compound of formula (III)

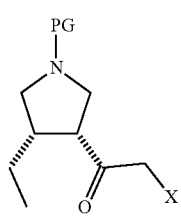

(III)

wherein X is Br or Cl;

c) reacting the compound of formula (III) with a compound of formula (IV)

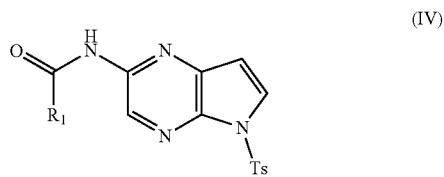

(IV)

to produce a compound of formula (V)

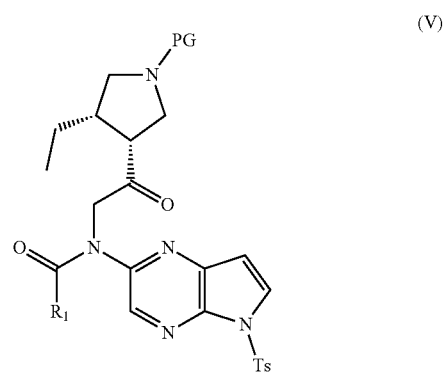

(V)

wherein $R_1$ is selected from the group consisting of alkyl, aryl, and $-OR_2$; $R_2$ is alkyl; and Ts is tosyl;

d) contacting the compound of formula (V) with a perfluoro acid anhydride and an organic base to form a compound of formula (VI)

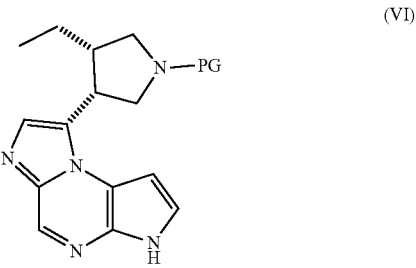

(VI)

e) deprotecting the compound of formula (VI) and forming a pharmaceutically acceptable salt of the compound of formula (VII):

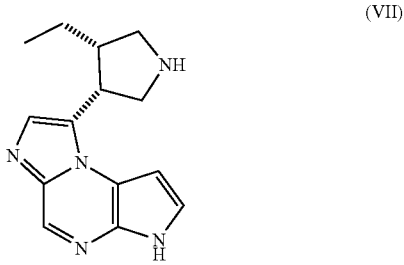

(VII)

f) reacting the pharmaceutically acceptable salt of the compound of formula (VII) with 2,2,2-trifluoroethylamine to produce Compound 1.

In another aspect, the present disclosure relates to a process for preparing Compound 1, or a pharmaceutically acceptable salt thereof. The process comprises:

a) reacting a compound of formula (Ib)

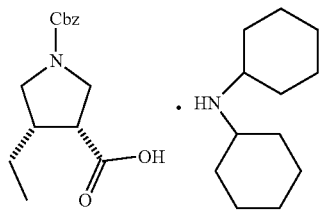
(Ib)

with trimethylsulfoxonium chloride in the presence of carbonyldiimidazole and a strong base to form a compound of formula (IIa)

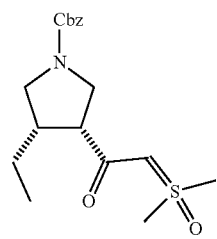
(IIa)

wherein Cbz is carboxybenzyl;

b) contacting the compound of formula (IIa) with lithium bromide and a sulfonic acid to form a compound of formula (IIIa)

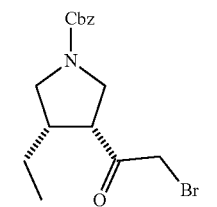
(IIIa)

c) reacting the compound of formula (IIIa) with a compound of formula (IVa)

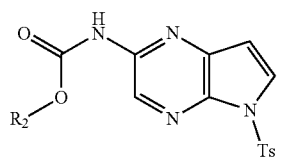
(IVa)

in the presence of lithium tert-butoxide to produce a compound of formula (Va)

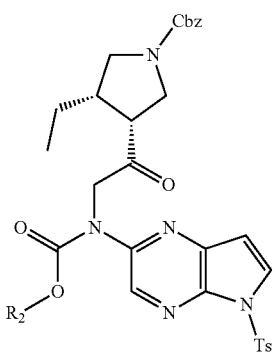
(Va)

wherein $R_2$ is methyl or ethyl; and Ts is tosyl;

d) contacting the compound of formula (Va) with a perfluoro acid anhydride and an organic base to form a compound of formula (VIa)

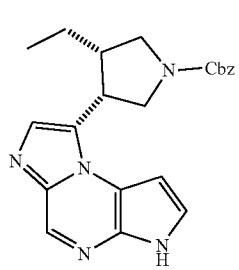
(VIa)

e) deprotecting the compound of formula (VIa) to form a compound of formula (VII)

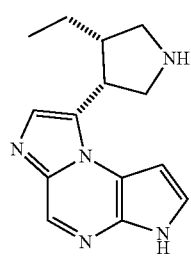
(VII)

f) contacting the compound of formula (VII) with hydrochloric acid to form a compound of formula (VIIa)

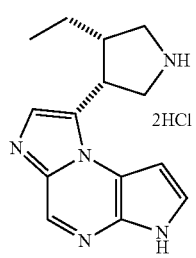
(VIIa)

g) reacting the compound of formula (VIIa) with 2,2,2-trifluoroethylamine in the presence of carbonyldiimidazole to produce Compound 1.

In another aspect, the present disclosure relates to a process for preparing Compound 1. The process comprises:

a) reacting a compound of formula (I)

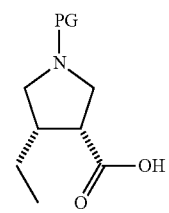

(I)

or a pharmaceutically acceptable salt thereof with trimethylsulfoxonium chloride to form a compound of formula (II)

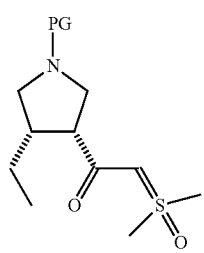

(II)

wherein PG is a protecting group;

b) contacting the compound of formula (II) with LiX and a sulfonic acid to form a compound of formula (III)

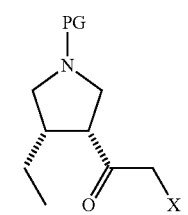

(III)

wherein X is Br or Cl;

c) reacting the compound of formula (III) with a compound of formula (IV)

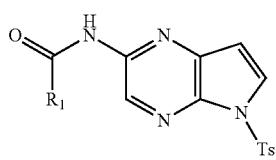

(IV)

to produce a compound of formula (V)

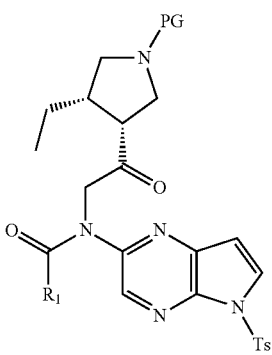

(V)

wherein $R_1$ is selected from the group consisting of alkyl, aryl, and $-OR_2$; $R_2$ is alkyl; and Ts is tosyl;

d) contacting the compound of formula (V) with a perfluoro acid anhydride and an organic base to produce a compound of formula (VI)

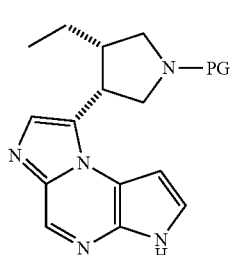

(VI)

e) deprotecting the compound of formula (VI) to form a compound of formula (VII)

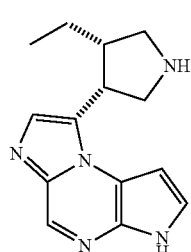

(VII)

and contacting the compound of formula (VII) with hydrochloric acid to form the compound of formula (VIIb)

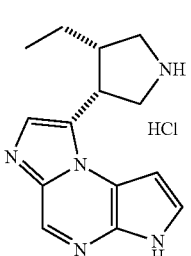

(VIIb)

f) contacting the compound of formula (VIIb) with a base to form the compound of formula (VII);

g) reacting the compound of formula (VII) with 2,2,2-trifluoroethylamine to produce Compound 1;

h) contacting Compound 1 with L-tartaric acid to produce a tartrate salt of Compound 1; and i) contacting the tartrate salt with sodium carbonate and sodium bicarbonate to produce Compound 1.

In another aspect, the present disclosure relates to a process for preparing Compound 1, or a pharmaceutically acceptable salt thereof. The process comprises:

a) converting a compound of formula (XIa):

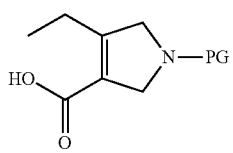

(XIa)

to a compound of formula (I):

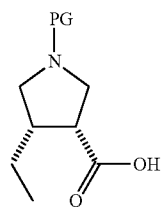

(I)

wherein PG is a protecting group;

b) reacting the compound of formula (I) with trimethylsulfoxonium chloride to form a compound of formula (II)

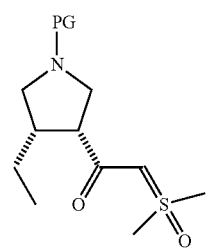

(II)

c) contacting the compound of formula (II) with an anhydrous source of HBr or HCl to form a compound of formula (III)

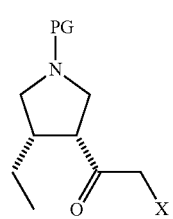

(III)

wherein X is Br or Cl;

d) reacting the compound of formula (III) with a compound of formula (IV)

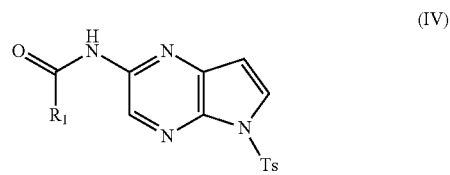

(IV)

to produce a compound of formula (V)

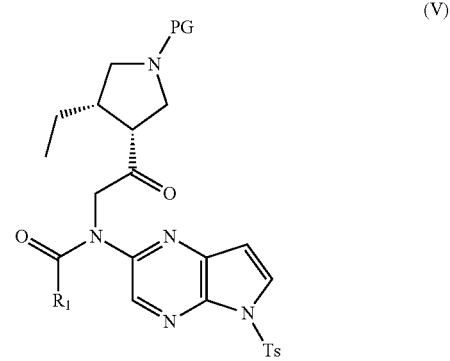

(V)

wherein $R_1$ is selected from the group consisting of alkyl, aryl, and $-OR_2$; $R_2$ is alkyl; and Ts is tosyl;

e) contacting the compound of formula (V) with a perfluoro acid anhydride and an organic base to form a compound of formula (VI)

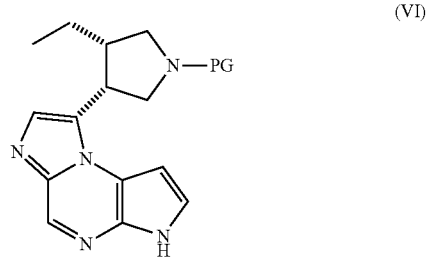

(VI)

f) deprotecting the compound of formula (VI) and forming a pharmaceutically acceptable salt of the compound of formula (VII):

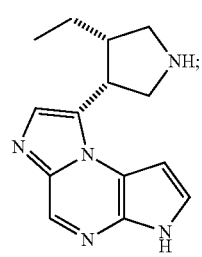

(VII)

and g) reacting the pharmaceutically acceptable salt of the compound of formula (VII) with 2,2,2-trifluoroethylamine to produce Compound 1.

In another aspect, the present disclosure relates to a compound of formula (II):

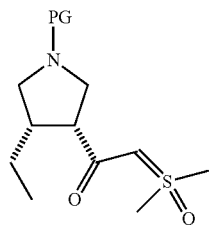

(II)

wherein PG is a protecting group.

In another aspect, the disclosure relates to a process for preparing a compound of formula (II):

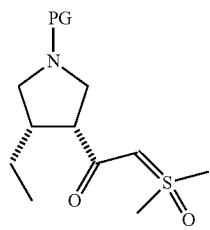

(II)

wherein PG is a protecting group, the process comprising reacting a compound of formula (I)

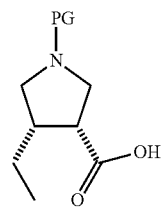

(I)

or a pharmaceutically acceptable salt thereof with trimethylsulfoxonium chloride to form the compound of formula (II).

In another aspect, the present disclosure is directed to a process for the preparation of a compound of formula (III):

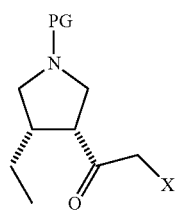

(III)

the process comprising contacting a compound of formula (II)

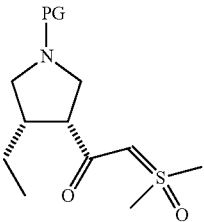

(II)

with LiX and a sulfonic acid to form the compound of formula (III); wherein PG is a protecting group; and X is Br or Cl.

In another aspect, the present disclosure relates to a compound of formula (Va)

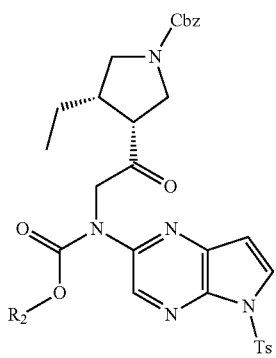

(Va)

wherein $R_2$ is methyl or ethyl; and Ts is tosyl.

In another aspect, the present disclosure relates to a process for preparing a compound of formula (V)

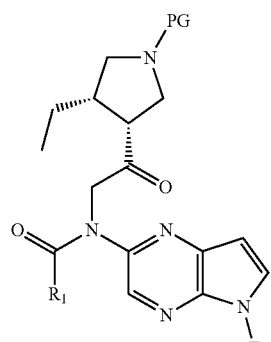

(V)

the process comprising:

a) converting a compound of formula (XIa):

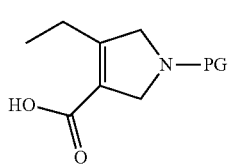

(XIa)

to a compound of formula (I)

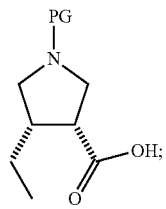
(I)

b) reacting the compound of formula (I) with trimethyl-sulfoxonium chloride to form a compound of formula (II)

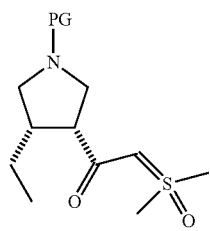
(II)

c) contacting the compound of formula (II) with an anhydrous source of HBr or HCl to form a compound of formula (III)

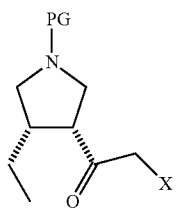
(III)

d) reacting the compound of formula (III) with a compound of formula (IV)

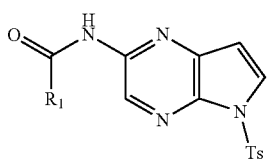
(IV)

to produce the compound of formula (V);
wherein:
PG is a protecting group;
X is Br or Cl;
$R_1$ is selected from the group consisting of alkyl, aryl, and —$OR_2$;
$R_2$ is alkyl; and
Ts is tosyl.

In another aspect, the disclosure is directed to a process for preparing a crystalline compound of formula (V)

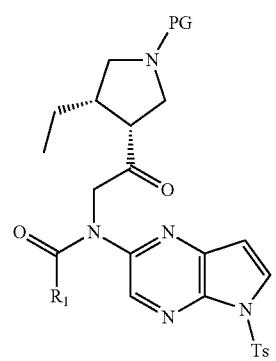
(V)

the process comprising:
a) reacting a compound of formula (III)

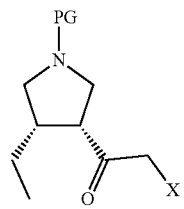
(III)

with a compound of formula (IV):

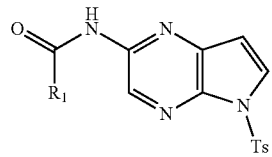
(IV)

to produce the compound of formula (V);
wherein:
PG is a protecting group;
X is Br or C;
$R_1$ is —$OR_2$;
$R_2$ is methyl or ethyl; and
Ts is tosyl.

In another aspect, the present disclosure relates to a compound of formula (IVa):

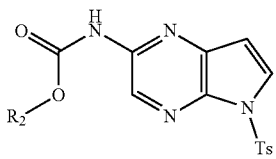
(IVa)

wherein $R_2$ is methyl or ethyl, and Ts is tosyl.

In another aspect, the present disclosure relates to a process for preparing a compound of formula (IVa):

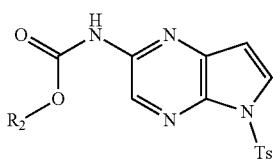
(IVa)

wherein $R_2$ is methyl or ethyl, and Ts is tosyl, the process comprising:
a) reacting a compound of formula (XVII)

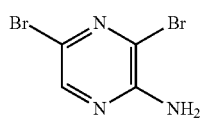
(XVII)

with trimethylsilylacetylene in the presence of a catalyst to form a compound of formula (XVIII):

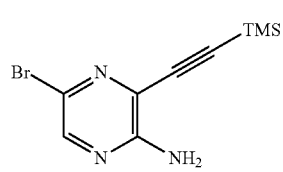
(XVIII)

wherein TMS is trimethylsilyl;
b) contacting the compound of formula (XVIII) with p-toluenesulfonyl chloride in the presence of a base to form a compound of formula (XIX)

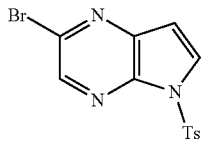
(XIX)

wherein Ts is tosyl; and
c) reacting the compound of formula (XIX) with a carbamate in the presence of a catalyst and a ligand to form the compound of formula (IVa), wherein the carbamate is selected from the group consisting of methyl carbamate and ethyl carbamate.

In another aspect, the present disclosure relates to a compound of formula (VII):

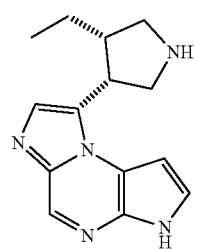
(VII)

or a pharmaceutically acceptable salt thereof.

In another aspect, the present disclosure relates to a process for preparing a compound of formula (Ib)

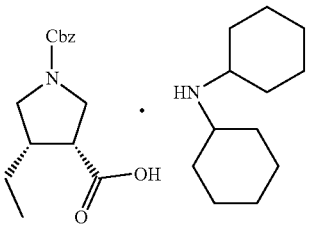
(Ib)

wherein Cbz is carboxybenzyl, the process comprising:
(i) reacting carboxybenzyl-glycine ethyl ester with ethyl acrylate to form a compound of formula (VIII):

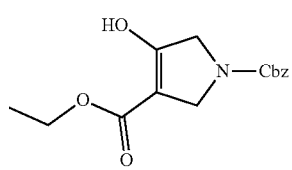
(VIII)

(ii) protecting the compound of formula (VIII) to form a compound of formula (IX):

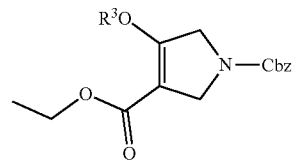
(IX)

wherein $R^3$ is selected from the group consisting of $CF_3SO_2$—; $CH_3SO_2$—; and tosyl;
(iii) contacting the compound of formula (IX) with one of ethyl boronic acid, ethyl magnesium bromide, or ethyl zinc chloride in the presence of a catalyst to form a compound of formula (X):

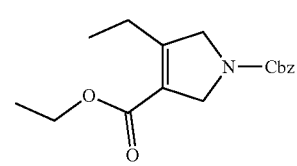
(X)

(iv) hydrolyzing the compound of formula (X) to produce the compound of formula (XI):

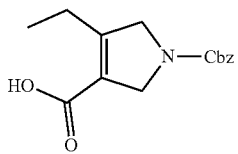

(XI)

(v) converting the compound of formula (XI) to the compound of formula (XII):

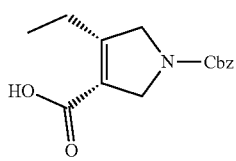

(XII)

(vi) contacting the compound of formula (XII) with dicyclohexylamine to form the compound of formula (Ib).

In another aspect, the present disclosure relates to the dicyclohexylamine salt of (3R,4S)-1-((benzyloxy)carbonyl)-4-ethylpyrrolidine-3-carboxylate.

In one aspect, the present disclosure relates to pharmaceutically acceptable solid state forms of Compound 1.

In another aspect, the present disclosure relates to Amorphous Freebase of Compound 1.

In another aspect, the present disclosure relates to crystalline Compound 1.

In another aspect, the present disclosure relates to crystalline hydrates of Compound 1.

In another aspect, the present disclosure relates to crystalline tartrates of Compound 1.

In another aspect, the present disclosure relates to the Freebase Hydrate Form C of Compound 1.

In another aspect, the present disclosure relates to the Freebase Hydrate Form B of Compound 1.

In another aspect, the present disclosure relates to crystalline anhydrates of Compound 1.

In another aspect, the present disclosure relates to the Freebase Anhydrate Form D of Compound 1.

In another aspect, the present disclosure relates to pharmaceutical compositions comprising one or more solid state forms of Compound 1, and a pharmaceutically acceptable carrier.

In another aspect, the present disclosure is directed to a pharmaceutical composition comprising one or more solid state forms of Compound 1, from about 10 w/w % to about 35 w/w % of an organic acid selected from the group consisting of tartaric acid, fumaric acid, citric acid, succinic acid, malic acid, and combinations thereof, and a pharmaceutically acceptable carrier. In one embodiment, the solid state form is Tartrate Hydrate. In one embodiment, the solid state form is Freebase Hydrate Form C.

In another aspect, the present disclosure relates to pharmaceutical compositions comprising one or more solid state forms of Compound 1, and, optionally, one or more additional therapeutic agents.

In another aspect, the present disclosure relates to methods of treating a JAK-associated condition (such as rheumatoid arthritis) in a human subject suffering from or susceptible to such a condition comprising administering to the subject a therapeutically effective amount of a solid state form of Compound 1. In another aspect, the disclosure relates to a pharmaceutical composition comprising a therapeutically effective amount of a solid state form of Compound 1 as described in the present disclosure, for use in treatment of a JAK-associated condition (such as rheumatoid arthritis) in a subject, particularly in a human subject suffering from or susceptible to the condition.

In another aspect, the present disclosure relates to methods of treating rheumatoid arthritis, wherein the term "rheumatoid arthritis" includes juvenile rheumatoid arthritis, juvenile idiopathic arthritis, ankylosing spondylitis disease, Sjogren's syndrome, psoriatic arthritis.

In another aspect, the present disclosure relates to methods of treating inflammatory bowel disease, wherein the term "inflammatory bowel disease" includes Crohn's disease, pediatric Crohn's disease and ulcerative colitis.

In another aspect, the present disclosure relates to a method of treating a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis and systemic lupus erythematosus in a human subject suffering from or susceptible to such a condition, the method comprising administering to the subject a therapeutically effective amount a solid state form of Compound 1. In another aspect, the disclosure relates to a pharmaceutical composition comprising a therapeutically effective amount of a solid state form of Compound 1 as described in the present disclosure, for use in treatment of a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis, and systemic lupus erythematosus in a subject, particularly in a human subject suffering from or susceptible to the condition.

In another aspect, the present disclosure relates to methods of treating a JAK-associated condition (such as rheumatoid arthritis) in a human subject suffering from or susceptible to such a condition comprising administering to the subject a solid state form of Compound 1, in combination with one or more additional therapeutic agents (e.g., a therapeutic agent for treating rheumatoid arthritis that is not a JAK inhibitor). In another aspect, the disclosure relates to a pharmaceutical composition comprising a solid state form of Compound 1, as described in the present disclosure, in combination with one or more additional therapeutic agents (e.g., a therapeutic agent for treating rheumatoid arthritis that is not a JAK inhibitor), for use in treatment of a JAK-associated condition (such as rheumatoid arthritis) in a subject, particularly in a human subject suffering from or susceptible to the condition.

In another aspect, the present disclosure relates to a method of treating moderate to severely active rheumatoid arthritis, the method comprising administering a therapeutically effective amount of Compound 1 in one or more forms as disclosed herein to a subject suffering from or susceptible to the condition. In a particular aspect, such a method may comprise administering 7.5 mg once daily or 15 mg once daily, or 30 mg once daily, or 45 mg once daily of the Compound 1, in one or more forms as disclosed herein, to the subject. In this or another particular aspect, the subject may be administered the Compound 1 in Freebase Form C. In this or yet another particular aspect, the subject may have an inadequate response to methotrexate. In this or yet another particular aspect, the subject may have an inadequate response to biologics medicines approved for rheumatoid arthritis. In this or yet another particular aspect, the subject may have not previously been administered biologics medicines approved for rheumatoid arthritis.

In another aspect, the present disclosure relates to a method of treating an adult subject having moderate to severely active rheumatoid arthritis, the method comprising administering to the subject: a) about 7.5 mg of Compound 1 freebase, or a pharmaceutically acceptable salt thereof, or a crystalline hydrate or a crystalline anhydrate of Compound 1 in an amount sufficient to deliver to the subject about 7.5 mg of Compound 1 freebase equivalent; or b) about 15 mg of Compound 1 freebase, or a pharmaceutically acceptable salt thereof, or a crystalline hydrate or a crystalline anhydrate of Compound 1 in an amount sufficient to deliver to the subject about 15 mg of Compound 1 freebase equivalent; or c) about 30 mg of Compound 1 freebase, or a pharmaceutically acceptable salt thereof, or a crystalline hydrate or a crystalline anhydrate of Compound 1 in an amount sufficient to deliver to the subject about 30 mg of Compound 1 freebase equivalent; or d) about 45 mg of Compound 1 freebase, or a pharmaceutically acceptable salt thereof, or a crystalline hydrate or a crystalline anhydrate of Compound 1 in an amount sufficient to deliver to the subject about 45 mg of Compound 1 freebase equivalent. In one embodiment, the present disclosure is directed to a pharmaceutical composition for use in treating an adult subject having moderate to severely active rheumatoid arthritis, the use comprising administering the pharmaceutical composition to the subject, wherein the pharmaceutical composition comprises a) about 7.5 mg of Compound 1 freebase, or a pharmaceutically acceptable salt thereof, or a crystalline hydrate or a crystalline anhydrate of Compound 1 in an amount sufficient to deliver to the subject about 7.5 mg of Compound 1 freebase equivalent; or b) about 15 mg of Compound 1 freebase, or a pharmaceutically acceptable salt thereof, or a crystalline hydrate or a crystalline anhydrate of Compound 1 in an amount sufficient to deliver to the subject about 15 mg of Compound 1 freebase equivalent; or c) about 30 mg of Compound 1 freebase, or a pharmaceutically acceptable salt thereof, or a crystalline hydrate or a crystalline anhydrate of Compound 1 in an amount sufficient to deliver to the subject about 30 mg of Compound 1 freebase equivalent; or d) about 45 mg of Compound 1 freebase, or a pharmaceutically acceptable salt thereof, or a crystalline hydrate or a crystalline anhydrate of Compound 1 in an amount sufficient to deliver to the subject about 45 mg of Compound 1 freebase equivalent.

In another embodiment, the present disclosure relates to a method of treating structural damage associated with rheumatoid arthritis in an adult subject, the method comprising administering to the subject: a) about 7.5 mg per day of Compound 1 freebase or a pharmaceutically acceptable salt thereof, or a crystalline hydrate or crystalline anhydrate of Compound 1 in an amount sufficient to deliver to the subject about 7.5 mg per day of Compound 1 freebase equivalent; or b) about 15 mg per day of Compound 1 freebase or a pharmaceutically acceptable salt thereof, or a crystalline hydrate or crystalline anhydrate of Compound 1 in an amount sufficient to deliver to the subject about 15 mg per day of Compound 1 freebase equivalent; or c) about 30 mg per day of Compound 1 freebase or a pharmaceutically acceptable salt thereof, or a crystalline hydrate or crystalline anhydrate of Compound 1 in an amount sufficient to deliver to the subject about 30 mg per day of Compound 1 freebase equivalent; or d) about 45 mg per day of Compound 1 freebase or a pharmaceutically acceptable salt thereof, or a crystalline hydrate or crystalline anhydrate of Compound 1 in an amount sufficient to deliver to the subject about 45 mg per day of Compound 1 freebase equivalent; such that the structural damage in the adult subject is inhibited or lessened. In one embodiment, the disclosure relates to a pharmaceutical composition for use in treating structural damage associated with rheumatoid arthritis in an adult subject, the use comprising administering the pharmaceutical composition to the subject, wherein the pharmaceutical composition comprises: a) about 7.5 mg per day of Compound 1 freebase or a pharmaceutically acceptable salt thereof, or a crystalline hydrate or crystalline anhydrate of Compound 1 in an amount sufficient to deliver to the subject about 7.5 mg per day of Compound 1 freebase equivalent; or b) about 15 mg per day of Compound 1 freebase or a pharmaceutically acceptable salt thereof, or a crystalline hydrate or crystalline anhydrate of Compound 1 in an amount sufficient to deliver to the subject about 15 mg per day of Compound 1 freebase equivalent; or c) about 30 mg per day of Compound 1 freebase or a pharmaceutically acceptable salt thereof, or a crystalline hydrate or crystalline anhydrate of Compound 1 in an amount sufficient to deliver to the subject about 30 mg per day of Compound 1 freebase equivalent; or d) about 45 mg per day of Compound 1 freebase or a pharmaceutically acceptable salt thereof, or a crystalline hydrate or crystalline anhydrate of Compound 1 in an amount sufficient to deliver to the subject about 45 mg per day of Compound 1 freebase equivalent; such that the structural damage in the adult subject is inhibited or lessened.

In another aspect, the disclosure is directed to a method of treating moderate to severely active rheumatoid arthritis in an adult subject, the method comprising administering to the subject: a) about 7.5 mg per day of Compound 1 freebase or a pharmaceutically acceptable salt thereof, or a crystalline hydrate or crystalline anhydrate of Compound 1 in an amount sufficient to deliver to the subject about 7.5 mg per day of Compound 1 freebase equivalent; or b) about 15 mg per day of Compound 1 freebase or a pharmaceutically acceptable salt thereof, or a crystalline hydrate or crystalline anhydrate of Compound 1 in an amount sufficient to deliver to the subject about 15 mg per day of Compound 1 freebase equivalent; or c) about 30 mg per day of Compound 1 freebase or a pharmaceutically acceptable salt thereof, or a crystalline hydrate or crystalline anhydrate of Compound 1 in an amount sufficient to deliver to the subject about 30 mg per day of Compound 1 freebase equivalent; or d) about 45 mg per day of Compound 1 freebase or a pharmaceutically acceptable salt thereof, or a crystalline hydrate or crystalline anhydrate of Compound 1 in an amount sufficient to deliver to the subject about 45 mg per day of Compound 1 freebase equivalent; wherein the subject has symptoms selected from the group consisting of at least 6 swollen joints, at least 6 tender joints, and combinations thereof prior to treating. In one embodiment, the disclosure is directed to a pharmaceutical composition for use in treating moderate to severely active rheumatoid arthritis in an adult subject, the use comprising administering the pharmaceutical composition to the subject, wherein the pharmaceutical composition comprises: a) about 7.5 mg per day of Compound 1 freebase or a pharmaceutically acceptable salt thereof, or a crystalline hydrate or crystalline anhydrate of Compound 1 in an amount sufficient to deliver to the subject about 7.5 mg per day of Compound 1 freebase equivalent; or b) about 15 mg per day of Compound 1 freebase or a pharmaceutically acceptable salt thereof, or a crystalline hydrate or crystalline anhydrate of Compound 1 in an amount sufficient to deliver to the subject about 15 mg per day of Compound 1 freebase equivalent; or c) about 30 mg per day of Compound 1 freebase or a pharmaceutically acceptable salt thereof, or a crystalline hydrate or crystalline anhydrate of Compound 1 in an amount sufficient to deliver to the subject about 30 mg per day of Compound 1 freebase equivalent; or d) about 45 mg per day of Compound 1 freebase or a pharmaceutically acceptable salt thereof, or a crystalline hydrate or crystalline anhydrate of Compound 1 in an amount sufficient to deliver to the subject about 45 mg per day of Compound 1 freebase equivalent; wherein the subject has symptoms selected from the group consisting of at least 6 swollen joints, at least 6 tender joints, and combinations thereof prior to treating.

In another aspect, the disclosure is directed to a method of reducing signs and symptoms of rheumatoid arthritis in an adult subject with moderately to severely active rheumatoid arthritis, the method comprising administering to the subject: a) about 7.5 mg per day of Compound 1 freebase or a pharmaceutically acceptable salt thereof, or a crystalline hydrate or crystalline anhydrate of Compound 1 in an amount sufficient to deliver to the subject about 7.5 mg of Compound 1 freebase equivalent; or b) about 15 mg per day of Compound 1 freebase or a pharmaceutically acceptable salt thereof, or a crystalline hydrate or crystalline anhydrate of Compound 1 in an amount sufficient to deliver to the subject about 15 mg of Compound 1 freebase equivalent; or c) about 30 mg per day of Compound 1 freebase or a pharmaceutically acceptable salt thereof, or a crystalline hydrate or crystalline anhydrate of Compound 1 in an amount sufficient to deliver to the subject about 30 mg of Compound 1 freebase equivalent; or d) about 45 mg per day of Compound 1 freebase or a pharmaceutically acceptable salt thereof, or a crystalline hydrate or crystalline anhydrate of Compound 1 in an amount sufficient to deliver to the subject about 45 mg of Compound 1 freebase equivalent. In one embodiment, the disclosure is directed to a pharmaceutical composition for use in reducing signs and symptoms of rheumatoid arthritis in an adult subject with moderately to severely active rheumatoid arthritis, the use comprising administering the pharmaceutical composition to the subject, wherein the pharmaceutical composition comprises: a) about 7.5 mg per day of Compound 1 freebase or a pharmaceutically acceptable salt thereof, or a crystalline hydrate or crystalline anhydrate of Compound 1 in an amount sufficient to deliver to the subject about 7.5 mg of Compound 1 freebase equivalent; or b) about 15 mg per day of Compound 1 freebase or a pharmaceutically acceptable salt thereof, or a crystalline hydrate or crystalline anhydrate of Compound 1 in an amount sufficient to deliver to the subject about 15 mg of Compound 1 freebase equivalent; or c) about 30 mg per day of Compound 1 freebase or a pharmaceutically acceptable salt thereof, or a crystalline hydrate or crystalline anhydrate of Compound 1 in an amount sufficient to deliver to the subject about 30 mg of Compound 1 freebase equivalent; or d) about 45 mg per day of Compound 1 freebase or a pharmaceutically acceptable salt thereof, or a crystalline hydrate or crystalline anhydrate of Compound 1 in an amount sufficient to deliver to the subject about 45 mg of Compound 1 freebase equivalent.

In another aspect, the present disclosure relates to kits comprising one or more pharmaceutical compositions comprising a solid state form of Compound 1. The kit optionally can comprise another pharmaceutical composition comprising one or more additional therapeutic agents and/or instructions, for example, instructions for using the kit.

In another aspect, the present disclosure relates to methods for the preparation of a solid state form of Compound 1.

In another aspect, the present disclosure relates to solid state forms of Compound 1 prepared in accordance with such methods.

In another aspect, the present disclosure relates to a method of treating an adult subject having moderate to severely active rheumatoid arthritis, the method comprising administering to the subject about 7.5 mg, or about 15 mg, or about 30 mg, or about 45 mg of Compound 1 freebase, or a crystalline hydrate of Compound 1 in an amount sufficient to deliver to the subject about 7.5 mg, or about 15 mg, or about 30 mg, or about 45 mg of Compound 1 freebase equivalent. In this or another particular aspect, the hydrate may be a hemihydrate. In this or another aspect, the hemihydrate may be Freebase Hydrate Form C. In this or yet another particular aspect, the subject may have an inadequate response or tolerance to one or more disease-modifying antirheumatic drugs (DMARDS), such as methotrexate. In this or yet another particular aspect, the subject may have not previously been administered DMARDS. In this or yet another particular aspect, the subject may further be administered one or more DMARD.

In another aspect, the present disclosure relates to a method of treating structural damage associated with rheumatoid arthritis in an adult subject, the method comprising administering to the subject about 7.5 mg, or about 15 mg, or about 30 mg, or about 45 mg per day of Compound 1 freebase or a crystalline hydrate of Compound 1 in an amount sufficient to deliver to the subject about 7.5 mg, or about 15 mg, or about 30 mg, or about 45 mg per day of Compound 1 freebase equivalent, such that the structural damage in the adult subject is inhibited or lessened. In this or another particular aspect, the hydrate may be a hemihydrate. In this or another aspect, the hemihydrate may be Freebase Hydrate Form C.

In another aspect, the present disclosure relates to a method of treating moderate to severely active rheumatoid arthritis in an adult subject, the method comprising administering to the subject about 7.5 mg, or about 15 mg, or about 30 mg, or about 45 mg per day of Compound 1 freebase or a crystalline hydrate of Compound 1 in an amount sufficient to deliver to the subject about 7.5 mg, or about 15 mg, or about 30 mg, or about 45 mg per day of Compound 1 freebase equivalent, wherein the subject has symptoms selected from the group consisting of at least 6 swollen joints, at least 6 tender joints, and combinations thereof prior to treating. In this or another particular aspect, the hydrate may be a hemihydrate. In this or another aspect, the hemihydrate may be Freebase Hydrate Form C.

In another aspect, the present disclosure relates to a method of reducing signs and symptoms of rheumatoid arthritis in an adult subject with moderately to severely active rheumatoid arthritis, the method comprising administering to the subject about 7.5 mg per day of Compound 1 freebase or a crystalline hydrate of Compound 1 in an amount sufficient to deliver to the subject about 7.5 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a method of reducing signs and symptoms of rheumatoid arthritis in an adult subject with moderately to severely active rheumatoid arthritis, the method comprising administering to the subject about 15 mg per day of Compound 1 freebase or a crystalline hydrate of Compound 1 in an amount sufficient to deliver to the subject about 15 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a method of reducing signs and symptoms of rheumatoid arthritis in an adult subject with moderately to severely active rheumatoid arthritis, the method comprising administering to the subject about 30 mg per day of Compound 1 freebase or a crystalline hydrate of Compound 1 in an amount sufficient to deliver to the subject about 30 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a method of reducing signs and symptoms of rheumatoid arthritis in an adult subject with moderately to severely active rheumatoid arthritis, the method comprising administering to the subject about 45 mg per day of Compound 1 freebase or a crystalline hydrate of Compound 1 in an amount sufficient to deliver to the subject about 45 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a pharmaceutical composition comprising a crystalline hydrate of Compound 1 and a pharmaceutically acceptable carrier, wherein the composition comprises the crystalline hydrate in an amount sufficient to deliver about 7.5 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a pharmaceutical composition comprising a crystalline hydrate of Compound 1 and a pharmaceutically acceptable carrier, wherein the composition comprises the crystalline hydrate in an amount sufficient to deliver about 15 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a pharmaceutical composition comprising a crystalline hydrate of Compound 1 and a pharmaceutically acceptable carrier, wherein the composition comprises the crystalline hydrate in an amount sufficient to deliver about 30 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a pharmaceutical composition comprising a crystalline hydrate of Compound 1 and a pharmaceutically acceptable carrier, wherein the composition comprises the crystalline hydrate in an amount sufficient to deliver about 45 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a method of treating an adult subject having moderate to severely active rheumatoid arthritis, the method comprising administering to the subject about 7.5 mg, or about 15 mg, or about 30 mg, or about 45 mg of a crystalline hydrate of Compound 1. In this or another particular aspect, the hydrate may be a hemihydrate. In this or another aspect, the hemihydrate may be Freebase Hydrate Form C.

In another aspect, the present disclosure relates to a method of treating structural damage associated with rheumatoid arthritis in an adult subject, the method comprising administering to the subject about 7.5 mg, or about 15 mg, or about 30 mg, or about 45 mg per day of a crystalline hydrate of Compound 1, such that the structural damage in the adult subject is inhibited or lessened. In this or another particular aspect, the hydrate may be a hemihydrate. In this or another aspect, the hemihydrate may be Freebase Hydrate Form C.

In another aspect, the present disclosure relates to a method of treating moderate to severely active rheumatoid arthritis in an adult subject, the method comprising administering to the subject about 7.5 mg, or about 15 mg, or about 30 mg, or about 45 mg per day of a crystalline hydrate of Compound 1, wherein the subject has symptoms selected from the group consisting of at least 6 swollen joints, at least 6 tender joints, and combinations thereof prior to treating. In this or another particular aspect, the hydrate may be a hemihydrate. In this or another aspect, the hemihydrate may be Freebase Hydrate Form C.

In another aspect, the present disclosure relates to a method of reducing signs and symptoms of rheumatoid arthritis in an adult subject with moderately to severely active rheumatoid arthritis, the method comprising administering to the subject about 7.5 mg, or about 15 mg, or about 30 mg, or about 45 mg per day of a crystalline hydrate of Compound 1. In this or another particular aspect, the hydrate may be a hemihydrate. In this or another aspect, the hemihydrate may be Freebase Hydrate Form C.

In another aspect, the present disclosure is directed to an extended release formulation for oral administration comprising Compound 1 or a pharmaceutically acceptable salt thereof, a hydrophilic polymer, and a pH modifier, wherein the hydrophilic polymer, in contact with water, forms a gel layer that provides an environment suitable for Compound 1 and the pH modifier to dissolve.

In another aspect, the present disclosure is directed to a process for preparing a pharmaceutical composition, the process comprising: (a) combining Compound 1 or a pharmaceutically acceptable salt thereof, or a solid state form of Compound 1, and at least a portion of one additional composition component to form a dry granulation mixture; (b) contacting the dry granulation mixture with a granulation fluid to form a wet granulation mixture; (c) drying the wet granulation mixture to form a granulated material; (d) milling the granulated material to form a milled granulated material; (e) combining the milled granulation material with any remaining composition components; and (f) compressing the composition to form the pharmaceutical composition.

In one aspect, the present disclosure is directed to a method for treating atopic dermatitis in a patient, comprising orally administering to a patient suffering from atopic dermatitis a solid dosage form comprising about 7.5 mg, 15 mg, or 30 mg free base equivalent of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide or a pharmaceutically acceptable salt thereof once daily for a time period sufficient to treat the atopic dermatitis. In one aspect, the patient is an adult. In one aspect, the adult patient has moderate to severe atopic dermatitis. In one aspect, the adult patient had inadequately responded to treatment with topical corticosteroids or topical calcineurin inhibitors. In one aspect, the time period sufficient to treat the atopic dermatitis is at least 2 weeks. In one aspect, the time period sufficient to treat the atopic dermatitis is at least 16 weeks.

In one aspect, the present disclosure is directed to a method for treating atopic dermatitis in a patient, comprising orally administering to a patient suffering from atopic dermatitis a solid dosage form comprising about 7.5 mg, 15 mg or 30 mg freebase equivalent of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide or a pharmaceutically acceptable salt thereof once daily for a time period sufficient to treat the atopic dermatitis, wherein the solid dosage form comprises a solid form of (3S,4R)-3-ethyl-4-(3H-imidazo[1,2-a]pyrrolo[2,3-e]pyrazin-8-yl)-N-(2,2,2-trifluoroethyl) pyrrolidine-1-carboxamide or a pharmaceutically acceptable salt thereof selected from the group consisting of amorphous freebase, freebase hydrate Form C, freebase anhydrate Form D, and tartrate tetrahydrate. In one aspect, the solid form is the freebase hydrate Form C. In one aspect, the patient is an adult. In one aspect, the adult patient has moderate to severe atopic dermatitis. In one aspect, the adult patient had inadequately responded to treatment with topical corticosteroids or topical calcineurin inhibitors. In one aspect, the time period sufficient to treat the atopic dermatitis is at least 2 weeks. In one aspect, the time period sufficient to treat the atopic dermatitis is at least 16 weeks.

In one aspect, the present disclosure is directed to a method for treating atopic dermatitis in a patient, comprising orally administering to a human subject suffering from atopic dermatitis a solid dosage form comprising about 7.5 mg, 15 mg or 30 mg freebase equivalents of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide or a pharmaceutically acceptable salt thereof, a release control polymer and an acidic pH modifier, once daily for a time period sufficient to treat the atopic dermatitis, wherein the solid dosage form provides for extended release of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide or a pharmaceutically acceptable salt thereof. In one aspect, the patient is an adult. In one aspect, the release control polymer is a hydrophilic polymer and the acidic pH modifier is an organic acid. In one aspect, the time period sufficient to treat the atopic dermatitis is at least 2 weeks. In one aspect, the time period sufficient to treat the atopic dermatitis is at least 16 weeks.

BRIEF DESCRIPTION OF THE DRAWINGS

FIG. 34A-34D shows the dose-normalized Compound 1 mean $C_{max}$ and AUC after administration of single doses in healthy subjects (FIG. 34A—single dose, $C_{max}$; FIG. 34C—single dose, $AUC_\infty$) and multiple-doses in healthy subjects and subjects with rheumatoid arthritis (FIG. 34B—multiple-doses, $C_{max}$; FIG. 34D—multiple-doses, $AUC_{0-12}$).

FIG. 36A shows the ACR20, ACR50, and ACR70 response rate at week 12 following administration of placebo or various doses of Compound 1 to subjects with active rheumatoid arthritis and prior inadequate response or intolerance to an anti-TNF biologic agent (*P<0.05; P<0.01; *P<0.001 relative to placebo; modified intent-to-treat population (NRI)).

FIG. 41 shows the ACR20, ACR50, and ACR70 responses at week 12 following administration of placebo or various doses of Compound 1 to subjects with active rheumatoid arthritis and inadequate response to methotrexate (*P<0.05; P<0.01; *P<0.001 relative to placebo; modified intent-to-treat population with NRI of missing values).

FIG. 47 is an example of the Patient Oriented Eczema Measure.

FIG. 48 is an example of the Pruritus (Itch) Numerical Rate Scale.

DETAILED DESCRIPTION OF THE INVENTION

Figure 1A:
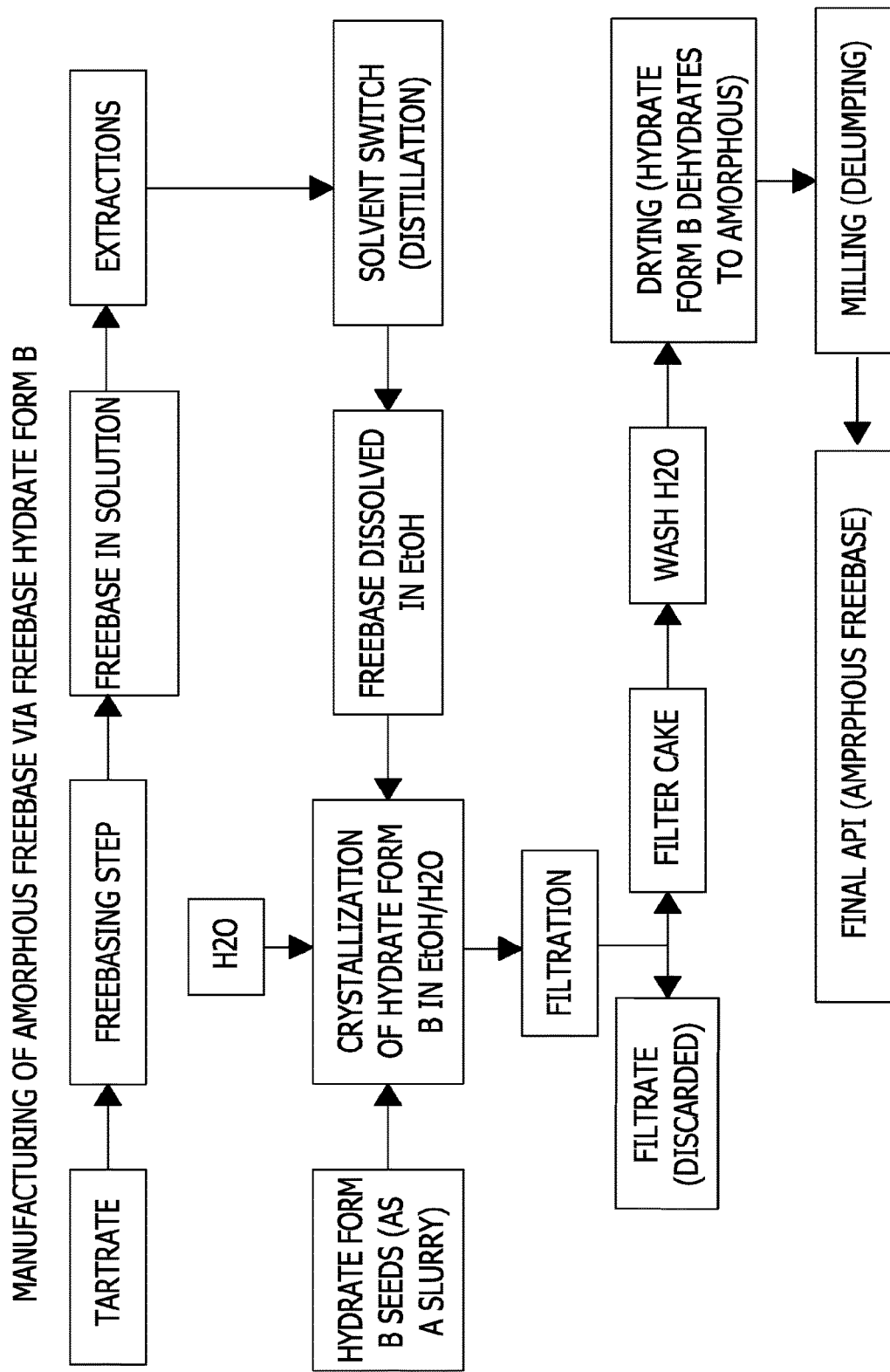
FIG. 1A schematically illustrates one method of preparing the Amorphous Freebase.

This written description uses examples to disclose the invention and also to enable any person skilled in the art to practice the invention, including making and using any of the disclosed solid state forms or compositions, and performing any of the disclosed methods or processes. The patentable scope of the invention is defined by the claims, and may include other examples that occur to those skilled in the art. Such other examples are intended to be within the scope of the claims if they have elements that do not differ from the literal language of the claims, or if they include equivalent elements.

I. DEFINITIONS

Section headings as used in this section and the entire disclosure are not intended to be limiting.

Where a numeric range is recited, each intervening number within the range is explicitly contemplated with the same degree of precision. For example, for the range 6 to 9, the numbers 7 and 8 are contemplated in addition to 6 and 9, and for the range 6.0 to 7.0, the numbers 6.0, 6.1, 6.2, 6.3, 6.4, 6.5, 6.6, 6.7, 6.8, 6.9 and 7.0 are explicitly contemplated. In the same manner, all recited ratios also include all sub-ratios falling within the broader ratio.

The singular forms "a," "an" and "the" include plural referents unless the context clearly dictates otherwise.

The term "about" generally refers to a range of numbers that one of skill in the art would consider equivalent to the recited value (i.e., having the same function or result). In many instances, the term "about" may include numbers that are rounded to the nearest significant figure.

The term "alkyl" refers to straight chained or branched hydrocarbons which are completely saturated. For purposes of exemplification, which should not be construed as limiting the scope of this invention, examples of alkyls include methyl, ethyl, propyl, isopropyl, butyl, pentyl, hexyl, and isomers thereof.

The term "alkenyl" refers to a hydrocarbon moiety containing two to eight carbons, including straight chained or branched hydrocarbons which contain one or more double bonds. Non-limiting examples of alkenyls are ethenyl, propenyl, and butenyl.

The term "amorphous" as applied to a compound refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ("glass transition").

The term "anhydrate" as applied to a compound refers to a solid state wherein the compound contains no structural water within the crystal lattice.

The term "aryl" refers to a mono-, bi-, or tricyclic aromatic hydrocarbon radical. Examples include phenyl, naphthyl, biphenyl, and 1,2,3,4-tetrahydronaphthyl.

Unless the context requires otherwise, the terms "comprise," "comprises," and "comprising" are used on the basis and clear understanding that they are to be interpreted inclusively, rather than exclusively, and that Applicant intends each of those words to be so interpreted in construing this patent, including the claims below.

The term "crystalline" as applied to a compound refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ("melting point").

The term "crystalline purity" means the crystalline purity of a compound with regard to a particular crystalline form of the compound as determined by the powder X-ray diffraction analytical methods described in this application.

The term "crystallization" as used throughout this application can refer to crystallization and/or recrystallization depending upon the applicable circumstances relating to the preparation of the compound.

The term "pharmaceutically acceptable" (such as in the recitation of a "pharmaceutically acceptable salt" or a "pharmaceutically acceptable diluent") refers to a material that is compatible with administration to a human subject, e.g., the material does not cause an undesirable biological effect. Examples of pharmaceutically acceptable salts are described in "Handbook of Pharmaceutical Salts: Properties, Selection, and Use" by Stahl and Wermuth (Wiley-VCH, Weinheim, Germany, 2002). Examples of pharmaceutically acceptable excipients are described in the "Handbook of Pharmaceutical Excipients," Rowe et al., Ed. (Pharmaceutical Press, 7th Ed., 2012).

The term "subject" refers to a human subject.

The terms "treating" and "treatment" refer to ameliorating, suppressing, eradicating, reducing the severity of, decreasing the frequency of incidence of, preventing, reducing the risk of, slowing the progression of damage caused by or delaying the onset of the condition or improving the quality of life of a patient suffering from the condition.

The term "Xantphos" refers to 4,5-Bis(diphenylphosphino)-9,9-dimethylxanthene.

The abbreviation "2-Me THF" refers to 2-methyl tetrahydrofuran.

The abbreviation "ACN" refers to acetonitrile.

The abbreviation "AcOH" refers to acetic acid.

As used herein, the term "$AUC_{24,ss}$" refers to the steady-state area under the plasma concentration time curve from time zero to twenty-four hours after administration of the referent drug. The term "$AUC_{12,ss}$" refers to the steady-state area under the plasma concentration time curve from time zero to twelve hours after administration of the referent drug.

As used herein, the term "$AUC_{inf}$" refers to the area under the plasma concentration time curve from time zero to infinity following a single dose, calculated using the trapezoidal rule. $AUC_{inf}=AUC_t+C_{last}/k$, where $C_{last}$ is the last measured concentration and k is the calculated terminal elimination rate constant.

As used herein, the term "$AUC_t$" refers to the area under the plasma concentration time curve from the time of administration of the referent drug to the time of the last measured concentration calculated using the trapezoidal rule. "$AUC_{24}$" refers to the area under the plasma concentration time curve from time zero to twenty-four hours after administration of the referent drug following a single dose.

The abbreviation "Bn" refers to benzyl.

As used herein, the term "$C_{12}$" is the plasma concentration of the referent drug observed 12 hours after administration of a single dose, or the indicated number of doses, of the referent drug. The term "$C_{12,ss}$" refers to the $C_{12}$ as measured at a steady-state.

As used herein, the term "$C_{24}$" is the plasma concentration of the referent drug observed 24 hours after administration of a single dose, or the indicated number of doses, of the referent drug. The term "$C_{24,ss}$" refers to the $C_{24}$ as measured at a steady-state.

The abbreviation "Cbz" refers to carboxybenzyl.

The abbreviation "CDI" refers to carbonyldiimidazole.

The abbreviation "% CV" refers to the coefficient of variation, expressed as a percent. % CV is calculated according to the following equation: % CV=(SD/x)*100, wherein x is the mean value and SD is the standard deviation.

As used herein, the term "$C_{max}$" refers to the plasma concentration of the referent drug at $T_{max}$, expressed herein as ng/mL, produced by the oral ingestion of a single dose, or indicated number of doses, of the dosage form or pharmaceutical composition, such as the dosage forms and compositions of the present disclosure. Unless specifically indicated, $C_{max}$ refers to the overall maximum observed concentration.

As used herein, the term "$C_{max,ss}$" refers to the steady-state $C_{max}$ of the referent drug during a dosage interval.

As used herein, the term "$C_{min,ss}$" refers to the minimum steady-state plasma concentration of the referent drug during a dosage interval.

As used herein, the term "$C_{trough}$" refers to the trough plasma concentration of the referent drug, as measured at the end of a dosing interval at steady state.

The abbreviation "DBU" refers to 1,8-diazabicyclo[5.4.0]undec-7-ene.

The abbreviation "DCHA" refers to dicyclohexylamine.

The abbreviation "DCM" refers to dichloromethane.

The abbreviation "DIPEA" refers to diisopropylethylamine.

The abbreviation "DMA" refers to dimethylacetamide, or N,N-dimethylacetamide.

The abbreviation "DMAP" refers to 4-dimethylaminopyridine.

The abbreviation "DSC" means differential scanning calorimetry.

As used herein, the term "entry into a use environment" means contact of a formulation of the disclosure with the gastric fluids of the subject to whom it is administered, or with a fluid intended to simulate gastric fluid.

The abbreviation "$EtB(OH)_2$" refers to ethyl boronic acid.

The abbreviation "EtOAc" refers to ethyl acetate.

The abbreviation "$Fe(acac)_3$" refers to iron(III) acetylacetonate.

The abbreviation "HDPE" refers to high-density polyethylene.

The abbreviation "HOAc" refers to acetic acid.

The abbreviation "HPMC" refers to hydroxypropyl methylcellulose.

The abbreviation "IPAc" refers to isopropyl acetate.

The abbreviation "KOtBu" refers to potassium tert-butoxide.

The abbreviation LiOtBu" refers to lithium tert-butoxide.

The abbreviation "$Me_3SOCl$" refers to trimethylsulfoxonium chloride.

The abbreviations "MeOH" and "EtOH" refer to methanol and ethanol, respectively.

The abbreviation "MS" means mass spectrometry.

The abbreviation "MTBE" refers to methyl tert-butyl ether.

The abbreviation "MTX" refers to methotrexate.

The abbreviations "NaOBu" or "NaOtBu" refer to sodium tert-butoxide.

The abbreviation "Ni(acac)₂" refers to nickel (II) acetylacetonate.

The abbreviation "NMM" refers to N-methyl morpholine.

The abbreviation "Pd/C" refers to palladium on carbon.

The abbreviation "PdCl₂(dppf)" refers to [1,1'-Bis(diphenylphosphino)ferrocene]dichloropalladium(II).

The abbreviation "PdCl₂(Ph₃P)₂" refers to bis(triphenylphosphine)palladium(II) dichloride:

The abbreviation "Pd(OAc)₂" refers to palladium (II) acetate.

The abbreviation "Pd(OH₂)/C" refers to palladium hydroxide on carbon.

The abbreviation "PFPAA" refers to pentafluoropropionic anhydride.

The abbreviation "pTsOH" refers to p-toluenesulfonic acid.

The abbreviation "PVA" refers to polyvinyl acetate.

The abbreviation "PXRD" means powder X-ray diffraction.

The abbreviation "(S)-Segphos Ru(OAc)₂" or "Ru(OAc)₂-Segphos" refers to diacetato[(S)-(−)5,5'-bis(diphenylphosphino)-4,4'-bi-1,3-benzodioxole]ruthenium(II).

As used herein, the term "$t_{1/2}$" refers to the terminal half-life of the referent drug after oral ingestion of a single dose, or indicated number of doses, of the referent drug. The term "$t_{1/2,ss}$" refers to the terminal half-life as measured at a steady-state.

The abbreviation "TCS" refers to topical corticosteroids and includes hydrocortisone (1%), triamcinolone acetonide (0.1%) cream, fluocinolone acetonide ointment (0.025%), betamethasone dipropionate (0.05%) ointment and clobetasol propionate (0.05%) cream.

The abbreviation "TEA" refers to triethylamine.

The abbreviation "TFAA" refers to trifluoroacetic anhydride.

The abbreviation "TF₂O" refers to trifluoromethanesulfonic anhydride.

The abbreviation "TGA" means thermogravimetric analysis.

The abbreviation "TGA-MS" means thermogravimetric analysis-mass spectrometer.

The abbreviation "THF" refers to tetrahydrofuran.

As used herein, the term "$T_{max}$" refers to the time to peak plasma concentration of the referent drug after oral ingestion of a single dose, or indicated number of doses, of the referent drug.

As used herein, the term "$T_{max,ss}$" refers to the time to peak plasma concentration of the referent drug after oral ingestion of the referent drug at steady-state.

The abbreviation "TMS" refers to trimethylsilyl.

The term "triflate" refers to trifluoromethanesulfonate.

The abbreviation "v/v" refers to volume/volume.

The abbreviation "w/w" refers to weight/weight.

For clarity and convenience purposes only, the convention is utilized herein of designating the time of drug administration or initiation of dissolution testing as zero (0) hours (t=0 hours) and times following administration in appropriate time units, for example, t=30 minutes or t=2 hours, etc.

II. PROCESSES FOR PREPARING (3S,4R)-3-ETHYL-4-(3H-IMIDAZO[1,2-A]PYRROLO[2,3-E]PYRAZIN-8-YL)-N-(2,2,2-TRIFLUOROETHYL)PYRROLIDINE-1-CARBOXAMIDE (COMPOUND 1) AND INTERMEDIATES

The present disclosure relates to improved processes for preparing (3S,4R)-3-ethyl-4-(3H-imidazo[1,2-a]pyrrolo[2, 3-e]pyrazin-8-yl)-N-(2,2,2-trifluoroethyl)pyrrolidine-1-carboxamide (referred to herein as "Compound 1" or as "Compound 1 freebase"), to pharmaceutically acceptable salts of Compound 1, and to intermediates used in the preparation of Compound 1. Compound 1 has the structure shown below:

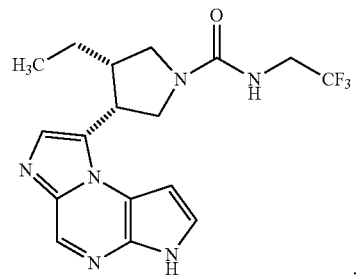

Methods for making and using this compound are described, for example, in International Application WO 2011/068881A1, which is incorporated by reference in this application.

Previously disclosed processes for preparing Compound 1, and pharmaceutically acceptable salts thereof suffer from several drawbacks. In particular, these processes involve the use of particularly hazardous reagents, such as trimethylsilyldiazomethane or diazomethane, and/or do not produce a crystalline product. The processes of the present disclosure overcome these drawbacks by avoiding the use of these hazardous reagents, and producing crystalline intermediates, which aid in purification.

Compounds of the present disclosure may be prepared using synthetic transformations such as those illustrated in Schemes I-XVI. Starting materials are commercially available, may be prepared by the procedures described herein, by literature procedures, or by procedures that would be well known to one skilled in the art of organic chemistry (see, for example, Larock, R. C. "Comprehensive Organic Transformations: A Guide to Functional Group Preparations, 2$^{nd}$ edition", 1999, Wiley-VCH or Greene, T. W. and Wuts, P. G. M. "Protective Groups in Organic Synthesis, 3$^{rd}$ Edition", 1999, Wiley-Interscience).

A. Preparation of Compound 1

In one aspect, the present disclosure is directed to a process for preparing Compound 1, or a pharmaceutically acceptable salt thereof. A process for preparing Compound 1 is illustrated in Scheme I. Reaction of protected (3R,4S)-4-ethylpyrrolidine-3-carboxylic acid (I) or a pharmaceutically acceptable salt thereof with trimethylsulfoxonium chloride gives sulfur ylide (II). Contacting sulfur ylide (II) with LiX and a sulfonic acid yields the corresponding halomethyl ketone (III). Reaction of (III) with (IV) in the presence of a base yields (V). Cyclization of (V) in the presence of a perfluoro acid anhydride and an organic base produces (VI). Removal of the protecting group and contacting the deprotected compound with an acid yields a pharmaceutically acceptable salt of (VII). Reacting the pharmaceutically acceptable salt of (VII) with 2,2,2-trifluoroethylamine produces Compound 1.

Scheme I

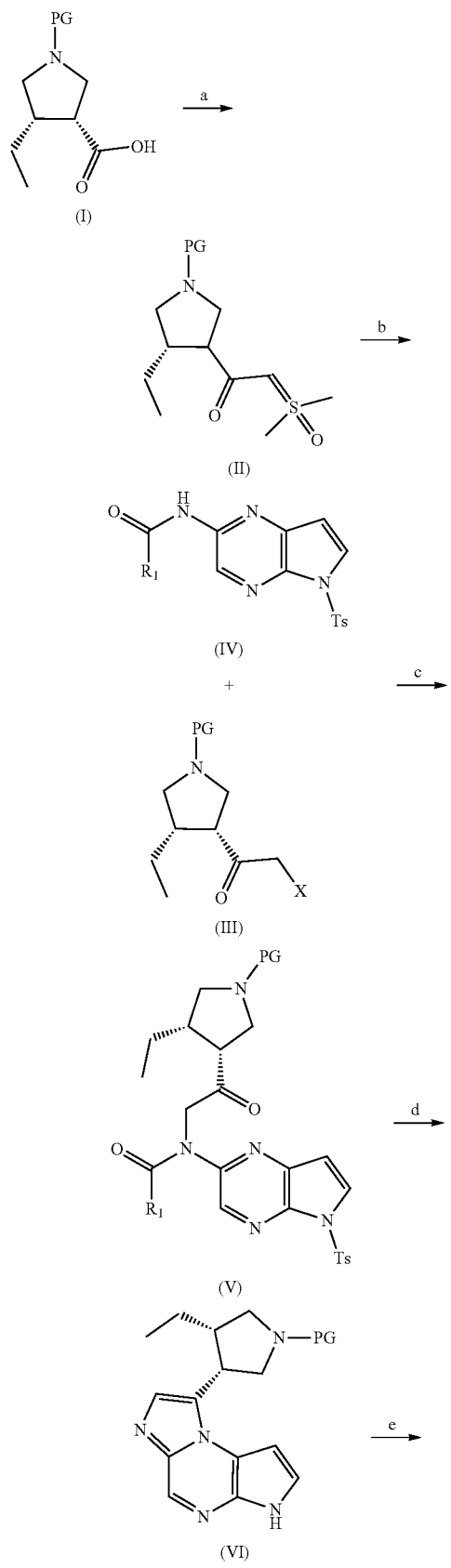

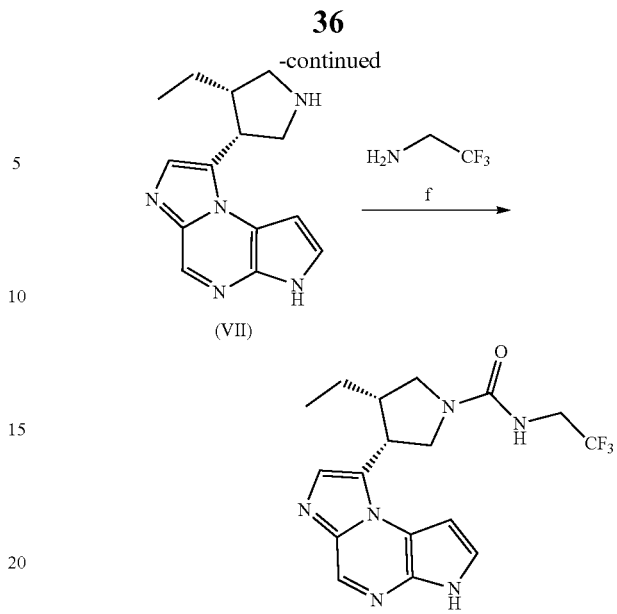

wherein:

PG is a protecting group;

X is Br or Cl;

$R_1$ is selected from the group consisting of alkyl, aryl, and —$OR_2$;

$R_2$ is alkyl; and

Ts is tosyl.

The protecting group may be any suitable protecting group known in the art. In some embodiments, the protecting group is selected from the group consisting of carboxybenzyl, p-methoxybenzyl carbonyl, benzyl, p-methoxybenzyl, and 3,4-dimethoxyenzyl. In another embodiment, the protecting group is carboxybenzyl.

In another embodiment, $R_1$ is —$OR_2$, and $R_2$ is methyl or ethyl. In such embodiments, the compound of formula (IV) is a compound of formula (IVa):

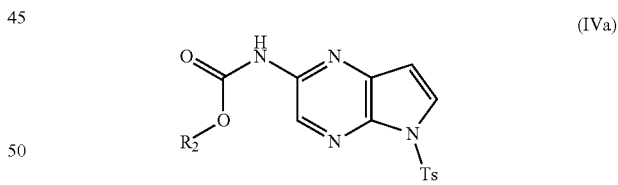

wherein $R_2$ is methyl or ethyl. It has surprisingly been discovered that when $R_2$ is ethyl or methyl, the compound of formula (V) and subsequent downstream compounds can be isolated as crystalline solids, which aids in purification of these intermediates. In contrast, previously known processes, which use compounds where $R_2$ is t-butyl, result in formation of compounds of formula (V) which are isolated as amorphous solids.

In certain embodiments, a pharmaceutically acceptable salt of a compound of the compound of formula (I) is used in the reaction of step (a). In one embodiment, the pharmaceutically acceptable salt of the compound of formula (I) is selected from the group consisting of the naphthalene ethane amine salt (Ia) and the dicyclohexylamine salt (Ib)

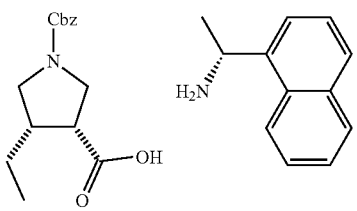

(Ia)

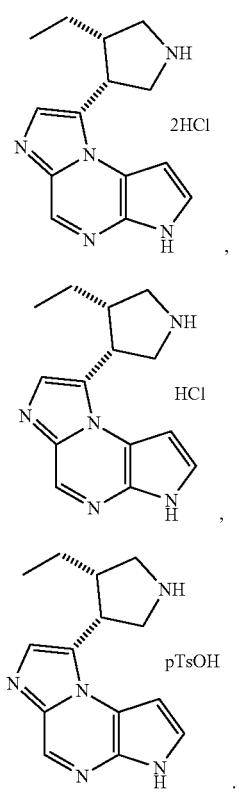

wherein Cbz is carboxybenzyl.

In one embodiment, the pharmaceutically acceptable salt of compound (VII) is selected from the group consisting of (VIIa), (VIIb), and (VIIc)

Another process for preparing Compound 1 is illustrated in Scheme Ia. Reaction of (3R,4S)-1-((benzyloxy)carbonyl)-4-ethylpyrrolidine-3-carboxylate dicyclohexylamine salt (Ib) with trimethylsulfoxonium chloride in the presence of carbonyldiimidazole and a strong base gives sulfur ylide (IIa). Contacting sulfur ylide (IIa) with lithium bromide and a sulfonic acid yields the corresponding bromomethyl ketone (IIIa). Reaction of (IIIa) with alkyl 5-tosyl-5H-pyrrolo[2,3-b]pyrazin-2-ylcarbamate (IVa) in the presence of lithium tert-butoxide yields (Va). Cyclization of (Va) in the presence of a perfluoro acid anhydride and an organic base produces (VIa). Removal of the carboxybenzyl protecting group and contacting the deprotected compound with hydrochloric acid yields the pharmaceutically acceptable salt (VIIa). Reacting the pharmaceutically acceptable salt (VIIa) with 2,2,2-trifluoroethylamine produces Compound 1.

Scheme Ia

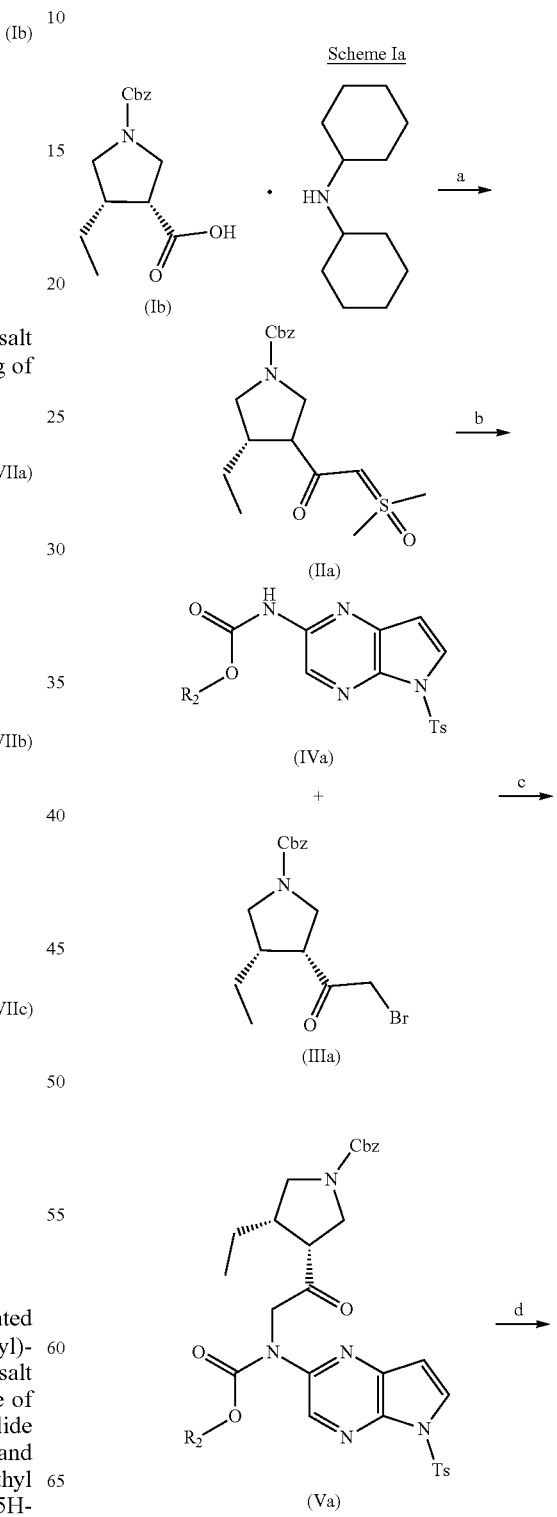

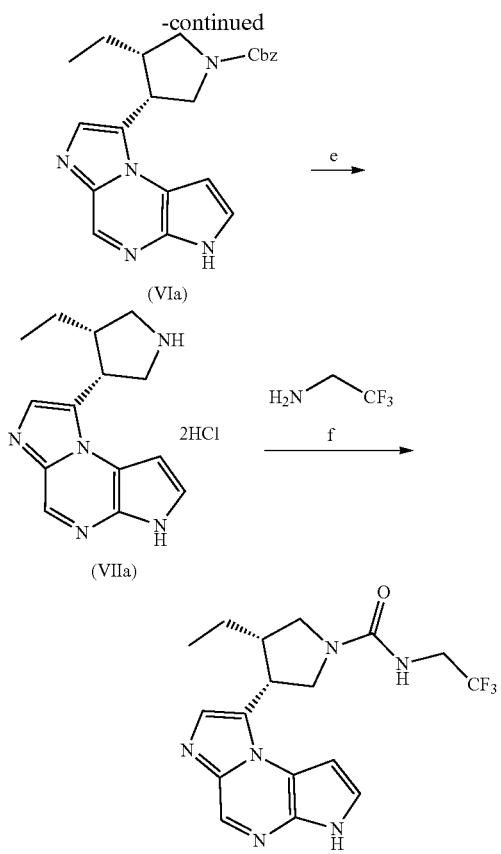

wherein:
Cbz is carboxybenzyl;
Ts is tosyl; and
R₂ is methyl or ethyl.

The reaction in step (a) of Schemes I and Ia is generally accomplished in the presence of a coupling agent, such as carbonyldiimidazole (CDI), and a strong base. The strong base may be, for example, potassium tert-butoxide, sodium tert-butoxide, or combinations thereof. The step (a) reaction may be conducted in any suitable solvent including, but not limited to, tetrahydrofuran, water, and methyl tert-butyl ether. In one embodiment, the reaction is conducted in the presence of carbonyldiimidazole and potassium tert-butoxide.

More particularly, in certain embodiments, a solution of a compound of formula (I), (Ia), or (Ib) in solvent is slowly added (e.g., over 30 minutes) to a slurry of CDI in solvent, and the resulting mixture is stirred at room temperature for 30 minutes to 12 hours, and typically for about 1 hour. The resulting solution is slowly added (e.g., over 15 minutes) to a suspension of the trimethylsulfoxonium chloride, strong base, and solvent, while maintaining the internal temperature below −1° C. In another embodiment, the reaction is quenched and the resulting compound of formula (II) or (IIa) is isolated prior to step (b).

In some embodiments, the reaction of step (a) may further involve contact of (Ia) or (Ib) with an acid prior to reaction with the trimethylsulfoxonium chloride, in order to extract the amine to obtain a compound of formula (I). Suitable acids include any mineral acid or organic acid, such as phosphoric acid, hydrochloric acid (HCl), acetic acid (HOAc), citric acid, and the like. The compound of formula (I) may subsequently be taken up in a suitable solvent, and reacted with trimethylsulfoxonium chloride, as described herein. In one embodiment, a pharmaceutically acceptable salt of a compound of formula (I) is used in step (a), wherein the pharmaceutically acceptable salt is (Ia) or (Ib), and the reaction of step (a) is conducted according to the procedure set forth in Step A of Example 3.

In step (b) of Schemes I and Ia, a compound of formula (II) or (IIa) is contacted with LiX and a sulfonic acid to form a compound of formula (III) or (IIIa), respectively. In one embodiment, the sulfonic acid is selected from the group consisting of methanesulfonic acid and p-toluenesulfonic acid. In one embodiment, the sulfonic acid is p-toluenesulfonic acid. LiX may be selected from lithium bromide and lithium chloride. In one embodiment, LiX is lithium bromide. In one embodiment, the reaction is conducted in lithium bromide and p-toluenesulfonic acid. The reaction of step (b) may be conducted in any suitable solvent including, but not limited to tetrahydrofuran, ethyl acetate, heptanes, ethanol, water, and combinations thereof.

More particularly, in certain embodiments, the sulfonic acid is added to a solution of the compound of formula (II) or (IIa) and LiX in a solvent. The resulting mixture is warmed to about 35° C. to about 65° C. and stirred overnight. In one embodiment, the mixture is warmed to about 40° C. and stirred overnight. The mixture is cooled to room temperature and washed. The compound of formula (III) or (IIIa) may be isolated, or optionally used in the next step without purification.

In step (c) of Schemes I and Ia a compound of formula (III) or (IIIa) are reacted with a compound of formula (IV) or (IVa) (prepared as described herein). The step (c) reaction is conducted in the presence of a base, such as lithium tert-butoxide, sodium tert-butoxide, or combinations thereof. In one embodiment, the base is lithium tert-butoxide. The reaction of step (c) may be conducted in any suitable solvent including, but not limited to dimethylacetamide, tetrahydrofuran, dichloromethane, ethyl acetate, heptanes, and combinations thereof.

More particularly, in certain embodiments, the base is added to a cooled suspension of the compound of formula (III) or (IIIa) in a solvent. The resulting solution is stirred for about 30 minutes to about 12 hours, or about 30 minutes, and cooled to about −20° C. to about 0°, or about −10° C. In one embodiment, the solution is stirred for about 30 minutes and cooled to about −20° C. to about 0°. A solution of a compound of formula (IV) or (IVa) in a solvent is slowly added (e.g., over 30 minutes), and the resulting mixture is stirred for about 30 minutes to about 6 hours, or about 30 minutes, at a temperature of about −20° C. to about 0° C., or about −10° C. In one embodiment, following addition of the solution of the compound of formula (IV) or (IVa) in a solvent, the resulting mixture is stirred for about 30 minutes at a temperature of about −10° C. In one embodiment, the reaction is quenched, and, in some embodiments, the resulting product (V) or (Va) is isolated prior to step (d).

In step (d) of Schemes I and Ia, a compound of formula (V) or (Va) is contacted with a perfluoro acid anhydride and an organic base to form a compound of formula (VI) or (VIa), respectively. Non-limiting examples of suitable organic bases include pyridine, triethylamine, and combinations thereof. Examples of suitable perfluoro acid anhydrides include trifluoroacetic anhydride, pentafluoropropionic anhydride, heptafluorobutyric anhydride, and combinations thereof. In certain embodiments, the organic base is pyridine and the perfluoro acid anhydride is trifluoroacetic anhydride. In other embodiments, the organic base is triethylamine, and the perfluoro acid anhydride is pentafluoropropionic anhydride. Suitable solvents for use in step (d) include, but are not limited to acetonitrile, toluene, and combinations thereof.

More particularly, in certain embodiments, the organic base and the perfluoro acid anhydride are charged into a solution of a compound of formula (V) or (Va) in solvent. The resulting mixture is warmed to about 55° C. to about 75° C., or about 55° C., and stirred for about 4 hours to about 18 hours, or about 6 hours. In one embodiment, the mixture of perfluoro acid anhydride and the compound of formula (V) or (Va) is warmed to about 55° C. and stirred for about 4 hours to about 18 hours. In one embodiment, the mixture is stirred for about 6 hours. Upon completion of the reaction, in some embodiments, the reaction mixture may be cooled, and concentrated prior to contacting with a hydroxide solution to quench excess reagents, and remove the tosyl protecting group. Suitable hydroxide solutions include a sodium hydroxide (NaOH) solution, a potassium hydroxide (KOH) solution, and the like. The resulting mixture may be stirred at room temperature to about 85° C., including at about 55° C., for about 30 minutes to about 8 hours. In one embodiment, the mixture is stirred for about 1 hour. Upon completion, the solvent may optionally be removed and switched to methanol, ethanol, isopropanol, or other suitable solvents prior to step (e).

In step (e) of Schemes I and Ia, a compound of formula (VI) or (VIa) is deprotected, and a pharmaceutically acceptable salt of compound (VII), such as (VIIa), (VIIb), or (VIIc) is formed. The protecting group on the compound of formula (VI) or (VIa) may be removed using any suitable means known in the art. In one embodiment, deprotection occurs by contacting the compound of formula (VI) or (VIa) with palladium on carbon (e.g., Pd/C or Pd(OH$_2$)/C) under hydrogen pressure. In other embodiments, deprotection occurs by contacting the compound of formula (VI) or (VIa) with an acid. Non-limiting examples of suitable acids include hydrochloric acid (HCl), hydrobromic acid (HBr), hydrobromic acid in acetic acid (e.g., HBr/HOAc), and the like. In other embodiments, deprotection occurs by subjecting the compound of formula (VI) or (VIa) to heating, e.g., at a temperature of from room temperature to about 85° C., including about 50° C. Upon deprotection, the compound of formula (VII) is contacted with the appropriate acid (e.g., hydrochloric acid or p-toluenesulfonic acid) to form the pharmaceutically acceptable salt.

Step (e) may occur in any suitable solvent including, but not limited to ethanol, isopropyl acetate, ethyl acetate, and combinations thereof.

More particularly, in some embodiments, palladium on carbon and the compound of formula (VI) or (VIa) in solvent are mixed under hydrogen pressure at about 1 psig to about 100 psig. In another embodiment, the hydrogen pressure is about 20 psig. The mixture is agitated for about 2 hours to about 24 hours, including about 16 hours, at about 20° C. to about 85° C., including about 50° C. In one embodiment, the mixture is agitated for about 16 hours at about 20° C. to about 80° C. In one embodiment, the mixture is agitated for about 16 hours at about 50° C. Upon completion of the reaction, the reaction mixture is cooled and filtered, followed by addition of the appropriate acid. The resulting salt is optionally isolated prior to step (f).

In step (f), the salt produced in step (e) is reacted with 2,2,2-trifluoroethylamine to produce Compound 1. The step (f) reaction is conducted in the presence of a coupling agent, such as carbonyldiimidazole (CDI), and optionally buffers, such as dipotassium phosphate, potassium hydroxide, and combinations thereof. In one embodiment, the step (f) reaction is conducted in the presence of CDI, dipotassium phosphate, and potassium hydroxide. The step (f) reaction may be conducted in any suitable solvent including, but not limited to, tetrahydrofuran, ethyl acetate, heptanes, ethanol, water, and combinations thereof.

More particularly, in certain embodiments, 2,2,2-trifluoroethyl amine is added slowly (e.g., over 20 minutes) to a slurry of CDI in solvent, while maintaining an internal temperature of less than 30° C. The resulting solution is stirred for about 10 minutes to about 12 hours, and in one embodiment for about 1 hour, to form an imidazolide solution. The pH of a biphasic mixture of the pharmaceutically acceptable salt from step (e) in buffer and solvent is adjusted to about 7 to about 11, and in one embodiment to about 9, by addition of a base. The imidazolide solution is added, and the resulting mixture is mixed at about 25° C. while maintaining a pH of about 9 by portionwise addition of base for about 30 minutes to about 18 hours. In one embodiment, the mixture formed after addition of the imidazolide solution is mixed at about 25° C. while maintaining a pH of about 9 by portionwise addition of base for about 1 hour. In one embodiment, upon completion, the reaction is quenched and the resulting product isolated.

In one embodiment, Compound 1 is prepared according to the process set forth in Scheme Ia. In certain embodiments, the process may further comprise preparation of (Ib) according to the process set forth in Scheme V herein.

An alternate process for preparing Compound 1 is illustrated in Scheme II. Reaction of protected (3R,4S)-4-ethylpyrrolidine-3-carboxylic acid (I) or a pharmaceutically acceptable salt thereof with trimethylsulfoxonium chloride gives sulfur ylide (II). Contacting sulfur ylide (II) with LiX and a sulfonic acid yields the corresponding halomethyl ketone (III). Reaction of (III) with (IV) in the presence of a base yields (V). Cyclization of (V) in the presence of a perfluoro acid anhydride and an organic base produces (VI). Removal of the protecting group and contacting the deprotected compound (VII) (not shown) with hydrochloric acid yields pharmaceutically acceptable salt (VIIb). The pharmaceutically acceptable salt (VIIb) is converted to the freebase (VII), which is reacted with 2,2,2-trifluoroethylamine to produce Compound 1. Compound 1 is contacted with L-tartaric acid to form the corresponding tartrate salt, followed by formation of the Compound 1 freebase.

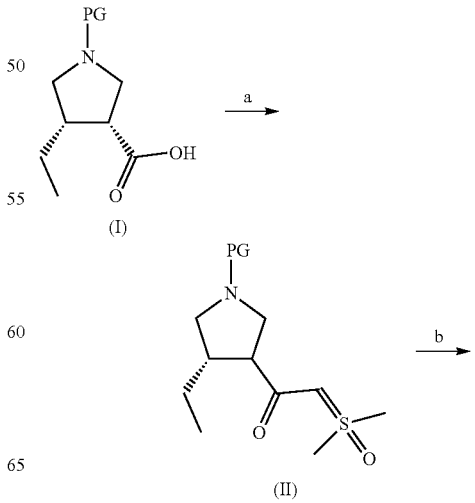

Scheme II

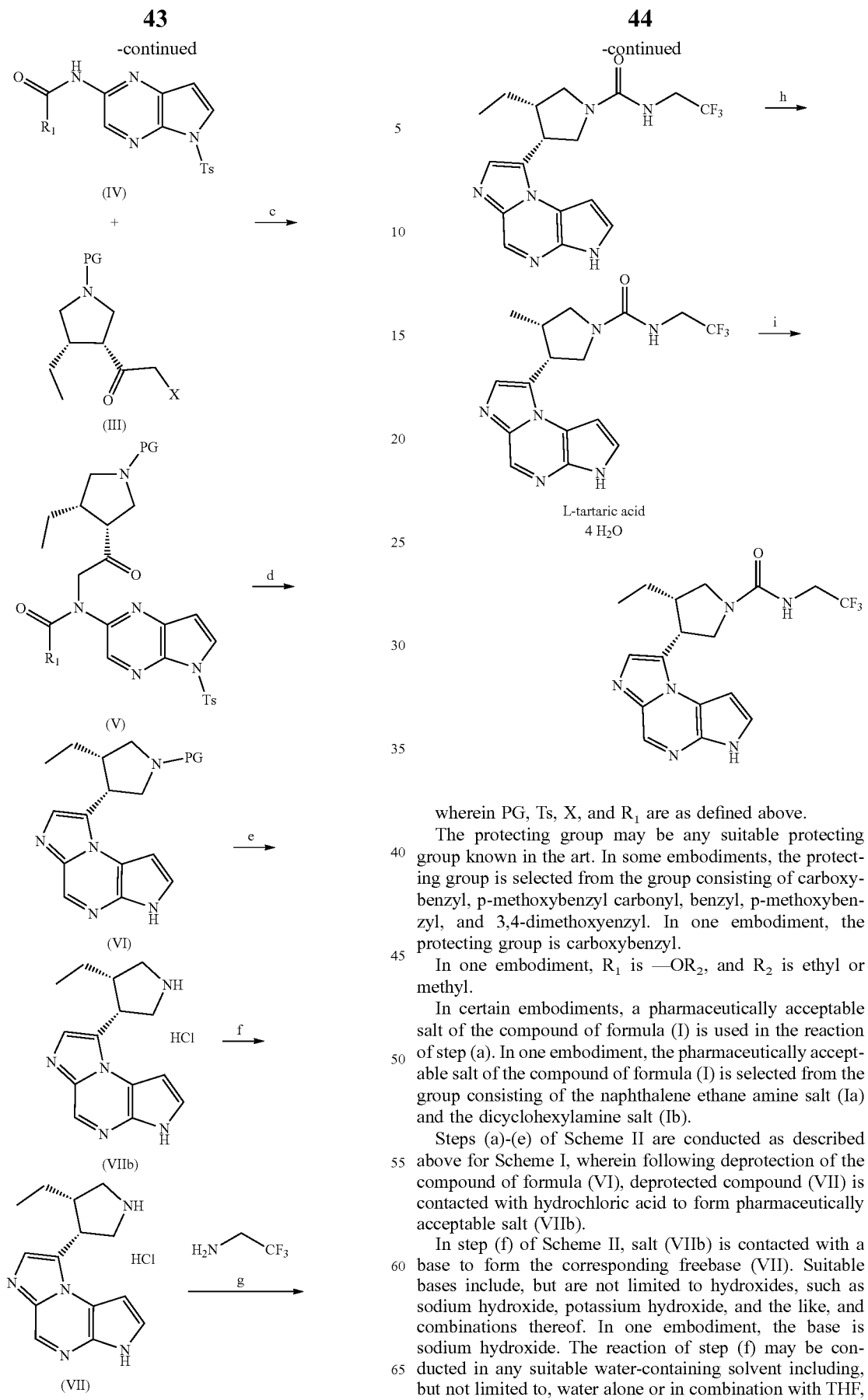

wherein PG, Ts, X, and $R_1$ are as defined above.

The protecting group may be any suitable protecting group known in the art. In some embodiments, the protecting group is selected from the group consisting of carboxybenzyl, p-methoxybenzyl carbonyl, benzyl, p-methoxybenzyl, and 3,4-dimethoxyenzyl. In one embodiment, the protecting group is carboxybenzyl.

In one embodiment, $R_1$ is —$OR_2$, and $R_2$ is ethyl or methyl.

In certain embodiments, a pharmaceutically acceptable salt of the compound of formula (I) is used in the reaction of step (a). In one embodiment, the pharmaceutically acceptable salt of the compound of formula (I) is selected from the group consisting of the naphthalene ethane amine salt (Ia) and the dicyclohexylamine salt (Ib).

Steps (a)-(e) of Scheme II are conducted as described above for Scheme I, wherein following deprotection of the compound of formula (VI), deprotected compound (VII) is contacted with hydrochloric acid to form pharmaceutically acceptable salt (VIIb).

In step (f) of Scheme II, salt (VIIb) is contacted with a base to form the corresponding freebase (VII). Suitable bases include, but are not limited to hydroxides, such as sodium hydroxide, potassium hydroxide, and the like, and combinations thereof. In one embodiment, the base is sodium hydroxide. The reaction of step (f) may be conducted in any suitable water-containing solvent including, but not limited to, water alone or in combination with THF, 2-methyl tetrahydrofuran, ethanol, methanol, and the like.

In step (g) compound (VII) is reacted with 2,2,2-trifluoroethylamine to produce Compound 1. The step (g) reaction is conducted in the presence of a coupling agent, such as CDI. Step (g) in Scheme II is conducted using similar reagents and under similar conditions as those set forth above for step (f) of Scheme I.

In step (h) of Scheme II, Compound 1 is contacted with L-tartaric acid to form the corresponding tartrate salt (step (h)). Formation of the tartrate salt advantageously aids in removal of impurities prior to isolation of the freebase. In one embodiment, the tartrate salt may be formed using the procedure described in Example 8, Method B, only without drying the tartrate salt prior to step (i). The tartrate salt is subsequently converted back to the freebase form (step (i)) to produce Compound 1. In particular, in step (i) the tartrate salt may be contacted with a base, such as an inorganic base, to produce the corresponding freebase. Suitable bases include, but are not limited to, sodium bicarbonate, sodium carbonate, sodium hydroxide, potassium carbonate, potassium bicarbonate, potassium hydroxide, and the like, or combinations thereof. In one embodiment, the tartrate salt is contacted with sodium bicarbonate and sodium carbonate to produce the corresponding freebase.

Suitable solvents for use in step (h) include, but are not limited to, isopropyl acetate, methyl tert-butyl ether, water, isopropyl alcohol, and combinations thereof. Suitable solvents for use in step (i) include, but are not limited to, ethyl acetate, ethanol, water, and combinations thereof.

In some embodiments, the products of steps (d), (e), (g), and (h) of Scheme II are not isolated prior to the subsequent step.

An alternate process for preparing Compound 1 is illustrated in Scheme III. Compound (XIa) is hydrogenated to produce (I). Reaction of protected (3R,4S)-4-ethylpyrrolidine-3-carboxylic acid (I) with trimethylsulfoxonium chloride gives sulfur ylide (II). Contacting sulfur ylide (II) with an anhydrous source of HBr or HCl yields the corresponding halomethyl ketone (III). Reaction of (III) with (IV) in the presence of a base yields (V). Cyclization of (V) in the presence of a perfluoro acid anhydride and an organic base produces (VI). Removal of the protecting group and contacting the deprotected compound with an acid yields a pharmaceutically acceptable salt of (VII). Reacting the pharmaceutically acceptable salt of (VII) with 2,2,2-trifluoroethylamine produces Compound 1.

Scheme III

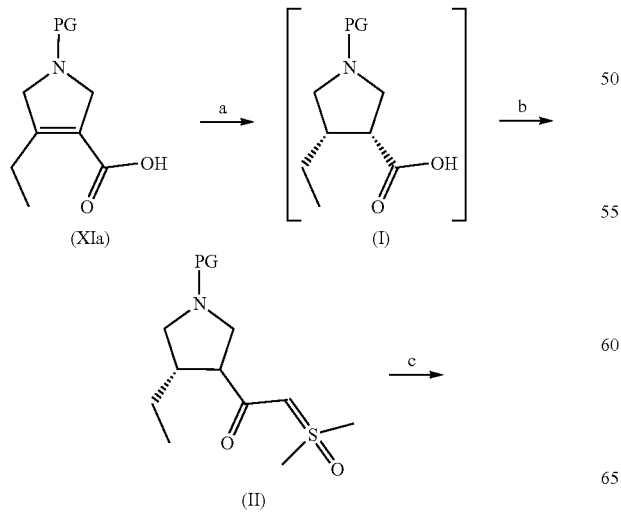

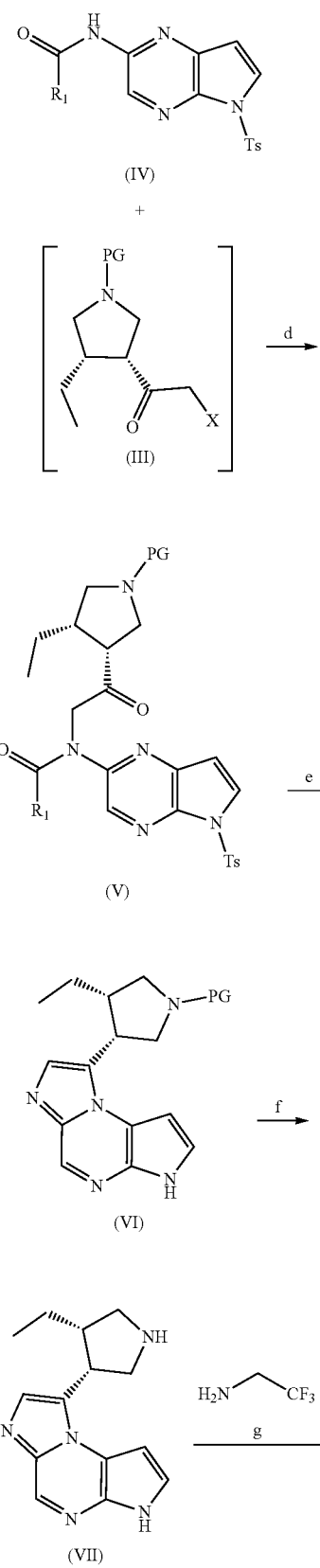

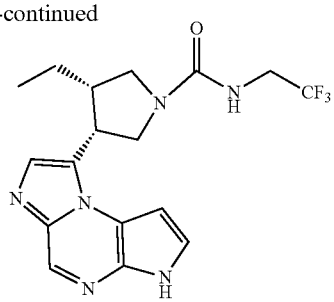

wherein:

PG is a protecting group;

X is Br or Cl;

R₁ is selected from the group consisting of alkyl, aryl, and —OR₂;

R₂ is alkyl; and

Ts is tosyl.

The protecting group may be any suitable protecting group known in the art. In some embodiments, the protecting group is selected from the group consisting of carboxybenzyl, p-methoxybenzyl carbonyl, benzyl, p-methoxybenzyl, and 3,4-dimethoxyenzyl. In another embodiment, the protecting group is carboxybenzyl.

In another embodiment, R₁ is —OR₂, and R₂ is methyl or ethyl. In such embodiments, the compound of formula (IV) is a compound of formula (IVa):

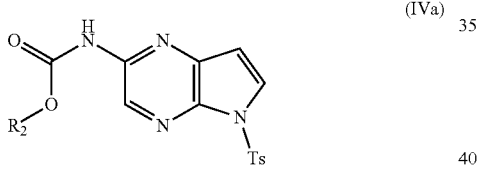

wherein R₂ is methyl or ethyl. It has surprisingly been discovered that when R₂ is ethyl or methyl, the compound of formula (V) and subsequent downstream compounds can be isolated as crystalline solids, which aids in purification of these intermediates. In contrast, previously known processes, which use compounds where R₂ is t-butyl, result in formation of compounds of formula (V) which are isolated as amorphous solids.

Another process for preparing Compound 1 is illustrated in Scheme IIIa. 1-((benzyloxy)carbonyl)-4-ethyl-2,5-dihydro-1H-pyrrole-3-carboxylic acid (XI) is hydrogenated to produce (XII). Reaction of (3R,4S)-1-((benzyloxy)carbonyl)-4-ethylpyrrolidine-3-carboxylate (XII) with trimethylsulfoxonium chloride gives sulfur ylide (IIa) Contacting sulfur ylide (IIa) with an anhydrous source of HBr yields the corresponding bromomethyl ketone (IIIa). Reaction of (IIIa) with alkyl 5-tosyl-5H-pyrrolo[2,3-b]pyrazine-2-ylcarbamate (IVa) in the presence of lithium tert-butoxide yields (Va). Cyclization of (Va) in the presence of a perfluoro acid anhydride and an organic base produces (VIa). Removal of the carboxybenzyl protecting group and contacting the deprotected compound with hydrochloric acid yields the pharmaceutically acceptable salt (VIIa). Reacting the pharmaceutically acceptable salt (VIIa) with 2,2,2-trifluoroethylamine produces Compound 1.

Scheme IIIa

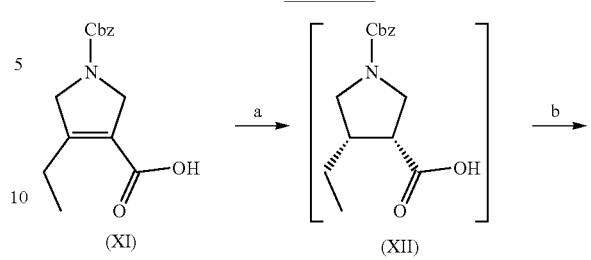

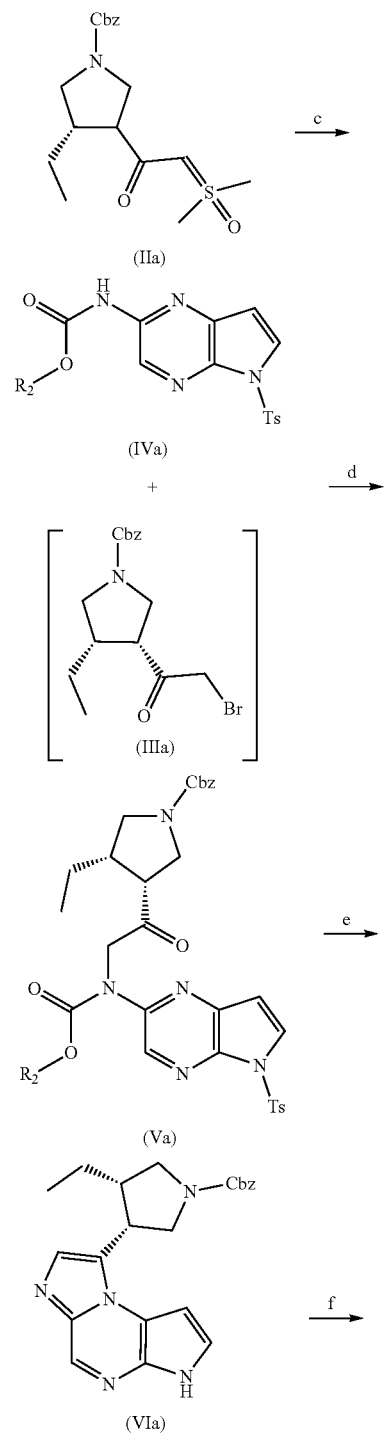

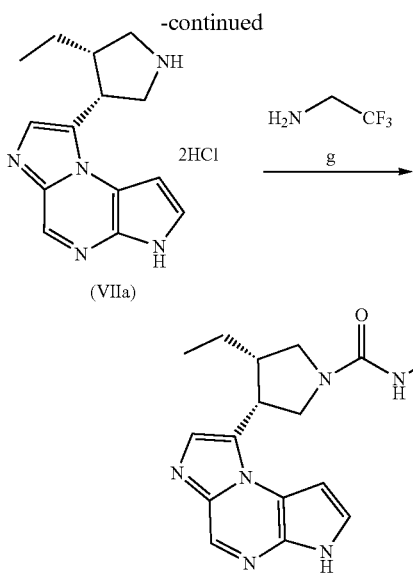

wherein:
Cbz is carboxybenzyl;
Ts is tosyl; and
$R_2$ is methyl or ethyl.

In step (a) of Schemes III and IIIa, (XIa) or (XI) (which may be prepared as described in Scheme V) is converted to (I) or (XII), respectively. In particular, in step (a), compound (XI) or (XIa) may be contacted with a catalyst, such as a ruthenium catalyst. Any catalyst comprising a chiral phosphine may be used. One particular example of a suitable catalyst is diacetato[(S)-(-)5,5'-bis(diphenylphosphino)-4, 4'-bi-1,3-benzodioxole]ruthenium(II) (i.e., (S)-Segphos Ru(OAc)$_2$). Suitable solvents for use in step (a) include, but are not limited to, methanol, triethylamine, and combinations thereof.

In particular, in certain embodiments, a solution of (XI) or (XIa) and the catalyst in solvent is hydrogenated at about 30° C. to about 100° C. for from about 1 hour to about 18 hours. In one embodiment, the solution of (XI) or (XIa) and the catalyst in solvent is hydrogenated at about 580 psi. In one embodiment, the solution of (XI) or (XIa) and the catalyst in solvent is hydrogenated at about 200 psi gauge (psig). In one embodiment, the solution of (XI) or (XIa) and the catalyst in solvent is hydrogenated at about 80° C. for from about 1 hour to about 8 hours, or for about 2 hours, or for about 4 hours. Upon completion, the reaction mixture is cooled to room temperature, filtered, and concentrated. In one particular embodiment, step (a) of Schemes III and IIIa is performed as described in Step A of Example 4.

The reaction in step (b) of Schemes III and IIIa, is generally accomplished in the presence of a coupling agent, such as carbonyldiimidazole (CDI), and a strong base. The strong base may be, for example, potassium tert-butoxide, sodium tert-butoxide, or combinations thereof. The step (b) reaction may be conducted in any suitable solvent including, but not limited to, tetrahydrofuran, water, and methyl tert-butyl ether. In one embodiment, the reaction is conducted in the presence of carbonyldiimidazole and potassium tert-butoxide.

More particularly, in certain embodiments, a suspension of trimethylsulfoxonium chloride, strong base, and solvent is heated (e.g., to about 35° C. to about 65° C., or to about 45° C.) for about 30 minutes to about 8 hours, or for about 1 hour, followed by cooling. In one embodiment, the suspension is cooled to a temperature of about −1° C. or less, or to about −5° C. or less. In some embodiments, the concentrated filtrate from step (a) is diluted with a suitable solvent (e.g., tetrahydrofuran), and to this solution is slowly added (e.g., over 30 minutes to 1 hour, or over 30 minutes) CDI. The resulting mixture is stirred at room temperature for 30 minutes to 12 hours, and typically for about 1 hour. The resulting solution is slowly added (e.g., over 15 minutes to 1 hour, or over 1 hour) to the suspension of the trimethylsulfoxonium chloride, strong base, and solvent, while maintaining the internal temperature below −1° C. In embodiments, the reaction may be stirred for about 30 minutes to about 8 hours, or for about 1 hour at a temperature of below about −1° C., or at about −5° C. In another embodiment, the reaction is quenched and the resulting compound of formula (II) or (IIa) is isolated prior to step (c). In one particular embodiment, step (b) of Schemes III or IIIa is performed as described in Step A of Example 4.

Steps (a) and (b) of Schemes III and IIIa advantageously allow for preparation of a protected (3R,4S)-4-ethylpyrrolidine-3-carboxylic acid without formation and isolation of the naphthalene ethane amine salt (Ia) or the dicyclohexylamine salt (Ib), or isolation of (I) or (XI).

In step (c) of Schemes III and IIIa, a compound of formula (II) or (IIa) is contacted with an anhydrous source of HBr or HCl to form a compound of formula (III) or (IIIa), respectively. In particular, the anhydrous source of HBR or HCl comprises no more than 0.2% water (by volume), or no more than about 0.15% water (by volume). The reaction of step (c) may be conducted in any suitable solvent including, tetrahydrofuran.

More particularly, in certain embodiments, (II) or (IIa) is combined with the HBr or HCl in a suitable solvent. In one embodiment, the solvents are tetrahydrofuran and acetic acid. In one embodiment, the solvent comprises no more than 0.2% water (by volume). In one embodiment, (II) or (IIa) is combined with a solvent (e.g., THF) and a solution of HBr in HOAc. The resulting mixture is warmed to about 35° C. to about 65° C., or about 40° C. and agitated. In one embodiment, the mixture is agitated for about 4 to about 12 hours, or for about 5 hours. In one embodiment, the mixture is warmed to about 40° C. and agitated (e.g., stirred) for about 5 hours. In one embodiment, the mixture is cooled to room temperature (e.g., around 20° C.) and distilled, followed by washing. In one particular embodiment, the product (compound (III) or (IIIa)) is concentrated to dryness, and resuspended in a solvent (e.g., N,N-dimethylacetamide) to form a solution of (III) or (IIIa) for use in step (d). In one embodiment, step (c) of Schemes III or IIIa is performed as described in Step B of Example 4.

Step (c) advantageously produces the halomethyl ketone (III) or (IIIa) in higher purity than Scheme I or Ia.

In step (d) of Schemes III and IIIa, a compound of formula (III) or (IIIa) is reacted with a compound of formula (IV) or (IVa) (prepared as described herein). The step (d) reaction is conducted in the presence of a base, such as lithium tert-butoxide, sodium tert-butoxide, or combinations thereof. In one embodiment, the base is lithium tert-butoxide. The reaction of step (d) may be conducted in any suitable solvent including, but not limited to dimethylacetamide, tetrahydrofuran, dichloromethane, ethyl acetate, heptanes, and combinations thereof.

More particularly, in certain embodiments, the base is slowly added (e.g., over about 30 minutes) to a cooled suspension of the compound of formula (IV) or (IVa) in a solvent. In one embodiment, the suspension of the compound of formula (IV) or (IVa) is cooled to about 0° C. The resulting solution is stirred for about 30 minutes to about 12 hours, or about 30 minutes, and cooled to about −20° C. to about 0° C., or about −10° C. In one embodiment, the solution is stirred for about 30 minutes and cooled to about −20° C. to about 0° C., or about −10° C. The halomethyl ketone solution prepared in step (c) is then slowly added (e.g., over about 1 hour), and the resulting mixture is agitated (e.g., stirred) for about 30 minutes to about 6 hours, or about 30 minutes, at a temperature of about −20° C. to about 0° C., or about −10° C. In one embodiment, following addition of the step (c) solution, the resulting mixture is stirred for about 30 minutes at a temperature of about −10° C. In one embodiment, the reaction is quenched, and, in some embodiments, the resulting product (V) or (Va) is isolated prior to step (e). In one embodiment, step (d) of Schemes III and IIIa is performed as described in Step C of Example 4.

Steps (e)-(g) of Schemes III and IIIa may be conducted as described above for steps (d)-(f) of Scheme I, respectively.

In one embodiment, Compound 1 is prepared according to the process set forth in Scheme IIIa.

B. Preparation of Compounds of Formula (I), (Ia), (Ib), and (XIa)

The processes for preparing Compound 1 disclosed herein may use a compound of formula (I), or a pharmaceutically acceptable salt thereof, and/or a compound of formula (XI) or (XIa). In one embodiment, the processes use either the naphthalene ethane amine salt of formula (Ia), or the dicyclohexylamine salt of formula (Ib). Compounds of formula (I) and (Ia) and their preparation are described in, for example, US 2013/0072470, which is herein incorporated by reference. (Ia) can also be prepared as described in Scheme IV, set forth below. (Ib) can be prepared as described in Scheme V, set forth below. Compounds of formula (I) wherein PG is Cbz (i.e., compounds of formula (XII)) can be prepared using the procedure set forth in Scheme IV or V. Compounds of formula (XI) can be prepared using the procedure set forth in Scheme V. Other protecting groups may be substituted for Cbz using techniques known to those skilled in the art.

Formula (Ia)

The preparation of (Ia) has been previously described (see, e.g., US 2013/0072470, Example 12, which is herein incorporated by reference). One suitable process for preparing the naphthalene ethane amine salt of the compound of formula (I) is illustrated in Scheme IV. Ethyl pent-2-ynoate is hydrogenated with a Lindlar catalyst to form (Z)-ethyl pent-2-enoate. The (Z)-ethyl pent-2-enoate is reacted with N-(methoxymethyl)-N-(trimethylsilyl methyl)benzylamine to form (XIII). (XIII) is deprotected to form (XIV), followed by hydrolysis of (XIV) to form (XV). (XV) is reacted with N-(benzyloxycarbonyloxy) succinimide to form (XVI). The protected (XVI) is contacted with (R)-1-(naphthalene-1-yl) ethanamine to form (Ia).

Scheme IV

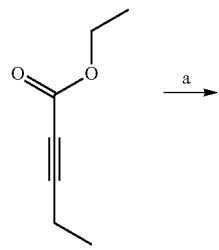

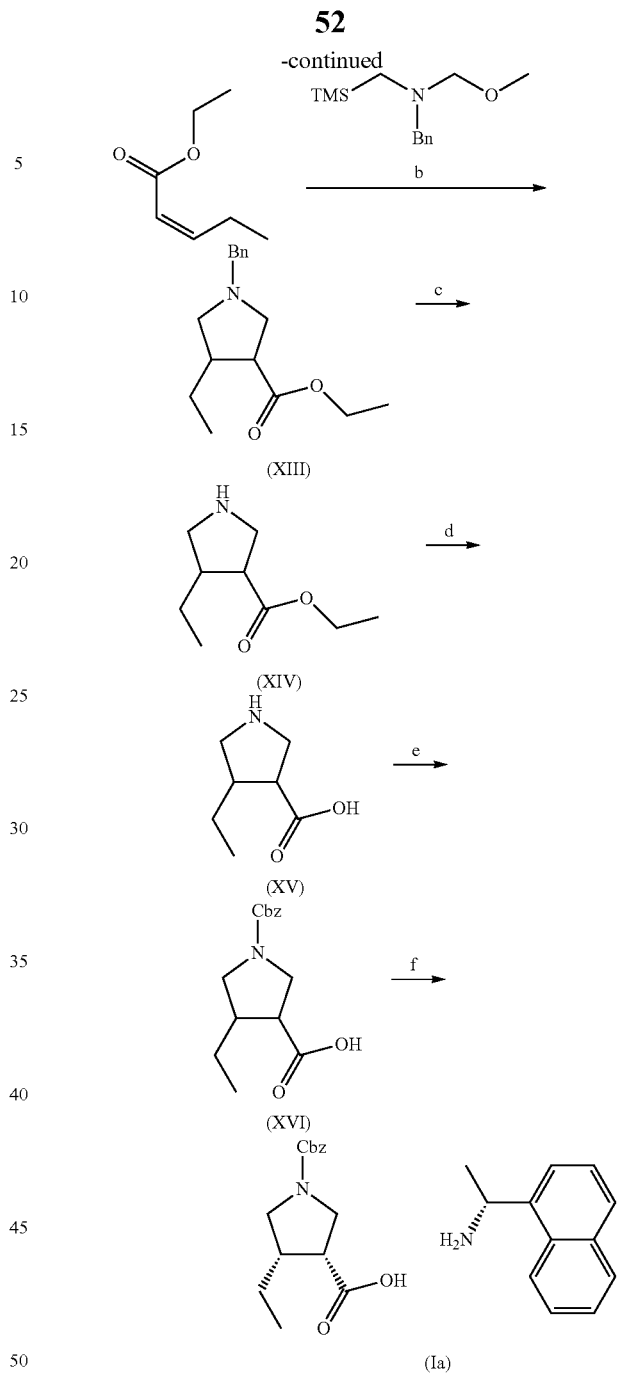

wherein:
TMS is trimethylsilyl;
Cbz is carboxybenzyl; and
Bn is benzyl.

In step (a) of Scheme IV, ethyl pent-2-ynoate is hydrogenated with a Lindlar catalyst to form (Z)-ethyl pent-2-enoate. In particular, in certain embodiments, the ethyl pent-2-ynoate is added to a slurry of the Lindlar catalyst in solvent (e.g., THF) and organic base (e.g., pyridine). The reaction mixture is sparged with hydrogen (e.g., for about 15 hours). In one embodiment, upon reaction completion, the reaction mixture is filtered, and the (Z)-ethyl pent-2-enoate washed prior to step (b).

In step (b) of Scheme IV, the (Z)-ethyl pent-2-enoate is reacted with N-(methoxymethyl)-N-(trimethylsilyl methyl)

benzylamine to form (XIII). In particular, trifluoroacetic acid (TFA) is added to a solution of the (Z)-ethyl pent-2-enoate and N-(methoxymethyl)-N-(trimethylsilyl methyl) benzylamine in solvent (e.g., dichloromethane (DCM)). After about 2 days, the reaction mixture is concentrated to provide (XIII).

In steps (c) and (d) of Scheme IV, (XIII) is deprotected to form (XIV), followed by hydrolysis of (XIV) to form (XV). (XIII) may be deprotected using any suitable means known in the art, including those set forth above for step (e) of Scheme I. In one embodiment, (XIII) is deprotected by contacting (XIII) with a catalyst (e.g., a palladium catalyst such as Pd/C or Pd(OH$_2$)/C) under hydrogen pressure. In one embodiment, the resulting mixture is filtered to provide (XIV). In step (d), (XIV) is contacted with an acid (e.g., HCl). In one embodiment, the reaction mixture is heated (e.g., to about 100° C.), typically for about 24 hours. The reaction mixture is cooled and concentrated. In step (e), the reaction mixture from step (d) containing (XV) is reacted with N-(benzyloxycarbonyloxy) succinimide (e.g., for about 15 hours) to form (XVI).

In step (f) of Scheme IV, (XVI) is contacted with (R)-1-(naphthalene-1-yl)ethanamine to form (Ia).

Formula (Ib)

In some embodiments, the present disclosure is directed to compound (Ib) and a process for preparing compound (Ib). A process for preparing the dicyclohexylamine salt of the compound of formula (I) is illustrated in Scheme V. Carboxybenzyl-glycine ethyl ester is reacted with ethyl acrylate to form (VIII). Protection of (VIII) yields (IX). Contacting (IX) with one of ethyl boronic acid, ethyl magnesium bromide, or ethyl zinc chloride in the presence of a catalyst results in (X). (X) is hydrolyzed to produce (XI), which is hydrogenated to produce (XII). (XII) is contacted with dicyclohexylamine to form (Ib).

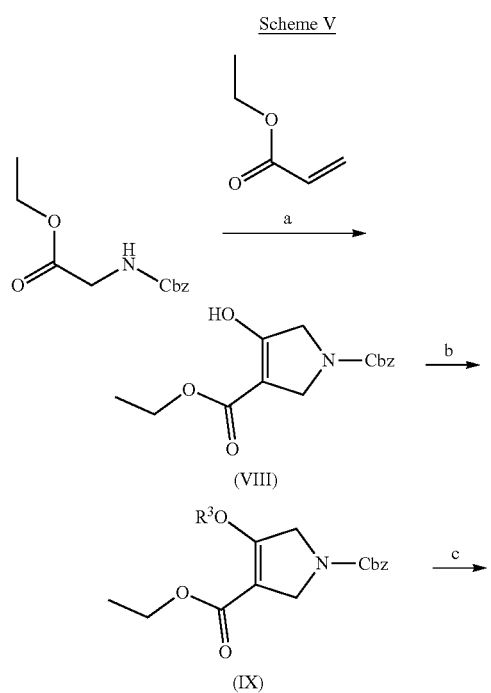

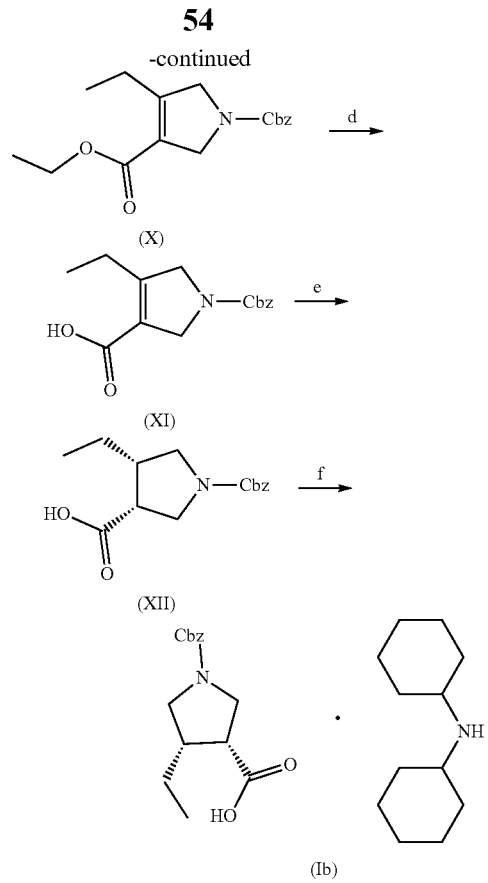

wherein
Cbz is carboxybenzyl; and
R$^3$ is selected from the group consisting of CF$_3$SO$_2$—, CH$_3$SO$_2$—, and tosyl.

In step (a) of Scheme V, carboxybenzyl-glycine ethyl ester is reacted with ethyl acrylate to form (VIII). The step (a) reaction is conducted in the presence of a strong base. Suitable bases include, but are not limited to, sodium tert-butoxide, potassium tert-butoxide, and lithium tert-butoxide. In one embodiment, the strong base is sodium tert-butoxide. In one embodiment, the step (a) reaction is conducted in an organic solvent, such as tetrahydrofuran, 1,4-dioxane, 1,2-dimethoxyethane, 2-methyl tetrahydrofuran, and the like, and combinations thereof.

In particular, in certain embodiments, the base is slowly added (e.g., over 1 hour) to a mixture of the carboxybenzyl-glycine ethyl ester and ethyl acrylate in solvent at about –5° C. to about 20° C. In one embodiment, the base is slowly added (e.g., over 1 hour) to a mixture of the carboxybenzyl-glycine ethyl ester and ethyl acrylate in solvent at about 0° C. The resulting mixture is warmed to room temperature, and stirred overnight. In one embodiment, upon completion, the reaction is quenched and the product crystallized. The product may optionally be isolated prior to step (b).

In step (b) of Scheme V, the compound of formula (VIII) is protected to form (IX). In one embodiment, the compound of formula (VIII) is reacted with a reagent selected from the group consisting of trifluoromethanesulfonic anhydride, methanesulfonyl chloride, and p-toluenesulfonyl chloride to form (IX). In one embodiment, the step (b) reaction is conducted in the presence of an organic base. Suitable organic bases include, but are not limited to, diisopropylethylamine (DIPEA), 4-dimethylamino pyridine (DMAP), triethylamine (TEA), pyridine, N-methylmorpholine (NMM), and combinations thereof. The step (b) reaction may be conducted in any suitable solvent including, but not limited to, triethylamine, N-methylmorpholine, pyridine, diisopropyl ether, and combinations thereof.

In particular, in certain embodiments, the trifluoromethanesulfonic anhydride, methanesulfonyl chloride, or p-toluenesulfonyl chloride is added to a mixture of (VIII) in solvent at about −5° C. to about 20° C. In one embodiment, the trifluoromethanesulfonic anhydride, methanesulfonyl chloride, or p-toluenesulfonyl chloride is added to a mixture of (VIII) in solvent at a temperature of about 0° C. The organic base is subsequently slowly added (e.g., over about 30 minutes), and the mixture warmed to room temperature and stirred for about 30 minutes to about 18 hours. In one embodiment, the mixture is stirred for about 1 hour. Upon completion, the reaction is preferably quenched and the product washed. In some embodiments, a solution of (IX) in solvent is prepared and used directly in step (c).

In step (c) of Scheme V, (IX) is contacted with one of ethyl boronic acid, ethyl magnesium bromide, or ethyl zinc chloride in the presence of a catalyst to produce (X). Any suitable catalyst known in the art may be used. In certain embodiments, the catalyst is a palladium catalyst, such as $PdCl_2(dppf)$. In some embodiments, the catalyst is a nickel catalyst, such as $Ni(acac)_2$. In some embodiments, the catalyst is an iron catalyst, and in particular a Fe(III) catalyst, such as $FeCl_3$ and $Fe(acac)_3$. Step (c) may be conducted in a buffer. Suitable buffers include, but are not limited to, potassium carbonate, sodium carbonate, potassium phosphate tribasic, and combinations thereof. Suitable solvents for use in step (c) include, but are not limited to, toluene, water, dioxane, tetrahydrofuran, and combinations thereof.

In particular, in certain embodiments, the ethyl boronic acid and buffer is added to the solution of (IX) in solvent prepared in step (b). A suitable catalyst may then be added, and the resulting mixture warmed to about 75° C. to about 110° C., or about 85° C., and stirred for about 4 hours to about 18 hours, or about 6 hours. In one embodiment, the mixture is warmed to about 85° C., and stirred for about 6 hours. Upon completion, the reaction mixture is cooled to room temperature, and the product filtered. In one embodiment, the product is isolated prior to step (d).

In step (d), (X) is hydrolyzed to produce (XI). (X) may be hydrolyzed using any suitable means known in the art. In one embodiment, (X) is contacted with an alkali metal hydroxide. The alkali metal hydroxide may be selected from the group consisting of sodium hydroxide and lithium hydroxide. In one embodiment, the alkali metal hydroxide is sodium hydroxide. Any suitable solvent may be used in the step (d) reaction including, but not limited to, tetrahydrofuran, water, dioxane, and combinations thereof.

In particular, in certain embodiments, the alkali metal hydroxide is added to a solution of (X) in solvent. The resulting mixture is warmed to about 20° C. to about 65° C., and stirred for about 2 hours to about 18 hours. In one embodiment, the mixture is warmed to about 50° C., and stirred for about 2 hours to about 18 hours. In one embodiment, the mixture is stirred for about 7 hours. Upon completion, the mixture is cooled to room temperature, the pH adjusted to about 9, and the solvent removed. In one embodiment, the product is washed and isolated prior to step (e).

In steps (e) and (f) of Scheme V, (XI) is converted to (XII), and (XII) is contacted with dicyclohexylamine to form (Ib). In particular, in step (e) compound (XI) may be contacted with a catalyst, such as a ruthenium catalyst. Any catalyst comprising a chiral phosphine may be used. One particular example of a suitable catalyst is diacetato[(S)-(−)5,5'-bis(diphenylphosphino)-4,4'-bi-1,3-benzodioxole]ruthenium(II) (i.e., (S)-Segphos $Ru(OAc)_2$). Suitable solvents for use in step (e) include, but are not limited to, methanol, triethylamine, and combinations thereof.

In particular, in certain embodiments, a solution of (XI) and the catalyst in solvent is hydrogenated at about 30° C. to about 100° C. for from about 1 hour to about 18 hours. In one embodiment, the solution of (XI) and the catalyst in solvent is hydrogenated at about 580 psi. In one embodiment, the solution of (XI) and the catalyst in solvent is hydrogenated at about 80° C. for from about 1 hour to about 8 hours, or for about 2 hours. Upon completion, the reaction mixture is cooled to room temperature, filtered, and concentrated. In one embodiment, the product is washed, and transferred to a suitable solvent, such as acetonitrile, prior to step (f). In step (f), additional solvent (e.g., acetonitrile) and dicyclohexylamine are added, and the mixture is heated to about 50° C. to about 80° C. In one embodiment, the mixture is heated to about 80° C. The resulting solution is cooled to room temperature and stirred for about 1 hour to about 18 hours. In one embodiment, the mixture is cooled to room temperature and stirred for about 1 hour. The resulting product (Ib) may be isolated prior to use in preparation of Compound 1.

C. Intermediate Compounds

In some embodiments, the present disclosure is directed to intermediate compounds useful in the preparation of Compound 1, as well as to processes for preparing the intermediate compounds.

Formula (IVa)

In one embodiment, the present disclosure is directed to a compound of formula (IVa).

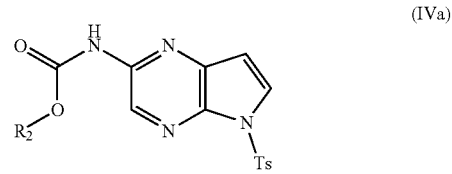

(IVa)

wherein $R_2$ and Ts are as defined above.

As discussed herein and as depicted in Schemes I, II, and III, compounds of formula (Na) may be reacted with a compound of formula (III) or (IIIa) to produce a compound of formula (V) or (Va). Advantageously, the methyl or ethyl carbamate moiety present on the compound of formula (IVa) results in a crystalline product when the compound of formula (IVa) is reacted with a compound of formula (III) or (IIIa) in Schemes I, II, or III.

In another aspect, the present disclosure is directed to a process for preparing a compound of formula (IVa). One suitable process for preparing a compound of formula (IVa) is illustrated in Scheme VI. In particular, (XVII) is reacted with trimethylsilylacetylene in the presence of a catalyst to form (XVIII). (XVIII) is contacted with p-toluenesulfonyl chloride in the presence of a base to form (XIX). (XIX) is reacted with an ethyl or methyl carbamate in the presence of a catalyst and a ligand to form a compound of formula (IVa).

Scheme VI

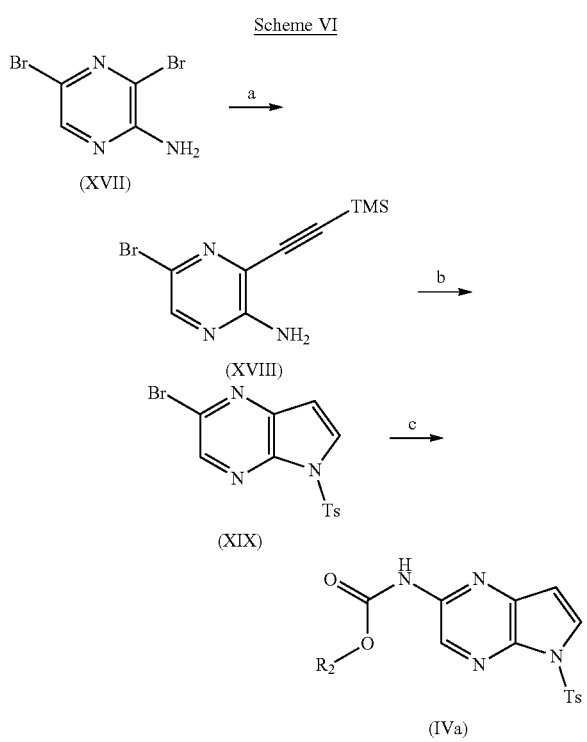

wherein:
R₂ is methyl or ethyl;
Ts is tosyl; and
TMS is trimethylsilyl.

In step (a) of Scheme VI, compound (XVII), which is commercially available, is reacted with trimethylsilylacetylene in the presence of a catalyst to form (XVIII). Any suitable catalyst known in the art may be used. In some embodiments, the catalyst is a palladium catalyst, such as bis(triphenylphosphine)palladium (II) dichloride (PdCl$_2$(Ph$_3$P)$_2$). Step (a) is typically conducted in the presence of copper (I) iodide (CuI). Any suitable solvent may be used in step (a), including, but not limited to, triethylamine.

In particular, in certain embodiments, the catalyst is added to a solution of (XVII) and CuI in solvent. The reaction mixture is cooled (e.g., to about −5 to 0° C.), and a solution of the trimethylsilylacetylene in solvent is slowly added (e.g., over about 15 minutes). The reaction mixture is stirred at about −5 to 0° C. (e.g., for about 1.5 hours), and allowed to warm to room temperature overnight. In one embodiment, the reaction mixture is filtered and washed, and the product isolated prior to step (b).

In step (b) of Scheme VI, (XVIII) is contacted with p-toluenesulfonyl chloride in the presence of a base to form (XIX). Suitable bases for use in step (b) include, but are not limited to, potassium tert-butoxide, sodium hydride, and the like, and combinations thereof. Suitable solvents for use in step (b) include, but are not limited to, dimethylformamide.

In particular, in certain embodiments, the base is added to a solution of (XVIII) in solvent (e.g., at about 0° C.). The p-toluenesulfonyl chloride is subsequently added, and the mixture is allowed to warm to room temperature. After reaction (e.g., for about 16 hours), the reaction mixture is poured into ice cold water, and the precipitate is collected. In one embodiment, the product is isolated and purified prior to step (c).

In step (c) of Scheme VI, (XIX) is reacted with an ethyl or methyl carbamate in the presence of a catalyst and a ligand to form a compound of formula (IVa). The reaction may be conducted in the presence of buffers, such as potassium carbonate, tetramethylammonium hydroxide, and the like. Any suitable catalyst known in the art may be used in step (c). In one embodiment, the catalyst is a palladium catalyst, such as palladium (II) acetate. Suitable ligands for use in step (c) include bidentate ligands, such as Xantphos. In one embodiment, the catalyst is palladium (II) acetate and the ligand is Xantphos. Suitable solvents for use in step (c) include, but are not limited to, dioxane, toluene, and tetrahydrofuran.

In particular, in certain embodiments, a degassed mixture of the catalyst, ligand, (XIX), carbamate, and the buffer in solvent is heated to about 75° C. to about 110° C., or about 95° C., and stirred overnight. After completion, the reaction mixture is cooled to about 30° C. to about 60° C. In one embodiment, the reaction mixture is cooled to about 50° C. Optionally, additional solvent may be added, and the resulting solution filtered. In another embodiment, the product is washed and isolated prior to use in preparation of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide.

Compound (XVII) used in Scheme VI is commercially available. The preparation of compounds (XVIII) and (XIX) are also described in Example 1 of WO 2011/068881, which is herein incorporated by reference.

Formula (II)

In one aspect, the present disclosure is directed to a compound of formula (II):

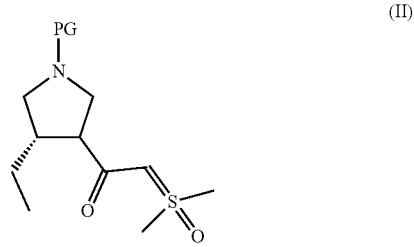

(II)

wherein PG is a protecting group.

The protecting group may be any suitable protecting group known in the art. In some embodiments, the protecting group is selected from the group consisting of carboxybenzyl, p-methoxybenzyl carbonyl, benzyl, p-methoxybenzyl, and 3,4-dimethoxyenzyl.

In one preferred embodiment, the protecting group is carboxybenzyl, and the compound of formula (II) is compound (IIa):

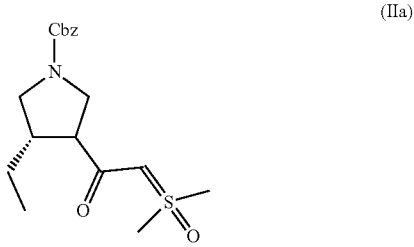 [SMILES: CC[C@@H]1CN(C(=O)OCc2ccccc2)CC1C(=O)C=S(C)(C)=O]

(IIa)

wherein Cbz is carboxybenzyl.

In another aspect, the present disclosure is directed to a process for preparing a compound of formula (II) or (IIa). One process for preparing a compound of formula (II) or (IIa) is illustrated in Scheme VII. In Scheme VII, a compound of formula (I) or a pharmaceutically acceptable salt thereof is reacted with trimethylsulfoxonium chloride to form a compound of formula (II). In one particular embodiment, the pharmaceutically acceptable salt is a compound of formula (Ib).

Scheme VII

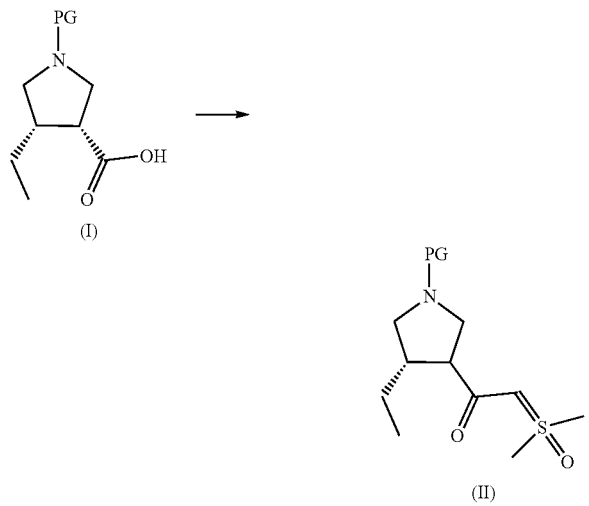

wherein PG is a protecting group as defined herein.

The reaction of Scheme VII is generally accomplished in the presence of a coupling agent, such as carbonyldiimidazole (CDI), and a strong base. The strong base may be, for example, potassium tert-butoxide, sodium tert-butoxide, or combinations thereof. The Scheme VII reaction may be conducted in any suitable solvent including, but not limited to, tetrahydrofuran, water, and methyl tert-butyl ether. In one embodiment, the reaction is conducted in the presence of carbonyldiimidazole and potassium tert-butoxide. In one embodiment, the reaction of Scheme VII is conducted under the conditions described above for step (a) of Scheme I.

Another process for preparing a compound of formula (II) or (IIa) is illustrated in Scheme VIII. In step (a) of Scheme VIII, a compound of formula (XIa) is hydrogenated to a compound of formula (I), and in step (b) of Scheme VIII, the compound of formula (I) is reacted with trimethylsulfoxonium chloride to form a compound of formula (II).

Scheme VIII

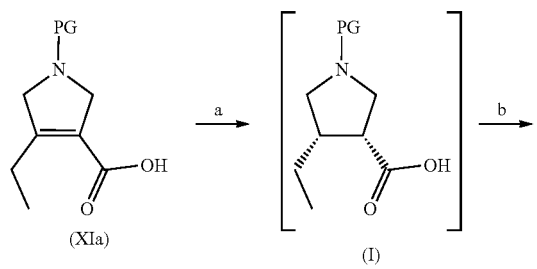

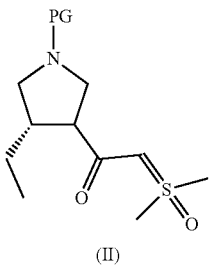

wherein PG is a protecting group as defined herein.

In step (a) of Scheme VIII, the compound of formula (XIa) may be contacted with a catalyst, such as a ruthenium catalyst. Any catalyst comprising a chiral phosphine may be used. One particular example of a suitable catalyst is diacetato[(S)-(−)5,5'-bis(diphenylphosphino)-4,4'-bi-1,3-benzodioxole]ruthenium(II) (i.e., (S)-Segphos Ru(OAc)$_2$). Suitable solvents for use in step (a) include, but are not limited to, methanol, triethylamine, and combinations thereof. In one embodiment, the reaction of step (a) of Scheme VIII is conducted under the conditions described above for step (a) of Scheme III.

The reaction in step (b) of Scheme VIII is generally accomplished in the presence of a coupling agent, such as carbonyldiimidazole (CDI), and a strong base. The strong base may be, for example, potassium tert-butoxide, sodium tert-butoxide, or combinations thereof. The step (b) reaction may be conducted in any suitable solvent including, but not limited to, tetrahydrofuran, water, and methyl tert-butyl ether. In one embodiment, the reaction is conducted in the presence of carbonyldiimidazole and potassium tert-butoxide. In one embodiment, the reaction of step (b) of Scheme VIII is conducted under the conditions described above for step (b) of Scheme III.

Formula (III)

In another embodiment, the present disclosure is directed to a process for preparing a compound of formula (III):

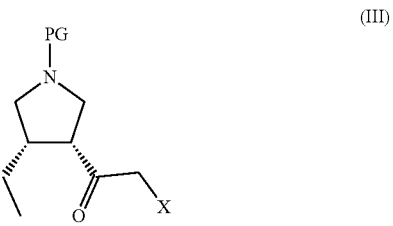

wherein PG is a protecting group, and X is Br or Cl.

The protecting group may be any suitable protecting group known in the art. In some embodiments, the protecting group is selected from the group consisting of carboxybenzyl, p-methoxybenzyl carbonyl, benzyl, p-methoxybenzyl, and 3,4-dimethoxyenzyl.

In one preferred embodiment, the protecting group is carboxybenzyl and X is Br, and the compound of formula (III) is compound (IIIa)

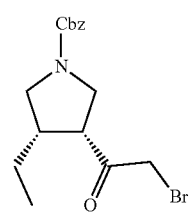

wherein Cbz is carboxybenzyl.

One process for preparing a compound of formula (III) or (IIIa) is illustrated in Scheme IX.

Scheme IX

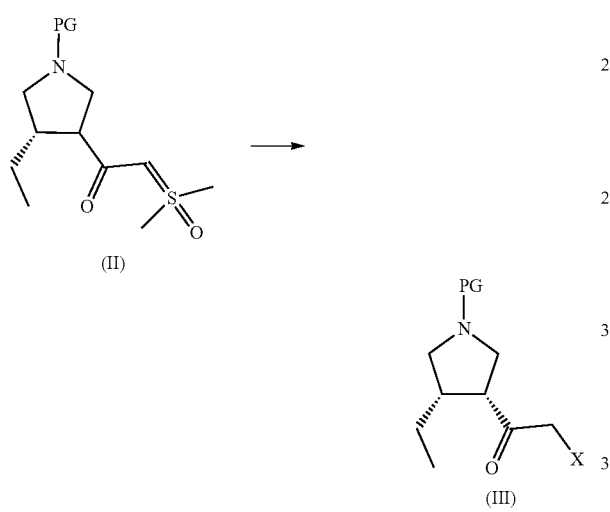

wherein PG and X are as defined herein.

Referring to Scheme IX, in one embodiment, a compound of formula (II) is contacted with LiX and a sulfonic acid to form a compound of formula (III). In this embodiment, the sulfonic acid is selected from the group consisting of methanesulfonic acid and p-toluenesulfonic acid. In one embodiment, the sulfonic acid is p-toluenesulfonic acid. LiX may be selected from lithium bromide and lithium chloride. In one embodiment, LiX is lithium bromide. In one embodiment, the reaction is conducted in lithium bromide and p-toluenesulfonic acid. The reaction may be conducted in any suitable solvent including, but not limited to tetrahydrofuran, ethyl acetate, heptanes, ethanol, water, and combinations thereof. In one embodiment, the reaction of Scheme XI is conducted under the conditions described above for step (b) of Scheme I.

Referring to Scheme IX, in an alternate embodiment, the compound of formula (II) is contacted with an anhydrous source of HBr or HCl to form the compound of formula (III). The reaction may be conducted in any suitable solvent including, but not limited to, tetrahydrofuran, ethyl acetate, acetic acid, N,N-dimethylacetamide, heptanes, and combinations thereof. In one embodiment, the reaction of Scheme IX is conducted under the conditions described above for step (c) of Scheme III.

In some embodiments, the process for preparing a compound of formula (III) or (IIIa) may further comprise preparing a compound of formula (II). One such process is illustrated in Scheme X.

Scheme X

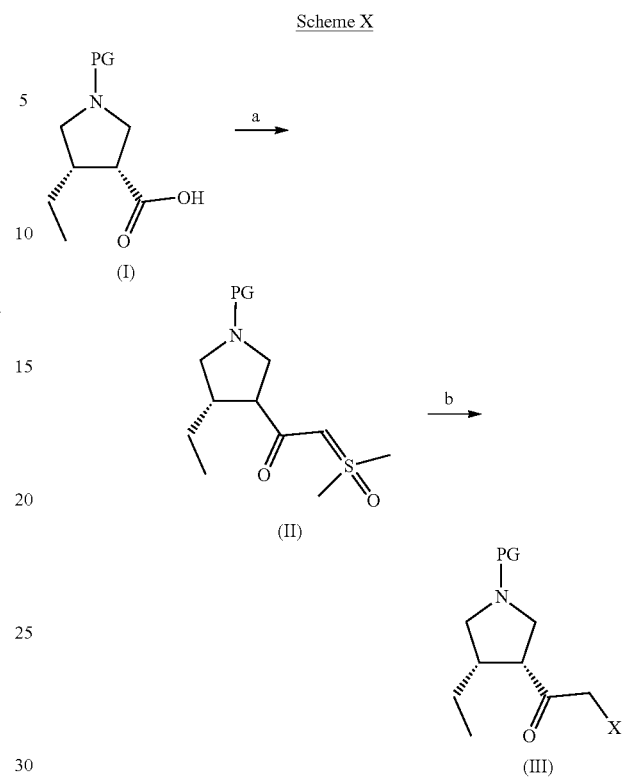

wherein PG and X are as defined above.

In Scheme X, a compound of formula (I) or a pharmaceutically acceptable salt thereof is reacted with trimethylsulfoxonium chloride in the presence of carbonyldiimidazole and a strong base (e.g., potassium tert-butoxide, sodium tert-butoxide, and combinations thereof) to form a compound of formula (II). The compound of formula (II) is then contacted with LiX and a sulfonic acid to form a compound of formula (III), as described above in Scheme IX. In one embodiment, step (a) of Scheme X is conducted under the conditions described above for step (a) of Scheme I. In one embodiment, the protecting group is carboxybenzyl, and the compound of formula (II) is compound (IIa). In another embodiment, in step (a) of Scheme X, a pharmaceutically acceptable salt of a compound of formula (I) is reacted with trimethylsulfoxonium chloride to form a compound of formula (II). In one embodiment, the salt is (Ia) or (Ib).

In some embodiments, the process for preparing a compound of formula (III) or (IIIa) may further comprise preparing a compound of Formula (I) and (II). One such process is illustrated in Scheme XI.

Scheme XI

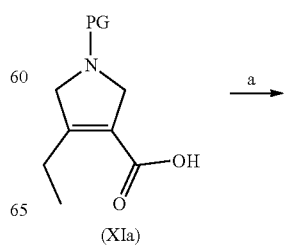

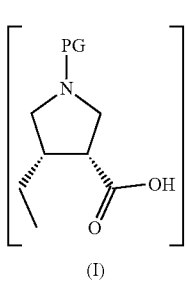

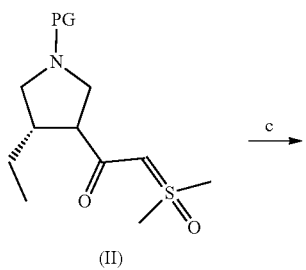

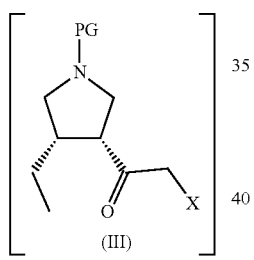

wherein PG and X are as defined above.

In step (a) of Scheme XI, a compound of formula (XIa) is hydrogenated to a compound of formula (I), and in step (b), the compound of formula (I) is reacted with trimethylsulfoxonium chloride in the presence of CDI and a strong base (e.g., KOtBu, NatOBu, and combinations thereof) to form a compound of formula (II). The compound of formula (II) is then contacted with an anhydrous source of HBr or HCl to form the compound of formula (III), as described above for Scheme IX. In one embodiment, the protecting group is carboxybenzyl, and the compound of formula (XIa), (I), and (II) is compound (XI), (XII), and (IIa), respectively. In one embodiment, step (a), step (b), and step (c) of Scheme XI are conducted under the conditions described above for step (a), step (b), and step (c) of Scheme III, respectively.

Formulae (V) and (Va)

In another embodiment, the present disclosure is directed to a compound of formula (Va):

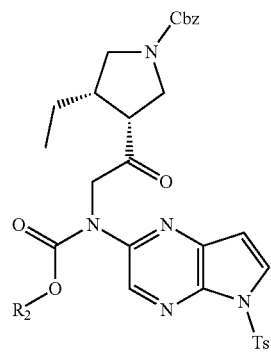

wherein $R_2$, Cbz, and Ts are as defined above.

In another aspect, the present disclosure is directed to a process for preparing a compound of formula (V) or (Va). One process for preparing a compound of formula (V) or (Va) is illustrated in Scheme XII. In Scheme XII, a compound of formula (I) or a pharmaceutically acceptable salt thereof is reacted with trimethylsulfoxonium chloride to form a compound of formula (II). Contacting the compound of formula (II) with LiX and a sulfonic acid yields the corresponding halomethyl ketone (III). Reaction of a compound of formula (III) with a compound of formula (IV) in the presence of a base yields a compound of formula (V).

Scheme XII

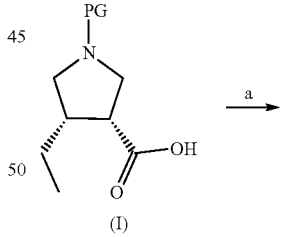

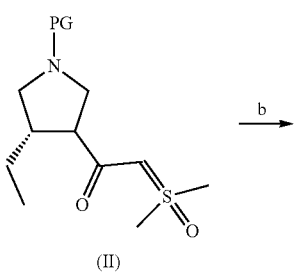

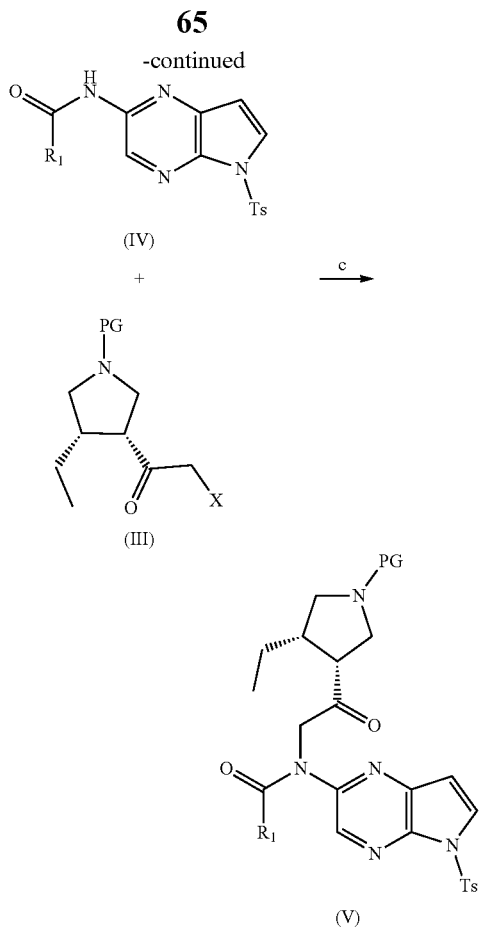

wherein PG, Ts, R$_1$, and X are as defined above.

The protecting group may be any suitable protecting group known in the art. In some embodiments, the protecting group is selected from the group consisting of carboxybenzyl, p-methoxybenzyl carbonyl, benzyl, p-methoxybenzyl, and 3,4-dimethoxyenzyl.

In one embodiment, the protecting group is carboxybenzyl, and the compound is a compound of formula (Va). In one embodiment, the protecting group is carboxybenzyl, and X is Br.

In one embodiment, R$_1$ is —OR$_2$, and R$_2$ is methyl or ethyl. In such embodiments, the compound of formula (IV) is a compound of formula (IVa).

In certain embodiments, a pharmaceutically acceptable salt of a compound of formula (I) is used in the reaction of step (a) of Scheme XII. In one embodiment, the pharmaceutically acceptable salt of the compound of formula (I) is selected from the group consisting of the naphthalene ethane amine salt (Ia) and the dicyclohexylamine salt (Ib).

The reaction in step (a) of Scheme XII is generally accomplished in the presence of a coupling agent, such as carbonyldiimidazole (CDI), and a strong base. The strong base may be, for example, potassium tert-butoxide, sodium tert-butoxide, or combinations thereof. The step (a) reaction may be conducted in any suitable solvent including, but not limited to, tetrahydrofuran, water, and methyl tert-butyl ether. In one embodiment, the reaction is conducted in the presence of carbonyldiimidazole and potassium tert-butoxide.

In step (b) of Scheme XII, a compound of formula (II) or (IIa) is contacted with LiX and a sulfonic acid to form a compound of formula (III) or (IIIa), respectively. In one embodiment, the sulfonic acid is selected from the group consisting of methanesulfonic acid and p-toluenesulfonic acid. In one embodiment, the sulfonic acid is p-toluenesulfonic acid. LiX may be selected from lithium bromide and lithium chloride. In one embodiment, LiX is lithium bromide. In one embodiment, the reaction is conducted in lithium bromide and p-toluenesulfonic acid. The reaction of step (b) may be conducted in any suitable solvent including, but not limited to tetrahydrofuran, ethyl acetate, heptanes, ethanol, water, and combinations thereof.

In step (c) of Scheme XII, a compound of formula (III) or (IIIa) is reacted with a compound of formula (IV) or (IVa) (prepared as described herein). The step (c) reaction is conducted in the presence of a base, such as lithium tert-butoxide, sodium tert-butoxide, or combinations thereof. In one embodiment, the base is lithium tert-butoxide. The reaction of step (c) may be conducted in any suitable solvent including, but not limited to dimethylacetamide, tetrahydrofuran, dichloromethane, ethyl acetate, heptanes, and combinations thereof.

In One embodiment, steps (a), (b), and (c) of Scheme XII are conducted under the conditions set forth herein for the corresponding step of Scheme I.

In another aspect, the present disclosure is directed to an alternate process for preparing a compound of formula (V) or (Va). One process for preparing a compound of formula (V) or (Va) is illustrated in Scheme XIII. In Scheme XIII, a compound of formula (XIa) is hydrogenated to a compound of formula (I), and the compound of formula (I) is reacted with trimethylsulfoxonium chloride to form a compound of formula (II). Contacting the compound of formula (II) with an anhydrous source of HBr or HCl yields the corresponding halomethyl ketone (III). Reaction of a compound of formula (III) with a compound of formula (IV) in the presence of a base yields a compound of formula (V).

Scheme XIII

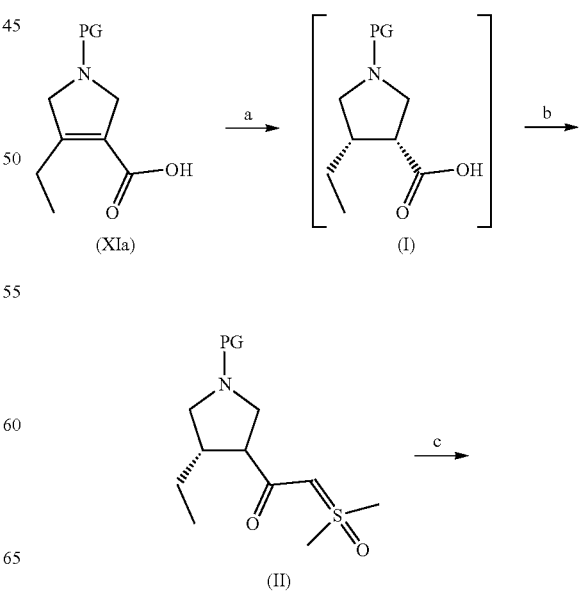

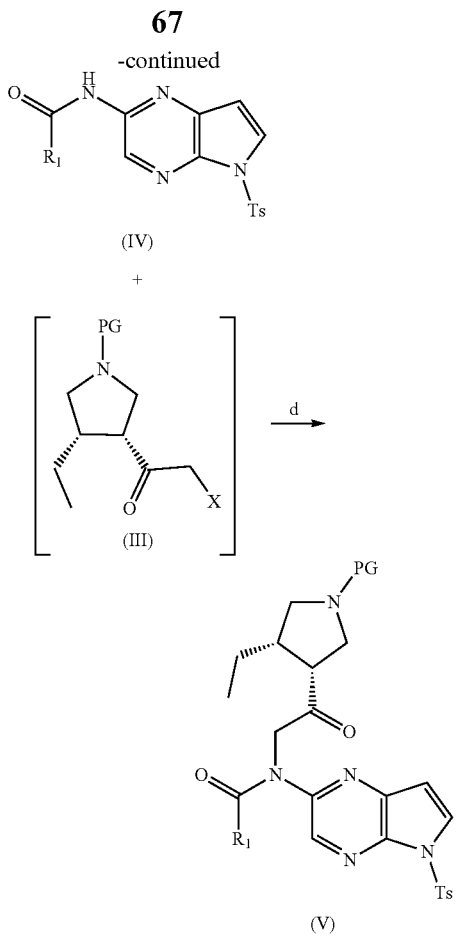

wherein PG, Ts, $R_1$, and X are as defined above.

The protecting group may be any suitable protecting group, such as described herein. In one embodiment, the protecting group is carboxybenzyl, and the compound of formula (XIa), (I), (II), (III), (IV), and (V) is compound (XI), (XII), (IIa), (IIIa), (IVa), and (Va), respectively. In one embodiment, the protecting group is carboxybenzyl, and X is Br. In One embodiment, $R_1$ is —$OR_2$ and $R_2$ is methyl or ethyl. In such embodiments, the compound of formula (IV) is a compound of formula (IVa).

In step (a) of Scheme XIII, the compound of formula (XIa) may be contacted with a catalyst, such as a ruthenium catalyst. Any catalyst comprising a chiral phosphine may be used. One particular example of a suitable catalyst is diacetato[(S)-(−)5,5'-bis(diphenylphosphino)-4,4'-bi-1,3-benzodioxole]ruthenium(II) (i.e., (S)-Segphos Ru(OAc)$_2$). Suitable solvents for use in step (a) include, but are not limited to, methanol, triethylamine, and combinations thereof. In one embodiment, the reaction of step (a) of Scheme XIII is conducted under the conditions described above for step (a) of Scheme III.

The reaction in step (b) of Scheme XIII is generally accomplished in the presence of a coupling agent, such as carbonyldiimidazole (CDI), and a strong base. The strong base may be, for example, potassium tert-butoxide, sodium tert-butoxide, or combinations thereof. The step (b) reaction may be conducted in any suitable solvent including, but not limited to, tetrahydrofuran, water, and methyl tert-butyl ether. In one embodiment, the reaction is conducted in the presence of carbonyldiimidazole and potassium tert-butoxide. In one embodiment, the reaction of step (b) of Scheme XIII is conducted under the conditions described above for step (b) of Scheme III.

In step (c) of Scheme XIII, the compound of formula (II) is contacted with an anhydrous source of HBr or HCl to form the compound of formula (III). The reaction may be conducted in any suitable solvent including, but not limited to, tetrahydrofuran, ethyl acetate, acetic acid, N,N-dimethylacetamide, heptanes, and combinations thereof. In one embodiment, the reaction of step (c) of Scheme XIII is conducted under the conditions described above for step (c) of Scheme III.

In step (d) of Scheme XIII, the compound of formula (III) is reacted with a compound of formula (IV) or (IVa) (prepared as described herein). The step (d) reaction is conducted in the presence of a base, such as lithium tert-butoxide, sodium tert-butoxide, or combinations thereof. In one embodiment, the base is lithium tert-butoxide. The reaction of step (d) may be conducted in any suitable solvent including, but not limited to dimethylacetamide, tetrahydrofuran, dichloromethane, ethyl acetate, heptanes, and combinations thereof. In one embodiment, the reaction of step (d) of Scheme XIII is conducted under the conditions described above for step (d) of Scheme III.

As discussed herein, it has surprisingly been discovered that when $R_1$ is —$OR_2$, and $R_2$ is ethyl or methyl, the compound of formula (V) and subsequent downstream compounds can be isolated as crystalline solids, which aids in purification of these intermediates. Thus, in another aspect, the present disclosure is directed to a process for preparing a crystalline compound of formula (V). The process comprises a) reacting a compound of formula (III):

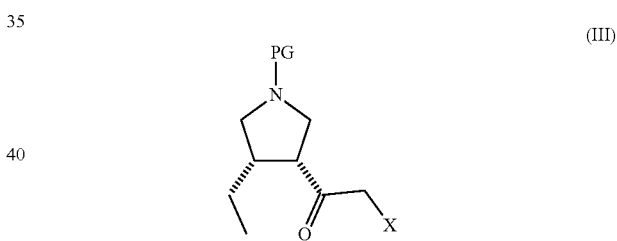

with a compound of formula (IV):

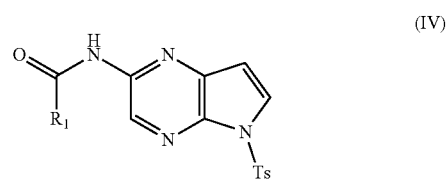

to produce the compound of formula (V); wherein: PG is a protecting group; X is Br or Cl; $R_1$ is —$OR_2$; $R_2$ is methyl or ethyl; and Ts is tosyl. In one embodiment, the process is conducted under the conditions set forth above for step c) in Scheme XII or step (d) in Scheme XIII.

Formula (VII)

In another embodiment, the present disclosure is directed to compound (VII):

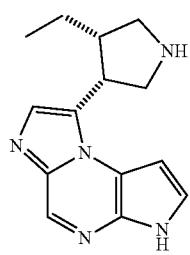

(VII)

or a pharmaceutically acceptable salt thereof.

In one embodiment, the pharmaceutically acceptable salt of (VII) is selected from the group consisting of (VIIa), (VIIb), and (VIIc):

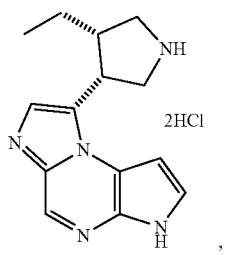

(VIIa)

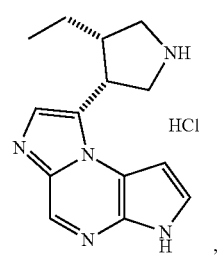

(VIIb)

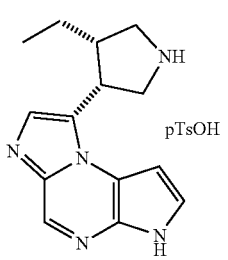

(VIIc)

In some embodiments, any of the processes for preparing (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide that are disclosed herein may further comprise forming one of the solid state forms described herein in Section III.

III. SOLID STATE FORMS

The present disclosure also relates to solid state forms of Compound 1. As with all pharmaceutical compounds and compositions, the chemical and physical properties of Compound 1 are important in its commercial development. These properties include, but are not limited to: (1) packing properties such as molar volume, bulk density and hygroscopicity, (2) thermodynamic properties such as melting temperature, vapor pressure and solubility, (3) kinetic properties such as dissolution rate and stability (including stability at ambient conditions, especially to moisture and under storage conditions), (4) surface properties such as surface area, wettability, interfacial tension and shape, (5) mechanical properties such as hardness, tensile strength, compactibility, handling, flow and blend; and (6) filtration properties. These properties can affect, for example, the processing and storage of the compound and pharmaceutical compositions comprising the compound.

Solid state forms of Compound 1 that improve upon one or more of these properties relative to other solid state forms of the compound are desirable. Isolating pharmaceutically acceptable solid state forms of the compound that can be manufactured and formulated on a commercial-scale has been a challenge.

The Amorphous Freebase form of Compound 1 generally has greater solubility, and increased bioavailability relative to most of the corresponding crystalline forms of the compound. The Amorphous Freebase also has acceptable chemical stability. However, it is hygroscopic, and environmental controls potentially are required to ensure appropriate control of potency and water content during storage, dispensing, and handling of the Amorphous Freebase. In addition, the Amorphous Freebase exhibits an oiling-out limit close to the solubility curve during manufacturing.

Crystalline Hydrochloride Solvate Form AA, crystalline Hydrochloride Solvate Form BB, and crystalline Hydrochloride Solvate Form CC generally convert to an amorphous hydrochloride upon ambient drying. The resulting amorphous hydrochloride is hygroscopic. Yields obtained for each of the crystalline hydrochlorides generally have been low. Hydrochloride Solvate Form AA, Hydrochloride Solvate Form BB, and Hydrochloride Solvate form CC may not be suitable for large scale manufacturing.

The crystalline L-Maleate forms generally may be less chemically stable than the Amorphous Freebase, the Freebase Hydrate Form C, and the Tartrate Hydrate, and may not exhibit pharmaceutically acceptable stability for use as an active ingredient in a pharmaceutical dosage form.

The Tartrate Hydrate form has acceptable chemical stability, high solubility, generally good impurity rejection during isolation and is not hygroscopic. However, the Tartrate Hydrate presented challenges because of lack of physical stability which also impacted manufacturing. The Tartrate Hydrate dehydrated into Amorphous at low relative humidity and high temperature, e.g., <10% RH at 25° C. Shearing and compression potentially cause conversion to the amorphous tartrate, and therefore it is not suitable for compressing into tablet form. Additionally, the filter cake solidified during drying, resulting in the need for additional controls during drying.

Freebase Hydrate Form B has been manufactured on a large scale without the need for labor-intensive and expensive techniques such as spray-drying. It also provided for appropriate control of the bulk properties of the Amorphous Freebase. However, the Amorphous Freebase exhibited poor impurity rejection when isolated via Freebase Hydrate Form B, and required a dry environment for storage and control of relative humidity during manufacturing and packaging.

The Freebase Hydrate Form B was not physically stable. It desolvated (or dehydrated) and converted to the Amorphous Freebase upon drying. Although the Freebase Hydrate Form B generally did not exhibit pharmaceutically acceptable physical stability for use as an active ingredient in a pharmaceutical dosage form, it may be a useful intermediate in the preparation of other solid state forms such as the Amorphous Freebase.

After years of experimentation, Freebase Hydrate Form C was serendipitously discovered when attempting to scale up the Amorphous Freebase. It offers many surprising and superior properties over the Amorphous Freebase, the Tartrate Hydrate and other forms of Compound 1.

Freebase Hydrate Form C generally exhibits excellent chemical stability, physical stability, and solid state properties, including low hygroscopicity and prismatic morphology. Freebase Hydrate Form C has improved bulk properties such as powder flow, bulk density, which are beneficial in the formulation process. In addition, Freebase Hydrate Form C offers at least the following unexpected advantages over the other forms: 1) efficient purification is obtained since there is no need to use the tartrate crystal; 2) the seeding step is straightforward since Freebase Hydrate Form C can be stored at normal conditions; 3) the drying step can be carried out at normal conditions with standard equipment since no dehydration occurs up to around 110° C.; 4) Freebase Hydrate Form C can be crystallized in different particle sizes. Large-scale manufacture of the Freebase Hydrate Form C is relatively straightforward with minimal scaling, good yield, good impurity rejection, fast filtration, conventional drying, and minimal milling issues. In addition, Freebase Hydrate Form C can be grown into different particle sizes.

Freebase Anhydrate Form D can be manufactured only when the water content of the crystallization solvent is low, and will convert to Freebase Hydrate Form C in solutions at high water content. The manufacture of Freebase Anhydrate Form D thus requires strict control of water content. Freebase Anhydrate Form D is slow to crystallize, and difficult to manufacture in higher yield. This anhydrate is reversibly hygroscopic (up to 1.8% water at 90% RH at 25° C.), and is metastable relative to Freebase Hydrate Form C at typical environmental conditions (e.g., above 2.4% RH at 23° C.) used during storage for downstream processing. Freebase Hydrate Form C will convert to Freebase Anhydrate Form D in a solution of ethyl acetate with low water content.

The sections below discuss solid state forms that have been identified and selected properties of those solid state forms.

A. Amorphous Freebase

In one embodiment, the solid state form is amorphous Compound 1 (the "Amorphous Freebase"). In one aspect, the Amorphous Freebase comprises less than about 13% by weight water. In another aspect, the Amorphous Freebase comprises less than about 12% by weight water. In another aspect, the Amorphous Freebase comprises less than about 10% by weight water. In another aspect, the Amorphous Freebase comprises less than about 9% by weight water. In another aspect, the Amorphous Freebase comprises less than about 8% by weight water. In another aspect, the Amorphous Freebase comprises less than about 7% by weight water. In another aspect, the Amorphous Freebase comprises less than about 6% by weight water. In another aspect, the Amorphous Freebase comprises less than about 5% by weight water. In another aspect, the Amorphous Freebase comprises less than about 4% by weight water. In another aspect, the Amorphous Freebase comprises less than about 3% by weight water. In another aspect, the Amorphous Freebase comprises less than about 2% by weight water. In another aspect, the Amorphous Freebase comprises less than about 1% by weight water. In another aspect, the Amorphous Freebase has a glass transition temperature onset at about 119° C. In another aspect, the Amorphous Freebase has a glass transition temperature midpoint at about 122° C. In another aspect, the Amorphous Freebase has a glass transition temperature onset at about 119° C. and a glass transition temperature midpoint at about 122° C. The Amorphous Freebase is further described in the Examples of the application.

The Amorphous Freebase generally has greater solubility, and increased bioavailability, relative to the corresponding crystalline forms of the compound. The Amorphous Freebase also has acceptable chemical stability. For example, when chemical stability was evaluated in closed vials at 30° C./65% relative humidity and 40° C./75% relative humidity over 12 weeks, and at 50° C./75% relative humidity over 6 weeks, no degradation of the Amorphous Freebase was observed in the closed vials under any of those conditions. In addition, the Amorphous Freebase exhibits acceptable stability to light and peroxide. The Amorphous Freebase, however, is hygroscopic and can comprise as much as 12% by weight water at 25° C./90% relative humidity. Environmental controls potentially are required to ensure appropriate control of potency and water content during storage, dispensing, and handling of the Amorphous Freebase.

The Amorphous Freebase can be prepared, for example, using anti-solvent crystallization to prepare the Freebase Solvate Form A or Freebase Hydrate Form B (described below) followed by dehydration or desolvation to yield the Amorphous Freebase. This crystallization/dehydration/desolvation method allows for the large-scale manufacture of the Amorphous Freebase without the need for labor-intensive and expensive techniques such as spray-drying. It also provides for appropriate control of the bulk properties of the Amorphous Freebase (i.e., particle size, flow properties etc.). When the Amorphous Freebase is prepared by desolvation of the Freebase Solvate Form A or dehydration of the Freebase Hydrate Form B, the Amorphous Freebase generally retains the morphology of the Freebase Solvate Form A or Freebase Hydrate Form B (i.e., blades with hexagonal crystal faces when prepared by dehydration of Freebase Hydrate Form B, or irregular when desolvated from Freebase Solvate Form A).

The process volumes required for crystallization during the large-scale manufacture of the Freebase Solvate Form A or Freebase Hydrate Form B generally are within conventional processing volumes, but impurity rejection potentially may be lower than desired. Drying and dehydration/desolvation of the Freebase Hydrate Form B/Freebase Solvate Form A to the Amorphous Freebase generally can be carried out with standard equipment under conventional conditions and the isolated Amorphous Freebase typically can be co-milled without adversely impacting the amorphous state.

B. Crystalline Freebase Solvates and Hydrates

In another embodiment, the solid state form is a crystalline freebase of Compound 1. In one aspect, the crystalline freebase is a solvate. In another aspect, the crystalline freebase is an isopropyl acetate/water solvate (the "Freebase Solvate Form A"). In another aspect, the crystalline freebase is a hydrate (the "Freebase Hydrate Form B"). The Freebase Solvate Form A and the Freebase Hydrate Form B are further described in the Examples of the application.

In one embodiment, the crystalline freebase solvate or hydrate has an X-ray powder diffraction pattern characterized by peaks at 3.1±0.2, 9.3±0.2, and 12.0±0.2 degrees two theta when measured at about 25° C. with monochromatic K$\alpha$1 radiation.

In one embodiment, the crystalline freebase solvate or hydrate has an X-ray powder diffraction pattern characterized by peaks at 3.1±0.2, 9.3±0.2, and 12.0±0.2 degrees two theta, and that is further characterized by a peak at one or more of 13.7±0.2, 20.8±0.2 and 25.0±0.2 degrees two theta when measured at about 25° C. with monochromatic Kα1 radiation.

In one embodiment, the crystalline freebase solvate or hydrate has an X-ray powder diffraction pattern characterized by peaks at 3.1±0.2, 9.3±0.2, 12.0±0.2, and 20.8±0.2 degrees two theta, when measured at about 25° C. with monochromatic Kα1 radiation.

In one embodiment, the crystalline freebase solvate or hydrate has an X-ray powder diffraction pattern characterized by peaks at 3.1±0.2, 9.3±0.2, 12.0±0.2, and 25.0±0.2 degrees two theta, when measured at about 25° C. with monochromatic Kα1 radiation.

In one embodiment, the crystalline freebase solvate or hydrate has an X-ray powder diffraction pattern characterized by peaks at 3.1±0.2, 9.3±0.2, 12.0±0.2, 20.8±0.2, and 25.0±0.2 degrees two theta, when measured at about 25° C. with monochromatic Kα1 radiation.

In one embodiment, the crystalline freebase solvate or hydrate has an X-ray powder diffraction pattern characterized by peaks at 3.1±0.2, 9.3±0.2, 12.0±0.2, 13.7±0.2, 20.8±0.2, and 25.0±0.2 degrees two theta when measured at about 25° C. with monochromatic Kα1 radiation.

In one embodiment, the crystalline freebase solvate or hydrate has an X-ray powder diffraction pattern without a significant peak at one or more of 15.1±0.2, and 21.7±0.2 degrees two theta when measured at about 25° C. with monochromatic Kα1 radiation.

In one embodiment, the crystalline freebase solvate or hydrate has an X-ray powder diffraction pattern without a significant peak at one or more of 3.9±0.2, 6.8±0.2, and 14.1±0.2 degrees two theta when measured at about 25° C. with monochromatic Kα1 radiation.

In one embodiment, the crystalline freebase solvate or hydrate has an X-ray powder diffraction pattern without a significant peak at one or more of 15.1±0.2, and 21.7±0.2 degrees two theta, and without a significant peak at one or more of 3.9±0.2, 6.8±0.2, and 14.1 t 0.2 degrees two theta, when measured at about 25° C. with monochromatic Kα1 radiation.

In one embodiment, the crystalline freebase solvate or hydrate has an X-ray powder diffraction pattern characterized by peaks at 3.1±0.2, 9.3±0.2, and 12.0±0.2 degrees two theta, and without a significant peak at one or more of 15.1±0.2, and 21.7±0.2 degrees two theta, when measured at about 25° C. with monochromatic Kα1 radiation.

In one embodiment, the crystalline freebase solvate or hydrate has an X-ray powder diffraction pattern characterized by peaks at 3.1±0.2, 9.3±0.2, and 12.0±0.2 degrees two theta, and without a significant peak at one or more of 3.9±0.2, 6.8±0.2, and 14.1±0.2 degrees two theta, when measured at about 25° C. with monochromatic Kα1 radiation.

In one embodiment, the crystalline freebase solvate or hydrate has an X-ray powder diffraction pattern characterized by peaks at 3.1±0.2, 9.3±0.2, and 12.0±0.2 degrees two theta, and without a significant peak at one or more of 15.1±0.2, and 21.7±0.2 degrees two theta, and without a significant peak at one or more of 3.9±0.2, 6.8±0.2, and 14.1±0.2 degrees two theta, when measured at about 25° C. with monochromatic Kα1 radiation.

In one embodiment, the crystalline freebase solvate or hydrate has an X-ray powder diffraction pattern characterized by peaks at 3.1±0.2, 9.3±0.2, and 12.0±0.2, 13.7±0.2, 20.8±0.2, and 25.0±0.2 degrees two theta, and without a significant peak at one or more of 15.1±0.2, and 21.7±0.2 degrees two theta, when measured at about 25° C. with monochromatic Kα1 radiation.

In one embodiment, the crystalline freebase solvate or hydrate has an X-ray powder diffraction pattern characterized by peaks at 3.1±0.2, 9.3±0.2, and 12.0±0.2, 13.7±0.2, 20.8±0.2, and 25.0±0.2 degrees two theta, and without a significant peak at one or more of 3.9±0.2, 6.8±0.2, and 14.1±0.2 degrees two theta, when measured at about 25° C. with monochromatic Kα1 radiation.

In one embodiment, the crystalline freebase solvate or hydrate has an X-ray powder diffraction pattern characterized by peaks at 3.1±0.2, 9.3±0.2, and 12.0±0.2, 13.7±0.2; 20.8±0.2, and 25.0±0.2 degrees two theta, and without a significant peak at one or more of 15.1±0.2, and 21.7±0.2 degrees two theta, and without a significant peak at one or more of 3.9±0.2, 6.8±0.2, and 14.1±0.2 degrees two theta, when measured at about 25° C. with monochromatic Kα1 radiation.

In one embodiment, the crystalline freebase solvate or hydrate has an X-ray powder diffraction pattern characterized by peaks substantially at the positions listed in Table 16-A ±0.2 degrees two theta, when measured at about 25° C. with monochromatic Kα1 radiation.

In one embodiment, the crystalline freebase solvate or hydrate has an X-ray powder diffraction pattern characterized by peaks substantially at the positions listed in Table 16-B ±0.2 degrees two theta, when measured at about 25° C. with monochromatic Kα1 radiation.

In one embodiment, the crystalline freebase solvate or hydrate has an X-ray powder diffraction pattern characterized by peaks substantially at the positions listed in Table 16-B ±0.2 degrees two theta that have a relative intensity of at least 10.0%, when measured at about 25° C. with monochromatic Kα1 radiation.

In further aspects of each of the above embodiments, the significant peak values have a variation of ±0.1 degrees two theta rather than ±0.2 degrees two theta. In still further aspects of each of the above embodiments, the significant peak values have a variation of ±0.05 degrees two theta rather than ±0.2 degrees two theta.

Figure 3A:
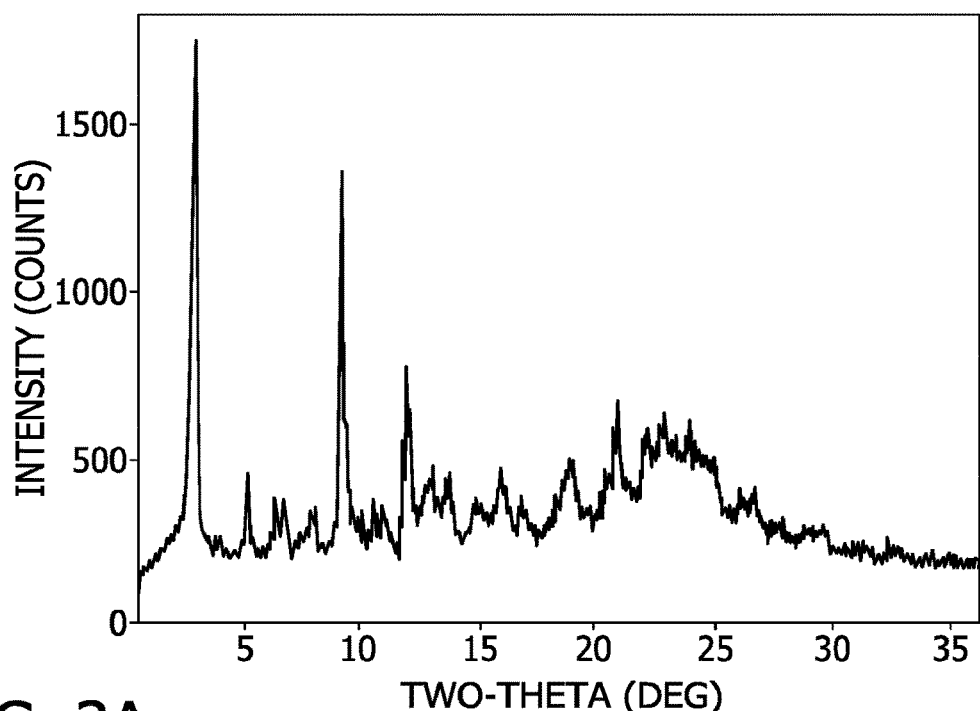
FIG. 3A is a powder X-ray diffraction pattern corresponding to the Freebase Solvate Form A (Isopropyl Acetate/Water Solvate).
Figure 3B:
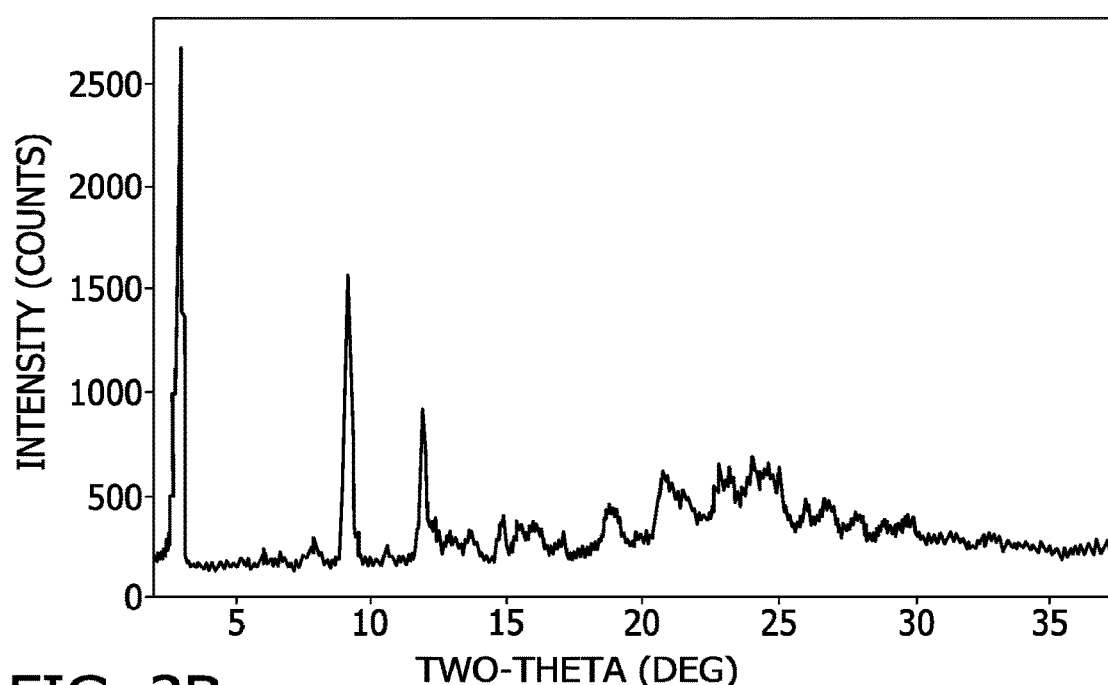
FIG. 3B is a powder X-ray diffraction pattern corresponding to the Freebase Hydrate Form B.

In one embodiment, the crystalline freebase has an X-ray powder diffraction pattern substantially as shown in FIG. 3B.

In one embodiment, the crystalline freebase has a thermogravimetric analysis profile showing a weight loss of about 5% to about 6% between about 100° C. and about 160° C. when heated at a rate of 10° C./minute.

Figure 4A:
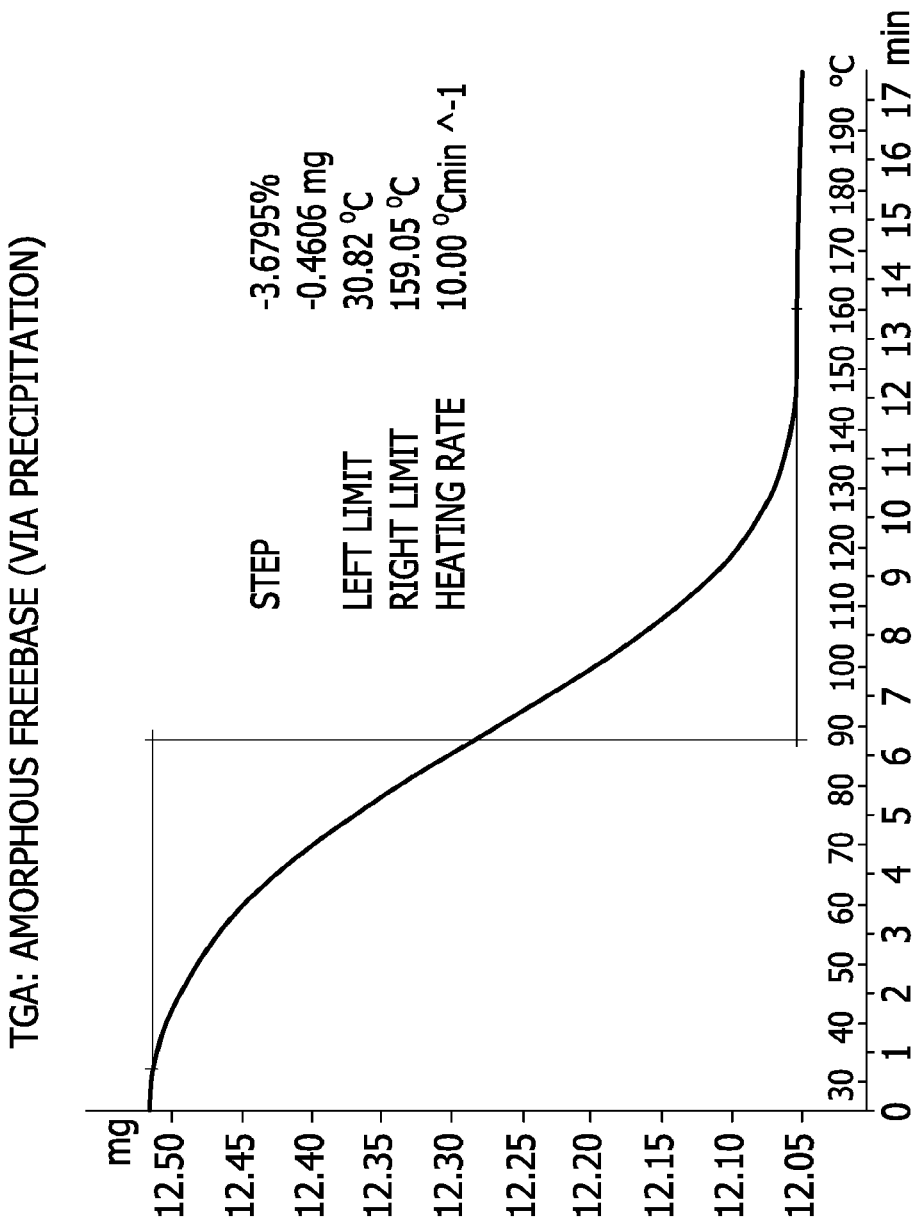
FIGS. 4A and 4B are thermogravimetric analysis thermograms corresponding to the Amorphous Freebase (via precipitation) and the Amorphous Freebase (via dehydration), respectively.
Figure 4B:
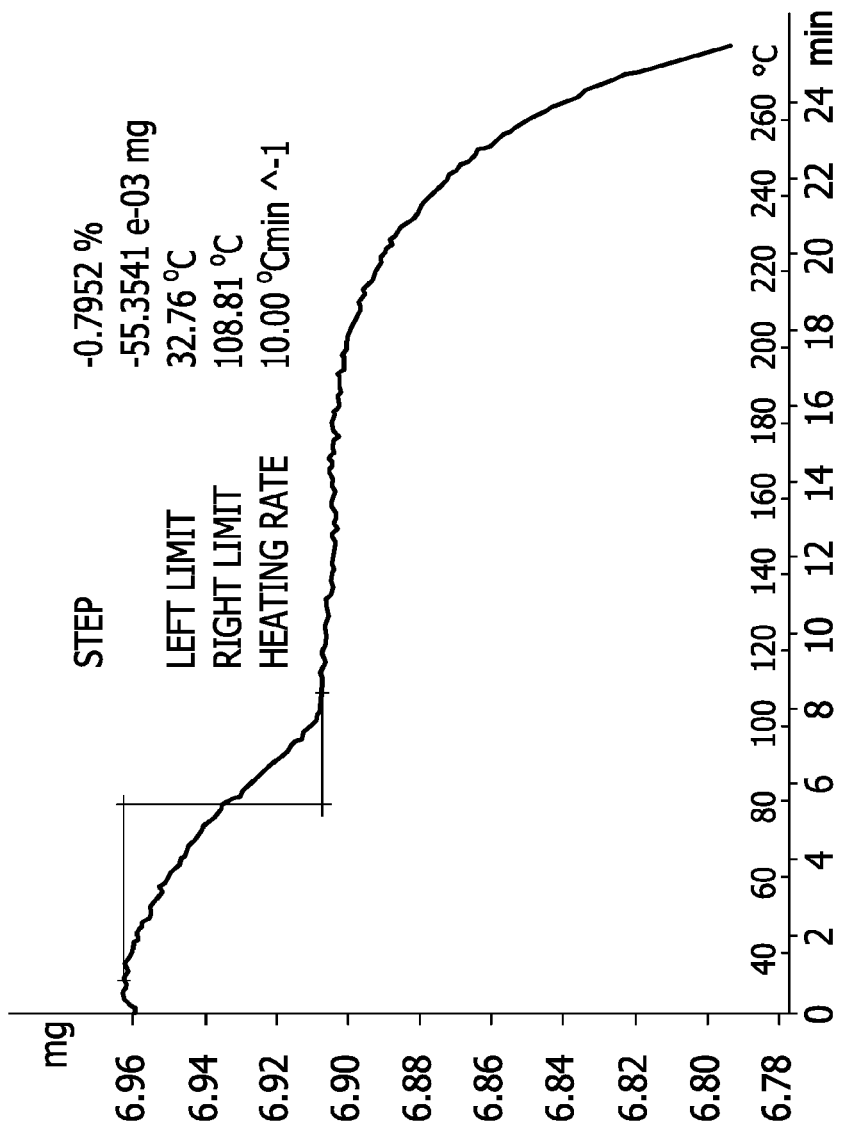
Figure 4C:
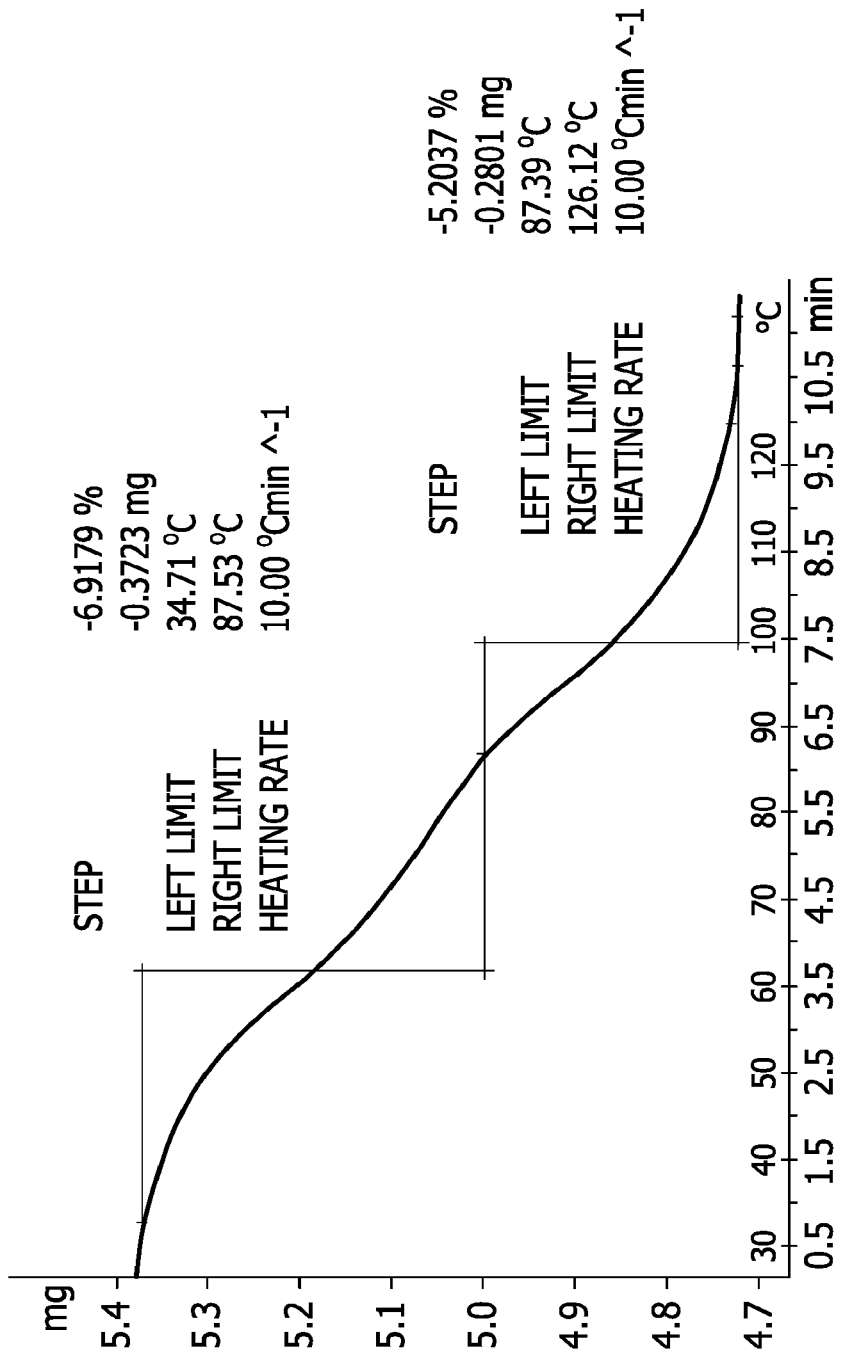
FIG. 4C is a thermogravimetric analysis thermogram corresponding to the Freebase Solvate Form A.
Figure 4D:
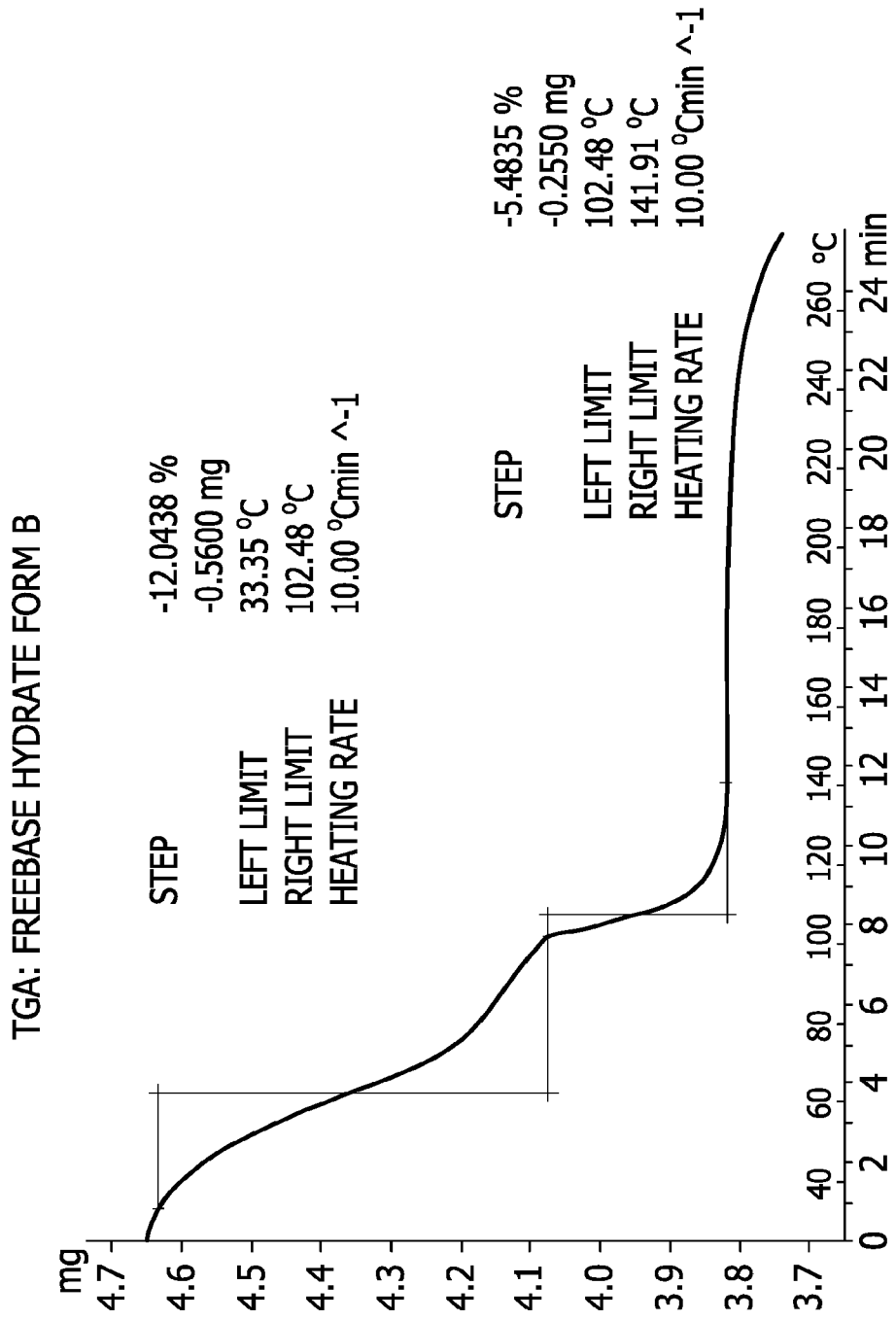
FIG. 4D is a thermogravimetric analysis thermogram corresponding to the Freebase Hydrate Form B.

In one embodiment, the crystalline freebase has a thermogravimetric analysis profile substantially as shown in FIG. 4D.

In one embodiment, the crystalline freebase has a differential scanning calorimetry profile comprising a first endotherm between about 25° C. to about 100° C. when heated at a rate of 10° C./minute.

In one embodiment, the crystalline freebase has a differential scanning calorimetry profile comprising a first endotherm between about 59.90° C. to about 98.79° C. when heated at a rate of 10° C./minute.

In one embodiment, the crystalline freebase has a differential scanning calorimetry profile comprising a second endotherm between about 100° C. to about 160° C. when heated at a rate of 10° C./minute.

In one embodiment, the crystalline freebase has a differential scanning calorimetry profile comprising a second endotherm between about 109.31° C. to about 132.94° C. when heated at a rate of 10° C./minute.

In one embodiment, the crystalline freebase has a differential scanning calorimetry profile comprising a first endotherm between about 25° C. to about 100° C., and a second endotherm between about 100° C. to about 160° C., when heated at a rate of 10° C./minute.

Figure 5A:
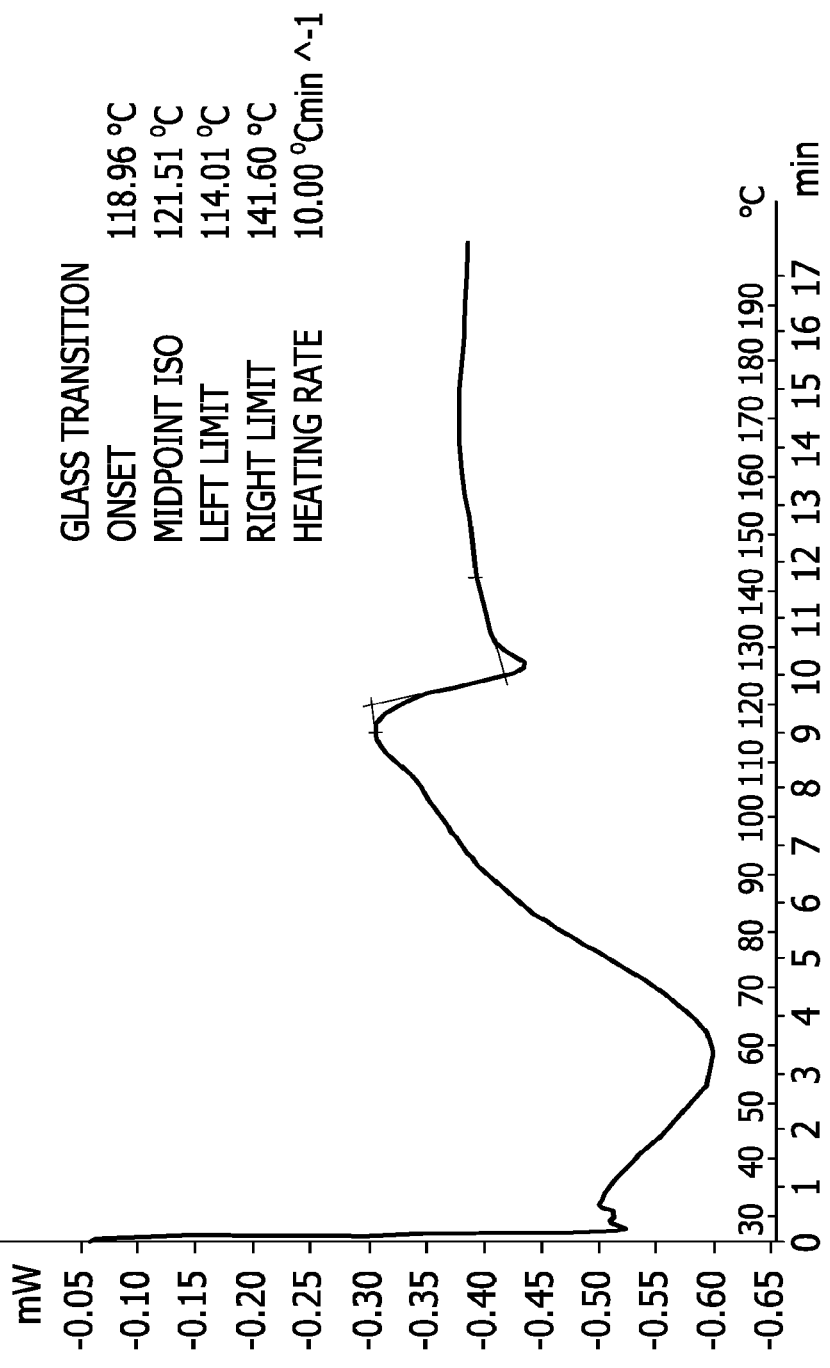
FIG. 5A is a differential scanning calorimetry thermogram corresponding to the Amorphous Freebase (via dehydration).
Figure 5B:
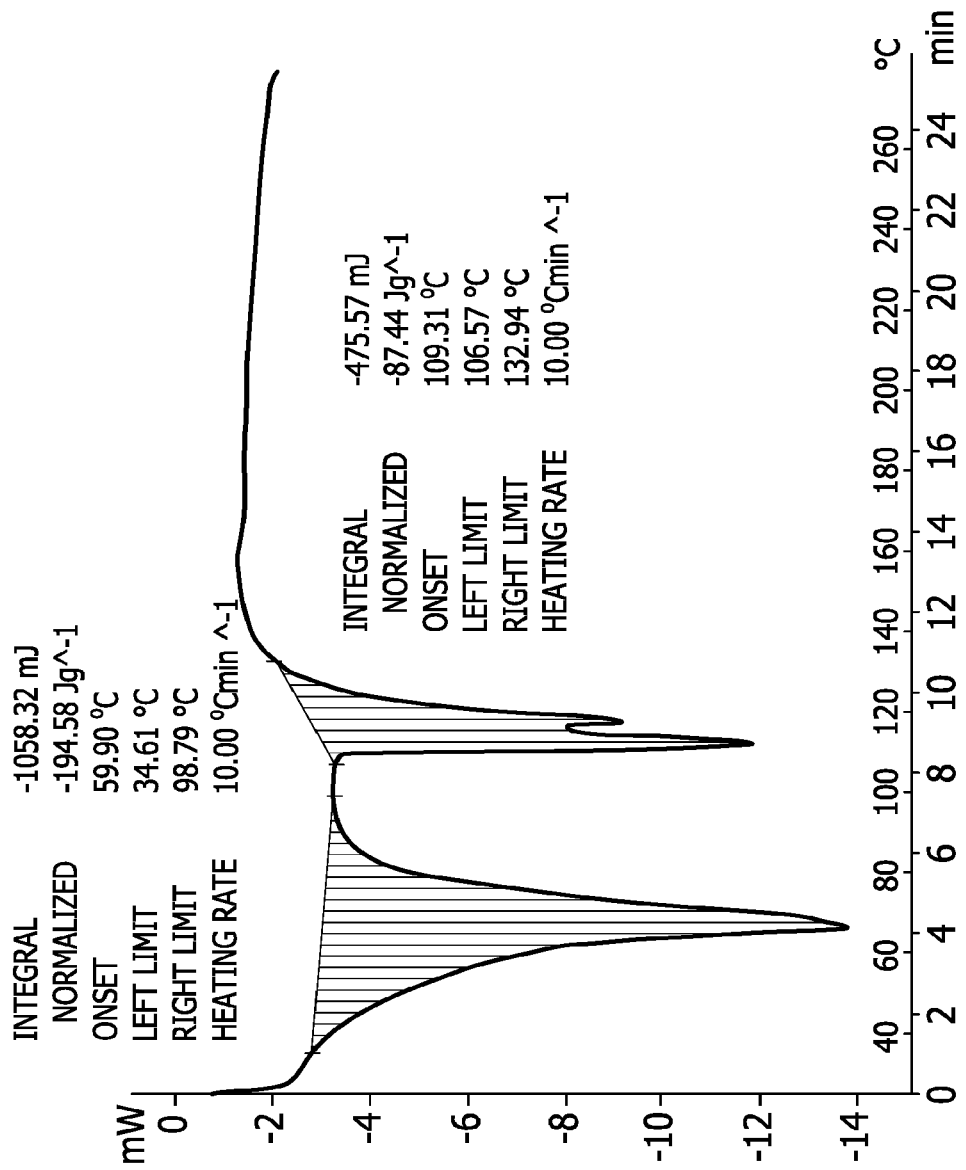
FIG. 5B is a differential scanning calorimetry thermogram corresponding to the Freebase Hydrate Form B.

In one embodiment, the crystalline freebase has a differential scanning calorimetry profile substantially as shown in FIG. 5B.

In one embodiment, the crystalline freebase has a thermogravimetric analysis profile showing a weight loss of about 5% to about 6% between about 100° C. and about 160° C. when heated at a rate of 10° C./minute; and a differential scanning calorimetry profile comprising a first endotherm between about 25° C. to about 100° C. and/or a second endotherm between about 100° C. to about 160° C., when heated at a rate of 10° C./minute. In one aspect, the differential scanning calorimetry profile comprises a first endotherm between about 25° C. to about 100° C. when heated at a rate of 10° C./minute. In another aspect, the differential scanning calorimetry profile comprises a second endotherm between about 100° C. to about 160° C. when heated at a rate of 10° C./minute. In another aspect, the differential scanning calorimetry profile comprises a first endotherm between about 25° C. to about 100° C., and a second endotherm between about 100° C. to about 160° C., when heated at a rate of 10° C./minute.

In one embodiment, the crystalline freebase has a thermogravimetric analysis profile showing a weight loss of about 5% to about 6% between about 100° C. and about 160° C. when heated at a rate of 10° C./minute; and a differential scanning calorimetry profile comprising a first endotherm between about 59.90° C. to about 98.79° C. and/or a second endotherm between about 109.31° C. to about 132.94° C., when heated at a rate of 10° C./minute. In one aspect, the differential scanning calorimetry profile comprises a first endotherm between about 59.90° C. to about 98.79° C. when heated at a rate of 10° C./minute. In another aspect, the differential scanning calorimetry profile comprises a second endotherm between about 109.31° C. to about 132.94° C. when heated at a rate of 10° C./minute. In another aspect, the differential scanning calorimetry profile comprises a first endotherm between about 59.90° C. to about 98.79° C., and a second endotherm between about 109.31° C. to about 132.94° C., when heated at a rate of 10° C./minute.

In one embodiment, the crystalline freebase has an X-ray diffraction pattern as previously described above, and further has at least one of the following: (a) a thermogravimetric analysis profile showing a weight loss of about 5% to about 6% between about 100° C. and about 160° C. when heated at a rate of 10° C./minute; and (b) a differential scanning calorimetry profile comprising a first endotherm between about 25° C. to about 100° C., and/or a second endotherm between about 100° C. to about 160° C., when heated at a rate of 10° C./minute. In one aspect, the differential scanning calorimetry profile comprises a first endotherm between about 25° C. to about 100° C. when heated at a rate of 10° C./minute. In another aspect, the differential scanning calorimetry profile comprises a second endotherm between about 100° C. to about 160° C. when heated at a rate of 10° C./minute. In another aspect, the differential scanning calorimetry profile comprises a first endotherm between about 25° C. to about 100° C., and a second endotherm between about 100° C. to about 160° C., when heated at a rate of 10° C./minute.

In one embodiment, the crystalline freebase has an X-ray diffraction pattern as previously described above, and further has a thermogravimetric analysis profile showing a weight loss of about 5% to about 6% between about 100° C. and about 160° C. when heated at a rate of 10° C./minute.

In one embodiment, the crystalline freebase has an X-ray diffraction pattern as previously described above, and further has a differential scanning calorimetry profile comprising a first endotherm between about 25° C. to about 100° C., and/or a second endotherm between about 100° C. to about 160° C., when heated at a rate of 10° C./minute. In one aspect, the differential scanning calorimetry profile comprises a first endotherm between about 25° C. to about 100° C. when heated at a rate of 10° C./minute. In another aspect, the differential scanning calorimetry profile comprises a second endotherm between about 100° C. to about 160° C. when heated at a rate of 10° C./minute. In another aspect, the differential scanning calorimetry profile comprises a first endotherm between about 25° C. to about 100° C., and a second endotherm between about 100° C. to about 160° C., when heated at a rate of 10° C./minute.

In one embodiment, the crystalline freebase has an X-ray diffraction pattern as previously described above; a thermogravimetric analysis profile showing a weight loss of about 5% to about 6% between about 100° C. and about 160° C. when heated at a rate of 10° C./minute; and a differential scanning calorimetry profile comprising a first endotherm between about 25° C. to about 100° C., and/or a second endotherm between about 100° C. to about 160° C., when heated at a rate of 10° C./minute. In one aspect, the differential scanning calorimetry profile comprises a first endotherm between about 25° C. to about 100° C. when heated at a rate of 10° C./minute. In another aspect, the differential scanning calorimetry profile comprises a second endotherm between about 100° C. to about 160° C. when heated at a rate of 10° C./minute. In another aspect, the differential scanning calorimetry profile comprises a first endotherm between about 25° C. to about 100° C., and a second endotherm between about 100° C. to about 160° C., when heated at a rate of 10° C./minute.

The Freebase Solvate Form A and Freebase Hydrate Form B are not physically stable. As discussed above, they desolvate (or dehydrate) and convert to the Amorphous Freebase upon drying. Although the Freebase Solvate Form A and Freebase Hydrate Form B generally do not exhibit pharmaceutically acceptable physical stability for use as an active ingredient in a pharmaceutical dosage form, they are useful intermediates in the preparation of other solid state forms such as the Amorphous Freebase.

C. Crystalline Freebase Hydrate Form C (Hemihydrate)

In another embodiment, the solid state form is a crystalline hydrate, wherein the crystalline hydrate is a hemihydrate. In another embodiment, the solid state form is crystalline hemihydrate of Compound 1 having a powder X-ray diffraction pattern corresponding to Freebase Hydrate Form C. The Freebase Hydrate Form C is further described in the Examples of the application.

In one embodiment, the Freebase Hydrate Form C has an X-ray powder diffraction pattern characterized by peaks at 13.4±0.2, 15.1±0.2, and 21.7±0.2 degrees two theta when measured at about 25° C. with monochromatic Kα1 radiation.

In one embodiment, the Freebase Hydrate Form C has an X-ray powder diffraction pattern characterized by peaks at 13.4±0.2, 15.1±0.2, and 21.7±0.2 degrees two theta, and that is further characterized by a peak at one or more of 7.7±0.2, 7.9±0.2, 9.6±0.2, 10.3±0.2, 13.9±0.2, 15.5±0.2, 15.9±0.2, 17.0±0.2, 17.2±0.2, 17.8±0.2, 18.1±0.2, 18.3±0.2, 19.3±0.2, 19.7±0.2, 20.5±0.2, 20.9±0.2, 21.9±0.2, 22.2±0.2, 23.5±0.2, 24.4±0.2, 24.9±0.2, 28.2±0.2, and 29.5±0.2 degrees two theta when measured at about 25° C. with monochromatic Kα1 radiation.

In one embodiment, the Freebase Hydrate Form C has an X-ray powder diffraction pattern that is characterized by peaks at 13.4±0.2, 15.1±0.2, 15.5±0.2, and 21.7±0.2 degrees two theta when measured at about 25° C. with monochromatic Kα1 radiation.

In one embodiment, the Freebase Hydrate Form C has an X-ray powder diffraction pattern that is characterized by peaks at 13.4±0.2, 15.1±0.2, 17.0±0.2, and 21.7±0.2 degrees two theta when measured at about 25° C. with monochromatic Kα1 radiation.

In one embodiment, the Freebase Hydrate Form C has an X-ray powder diffraction pattern that is characterized by peaks at 13.4±0.2, 15.1±0.2, 20.9±0.2, and 21.7±0.2 degrees two theta when measured at about 25° C. with monochromatic Kα1 radiation.

In one embodiment, the Freebase Hydrate Form C has an X-ray powder diffraction pattern that is characterized by peaks at 13.4±0.2, 15.1±0.2, 15.5±0.2, 17.0±0.2, 20.9±0.2, and 21.7±0.2 degrees two theta when measured at about 25° C. with monochromatic Kα1 radiation.

In one embodiment, the Freebase Hydrate Form C has an X-ray powder diffraction pattern characterized by peaks at 15.5±0.2, 13.4±0.2, 15.1±0.2, 19.3±0.2, 20.5±0.2, and 21.7±0.2 degrees two theta when measured at about 25° C. with monochromatic Kα1 radiation.

In one embodiment, the Freebase Hydrate Form C has an X-ray powder diffraction pattern without a significant peak at one or more of 3.1±0.2, 9.3±0.2, and 12.0±0.2 degrees two theta, when measured at about 25° C. with monochromatic Kα1 radiation.

In one embodiment, the Freebase Hydrate Form C has an X-ray powder diffraction pattern without a significant peak at one or more of 3.9±0.2, 6.8±0.2, and 14.1±0.2 degrees two theta, when measured at about 25° C. with monochromatic Kα1 radiation.

In one embodiment, the Freebase Hydrate Form C has an X-ray powder diffraction pattern without a significant peak at one or more of 3.1±0.2, 9.3±0.2, and 12.0±0.2 degrees two theta, and without a significant peak at one or more of 3.9±0.2, 6.8±0.2, and 14.1±0.2 degrees two theta, when measured at about 25° C. with monochromatic Kα1 radiation.

In one embodiment, the Freebase Hydrate Form C has an X-ray powder diffraction pattern characterized by peaks at 13.4±0.2, 15.1±0.2, and 21.7±0.2 degrees two theta, and without a significant peak at one or more of 3.1±0.2, 9.3±0.2, and 12.0±0.2 degrees two theta, when measured at about 25° C. with monochromatic Kα1 radiation.

In one embodiment, the Freebase Hydrate Form C has an X-ray powder diffraction pattern characterized by peaks at 13.4±0.2, 15.1±0.2, and 21.7±0.2 degrees two theta, and without a significant peak at one or more of 3.9±0.2, 6.8±0.2, and 14.1±0.2 degrees two theta, when measured at about 25° C. with monochromatic Kα1 radiation.

In one embodiment, the Freebase Hydrate Form C has an X-ray powder diffraction pattern characterized by peaks at 13.4±0.2, 15.1±0.2, and 21.7±0.2 degrees two theta, and without a significant peak at one or more of 3.1±0.2, 9.3±0.2, and 12.0±0.2 degrees two theta, and without a significant peak at one or more of 3.9±0.2, 6.8±0.2, and 14.1±0.2 degrees two theta, when measured at about 25° C. with monochromatic Kα1 radiation.

In one embodiment, the Freebase Hydrate Form C has an X-ray powder diffraction pattern characterized by peaks at 15.5±0.2, 13.4±0.2, 15.1±0.2, 19.3±0.2, 20.5±0.2, and 21.7±0.2 degrees two theta, and without a significant peak at one or more of 3.1±0.2, 9.3±0.2, and 12.0±0.2 degrees two theta, when measured at about 25° C. with monochromatic Kα1 radiation.

In one embodiment, the Freebase Hydrate Form C has an X-ray powder diffraction pattern characterized by peaks at 15.5±0.2, 13.4±0.2, 15.1±0.2, 19.3±0.2, 20.5±0.2, and 21.7±0.2 degrees two theta, and without a significant peak at one or more of 3.9±0.2, 6.8±0.2, and 14.1±0.2 degrees two theta, when measured at about 25° C. with monochromatic Kα1 radiation.

In one embodiment, the Freebase Hydrate Form C has an X-ray powder diffraction pattern characterized by peaks at 15.5±0.2, 13.4±0.2, 15.1±0.2, 19.3±0.2, 20.5±0.2, and 21.7±0.2 degrees two theta, and without a significant peak at one or more of 3.1±0.2, 9.3±0.2, and 12.0±0.2 degrees two theta, and without a significant peak at one or more of 3.9±0.2, 6.8±0.2, and 14.1±0.2 degrees two theta, when measured at about 25° C. with monochromatic Kα1 radiation.

In one embodiment, the Freebase Hydrate Form C has an X-ray powder diffraction pattern characterized by peaks substantially at the positions listed in Table 16-C ±0.2 degrees two theta, when measured at about 25° C. with monochromatic Kα1 radiation.

In one embodiment, the Freebase Hydrate Form C has an X-ray powder diffraction pattern characterized by peaks substantially at the positions listed in Table 16-C ±0.2 degrees two theta that have a relative intensity of at least 10.0%, when measured at about 25° C. with monochromatic Kα1 radiation.

In further aspects of each of the above embodiments, the significant peak values have a variation oft 0.1 degrees two theta rather than ±0.2 degrees two theta. In still further aspects of each of the above embodiments, the significant peak values have a variation of ±0.05 degrees two theta rather than ±0.2 degrees two theta.

Figure 3C:
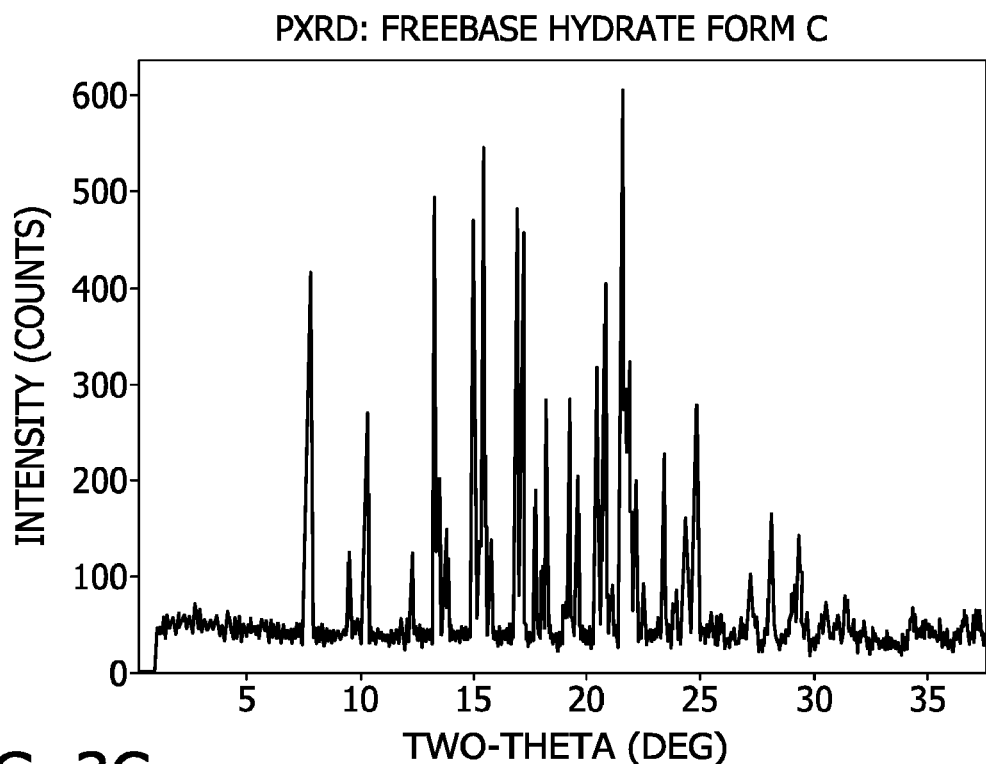
FIG. 3C is a powder X-ray diffraction pattern corresponding to the Freebase Hydrate Form C.

In one embodiment, the Freebase Hydrate Form C has an X-ray powder diffraction pattern substantially as shown in FIG. 3C when measured at about 25° C. with monochromatic Kα1 radiation.

In one embodiment, the Freebase Hydrate Form C has a thermogravimetric analysis profile showing a weight loss of about 2.3% to about 2.6% between about 120° C. and 160° C. when heated at a rate of 10° C./minute.

In one embodiment, the Freebase Hydrate Form C has a thermogravimetric analysis profile showing a weight loss of about 2.3% to about 2.6% between about 114.52° C. and 168.15° C. when heated at a rate of 10° C./minute.

Figure 4E:
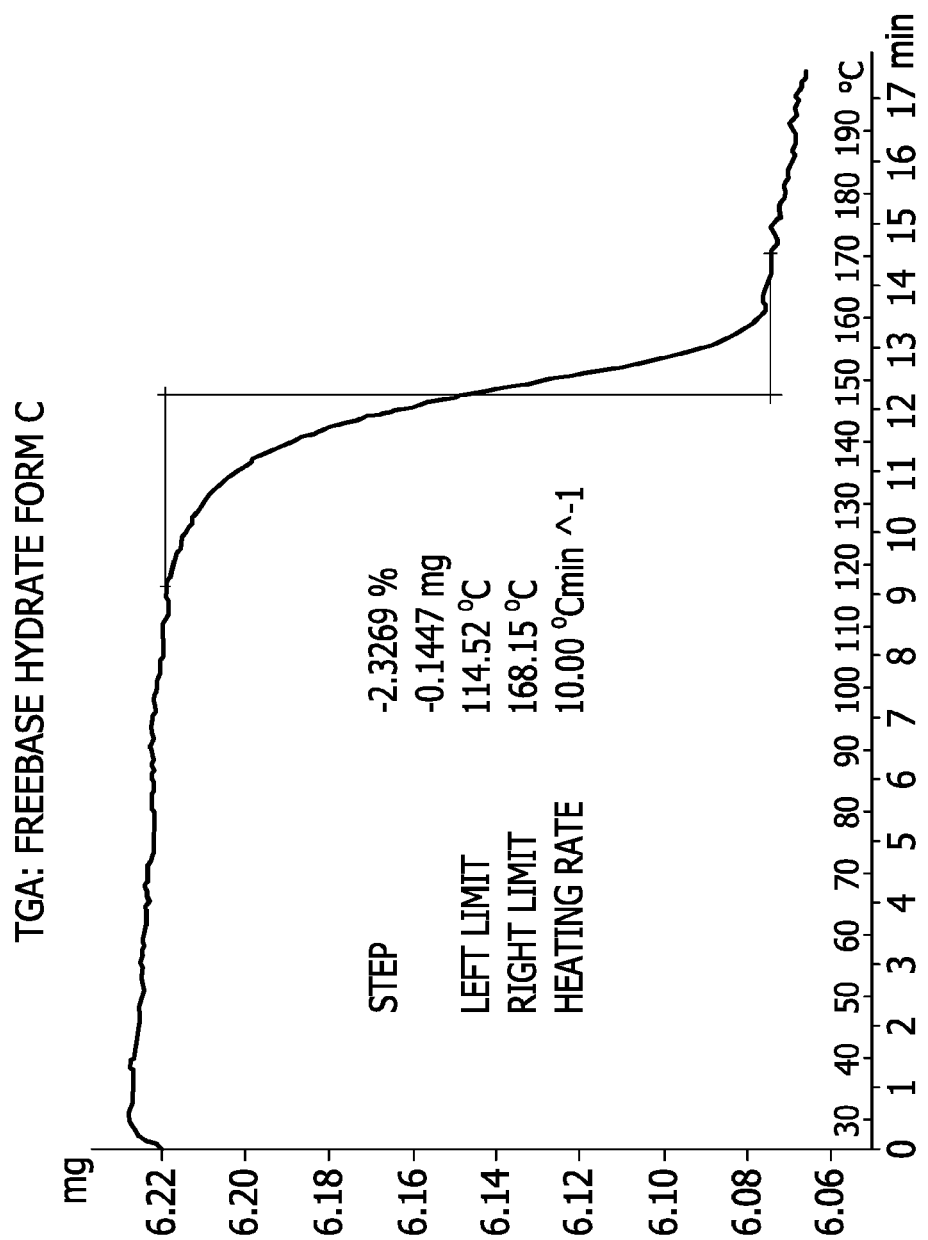
FIG. 4E is a thermogravimetric analysis thermogram corresponding to the Freebase Hydrate Form C.

In one embodiment, the Freebase Hydrate Form C has a thermogravimetric analysis profile substantially as shown in FIG. 4E.

In one embodiment, the Freebase Hydrate Form C has a differential scanning calorimetry profile comprising an endotherm between about 120° C. and about 170° C. when heated at a rate of 10° C./minute.

In one embodiment, the Freebase Hydrate Form C has a differential scanning calorimetry profile comprising an endotherm between about 134.70° C. and about 167.53° C. when heated at a rate of 10° C./minute.

Figure 5C:
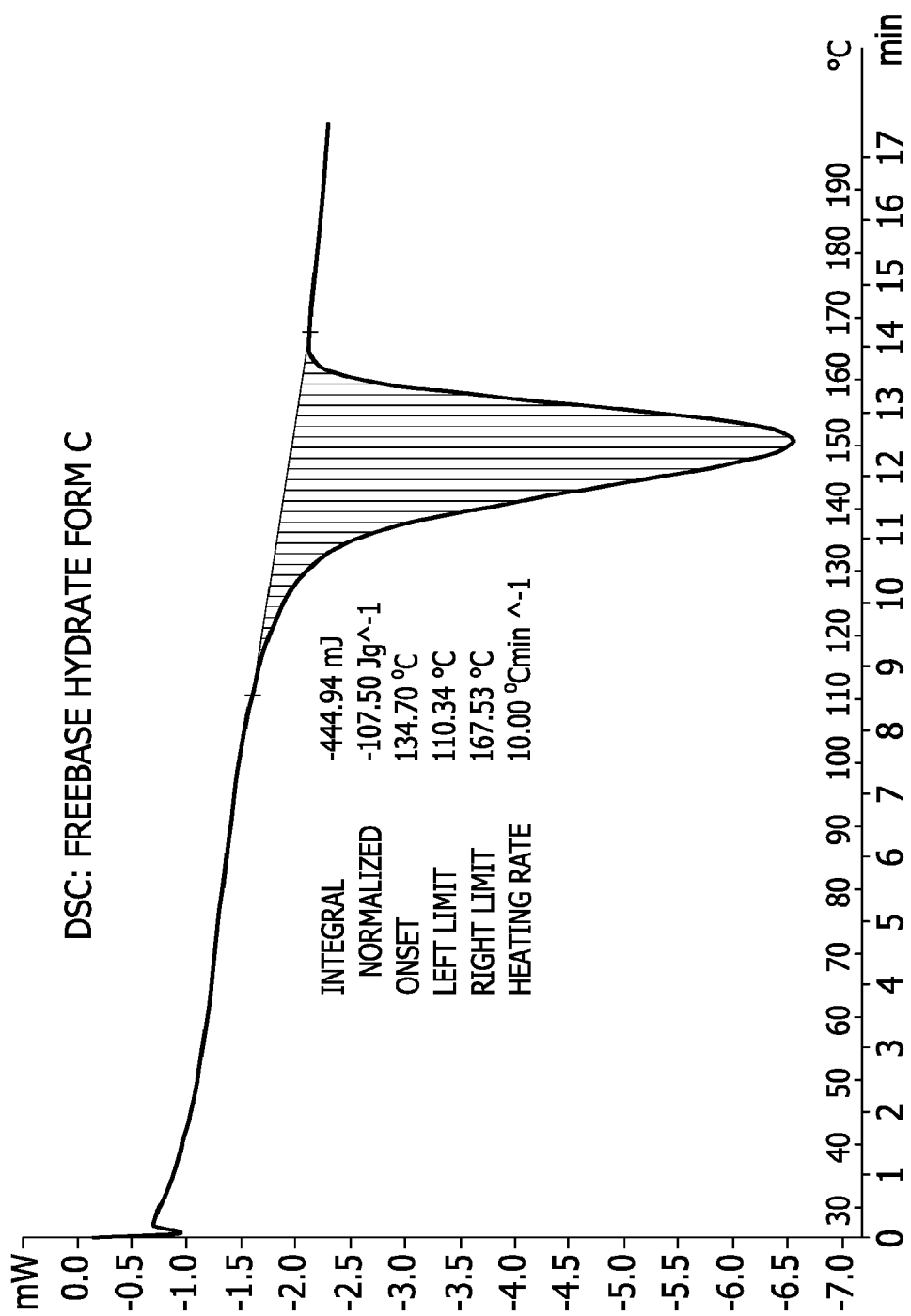
FIG. 5C is a differential scanning calorimetry thermogram corresponding to the Freebase Hydrate Form C.

In one embodiment, the Freebase Hydrate Form C has a differential scanning calorimetry profile substantially as shown in FIG. 5C.

In one embodiment, the Freebase Hydrate Form C has a moisture sorption isotherm profile showing a weight gain of about 0% to about 0.2% when relative humidity is increased from about 0% relative humidity to about 90% relative humidity at a temperature of 25° C.

Figure 6A:
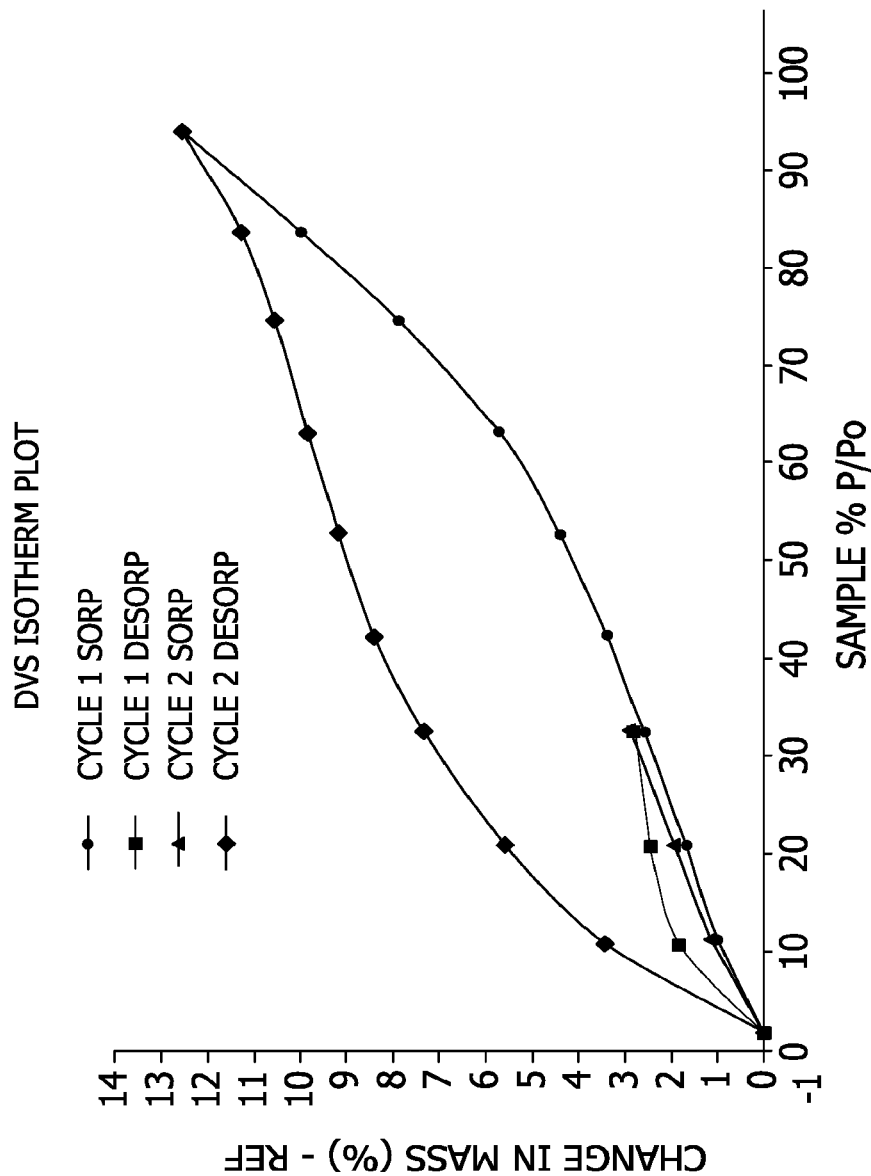
FIG. 6A is a moisture sorption isotherm corresponding to the Amorphous Freebase (via dehydration).
Figure 6B:
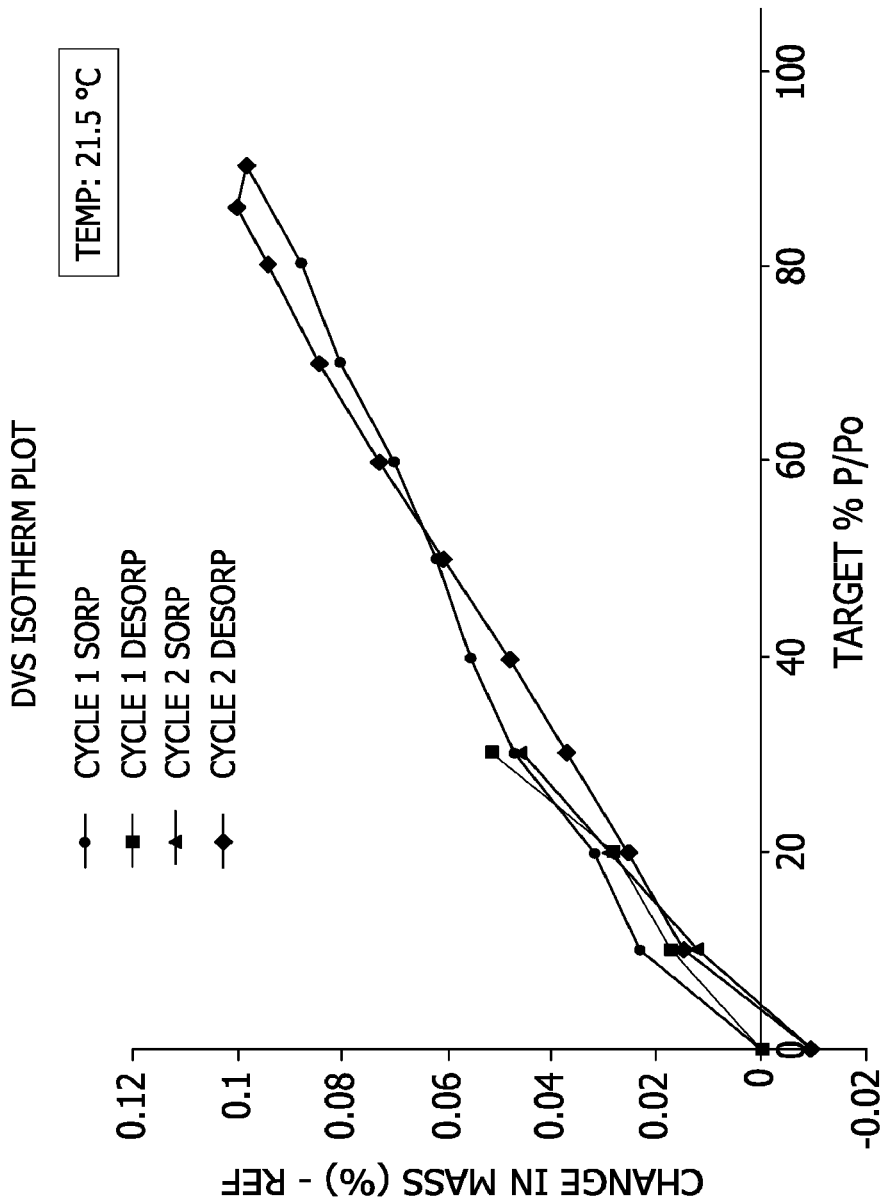
FIG. 6B is a moisture sorption isotherm corresponding to the Freebase Hydrate Form C.

In one embodiment, the Freebase Hydrate Form C has a moisture sorption isotherm profile substantially as shown in FIG. 6B.

In one embodiment, the Freebase Hydrate Form C has a thermogravimetric analysis profile showing a weight loss of about 2.3% to about 2.6% between about 120° C. and 160° C. when heated at a rate of 10° C./minute; and a differential scanning calorimetry profile comprising an endotherm between about 120 and about 170° C. when heated at a rate of 10° C./minute.

In one embodiment, the Freebase Hydrate Form C has a thermogravimetric analysis profile showing a weight loss of about 2.3% to about 2.6% between about 120° C. and 160° C. when heated at a rate of 10° C./minute; and a moisture sorption isotherm profile showing a weight gain of about 0% to about 0.2% when relative humidity is increased from about 0% relative humidity to about 90% relative humidity at a temperature of 25° C.

In one embodiment, the Freebase Hydrate Form C has a differential scanning calorimetry profile comprising an endotherm between about 120 and about 170° C. when heated at a rate of 10° C./minute; and a moisture sorption isotherm profile showing a weight gain of about 0% to about 0.2% when relative humidity is increased from about 0% relative humidity to about 90% relative humidity at a temperature of 25° C.

In one embodiment, the Freebase Hydrate Form C has a thermogravimetric analysis profile showing a weight loss of about 2.3% to about 2.6% between about 120° C. and 160° C. when heated at a rate of 10° C./minute; a differential scanning calorimetry profile comprising an endotherm between about 120 and about 170° C. when heated at a rate of 10° C./minute; and a moisture sorption isotherm profile showing a weight gain of about 0% to about 0.2% when relative humidity is increased from about 0% relative humidity to about 90% relative humidity at a temperature of 25° C.

In one embodiment, the Freebase Hydrate Form C has a thermogravimetric analysis profile showing a weight loss of about 2.3% to about 2.6% between about 120° C. and 160° C. when heated at a rate of 10° C./minute; a differential scanning calorimetry profile comprising an endotherm between about 134.70 and about 167.53° C. when heated at a rate of 10° C./minute; and a moisture sorption isotherm profile showing a weight gain of about 0% to about 0.2% when relative humidity is increased from about 0% relative humidity to about 90% relative humidity at a temperature of 25° C.

In one embodiment, the Freebase Hydrate Form C has an orthorhombic lattice type.

In one embodiment, the Freebase Hydrate Form C has a P212121 space group.

In one embodiment, the Freebase Hydrate Form C has unit cell a, b and c values of about 12.7 Å, about 13.1 Å, and about 22.6 Å, respectively.

In one embodiment, the Freebase Hydrate Form C has an X-ray diffraction pattern as previously described above, and at least one of the following: (a) a thermogravimetric analysis profile showing a weight loss of about 2.3% to about 2.6% between about 120° C. and 160° C. when heated at a rate of 10° C./minute; (b) a differential scanning calorimetry profile comprising an endotherm between about 120 and about 170° C. when heated at a rate of 10° C./minute; and/or (c) a moisture sorption isotherm profile showing a weight gain of about 0% to about 0.2% when relative humidity is increased from about 0% relative humidity to about 90% relative humidity at a temperature of 25° C.

In one embodiment, the Freebase Hydrate Form C has an X-ray diffraction pattern as previously described above, and a thermogravimetric analysis profile showing a weight loss of about 2.3% to about 2.6% between about 120° C. and 160° C. when heated at a rate of 10° C./minute.

In one embodiment, the Freebase Hydrate Form C has an X-ray diffraction pattern as previously described above, and a differential scanning calorimetry profile comprising an endotherm between about 120 and about 170° C. when heated at a rate of 10° C./minute.

In one embodiment, the Freebase Hydrate Form C has an X-ray diffraction pattern as previously described above, and a moisture sorption isotherm profile showing a weight gain of about 0% to about 0.2% when relative humidity is increased from about 0% relative humidity to about 90% relative humidity at a temperature of 25° C.

In one embodiment, the Freebase Hydrate Form C has an X-ray diffraction pattern as previously described above; a thermogravimetric analysis profile showing a weight loss of about 2.3% to about 2.6% between about 120° C. and 160° C. when heated at a rate of 10° C./minute; and a differential scanning calorimetry profile comprising an endotherm between about 120 and about 170° C. when heated at a rate of 10° C./minute.

In one embodiment, the Freebase Hydrate Form C has an X-ray diffraction pattern as previously described above; a thermogravimetric analysis profile showing a weight loss of about 2.3% to about 2.6% between about 120° C. and 160° C. when heated at a rate of 10° C./minute; and a moisture sorption isotherm profile showing a weight gain of about 0% to about 0.2% when relative humidity is increased from about 0% relative humidity to about 90% relative humidity at a temperature of 25° C.

In one embodiment, the Freebase Hydrate Form C has an X-ray diffraction pattern as previously described above; a differential scanning calorimetry profile comprising an endotherm between about 120 and about 170° C. when heated at a rate of 10° C./minute; and a moisture sorption isotherm profile showing a weight gain of about 0% to about 0.2% when relative humidity is increased from about 0% relative humidity to about 90% relative humidity at a temperature of 25° C.

In one embodiment, the Freebase Hydrate Form C has an X-ray diffraction pattern as previously described above; a thermogravimetric analysis profile showing a weight loss of about 2.3% to about 2.6% between about 120° C. and 160° C. when heated at a rate of 10° C./minute; a differential scanning calorimetry profile comprising an endotherm between about 120 and about 170° C. when heated at a rate of 10° C./minute; and a moisture sorption isotherm profile showing a weight gain of about 0% to about 0.2% when relative humidity is increased from about 0% relative humidity to about 90% relative humidity at a temperature of 25° C.

The Freebase Hydrate Form C generally exhibits good chemical stability, physical stability, and solid state properties (including low hygroscopicity). Large-scale manufacture of the Freebase Hydrate Form C is relatively straightforward with minimal scaling, good yield, good impurity rejection, fast filtration, conventional drying, and minimal milling issues (even after subjecting the isolated material to high energy pinmilling). In addition, different particle sizes can be achieved through appropriate control of the crystallization process.

D. Crystalline Freebase Anhydrate Form D

In another embodiment, the solid state form is a crystalline anhydrate freebase of Compound 1 having a powder X-ray diffraction pattern corresponding to Freebase Anhydrate Form D. The Freebase Anhydrate Form D is further described in the Examples of the application.

In one embodiment the Freebase Anhydrate Form D has an X-ray powder diffraction pattern characterized by peaks at 8.0±0.2, 9.7±0.2, 14.2±0.2, 14.5±0.2, and 20.3±0.2 degrees two theta when measured at about 25° C. with monochromatic Kα1 radiation.

In one embodiment, the Freebase Anhydrate Form D has an X-ray powder diffraction pattern characterized by peaks at 8.0±0.2, 9.7±0.2, 14.2±0.2, 14.5±0.2, and 20.3±0.2 degrees two theta, and that is further characterized by a peak at one or more of 4.0±0.2, 18.4±0.2, 19.0±0.2, 23.0±0.2, and 24.7±0.2 degrees two theta, when measured at about 25° C. with monochromatic Kα1 radiation.

In one embodiment, the Freebase Anhydrate Form D has an X-ray powder diffraction pattern characterized by peaks at 4.0±0.2, 8.0±0.2, 9.7±0.2, 14.2±0.2, 14.5±0.2; and 20.3±0.2 degrees two theta, when measured at about 25° C. with monochromatic Kα1 radiation.

In one embodiment, the Freebase Anhydrate Form D has an X-ray powder diffraction pattern characterized by peaks at 8.0±0.2, 9.7±0.2, 14.2±0.2, 14.5±0.2, 18.4±0.2 and 20.3±0.2 degrees two theta, when measured at about 25° C. with monochromatic Kα1 radiation.

In one embodiment, the Freebase Anhydrate Form D has an X-ray powder diffraction pattern characterized by peaks at 8.0±0.2, 9.7±0.2, 14.2±0.2, 14.5±0.2, 19.0±0.2 and 20.3±0.2 degrees two theta, when measured at about 25° C. with monochromatic Kα1 radiation.

In one embodiment, the Freebase Anhydrate Form D has an X-ray powder diffraction pattern characterized by peaks at 4.0±0.2, 8.0±0.2, 9.7±0.2, 14.2±0.2, 14.5±0.2, 19.0±0.2 and 20.3±0.2 degrees two theta, when measured at about 25° C. with monochromatic Kα1 radiation.

In one embodiment, the Freebase Anhydrate Form D has an X-ray powder diffraction pattern characterized by peaks at 8.0±0.2, 9.7±0.2, 14.2±0.2, 14.5±0.2, 20.3±0.2, and 23.0±0.2 degrees two theta, when measured at about 25° C. with monochromatic Kα1 radiation.

In one embodiment, the Freebase Anhydrate Form D has an X-ray powder diffraction pattern characterized by peaks at 8.0±0.2, 9.7±0.2, 14.2±0.2, 14.5±0.2, 20.3±0.2, and 24.7±0.2 degrees two theta, when measured at about 25° C. with monochromatic Kα1 radiation.

In one embodiment, the Freebase Anhydrate Form D has an X-ray powder diffraction pattern characterized by peaks at 4.0±0.2, 14.5±0.2, and 19.0±0.2 degrees two theta, when measured at about 25° C. with monochromatic Kα1 radiation.

In one embodiment, the Freebase Anhydrate Form D has an X-ray powder diffraction pattern characterized by peaks at 4.0±0.2, 14.5±0.2, and 19.0±0.2 degrees two theta, and that is further characterized by a peak at one or more of 8.0±0.2, 9.7±0.2, 14.2±0.2, 18.4±0.2, 20.3±0.2, 23.0±0.2, and 24.7±0.2 degrees two theta, when measured at about 25° C. with monochromatic Kα1 radiation.

In one embodiment, the Freebase Anhydrate Form D has an X-ray powder diffraction pattern without a significant peak at one or more of 3.1±0.2, 9.3±0.2, and 20.8±0.2 degrees two theta, when measured at about 25° C. with monochromatic Kα1 radiation.

In one embodiment, the Freebase Anhydrate Form D has an X-ray powder diffraction pattern without a significant peak at one or more of 6.8±0.2, 15.7±0.2, and 21.9±0.2 degrees two theta, when measured at about 25° C. with monochromatic Kα1 radiation.

In one embodiment, the Freebase Anhydrate Form D has an X-ray powder diffraction pattern without a significant peak at one or more of 13.4±0.2, 15.5±0.2, and 21.7±0.2 degrees two theta, when measured at about 25° C. with monochromatic Kα1 radiation.

In one embodiment, the Freebase Anhydrate Form D has an X-ray powder diffraction pattern without a significant peak at one or more of 13.4±0.2, 15.5±0.2, and 21.7±0.2 degrees two theta, and without a significant peak at one or more of 6.8±0.2, 15.7±0.2; and 21.9±0.2 degrees two theta, and without a significant peak at one or more of 3.1±0.2, 9.3±0.2, and 20.8±0.2 degrees two theta, when measured at about 25° C. with monochromatic Kα1 radiation.

In one embodiment the Freebase Anhydrate Form D has an X-ray powder diffraction pattern characterized by peaks at 8.0±0.2, 9.7±0.2, 14.2±0.2, 14.5±0.2, and 20.3±0.2 degrees two theta, and without a significant peak at one or more of 3.1±0.2, 9.3±0.2, and 20.8±0.2 degrees two theta, when measured at about 25° C. with monochromatic Kα1 radiation.

In one embodiment the Freebase Anhydrate Form D has an X-ray powder diffraction pattern characterized by peaks at 8.0±0.2, 9.7±0.2, 14.2±0.2, 14.5±0.2, and 20.3±0.2 degrees two theta, and without a significant peak at one or more of 6.8±0.2, 15.7±0.2, and 21.9±0.2 degrees two theta, when measured at about 25° C. with monochromatic Kα1 radiation.

In one embodiment the Freebase Anhydrate Form D has an X-ray powder diffraction pattern characterized by peaks at 8.0±0.2, 9.7±0.2, 14.2±0.2, 14.5±0.2, and 20.3±0.2 degrees two theta, and without a significant peak at one or more of 13.4±0.2, 15.5±0.2, and 21.7±0.2 degrees two theta, when measured at about 25° C. with monochromatic Kα1 radiation.

In one embodiment the Freebase Anhydrate Form D has an X-ray powder diffraction pattern characterized by peaks at 8.0±0.2, 9.7±0.2, 14.2±0.2, 14.5±0.2, and 20.3±0.2 degrees two theta, and without a significant peak at one or more of 3.1±0.2, 9.3±0.2, and 20.8±0.2 degrees two theta, and without a significant peak at one or more of 6.8±0.2, 15.7±0.2, and 21.9±0.2 degrees two theta, and without a significant peak at one or more of 13.4±0.2, 15.5±0.2, and 21.7±0.2 degrees two theta, when measured at about 25° C. with monochromatic Kα1 radiation.

In one embodiment the Freebase Anhydrate Form D has an X-ray powder diffraction pattern characterized by peaks at 4.0±0.2, 8.0±0.2, 9.7±0.2, 14.2±0.2, 14.5±0.2, 19.0±0.2, and 20.3±0.2 degrees two theta, and without a significant peak at one or more of 3.1±0.2, 9.3±0.2, and 20.8±0.2 degrees two theta, when measured at about 25° C. with monochromatic Kα1 radiation.

In one embodiment the Freebase Anhydrate Form D has an X-ray powder diffraction pattern characterized by peaks at 4.0±0.2, 8.0±0.2, 9.7±0.2, 14.2±0.2, 14.5±0.2, 19.0±0.2, and 20.3±0.2 degrees two theta, and without a significant peak at one or more of 6.8±0.2, 15.7±0.2, and 21.9±0.2 degrees two theta, when measured at about 25° C. with monochromatic Kα1 radiation.

In one embodiment the Freebase Anhydrate Form D has an X-ray powder diffraction pattern characterized by peaks at 4.0±0.2, 8.0±0.2, 9.7±0.2, 14.2±0.2, 14.5±0.2, 19.0±0.2, and 20.3±0.2 degrees two theta, and without a significant peak at one or more of 13.4±0.2, 15.5±0.2, and 21.7±0.2 degrees two theta, when measured at about 25° C. with monochromatic Kα1 radiation.

In one embodiment the Freebase Anhydrate Form D has an X-ray powder diffraction pattern characterized by peaks at 4.0±0.2, 8.0±0.2, 9.7±0.2, 14.2±0.2, 14.5±0.2, 19.0±0.2, and 20.3±0.2 degrees two theta, and without a significant peak at one or more of 3.1±0.2, 9.3±0.2, and 20.8±0.2 degrees two theta, and without a significant peak at one or more of 6.8±0.2, 15.7±0.2, and 21.9±0.2 degrees two theta, and without a significant peak at one or more of 13.4±0.2, 15.5±0.2, and 21.7±0.2 degrees two theta, when measured at about 25° C. with monochromatic Kα1 radiation.

In one embodiment, the Freebase Anhydrate Form D has an X-ray powder diffraction pattern characterized by peaks substantially at the positions listed in Table 16-J ±0.2 degrees two theta, when measured at about 25° C. with monochromatic Kα1 radiation.

In one embodiment, the Freebase Anhydrate Form D has an X-ray powder diffraction pattern characterized by peaks substantially at the positions listed in Table 16-J ±0.2 degrees two theta that have a relative intensity of at least 10.0%, when measured at about 25° C. with monochromatic Kα1 radiation.

In further aspects of each of the above embodiments, the significant peak values have a variation of ±0.1 degrees two theta rather than ±0.2 degrees two theta. In still further aspects of each of the above embodiments, the significant peak values have a variation of ±0.05 degrees two theta rather than ±0.2 degrees two theta.

Figure 3D:
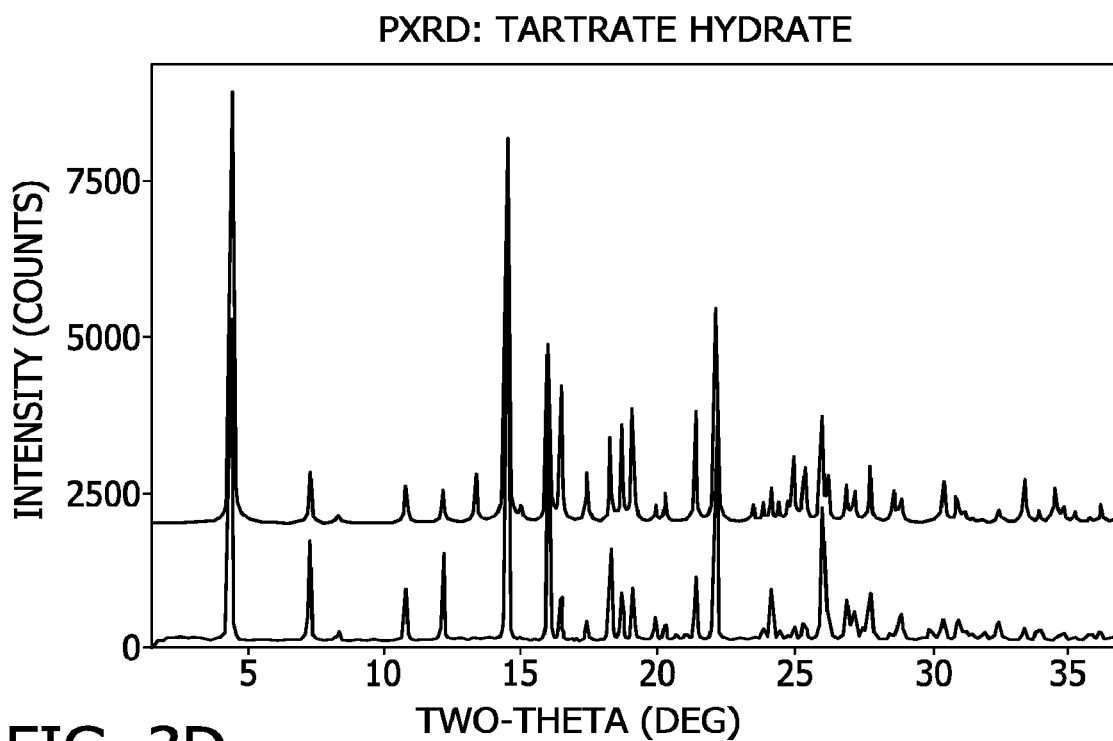
FIG. 3D is a powder X-ray diffraction pattern corresponding to the Tartrate Hydrate. The experimental PXRD pattern is shown at the bottom of FIG. 3D and the calculated PXRD pattern is shown at the top of FIG. 3D.
Figure 3E:
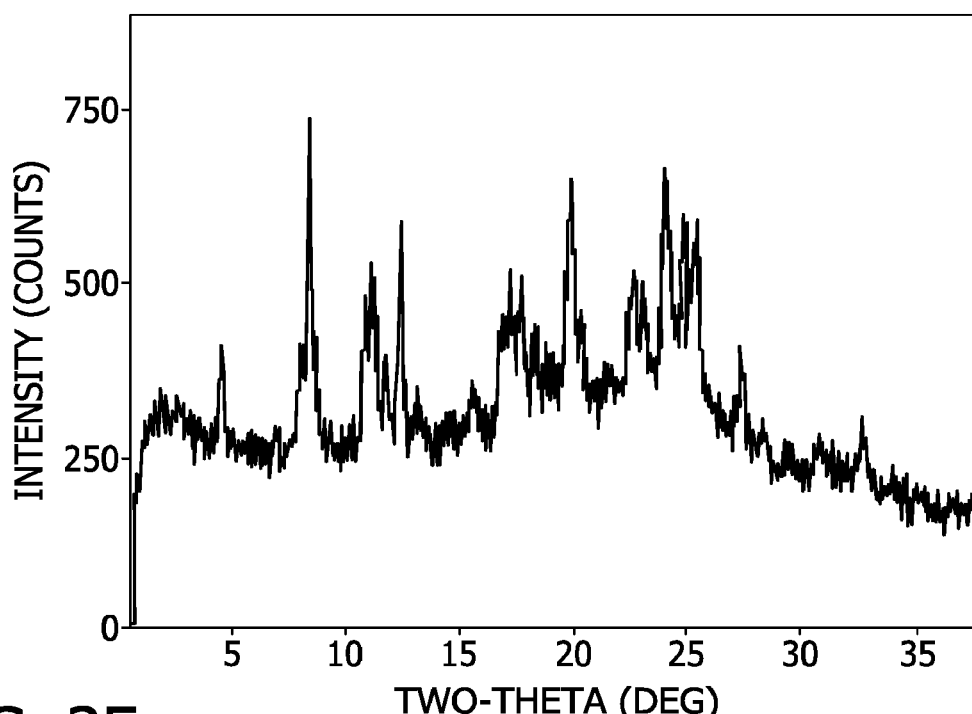
FIG. 3E is a powder X-ray diffraction pattern corresponding to the Hydrochloride Solvate Form AA.
Figure 3F:
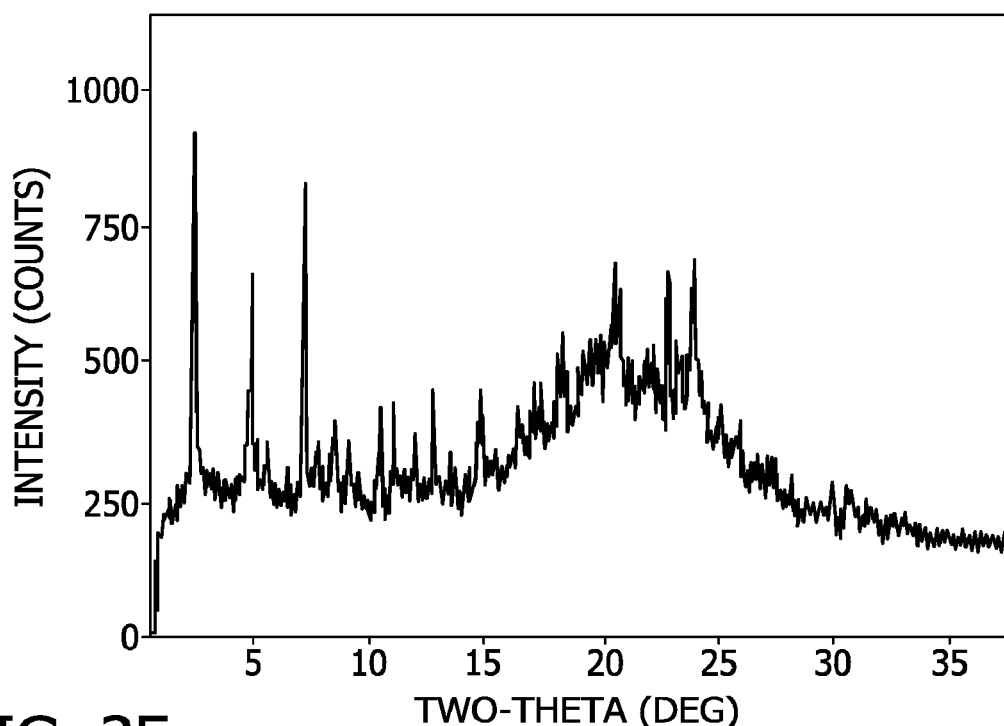
FIG. 3F is powder X-ray diffraction pattern corresponding to the Hydrochloride Solvate Form BB.
Figure 3G:
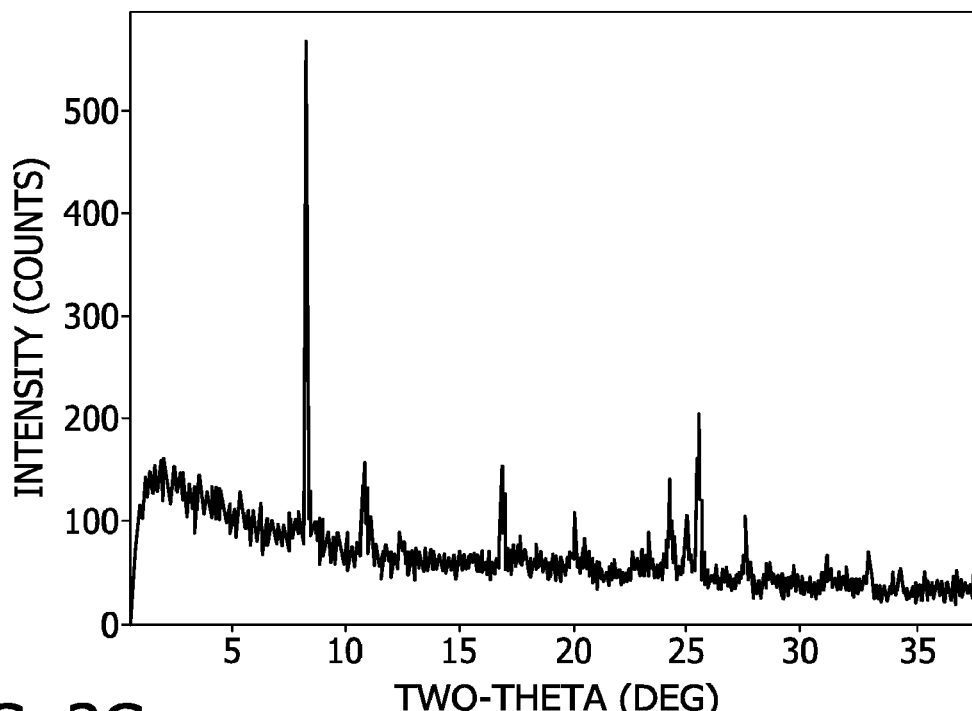
FIG. 3G is a powder X-ray diffraction pattern corresponding to the Hydrochloride Solvate Form CC.
Figure 3H:
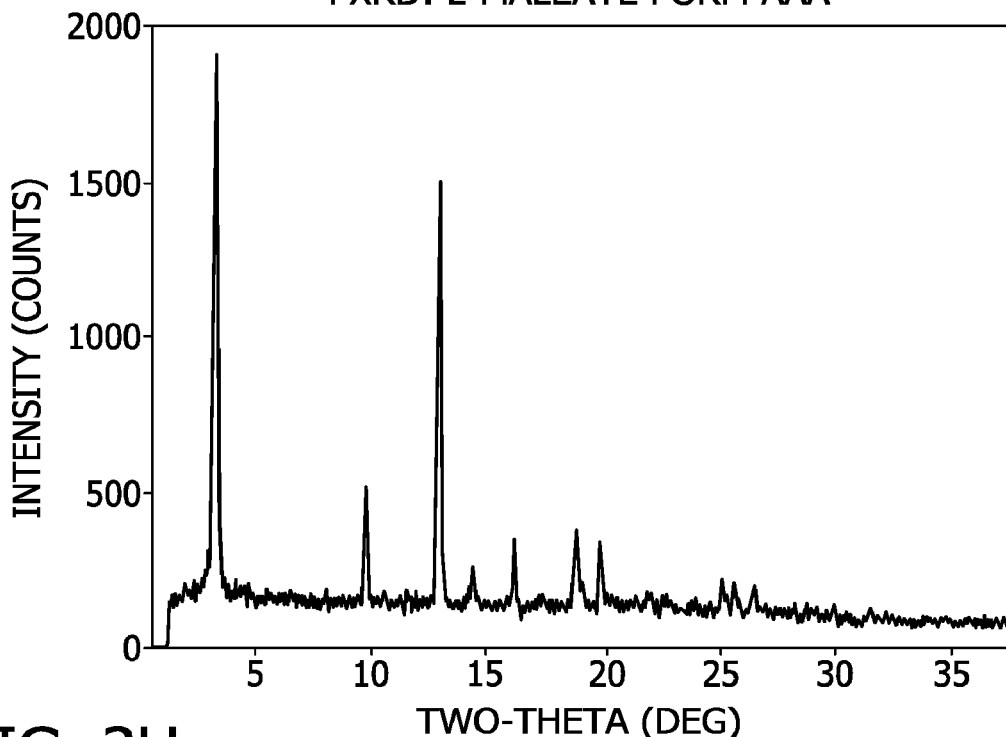
FIG. 3H is a powder X-ray diffraction pattern corresponding to L-Maleate Form AAA.
Figure 3I:
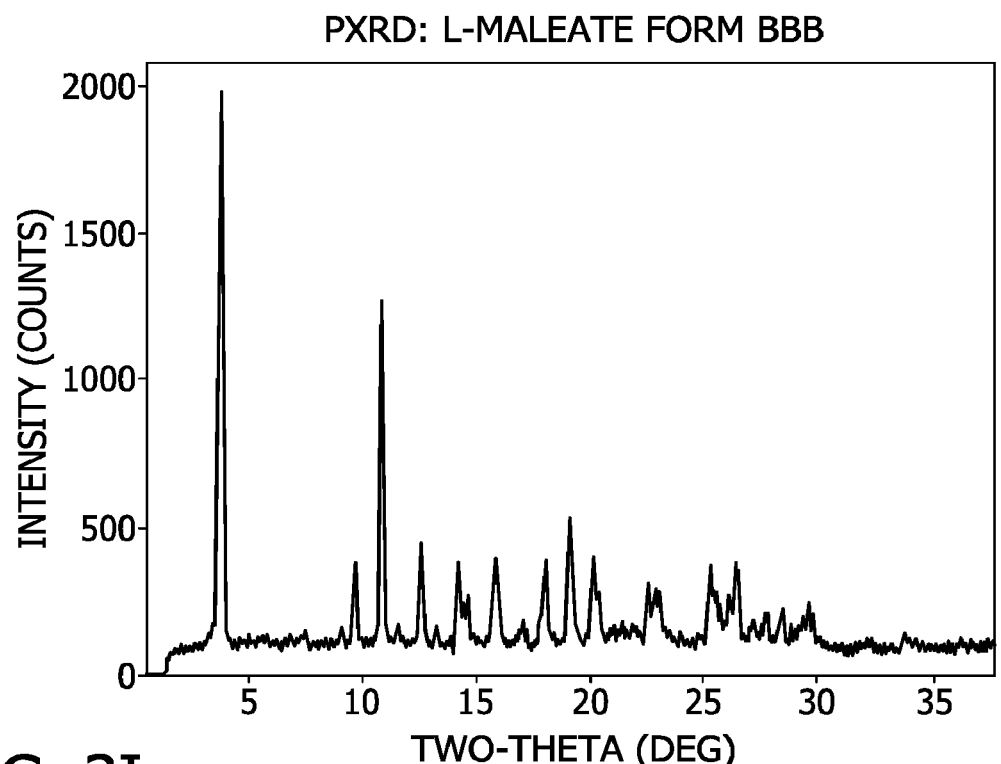
FIG. 3I is a powder X-ray diffraction pattern corresponding to L-Maleate Form BBB.
Figure 3J:
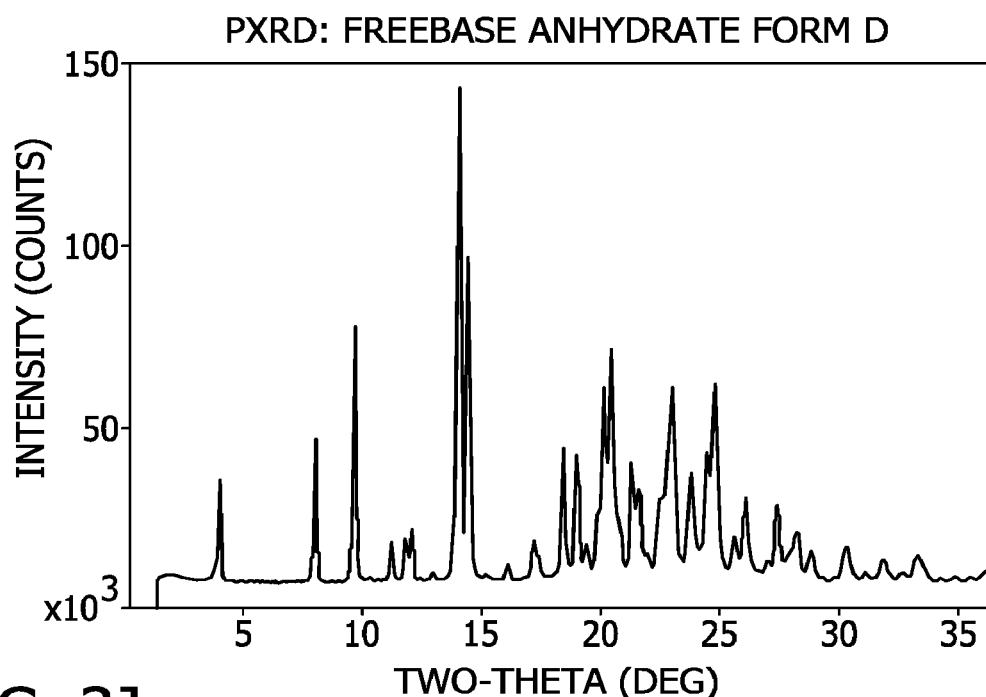
FIG. 3J is a powder X-ray diffraction pattern corresponding to Freebase Anhydrate Form D.

In one embodiment, the Freebase Anhydrate Form D has an X-ray powder diffraction pattern substantially as shown in FIG. 3J when measured at about 25° C. with monochromatic Kα1 radiation.

In one embodiment, the Freebase Anhydrate Form D has a thermogravimetric analysis profile showing a weight loss of about 0.5% to about 0.8% between about 43° C. and 188° C. when heated at a rate of 10° C./minute.

In one embodiment, the Freebase Anhydrate Form D has a thermogravimetric analysis profile showing a weight loss of about 0.5% to about 0.8% between about 41.36° C. and 190.48° C. when heated at a rate of 10° C./minute.

In one embodiment, the Freebase Anhydrate Form D has a thermogravimetric analysis profile showing a weight loss of about 0.45% to about 0.55% between about 43° C. and 100° C. when heated at a rate of 10° C./minute.

In one embodiment, the Freebase Anhydrate Form D has a thermogravimetric analysis profile showing a weight loss of about 0.5% between about 43° C. and 100° C. when heated at a rate of 10° C./minute.

Figure 4F:
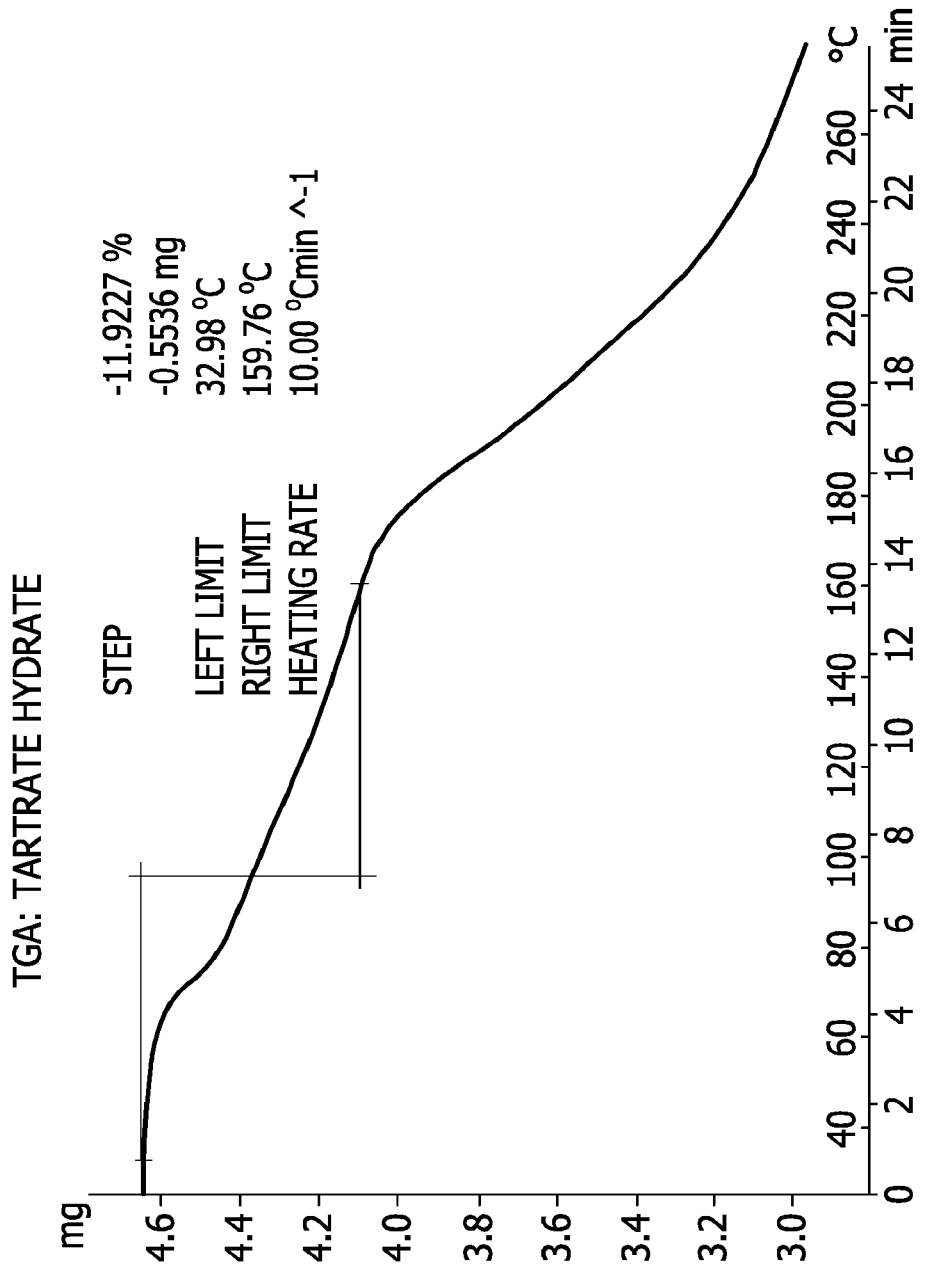
FIG. 4F is a thermogravimetric analysis thermogram corresponding to the Tartrate Hydrate.
Figure 4G:
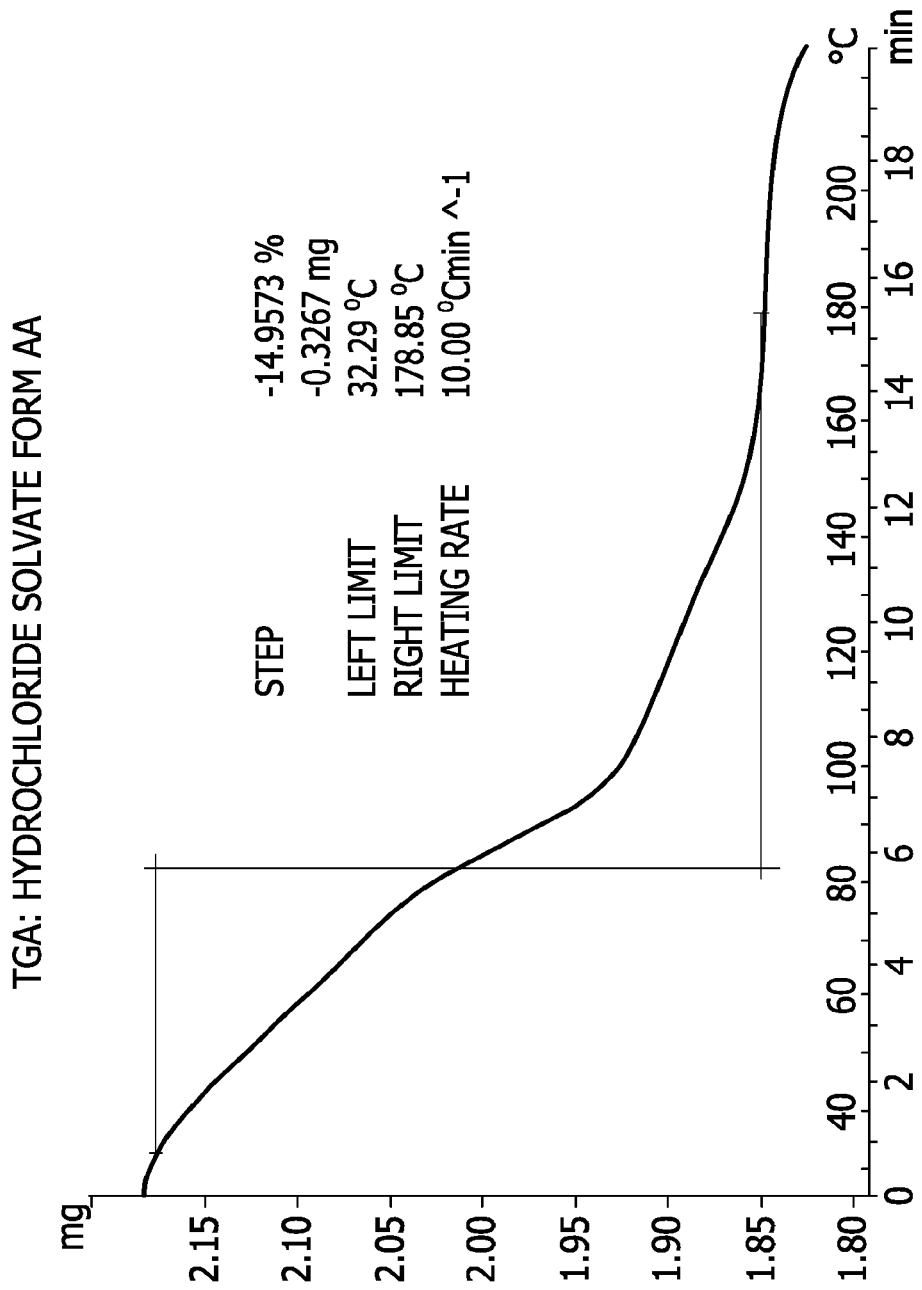
FIG. 4G is a thermogravimetric analysis thermogram corresponding to the Hydrochloride Solvate Form AA.
Figure 4H:
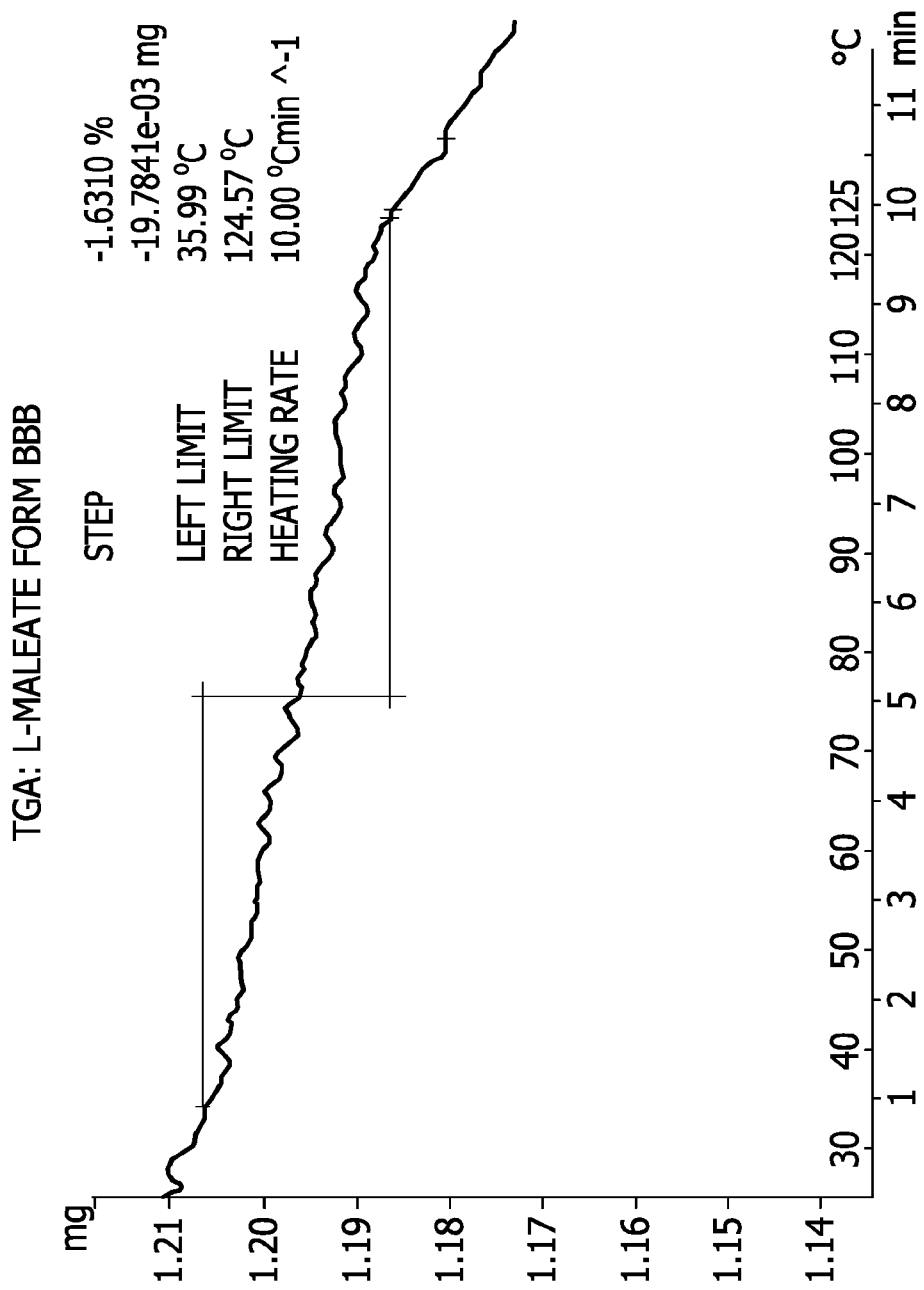
FIG. 4H is a thermogravimetric analysis thermogram corresponding to L-Maleate Form BBB.
Figure 4I:
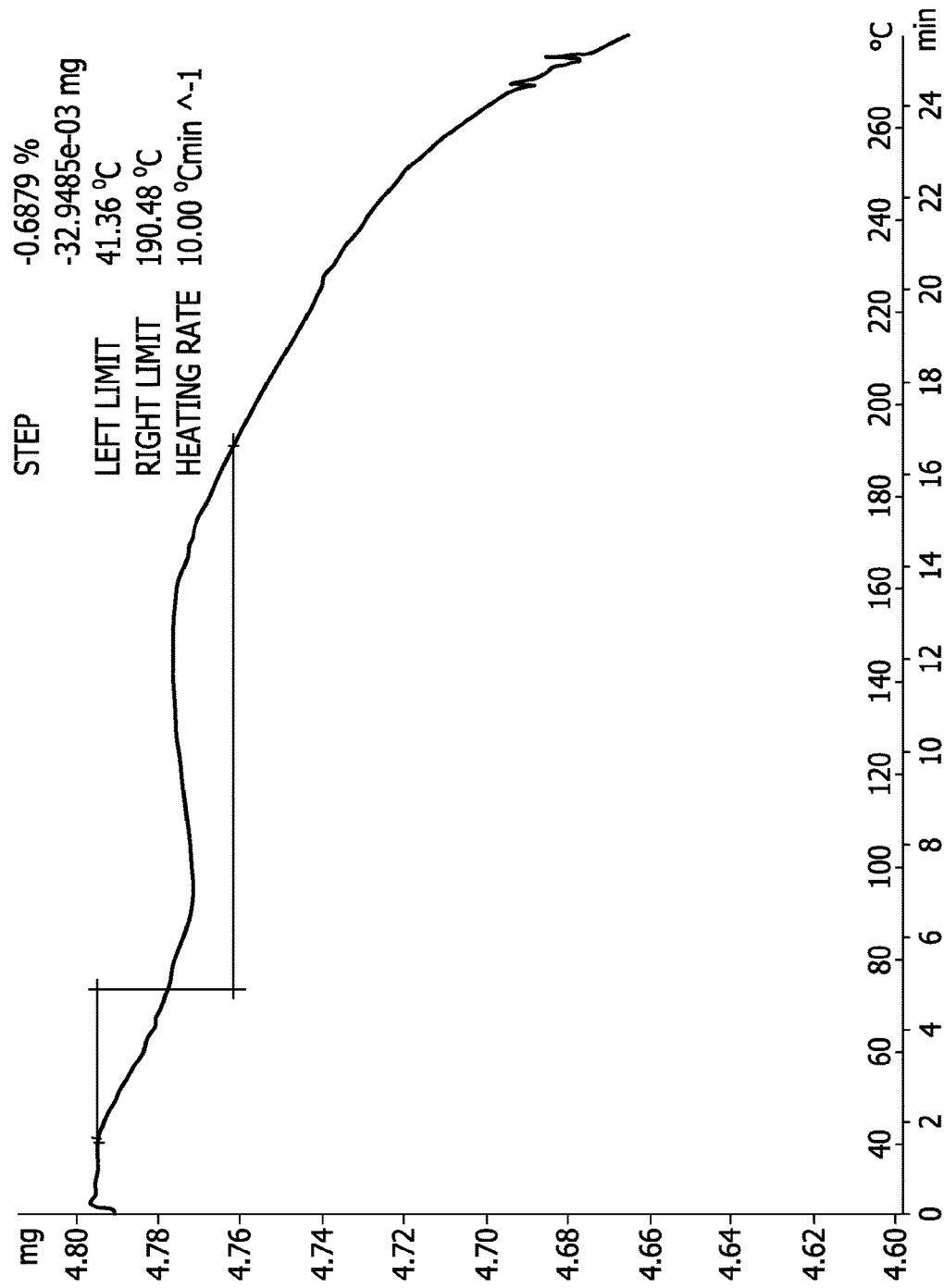
FIG. 4I is a thermogravimetric analysis thermogram corresponding to Freebase Anhydrate Form D.

In one embodiment, the Freebase Anhydrate Form D has a thermogravimetric analysis profile substantially as shown in FIG. 4I.

In one embodiment, the Freebase Anhydrate Form D has a differential scanning calorimetry profile comprising an endotherm between about 180° C. and about 220° C. when heated at a rate of 10° C./minute.

In one embodiment, the Freebase Anhydrate Form D has a differential scanning calorimetry profile comprising an endotherm between about 199.55° C. and about 217.41° C. when heated at a rate of 10° C./minute.

In one embodiment, the Freebase Anhydrate Form D has a differential scanning calorimetry profile comprising an endotherm with an onset melting point of about 199.55° C. and a melting enthalpy of about 85.4 J/g.

Figure 5D:
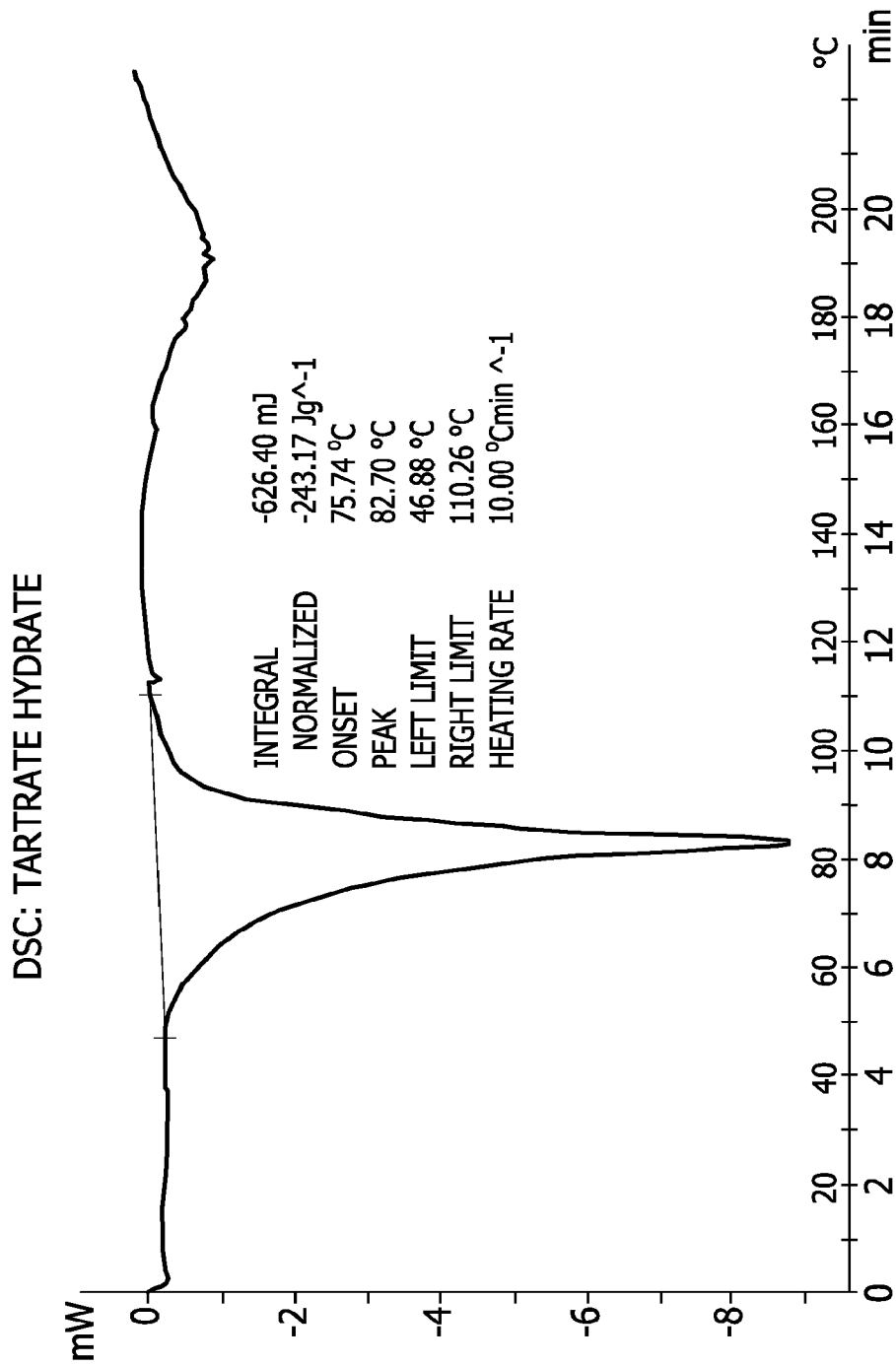
FIG. 5D is a differential scanning calorimetry thermogram corresponding to the Tartrate Hydrate.
Figure 5E:
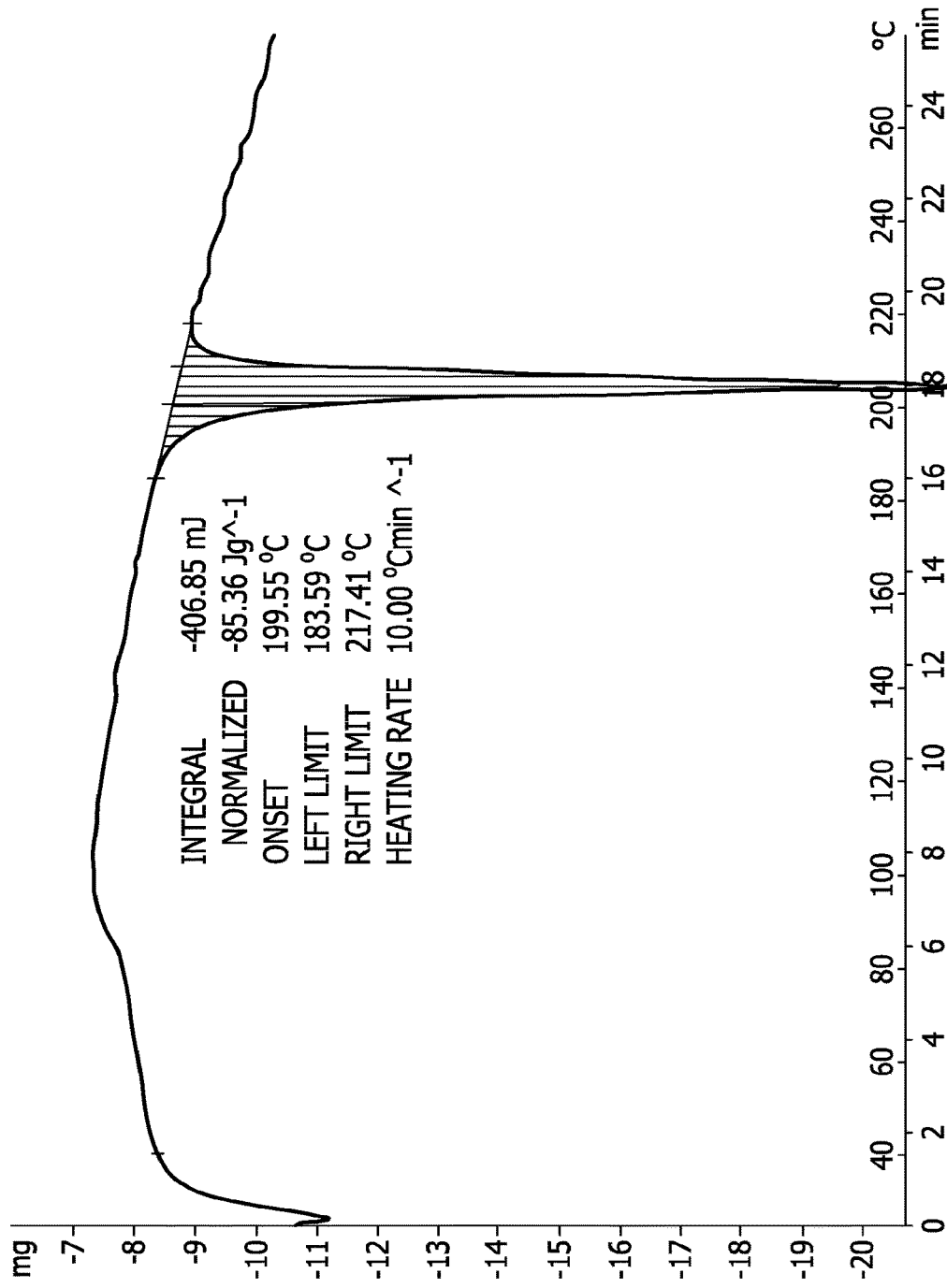
FIG. 5E is a differential scanning calorimetry thermogram corresponding to the Freebase Anhydrate Form D.

In one embodiment, the Freebase Anhydrate Form D has a differential scanning calorimetry profile substantially as shown in FIG. 5E.

In one embodiment, the Freebase Anhydrate Form D has a moisture sorption isotherm profile showing a weight gain of about 1.6% to about 2.0% when relative humidity is increased from about 0% relative humidity to about 90% relative humidity at a temperature of 25° C.

Figure 6C:
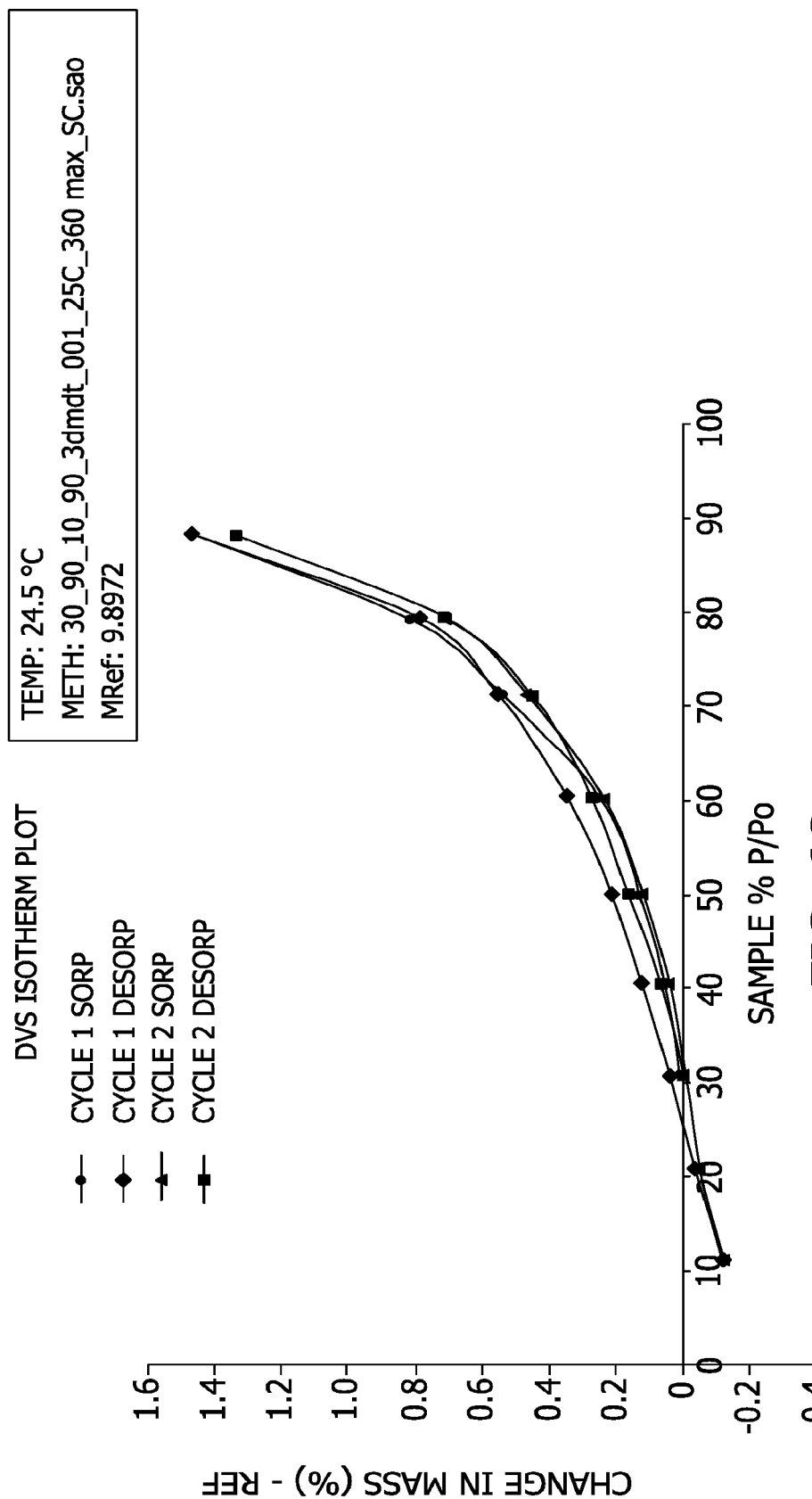
FIG. 6C is a moisture sorption isotherm corresponding to the Tartrate Hydrate.
Figure 6D:
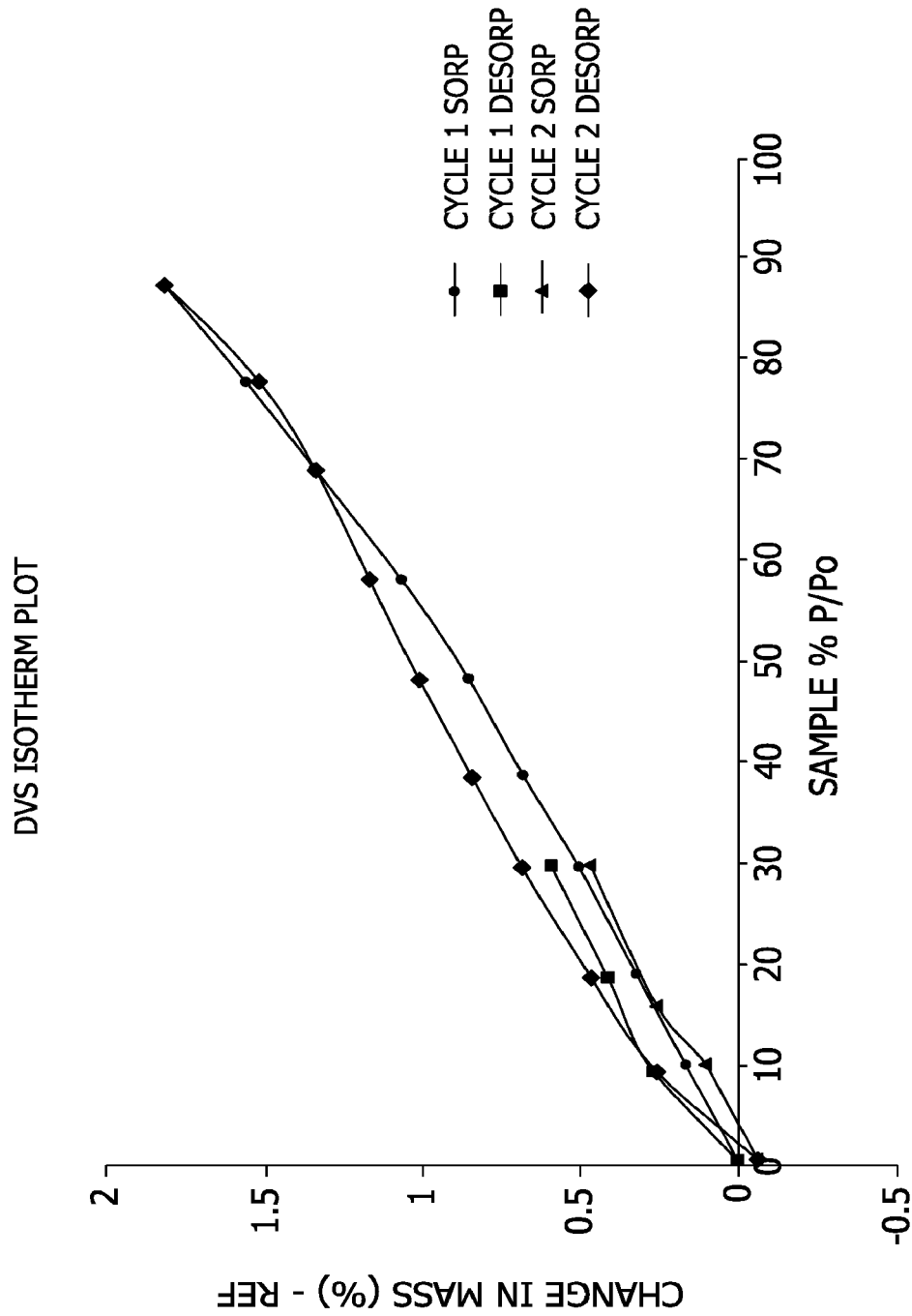
FIG. 6D is a moisture sorption isotherm corresponding to the Freebase Anhydrate Form D.

In one embodiment, the Freebase Anhydrate Form D has a moisture sorption isotherm profile substantially as shown in FIG. 6D.

In one embodiment, the Freebase Anhydrate Form D has a thermogravimetric analysis profile showing a weight loss of about 0.5% to about 0.8% between about 43° C. and 188° C. when heated at a rate of 10° C./minute; and a differential scanning calorimetry profile comprising an endotherm between about 180° C. and about 220° C. when heated at a rate of 10° C./minute.

In one embodiment, the Freebase Anhydrate Form D has a thermogravimetric analysis profile showing a weight loss of about 0.5% to about 0.8% between about 43° C. and 188° C. when heated at a rate of 10° C./minute; and a moisture sorption isotherm profile showing a weight gain of about 1.6% to about 2.0% when relative humidity is increased from about 0% relative humidity to about 90% relative humidity at a temperature of 25° C.

In one embodiment, the Freebase Anhydrate Form D has a differential scanning calorimetry profile comprising an endotherm between about 180° C. and about 220° C. when heated at a rate of 10° C./minute; and a moisture sorption isotherm profile showing a weight gain of about 1.6% to about 2.0% when relative humidity is increased from about 0% relative humidity to about 90% relative humidity at a temperature of 25° C.

In one embodiment, the Freebase Anhydrate Form D has a thermogravimetric analysis profile showing a weight loss of about 0.5% to about 0.8% between about 43° C. and 188° C. when heated at a rate of 10° C./minute; a differential scanning calorimetry profile comprising an endotherm between about 180° C. and about 220° C. when heated at a rate of 10° C./minute; and a moisture sorption isotherm profile showing a weight gain of about 1.6% to about 2.0% when relative humidity is increased from about 0% relative humidity to about 90% relative humidity at a temperature of 25° C.

In one embodiment, the Freebase Anhydrate Form D has a thermogravimetric analysis profile showing a weight loss of about 0.5% to about 0.8% between about 43° C. and 188° C. when heated at a rate of 10° C./minute; a differential scanning calorimetry profile comprising an endotherm between about 199.55° C. and about 217.41° C. when heated at a rate of 10° C./minute; and a moisture sorption isotherm profile showing a weight gain of about 1.6% to about 2.0% when relative humidity is increased from about 0% relative humidity to about 90% relative humidity at a temperature of 25° C.

In one embodiment, the Freebase Anhydrate Form D has an orthorhombic lattice type.

In one embodiment, the Freebase Anhydrate Form D has a P2$_1$2$_1$2 space group.

In one embodiment, the Freebase Anhydrate Form D has unit cell a, b and c values of about 43.8 Å, about 8.6 Å, and about 9.2 Å, respectively.

In one embodiment, the Freebase Anhydrate Form D has an X-ray diffraction pattern as previously described above, and at least one of the following: (a) a thermogravimetric analysis profile showing a weight loss of about 0.5% to about 0.8% between about 43° C. and 188° C. when heated at a rate of 10° C./minute; (b) a differential scanning calorimetry profile comprising an endotherm between about 180° C. and about 220° C. when heated at a rate of 10° C./minute; and/or (c) a moisture sorption isotherm profile showing a weight gain of about 1.6% to about 2.0% when relative humidity is increased from about 0% relative humidity to about 90% relative humidity at a temperature of 25° C.

In one embodiment, the Freebase Anhydrate Form D has an X-ray diffraction pattern as previously described above, and a thermogravimetric analysis profile showing a weight loss of about 0.5% to about 0.8% between about 43° C. and 188° C. when heated at a rate of 10° C./minute.

In one embodiment, the Freebase Anhydrate Form D has an X-ray diffraction pattern as previously described above, and a differential scanning calorimetry profile comprising an endotherm between about 180° C. and about 220° C. when heated at a rate of 10° C./minute.

In one embodiment, the Freebase Anhydrate Form D has an X-ray diffraction pattern as previously described above, and a moisture sorption isotherm profile showing a weight gain of about 1.6% to about 2.0% when relative humidity is increased from about 0% relative humidity to about 90% relative humidity at a temperature of 25° C.

In one embodiment, the Freebase Anhydrate Form D has an X-ray diffraction pattern as previously described above; a thermogravimetric analysis profile showing a weight loss of about 0.5% to about 0.8% between about 43° C. and 188° C. when heated at a rate of 10° C./minute; and a differential scanning calorimetry profile comprising an endotherm between about 180° C. and about 220° C. when heated at a rate of 10° C./minute.

In one embodiment, the Freebase Anhydrate Form D has an X-ray diffraction pattern as previously described above; a thermogravimetric analysis profile showing a weight loss of about 0.5% to about 0.8% between about 43° C. and 188° C. when heated at a rate of 10° C./minute; and a moisture sorption isotherm profile showing a weight gain of about 1.6% to about 2.0% when relative humidity is increased from about 0% relative humidity to about 90% relative humidity at a temperature of 25° C.

In one embodiment, the Freebase Anhydrate Form D has an X-ray diffraction pattern as previously described above; a differential scanning calorimetry profile comprising an endotherm between about 180° C. and about 220° C. when heated at a rate of 10° C./minute; and a moisture sorption isotherm profile showing a weight gain of about 1.6% to about 2.0% when relative humidity is increased from about 0% relative humidity to about 90% relative humidity at a temperature of 25° C.

In one embodiment, the Freebase Anhydrate Form D has an X-ray diffraction pattern as previously described above; a thermogravimetric analysis profile showing a weight loss of about 0.5% to about 0.8% between about 43° C. and 188° C. when heated at a rate of 10° C./minute; a differential scanning calorimetry profile comprising an endotherm between about 180° C. and about 220° C. when heated at a rate of 10° C./minute; and a moisture sorption isotherm profile showing a weight gain of about 1.6% to about 2.0% when relative humidity is increased from about 0% relative humidity to about 90% relative humidity at a temperature of 25° C.

Freebase Anhydrate Form D is reversibly hygroscopic (up to 1.8% water at 90% RH at 25° C.), and is metastable relative to Freebase Hydrate Form C at typical environmental conditions (e.g., above 2.4% RH at 23° C.) used during storage for downstream processing. The manufacture of Freebase Anhydrate Form D requires strict control of water, as the Freebase Anhydrate Form D can be manufactured only when the water content of the crystallization solvent is low (e.g., less than 0.15% at 23° C., corresponding to a water activity of 2.4%), and will convert to Freebase Hydrate Form C in solution at high water content. Freebase Anhydrate Form D is slow to crystallize, and difficult to manufacture in higher yield.

E. Crystalline Tartrate

In another embodiment, the solid state form is a tartrate of Compound 1. In one aspect, the tartrate is amorphous. In another aspect, the tartrate is crystalline. In another aspect, the crystalline tartrate is a solvate. In another aspect, the crystalline tartrate is a hydrate. In another aspect, the tartrate is a crystalline L-tartrate. In another aspect, the crystalline L-tartrate is a hydrate. In another aspect, the crystalline tartrate is a tetrahydrate (the "Tartrate Hydrate"). The Tartrate Hydrate (a tetrahydrate) is further described in the Examples of the application.

In one embodiment, the Tartrate Hydrate has an X-ray powder diffraction pattern characterized by peaks at 3.9±0.2, 6.8±0.2, and 14.1±0.2 degrees two theta when measured at about 25° C. with monochromatic Kα1 radiation.

In one embodiment, the Tartrate Hydrate has an X-ray powder diffraction pattern characterized by peaks at 3.9±0.2, 6.8±0.2, 14.1±0.2, 15.7±0.2, 21.9±0.2, and 25.9±0.2 degrees two theta when measured at about 25° C. with monochromatic Kα1 radiation.

In one embodiment, the Tartrate Hydrate has an X-ray powder diffraction pattern without a significant peak at one or more of 13.4±0.2 and 15.1±0.2 degrees two theta, when measured at about 25° C. with monochromatic Kα1 radiation.

In one embodiment, the Tartrate Hydrate has an X-ray powder diffraction pattern without a significant peak at one or more of 3.1±0.2, 9.3±0.2, and 12.0±0.2 degrees two theta, when measured at about 25° C. with monochromatic Kα1 radiation.

In one embodiment, the Tartrate Hydrate has an X-ray powder diffraction pattern without a significant peak at one or more of 13.4±0.2 and 15.1±0.2 degrees two theta, and without a significant peak at one or more of 3.1±0.2 and 9.3±0.2 degrees two theta, when measured at about 25° C. with monochromatic Kα1 radiation.

In one embodiment, the Tartrate Hydrate has an X-ray powder diffraction pattern characterized by peaks at 3.9±0.2, 6.8±0.2, and 14.1±0.2 degrees two theta, and without a significant peak at one or more of 13.4±0.2 and 15.1±0.2 degrees two theta, when measured at about 25° C. with monochromatic Kα1 radiation.

In one embodiment, the Tartrate Hydrate has an X-ray powder diffraction pattern characterized by peaks at 3.9±0.2, 6.8±0.2, and 14.1±0.2 degrees two theta, and without a significant peak at one or more of 3.1±0.2, 9.3±0.2, and 12.0±0.2 degrees two theta, when measured at about 25° C. with monochromatic Kα1 radiation.

In one embodiment, the Tartrate Hydrate has an X-ray powder diffraction pattern characterized by peaks at 3.9±0.2, 6.8±0.2, and 14.1±0.2 degrees two theta, and without a significant peak at one or more of 13.4±0.2 and 15.1±0.2 degrees two theta, and without a significant peak at one or more of 3.1±0.2, 9.3±0.2, and 12.0±0.2 degrees two theta, when measured at about 25° C. with monochromatic Kα1 radiation.

In one embodiment, the Tartrate Hydrate has an X-ray powder diffraction pattern characterized by peaks at 3.9±0.2, 6.8±0.2, 14.1±0.2, 15.7±0.2, 21.9±0.2 degrees two theta, and without a significant peak at one or more of 13.4±0.2 and 15.1±0.2 degrees two theta, when measured at about 25° C. with monochromatic Kα1 radiation.

In one embodiment, the Tartrate Hydrate has an X-ray powder diffraction pattern characterized by peaks at 3.9±0.2, 6.8±0.2, 14.1±0.2, 15.7±0.2, 21.9±0.2 degrees two theta, and without a significant peak at one or more of 3.1±0.2, 9.3±0.2, and 12.0±0.2 degrees two theta.

In one embodiment, the Tartrate Hydrate has an X-ray powder diffraction pattern characterized by peaks at 3.9±0.2, 6.8±0.2, 14.1±0.2, 15.7±0.2, 21.9±0.2 degrees two theta, and without a significant peak at one or more of 13.4±0.2 and 15.1±0.2 degrees two theta, and without a significant peak at one or more of 3.1±0.2, 9.3±0.2, and 12.0±0.2 degrees two theta.

In further aspects of each of the above embodiments, the significant peak values have a variation of ±0.1 degrees two theta rather than ±0.2 degrees two theta. In still further aspects of each of the above embodiments, the significant peak values have a variation oft 0.05 degrees two theta rather than ±0.2 degrees two theta.

In one embodiment, the Tartrate Hydrate has an X-ray powder diffraction pattern substantially as shown in FIG. 3D, when measured at about 25° C. with monochromatic Kα1 radiation.

In one embodiment, the Tartrate Hydrate has a thermogravimetric analysis profile showing a weight loss of about 11.8% to about 12.2% between about 25° C. and 160° C. when heated at a rate of 10° C./minute.

In one embodiment, the Tartrate Hydrate has a thermogravimetric analysis profile showing a weight loss of about 11.8% to about 12.2% between about 32.98° C. and 159.76° C. when heated at a rate of 10° C./minute.

In one embodiment, the Tartrate Hydrate has a thermogravimetric analysis profile substantially as shown in FIG. 4F.

In one embodiment, the Tartrate Hydrate has a differential scanning calorimetry profile comprising an endotherm between about 60° C. and about 100° C. when heated at a rate of 10° C./minute.

In one embodiment, the Tartrate Hydrate has a differential scanning calorimetry profile comprising an endotherm between about 75.74° C. and about 110.26° C. when heated at a rate of 10° C./minute.

In one embodiment, the Tartrate Hydrate has a differential scanning calorimetry profile substantially as shown in FIG. 5D.

In one embodiment, the Tartrate Hydrate has a thermogravimetric analysis profile showing a weight loss of about 11.8% to about 12.2% between about 25° C. and 160° C. when heated at a rate of 10° C./minute; and a differential scanning calorimetry profile comprising an endotherm between about 60° C. and about 100° C. when heated at a rate of 10° C./minute.

In one embodiment, the Tartrate Hydrate has a moisture sorption isotherm profile showing a weight gain of about 1% to about 2% when relative humidity is increased from about 10% relative humidity to about 90% relative humidity at a temperature of 25° C.

In one embodiment, the Tartrate Hydrate has a moisture sorption isotherm profile substantially as shown in FIG. 6C.

In one embodiment, the Tartrate Hydrate has a thermogravimetric analysis profile showing a weight loss of about 11.8% to about 12.2% between about 25° C. and 160° C. when heated at a rate of 10° C./minute; a differential scanning calorimetry profile comprising an endotherm between about 60° C. and about 100° C. when heated at a rate of 10° C./minute; and a moisture sorption isotherm profile showing a weight gain of about 1% to about 2% when relative humidity is increased from about 10% relative humidity to about 90% relative humidity at a temperature of 25° C.

In one embodiment, the Tartrate Hydrate has an X-ray diffraction pattern as previously described above, and at least one of the following: (a) a thermogravimetric analysis profile showing a weight loss of about 11.8% to about 12.2% between about 25° C. and 160° C. when heated at a rate of 10° C./minute; (b) a differential scanning calorimetry profile comprising an endotherm between about 60° C. and about 100° C. when heated at a rate of 10° C./minute; and/or (c) a moisture sorption isotherm profile showing a weight gain of about 1% to about 2% when relative humidity is increased from about 10% relative humidity to about 90% relative humidity at a temperature of 25° C.

In one embodiment, the Tartrate Hydrate has an X-ray diffraction pattern as previously described above, and a thermogravimetric analysis profile showing a weight loss of about 11.8% to about 12.2% between about 25° C. and 160° C. when heated at a rate of 10° C./minute.

In one embodiment, the Tartrate Hydrate has an X-ray diffraction pattern as previously described above, and a differential scanning calorimetry profile comprising an endotherm between about 60° C. and about 100° C. when heated at a rate of 10° C./minute.

In one embodiment, the Tartrate Hydrate has an X-ray diffraction pattern as previously described above, and a moisture sorption isotherm profile showing a weight gain of about 1% to about 2% when relative humidity is increased from about 10% relative humidity to about 90% relative humidity at a temperature of 25° C.

In one embodiment, the Tartrate Hydrate has an X-ray diffraction pattern as previously described above; a thermogravimetric analysis profile showing a weight loss of about 11.8% to about 12.2% between about 25° C. and 160° C. when heated at a rate of 10° C./minute; and a differential scanning calorimetry profile comprising an endotherm between about 60° C. and about 100° C. when heated at a rate of 10° C./minute.

In one embodiment, the Tartrate Hydrate has an X-ray diffraction pattern as previously described above; a thermogravimetric analysis profile showing a weight loss of about 11.8% to about 12.2% between about 25° C. and 160° C. when heated at a rate of 10° C./minute; and a moisture sorption isotherm profile showing a weight gain of about 1% to about 2% when relative humidity is increased from about 10% relative humidity to about 90% relative humidity at a temperature of 25° C.

In one embodiment, the Tartrate Hydrate has an X-ray diffraction pattern as previously described above; a differential scanning calorimetry profile comprising an endotherm between about 60° C. and about 100° C. when heated at a rate of 10° C./minute; and a moisture sorption isotherm profile showing a weight gain of about 1% to about 2% when relative humidity is increased from about 10% relative humidity to about 90% relative humidity at a temperature of 25° C.

In one embodiment, the Tartrate Hydrate has an X-ray diffraction pattern as previously described above; a thermogravimetric analysis profile showing a weight loss of about 11.8% to about 12.2% between about 25° C. and 160° C. when heated at a rate of 10° C./minute; a differential scanning calorimetry profile comprising an endotherm between about 60° C. and about 100° C. when heated at a rate of 10° C./minute; and a moisture sorption isotherm profile showing a weight gain of about 1% to about 2% when relative humidity is increased from about 10% relative humidity to about 90% relative humidity at a temperature of 25° C.

The Tartrate Hydrate has acceptable chemical stability and exhibits acceptable stability to light and peroxide. For example, when chemical stability was evaluated in closed vial's at 30° C./65% relative humidity and 40° C./75% relative humidity over 12 weeks, and at 50° C./75% relative humidity over 6 weeks, no degradation of the Tartrate Hydrate was observed in the closed vials under any of the conditions. The Tartrate Hydrate has good solubility (BCS Class I) and is not hygroscopic. The Tartrate Hydrate, however, potentially will convert to an amorphous tartrate below 10% relative humidity, when heated, or when compressed or under shear.

The Tartrate Hydrate can be manufactured, for example, using anti-solvent crystallization. Impurity rejection during the large-scale manufacture of the Tartrate Hydrate generally is good, but scaling may be greater than desired and specific anti-solvent addition controls and process volume restrictions potentially may be required. In addition, appropriate control of the filtration, washing, and drying steps may be required to minimize consolidation of the wet cake and formation of hard lumps in the isolated material. For example, control of the relative humidity (e.g., greater than 10% and less than 100% relative humidity), temperature (e.g., crystallization at about 10° C. works well), and mixing rate may be required during drying to minimize the formation of hard lumps in the isolated material. Insufficient control of the drying conditions potentially will produce a consolidated, harder material that may be difficult to break up during subsequent processing. As previously noted, shearing and compression potentially will cause conversion to the amorphous tartrate. The dried material typically is milled with mechanical impact mills (e.g., Fitzmills and pin mills) because shear-based mills (e.g., comills) can lead to loss of crystallinity. In addition, loss of crystallinity potentially can result from pressure or compression forces during formulation (such as would be required for tableting).

F. Crystalline Hydrochloride

In another embodiment, the solid state form is a crystalline hydrochloride of Compound 1. In one aspect, the crystalline hydrochloride corresponds to crystalline Hydrochloride Solvate Form AA. In another aspect, the crystalline hydrochloride corresponds to crystalline Hydrochloride Solvate Form BB. In another aspect, the crystalline hydrochloride corresponds to crystalline Hydrochloride Solvate Form CC. Hydrochloride Solvate Form AA, Hydrochloride Solvate Form BB, and Hydrochloride Solvate Form CC are further described in the Examples of the application.

Hydrochloride Solvate Form AA, Hydrochloride Solvate Form BB, and Hydrochoride Solvate Form CC appear to be solvates and generally convert to an amorphous hydrochloride upon ambient drying. The resulting amorphous hydrochloride is hygroscopic. Yields obtained for each of the crystalline hydrochlorides generally have been in the 10% to 15% range.

G. Crystalline L-Maleate

In another embodiment, the solid state form is a crystalline L-maleate of Compound 1. In one aspect, the crystalline L-maleate corresponds to crystalline L-Maleate Form AAA. In another aspect, the crystalline L-maleate corresponds to crystalline L-Maleate Form BBB. L-Maleate Form AAA and L-Maleate Form BBB are further described in the Examples of the application.

Because L-maleic acid will react with Compound 1, the L-Maleate Form AAA and L-Maleate Form BBB generally are less chemically stable than the Amorphous Freebase, the Freebase Hydrate Form C, and the Tartrate Hydrate and do not exhibit pharmaceutically acceptable stability for use as an active ingredient in a pharmaceutical dosage form.

H. Crystalline Purity

In additional embodiments of the solid state forms discussed above, the solid state form has a pharmaceutically acceptable crystalline purity (or a pharmaceutically acceptable amorphous purity in the case of the Amorphous Freebase). For example, in one aspect, Compound 1 comprises at least about 75% by weight of the desired solid state form. In another aspect, at least 80% by weight is the desired solid state form. In another aspect, at least 85% by weight is the desired solid state form. In another aspect, at least 90% by weight is the desired solid state form. In another aspect, at least 95% by weight is the desired solid state form. In another aspect, at least 96% by weight is the desired solid state form. In another aspect, at least 97% by weight is the desired solid state form. In another aspect, at least 98% by weight is the desired solid state form. In another aspect, at least 99% by weight is the desired solid state form. In another aspect, Compound 1 is present as the substantially crystalline pure (or amorphous pure in the case of the Amorphous Freebase) solid state form. In a preferred aspect, the solid state form is the Amorphous Freebase. In another aspect, the solid state form is Freebase Anhydrate Form D. In a more preferred aspect, the solid state form is the Freebase Hydrate Form B. In a particularly preferred aspect, the solid state form is the Freebase Hydrate Form C. In a preferred aspect, the solid state form is the Tartrate Hydrate.

IV. METHODS OF TREATMENT

The present disclosure also relates to methods of treating a JAK-associated condition in a subject, particularly a human subject suffering from or susceptible to the condition, comprising administering to the subject a therapeutically effective amount of Compound 1 freebase or a pharmaceutically acceptable salt thereof or one or more solid state forms of Compound 1 as described in the present disclosure. Another aspect of the disclosure relates to Compound 1 freebase or a pharmaceutically acceptable salt thereof or one or more solid state forms of Compound 1 as described in the present disclosure for use in treatment of a JAK-associated condition in a subject, particularly in a human subject suffering from or susceptible to the condition, the use comprising administering to the subject a therapeutically effective amount of Compound 1 freebase or a pharmaceutically acceptable salt thereof or one or more solid state forms of Compound 1. In one aspect, the condition is a JAK-1-associated condition. In another aspect, the solid state form is the Amorphous Freebase. In another aspect, the solid state form is the Freebase Hydrate Form B. In another aspect, the solid state form is the Freebase Hydrate Form C. In another aspect, the solid state form is the Tartrate Hydrate. In another aspect, the solid state form is the Freebase Anhydrate Form D.

In one embodiment, the present disclosure relates to methods of treating a condition selected from the group consisting of immunomodulation, inflammation, and proliferative disorders (such as cancer) in a subject, wherein the method comprises administering to the subject, particularly a human subject suffering from or susceptible to the condition, a therapeutically effective amount of Compound 1 freebase or a pharmaceutically acceptable salt thereof or a solid state form of Compound 1. In another aspect, the present disclosure relates to Compound 1 freebase or a pharmaceutically acceptable salt thereof or a solid state form of Compound 1 for use in treatment of a condition selected from the group consisting of immunomodulation, inflammation, and proliferative disorders (such as cancer) in a subject, particularly in a human subject suffering from or susceptible to the condition, the use comprising administering to the subject a therapeutically effective amount of Compound 1 freebase or a pharmaceutically acceptable salt thereof or a solid state form of Compound 1. In one aspect, the solid state form is the Amorphous Freebase. In another aspect, the solid state form is the Freebase Anhydrate Form D. In another aspect, the solid state form is the Freebase Hydrate Form B. In another aspect, the solid state form is the Freebase Hydrate Form C. In another aspect, the solid state form is the Tartrate Hydrate.

In one embodiment, the present disclosure relates to methods of treating a condition selected from the group consisting of rheumatoid arthritis, multiple sclerosis, experimental allergic encephalomyelitis, systemic lupus erythematosus, Crohn's disease, atopic dermatitis, vasculitis, cardiomyopathy, psoriasis, Reiter's syndrome, glomerulonephritis, ulcerative colitis, allergic asthma, insulin-dependent diabetes, peripheral neuropathy, uveitis, fibrosing alveolitis, type I diabetes, juvenile diabetes, juvenile arthritis, Castleman disease, neutropenia, endometriosis, autoimmune thyroid disease, sperm and testicular autoimmunity, scleroderma, axonal and neuronal neuropathies, allergic rhinitis, Sjogren's syndrome, hemolytic anemia, Graves' disease, Hashimoto's thyroiditis, IgA nephropathy, amyloidosis, ankylosing spondylitis, Behcet's disease, sarcoidosis, vesiculobullous dermatosis, myositis, primary biliary cirrhosis, polymyalgia rheumatica, autoimmune immunodeficiency, Chagas disease, Kawasaki syndrome, psoriatic arthritis, celiac sprue, myasthenia gravis, autoimmune myocarditis, POEMS syndrome, and chronic fatigue syndrome in a subject, wherein the method comprises administering to the subject, particularly a human subject suffering from or susceptible to the condition, a therapeutically effective amount of Compound 1 freebase or a pharmaceutically acceptable salt thereof or a solid state form of Compound 1. In another aspect, the present disclosure relates to Compound 1 freebase or a pharmaceutically acceptable salt thereof or a solid state form of Compound 1 for use in treatment of a condition selected from the group consisting of rheumatoid arthritis, multiple sclerosis, experimental allergic encephalomyelitis, systemic lupus erythematosus, Crohn's disease, atopic dermatitis, vasculitis, cardiomyopathy, psoriasis, Reiter's syndrome, glomerulonephritis, ulcerative colitis, allergic asthma, insulin-dependent diabetes, peripheral neuropathy, uveitis, fibrosing alveolitis, type I diabetes, juvenile diabetes, juvenile arthritis, Castleman disease, neutropenia, endometriosis, autoimmune thyroid disease, sperm and testicular autoimmunity, scleroderma, axonal and neuronal neuropathies, allergic rhinitis, Sjogren's syndrome, hemolytic anemia, Graves' disease, Hashimoto's thyroiditis, IgA nephropathy, amyloidosis, ankylosing spondylitis, Behcet's disease, sarcoidosis, vesiculobullous dermatosis, myositis, primary biliary cirrhosis, polymyalgia rheumatica, autoimmune immunodeficiency, Chagas disease, Kawasaki syndrome, psoriatic arthritis, celiac sprue, myasthenia gravis, autoimmune myocarditis, POEMS syndrome, and chronic fatigue syndrome in a subject, particularly in a human subject suffering from or susceptible to the condition, the use comprising administering to the subject a therapeutically effective amount of Compound 1 freebase or a pharmaceutically acceptable salt thereof or a solid state form of Compound 1. In one aspect, the solid state form is the Amorphous Freebase. In another aspect, the solid state form is the Freebase Hydrate Form B. In another aspect, the solid state form is the Freebase Hydrate Form C. In another aspect, the solid state form is the Tartrate Hydrate. In another aspect, the solid state form is the Freebase Anhydrate Form D.

In one embodiment, the present disclosure relates to methods of treating a condition selected from the group consisting of rheumatoid arthritis (including moderate to severe rheumatoid arthritis), systemic lupus erythematosus, multiple sclerosis, Crohn's disease (including moderate to severe Crohn's disease), psoriasis (including moderate to severe chronic plaque psoriasis), ulcerative colitis (including moderate to severe ulcerative colitis), ankylosing spondylitis, psoriatic arthritis, juvenile idiopathic arthritis (including moderate to severe polyarticular juvenile idiopathic arthritis), diabetic nephropathy, dry eye syndrome, Sjogren's syndrome, alopecia areata, vitiligo, and atopic dermatitis in a subject, wherein the method comprises administering to the subject, particularly a human subject suffering from or susceptible to the condition, a therapeutically effective amount of Compound 1 freebase or a pharmaceutically acceptable salt thereof or a solid state form of Compound 1. In another aspect, the present disclosure relates to Compound 1 freebase or a pharmaceutically acceptable salt thereof or a solid state form of Compound 1 for use in treatment of a condition selected from the group consisting of rheumatoid arthritis (including moderate to severe rheumatoid arthritis), systemic lupus erythematosus, multiple sclerosis, Crohn's disease (including moderate to severe Crohn's disease), psoriasis (including moderate to severe chronic plaque psoriasis), ulcerative colitis (including moderate to severe ulcerative colitis), ankylosing spondylitis, psoriatic arthritis, juvenile idiopathic arthritis (including moderate to severe polyarticular juvenile idiopathic arthritis), diabetic nephropathy, dry eye syndrome, Sjogren's syndrome, alopecia areata, vitiligo, and atopic dermatitis in a subject, particularly in a human subject suffering from or susceptible to the condition, the use comprising administering to the subject a therapeutically effective amount of Compound 1 freebase or a pharmaceutically acceptable salt thereof or a solid state form of Compound 1. In one aspect, the solid state form is the Amorphous Freebase. In another aspect, the solid state form is the Freebase Hydrate Form B. In another aspect, the solid state form is the Freebase Hydrate Form C. In another aspect, the solid state form is the Tartrate Hydrate. In another aspect, the solid state form is the Freebase Anhydrate Form D.

In one embodiment, the present disclosure relates to methods of treating a condition selected from the group consisting of an ocular condition, systemic inflammatory response syndrome, juvenile rheumatoid arthritis, systemic onset juvenile rheumatoid arthritis, type III hypersensitivity reactions, type IV hypersensitivity, inflammation of the aorta, iridocyclitis/uveitis/optic neuritis, juvenile spinal muscular atrophy, diabetic retinopathy or microangiopathy, chronic inflammation, ulcerative colitis, inflammatory bowel disease, allergic diseases, dermatitis scleroderma, acute or chronic immune disease associated with organ transplantation, psoriatic arthropathy, ulcerative colitic arthropathy, autoimmune bullous disease, autoimmune haemolytic anaemia, rheumatoid arthritis associated interstitial lung disease, systemic lupus erythematosus associated lung disease, dermatomyositis/polymyositis associated lung disease, Sjögren's syndrome/disease associated lung disease, ankylosing spondylitis and ankylosing spondylitis-associated lung disease, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, psoriasis type 1, psoriasis type 2, plaque psoriasis, moderate to severe chronic plaque psoriasis, autoimmune neutropenia, sperm autoimmunity, multiple sclerosis (all subtypes), acute rheumatic fever, rheumatoid spondylitis, Sjögren's syndrome, and autoimmune thrombocytopaenia in a subject, wherein the method comprises administering to the subject, particularly a human subject suffering from or susceptible to the condition, a therapeutically effective amount of Compound 1 freebase or a pharmaceutically acceptable salt thereof or a solid state form of Compound 1. In another aspect, the present disclosure relates to Compound 1 freebase or a pharmaceutically acceptable salt thereof or a solid state form of Compound 1 for use in treatment of a condition selected from the group consisting of an ocular condition, systemic inflammatory response syndrome, juvenile rheumatoid arthritis, systemic onset juvenile rheumatoid arthritis, type III hypersensitivity reactions, type IV hypersensitivity, inflammation of the aorta, iridocyclitis/uveitis/optic neuritis, juvenile spinal muscular atrophy, diabetic retinopathy or microangiopathy, chronic inflammation, ulcerative colitis, inflammatory bowel disease, allergic diseases, dermatitis scleroderma, acute or chronic immune disease associated with organ transplantation, psoriatic arthropathy, ulcerative colitic arthropathy, autoimmune bullous disease, autoimmune haemolytic anaemia, rheumatoid arthritis associated interstitial lung disease, systemic lupus erythematosus associated lung disease, dermatomyositis/polymyositis associated lung disease, Sjögren's syndrome/disease associated lung disease, ankylosing spondylitis and ankylosing spondylitis-associated lung disease, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, psoriasis type 1, psoriasis type 2, plaque psoriasis, moderate to severe chronic plaque psoriasis, autoimmune neutropenia, sperm autoimmunity, multiple sclerosis (all subtypes), acute rheumatic fever, rheumatoid spondylitis, Sjögren's syndrome, and autoimmune thrombocytopaenia in a subject, particularly in a human subject suffering from or susceptible to the condition, the use comprising administering to the subject a therapeutically effective amount of Compound 1 freebase or a pharmaceutically acceptable salt thereof or a solid state form of Compound 1. In one aspect, the solid state form is the Amorphous Freebase. In another aspect, the solid state form is the Freebase Hydrate Form B. In another aspect, the solid state form is the Freebase Hydrate Form C. In another aspect, the solid state form is the Tartrate Hydrate. In another aspect, the solid state form is the Freebase Anhydrate Form D.

In one embodiment, the present disclosure relates to methods of treating a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis, and systemic lupus erythematosus in a subject, wherein the method comprises administering to the subject a therapeutically effective amount of Compound 1 freebase or a pharmaceutically acceptable salt thereof or a solid state form of Compound 1. In another aspect, the present disclosure relates to Compound 1 freebase or a pharmaceutically acceptable salt thereof or a solid state form of Compound 1 for use in treatment of a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis, and systemic lupus erythematosus in a subject, particularly in a human subject suffering from or susceptible to the condition, the use comprising administering to the subject a therapeutically effective amount of Compound 1 freebase or a solid state form of Compound 1. In one aspect, the solid state form is the Amorphous Freebase. In another aspect, the solid state form is the Freebase Hydrate Form B. In another aspect, the solid state form is the Freebase Hydrate Form C. In another aspect, the solid state form is the Tartrate Hydrate. In another aspect, the solid state form is the Freebase Anhydrate Form D.

In one embodiment, the present disclosure relates to methods of treating a condition selected from the group consisting of rheumatoid arthritis, Crohn's disease, ankylosing spondylitis, psoriatic arthritis, psoriasis, ulcerative colitis, systemic lupus erythematosus, lupus nephritis, diabetic nephropathy, dry eye syndrome, Sjogren's syndrome, alopecia areata, vitiligo, and atopic dermatitis in a subject, wherein the method comprises administering to the subject a therapeutically effective amount of Compound 1 freebase or a pharmaceutically acceptable salt thereof or a solid state form of Compound 1. In another aspect, the present disclosure relates to Compound 1 freebase or a pharmaceutically acceptable salt thereof or a solid state form of Compound 1 for use in treatment of a condition selected from the group consisting of rheumatoid arthritis, Crohn's disease, ankylosing spondylitis, psoriatic arthritis, psoriasis, ulcerative colitis, systemic lupus erythematosus, lupus nephritis, diabetic nephropathy, dry eye syndrome, Sjogren's syndrome, alopecia areata, vitiligo, and atopic dermatitis in a subject, particularly in a human subject suffering from or susceptible to the condition, the use comprising administering to the subject a therapeutically effective amount of Compound 1 freebase or a pharmaceutically acceptable salt thereof or a solid state form of Compound 1. In one aspect, the solid state form is the Amorphous Freebase. In another aspect, the solid state form is the Freebase Hydrate Form B. In another aspect, the solid state form is the Freebase Hydrate Form C. In another aspect, the solid state form is the Tartrate Hydrate. In another aspect, the solid state form is the Freebase Anhydrate Form D.

In one embodiment, the present disclosure relates to methods of treating arthritis in a subject, wherein the method comprises administering to the subject a therapeutically effective amount of Compound 1 freebase or a pharmaceutically acceptable salt thereof or a solid state form of Compound 1. In another aspect, the present disclosure relates to Compound 1 freebase or a pharmaceutically acceptable salt thereof or a solid state form of Compound 1 for use in treatment of arthritis in a subject, particularly in a human subject suffering from or susceptible to arthritis, the use comprising administering to the subject a therapeutically effective amount of Compound 1 freebase or a pharmaceutically acceptable salt thereof or a solid state form of Compound 1. In one aspect, the arthritis is selected from the group consisting of rheumatoid arthritis, juvenile idiopathic arthritis, and psoriatic arthritis. In another aspect, the arthritis is rheumatoid arthritis. In another aspect, the arthritis is juvenile idiopathic arthritis. In another aspect, the arthritis is psoriatic arthritis. In another aspect, the solid state form is the Amorphous Freebase. In another aspect, the solid state form is the Freebase Hydrate Form B. In another aspect, the solid state form is the Freebase Hydrate Form C. In another aspect, the solid state form is the Tartrate Hydrate. In another aspect, the solid state form is the Freebase Anhydrate Form D. In another aspect, the solid state form is the Freebase Solvate Form A. In another aspect, the solid state form is the Hydrochloride Solvate form AA. In another aspect, the solid state form is the Hydrochloride Solvate Form BB. In another aspect, the solid state form is the Hydrochloride Solvate Form CC. In another aspect, the solid state form is the L-Maleate Form AAA. In another aspect, the solid state form is the L-Maleate Form BBB.

In one embodiment, the present disclosure relates to methods of treating a spondyloarthropathy in a subject, wherein the method comprises administering to the subject a therapeutically effective amount of Compound 1 freebase or a pharmaceutically acceptable salt thereof or a solid state form of Compound 1. In another aspect, the present disclosure relates to Compound 1 freebase or a pharmaceutically acceptable salt thereof or a solid state form of Compound 1 for use in treatment of spondyloarthropathy, particularly in a human subject suffering from or susceptible to spondyloarthropathy, the use comprising administering to the subject a therapeutically effective amount of Compound 1 freebase or a pharmaceutically acceptable salt thereof or a solid state form of Compound 1. In one aspect, the spondyloarthropathy is ankylosing spondylitis. In another aspect, the solid state form is the Amorphous Freebase. In another aspect, the solid state form is the Freebase Hydrate Form B. In another aspect, the solid state form is the Freebase Hydrate Form C. In another aspect, the solid state form is the Tartrate Hydrate. In another aspect, the solid state form is the Freebase Anhydrate Form D. In another aspect, the solid state form is the Freebase Solvate Form A. In another aspect, the solid state form is the Hydrochloride Solvate form AA. In another aspect, the solid state form is the Hydrochloride Solvate Form BB. In another aspect, the solid state form is the Hydrochloride Solvate Form CC. In another aspect, the solid state form is the L-Maleate Form AAA. In another aspect, the solid state form is the L-Maleate Form BBB.

In one embodiment, the present disclosure relates to methods of treating a gastrointestinal condition in a subject, wherein the method comprises administering to the subject a therapeutically effective amount of Compound 1 freebase or a pharmaceutically acceptable salt thereof or a solid state form of Compound 1. In another aspect, the present disclosure relates to Compound 1 freebase or a pharmaceutically acceptable salt thereof or a solid state form of Compound 1 for use in treatment of a gastrointestinal condition, particularly in a human subject suffering from or susceptible to a gastrointestinal condition, the use comprising administering to the subject a therapeutically effective amount of Compound 1 freebase or a pharmaceutically acceptable salt thereof or a solid state form of Compound 1. In one aspect, the gastrointestinal condition is selected from the group consisting of Crohn's disease and ulcerative colitis. In another aspect, the gastrointestinal condition is Crohn's disease. In another aspect, the gastrointestinal condition is ulcerative colitis. In another aspect, the solid state form is the Amorphous Freebase. In another aspect, the solid state form is the Freebase Hydrate Form B. In another aspect, the solid state form is the Freebase Hydrate Form C. In another aspect, the solid state form is the Tartrate Hydrate. In another aspect, the solid state form is the Freebase Anhydrate Form D. In another aspect, the solid state form is the Freebase Solvate Form A. In another aspect, the solid state form is the Hydrochloride Solvate form AA. In another aspect, the solid state form is the Hydrochloride Solvate Form BB. In another aspect, the solid state form is the Hydrochloride Solvate Form CC. In another aspect, the solid state form is the L-Maleate Form AAA. In another aspect, the solid state form is the L-Maleate Form BBB.

In one embodiment, the present disclosure relates to methods of treating a skin condition, wherein the method comprises administering to the subject a therapeutically effective amount of Compound 1 freebase or a pharmaceutically acceptable salt thereof or a solid state form of Compound 1. In another aspect, the present disclosure relates to Compound 1 freebase or a pharmaceutically acceptable salt thereof or a solid state form of Compound 1 for use in treatment of a skin condition, particularly in a human subject suffering from or susceptible to a skin condition, the use comprising administering to the subject a therapeutically effective amount of Compound 1 freebase or a pharmaceutically acceptable salt thereof or a solid state form of Compound 1. In one aspect, the skin condition is selected from the group consisting of psoriasis, plaque psoriasis, nail psoriasis, and hidradenitis suppurativa. In another aspect, the skin condition is psoriasis. In another aspect, the skin condition is plaque psoriasis. In another aspect, the skin condition is nail psoriasis. In another aspect, the skin condition is hidradenitis suppurativa. In another aspect, the skin condition is atopic dermatitis. In another aspect, the solid state form is the Amorphous Freebase. In another aspect, the solid state form is the Freebase Hydrate Form B. In another aspect, the solid state form is the Freebase Hydrate Form C. In another aspect, the solid state form is the Tartrate Hydrate. In another aspect, the solid state form is the Freebase Anhydrate Form D. In another aspect, the solid state form is the Freebase Solvate Form A. In another aspect, the solid state form is the Hydrochloride Solvate form AA. In another aspect, the solid state form is the Hydrochloride Solvate Form BB. In another aspect, the solid state form is the Hydrochloride Solvate Form CC. In another aspect, the solid state form is the L-Maleate Form AAA. In another aspect, the solid state form is the L-Maleate Form BBB.

The therapeutically effective dose level for any particular subject will depend upon the specific situation and can depend upon a variety of factors including the type, age, weight, sex, diet, and condition of the subject being treated; the severity of the pathological condition; activity of the specific compound employed; the specific composition employed; the age, body weight, general health, sex and diet of the subject; the route of administration; the duration of the treatment; pharmacological considerations, such as the activity, efficacy, pharmacokinetic, and toxicology profiles of the particular compound or salt used; whether a drug delivery system is utilized; drugs used in combination or coincidental with the specific compound employed; and like factors well-known in the medical arts. An ordinarily skilled physician provided with the disclosure of the present application will be able to determine appropriate dosages and regimens for administration of the therapeutic agent to the subject, and to adjust such dosages and regimens as necessary during the course of treatment, in accordance with methods well-known in the therapeutic arts. It is well within the skill of the art to start doses of the compound at levels lower than required to achieve the desired therapeutic effect and to gradually increase the dosage until the desired effect is achieved. Thus, the dosage regimen actually employed can vary widely, and therefore, can derive from the preferred dosage regimen set forth below.

The total daily dose of the solid state form (administered in single or divided doses) typically is from about 0.001 to about 100 mg/kg, or from about 0.001 to about 30 mg/kg, or from about 0.001 to about 15 mg/kg. In another embodiment, the total daily dose is from about 0.01 to about 10 mg/kg (i.e., mg of the compound or salt per kg body weight). Dosage unit compositions can contain such amounts or submultiples thereof to make up the daily dose. In many instances, the administration of the compound or salt will be repeated a plurality of times. Multiple doses per day typically may be used to increase the total daily dose, if desired.

In one embodiment, the daily dose of the solid state form administered to the subject is from about 0.01 mg to about 3000 mg. In one aspect, the daily dose is from about 0.1 mg to about 1000 mg. In another aspect, the daily dose is from is from about 1 mg to about 500 mg. In another aspect, the daily dose is from about 1 mg to about 250 mg. In another aspect, the daily dose is from about 1 mg to about 100 mg. In another aspect, the daily dose is from about 1 mg to about 50 mg. In another aspect, the daily dose is from about 1 mg to about 45 mg. In another aspect, the daily dose is from about 1 mg to about 30 mg. In another aspect, the daily dose is from about 1 mg to about 25 mg. In another aspect, the daily dose is from about 1 mg to about 24 mg. In another aspect, the daily dose is from about 1 mg to about 15 mg. In another aspect, the daily dose is from about 1 mg to about 7.5 mg. In another aspect, the daily dose is from about 25 mg to about 50 mg. In another aspect, the daily dose is from about 1 mg to about 10 mg. In another aspect, the daily dose is from about 10 mg to about 20 mg. In another aspect, the daily dose is from about 20 mg to about 30 mg. In another aspect, the daily dose is from about 30 mg to about 40 mg. In another aspect, the daily dose is from about 7.5 mg to about 45 mg. In another aspect, the daily dose is from about 15 mg to about 30 mg. In another aspect, the daily dose is about 3 mg. In another aspect, the daily dose is about 6 mg. In another aspect, the daily dose is about 7.5 mg. In another aspect, the daily dose is about 12 mg. In another aspect, the daily dose is about 15 mg. In another aspect, the daily dose is about 18 mg. In another aspect, the daily dose is about 24 mg. In another aspect, the daily dose is about 30 mg. In another aspect, the daily dose is about 36 mg. In another aspect, the daily dose is about 45 mg.

In one embodiment, a dose of about 3 mg, about 6 mg, about 12 mg, or about 24 mg per unit dosage form (e.g., per tablet or capsule) of a solid state form of Compound 1 is administered orally BID (twice daily) in equal amounts (e.g., twice a day, about 3 mg each time) to a human subject.

In one embodiment, the disclosure relates to a method of treating a subject having rheumatoid arthritis, the method comprising administering to the subject about 3 mg, per unit dosage form (e.g., per tablet or capsule) of a solid state form of Compound 1 orally BID (twice daily) in equal amounts (e.g., twice a day, about 3 mg each time). In another aspect, the present disclosure relates a solid state form of Compound 1 for use in treating rheumatoid arthritis in a subject, particularly in a human subject suffering from or susceptible to rheumatoid arthritis, the use comprising administering to the subject about 3 mg, per unit dosage form (e.g., per tablet or capsule) of a solid state form of Compound 1 orally BID (twice daily) in equal amounts (e.g., twice a day, about 3 mg each time).

In one embodiment, the disclosure relates to a method of treating a subject having rheumatoid arthritis, the method comprising administering to the subject about 6 mg, per unit dosage form (e.g., per tablet or capsule) of a solid state form of Compound 1 orally BID (twice daily) in equal amounts (e.g., twice a day, about 6 mg each time). In another aspect, the present disclosure relates a solid state form of Compound 1 for use in treating rheumatoid arthritis in a subject, particularly in a human subject suffering from or susceptible to rheumatoid arthritis, the use comprising administering to the subject about 6 mg, per unit dosage form (e.g., per tablet or capsule) of a solid state form of Compound 1 orally BID (twice daily) in equal amounts (e.g., twice a day, about 6 mg each time).

In one embodiment, the disclosure relates to a method of treating a subject having rheumatoid arthritis, the method comprising administering to the subject about 12 mg, per unit dosage form (e.g., per tablet or capsule) of a solid state form of Compound 1 orally BID (twice daily) in equal amounts (e.g., twice a day, about 12 mg each time). In another aspect, the present disclosure relates a solid state form of Compound 1 for use in treating rheumatoid arthritis in a subject, particularly in a human subject suffering from or susceptible to rheumatoid arthritis, the use comprising administering to the subject about 12 mg, per unit dosage form (e.g., per tablet or capsule) of a solid state form of Compound 1 orally BID (twice daily) in equal amounts (e.g., twice a day, about 12 mg each time).

In one embodiment, the disclosure relates to a method of treating a subject having rheumatoid arthritis, the method comprising administering to the subject about 24 mg, per unit dosage form (e.g., per tablet or capsule) of a solid state form of Compound 1 orally BID (twice daily) in equal amounts (e.g., twice a day, about 24 mg each time). In another aspect, the present disclosure relates a solid state form of Compound 1 for use in treating rheumatoid arthritis in a subject, particularly in a human subject suffering from or susceptible to rheumatoid arthritis, the use comprising administering to the subject about 24 mg, per unit dosage form (e.g., per tablet or capsule) of a solid state form of Compound 1 orally BID (twice daily) in equal amounts (e.g., twice a day, about 24 mg each time).

In another embodiment, the methods or uses comprise administering orally QD (once daily) to a human subject a dose of about 7.5 mg per unit dosage form (e.g., per tablet or capsule) of Compound 1 freebase or a pharmaceutically acceptable salt thereof.

In another embodiment, the methods or uses comprise administering orally QD (once daily) to a human subject a dose of about 7.5 mg per unit dosage form (e.g., per tablet or capsule) of a solid state form of Compound 1. In one embodiment, the methods or uses comprise administering orally QD (once daily) to a human subject a solid state form of Compound 1 in an amount sufficient to deliver 7.5 mg per unit dosage form (e.g., per tablet or capsule) of Compound 1 freebase equivalent to the subject. In one embodiment, the solid state form is the Amorphous Freebase. In one embodiment, the solid state form is the Freebase Hydrate Form B. In one embodiment, the solid state form is the Freebase Hydrate Form C. In one embodiment, the solid state form is the Tartrate Hydrate. In another aspect, the solid state form is the Freebase Anhydrate Form D.

In another embodiment, the methods or uses comprise administering orally QD (once daily) to a human subject a dose of about 15 mg per unit dosage form (e.g., per tablet or capsule) of Compound 1 freebase or a pharmaceutically acceptable salt thereof.

In another embodiment, the methods or uses comprise administering orally QD (once daily) to a human subject a dose of about 15 mg per unit dosage form (e.g., per tablet or capsule) of a solid state form of Compound 1. In one embodiment, the methods or uses comprise administering orally QD (once daily) to a human subject a solid state form of Compound 1 in an amount sufficient to deliver 15 mg per unit dosage form (e.g., per tablet or capsule) of Compound 1 freebase equivalent to the subject. In one embodiment, the solid state form is the Amorphous Freebase. In one embodiment, the solid state form is the Freebase Hydrate Form B. In one embodiment, the solid state form is the Freebase Hydrate Form C. In one embodiment, the solid state form is the Tartrate Hydrate. In another aspect, the solid state form is the Freebase Anhydrate Form D.

In another embodiment, the methods or uses comprise administering orally QD (once daily) to a human subject a dose of about 24 mg of Compound 1 freebase or a pharmaceutically acceptable salt thereof. The 24 mg QD dose of Compound 1 freebase or a pharmaceutically acceptable salt thereof may be administered as either a single dosage form comprising about 24 mg per unit dosage form (e.g., per tablet or capsule) of Compound 1 freebase or a pharmaceutically acceptable salt thereof, or two dosage forms comprising about 12 mg per unit dosage form (e.g., per tablet or capsule) of Compound 1 freebase or a pharmaceutically acceptable salt thereof administered simultaneously.

In another embodiment, the methods or uses comprise administering orally QD (once daily) to a human subject a dose of about 24 mg of a solid state form of Compound 1. In one embodiment, the methods or uses comprise administering orally QD (once daily) to a human subject a solid state form of Compound 1 in an amount sufficient to deliver 24 mg of Compound 1 freebase equivalent to the subject. The 24 mg QD dose of the solid state form of Compound 1 may be administered as either a single dosage form comprising about 24 mg per unit dosage form (e.g., per tablet or capsule) of the solid state form of Compound 1, or two dosage forms comprising about 12 mg per unit dosage form (e.g., per tablet or capsule) of the solid state form of Compound 1 administered simultaneously. In one embodiment, the solid state form is the Amorphous Freebase. In one embodiment, the solid state form is the Freebase Hydrate Form B. In one embodiment, the solid state form is the Freebase Hydrate Form C. In one embodiment, the solid state form is the Tartrate Hydrate. In another aspect, the solid state form is the Freebase Anhydrate Form D.

In another embodiment, the methods or uses comprise administering orally QD (once daily) to a human subject a dose of about 30 mg per unit dosage form (e.g., per tablet or capsule) of Compound 1 freebase or a pharmaceutically acceptable salt thereof.

In another embodiment, the methods or uses comprise administering orally QD (once daily) to a human subject a dose of about 30 mg per unit dosage form (e.g., per tablet or capsule) of a solid state form of Compound 1. In one embodiment, the methods or uses comprise administering orally QD (once daily) to a human subject a solid state form of Compound 1 in an amount sufficient to deliver 30 mg per unit dosage form (e.g., per tablet or capsule) of Compound 1 freebase equivalent to the subject. In one embodiment, the solid state form is the Amorphous Freebase. In one embodiment, the solid state form is the Freebase Hydrate Form B. In one embodiment, the solid state form is the Freebase Hydrate Form C. In one embodiment, the solid state form is the Tartrate Hydrate. In another aspect, the solid state form is the Freebase Anhydrate Form D.

In another embodiment, the methods or uses comprise administering orally QD (once daily) to a human subject a dose of about 36 mg per unit dosage form (e.g., per tablet or capsule) of Compound 1 freebase or a pharmaceutically acceptable salt thereof.

In another embodiment, the methods or uses comprise administering orally QD (once daily) to a human subject a dose of about 36 mg per unit dosage form (e.g., per tablet or capsule) of a solid state form of Compound 1. In one embodiment, the methods or uses comprise administering orally QD (once daily) to a human subject a solid state form of Compound 1 in an amount sufficient to deliver 36 mg per unit dosage form (e.g., per tablet or capsule) of Compound 1 freebase equivalent to the subject. In one embodiment, the solid state form is the Amorphous Freebase. In one embodiment, the solid state form is the Freebase Hydrate Form B. In one embodiment, the solid state form is the Freebase Hydrate Form C. In one embodiment, the solid state form is the Tartrate Hydrate. In another aspect, the solid state form is the Freebase Anhydrate Form D.

In another embodiment, the methods or uses comprise administering orally QD (once daily) to a human subject a dose of about 45 mg per unit dosage form (e.g., per tablet or capsule) of Compound 1 freebase or a pharmaceutically acceptable salt thereof.

In another embodiment, the methods or uses comprise administering orally QD (once daily) to a human subject a dose of about 45 mg per unit dosage form (e.g., per tablet or capsule) of a solid state form of Compound 1. In one embodiment, the methods or uses comprise administering orally QD (once daily) to a human subject a solid state form of Compound 1 in an amount sufficient to deliver 45 mg per unit dosage form (e.g., per tablet or capsule) of Compound 1 freebase equivalent to the subject. In one embodiment, the solid state form is the Amorphous Freebase. In one embodiment, the solid state form is the Freebase Hydrate Form B. In one embodiment, the solid state form is the Freebase Hydrate Form C. In one embodiment, the solid state form is the Tartrate Hydrate. In another aspect, the solid state form is the Freebase Anhydrate Form D.

In certain embodiments, Compound 1 freebase or a pharmaceutically acceptable salt thereof and/or solid state forms thereof can be used to treat rheumatoid arthritis (RA), including reducing signs and symptoms of RA, inducing a major clinical response, inhibiting the progression of or treating structural damage associated with RA, and improving physical function in adult subjects, such as adult subjects with moderately to severely active RA. In one embodiment, Compound 1 freebase or a pharmaceutically acceptable salt thereof and/or solid state forms thereof are used to treat RA in adult subjects. In one embodiment, Compound 1 freebase or a pharmaceutically acceptable salt thereof and/or solid state forms thereof are used to reduce signs and symptoms of RA in adult subjects. In one embodiment, Compound 1 freebase or a pharmaceutically acceptable salt thereof and/or solid state forms thereof induce a major clinical response in adult subjects with RA. In one embodiment, Compound 1 freebase or a pharmaceutically acceptable salt thereof and/or solid state forms thereof are used to inhibit the progression of structural damage associated with RA in adult subjects. In one embodiment, Compound 1 freebase and/or solid state forms thereof are used to treat structural damage associated with RA in adult subjects. In one embodiment, Compound 1 freebase or a pharmaceutically acceptable salt thereof and/or solid state forms thereof are used to improve physical function in adult subjects. In one embodiment, the adult subjects have RA. In another embodiment, the adult subjects have moderately to severely active RA.

Compound 1 freebase or a pharmaceutically acceptable salt thereof or solid state forms thereof may be used alone, or in combination with methotrexate or other non-biologic disease-modifying anti-rheumatic drugs (DMARDs), and/or in combination with anti-TNFα biological agents, such as TNF antagonists like chimeric, humanized or human TNF antibodies, adalimumab (such as HUMIRA™ brand adalimumab), infliximab such as CA2 (REMICADE™ brand infliximab), golimumab such as SIMPONI™ (golimumab), certolizumab pegol such as CIMZIA™, tocilizumab such as ACTEMRA™, CDP 571, and soluble p55 or p75 TNF receptors, derivatives, thereof, etanercept such as p75TNFR1gG (ENBREL™ brand etanercept) or p55TNFR1gG (lenercept).

Patients having active rheumatoid arthritis (RA) may be diagnosed according to 1987-revised American College of Rheumatology (ACR) classification criteria or the 2010 ACR/EULAR criteria. In certain embodiments, RA may be diagnosed based on patients having at least 6 swollen and 6 tender joints. In certain embodiments, patients treatable with Compound 1 or solid state forms thereof may include those who have failed therapy with at least one (e.g., at least one but no more than four) DMARDs and/or have inadequate response to methotrexate, adalimumab, infliximab, etanercept, or other anti-TNFα biological agents, or non-anti-TNF biologics.

In certain embodiments, Compound 1 freebase or a pharmaceutically acceptable salt thereof or solid state forms thereof halt disease progression, and/or relieves at least a symptom of the disease, which may be detected or monitored by X-ray results, including radiographic progression of joint damage.

In certain embodiments, therapeutic efficacy can be measured by improvements in ACR20, ACR50, and/or ACR70, either in individual patients or a population of patients in need of treatment. In certain embodiments, statistically significant improvement (as compared placebo or untreated control) over a treatment period (e.g., 1 week, 2 weeks, 4 weeks, 6 weeks, 8 weeks, 12 weeks, 2 months, 3 months, 6 months, 1 year, 2 years, 5 years, 10 years or more) in one or more of the ACR criteria is achieved. Statistical significance is manifested by a p value of less than 0.05, or less than 0.01.

Components of the ACR responses are well known in the art, and may include the median number of tender joints, the median number of swollen joints, physician global assessment such as one measured by visual analog scale (VAS), patient global assessment such as one measured by visual analog scale, pain such as one measured by visual analog scale, disability index of the Health Assessment Questionnaire (HAQ-DI score), and C-reactive protein (CRP) (mg/dL).

In certain embodiments, an ACR20 response is determined based on a 20% or greater improvement in tender joint count (TJC) and swollen joint count (SJC) and greater than or equal to 3 of the 5 measures of Patient's Assessment of Pain (VAS), Patient's Global Assessment of Disease Activity (VAS), Physician's Global Assessment of Disease Activity (VAS), HAQ-DI, or high sensitivity C-reactive protein (hsCRP). In some embodiments, an ACR50 response is determined based on a 50% or greater improvement in TJC and SJC and greater than or equal to 3 of the 5 measures of Patient's Assessment of Pain (VAS), Patient's Global Assessment of Disease Activity (VAS), Physician's Global Assessment of Disease Activity (VAS), HAQ-DI, or hsCRP. An ACR70 response is determined based on a 70% or greater improvement in TJC and SJC and greater than or equal to 3 of the 5 measures of Patient's Assessment of Pain (VAS), Patient's Global Assessment of Disease Activity (VAS), Physician's Global Assessment of Disease Activity (VAS), HAQ-DI, or hsCRP. In certain embodiments, the ACR20, ACR50, or ACR70 response occurs by week 12 of treatment.

In certain embodiments, a DAS28 (disease activity score based on the 28 joints examined) score is determined as a composite score derived from four of the following measures: examination of joints for swelling and tenderness, global scores of pain and overall status, blood markers of inflammation (e.g. ESR (erythrocyte sedimentation rate) and CRP (C reactive protein), referred to herein as DAS28 (CRP)), questionnaires (e.g. the HAQ (health assessment questionnaire) which assess function) and X-rays and other imaging techniques such as ultrasound and MRI.

In certain embodiments, structural joint damage can be assessed radiographically and expressed as change in Total Sharp Score (TSS) and its components, the erosion score and Joint Space Narrowing (JSN) score, for example, at week 12 compared to baseline, or at week 24 as compared to baseline.

In certain embodiments, improvement in signs and symptoms of the disease can be measured by patient physical function response, such as disability index of Health Assessment Questionnaire (HAQ-DI), and/or the health-outcomes as assessed by The Short Form Health Survey (SF 36). In one embodiment, improvement in signs and symptoms of the disease is measured by HAQ-DI, including the minimal clinically important difference (MCID) of −0.22. Improvement can also be measured by one or both of Physical Component Summary (PCS) and the Mental Component Summary (MCS). Improvements can further be measured by Work Instability Scale for RA (RA-WIS) (see Gilworth et al., Arthritis & Rheumatism (Arthritis Care & Research) 49(3): 349-354, 2003, incorporated by reference).

In one embodiment, the disclosure relates to a method of treating rheumatoid arthritis in a subject, the method comprising administering to the subject, particularly a human subject suffering from or susceptible to rheumatoid arthritis, about 7.5 mg, per unit dosage form (e.g., per tablet or capsule) of Compound 1 freebase or a pharmaceutically acceptable salt thereof orally QD (once daily). In another aspect, the present disclosure relates to Compound 1 freebase or a pharmaceutically acceptable salt thereof for use in treatment of rheumatoid arthritis in a subject, particularly in a human subject suffering from or susceptible to rheumatoid arthritis, the use comprising administering to the subject about 7.5 mg, per unit dosage form (e.g., per tablet or capsule) of Compound 1 freebase or a pharmaceutically acceptable salt thereof orally QD (once daily). In one embodiment, the subject has moderately to severely active rheumatoid arthritis. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 7.5 mg, per unit dosage form (e.g., per tablet or capsule) of a solid state form of Compound 1 orally QD (once daily). In one embodiment, the method comprising administering to the subject a solid state form of Compound 1 orally QD (once daily) in an amount sufficient to deliver 7.5 mg, per unit dosage form (e.g., per tablet or capsule) of Compound 1 freebase equivalent to the subject. In another aspect, the present disclosure relates to a solid state form of Compound 1 for use in treatment of rheumatoid arthritis in a subject, particularly in a human subject suffering from or susceptible to rheumatoid arthritis, the use comprising administering to the subject about 7.5 mg, per unit dosage form (e.g., per tablet or capsule) of a solid state form of Compound 1 orally QD (once daily). In one embodiment, the solid state form delivers about 7.5 mg, per unit dosage form (e.g., per tablet or capsule) of Compound 1 freebase equivalent to the subject. In one embodiment, the solid state form is the Freebase Hydrate Form B. In one embodiment, the solid state form is the Freebase Hydrate Form C. In one embodiment, the solid state form is the Tartrate Hydrate. In one embodiment, the solid state form is Freebase Anhydrate Form D. In one embodiment, the subject has moderately to severely active rheumatoid arthritis. In another aspect, the solid state form is the Freebase Solvate Form A. In another aspect, the solid state form is the Hydrochloride Solvate form AA. In another aspect, the solid state form is the Hydrochloride Solvate Form BB. In another aspect, the solid state form is the Hydrochloride Solvate Form CC. In another aspect, the solid state form is the L-Maleate Form AAA. In another aspect, the solid state form is the L-Maleate Form BBB. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 15 mg, per unit dosage form (e.g., per tablet or capsule) of Compound 1 freebase or a pharmaceutically acceptable salt thereof orally QD (once daily). In another aspect, the present disclosure relates to Compound 1 freebase or a pharmaceutically acceptable salt thereof for use in treatment of rheumatoid arthritis in a subject, particularly in a human subject suffering from or susceptible to rheumatoid arthritis, the use comprising administering to the subject about 15 mg, per unit dosage form (e.g., per tablet or capsule) of Compound 1 freebase or a pharmaceutically acceptable salt thereof orally QD (once daily). In one embodiment, the subject has moderately to severely active rheumatoid arthritis. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 15 mg, per unit dosage form (e.g., per tablet or capsule) of a solid state form of Compound 1 orally QD (once daily). In one embodiment, the method comprising administering to the subject a solid state form of Compound 1 orally QD (once daily) in an amount sufficient to deliver 15 mg, per unit dosage form (e.g., per tablet or capsule) of Compound 1 freebase equivalent to the subject. In another aspect, the present disclosure relates to a solid state form of Compound 1 for use in treatment of rheumatoid arthritis in a subject, particularly in a human subject suffering from or susceptible to rheumatoid arthritis, the use comprising administering to the subject about 15 mg, per unit dosage form (e.g., per tablet or capsule) of a solid state form of Compound 1 orally QD (once daily). In one embodiment, the solid state form delivers about 15 mg, per unit dosage form (e.g., per tablet or capsule) of Compound 1 freebase equivalent to the subject. In one embodiment, the solid state form is the Freebase Hydrate Form B. In one embodiment, the solid state form is the Freebase Hydrate Form C. In one embodiment, the solid state form is the Tartrate Hydrate. In one embodiment, the solid state form is Freebase Anhydrate Form D. In one embodiment, the subject has moderately to severely active rheumatoid arthritis. In another aspect, the solid state form is the Freebase Solvate Form A. In another aspect, the solid state form is the Hydrochloride Solvate form AA. In another aspect, the solid state form is the Hydrochloride Solvate Form BB. In another aspect, the solid state form is the Hydrochloride Solvate Form CC. In another aspect, the solid state form is the L-Maleate Form AAA. In another aspect, the solid state form is the L-Maleate Form BBB. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 24 mg of Compound 1 freebase or a pharmaceutically acceptable salt thereof orally QD (once daily). In another aspect, the present disclosure relates to Compound 1 freebase or a pharmaceutically acceptable salt thereof for use in treatment of rheumatoid arthritis in a subject, particularly in a human subject suffering from or susceptible to rheumatoid arthritis, the use comprising administering to the subject about 24 mg of Compound 1 freebase or a pharmaceutically acceptable salt thereof orally QD (once daily). The 24 mg dose of Compound 1 freebase or a pharmaceutically acceptable salt thereof may be administered as either a single dosage form comprising about 24 mg per unit dosage form (e.g., per tablet or capsule) of Compound 1 freebase or a pharmaceutically acceptable salt thereof, or two dosage forms comprising about 12 mg per unit dosage form (e.g., per tablet or capsule) of Compound 1 freebase or a pharmaceutically acceptable salt thereof administered simultaneously. In one embodiment, the subject has moderately to severely active rheumatoid arthritis. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 24 mg of a solid state form of Compound 1 orally QD (once daily). In one embodiment, the method comprising administering to the subject a solid state form of Compound 1 orally QD (once daily) in an amount sufficient to deliver 24 mg of Compound 1 freebase equivalent to the subject. In another aspect, the present disclosure relates to a solid state form of Compound 1 for use in treatment of rheumatoid arthritis in a subject, particularly in a human subject suffering from or susceptible to rheumatoid arthritis, the use comprising administering to the subject about 24 mg of a solid state form of Compound 1 orally QD (once daily). In one embodiment, the solid state form delivers about 24 mg of Compound 1 freebase equivalent to the subject. The 24 mg dose of the solid state form of Compound 1 may be administered as either a single dosage form comprising about 24 mg per unit dosage form (e.g., per tablet or capsule) of the solid state form of Compound 1, or two dosage forms comprising about 12 mg per unit dosage form (e.g., per tablet or capsule) of the solid state form of Compound 1 administered simultaneously. In one embodiment, the solid state form is the Freebase Hydrate Form B. In one embodiment, the solid state form is the Freebase Hydrate Form C. In one embodiment, the solid state form is the Tartrate Hydrate. In one embodiment, the solid state form is the Freebase Anhydrate Form D. In another aspect, the solid state form is the Freebase Solvate Form A. In another aspect, the solid state form is the Hydrochloride Solvate form AA. In another aspect, the solid state form is the Hydrochloride Solvate Form BB. In another aspect, the solid state form is the Hydrochloride Solvate Form CC. In another aspect, the solid state form is the L-Maleate Form AAA. In another aspect, the solid state form is the L-Maleate Form BBB. In one embodiment, the subject has moderately to severely active rheumatoid arthritis. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 30 mg, per unit dosage form (e.g., per tablet or capsule) of Compound 1 freebase or a pharmaceutically acceptable salt thereof orally QD (once daily). In another aspect, the present disclosure relates to Compound 1 freebase or a pharmaceutically acceptable salt thereof for use in treatment of rheumatoid arthritis in a subject, particularly in a human subject suffering from or susceptible to rheumatoid arthritis, the use comprising administering to the subject about 30 mg, per unit dosage form (e.g., per tablet or capsule) of Compound 1 freebase or a pharmaceutically acceptable salt thereof orally QD (once daily). In one embodiment, the subject has moderately to severely active rheumatoid arthritis. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 30 mg, per unit dosage form (e.g., per tablet or capsule) of a solid state form of Compound 1 orally QD (once daily). In one embodiment, the method comprising administering to the subject a solid state form of Compound 1 orally QD (once daily) in an amount sufficient to deliver 30 mg, per unit dosage form (e.g., per tablet or capsule) of Compound 1 freebase equivalent to the subject. In another aspect, the present disclosure relates to a solid state form of Compound 1 for use in treatment of rheumatoid arthritis in a subject, particularly in a human subject suffering from or susceptible to rheumatoid arthritis, the use comprising administering to the subject about 30 mg, per unit dosage form (e.g., per tablet or capsule) of a solid state form of Compound 1 orally QD (once daily). In one embodiment, the solid state form delivers about 30 mg, per unit dosage form (e.g., per tablet or capsule) of Compound 1 freebase equivalent to the subject. In one embodiment, the solid state form is the Freebase Hydrate Form B. In one embodiment, the solid state form is the Freebase Hydrate Form C. In one embodiment, the solid state form is the Tartrate Hydrate. In one embodiment, the solid state form is the Freebase Anhydrate Form D. In one embodiment, the subject has moderately to severely active rheumatoid arthritis. In another aspect, the solid state form is the Freebase Solvate Form A. In another aspect, the solid state form is the Hydrochloride Solvate form AA. In another aspect, the solid state form is the Hydrochloride Solvate Form BB. In another aspect, the solid state form is the Hydrochloride Solvate Form CC. In another aspect, the solid state form is the L-Maleate Form AAA. In another aspect, the solid state form is the L-Maleate Form BBB. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 36 mg, per unit dosage form (e.g., per tablet or capsule) of Compound 1 freebase or a pharmaceutically acceptable salt thereof orally QD (once daily). In another aspect, the present disclosure relates to Compound 1 freebase or a pharmaceutically acceptable salt thereof for use in treatment of rheumatoid arthritis in a subject, particularly in a human subject suffering from or susceptible to rheumatoid arthritis, the use comprising administering to the subject about 36 mg, per unit dosage form (e.g., per tablet or capsule) of Compound 1 freebase or a pharmaceutically acceptable salt thereof orally QD (once daily). In one embodiment, the subject has moderately to severely active rheumatoid arthritis. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 36 mg, per unit dosage form (e.g., per tablet or capsule) of a solid state form of Compound 1 orally QD (once daily). In one embodiment, the method comprising administering to the subject a solid state form of Compound 1 orally QD (once daily) in an amount sufficient to deliver 36 mg, per unit dosage form (e.g., per tablet or capsule) of Compound 1 freebase equivalent to the subject. In another aspect, the present disclosure relates to a solid state form of Compound 1 for use in treatment of rheumatoid arthritis in a subject, particularly in a human subject suffering from or susceptible to rheumatoid arthritis, the use comprising administering to the subject about 36 mg, per unit dosage form (e.g., per tablet or capsule) of a solid state form of Compound 1 orally QD (once daily). In one embodiment, the solid state form delivers about 36 mg, per unit dosage form (e.g., per tablet or capsule) of Compound 1 freebase equivalent to the subject. In one embodiment, the solid state form is the Freebase Hydrate Form B. In one embodiment, the solid state form is the Freebase Hydrate Form C. In one embodiment, the solid state form is the Tartrate Hydrate. In one embodiment, the solid state form is the Freebase Anhydrate Form D. In one embodiment, the subject has moderately to severely active rheumatoid arthritis. In another aspect, the solid state form is the Freebase Solvate Form A. In another aspect, the solid state form is the Hydrochloride Solvate form AA. In another aspect, the solid state form is the Hydrochloride Solvate Form BB. In another aspect, the solid state form is the Hydrochloride Solvate Form CC. In another aspect, the solid state form is the L-Maleate Form AAA. In another aspect, the solid state form is the L-Maleate Form BBB. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 45 mg, per unit dosage form (e.g., per tablet or capsule) of Compound 1 freebase or a pharmaceutically acceptable salt thereof orally QD (once daily). In another aspect, the present disclosure relates to Compound 1 freebase or a pharmaceutically acceptable salt thereof for use in treatment of rheumatoid arthritis in a subject, particularly in a human subject suffering from or susceptible to rheumatoid arthritis, the use comprising administering to the subject about 45 mg, per unit dosage form (e.g., per tablet or capsule) of Compound 1 freebase or a pharmaceutically acceptable salt thereof orally QD (once daily). In one embodiment, the subject has moderately to severely active rheumatoid arthritis. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 45 mg, per unit dosage form (e.g., per tablet or capsule) of a solid state form of Compound 1 orally QD (once daily). In one embodiment, the method comprising administering to the subject a solid state form of Compound 1 orally QD (once daily) in an amount sufficient to deliver 45 mg, per unit dosage form (e.g., per tablet or capsule) of Compound 1 freebase equivalent to the subject. In another aspect, the present disclosure relates to a solid state form of Compound 1 for use in treatment of rheumatoid arthritis in a subject, particularly in a human subject suffering from or susceptible to rheumatoid arthritis, the use comprising administering to the subject about 45 mg, per unit dosage form (e.g., per tablet or capsule) of a solid state form of Compound 1 orally QD (once daily). In one embodiment, the solid state form delivers about 45 mg, per unit dosage form (e.g., per tablet or capsule) of Compound 1 freebase equivalent to the subject. In one embodiment, the solid state form is the Freebase Hydrate Form B. In one embodiment, the solid state form is the Freebase Hydrate Form C. In one embodiment, the solid state form is the Tartrate Hydrate. In one embodiment, the solid state form is the Freebase Anhydrate Form D. In one embodiment, the subject has moderately to severely active rheumatoid arthritis. In another aspect, the solid state form is the Freebase Solvate Form A. In another aspect, the solid state form is the Hydrochloride Solvate form AA. In another aspect, the solid state form is the Hydrochloride Solvate Form BB. In another aspect, the solid state form is the Hydrochloride Solvate Form CC. In another aspect, the solid state form is the L-Maleate Form AAA. In another aspect, the solid state form is the L-Maleate Form BBB. In one embodiment, the subject is an adult.

In one embodiment, the disclosure relates to a method of treating moderate to severely active rheumatoid arthritis in an adult subject, particularly in a human subject suffering from or susceptible to moderate to severely active rheumatoid arthritis, the method comprising administering to the subject a therapeutically effective amount of Compound 1 (freebase), or a pharmaceutically acceptable salt thereof or a solid state form of Compound 1. In one embodiment, the method comprises administering to the subject about 7.5 mg or about 15 mg or about 30 mg or about 45 mg, per unit dosage form (e.g., per tablet or capsule) of Compound 1 (freebase), or a pharmaceutically acceptable salt thereof or a solid state form of Compound 1 in an amount sufficient to deliver to the subject about 7.5 mg or about 15 mg or about 30 mg or about 45 mg, per unit dosage form (e.g., per tablet or capsule) of Compound 1 freebase equivalent. In one embodiment, the method comprises administering to the subject about 7.5 mg or about 15 mg or about 30 mg or about 45 mg, per unit dosage form (e.g., per tablet or capsule) of Compound 1 (freebase), or a pharmaceutically acceptable salt thereof or a solid state form of Compound 1. In one embodiment, the Compound 1 (freebase) or a pharmaceutically acceptable salt thereof or the solid state form of Compound 1 is administered to the subject orally QD (once daily). In another aspect, the disclosure relates to Compound 1 freebase or a pharmaceutically acceptable salt thereof or a solid state form of Compound 1 (e.g., a crystalline hydrate or crystalline anhydrate), as described in the present disclosure, for use in treatment of moderate to severely active rheumatoid arthritis in an adult subject, particularly in a human subject suffering from or susceptible to moderate to severely active rheumatoid arthritis, the use comprising administering to the subject a therapeutically effective amount of Compound 1 freebase or a pharmaceutically acceptable salt thereof or a solid state form of Compound 1. In one embodiment, the solid state form is a crystalline hydrate. In one embodiment, the crystalline hydrate is the Freebase Hydrate Form B. In one embodiment, the crystalline hydrate is a hemihydrate. In one embodiment, the hemihydrate is Freebase Hydrate Form C. In one embodiment, the solid state form is a crystalline anhydrate. In one embodiment, the crystalline anhydrate is Freebase Anhydrate Form D. In one embodiment, the solid state form is the Freebase Solvate Form A. In another aspect, the solid state form is the Hydrochloride Solvate form AA. In one embodiment, the solid state form is the Hydrochloride Solvate Form BB. In one embodiment, the solid state form is the Hydrochloride Solvate Form CC. In one embodiment, the solid state form is the L-Maleate Form AAA. In one embodiment, the solid state form is the L-Maleate Form BBB. In one embodiment, the Compound 1 (freebase) or a pharmaceutically acceptable salt thereof or the solid state form of Compound 1 is in a once daily extended release formulation. In one embodiment, the formulation delivers about 7.5 mg or about 15 mg or about 30 mg or about 45 mg per unit dosage form (e.g., per tablet or capsule) of Compound 1 (freebase equivalent) or a solid state form of Compound 1 orally QD (once daily).

In one embodiment, the subject having moderate to severely active rheumatoid arthritis has, prior to treatment, at least one of the following identifying characteristics: at least 6 swollen joints (based on 66 joint counts), at least 6 tender joints (based on 68 joint counts), high-sensitivity C-reactive protein (hsCRP) greater than the upper limit of normal (ULN), or positive test results for both rheumatoid factor (RF) and anti-cyclic citrullinated peptide (CCP). In one embodiment, the subject having moderate to severely active rheumatoid arthritis has, prior to treatment, at least 6 swollen joints (based on 66 joint counts) and at least 6 tender joints (based on 68 joint counts). Methods for assessing tender and swollen joints are known, and described in, for example, Scott, et al., Clinical and Experimental Rheumatology, 2014, Vol. 32 (Supp. 85), S7-S12.

Thus, in another embodiment, the present disclosure is directed to a method of treating moderate to severely active rheumatoid arthritis in an adult subject, particularly in a human subject suffering from or susceptible to moderate to severely active rheumatoid arthritis, the method comprising administering to the subject a therapeutically effective amount of Compound 1 (freebase), or a pharmaceutically acceptable salt thereof or a solid state form of Compound 1 (e.g., a crystalline hydrate or a crystalline anhydrate) as described herein, wherein the subject has symptoms selected from the group consisting of at least 6 swollen joints, at least 6 tender joints, and combinations thereof prior to treating. In one embodiment, the method comprises administering to the subject about 7.5 mg or about 15 mg or about 30 mg or about 45 mg, per unit dosage form (e.g., per tablet or capsule), per day of Compound 1 (freebase) or a pharmaceutically acceptable salt thereof or a solid state form of Compound 1 in an amount sufficient to deliver to the subject about 7.5 or about 15 mg or about 30 mg or about 45 mg, per unit dosage form (e.g., per tablet or capsule), per day of Compound 1 freebase equivalent, wherein the subject has symptoms selected from the group consisting of at least 6 swollen joints, at least 6 tender joints, and combinations thereof prior to treating. In one embodiment, the method comprises administering to the subject about 7.5 mg or about 15 mg or about 30 mg or about 45 mg, per unit dosage form (e.g., per tablet or capsule) of a solid state form of Compound 1. In another aspect, the disclosure relates to Compound 1 freebase or a pharmaceutically acceptable salt thereof or a solid state form of Compound 1 (e.g., a crystalline hydrate or crystalline anhydrate), as described in the present disclosure, for use in treatment of moderate to severely active rheumatoid arthritis in an adult subject, particularly in a human subject suffering from or susceptible to moderate to severely active rheumatoid arthritis, wherein the subject has symptoms selected from the group consisting of at least 6 swollen joints, at least 6 tender joints, and combinations thereof prior to treating, the use comprising administering to the subject a therapeutically effective amount of Compound 1 freebase or a pharmaceutically acceptable salt thereof or a solid state form of Compound 1. In one embodiment, the therapeutically effective amount of the solid state form of Compound 1 delivers to the subject about 7.5 mg or about 15 mg or about 30 mg or about 45 mg per unit dosage form (e.g., per tablet or capsule) of Compound 1 (freebase equivalent) or a solid state form of Compound 1 orally QD (once daily). In one embodiment, the Compound 1 (freebase) or a pharmaceutically acceptable salt thereof or the solid state form of Compound 1 is in a once daily extended release formulation. In one embodiment, the Compound 1 (freebase) or a pharmaceutically acceptable salt thereof or the solid state form of Compound 1 is administered to the subject orally QD (once daily). In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is Tartrate Hydrate. In one embodiment, the symptoms result from the progression of structural damage assessed by radiograph.

In one embodiment, the present disclosure is directed to a method of treating moderate to severely active rheumatoid arthritis in an adult subject, particularly in a human subject suffering from or susceptible to moderate to severely active rheumatoid arthritis, the method comprising administering to the subject about 7.5 mg, per unit dosage form (e.g., per tablet or capsule), per day of Compound 1 (freebase), or a pharmaceutically acceptable salt thereof or a solid state form of Compound 1 in an amount sufficient to deliver to the subject about 7.5 mg, per unit dosage form (e.g., per tablet or capsule), per day of Compound 1 freebase equivalent, wherein the subject has symptoms selected from the group consisting of at least 6 swollen joints, at least 6 tender joints, and combinations thereof prior to treating. In one embodiment, the method comprises administering to the subject about 7.5 mg, per unit dosage form (e.g., per tablet or capsule), per day of a solid state form of Compound 1. In another aspect, the disclosure relates to Compound 1 freebase or a pharmaceutically acceptable salt thereof or a solid state form of Compound 1 for use in treatment of moderate to severely active rheumatoid arthritis in an adult subject, particularly in a human subject suffering from or susceptible to moderate to severely active rheumatoid arthritis, wherein the subject has symptoms selected from the group consisting of at least 6 swollen joints, at least 6 tender joints, and combinations thereof prior to treating, the use comprising administering to the subject about 7.5 mg, per unit dosage form (e.g., per tablet or capsule) of Compound 1 freebase or a pharmaceutically acceptable salt thereof or a solid state form of Compound 1. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate. In one embodiment, the Compound 1 freebase or a pharmaceutically acceptable salt thereof or the solid state form of Compound 1 is administered orally QD (once daily). In one embodiment, the Compound 1 freebase or a pharmaceutically acceptable salt thereof or the solid state form of Compound 1 is in a once daily extended release formulation. In one embodiment, the symptoms result from the progression of structural damage assessed by radiograph.

In one embodiment, the present disclosure is directed to a method of treating moderate to severely active rheumatoid arthritis in an adult subject, particularly in a human subject suffering from or susceptible to moderate to severely active rheumatoid arthritis, the method comprising administering to the subject about 15 mg, per unit dosage form (e.g., per tablet or capsule), per day of Compound 1 (freebase), or a pharmaceutically acceptable salt thereof or a solid state form of Compound 1 in an amount sufficient to deliver to the subject about 15 mg, per unit dosage form (e.g., per tablet or capsule), per day of Compound 1 freebase equivalent, wherein the subject has symptoms selected from the group consisting of at least 6 swollen joints, at least 6 tender joints, and combinations thereof prior to treating. In one embodiment, the method comprises administering to the subject about 15 mg, per unit dosage form (e.g., per tablet or capsule), per day of a solid state form of Compound 1. In another aspect, the disclosure relates to Compound 1 freebase or a pharmaceutically acceptable salt thereof or a solid state form of Compound 1 for use in treatment of moderate to severely active rheumatoid arthritis in an adult subject, particularly in a human subject suffering from or susceptible to moderate to severely active rheumatoid arthritis, wherein the subject has symptoms selected from the group consisting of at least 6 swollen joints, at least 6 tender joints, and combinations thereof prior to treating, the use comprising administering to the subject about 15 mg, per unit dosage form (e.g., per tablet or capsule) of Compound 1 freebase or a pharmaceutically acceptable salt thereof or a solid state form of Compound 1. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate. In one embodiment, the Compound 1 freebase or a pharmaceutically acceptable salt thereof or the solid state form of Compound 1 is administered orally QD (once daily). In one embodiment, the Compound 1 freebase or a pharmaceutically acceptable salt thereof or the solid state form of Compound 1 is in a once daily extended release formulation. In one embodiment, the symptoms result from the progression of structural damage assessed by radiograph.

In one embodiment, the present disclosure is directed to a method of treating moderate to severely active rheumatoid arthritis in an adult subject, particularly in a human subject suffering from or susceptible to moderate to severely active rheumatoid arthritis, the method comprising administering to the subject about 30 mg, per unit dosage form (e.g., per tablet or capsule), per day of Compound 1 (freebase), or a pharmaceutically acceptable salt thereof or a solid state form of Compound 1 in an amount sufficient to deliver to the subject about 30 mg, per unit dosage form (e.g., per tablet or capsule), per day of Compound 1 freebase equivalent, wherein the subject has symptoms selected from the group consisting of at least 6 swollen joints, at least 6 tender joints, and combinations thereof prior to treating. In one embodiment, the method comprises administering to the subject about 30 mg, per unit dosage form (e.g., per tablet or capsule), per day of a solid state form of Compound 1. In another aspect, the disclosure relates to Compound 1 freebase or a pharmaceutically acceptable salt thereof or a solid state form of Compound 1 for use in treatment of moderate to severely active rheumatoid arthritis in an adult subject, particularly in a human subject suffering from or susceptible to moderate to severely active rheumatoid arthritis, wherein the subject has symptoms selected from the group consisting of at least 6 swollen joints, at least 6 tender joints, and combinations thereof prior to treating, the use comprising administering to the subject about 30 mg, per unit dosage form (e.g., per tablet or capsule) of Compound 1 freebase or a pharmaceutically acceptable salt thereof or a solid state form of Compound 1. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate. In one embodiment, the Compound 1 freebase or a pharmaceutically acceptable salt thereof or the solid state form of Compound 1 is administered orally QD (once daily). In one embodiment, the Compound 1 freebase or a pharmaceutically acceptable salt thereof or the solid state form of Compound 1 is in a once daily extended release formulation. In one embodiment, the symptoms result from the progression of structural damage assessed by radiograph.

In one embodiment, the present disclosure is directed to a method of treating moderate to severely active rheumatoid arthritis in an adult subject, particularly in a human subject suffering from or susceptible to moderate to severely active rheumatoid arthritis, the method comprising administering to the subject about 45 mg, per unit dosage form (e.g., per tablet or capsule), per day of Compound 1 (freebase), or a pharmaceutically acceptable salt thereof or a solid state form of Compound 1 in an amount sufficient to deliver to the subject about 45 mg, per unit dosage form (e.g., per tablet or capsule), per day of Compound 1 freebase equivalent, wherein the subject has symptoms selected from the group consisting of at least 6 swollen joints, at least 6 tender joints, and combinations thereof prior to treating. In one embodiment, the method comprises administering to the subject about 45 mg, per unit dosage form (e.g., per tablet or capsule), per day of a solid state form of Compound 1. In another aspect, the disclosure relates to Compound 1 freebase or a pharmaceutically acceptable salt thereof or a solid state form of Compound 1 for use in treatment of moderate to severely active rheumatoid arthritis in an adult subject, particularly in a human subject suffering from or susceptible to moderate to severely active rheumatoid arthritis, wherein the subject has symptoms selected from the group consisting of at least 6 swollen joints, at least 6 tender joints, and combinations thereof prior to treating, the use comprising administering to the subject about 45 mg, per unit dosage form (e.g., per tablet or capsule) of Compound 1 freebase or a pharmaceutically acceptable salt thereof or a solid state form of Compound 1. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate. In one embodiment, the Compound 1 freebase or a pharmaceutically acceptable salt thereof or the solid state form of Compound 1 is administered orally QD (once daily). In one embodiment, the Compound 1 freebase or a pharmaceutically acceptable salt thereof or the solid state form of Compound 1 is in a once daily extended release formulation. In one embodiment, the symptoms result from the progression of structural damage assessed by radiograph.

In one embodiment, the adult subject receiving the treatment achieves an ACR20 response after treatment. In one embodiment, the adult subject achieves an ACR20 response after treatment for at least twelve weeks (e.g., at week 12 of treating). In another embodiment, the adult subject receiving the treatment achieves an ACR50 response after treatment. In one embodiment, the adult subject achieves an ACR50 response after treatment for at least twelve weeks (e.g., at week 12 of treating), or after at least twenty-four weeks (e.g., at week 24). In another embodiment, the adult subject receiving the treatment achieves an ACR70 response after treatment. In one embodiment, the adult subject achieves an ACR70 response after treatment for at least twelve weeks (e.g., at week 12 of treating). In certain embodiments, the adult subject achieves an ACR20 response, an ACR50 response, and/or an ACR70 response following treatment for at least twelve weeks (e.g., at week 12 of treating).

In one embodiment, the adult subject receiving the treatment achieves an ACR20 response after treatment for at least 8 weeks (e.g., at week 8 of treating). In another embodiment, the adult subject receiving the treatment achieves an ACR20 response after treatment for at least 6 weeks (e.g., at week 6 of treating). In another embodiment, the adult subject receiving the treatment achieves an ACR20 response after treatment for at least 4 weeks (e.g., at week 4 of treating). In another embodiment, the adult subject receiving the treatment achieves an ACR20 response after treatment for at least 2 weeks (e.g., at week 2 of treating).

In one embodiment, the adult subject receiving the treatment achieves an ACR50 response after treatment for at least 8 weeks (e.g., at week 8 of treating). In another embodiment, the adult subject receiving the treatment achieves an ACR50 response after treatment for at least 6 weeks (e.g., at week 6 of treating). In another embodiment, the adult subject receiving the treatment achieves an ACR50 response after treatment for at least 4 weeks (e.g., at week 4 of treating). In another embodiment, the adult subject receiving the treatment achieves an ACR50 response after treatment for at least 2 weeks (e.g., at week 2 of treating).

In one embodiment, the adult subject receiving the treatment achieves an ACR70 response after treatment for at least 8 weeks (e.g., at week 8 of treating). In another embodiment, the adult subject receiving the treatment achieves an ACR70 response after treatment for at least 6 weeks (e.g., at week 6 of treating). In another embodiment, the adult subject receiving the treatment achieves an ACR70 response after treatment for at least 4 weeks (e.g., at week 4 of treating).

In one embodiment, the adult subject receiving the treatment achieves a change in DAS28 score after treatment. In one embodiment, the change in DAS score is a decrease in DAS28(CRP) after treatment, as compared to baseline (i.e., DAS28(CRP) prior to treatment). In one embodiment, the adult subject achieves a decrease in DAS28 score as compared to baseline after treatment for at least twelve weeks (e.g., at week 12 of treating). In one embodiment, the adult subject achieves a decrease in DAS28(CRP) as compared to baseline after treatment for at least 12 weeks (e.g., at week 12 of treating). In another embodiment, the adult subject achieves a decrease in DAS28(CRP) as compared to baseline after treatment for at least 8 weeks (e.g., at week 8 of treating). In another embodiment, the adult subject achieves a decrease in DAS28(CRP) as compared to baseline after treatment for at least 6 weeks (e.g., at week 6 of treating). In another embodiment, the adult subject achieves a decrease in DAS28(CRP) as compared to baseline after treatment for at least 4 weeks (e.g., at week 4 of treating). In another embodiment, the adult subject achieves a decrease in DAS28(CRP) as compared to baseline after treatment for at least 2 weeks (e.g., at week 2 of treating).

In another embodiment, the adult subject receiving the treatment achieves a low disease activity (LDA) score or clinical remission after treatment. In one embodiment, the LDA score or clinical remission is measured as a DAS28 score (in particular, DAS28(CRP)) of 3.2 or less. In another embodiment, the LDA score or clinical remission is measured as a DAS28(CRP) of less than 2.6. In another embodiment, the LDA score or clinical remission is assessed using Clinical Disease Activity Index (CDAI) criteria. In one embodiment, the adult subject achieves a CDAI score of 10 or less after treatment. In another embodiment, the adult subject achieves a CDAI score of 2.8 or less after treatment. In one embodiment, the adult subject achieves the LDA score or clinical remission after treatment for at least 12 weeks (e.g., at week 12 of treating). In one embodiment, the adult subject achieves the LDA score or clinical remission after treatment for at least 8 weeks (e.g., at week 8 of treating). In one embodiment, the adult subject achieves the LDA score or clinical remission after treatment for at least 6 weeks (e.g., at week 6 of treating). In one embodiment, the adult subject achieves the LDA score or clinical remission after treatment for at least 4 weeks (e.g., at week 4 of treating). In one embodiment, the adult subject achieves the LDA score or clinical remission after treatment for at least 2 weeks (e.g., at week 2 of treating).

In one embodiment, the adult subject receiving the treatment achieves a change in mean modified Total Sharp Score (mTSS). In one embodiment, the adult subject receiving the treatment achieves a change in mTSS after treatment for at least twelve weeks (e.g., at week 12 of treating), or after treatment for at least twenty-four weeks (e.g., at week 24 of treating). In one embodiment, mTSS may be determined by scoring x-rays of the hand/wrist and feet joints for erosions and joint space narrowing. The erosion score and narrowing score are added to determine the total score.

In one embodiment, the adult subject receiving the treatment achieves a change in HAQ-DI score. In one embodiment, the adult subject receiving the treatment achieves a change in HAQ-DI score after treatment for at least twelve weeks (e.g., at week 12 of treating).

In one embodiment, the adult subject receiving the treatment achieves a change in Short Form 36 (SF-36) physical component score (PCS). In one embodiment, the adult subject receiving the treatment achieves a change in SF-36 PCS after treatment for at least twelve weeks (e.g., at week 12 of treating). SF-36 is a 36 item participant questionnaire with questions relating to participant health and daily activities.

In one embodiment, the adult subject receiving the treatment achieves a clinical remission (CR). In one embodiment, the adult subject receiving the treatment achieves a CR after treatment for at least twelve weeks (e.g., at week 12 of treating). In one embodiment, CR is determined based on DAS28 C-Reactive Protein (DAS28(CRP)) response rate. In one embodiment, CR is a DAS28(CRP) score of less than 2.6.

In one embodiment, the adult subject receiving the treatment achieves a change in functional assessment of chronic illness therapy (FACIT-F). In one embodiment, the adult subject receiving the treatment achieves a change in FACIT-F after treatment for at least twelve weeks (e.g., at week 12 of treating). FACIT-F is a participant questionnaire with 13 indexes rated on a 5 point scale. The indexes relate to the participant's level of fatigue during the past seven days.

In one embodiment, the adult subject receiving the treatment achieves a change in work instability score for rheumatoid arthritis (RA-WIS). In one embodiment, the adult subject receiving the treatment achieves a change in RA-WIS after treatment for at least twelve weeks (e.g., at week 12 of treating). RA-WIS is a participant questionnaire containing 23 questions relating to the participant's functioning in their work environment.

In one embodiment, the adult subject receiving the treatment achieves a change in morning stiffness severity. In one embodiment, the adult subject receiving the treatment achieves a change in morning stiffness severity after treatment for at least twelve weeks (e.g., at week 12 of treating). Morning stiffness severity is determined by the Patient's Assessment of Severity and Duration of Morning Stiffness questionnaire.

In one embodiment, the method or use comprises administering to the subject about 7.5 mg, per unit dosage form (e.g., per tablet or capsule), of Compound 1 (freebase), or a pharmaceutically acceptable salt thereof or a solid state form of Compound 1 in an amount sufficient to deliver to the subject about 7.5 mg, per unit dosage form (e.g., per tablet or capsule), of Compound 1 freebase equivalent to the subject, wherein the subject achieves an ACR20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 7.5 mg, per unit dosage form (e.g., per tablet or capsule), of Compound 1 (freebase), or a pharmaceutically acceptable salt thereof or a solid state form of Compound 1 in an amount sufficient to deliver to the subject about 7.5 mg, per unit dosage form (e.g., per tablet or capsule), of Compound 1 freebase equivalent, wherein the subject achieves an ACR50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In one embodiment, the method or use comprises administering to the subject about 7.5 mg, per unit dosage form (e.g., per tablet or capsule), of Compound 1 (freebase), or a pharmaceutically acceptable salt thereof or a solid state form of Compound 1 in an amount sufficient to deliver to the subject about 7.5 mg, per unit dosage form (e.g., per tablet or capsule), of Compound 1 freebase equivalent, wherein the subject achieves an ACR70 response at week 12 of treating. In one embodiment, the method or use comprises administering to the subject about 7.5 mg, per unit dosage form (e.g., per tablet or capsule), of Compound 1 (freebase), or a pharmaceutically acceptable salt thereof or a solid state form of Compound 1 in an amount sufficient to deliver to the subject about 7.5 mg, per unit dosage form (e.g., per tablet or capsule), of Compound 1 freebase equivalent, wherein the subject achieves a decrease in DAS28(CRP) as compared to baseline at week 12 of treating. In another embodiment, the subject achieves a decrease in DAS28(CRP) as compared to baseline at week 8 of treating. In another embodiment, the subject achieves a decrease in DAS28(CRP) as compared to baseline at week 6 of treating. In another embodiment, the subject achieves a decrease in DAS28(CRP) as compared to baseline at week 4 of treating. In another embodiment, the subject achieves a decrease in DAS28(CRP) as compared to baseline at week 2 of treating. In one embodiment, the method or use comprises administering about 7.5 mg, per unit dosage form (e.g., per tablet or capsule), of the solid state form to the subject. In one embodiment, the Compound 1 (freebase) or a pharmaceutically acceptable salt thereof or the solid state form is in a once daily extended release formulation. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate.

In one embodiment, the method or use comprises administering to the subject about 15 mg, per unit dosage form (e.g., per tablet or capsule), of Compound 1 (freebase), or a pharmaceutically acceptable salt thereof or a solid state form of Compound 1 in an amount sufficient to deliver to the subject about 15 mg, per unit dosage form (e.g., per tablet or capsule), of Compound 1 freebase equivalent, wherein the subject achieves an ACR20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 15 mg, per unit dosage form (e.g., per tablet or capsule), of Compound 1 (freebase), or a pharmaceutically acceptable salt thereof or a solid state form of Compound 1 in an amount sufficient to deliver to the subject about 15 mg, per unit dosage form (e.g., per tablet or capsule), of Compound 1 freebase equivalent, wherein the subject achieves an ACR50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In one embodiment, the method or use comprises administering to the subject about 15 mg, per unit dosage form (e.g., per tablet or capsule), of Compound 1 (freebase), or a pharmaceutically acceptable salt thereof or a solid state form of Compound 1 in an amount sufficient to deliver to the subject about 15 mg, per unit dosage form (e.g., per tablet or capsule), of Compound 1 freebase equivalent, wherein the subject achieves an ACR70 response at week 12 of treating. In another embodiment, the subject achieves an ACR70 response at week 8 of treating. In another embodiment, the subject achieves an ACR70 response at week 6 of treating. In one embodiment, the method or use comprises administering to the subject about 15 mg, per unit dosage form (e.g., per tablet or capsule), of Compound 1 (freebase), or a pharmaceutically acceptable salt thereof or a solid state form of Compound 1 in an amount sufficient to deliver to the subject about 15 mg, per unit dosage form (e.g., per tablet or capsule), of Compound 1 freebase equivalent, wherein the subject achieves a decrease in DAS28(CRP) as compared to baseline at week 12 of treating. In another embodiment, the subject achieves a decrease in DAS28(CRP) as compared to baseline at week 8 of treating. In another embodiment, the subject achieves a decrease in DAS28(CRP) as compared to baseline at week 6 of treating. In another embodiment, the subject achieves a decrease in DAS28(CRP) as compared to baseline at week 4 of treating. In another embodiment, the subject achieves a decrease in DAS28(CRP) as compared to baseline at week 2 of treating. In one embodiment, the method or use comprises administering about 15 mg, per unit dosage form (e.g., per tablet or capsule), of the solid state form to the subject. In one embodiment, the Compound 1 (freebase) or a pharmaceutically acceptable salt thereof or the solid state form is in a once daily extended release formulation. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate.

In one embodiment, the method or use comprises administering to the subject about 24 mg, per unit dosage form (e.g., per tablet or capsule), of Compound 1 (freebase), or a pharmaceutically acceptable salt thereof or a solid state form of Compound 1 in an amount sufficient to deliver to the subject about 24 mg, per unit dosage form (e.g., per tablet or capsule), of Compound 1 freebase equivalent, wherein the subject achieves an ACR20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 24 mg, per unit dosage form (e.g., per tablet or capsule), of Compound 1 (freebase), or a pharmaceutically acceptable salt thereof or a solid state form of Compound 1 in an amount sufficient to deliver to the subject about 24 mg, per unit dosage form (e.g., per tablet or capsule), of Compound 1 freebase equivalent, wherein the subject achieves an ACR50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In one embodiment, the method or use comprises administering to the subject about 24 mg, per unit dosage form (e.g., per tablet or capsule), of Compound 1 (freebase), or a pharmaceutically acceptable salt thereof or a solid state form of Compound 1 in an amount sufficient to deliver to the subject about 24 mg, per unit dosage form (e.g., per tablet or capsule), of Compound 1 freebase equivalent, wherein the subject achieves an ACR70 response at week 12 of treating. In another embodiment, the subject achieves an ACR70 response at week 8 of treating. In another embodiment, the subject achieves an ACR70 response at week 6 of treating. In one embodiment, the method or use comprises administering to the subject about 24 mg, per unit dosage form (e.g., per tablet or capsule), of Compound 1 (freebase), or a pharmaceutically acceptable salt thereof or a solid state form of Compound 1 in an amount sufficient to deliver to the subject about 24 mg, per unit dosage form (e.g., per tablet or capsule), of Compound 1 freebase equivalent, wherein the subject achieves a decrease in DAS28(CRP) as compared to baseline at week 12 of treating. In another embodiment, the subject achieves a decrease in DAS28(CRP) as compared to baseline at week 8 of treating. In another embodiment, the subject achieves a decrease in DAS28(CRP) as compared to baseline at week 6 of treating. In another embodiment, the subject achieves a decrease in DAS28(CRP) as compared to baseline at week 4 of treating. In another embodiment, the subject achieves a decrease in DAS28(CRP) as compared to baseline at week 2 of treating. In one embodiment, the method or use comprises administering about 24 mg, per unit dosage form (e.g., per tablet or capsule), of the solid state form to the subject. In one embodiment, the Compound 1 (freebase) or a pharmaceutically acceptable salt thereof or the solid state form is in a once daily extended release formulation. In one embodiment, the solid state form is a crystalline hydrate. In one embodiment, the crystalline ahydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate.

In one embodiment, the method or use comprises administering to the subject about 30 mg, per unit dosage form (e.g., per tablet or capsule), of Compound 1 (freebase), or a pharmaceutically acceptable salt thereof or a solid state form of Compound 1 in an amount sufficient to deliver to the subject about 30 mg, per unit dosage form (e.g., per tablet or capsule), of Compound 1 freebase equivalent, wherein the subject achieves an ACR20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 30 mg, per unit dosage form (e.g., per tablet or capsule), of Compound 1 (freebase), or a pharmaceutically acceptable salt thereof or a solid state form of Compound 1 in an amount sufficient to deliver to the subject about 30 mg, per unit dosage form (e.g., per tablet or capsule), of Compound 1 freebase equivalent, wherein the subject achieves an ACR50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In another embodiment, the subject achieves an ACR50 response at week 2 of treating. In one embodiment, the method or use comprises administering to the subject about 30 mg, per unit dosage form (e.g., per tablet or capsule), of Compound 1 (freebase), or a pharmaceutically acceptable salt thereof or a solid state form of Compound 1 in an amount sufficient to deliver to the subject about 30 mg, per unit dosage form (e.g., per tablet or capsule), of Compound 1 freebase equivalent, wherein the subject achieves an ACR70 response at week 12 of treating. In another embodiment, the subject achieves an ACR70 response at week 8 of treating. In one embodiment, the method or use comprises administering to the subject about 30 mg, per unit dosage form (e.g., per tablet or capsule), of Compound 1 (freebase), or a pharmaceutically acceptable salt thereof or a solid state form of Compound 1 in an amount sufficient to deliver to the subject about 30 mg, per unit dosage form (e.g., per tablet or capsule), of Compound 1 freebase equivalent, wherein the subject achieves a decrease in DAS28(CRP) as compared to baseline at week 12 of treating. In another embodiment, the subject achieves a decrease in DAS28(CRP) as compared to baseline at week 8 of treating. In another embodiment, the subject achieves a decrease in DAS28(CRP) as compared to baseline at week 6 of treating. In another embodiment, the subject achieves a decrease in DAS28(CRP) as compared to baseline at week 4 of treating. In another embodiment, the subject achieves a decrease in DAS28(CRP) as compared to baseline at week 2 of treating. In one embodiment, the method or use comprises administering about 30 mg, per unit dosage form (e.g., per tablet or capsule), of the solid state form to the subject. In one embodiment, the Compound 1 (freebase) or a pharmaceutically acceptable salt thereof or the solid state form is in a once daily extended release formulation. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate.

In one embodiment, the method or use comprises administering to the subject about 45 mg, per unit dosage form (e.g., per tablet or capsule), of Compound 1 (freebase), or a pharmaceutically acceptable salt thereof or a solid state form of Compound 1 in an amount sufficient to deliver to the subject about 45 mg, per unit dosage form (e.g., per tablet or capsule), of Compound 1 freebase equivalent, wherein the subject achieves an ACR20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 45 mg, per unit dosage form (e.g., per tablet or capsule), of Compound 1 (freebase), or a pharmaceutically acceptable salt thereof or a solid state form of Compound 1 in an amount sufficient to deliver to the subject about 45 mg, per unit dosage form (e.g., per tablet or capsule), of Compound 1 freebase equivalent, wherein the subject achieves an ACR50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In one embodiment, the method or use comprises administering to the subject about 45 mg, per unit dosage form (e.g., per tablet or capsule), of Compound 1 (freebase), or a pharmaceutically acceptable salt thereof or a solid state form of Compound 1 in an amount sufficient to deliver to the subject about 45 mg, per unit dosage form (e.g., per tablet or capsule), of Compound 1 freebase equivalent, wherein the subject achieves an ACR70 response at week 12 of treating. In another embodiment, the subject achieves an ACR70 response at week 8 of treating. In another embodiment, the subject achieves an ACR70 response at week 6 of treating. In another embodiment, the subject achieves an ACR70 response at week 4 of treating. In one embodiment, the method or use comprises administering to the subject about 45 mg, per unit dosage form (e.g., per tablet or capsule), of Compound 1 (freebase), or a pharmaceutically acceptable salt thereof or a solid state form of Compound 1 in an amount sufficient to deliver to the subject about 45 mg, per unit dosage form (e.g., per tablet or capsule), of Compound 1 freebase equivalent, wherein the subject achieves a decrease in DAS28(CRP) as compared to baseline at week 12 of treating. In another embodiment, the subject achieves a decrease in DAS28(CRP) as compared to baseline at week 8 of treating. In another embodiment, the subject achieves a decrease in DAS28(CRP) as compared to baseline at week 6 of treating. In another embodiment, the subject achieves a decrease in DAS28(CRP) as compared to baseline at week 4 of treating. In another embodiment, the subject achieves a decrease in DAS28(CRP) as compared to baseline at week 2 of treating. In one embodiment, the method or use comprises administering about 45 mg, per unit dosage form (e.g., per tablet or capsule), of the solid state form to the subject. In one embodiment, the Compound 1 (freebase) or a pharmaceutically acceptable salt thereof or the solid state form is in a once daily extended release formulation. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate.

In another embodiment, the adult subject is a subject who has had an inadequate response or intolerance to one or more disease-modifying antirheumatic drugs (DMARDs). In one embodiment, the DMARD is a conventional synthetic DMARD (csDMARD). In another embodiment, the DMARD is a biologic DMARD (bDMARD). Examples of csDMARDs include, but are not limited to, methotrexate (MTX), sulfasalazine, hydroxychloroquine, chloroquine, leflunomide, and azathioprine. Examples of bDMARDs include, but are not limited to, tocilizumab such as ACTEMRA™, etanercept such as p75TNFR1gG (ENBREL™ brand etanercept), adalimumab (such as HUMIRA™ brand adalimumab), and golimumab such as SIMPONI™ (golimumab). In one embodiment, the csDMARD is MTX. In one embodiment, the bDMARD is an anti-TNF biologic. An inadequate response or intolerance to one or more DMARDs can be measured using any of the indices described herein (e.g., failure to achieve an ACR20 response). In one embodiment, a subject having an inadequate response to a DMARD is a subject who does not achieve reduced disease activity, does not achieve an improvement in physical function, exhibits no evidence of stopping disease progression, or who experiences disease relapse after treatment with the DMARD. In one embodiment, a subject having an inadequate response to a DMARD is a subject who does not achieve an ACR20 response after treatment with the DMARD. In one embodiment, a subject having an inadequate tolerance (intolerance) to a DMARD is a subject who experiences toxicity or complicating co-morbidities after treatment with the DMARD.

In one embodiment, the adult subject is a subject who has had an inadequate response to stable methotrexate therapy. In one embodiment, the adult subject received methotrexate therapy for at least three months prior to treatment. In another embodiment, the adult subject received a stable dose of methotrexate of about 7.5 to about 25 mg per week for at least four weeks prior to treatment. In another embodiment, the adult subject is administered a stable dose of methotrexate (e.g., from about 7.5 to about 25 mg per week) during treatment with Compound 1. In another embodiment, the adult subject received a supplement of folic acid for at least four weeks prior to treatment. In another embodiment, the adult subject is administered a supplement of folic acid during treatment.

In one embodiment, the adult subject is a subject who has had an inadequate response or intolerance to at least one anti-TNF therapy. Anti-TNF biologic agents are described elsewhere herein, and include TNF antagonists such as chimeric, humanized or human TNF antibodies, adalimumab (such as HUMIRA™ brand adalimumab), infliximab such as CA2 (REMICADE™ brand infliximab), golimumab such as SIMPONI™ (golimumab), certolizumab pegol such as CIMZIA™, tocilizumab such as ACTEMRA™, CDP 571, and soluble p55 or p75 TNF receptors, derivatives, thereof, etanercept such as p75TNFR1gG (ENBREL™ brand etanercept) or p55TNFR1gG (lenercept). In one embodiment, the adult subject received methotrexate therapy for at least three months prior to treatment. In another embodiment, the adult subject received a stable dose of methotrexate of about 7.5 to about 25 mg per week for at least four weeks prior to treatment. In another embodiment, the adult subject is administered a stable dose of methotrexate (e.g., from about 7.5 to about 25 mg per week) during treatment with Compound 1. In another embodiment, the adult subject has been treated with at least one anti-TNF biologic agent for at least three months prior to treatment with Compound 1. In another embodiment, the adult subject received a supplement of folic acid for at least four weeks prior to treatment. In another embodiment, the adult subject is administered a supplement of folic acid during treatment In certain embodiments, the adult subject, who has had an inadequate response or tolerance to one or more DMARDS (including methotrexate and/or an anti-TNF biologic agent), achieves an ACR20 response, an ACR50 response, an ACR70 response, and/or a decrease in DAS28(CRP) as compared to baseline following treatment for at least twelve weeks (e.g., at week 12 of treating), and/or following treatment for at least 8 weeks (e.g., at week 8 of treating), and/or following treatment for at least 6 weeks (e.g., at week 6 of treating), and/or following treatment for at least 4 weeks (e.g., at week 4 of treating), and/or following treatment for at least 2 weeks (e.g., at week 2 of treating).

For instance, in one embodiment, the method or use comprises administering to the subject about 7.5 mg, per unit dosage form (e.g., per tablet or capsule), of Compound 1 (freebase), or a pharmaceutically acceptable salt thereof or a solid state form of Compound 1 in an amount sufficient to deliver to the subject about 7.5 mg, per unit dosage form (e.g., per tablet or capsule), of Compound 1 freebase equivalent, wherein the subject has had an inadequate response or intolerance to one or more DMARDS, and the subject achieves an ACR20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 7.5 mg, per unit dosage form (e.g., per tablet or capsule), of Compound 1 (freebase), or a pharmaceutically acceptable salt thereof or a solid state form of Compound 1 in an amount sufficient to deliver to the subject about 7.5 mg, per unit dosage form (e.g., per tablet or capsule), of Compound 1 freebase equivalent, wherein the subject has had an inadequate response or intolerance to one or more DMARDS, and the subject achieves an ACR 50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In one embodiment, the method or use comprises administering to the subject about 7.5 mg, per unit dosage form (e.g., per tablet or capsule), of Compound 1 (freebase), or a pharmaceutically acceptable salt thereof or a solid state form of Compound 1 in an amount sufficient to deliver to the subject about 7.5 mg, per unit dosage form (e.g., per tablet or capsule), of Compound 1 freebase equivalent, wherein the subject has had an inadequate response or intolerance to one or more DMARDS, and the subject achieves an ACR 70 response at week 12 of treating. In one embodiment, the method or use comprises administering to the subject about 7.5 mg, per unit dosage form (e.g., per tablet or capsule), of Compound 1 (freebase), or a pharmaceutically acceptable salt thereof or a solid state form of Compound 1 in an amount sufficient to deliver to the subject about 7.5 mg, per unit dosage form (e.g., per tablet or capsule), of Compound 1 freebase equivalent, wherein the subject has had an inadequate response or intolerance to one or more DMARDS, and the subject achieves a decrease in DAS28 (CRP) as compared to baseline at week 12 of treating. In another embodiment, the subject achieves a decrease in DAS28(CRP) as compared to baseline at week 8 of treating. In another embodiment, the subject achieves a decrease in DAS28(CRP) as compared to baseline at week 6 of treating. In another embodiment, the subject achieves a decrease in DAS28(CRP) as compared to baseline at week 4 of treating. In another embodiment, the subject achieves a decrease in DAS28(CRP) as compared to baseline at week 2 of treating. In one embodiment, the method or use comprises administering about 7.5 mg, per unit dosage form (e.g., per tablet or capsule), of the solid state form to the subject. In one embodiment, the Compound 1 (freebase) or a pharmaceutically acceptable salt thereof or the solid state form is in a once daily extended release formulation. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate.

In one embodiment, the method or use comprises administering to the subject about 15 mg, per unit dosage form (e.g., per tablet or capsule), of Compound 1 (freebase), or a pharmaceutically acceptable salt thereof or a solid state form of Compound 1 in an amount sufficient to deliver to the subject about 15 mg, per unit dosage form (e.g., per tablet or capsule), of Compound 1 freebase equivalent, wherein the subject has had an inadequate response or intolerance to one or more DMARDS, and the subject achieves an ACR 20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 15 mg, per unit dosage form (e.g., per tablet or capsule), of Compound 1 (freebase), or a pharmaceutically acceptable salt thereof or a solid state form of Compound 1 in an amount sufficient to deliver to the subject about 15 mg, per unit dosage form (e.g., per tablet or capsule), of Compound 1 freebase equivalent, wherein the subject has had an inadequate response or intolerance to one or more DMARDS, and the subject achieves an ACR 50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In one embodiment, the method or use comprises administering to the subject about 15 mg, per unit dosage form (e.g., per tablet or capsule), of Compound 1 (freebase), or a pharmaceutically acceptable salt thereof or a solid state form of Compound 1 in an amount sufficient to deliver to the subject about 15 mg, per unit dosage form (e.g., per tablet or capsule), of Compound 1 freebase equivalent, wherein the subject has had an inadequate response or intolerance to one or more DMARDS, and the subject achieves an ACR 70 response at week 12 of treating. In another embodiment, the subject achieves an ACR70 response at week 8 of treating. In another embodiment, the subject achieves an ACR70 response at week 6 of treating. In one embodiment, the method or use comprises administering to the subject about 15 mg, per unit dosage form (e.g., per tablet or capsule), of Compound 1 (freebase), or a pharmaceutically acceptable salt thereof or a solid state form of Compound 1 in an amount sufficient to deliver to the subject about 15 mg, per unit dosage form (e.g., per tablet or capsule), of Compound 1 freebase equivalent, wherein the subject has had an inadequate response or intolerance to one or more DMARDS, and the subject achieves a decrease in DAS28 (CRP) as compared to baseline at week 12 of treating. In another embodiment, the subject achieves a decrease in DAS28(CRP) as compared to baseline at week 8 of treating. In another embodiment, the subject achieves a decrease in DAS28(CRP) as compared to baseline at week 6 of treating. In another embodiment, the subject achieves a decrease in DAS28(CRP) as compared to baseline at week 4 of treating. In another embodiment, the subject achieves a decrease in DAS28(CRP) as compared to baseline at week 2 of treating. In one embodiment, the method or use comprises administering about 15 mg, per unit dosage form (e.g., per tablet or capsule), of the solid state form to the subject. In one embodiment, the Compound 1 (freebase) or a pharmaceutically acceptable salt thereof or the solid state form is in a once daily extended release formulation. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate.

In one embodiment, the method or use comprises administering to the subject about 24 mg, per unit dosage form (e.g., per tablet or capsule), of Compound 1 (freebase), or a pharmaceutically acceptable salt thereof or a solid state form of Compound 1 in an amount sufficient to deliver to the subject about 24 mg, per unit dosage form (e.g., per tablet or capsule), of Compound 1 freebase equivalent, wherein the subject has had an inadequate response or intolerance to one or more DMARDS, and the subject achieves an ACR 20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 24 mg, per unit dosage form (e.g., per tablet or capsule), of Compound 1 (freebase), or a pharmaceutically acceptable salt thereof or a solid state form of Compound 1 in an amount sufficient to deliver to the subject about 24 mg, per unit dosage form (e.g., per tablet or capsule), of Compound 1 freebase equivalent, wherein the subject has had an inadequate response or intolerance to one or more DMARDS, and the subject achieves an ACR 50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In another embodiment, the subject achieves an ACR50 response at week 2 of treating. In one embodiment, the method or use comprises administering to the subject about 24 mg, per unit dosage form (e.g., per tablet or capsule), of Compound 1 (freebase), or a pharmaceutically acceptable salt thereof or a solid state form of Compound 1 in an amount sufficient to deliver to the subject about 24 mg, per unit dosage form (e.g., per tablet or capsule), of Compound 1 freebase equivalent, wherein the subject has had an inadequate response or intolerance to one or more DMARDS, and the subject achieves an ACR 70 response at week 12 of treating. In one embodiment, the method or use comprises administering to the subject about 24 mg, per unit dosage form (e.g., per tablet or capsule), of Compound 1 (freebase), or a pharmaceutically acceptable salt thereof or a solid state form of Compound 1 in an amount sufficient to deliver to the subject about 24 mg, per unit dosage form (e.g., per tablet or capsule), of Compound 1 freebase equivalent, wherein the subject has had an inadequate response or intolerance to one or more DMARDS, and the subject achieves a decrease in DAS28(CRP) as compared to baseline at week 12 of treating. In another embodiment, the subject achieves a decrease in DAS28(CRP) as compared to baseline at week 8 of treating. In another embodiment, the subject achieves a decrease in DAS28(CRP) as compared to baseline at week 6 of treating. In another embodiment, the subject achieves a decrease in DAS28(CRP) as compared to baseline at week 4 of treating. In another embodiment, the subject achieves a decrease in DAS28(CRP) as compared to baseline at week 2 of treating. In one embodiment, the method or use comprises administering about 24 mg, per unit dosage form (e.g., per tablet or capsule), of the solid state form to the subject. In one embodiment, the Compound 1 (freebase) or a pharmaceutically acceptable salt thereof or the solid state form is in a once daily extended release formulation. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate.

In one embodiment, the method or use comprises administering to the subject about 30 mg, per unit dosage form (e.g., per tablet or capsule), of Compound 1 (freebase), or a pharmaceutically acceptable salt thereof or a solid state form of Compound 1 in an amount sufficient to deliver to the subject about 30 mg, per unit dosage form (e.g., per tablet or capsule), of Compound 1 freebase equivalent, wherein the subject has had an inadequate response or intolerance to one or more DMARDS, and the subject achieves an ACR 20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 30 mg, per unit dosage form (e.g., per tablet or capsule), of Compound 1 (freebase), or a pharmaceutically acceptable salt thereof or a solid state form of Compound 1 in an amount sufficient to deliver to the subject about 30 mg, per unit dosage form (e.g., per tablet or capsule), of Compound 1 freebase equivalent, wherein the subject has had an inadequate response or intolerance to one or more DMARDS, and the subject achieves an ACR 50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In another embodiment, the subject achieves an ACR50 response at week 2 of treating. In one embodiment, the method or use comprises administering to the subject about 30 mg, per unit dosage form (e.g., per tablet or capsule), of Compound 1 (freebase), or a pharmaceutically acceptable salt thereof or a solid state form of Compound 1 in an amount sufficient to deliver to the subject about 30 mg, per unit dosage form (e.g., per tablet or capsule), of Compound 1 freebase equivalent, wherein the subject has had an inadequate response or intolerance to one or more DMARDS, and the subject achieves an ACR 70 response at week 12 of treating. In one embodiment, the method or use comprises administering to the subject about 30 mg, per unit dosage form (e.g., per tablet or capsule), of Compound 1 (freebase), or a pharmaceutically acceptable salt thereof or a solid state form of Compound 1 in an amount sufficient to deliver to the subject about 30 mg, per unit dosage form (e.g., per tablet or capsule), of Compound 1 freebase equivalent, wherein the subject has had an inadequate response or intolerance to one or more DMARDS, and the subject achieves a decrease in DAS28(CRP) as compared to baseline at week 12 of treating. In another embodiment, the subject achieves a decrease in DAS28(CRP) as compared to baseline at week 8 of treating. In another embodiment, the subject achieves a decrease in DAS28(CRP) as compared to baseline at week 6 of treating. In another embodiment, the subject achieves a decrease in DAS28(CRP) as compared to baseline at week 4 of treating. In another embodiment, the subject achieves a decrease in DAS28(CRP) as compared to baseline at week 2 of treating. In one embodiment, the method or use comprises administering about 30 mg, per unit dosage form (e.g., per tablet or capsule), of the solid state form to the subject. In one embodiment, the Compound 1 (freebase) or a pharmaceutically acceptable salt thereof or the solid state form is in a once daily extended release formulation. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate.

In one embodiment, the method or use comprises administering to the subject about 45 mg, per unit dosage form (e.g., per tablet or capsule), of Compound 1 (freebase), or a pharmaceutically acceptable salt thereof or a solid state form of Compound 1 in an amount sufficient to deliver to the subject about 45 mg, per unit dosage form (e.g., per tablet or capsule), of Compound 1 freebase equivalent, wherein the subject has had an inadequate response or intolerance to one or more DMARDS, and the subject achieves an ACR 20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 45 mg, per unit dosage form (e.g., per tablet or capsule), of Compound 1 (freebase), or a pharmaceutically acceptable salt thereof or a solid state form of Compound 1 in an amount sufficient to deliver to the subject about 45 mg, per unit dosage form (e.g., per tablet or capsule), of Compound 1 freebase equivalent, wherein the subject has had an inadequate response or intolerance to one or more DMARDS, and the subject achieves an ACR 50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In one embodiment, the method or use comprises administering to the subject about 45 mg, per unit dosage form (e.g., per tablet or capsule), of Compound 1 (freebase), or a pharmaceutically acceptable salt thereof or a solid state form of Compound 1 in an amount sufficient to deliver to the subject about 45 mg, per unit dosage form (e.g., per tablet or capsule), of Compound 1 freebase equivalent, wherein the subject has had an inadequate response or intolerance to one or more DMARDS, and the subject achieves an ACR 70 response at week 12 of treating. In another embodiment, the subject achieves an ACR70 response at week 8 of treating. In another embodiment, the subject achieves an ACR70 response at week 6 of treating. In another embodiment, the subject achieves an ACR70 response at week 4 of treating. In one embodiment, the method or use comprises administering to the subject about 45 mg, per unit dosage form (e.g., per tablet or capsule), of Compound 1 (freebase), or a pharmaceutically acceptable salt thereof or a solid state form of Compound 1 in an amount sufficient to deliver to the subject about 45 mg, per unit dosage form (e.g., per tablet or capsule), of Compound 1 freebase equivalent, wherein the subject has had an inadequate response or intolerance to one or more DMARDS, and the subject achieves a decrease in DAS28(CRP) as compared to baseline at week 12 of treating. In another embodiment, the subject achieves a decrease in DAS28(CRP) as compared to baseline at week 8 of treating. In another embodiment, the subject achieves a decrease in DAS28(CRP) as compared to baseline at week 6 of treating. In another embodiment, the subject achieves a decrease in DAS28(CRP) as compared to baseline at week 4 of treating. In another embodiment, the subject achieves a decrease in DAS28(CRP) as compared to baseline at week 2 of treating. In one embodiment, the method or use comprises administering about 45 mg, per unit dosage form (e.g., per tablet or capsule), of the solid state form to the subject. In one embodiment, the Compound 1 (freebase) or a pharmaceutically acceptable salt thereof or the solid state form is in a once daily extended release formulation. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate.

In another embodiment, the adult subject is also administered a csDMARD or a bDMARD in a combination therapy, as described hereinafter. In certain embodiments, the DMARD is MTX. In certain embodiments, the adult subject receiving the combination therapy achieves an ACR20 response, an ACR50 response, an ACR70 response, and/or a decrease in DAS28(CRP) as compared to baseline following treatment. In particular embodiments, the adult subject receiving the combination therapy achieves an ACR20 response, an ACR50 response, an ACR70 response, and/or a decrease in DAS28(CRP) as compared to baseline at week 12 of treating, and/or at week 8 of treating, and/or at week 6 of treating, and/or at week 4 of treating, and/or at week 2 of treating. In one embodiment, the adult subject receiving the combination therapy is administered about 7.5 mg, per unit dosage form (e.g., per tablet or capsule), of Compound 1 (freebase), or a pharmaceutically acceptable salt thereof or a solid state form of Compound 1 in an amount sufficient to deliver to the subject about 7.5 mg, per unit dosage form (e.g., per tablet or capsule), of Compound 1 freebase equivalent. In one embodiment, the adult subject receiving the combination therapy is administered about 15 mg, per unit dosage form (e.g., per tablet or capsule), of Compound 1 (freebase), or a pharmaceutically acceptable salt thereof or a solid state form of Compound 1 in an amount sufficient to deliver to the subject about 15 mg, per unit dosage form (e.g., per tablet or capsule), of Compound 1 freebase equivalent. In one embodiment, the adult subject receiving the combination therapy is administered about 30 mg, per unit dosage form (e.g., per tablet or capsule), of Compound 1 (freebase), or a pharmaceutically acceptable salt thereof or a solid state form of Compound 1 in an amount sufficient to deliver to the subject about 30 mg, per unit dosage form (e.g., per tablet or capsule), of Compound 1 freebase equivalent. In one embodiment, the adult subject receiving the combination therapy is administered about 45 mg, per unit dosage form (e.g., per tablet or capsule), of Compound 1 (freebase), or a pharmaceutically acceptable salt thereof or a solid state form of Compound 1 in an amount sufficient to deliver to the subject about 45 mg, per unit dosage form (e.g., per tablet or capsule), of Compound 1 freebase equivalent. In one embodiment, the method comprises administering about 7.5 mg or about 15 mg or about 30 mg or about 45 mg, per unit dosage form (e.g., per tablet or capsule), of the solid state form to the subject. In one embodiment, the Compound 1 (freebase) or a pharmaceutically acceptable salt thereof or the solid state form is in a once daily extended release formulation. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate.

In another embodiment, any of the methods of treating an adult subject having moderate to severely active rheumatoid arthritis described herein may further comprises alleviating at least one symptom selected from the group consisting of bone erosion, cartilage erosion, inflammation, and vascularity. In another embodiment, the arthritis is further treated by alleviating at least one symptom selected from the group consisting of joint distortion, swelling, joint deformation, ankyloses on flexion, and severely impaired movement.

In another embodiment, the present disclosure relates to a method of treating structural damage associated with rheumatoid arthritis in an adult subject, particularly in a human subject suffering from or susceptible to structural damage associated with rheumatoid arthritis. The method comprises administering to the subject a therapeutically effective amount of Compound 1 (freebase), or a pharmaceutically acceptable salt thereof or a solid state form of Compound 1 (e.g., a crystalline hydrate or a crystalline anhydrate) as described herein, such that the structural damage in the adult subject is inhibited or lessened. In one embodiment, the method comprises administering to the subject about 7.5 mg or about 15 mg or about 30 mg or about 45 mg, per unit dosage form (e.g., per tablet or capsule), per day of Compound 1 (freebase) or a pharmaceutically acceptable salt thereof or a solid state form of Compound 1 in an amount sufficient to deliver to the subject about 7.5 mg or about 15 mg or about 30 mg or about 45 mg, per unit dosage form (e.g., per tablet or capsule), per day of Compound 1 freebase equivalent, such that the structural damage in the adult subject is inhibited or lessened. In one embodiment, the method comprises administering to the subject about 7.5 mg or about 15 mg or about 30 mg or about 45 mg, per unit dosage form (e.g., per tablet or capsule) of a solid state form of Compound 1, such that the structural damage in the adult subject is inhibited or lessened. In one embodiment, the Compound 1 (freebase) or a pharmaceutically acceptable salt thereof or the solid state form of Compound 1 is administered to the subject orally QD (once daily). In one embodiment, the structural damage is selected from the group consisting of loss of bone and/or cartilage, bone erosion, joint space narrowing as measured by radiography, and combinations thereof. In one embodiment, the structural damaged is inhibited or lessened when the structural damage is reduced by at least 20%, or at least 25%, or at least 30%, or at least 50%. In other embodiments, structural damage is inhibited or lessened when there is no further radiographic progression of the structural damage. In certain embodiments, structural joint damage can be assessed radiographically and expressed as change in Total Sharp Score (TSS) and its components, the erosion score and Joint Space Narrowing (JSN) score, for example, at week 12 compared to baseline. In another aspect, the disclosure relates to a solid state form (and in particular a crystalline hydrate) of Compound 1, as described in the present disclosure, for use in treatment of structural damage associated with rheumatoid arthritis, particularly in a human subject suffering from or susceptible to rheumatoid arthritis. In one embodiment, the solid state form is a crystalline hydrate. In one embodiment, the crystalline hydrate is the Freebase Hydrate Form B. In one embodiment, the crystalline hydrate is a hemihydrate. In one embodiment, the hemihydrate is Freebase Hydrate Form C. In one embodiment, the solid state form is a crystalline anhydrate. In one embodiment, the crystalline anhydrate is Freebase Anhydrate Form D. In one embodiment, the stolid state form is Tartrate Hydrate. In one embodiment, the Compound 1 (freebase) or a pharmaceutically acceptable salt thereof or the crystalline hydrate is in a once daily extended release formulation. In one embodiment, the Compound 1 (freebase) or a pharmaceutically acceptable salt thereof or the crystalline hydrate is in a once daily extended release formulation, and the formulation delivers about 7.5 mg or about 15 mg or about 30 mg or about 45 mg per unit dosage form (e.g., per tablet or capsule) of Compound 1 (freebase equivalent) orally QD (once daily).

In another aspect, the disclosure relates to Compound 1 freebase or a pharmaceutically acceptable salt thereof or a solid state form of Compound 1 (e.g., a crystalline hydrate or crystalline anhydrate), as described in the present disclosure for use in treatment of structural damage associated with rheumatoid arthritis in an adult subject, particularly in a human subject suffering from or susceptible to structural damage associated with rheumatoid arthritis, such that the structural damage in the adult subject is inhibited or lessened, the use comprising administering to the subject a therapeutically effective amount of Compound 1 freebase or a pharmaceutically acceptable salt thereof or a solid state form of Compound 1. In one embodiment, the solid state form is a crystalline hydrate. In one embodiment, the crystalline hydrate is Freebase Hydrate Form B. In one embodiment, the crystalline hydrate is a hemihydrate. In one embodiment, the hemihydrate is Freebase Hydrate Form C. In one embodiment, the solid state form is a crystalline anhydrate. In one embodiment, the crystalline anhydrate is Freebase Anhydrate Form D. In one embodiment, the Compound 1 (freebase) or a pharmaceutically acceptable salt thereof or the solid state form of Compound 1 is in a once daily extended release formulation. In one embodiment, the formulation delivers about 7.5 mg or about 15 mg or about 30 mg or about 45 mg per unit dosage form (e.g., per tablet or capsule) of Compound 1 (freebase equivalent) or a solid state form of Compound 1 orally QD (once daily).

In one embodiment, the present disclosure is directed to a method of treating structural damage associated with rheumatoid arthritis in an adult subject, particularly in a human subject suffering from or susceptible to structural damage associated with rheumatoid arthritis, the method comprising administering to the subject about 7.5 mg, per unit dosage form (e.g., per tablet or capsule), per day of Compound 1 (freebase), or a pharmaceutically acceptable salt thereof or a solid state form of Compound 1 in an amount sufficient to deliver to the subject about 7.5 mg, per unit dosage form (e.g., per tablet or capsule), per day of Compound 1 freebase equivalent, such that the structural damage in the adult subject is inhibited or lessened. In one embodiment, the method comprises administering to the subject about 7.5 mg, per unit dosage form (e.g., per tablet or capsule), per day of a solid state form of Compound 1. In another aspect, the disclosure relates to Compound 1 freebase or a pharmaceutically acceptable salt thereof or a solid state form of Compound 1, for use in treatment of structural damage associated with rheumatoid arthritis in an adult subject, particularly in a human subject suffering from or susceptible to structural damage associated with rheumatoid arthritis, such that the structural damage in the adult subject is inhibited or lessened, the use comprising administering to the subject about 7.5 mg, per unit dosage form (e.g., per tablet or capsule) of Compound 1 freebase or a pharmaceutically acceptable salt thereof or a solid state form of Compound 1. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate. In one embodiment, the Compound 1 freebase or a pharmaceutically acceptable salt thereof or the solid state form of Compound 1 is administered orally QD (once daily). In one embodiment, the Compound 1 freebase or a pharmaceutically acceptable salt thereof or the solid state form of Compound 1 is in a once daily extended release formulation. In one embodiment, the structural damage is selected from the group consisting of loss of bone and/or cartilage, bone erosion, joint space narrowing as measured by radiography, and combinations thereof.

In one embodiment, the present disclosure is directed to a method of treating structural damage associated with rheumatoid arthritis in an adult subject, particularly in a human subject suffering from or susceptible to structural damage associated with rheumatoid arthritis, the method comprising administering to the subject about 15 mg, per unit dosage form (e.g., per tablet or capsule), per day of Compound 1 (freebase), or a pharmaceutically acceptable salt thereof or a solid state form of Compound 1 in an amount sufficient to deliver to the subject about 15 mg, per unit dosage form (e.g., per tablet or capsule), per day of Compound 1 freebase equivalent, such that the structural damage in the adult subject is inhibited or lessened. In one embodiment, the method comprises administering to the subject about 15 mg, per unit dosage form (e.g., per tablet or capsule), per day of a solid state form of Compound 1. In another aspect, the disclosure relates to Compound 1 freebase or a pharmaceutically acceptable salt thereof or a solid state form of Compound 1, for use in treatment of structural damage associated with rheumatoid arthritis in an adult subject, particularly in a human subject suffering from or susceptible to structural damage associated with rheumatoid arthritis, such that the structural damage in the adult subject is inhibited or lessened, the use comprising administering to the subject about 15 mg, per unit dosage form (e.g., per tablet or capsule) of Compound 1 freebase or a pharmaceutically acceptable salt thereof or a solid state form of Compound 1. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate. In one embodiment, the Compound 1 freebase or a pharmaceutically acceptable salt thereof or the solid state form of Compound 1 is administered orally QD (once daily). In one embodiment, the Compound 1 freebase or a pharmaceutically acceptable salt thereof or the solid state form of Compound 1 is in a once daily extended release formulation. In one embodiment, the structural damage is selected from the group consisting of loss of bone and/or cartilage, bone erosion, joint space narrowing as measured by radiography, and combinations thereof.

In one embodiment, the present disclosure is directed to a method of treating structural damage associated with rheumatoid arthritis in an adult subject, particularly in a human subject suffering from or susceptible to structural damage associated with rheumatoid arthritis, the method comprising administering to the subject about 30 mg, per unit dosage form (e.g., per tablet or capsule), per day of Compound 1 (freebase), or a pharmaceutically acceptable salt thereof or a solid state form of Compound 1 in an amount sufficient to deliver to the subject about 30 mg, per unit dosage form (e.g., per tablet or capsule), per day of Compound 1 freebase equivalent, such that the structural damage in the adult subject is inhibited or lessened. In one embodiment, the method comprises administering to the subject about 30 mg, per unit dosage form (e.g., per tablet or capsule), per day of a solid state form of Compound 1. In another aspect, the disclosure relates to Compound 1 freebase or a pharmaceutically acceptable salt thereof or a solid state form of Compound 1, for use in treatment of structural damage associated with rheumatoid arthritis in an adult subject, particularly in a human subject suffering from or susceptible to structural damage associated with rheumatoid arthritis, such that the structural damage in the adult subject is inhibited or lessened, the use comprising administering to the subject about 30 mg, per unit dosage form (e.g., per tablet or capsule) of Compound 1 freebase or a pharmaceutically acceptable salt thereof or a solid state form of Compound 1. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate. In one embodiment, the Compound 1 freebase or a pharmaceutically acceptable salt thereof or the solid state form of Compound 1 is administered orally QD (once daily). In one embodiment, the Compound 1 freebase or a pharmaceutically acceptable salt thereof or the solid state form of Compound 1 is in a once daily extended release formulation. In one embodiment, the structural damage is selected from the group consisting of loss of bone and/or cartilage, bone erosion, joint space narrowing as measured by radiography, and combinations thereof.

In one embodiment, the present disclosure is directed to a method of treating structural damage associated with rheumatoid arthritis in an adult subject, particularly in a human subject suffering from or susceptible to structural damage associated with rheumatoid arthritis, the method comprising administering to the subject about 45 mg, per unit dosage form (e.g., per tablet or capsule), per day of Compound 1 (freebase), or a pharmaceutically acceptable salt thereof or a solid state form of Compound 1 in an amount sufficient to deliver to the subject about 45 mg, per unit dosage form (e.g., per tablet or capsule), per day of Compound 1 freebase equivalent, such that the structural damage in the adult subject is inhibited or lessened. In one embodiment, the method comprises administering to the subject about 45 mg, per unit dosage form (e.g., per tablet or capsule), per day of a solid state form of Compound 1. In another aspect, the disclosure relates to Compound 1 freebase or a pharmaceutically acceptable salt thereof or a solid state form of Compound 1, for use in treatment of structural damage associated with rheumatoid arthritis in an adult subject, particularly in a human subject suffering from or susceptible to structural damage associated with rheumatoid arthritis, such that the structural damage in the adult subject is inhibited or lessened, the use comprising administering to the subject 45 mg, per unit dosage form (e.g., per tablet or capsule) of Compound 1 freebase or a pharmaceutically acceptable salt thereof or a solid state form of Compound 1. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate. In one embodiment, the Compound 1 freebase or a pharmaceutically acceptable salt thereof or the solid state form of Compound 1 is administered orally QD (once daily). In one embodiment, the Compound 1 freebase or a pharmaceutically acceptable salt thereof or the solid state form of Compound 1 is in a once daily extended release formulation. In one embodiment, the structural damage is selected from the group consisting of loss of bone and/or cartilage, bone erosion, joint space narrowing as measured by radiography, and combinations thereof.

In another embodiment, the present disclosure is directed to a method of reducing signs and symptoms of rheumatoid arthritis in an adult subject, particularly in a human subject suffering from or susceptible to moderately to severely active rheumatoid arthritis. The method comprises administering to the subject a therapeutically effective amount of Compound 1 (freebase), or a pharmaceutically acceptable salt thereof or a solid state form of Compound 1 (e.g., a crystalline hydrate or a crystalline anhydrate) as described herein. In one embodiment, the method comprises administering to the subject about 7.5 mg or about 15 mg or about 30 mg or about 45 mg, per unit dosage form (e.g., per tablet or capsule), per day of Compound 1 (freebase) or a pharmaceutically acceptable salt thereof or a solid state form of Compound 1 in an amount sufficient to deliver to the subject about 7.5 mg or about 15 mg or about 30 mg or about 45 mg, per unit dosage form (e.g., per tablet or capsule), per day of Compound 1 freebase equivalent. In one embodiment, the method comprises administering to the subject about 7.5 mg or about 15 mg or about 30 mg or about 45 mg, per unit dosage form (e.g., per tablet or capsule) of a solid state form of Compound 1. In one embodiment, the Compound 1 (freebase) or a pharmaceutically acceptable salt thereof or the solid state form of Compound 1 is administered to the subject orally QD (once daily). In another aspect, the disclosure relates to Compound 1 freebase or a pharmaceutically acceptable salt thereof or a solid state form (and in particular a crystalline hydrate) of Compound 1, as described in the present disclosure, for use in reducing signs and symptoms of rheumatoid arthritis in an adult subject, particularly in a human subject suffering from or susceptible to moderate to severely active rheumatoid arthritis, the use comprising administering to the subject a therapeutically effective amount of Compound 1 freebase or a pharmaceutically acceptable salt thereof or a solid state form (and in particular a crystalline hydrate) of Compound 1. In one embodiment, the Compound 1 freebase or a pharmaceutically acceptable salt thereof or the solid state form of Compound 1 is in a once daily extended release formulation. In one embodiment, the formulation delivers about 7.5 mg or about 15 mg or about 30 mg or about 45 mg per unit dosage form (e.g., per tablet or capsule) of Compound 1 (freebase equivalent) or the solid state form of Compound 1 to the subject orally QD (once daily). In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate.

In one embodiment, the present disclosure is directed to a method of reducing the signs and symptoms of rheumatoid arthritis in an adult subject, particularly in a human subject suffering from or susceptible to moderately to severely active rheumatoid arthritis, the method comprising administering to the subject about 7.5 mg, per unit dosage form (e.g., per tablet or capsule), per day of Compound 1 (freebase), or a pharmaceutically acceptable salt thereof or a solid state form of Compound 1 in an amount sufficient to deliver to the subject about 7.5 mg, per unit dosage form (e.g., per tablet or capsule), per day of Compound 1 freebase equivalent. In one embodiment, the method comprises administering to the subject about 7.5 mg, per unit dosage form (e.g., per tablet or capsule), per day of a solid state form of Compound 1. In another aspect, the disclosure relates to Compound 1 freebase or a pharmaceutically acceptable salt thereof or a solid state form of Compound 1 for use in reducing signs and symptoms of rheumatoid arthritis in an adult subject, particularly in a human subject suffering from or susceptible to moderate to severely active rheumatoid arthritis, the use comprising administering to the subject about 7.5 mg, per unit dosage form (e.g., per tablet or capsule) of Compound 1 freebase or a pharmaceutically acceptable salt thereof or a solid state form of Compound 1. In one embodiment, the solid state form is a crystalline hydrate. In one embodiment, the crystalline hydrate is the Freebase Hydrate Form B. In one embodiment, the crystalline hydrate is a hemihydrate. In one embodiment, the hemihydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate. In one embodiment, the Compound 1 freebase or a pharmaceutically acceptable salt thereof or the solid state form of Compound 1 is administered orally QD (once daily). In one embodiment, the Compound 1 freebase or a pharmaceutically acceptable salt thereof or the solid state form of Compound 1 is in a once daily extended release formulation. In one embodiment, the Compound 1 (freebase) or a pharmaceutically acceptable salt thereof or the solid state form of Compound 1 is in a once daily extended release formulation, and the formulation delivers about 7.5 mg per unit dosage form (e.g., per tablet or capsule) of Compound 1 (freebase equivalent) or the solid state form of Compound 1 orally QD (once daily) to the subject.

In one embodiment, the present disclosure is directed to a method of reducing the signs and symptoms of rheumatoid arthritis in an adult subject, particularly in a human subject suffering from or susceptible to moderately to severely active rheumatoid arthritis, the method comprising administering to the subject about 15 mg, per unit dosage form (e.g., per tablet or capsule), per day of Compound 1 (freebase) or a pharmaceutically acceptable salt thereof or a solid state form of Compound 1 in an amount sufficient to deliver to the subject about 15 mg, per unit dosage form (e.g., per tablet or capsule), per day of Compound 1 freebase equivalent. In one embodiment, the method comprises administering to the subject about 15 mg, per unit dosage form (e.g., per tablet or capsule), per day of a solid state form of Compound 1. In another aspect, the disclosure relates to Compound 1 freebase or a pharmaceutically acceptable salt thereof or a solid state form of Compound 1 for use in reducing signs and symptoms of rheumatoid arthritis in an adult subject, particularly in a human subject suffering from or susceptible to moderate to severely active rheumatoid arthritis, the use comprising administering to the subject, about 15 mg, per unit dosage form (e.g., per tablet or capsule) of Compound 1 freebase or a pharmaceutically acceptable salt thereof or a solid state form of Compound 1. In one embodiment, the solid state form is a crystalline hydrate. In one embodiment, the crystalline hydrate is a hemihydrate. In one embodiment, the hemihydrate is Freebase Hydrate Form C. In one embodiment, the crystalline hydrate is the Freebase Hydrate Form B. In one embodiment, the solid state form is a crystalline anhydrate. In one embodiment, the crystalline anhydrate is the Freebase Anhydrate Form D. In one embodiment, the solid state form is the Tartrate Hydrate. In one embodiment, the Compound 1 freebase or the solid state form of Compound 1 is administered orally QD (once daily). In one embodiment, the Compound 1 (freebase) or a pharmaceutically acceptable salt thereof or the solid state form of Compound 1 is in a once daily extended release formulation. In one embodiment, the Compound 1 (freebase) or a pharmaceutically acceptable salt thereof or the solid state form of Compound 1 is in a once daily extended release formulation, and the formulation delivers about 15 mg per unit dosage form (e.g., per tablet or capsule) of Compound 1 (freebase equivalent) or the solid state form of Compound 1 orally QD (once daily) to the subject.

In another embodiment, the present disclosure is directed to a method of reducing signs and symptoms of rheumatoid arthritis in an adult subject, particularly in a human subject suffering from or susceptible to moderately to severely active rheumatoid arthritis. The method comprises administering to the subject about 30 mg, per unit dosage form (e.g., per tablet or capsule), per day of Compound 1 (freebase) or a pharmaceutically acceptable salt thereof or a solid state form of Compound 1 in an amount sufficient to deliver to the subject about 30 mg, per unit dosage form (e.g., per tablet or capsule), per day of Compound 1 freebase equivalent. In one embodiment, the method comprises administering to the subject about 30 mg, per unit dosage form (e.g., per tablet or capsule), per day of a solid state form of Compound 1. In another aspect, the disclosure relates to Compound 1 freebase or a pharmaceutically acceptable salt thereof or a solid state form of Compound 1 for use in reducing signs and symptoms of rheumatoid arthritis in an adult subject, particularly in a human subject suffering from or susceptible to moderate to severely active rheumatoid arthritis, the use comprising administering to the subject about 30 mg, per unit dosage form (e.g., per tablet or capsule) of Compound 1 freebase or a pharmaceutically acceptable salt thereof or a solid state form of Compound 1. In one embodiment, the solid state form is a crystalline hydrate. In one embodiment, the crystalline hydrate is a hemihydrate. In one embodiment, the hemihydrate is Freebase Hydrate Form C. In one embodiment, the crystalline hydrate is the Freebase Hydrate Form B. In one embodiment, the solid state form is a crystalline anhydrate. In one embodiment, the crystalline anhydrate is the Freebase Anhydrate Form D. In one embodiment, the solid state form is the Tartrate Hydrate. In one embodiment, the Compound 1 freebase or a pharmaceutically acceptable salt thereof or the solid state form of Compound 1 is administered orally QD (once daily). In one embodiment, the Compound 1 (freebase) or the crystalline hydrate is in a once daily extended release formulation. In one embodiment, the Compound 1 (freebase) or a pharmaceutically acceptable salt thereof or the solid state form of Compound 1 is in a once daily extended release formulation, and the formulation delivers about 30 mg per unit dosage form (e.g., per tablet or capsule) of Compound 1 (freebase equivalent) or the solid state form of Compound 1 orally QD (once daily) to the subject.

In one embodiment, the present disclosure is directed to a method of reducing the signs and symptoms of rheumatoid arthritis in an adult subject, particularly in a human subject suffering from or susceptible to moderately to severely active rheumatoid arthritis, the method comprising administering to the subject about 45 mg, per unit dosage form (e.g., per tablet or capsule), per day of Compound 1 (freebase), or a pharmaceutically acceptable salt thereof or a solid state form of Compound 1 in an amount sufficient to deliver to the subject about 45 mg, per unit dosage form (e.g., per tablet or capsule), per day of Compound 1 freebase equivalent. In one embodiment, the method comprises administering to the subject about 45 mg, per unit dosage form (e.g., per tablet or capsule), per day of a solid state form of Compound 1. In another aspect, the disclosure relates to Compound 1 freebase or a pharmaceutically acceptable salt thereof or a solid state form of Compound 1 for use in reducing signs and symptoms of rheumatoid arthritis in an adult subject, particularly in a human subject suffering from or susceptible to moderate to severely active rheumatoid arthritis, the use comprising administering to the subject about 45 mg, per unit dosage form (e.g., per tablet or capsule) of Compound 1 freebase or a pharmaceutically acceptable salt thereof or a solid state form of Compound 1. In one embodiment, the solid state form is a crystalline hydrate. In one embodiment, the crystalline hydrate is the Freebase Hydrate Form B. In one embodiment, the crystalline hydrate is a hemihydrate. In one embodiment, the hemihydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate. In one embodiment, the Compound 1 freebase or a pharmaceutically acceptable salt thereof or the solid state form of Compound 1 is administered orally QD (once daily). In one embodiment, the Compound 1 freebase or a pharmaceutically acceptable salt thereof or the solid state form of Compound 1 is in a once daily extended release formulation. In one embodiment, the Compound 1 (freebase) or a pharmaceutically acceptable salt thereof or the solid state form of Compound 1 is in a once daily extended release formulation, and the formulation delivers about 45 mg per unit dosage form (e.g., per tablet or capsule) of Compound 1 (freebase equivalent) or the solid state form of Compound 1 orally QD (once daily) to the subject.

In another aspect, the disclosure relates to a solid state form (and in particular a crystalline hydrate) of Compound 1, as described in the present disclosure, for use in reducing signs and symptoms of rheumatoid arthritis in an adult subject, particularly in a human subject suffering from or susceptible to rheumatoid arthritis.

In another embodiment, any of the methods of reducing signs and symptoms of rheumatoid arthritis described herein may further comprises alleviating at least one symptom selected from the group consisting of bone erosion, cartilage erosion, inflammation, and vascularity. In another embodiment, the arthritis is further treated by alleviating at least one symptom selected from the group consisting of joint distortion, swelling, joint deformation, ankyloses on flexion, and severely impaired movement.

In another embodiment, the Compound 1 freebase or a pharmaceutically acceptable salt thereof and/or solid state forms of Compound 1 used in any of the methods set forth herein may be administered to the subject in a once daily extended release solid oral dosage form. In particular, in one embodiment, the methods comprise once daily administration to the subject of an extended release (e.g., modified release) solid oral dosage form comprising the Compound 1 freebase or a pharmaceutically acceptable salt thereof or the solid state form of Compound 1, and a pharmaceutically acceptable polymeric carrier substantially contributing to the modification of the release of the Compound 1 freebase or a pharmaceutically acceptable salt thereof or the solid state form of Compound 1. In one aspect, the dosage form sustains release of the Compound 1 freebase or a pharmaceutically acceptable salt thereof or the solid state form of Compound 1 for from about 4 hours to about 24 hours following entry of the dosage form into a use environment. In one embodiment, the dosage form has a release rate of not more than about 60% after passage of about 4 hours following entry of the dosage form into a use environment. The term "entry into a use environment" refers to contact of the dosage form with gastric fluids of the subject to whom it is administered. As used herein, the term "release rate" refers to the percentage of the active ingredient (e.g., Compound 1 or a solid state form of Compound 1) in the dosage form that is released in the given time period, and under the specified conditions. In one embodiment, the dosage form comprises about 7.5 mg or about 15 mg or about 30 mg or about 45 mg, per unit dosage form (e.g., per tablet or capsule), of Compound 1 (freebase), or a pharmaceutically acceptable salt thereof or a solid state form of Compound 1 in an amount sufficient to deliver to the subject about 7.5 mg or about 15 mg or about 30 mg or about 45 mg, per unit dosage form (e.g., per tablet or capsule), per day of Compound 1 freebase equivalent. In one embodiment, the dosage form comprises about 7.5 mg or about 15 mg or about 30 mg or about 45 mg, per unit dosage form (e.g., per tablet or capsule), per day of a solid state form of Compound 1. In one embodiment, the solid state form is Freebase Hydrate Form B. In one embodiment, the solid state form is Freebase Hydrate Form C. In one embodiment, the solid state form is Freebase Anhydrate Form D. In one embodiment, the solid state form is Tartrate Hydrate. In one embodiment, the pharmaceutically acceptable polymeric carrier is a release control polymer, as set forth herein.

Thus, in one aspect, the dosage form sustains release of the Compound 1 freebase or a pharmaceutically acceptable salt thereof or the solid state form of Compound 1 for from about 4 hours to about 24 hours. In one embodiment, the dosage form releases the active ingredient (i.e., Compound 1 or a solid state form of Compound 1), at a release rate of not more than about 25%, or from about 10% to about 25%, or from about 15% to about 20%, or about 20% after passage of about 1 hour following entry into the use environment. In one embodiment, the dosage form releases the active ingredient at a release rate of not more than about 40%, or from about 20% to about 40%, or from about 25% to about 35% after passage of about 2 hours following entry into the use environment. In one embodiment, the dosage form releases the active ingredient at a release rate of not more than about 60%, or from about 30% to about 60%, or from about 40% to about 60%, or from about 45% to about 55% after passage of about 4 hours following entry into the use environment. In one embodiment, the dosage form releases the active ingredient at a release rate of not more than about 70% or from about 40% to about 70%, or from about 55% to about 70% after passage of about 6 hours following entry into the use environment. In one embodiment, the dosage form releases the active ingredient at a release rate of not more than about 80% or from about 55% to about 80%, or from about 60% to about 80% after passage of about 6 hours following entry into the use environment. In one embodiment, the dosage form releases the active ingredient at a release rate of not more than about 80%, or not less than about 50%, or not less than about 60%, or not less than about 70%, or not less than about 75%, or from about 50% to about 80%, or from about 60% to about 80%, or from about 65% to about 80% after passage of about 8 hours following entry into the use environment. In one embodiment, the dosage form releases the active ingredient at a release rate of not less than about 55%, or not less than about 60% or not less than about 70%, or not less than about 80%, or not less than about 85%, or from about 55% to about 90%, or from about 70% to about 90% after passage of about 10 hours following entry into the use environment. In one embodiment, the dosage form releases the active ingredient at a release rate of not less than about 65%, or not less than about 70%, or not less than about 80%, or not less than about 90%, or from about 65% to about 99%, or from about 80% to about 99%, or from about 90% to about 99% after passage of about 16 hours following entry into the use environment. In one embodiment, the dosage form releases the active ingredient at a release rate of not less than about 70%, or not less than about 80%, or not less than about 90%, or from about 70% to 100%, or from about 80% to 100% after passage of about 20 hours following entry into the use environment. In one aspect, the dosage form has a release rate of not more than about 60% after passage of about 4 hours following entry of the dosage form into a use environment, from about 50% to about 80% after passage of about 8 hours following entry of the dosage form into a use environment, from about 55% to about 90% after passage of about 10 hours following entry of the dosage form into a use environment, and from about 70% to 100% after passage of about 20 hours following entry of the dosage form into a use environment.

In one embodiment, the present disclosure is directed to a method of treating a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis, and systemic lupus erythematosus, the method comprising once daily administration to a subject suffering from or susceptible to the condition, of an extended release solid oral dosage form comprising about 7.5 mg or about 15 mg or about 30 mg or about 45 mg, per unit dosage form (e.g., per tablet or capsule), of Compound 1 freebase or a pharmaceutically acceptable salt thereof or a solid state form of Compound 1 in an amount sufficient to deliver to the subject about 7.5 mg, or about 15 mg, or about 30 mg, or about 45 mg, per unit dosage form (e.g., per tablet or capsule), of Compound 1 freebase equivalent, and a pharmaceutically acceptable polymeric carrier substantially contributing to the modification of the release of the Compound 1 freebase or a pharmaceutically acceptable salt thereof or the solid state form of Compound 1, wherein the dosage form sustains release of the Compound 1 freebase or a pharmaceutically acceptable salt thereof or the solid state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid state form of Compound 1. In one embodiment, the solid state form is Freebase Hydrate Form B. In one embodiment, the solid state form is Freebase Hydrate Form C. In one embodiment, the solid state form is Freebase Anhydrate Form D. In one embodiment, the solid state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment.

In another aspect, the disclosure is directed to an extended release solid oral dosage form comprising Compound 1 freebase or a pharmaceutically acceptable salt thereof or a solid state form of Compound 1 for use in treating a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis, and systemic lupus erythematosus, the use comprising once daily administration to a subject suffering from or susceptible to the condition, of the extended release solid oral dosage form, wherein the solid dosage form comprises about 7.5 mg or about 15 mg or about 30 mg or about 45 mg, per unit dosage form (e.g., per tablet or capsule) of Compound 1 freebase, or a pharmaceutically acceptable salt thereof or a solid state form of Compound 1 in an amount sufficient to deliver to the subject about 7.5 mg, or about 15 mg, or about 30 mg, or about 45 mg, per unit dosage form (e.g., per tablet or capsule), of Compound 1 freebase equivalent, and a pharmaceutically acceptable polymeric carrier substantially contributing to the modification of the release of the Compound 1 freebase or a pharmaceutically acceptable salt thereof or the solid state form of Compound 1, wherein the dosage form sustains release of the Compound 1 freebase or a pharmaceutically acceptable salt thereof or the solid state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid state form of Compound 1. In one embodiment, the solid state form is Freebase Hydrate Form B. In one embodiment, the solid state form is Freebase Hydrate Form C. In one embodiment, the solid state form is Freebase Anhydrate Form D. In one embodiment, the solid state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment.

In another embodiment, the disclosure is directed to a method of treating an adult subject having moderate to severely active rheumatoid arthritis, the method comprising once daily administration to the subject, particularly a human subject suffering from or susceptible to rheumatoid arthritis, of an extended release solid oral dosage form comprising about 7.5 mg, or about 15 mg, or about 30 mg, or about 45 mg, per unit dosage form (e.g., per tablet or capsule), of Compound 1 freebase or a pharmaceutically acceptable salt thereof or a solid state form of Compound 1 in an amount sufficient to deliver to the subject about 7.5 mg, or about 15 mg, or about 30 mg, or about 45 mg, per unit dosage form (e.g., per tablet or capsule), of Compound 1 freebase equivalent, and a pharmaceutically acceptable polymeric carrier substantially contributing to the modification of the release of the Compound 1 freebase or a pharmaceutically acceptable salt thereof or the solid state form of Compound 1, wherein the dosage form sustains release of the Compound 1 freebase or a pharmaceutically acceptable salt thereof or the solid state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid state form of Compound 1. In one embodiment, the solid state form is Freebase Hydrate Form B. In one embodiment, the solid state form is Freebase Hydrate Form C. In one embodiment, the solid state form is Freebase Anhydrate Form D. In one embodiment, the solid state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment. In one embodiment, the subject has symptoms selected from the group consisting of at least 6 swollen joints, at least 6 tender joints, and combinations thereof prior to treating.

In another aspect, the disclosure is directed to an extended release solid oral dosage form comprising Compound 1 freebase or a pharmaceutically acceptable salt thereof or a solid state form of Compound 1 for use in treating an adult subject having moderate to severely active rheumatoid arthritis, the use comprising once daily administration to the subject, particularly a subject suffering from or susceptible to moderately to severely active rheumatoid arthritis, of the extended release solid oral dosage form, wherein the solid dosage form comprises about 7.5 mg or about 15 mg or about 30 mg or about 45 mg, per unit dosage form (e.g., per tablet or capsule) of Compound 1 freebase or a pharmaceutically acceptable salt thereof, or a solid state form of Compound 1 in an amount sufficient to deliver to the subject about 7.5 mg, or about 15 mg, or about 30 mg, or about 45 mg, per unit dosage form (e.g., per tablet or capsule), of Compound 1 freebase equivalent, and a pharmaceutically acceptable polymeric carrier substantially contributing to the modification of the release of the Compound 1 freebase or a pharmaceutically acceptable salt thereof or the solid state form of Compound 1, wherein the dosage form sustains release of the Compound 1 freebase or a pharmaceutically acceptable salt thereof or the solid state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid state form of Compound 1. In one embodiment, the solid state form is Freebase Hydrate Form B. In one embodiment, the solid state form is Freebase Hydrate Form C. In one embodiment, the solid state form is Freebase Anhydrate Form D. In one embodiment, the solid state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment. In one embodiment, the subject has symptoms selected from the group consisting of at least 6 swollen joints, at least 6 tender joints, and combinations thereof prior to treating.

In one embodiment, the disclosure is directed to a method of treating structural damage associated with rheumatoid arthritis in an adult subject, the method comprising once daily administration to the subject, particularly a human subject suffering from or susceptible to rheumatoid arthritis, of an extended release solid oral dosage form comprising about 7.5 mg, or about 15 mg, or about 30 mg, or about 45 mg, per unit dosage form (e.g., per tablet or capsule), of Compound 1 freebase or a pharmaceutically acceptable salt thereof or a solid state form of Compound 1 in an amount sufficient to deliver to the subject about 7.5 mg, or about 15 mg, or about 30 mg, or about 45 mg, per unit dosage form (e.g., per tablet or capsule), of Compound 1 freebase or a pharmaceutically acceptable salt thereof equivalent, and a pharmaceutically acceptable polymeric carrier substantially contributing to the modification of the release of the Compound 1 freebase or a pharmaceutically acceptable salt thereof or the solid state form of Compound 1, wherein the dosage form sustains release of the Compound 1 freebase or a pharmaceutically acceptable salt thereof or the solid state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid state form of Compound 1. In one embodiment, the solid state form is Freebase Hydrate Form B. In one embodiment, the solid state form is Freebase Hydrate Form C. In one embodiment, the solid state form is Freebase Anhydrate Form D. In one embodiment, the solid state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment.

In another aspect, the disclosure is directed to an extended release solid oral dosage form comprising Compound 1 freebase or a pharmaceutically acceptable salt thereof or a solid state form of Compound 1 for use in treating structural damage associated with rheumatoid arthritis in an adult subject, the use comprising once daily administration to the subject, particularly a subject suffering from or susceptible to structural damage associated with rheumatoid arthritis, of the extended release solid oral dosage form, wherein the solid dosage form comprises about 7.5 mg or about 15 mg or about 30 mg or about 45 mg, per unit dosage form (e.g., per tablet or capsule) of Compound 1 freebase, or a pharmaceutically acceptable salt thereof or a solid state form of Compound 1 in an amount sufficient to deliver to the subject about 7.5 mg, or about 15 mg, or about 30 mg, or about 45 mg, per unit dosage form (e.g., per tablet or capsule), of Compound 1 freebase equivalent, and a pharmaceutically acceptable polymeric carrier substantially contributing to the modification of the release of the Compound 1 freebase or a pharmaceutically acceptable salt thereof or the solid state form of Compound 1, wherein the dosage form sustains release of the Compound 1 freebase or a pharmaceutically acceptable salt thereof or the solid state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid state form of Compound 1. In one embodiment, the solid state form is Freebase Hydrate Form B. In one embodiment, the solid state form is Freebase Hydrate Form C. In one embodiment, the solid state form is Freebase Anhydrate Form D. In one embodiment, the solid state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment.

In one embodiment, the disclosure is directed to a method of reducing signs and symptoms of rheumatoid arthritis in an adult subject, the method comprising once daily administration to the subject, particularly a human subject suffering from or susceptible to moderately to severely active rheumatoid arthritis, of an extended release solid oral dosage form comprising about 7.5 mg or about 15 mg or about 30 mg or about 45 mg, per unit dosage form (e.g., per tablet or capsule), of Compound 1 freebase or a pharmaceutically acceptable salt thereof or a solid state form of Compound 1 in an amount sufficient to deliver to the subject about 7.5 mg or about 15 mg or about 30 mg or about 45 mg, per unit dosage form (e.g., per tablet or capsule), of Compound 1 freebase equivalent, and a pharmaceutically acceptable polymeric carrier substantially contributing to the modification of the release of the Compound 1 freebase or a pharmaceutically acceptable salt thereof or the solid state form of Compound 1, wherein the dosage form sustains release of the Compound 1 freebase or a pharmaceutically acceptable salt thereof or the solid state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid state form of Compound 1. In one embodiment, the solid state form is Freebase Hydrate Form B. In one embodiment, the solid state form is Freebase Hydrate Form C. In one embodiment, the solid state form is Freebase Anhydrate Form D. In one embodiment, the solid state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment.

In another aspect, the disclosure is directed to an extended release solid oral dosage form comprising Compound 1 freebase or a pharmaceutically acceptable salt thereof or a solid state form of Compound 1 for use in reducing signs and symptoms associated with rheumatoid arthritis in an adult subject, the use comprising once daily administration to the subject, particularly a subject suffering from or susceptible to rheumatoid arthritis, of the extended release solid oral dosage form, wherein the solid dosage form comprises about 7.5 mg or about 15 mg or about 30 mg or about 45 mg, per unit dosage form (e.g., per tablet or capsule) of Compound 1 freebase, or a pharmaceutically acceptable salt thereof or a solid state form of Compound 1 in an amount sufficient to deliver to the subject about 7.5 mg, or about 15 mg, or about 30 mg, or about 45 mg, per unit dosage form (e.g., per tablet or capsule), of Compound 1 freebase equivalent, and a pharmaceutically acceptable polymeric carrier substantially contributing to the modification of the release of the Compound 1 freebase or a pharmaceutically acceptable salt thereof or the solid state form of Compound 1, wherein the dosage form sustains release of the Compound 1 freebase or a pharmaceutically acceptable salt thereof or the solid state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid state form of Compound 1. In one embodiment, the solid state form is Freebase Hydrate Form B. In one embodiment, the solid state form is Freebase Hydrate Form C. In one embodiment, the solid state form is Freebase Anhydrate Form D. In one embodiment, the solid state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment.

In the foregoing methods, in one embodiment, the pharmaceutically acceptable polymeric carrier comprises a release control polymer. In one embodiment, the release control polymer is hydroxypropylmethyl cellulose. In one embodiment, the dosage form comprises a pH modifier. In one embodiment, the pH modifier is tartaric acid. In one embodiment, the dosage form comprises from about 10 w/w % to about 35 w/w % tartaric acid. In one embodiment, the dosage form comprises about 10 w/w % tartaric acid. In one embodiment, the dosage form comprises about 20 w/w % tartaric acid. In one embodiment, the dosage form comprises about 30 w/w % tartaric acid.

In another embodiment the methods of the present disclosure further comprise administering Compound 1 or a solid state form thereof for at least 8 weeks. In another embodiment, the methods of the present disclosure comprise administering Compound 1 or a solid state form thereof for at least 12 weeks.

In another embodiment, the present disclosure relates to the use of a solid state form of Compound 1 for treating a condition as described in the various embodiments of the present disclosure.

In another embodiment, the present disclosure relates to a solid state form of Compound 1 for use in treatment of a condition as described in the various embodiments of the present disclosure.

V. COMBINATION THERAPY AND FIXED-DOSE COMBINATIONS

The present disclosure further relates to (i) methods of treatment and uses as previously described that further comprise the administration of one or more additional therapeutic agents (i.e., combination therapies), and (ii) pharmaceutical compositions as previously described that further comprise one or more additional therapeutic agents (i.e., fixed-dose combinations). When administered to a subject in combination with one or more additional therapeutic agents, the solid state form of Compound 1 and the additional therapeutic agent(s) can be administered as separate dosage forms or as a single dosage form comprising the solid state form of Compound 1 and the additional therapeutic agent(s). If administered as a separate dosage form, the additional therapeutic agent may be administered either simultaneously with, or sequentially with, the dosage form comprising the solid state form of Compound 1.

For example, the solid state forms of the present disclosure may be administered in a pharmaceutically acceptable form either alone or in combination with one or more additional agents that modulate a mammalian immune system or with anti-inflammatory agents. These agents may include but are not limited to cyclosporin A (e.g., SANDIMMUNE® or NEORAL®), rapamycin, FK-506 (tacrolimus), leflunomide, deoxyspergualin, mycophenolate (e.g., CELLCEPT®), azathioprine (e.g., IMURAN®), daclizumab (e.g., ZENAPAX®), OKT3 (e.g., ORTHOCLONE®), AtGam, aspirin, acetaminophen, aminosalicylate, ciprofloxacin, corticosteroid, metronidazole, probiotic, tacrolimus, ibuprofen, naproxen, piroxicam, and anti-inflammatory steroids (e.g., prednisolone or dexamethasone). In certain embodiments, the one or more additional agents are selected from the group consisting of aspirin, acetaminophen, aminosalicylate, ciprofloxacin, corticosteroid, cyclosporine, metronidazole, probiotic, tacrolimus, ibuprofen, naproxen, piroxicam, prednisolone, dexamethasone, anti-inflammatory steroid, methotrexate, chloroquine, azathioprine, hydroxychloroquine, penicillamine, sulfasalazine, leflunomide, tocilizumab, anakinra, abatacept, certolizumab pegol, golimumab, vedolizumab, natalizumab, ustekinumab, rituximab, efalizumab, belimumab, etanercept, infliximab, adalimumab, and immune modulator (e.g., activator) for CD4+CD25+ $T_{reg}$ cells.

Non-limiting examples of therapeutic agents for rheumatoid arthritis with which a compound of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-12, IL-15, IL-16, IL-21, IL-23, interferons, EMAP-II, GM-CSF, FGF, and PDGF. Compounds of the invention can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (39 or CD40L). Combinations of therapeutic agents may interfere at different points in the autoimmune and subsequent inflammatory cascade. Such examples may include TNF antagonists like chimeric, humanized or human TNF antibodies, adalimumab (such as HUMIRA™ brand adalimumab), infliximab such as CA2 (REMICADE™ brand infliximab), golimumab such as SIMPONI™ (golimumab), certolizumab pegol such as CIMZIA™, tocilizumab such as ACTEMRA™, CDP 571, and soluble p55 or p75 TNF receptors, derivatives, thereof, etanercept such as p75TNFR1gG (ENBREL™ brand etanercept) or p55TNFR1gG (lenercept), and also TNFα converting enzyme (TACE) inhibitors; similarly IL-1 inhibitors (Interleukin-1-converting enzyme inhibitors, IL-1RA etc.) may be effective for the same reason. Other combinations include Interleukin 11.

The solid state form may also be combined with nonbiologic DMARDS or other agents, such as methotrexate, 6-mercaptopurine, azathioprine sulphasalazine, mesalazine, olsalazine chloroquinine/hydroxychloroquine, penicillamine, aurothiomalate (intramuscular and oral), azathioprine, colchicine, corticosteroids (oral, inhaled and local injection), beta-2 adrenoreceptor agonists (salbutamol, terbutaline, salmeterol), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signalling by proinflammatory cytokines such as IL-1 (e.g., NIK, IKK, p38 or MAP kinase inhibitors), IL-1β converting enzyme inhibitors, T-cell signalling inhibitors such as kinase inhibitors, metalloproteinase inhibitors, sulfasalazine, and 6-mercaptopurines. The solid state form may also be combined with methotrexate.

Non-limiting examples of therapeutic agents for inflammatory bowel disease (IBD) with which the solid state form can be combined may include (but are not limited to) the following: budesonide; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as TNFα or IL-1 (e.g., NIK, IKK, or MAP kinase inhibitors); IL-1β converting enzyme inhibitors; TNFα converting enzyme inhibitors; T-cell signalling inhibitors such as kinase inhibitors; metalloprdteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and anti-inflammatory cytokines (e.g., IL-4, IL-10, IL-11, IL-13 and TGFβ). The solid state form may also be combined with methotrexate.

Examples of therapeutic agents for Crohn's disease with which the solid state form can lie combined include the following: TNF antagonists, for example, anti-TNF antibodies, adalimumab (such as HUMIRA™ brand adalimumab), infliximab such as CA2 (REMICADE™ brand infliximab), certolizumab pegol such as CIMZIA™, golimumab such as SIMPONI™ (golimumab), CDP 571, TNFR-Ig constructs, etanercept such as p75TNFRIgG (ENBREL™ brand etanercept) and lenercept such as p55TNFRIgG (Lenercept™) inhibitors and PDE4 inhibitors.

The solid state form can be combined with corticosteroids, for example, budesonide and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors; 6-mercaptopurine; IL-11; mesalamine; prednisone; azathioprine; mercaptopurine; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis (MS) with which the solid state form can be combined include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; cladribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of the invention can be combined with antibodies to cell surface molecules such as CD2, CD3, CD4, CD8, CD19, CD20, CD25, CD28, CD30, CD40, CD45, CD69, CD80, CD86, CD90 or their ligands. The solid state form may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adenosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g., soluble p55 or p75 TNF receptors, sIL-1RI, sIL-1RII, sIL-6R) and anti-inflammatory cytokines (e.g. IL-4, IL-10, IL-13 and TGFβ). Examples of therapeutic agents for multiple sclerosis in which a compound of the invention can be combined to include interferon-β, for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

The solid state form may also be combined with agents, such as alemtuzumab, dronabinol, daclizumab, mitoxantrone, xaliproden hydrochloride, fampridine, glatiramer acetate, natalizumab, sinnabidol, α-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for ankylosing spondylitis (AS) with which the solid state form can be combined include the following: ibuprofen, diclofenac, misoprostol, naproxen, meloxicam, indomethacin, diclofenac, celecoxib, rofecoxib, sulfasalazine, methotrexate, azathioprine, minocycline, prednisone, and anti-TNF antibodies, adalimumab (such as HUMIRA™ brand adalimumab), infliximab such as CA2 (REMICADE™ brand infliximab), CDP 571, TNFR-Ig constructs, etanercept such as p75TNFRIgG (ENBREL™ brand etanercept) and lenercept such as p55TNFRIgG (LENERCEPT™).

Non-limiting examples of therapeutic agents for psoriasis (Ps, such as moderate to severe plaque psoriasis) with which the solid state form can be combined include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874, ustekinumab, and adalimumab (such as HUMIRA™ brand adalimumab).

Non-limiting examples of therapeutic agents for psoriatic arthritis (PsA) with which the solid state form can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, adalimumab (such as HUMIRA™ brand adalimumab), and efalizumab.

Examples of therapeutic agents for SLE (Lupus) with which the solid state form can be combined include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budesonide, dexamethasone; cytotoxics, for example, azathioprine, cyclophosphamide, mycophenolate mofetil, methotrexate; inhibitors of PDE4 or purine synthesis inhibitor, for example CELLCEPT®. The solid state form may also be combined with agents such as sulfasalazine, 5-aminosalicylic acid, olsalazine, IMURAN® and agents which interfere with synthesis, production or action of proinflammatory cytokines such as IL-1, for example, caspase inhibitors like IL-1β converting enzyme inhibitors and IL-1ra. The solid state form may also be used with T cell signaling inhibitors, for example, tyrosine kinase inhibitors; or molecules that target T cell activation molecules, for example, CTLA-4-IgG or anti-B7 family antibodies, anti-PD-1 family antibodies. The solid state form can be combined with IL-11 or anti-cytokine antibodies, for example, fontolizumab (anti-IFNg antibody), or anti-receptor receptor antibodies, for example, anti-IL-6 receptor antibody and antibodies to B-cell surface molecules. The solid state form may also be used with LJP 394 (abetimus), agents that deplete or inactivate B-cells, for example, Rituximab (anti-CD20 antibody), lymphostat-B (anti-BlyS antibody), TNF antagonists, for example, anti-TNF antibodies, adalimumab (such as HUMIRA™ brand adalimumab), infliximab such as CA2 (REMICADE™ brand infliximab), CDP 571, TNFR-Ig constructs, etanercept such as p75TNFRIgG (ENBREL™ brand etanercept) and lenercept such as p55TNFRIgG (LENERCEPT™).

The solid state form may also be combined with an immune modulator for CD4+CD25+ $T_{reg}$ cells. $T_{reg}$ cells are essential for maintaining normal immune homeostasis. In patients with autoimmune diseases, reduced numbers or functional impairment of $T_{reg}$ cells has been observed, leading to loss of this finely-tuned mechanism. A humanized agonistic monoclonal antibody, BT-061, binds to a unique epitope of human CD4, and induces $T_{reg}$-specific signaling events that lead to their functional activation. Pre-clinical data using isolated $T_{reg}$ cells and rheumatoid arthritis synovial fluid indicate that BT-061 leads to suppression of CD4+ and CD8+ T effector cell proliferation, reduction of the expression of pro-inflammatory cytokines, and increase in the production of the anti-inflammatory cytokine TGFβ. Thus similar immune modulators for CD4+CD25+ $T_{reg}$ cells can also be co-administered with a compound of the invention for treating any of the inflammatory disease/disorder, or an autoimmune disease/disorder described herein, including but not limited to rheumatoid arthritis, Crohn's disease, ankylosing spondylitis, psoriatic arthritis, psoriasis, ulcerative colitis, systemic lupus erythematosus, lupus nephritis, diabetic nephropathy, dry eye syndrome, Sjogren's syndrome, alopecia areata, vitiligo, or atopic dermatitis. In certain embodiments, the combination treats rheumatoid arthritis, Crohn's disease, psoriasis, or psoriatic arthritis, including moderately to severely active rheumatoid arthritis, Crohn's disease, psoriasis, or psoriatic arthritis. In certain embodiments, the rheumatoid arthritis, Crohn's disease, psoriasis, or psoriatic arthritis patient being treated has inadequately responded to or has discontinued therapy due to loss of response to or intolerance to a first line therapy (such as a DMARD, including methotrexate) or an anti-TNFα therapy.

In certain embodiments, the immune modulator has one or more (or all) of the following properties: (1) activates a subset of CD4+ T cells comprising CD4+CD25+ regulatory T cells ($T_{reg}$), or CD4+CD25+ $T_{reg}$ cells; (2) binds only to a special epitope of the human CD4 antigen (such as the IgG-like C2 type 1 domain of CD4), which said epitope of human CD4 may be bound by a mouse IgG1 anti-CD4 monoclonal antibody B-F5 or a humanized version thereof, such as the BT-061 hB-F5 antibody tregalizumab as described in U.S. Pat. No. 7,452,981 (incorporated herein by reference, including all sequences of the VH and VL chains disclosed therein); (3) provides an activation signal to naturally occurring $T_{reg}$ cells but does not activate conventional T cells (e.g., CD4+ T cells that are not activated in (1), CD8+ cytotoxic T cells, etc.); and (4) is not a depleting anti-CD4 antibody that depletes CD4+ T cells, and/or does not appreciably trigger ADCC or CDC.

VI. PHARMACEUTICAL COMPOSITIONS

The present disclosure further relates, in part, to compositions comprising Compound 1 or a pharmaceutically acceptable salt thereof, or one or more solid state forms of Compound 1. Although the solid state form may be administered alone or in the form of a pharmaceutical composition, administration generally will be in the form of a pharmaceutical composition. In some embodiments, the composition comprises Compound 1 or a pharmaceutically acceptable salt thereof or a solid state form of Compound 1 in association with a pharmaceutically acceptable carrier. The preferred composition depends on the method of administration, and typically comprises one or more conventional pharmaceutically acceptable carriers, adjuvants, and/or vehicles (together referred to as "excipients"). Such compositions can be formulated for various routes of systemic or local delivery for example, by oral administration, topical administration, transmucosal administration, rectal administration, intravaginal administration, or administration by subcutaneous, intrathecal, intravenous, intramuscular, intraperitoneal, intranasal, intraocular or intraventricular injection.

Solid dosage forms for oral administration include, for example, capsules, tablets, pills, powders, and granules. In such solid dosage forms, the compounds or salts are ordinarily combined with one or more excipients. If administered per os, the compounds or salts can be mixed with, for example, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation, as can be provided in, for example, a dispersion of the compound or salt in hydroxypropylmethyl cellulose. In the case of capsules, tablets, and pills, the dosage forms also can comprise pH modifiers, such as sodium citrate; magnesium or calcium carbonate or bicarbonate; tartaric acid, fumaric acid, citric acid, succinic acid, malic acid, and phosphoric acid and combinations thereof. Tablets and pills additionally can be prepared with enteric coatings.

Liquid dosage forms for oral administration include, for example, pharmaceutically acceptable emulsions (including both oil-in-water and water-in-oil emulsions), solutions (including both aqueous and non-aqueous solutions), suspensions (including both aqueous and non-aqueous suspensions), syrups, and elixirs containing inert diluents commonly used in the art (e.g., water). Such compositions also can comprise, for example, wetting, emulsifying, suspending, sweeting and flavoring agents.

Parenteral administration includes subcutaneous injections, intravenous injections, intramuscular injections, intrasternal injections, and infusion. Injectable preparations (e.g., sterile injectable aqueous or oleaginous suspensions) can be formulated according to the known art using suitable dispersing, wetting agents, and/or suspending agents. Acceptable vehicles and solvents include, for example, water, 1,3-butanediol, Ringer's solution, isotonic sodium chloride solution, bland fixed oils (e.g., synthetic mono- or diglycerides), fatty acids (e.g., oleic acid), dimethyl acetamide, surfactants (e.g., ionic and non-ionic detergents), and/or polyethylene glycols.

Formulations for parenteral administration may, for example, be prepared from sterile powders or granules having one or more of the excipients mentioned for use in the formulations for oral administration. A compound or salt of the invention can be dissolved in water, polyethylene glycol, propylene glycol, ethanol, corn oil, cottonseed oil, peanut oil, sesame oil, benzyl alcohol, sodium chloride, and/or various pH modifiers. The pH may be adjusted, if necessary, with a suitable acid, base, or pH modifier.

Suppositories for rectal administration can be prepared by, for example, mixing a compound or salt of the invention with a suitable nonirritating excipient that is solid at ordinary temperatures, but liquid at the rectal temperature, and will therefore melt in the rectum to release the drug. Suitable excipients include, for example, cocoa butter; synthetic mono-, di-, or triglycerides, fatty acids, and/or polyethylene glycols.

Compound 1 or the solid state forms of the present disclosure can be formulated for administration topically to the skin or mucosa, i.e., dermally or transdermally. Such administration can include the use, e.g., of transdermal patches or iontophoresis devices.

Besides those representative dosage forms described above, pharmaceutically acceptable excipients and carriers are generally known to those skilled in the art and are thus included in the instant invention. Formulation of drugs is generally discussed in, for example, Hoover, J., Remington's Pharmaceutical Sciences (Mack Publishing Co., 1975) and Ansel's Pharmaceutical Dosage Forms and Drug Delivery Systems (Lippincott Williams & Wilkins, 2005).

Depending upon the route and frequency of administration, the pharmaceutical compositions of the present invention can contain, for example, from about 0.1 percent by weight to about 99 percent or more by weight of the active ingredient. The amount of active ingredient contained in the dosage unit composition employed for adult human treatment generally can range, for example, from about 0.01 mg to about 3000 mg. For the therapeutic uses described in this application, the amount of active ingredient contained in the dosage unit composition generally will be in the range, for example, from about 0.1 mg to about 1000 mg. In one embodiment, the amount of active ingredient contained in the dosage unit composition is in a range from about 1 mg to about 500 mg. In another embodiment, the amount of active ingredient contained in the dosage unit composition is in a range from about 1 mg to about 250 mg. In another embodiment, the amount of active ingredient contained in the dosage unit composition is in a range from about 1 mg to about 100 mg. In another embodiment, the amount of active ingredient contained in the dosage unit composition is in a range from about 1 mg to about 50 mg. In another embodiment, the amount of active ingredient contained in the dosage unit composition is in a range from about 1 mg to about 45 mg. In another embodiment, the amount of active ingredient contained in the dosage unit composition is in a range from about 1 mg to about 30 mg. In another embodiment, the amount of active ingredient contained in the dosage unit composition is in a range from about 1 mg to about 25 mg. In another embodiment, the amount of active ingredient contained in the dosage unit composition is in a range from about 1 mg to about 24 mg. In another embodiment, the amount of active ingredient contained in the dosage unit composition is in a range from about 1 mg to about 15 mg. In another embodiment, the amount of active ingredient contained in the dosage unit composition is in a range from about 1 mg to about 10 mg. In another embodiment, the amount of active ingredient contained in the dosage unit composition is in a range from about 1 mg to about 7.5 mg. In another embodiment, the amount of active ingredient contained in the dosage unit composition is in a range from about 10 mg to about 20 mg. In another embodiment, the amount of active ingredient contained in the dosage unit composition is in a range from about 20 mg to about 30 mg. In another embodiment, the amount of active ingredient contained in the dosage unit composition is in a range from about 30 mg to about 40 mg. In another embodiment, the amount of active ingredient contained in the dosage unit composition is in a range from about 7.5 mg to about 45 mg. In another embodiment, the amount of active ingredient contained in the dosage unit composition is in a range from about 15 mg to about 30 mg. In another embodiment, the amount of active ingredient contained in the dosage unit composition is about 3 mg. In another embodiment, the amount of active ingredient contained in the dosage unit composition is about 6 mg. In another embodiment, the amount of active ingredient contained in the dosage unit composition is about 7.5 mg. In another embodiment, the amount of active ingredient contained in the dosage unit composition is about 12 mg. In another embodiment, the amount of active ingredient contained in the dosage unit composition is about 15 mg. In another embodiment, the amount of active ingredient contained in the dosage unit composition is about 18 mg. In another embodiment, the amount of active ingredient contained in the dosage unit composition is about 24 mg. In another embodiment, the amount of active ingredient contained in the dosage unit composition is about 30 mg. In another embodiment, the amount of active ingredient contained in the dosage unit composition is about 36 mg. In another embodiment, the amount of active ingredient contained in the dosage unit composition is about 45 mg.

In one embodiment, the active ingredient contained in the dosage unit composition is Compound 1, or a pharmaceutically acceptable salt thereof. In one embodiment, the target or label amount of active ingredient (e.g., Compound 1) provided for inclusion in the compositions of the present disclosure refers to the amount of Compound 1 freebase. For instance, as discussed herein, Compound 1 may be prepared in several solid state forms including Amorphous Freebase, crystalline solvates and hydrates (e.g., Freebase Solvate Form A, Freebase Hydrate Form B), crystalline hemihydrates (e.g., Freebase Hydrate Form C), crystalline anhydrate (e.g., Freebase Anhydrate Form D), crystalline tartrate (e.g., Tartrate Hydrate), crystalline hydrochloride (e.g., Hydrochloride Solvate Form AA, Hydrochloride Solvate Form BB, Hydrochloride Solvate Form CC), and crystalline L-maleate (e.g., L-Maleate Form AAA, L-Maleate Form BBB, L-Maleate Form CCC). It should be understood that in embodiments, where the dosage unit composition comprises, e.g., a solvate, hydrate, hemihydrate, tartrate, hydrochloride, or L-maleate of Compound 1, the amount of solvate, hydrate, hemihydrate, tartrate, hydrochloride, or L-maleate of Compound 1 present in the dosage unit composition may be slightly higher than the target amount of Compound 1 (active ingredient), and preferably will be present in the dosage unit composition in an amount sufficient to deliver the target amount of Compound 1 freebase equivalent to a subject. For example, if the target amount of Compound 1 (active ingredient) in a dosage unit composition is 15 mg, a dosage unit composition comprising, for example, Freebase Hydrate Form C, may comprise the Freebase Hydrate Form C in an amount sufficient to deliver 15 mg of the Compound 1 freebase equivalent.

In one embodiment, the pharmaceutical composition is a tablet dosage form. In one aspect, the tablet is coated with a pharmaceutically acceptable polymer.

In one embodiment, tablet is a controlled-release formulation, such as an extended release tablet dosage form (also referred to herein as a modified release or sustained release formulation). Such formulations permit the sustained release of the active ingredient over an extended period of time, as compared to immediate release solid dosage forms, which permit the release of most or all of the active ingredient over a short period of time (e.g., typically around 60 minutes or less). In one aspect, the tablet comprises an active ingredient and at least one additive selected from the group consisting of a release control polymer, a filler, a glidant, a lubricant (e.g., for use in compacting the granules), a pH modifier, a surfactant, and combinations thereof. In one aspect, the tablet comprises an active ingredient, a release control polymer, a filler, a glidant, and a lubricant. In one aspect, the tablet comprises an active ingredient, a release control polymer, a filler, a glidant, a lubricant, and a pH modifier.

In certain embodiments, the release control polymer will be a hydrophilic polymer. Examples of suitable release control polymers include, but are not limited to a cellulose derivative with a viscosity of between 1000 and 150,000 mPA-s, hydroxypropylmethyl cellulose (e.g., Hypromellose 2208 or controlled release grades of hydroxypropylmethyl cellulose, including the E, F, and K series), copolymers of acrylic acid crosslinked with a polyalkenyl polyether (e.g., Carbopol® polymers), hydroxypropyl cellulose, hydroxyethyl cellulose, non-ionic homopolymers of ethylene oxide (e.g., Polyox™), water soluble natural gums of polysaccharides (e.g., xanthan gum, alginate, locust bean gum, etc.), crosslinked starch, polyvinyl acetates, polyvinylpyrrolidone, mixtures of polyvinyl acetates and polyvinyl pyrrolidone, and combinations thereof. In one embodiment, the release control polymer is selected from the group consisting of hydroxypropylmethyl cellulose, copolymers of acrylic acid crosslinked with a polyalkenyl polyether (e.g., Carbopol® polymers), and combinations thereof. Examples of suitable fillers ("bulking agents") include, but are not limited to, microcrystalline cellulose (e.g., Avicel® PH 101; Avicel® PH 102;), mannitol (e.g., Pearlitol® 100 SD or Pearlitol® 200 SD), lactose, sucrose, sorbitol, and the like. In one embodiment, the filler is selected from the group consisting of microcrystalline cellulose, mannitol, and combinations thereof. Examples of suitable glidants include, but are not limited to, silicone dioxide (e.g., colloidal silicon dioxide), calcium silicate, magnesium silicate, talc, and combinations thereof. In one embodiment, the glidant is colloidal silicone dioxide. Examples of suitable lubricants include, but are not limited to, polyethylene glycol (e.g., having a molecular weight of from 1000 to 6000), magnesium stearate, calcium stearate, sodium stearyl fumarate, talc, and the like. In one embodiment, the lubricant is magnesium stearate. Examples of suitable pH modifiers include, but are not limited to, organic acids, such as tartaric acid, citric acid, succinic acid, fumaric acid; sodium citrate; magnesium or calcium carbonate or bicarbonate; and combinations thereof. In one embodiment, the pH modifier is tartaric acid. Examples of suitable surfactants include sodium lauryl sulfate.

In one embodiment, the pharmaceutical composition comprises from about 10 w/w % to about 35 w/w % of a pH modifier, and in particular, tartaric acid, fumaric acid, citric acid, succinic acid, malic acid, or combinations thereof. In other embodiments, the formulation comprises from about 20 w/w % to about 35 w/w %, or from about 20 w/w % to about 30 w/w %, or from about 20 w/w % to about 25 w/w %, or about 10 w/w %, about 15 w/w. %, about 20 w/w %, about 25 w/w % or about 30 w/w % pH modifier. In one embodiment, the pH modifier is tartaric acid.

As discussed herein, sustained peak plasma concentrations can theoretically be achieved by means of sustained release matrix systems. However, when such systems are made of hydrophilic polymers, such as HPMC, they seldom provide pH independent drug release of pH-dependent soluble drugs, and they are normally incapable of attaining zero-order release except for practically insoluble drugs. Unexpectedly, is has now been discovered that when a pH modifier, such as tartaric acid, fumaric acid, citric acid, succinic acid, malic acid, or combinations thereof, is used in a hydrophilic sustained release matrix system, it allows Compound 1 or a pharmaceutically acceptable salt or solid state form thereof to be released at a steady rate regardless of the pH of the environment. In an unexpected finding, it was discovered that as a tablet containing the hydrophilic polymer matrix system erodes, Compound 1 reacts with the HPMC, creating a thicker gel layer which slows the release of Compound 1 from the tablet. The resulting gel layer provides an environment suitable for Compound 1 to dissolve.

Thus, in one embodiment, the pharmaceutical composition of the present disclosure exhibits a pH-independent release of the active ingredient (Compound 1). Advantageously, it has been discovered that including organic acids, such as a tartaric acid, in the composition as a pH modifier improves the release profile, and results in a pH independent release of the active ingredient. Without wishing to be bound to any particular theory, it is believed that the pH modifier and hydrophilic polymer create a microenvironment in which the active ingredient dissolves, and then is released. The release from the microenvironment occurs at approximately the same rate, regardless of pH. This is particularly advantageous, since the pH of the gastrointestinal tract may vary significantly from the stomach (e.g., pH of about 1.5-3), to the duodenum (e.g., pH of about 4-5); to the lower part of the small intestines (e.g., pH of about 6.5-7.5).

Thus, in one embodiment, the pharmaceutical composition is an extended release formulation comprising Compound 1, or a pharmaceutically acceptable salt or solid state form thereof, a hydrophilic polymer, and a pH modifier, wherein the hydrophilic polymer, in contact with water, forms a gel layer that provides an environment suitable for Compound 1, or a pharmaceutically acceptable salt or solid state form thereof, to dissolve. In some embodiments, the environment suitable for Compound 1, or a pharmaceutically acceptable salt or solid state form thereof, to dissolve has a pH equal to or less than about 3.8 at 37° C. In some such embodiments, the environment has a pH of from about 1.5 to about 3.7, or from about 2.0 to about 3.7, or from about 2.5 to about 3.6, or from about 3.0 to about 3.6, or from about 3.0 to about 3.5.

In one such embodiment, the environment suitable for Compound 1, or a pharmaceutically acceptable salt or solid state form thereof, to dissolve is as set forth above, and the extended release formulation comprises from about 10 w/w % to about 35 w/w % of a pH modifier, and in particular, tartaric acid, fumaric acid, citric acid, succinic acid, malic acid, or combinations thereof. In other embodiments, the formulation comprises, from about 20 w/w % to about 35 w/w %, or from about 20 w/w % to about 30 w/w %, or from about 20 w/w % to about 25 w/w %, or about 10 w/w %, about 15 w/w %, about 20 w/w %, about 25 w/w % or about 30 w/w % pH modifier. In any of these embodiments, the pH modifier may be selected from the group consisting of tartaric acid, fumaric acid, citric acid, succinic acid, malic acid, and combinations thereof. In one such embodiment, the pH modifier is selected from the group consisting of tartaric acid, fumaric acid, citric acid, succinic acid, and combinations thereof. In one such embodiment, the pH modifier is selected from the group consisting of tartaric acid and fumaric acid. In one embodiment, the pH modifier is tartaric acid. In one embodiment, the pH modifier is fumaric acid or citric acid. The weight % tartaric acid set forth herein is by weight of the uncoated composition (e.g., uncoated tablet). In any of the foregoing embodiments, the hydrophilic polymer may be a cellulose derivative with a viscosity of between 1000 and 150,000 mPA-s. In one embodiment, the hydrophilic polymer is selected from the group consisting of hydroxypropylmethyl cellulose, hydroxyethyl cellulose, and mixtures or combinations thereof. In one embodiment, the hydrophilic polymer is hydroxypropylmethyl cellulose. In one embodiment, the hydrophilic polymer is hydroxypropylmethyl cellulose Grade E, F, or K. In one embodiment, the hydrophilic polymer is Hypromellose 2208.

In one embodiment, the tablet is a compressed and/or milled tablet. For example, in some embodiments, the tablet is formed by blending the composition components (e.g., including the active ingredient and at least one pharmaceutically acceptable carrier). The composition can then be either directly compressed, or one or more of the composition components can be granulated prior to compression. In one embodiment, milling is performed using a mill fitted with any suitable size screen (e.g., a fitted with a screen size of from about 600 to about 1400 µm or about 610 µm or about 1397 µm). Compression can be done in a tablet press, such as in a steel die between two moving punches.

In other embodiments, the compressed and/or milled tablet is formulated using a wet granulation process. Use of wet granulation helps reduce and/or eliminate sticking that may occur when compression without wet granulation (e.g., direct compression) is used to formulate the tablets. In one embodiment, the wet granulation process may include the following steps: (a) combining the active ingredient (e.g., Compound 1 or a pharmaceutically acceptable salt thereof or a solid state form of Compound 1) and at least a portion of one additional composition component to form a dry granulation mixture; (b) contacting the dry granulation mixture with a granulation fluid to form a wet granulation mixture; (c) drying the wet granulation mixture to form a granulated material; (d) milling the granulated material to form a milled granulated material; (e) combining the milled granulation material with the remaining composition components; and (f) compressing the composition into the solid dosage unit (e.g., a tablet).

In step (a) of this process, the active ingredient may be combined with, for example, a portion of the release control polymer (e.g., HPMC), a portion of the filler (e.g., microcrystalline cellulose, such as Avicel® PH101), or both a portion of the release control polymer and a portion of the filler to form the dry granulation mixture. Any suitable portion of the release control polymer may be used in step (a). In one embodiment, from about 5 to 10 wt. % or from about 6 to 8 wt. % of the total amount of the release, control polymer in the composition is used in step (a).

In certain embodiments, the granulation fluid used in step (b) may comprise water, a suitable solvent (e.g., ethanol, isopropanol, etc.), or combinations thereof. In one embodiment, the granulation fluid comprises water. In one embodiment, the active ingredient may be combined with a portion of the filler, while a portion of the release control polymer (e.g., HPMC) is dissolved in a liquid, such as water, to form the granulation fluid. In one embodiment, the granulation fluid is sprayed on the dry granulation mixture.

The dried granulation material may be milled using, for example, a comill fit with any suitable screen size. In one embodiment, the screen size is from about 600 to about 900 microns, or from about 610 to about 813 microns. In one embodiment, the granulated material is milled using a comill fitted with a 610 μm screen. In one embodiment, the granulated material is milled using a comill fitted with a 813 μm screen.

In step (e), the milled granulation material is combined with any remaining composition components, such as any remaining filler (e.g., microcrystalline cellulose, such as Avicel® PH102), any remaining release control polymer, glidants, lubricants, pH modifiers, surfactants, and the like. In one embodiment, the filler and/or release control polymer included in the granulated material may be the same or different than the filler and/or release control polymer added in step (e). For instance, in one embodiment, the filler included in the granulated material (e.g., Avicel®PH101) may have a smaller particle size distribution than the filler added in step (e) (e.g., Avicel®PH102).

In one embodiment, the composition may be sieved, and the sieved composition blended, for example, after step (e), and prior to compressing the composition (step (1)). In one embodiment, the formulation is sieved prior to addition of any lubricant. In one embodiment, the pH modifier (e.g., tartaric acid) is optionally milled prior to combining with the granulated material.

In one embodiment, the present disclosure is directed to a process for preparing a pharmaceutical composition, the process comprising: (a) combining an active ingredient (e.g., Compound 1 or a pharmaceutically acceptable salt thereof or a solid state form of Compound 1) and at least a portion of one additional composition component to form a dry granulation mixture; (b) contacting the dry granulation mixture with a granulation fluid to form a wet granulation mixture; (c) drying the wet granulation mixture to form a granulated material; (d) milling the granulated material to form a milled granulated material; (e) combining the milled granulation material with the remaining composition components; and (f) compressing the composition to form the pharmaceutical composition. In one embodiment, the method further optionally comprises coating the pharmaceutical composition. In one embodiment, the disclosure is directed to a pharmaceutical composition prepared by this wet granulation process. In one embodiment, the pharmaceutical composition is a tablet. In one embodiment, the pH modifier (e.g., tartaric acid) is optionally milled prior to compressing. In one embodiment, the solid state form is Freebase Hydrate Form C.

In some embodiments, the compressed and/or milled tablet comprises a crystalline solid state form of Compound 1. In one embodiment, the crystalline solid state form is a crystalline hydrate. In one embodiment, the crystalline solid state form is Freebase Hydrate Form C. Advantageously, it has been discovered that crystalline Freebase Hydrate Form C is stable under mechanical processing, and exhibits minimal issues upon milling. In other embodiments, the crystalline solid state form is a crystalline anhydrate. In one embodiment, the crystalline anhydrate is Freebase Anhydrate Form D.

In some embodiments, the pharmaceutical composition is a compressed and/or milled tablet comprising Compound 1, wherein at least about 75% by weight of the Compound 1 present in the tablet is Freebase Hydrate Form C. In one aspect, at least 80% by weight is the Freebase Hydrate Form C. In another aspect, at least 85% by weight is the Freebase Hydrate Form C. In another aspect, at least 90% by weight is the Freebase Hydrate Form C. In another, at least 95% by weight is the Freebase Hydrate Form C. In another aspect, at least 96% by weight is the Freebase Hydrate Form C. In another aspect, at least 97% by weight is the Freebase Hydrate Form C. In another aspect, at least 98% by weight is the Freebase Hydrate Form C. In another aspect, at least 99% by weight is the Freebase Hydrate Form C.

In some embodiments, the pharmaceutical composition is a compressed and/or milled tablet comprising Compound 1, wherein at least about 75% by weight of the Compound 1 present in the tablet is the Amorphous Freebase. In one aspect, at least 80% by weight is the Amorphous Freebase. In another aspect, at least 85% by weight is the Amorphous Freebase. In another aspect, at least 90% by weight is the Amorphous Freebase. In another aspect, at least 95% by weight is the Amorphous Freebase. In another aspect, at least 96% by weight is the Amorphous Freebase. In another aspect, at least 97% by weight is the Amorphous Freebase. In another aspect, at least 98% by weight is the Amorphous Freebase. In another aspect, at least 99% by weight is the Amorphous Freebase.

In some embodiments, the pharmaceutical composition is a compressed and/or milled tablet comprising Compound 1, wherein at least about 75% by weight of the Compound 1 present in the tablet is the Freebase Hydrate Form B. In one aspect, at least 80% by weight is the Freebase Hydrate Form B. In another aspect, at least 85% by weight is the Freebase Hydrate Form B. In another aspect, at least 90% by weight is the Freebase Hydrate Form B. In another aspect, at least 95% by weight is the Freebase Hydrate Form B. In another aspect, at least 96% by weight is the Freebase Hydrate Form B. In another aspect, at least 97% by weight is the Freebase Hydrate Form B. In another aspect, at least 98% by weight is the Freebase Hydrate Form B. In another aspect, at least 99% by weight is the Freebase Hydrate Form B.

In some embodiments, the pharmaceutical composition is a compressed and/or milled tablet comprising Compound 1, wherein at least about 75% by weight of the Compound 1 present in the tablet is Freebase Anhydrate Form D. In one aspect, at least 80% by weight is the Freebase Anhydrate Form D. In another aspect, at least 85% by weight is the Freebase Anhydrate Form D. In another aspect, at least 90% by weight is the Freebase Anhydrate Form D. In another aspect, at least 95% by weight is the Freebase Anhydrate Form D. In another aspect, at least 96% by weight is the Freebase Anhydrate Form D. In another aspect, at least 97% by weight is the Freebase Anhydrate Form D. In another aspect, at least 98% by weight is the Freebase Anhydrate Form D. In another aspect, at least 99% by weight is the Freebase Anhydrate Form D.

In some embodiments, the pharmaceutical composition is a compressed and/or milled tablet comprising Compound 1, wherein at least about 75% by weight of the Compound 1 present in the tablet is the crystalline tartrate. In one aspect, at least 80% by weight is the crystalline tartrate. In another aspect, at least 85% by weight is the crystalline tartrate. In another aspect, at least 90% by weight is the crystalline tartrate. In another aspect, at least 95% by weight is the crystalline tartrate. In another aspect, at least 96% by weight is the crystalline tartrate. In another aspect, at least 97% by weight is the crystalline tartrate. In another aspect, at least 98% by weight is the crystalline tartrate. In another aspect, at least 99% by weight is the crystalline tartrate.

In one embodiment, the pharmaceutical composition is a tablet comprising a solid state form of Compound 1 and a pharmaceutically acceptable carrier, wherein the tablet is prepared by compressing the solid state form of Compound 1 and the pharmaceutically acceptable carrier. In one embodiment, the solid state form of Compound 1 is milled prior to compressing. In one embodiment, the solid state form is Freebase Hydrate Form C.

In some embodiments, the tablet further comprises a film coat. A film coat on the tablet further may contribute to the ease with which it can be swallowed. A film coat can also improve taste and provides an elegant appearance. In certain embodiments, the film-coat includes a polymeric film-forming material such as hydroxypropyl methylcellulose, hydroxypropylcellulose, and acrylate or methacrylate copolymers. Besides a film-forming polymer, the film-coat may further comprise a plasticizer, e.g. polyethylene glycol, a surfactant, e.g. polysorbates, and optionally a pigment, e.g. titanium dioxide or iron oxides. The film-coating may also comprise talc as anti-adhesive. In one embodiment, the film coat accounts for less than 5% by weight of a pharmaceutical composition of the present invention.

In another embodiment, the pharmaceutical composition is a capsule dosage form.

In another embodiment, the pharmaceutical composition comprises a crystalline hydrate of Compound 1, wherein at least about 75% by weight of Compound 1 present in the composition is the crystalline hydrate of Compound 1. In one aspect, at least 80% by weight is the crystalline hydrate. In another aspect, at least 85% by weight is the crystalline hydrate. In another aspect, at least 90% by weight is the crystalline hydrate. In another aspect, at least 95% by weight is the crystalline hydrate. In another aspect, at least 96% by weight is the crystalline hydrate. In another aspect, at least 97% by weight is the crystalline hydrate. In another aspect, at least 98% by weight is the crystalline hydrate. In another aspect, at least 99% by weight is the crystalline hydrate. In another aspect, the crystalline hydrate is the Freebase Hydrate Form C.

In another embodiment, the pharmaceutical composition comprises a crystalline tartrate of Compound 1, wherein at least about 75% by weight of Compound 1 present in the composition is the crystalline tartrate of Compound 1. In one aspect, at least 80% by weight is the crystalline tartrate. In another aspect, at least 85% by weight is the crystalline tartrate. In another aspect, at least 90% by weight is the crystalline tartrate. In another aspect, at least 95% by weight is the crystalline tartrate. In another aspect, at least 96% by weight is the crystalline tartrate. In another aspect, at least 97% by weight is the crystalline tartrate. In another aspect, at least 98% by weight is the crystalline tartrate. In another aspect, at least 99% by weight is the crystalline tartrate. In another aspect, the crystalline hydrate is the Tartrate Hydrate. In one embodiment, the pharmaceutical composition comprises a crystalline tartrate of Compound 1, from about 10 w/w % to about 35 w/w % of an organic acid selected from the group consisting of tartaric acid, fumaric acid, citric acid, succinic acid, malic acid, and combinations thereof, and a pharmaceutically acceptable carrier. In one embodiment, the crystalline hydrate is the Tartrate Hydrate.

In another embodiment, the pharmaceutical composition comprises the Amorphous Freebase, wherein at least about 75% by weight of Compound 1 present in the composition is the Amorphous Freebase. In one aspect, at least 80% by weight is the Amorphous Freebase. In another aspect, at least 85% by weight is the Amorphous Freebase. In another aspect, at least 90% by weight is the Amorphous Freebase. In another aspect, at least 95% by weight is the Amorphous Freebase. In another aspect, at least 96% by weight is the Amorphous Freebase. In another aspect, at least 97% by weight is the Amorphous Freebase. In another aspect, at least 98% by weight is the Amorphous Freebase. In another aspect, at least 99% by weight is the Amorphous Freebase.

In another embodiment, the pharmaceutical composition comprises a crystalline anhydrate of Compound 1, wherein at least about 75% by weight of Compound 1 present in the composition is the crystalline anhydrate of Compound 1. In one aspect, at least 80% by weight is the crystalline anhydrate. In another aspect, at least 85% by weight is the crystalline anhydrate. In another aspect, at least 90% by weight is the crystalline anhydrate. In another aspect, at least 95% by weight is the crystalline anhydrate. In another aspect, at least 96% by weight is the crystalline anhydrate. In another aspect, at least 97% by weight is the crystalline anhydrate. In another aspect, at least 98% by weight is the crystalline anhydrate. In another aspect, at least 99% by weight is the crystalline anhydrate. In another aspect, the crystalline anhydrate is the Freebase Anhydrate Form D.

In one embodiment, the present disclosure is directed to a pharmaceutical composition comprising about 15 mg of Compound 1 freebase or a pharmaceutically acceptable salt thereof or a solid state form of Compound 1, and a pharmaceutically acceptable carrier, wherein the solid state form of Compound 1 is selected from the group consisting of Amorphous Freebase, Freebase Hydrate Form B, Freebase Hydrate Form C, and Freebase Anhydrate Form D. In some such embodiments, the pharmaceutical composition is a once daily extended release dosage form (e.g., tablet or capsule).

In one embodiment, the present disclosure is directed to a pharmaceutical composition comprising about 15 mg of Compound 1 freebase or a pharmaceutically acceptable salt thereof or a solid state form of Compound 1, a pharmaceutically acceptable carrier, and a pH modifier, wherein the solid state form of Compound 1 is selected from the group consisting of Amorphous Freebase, Freebase Hydrate Form B, Freebase Hydrate Form C, and Freebase Anhydrate Form D. In one embodiment, the pharmaceutical composition comprises from about 10 wt % to about 30 wt. % of the pH modifier. In one embodiment, the pH modifier is tartaric acid. In some such embodiments, the pharmaceutical composition is a once daily extended release dosage form (e.g., tablet or capsule).

In one embodiment, the present disclosure is directed to a pharmaceutical composition comprising about 15 mg of a solid state form of Compound 1, a pharmaceutically acceptable carrier, and from about 10 w/w % to about 35 w/w % of tartaric acid, wherein the solid state form of Compound 1 is selected from the group consisting of Amorphous Freebase, Freebase Hydrate Form B, Freebase Hydrate Form C, and Freebase Anhydrate Form D. In some such embodiments, the pharmaceutical composition is a once daily extended release dosage form (e.g., tablet or capsule).

In one embodiment, the present disclosure is directed to a pharmaceutical composition comprising about 15 mg of Freebase Hydrate Form B, a pharmaceutically acceptable carrier, and from about 10 w/w % to about 35 w/w % of tartaric acid. In some such embodiments, the pharmaceutical composition is a once daily extended release dosage form (e.g., tablet or capsule).

In one embodiment, the present disclosure is directed to a pharmaceutical composition comprising about 15 mg of Amorphous Freebase, a pharmaceutically acceptable carrier, and from about 10 w/w % to about 35 w/w % of tartaric acid. In some such embodiments, the pharmaceutical composition is a once daily extended release dosage form (e.g., tablet or capsule).

In one embodiment, the present disclosure is directed to a pharmaceutical composition comprising about 15 mg of Freebase Anhydrate Form D, a pharmaceutically acceptable carrier, and from about 10 w/w % to about 35 w/w % of tartaric acid. In some such embodiments, the pharmaceutical composition is a once daily extended release dosage form (e.g., tablet or capsule).

In one embodiment, the present disclosure is directed to a pharmaceutical composition comprising about 15 mg of Freebase Hydrate Form C, a pharmaceutically acceptable carrier, and from about 10 w/w % to about 35 w/w % of tartaric acid. In some such embodiments, the pharmaceutical composition is a once daily extended release dosage form (e.g., tablet or capsule).

In one embodiment, the present disclosure is directed to a pharmaceutical composition comprising about 15 mg of Freebase Hydrate Form C, a pharmaceutically acceptable, carrier, and about 10 w/w % of tartaric acid. In some such embodiments, the pharmaceutical composition is a once daily extended release dosage form (e.g., tablet or capsule).

In one embodiment, the present disclosure is directed to a pharmaceutical composition comprising about 15 mg of Freebase Hydrate Form C, a pharmaceutically acceptable carrier, and about 20 w/w % of tartaric acid. In some such embodiments, the pharmaceutical composition is a once daily extended release dosage form (e.g., tablet or capsule).

In one embodiment, the present disclosure is directed to a pharmaceutical composition comprising about 15 mg of Freebase Hydrate Form C, a pharmaceutically acceptable carrier, and about 30 w/w % of tartaric acid. In some such embodiments, the pharmaceutical composition is a once daily extended release dosage form (e.g., tablet or capsule).

In one embodiment, the present disclosure is directed to a pharmaceutical composition comprising about 30 mg of Compound 1 freebase or a pharmaceutically acceptable salt thereof or a solid state form of Compound 1, and a pharmaceutically acceptable carrier, wherein the solid state form of Compound 1 is selected from the group consisting of Amorphous Freebase, Freebase Hydrate Form B, Freebase Hydrate Form C, and Freebase Anhydrate Form D. In some such embodiments, the pharmaceutical composition is a once daily extended release dosage form (e.g., tablet or capsule).

In one embodiment, the present disclosure is directed to a pharmaceutical composition comprising about 30 mg of Compound 1 freebase or a pharmaceutically acceptable salt thereof or a solid state form of Compound 1, a pharmaceutically acceptable carrier, and a pH modifier, wherein the solid state form of Compound 1 is selected from the group consisting of Amorphous Freebase, Freebase Hydrate Form B, Freebase Hydrate Form C, and Freebase Anhydrate Form D. In one embodiment, the pharmaceutical composition comprises from about 10 wt % to about 30 wt. % of the pH modifier. In one embodiment, the pH modifier is tartaric acid. In some such embodiments, the pharmaceutical composition is a once daily extended release dosage form (e.g., tablet or capsule).

In one embodiment, the present disclosure is directed to a pharmaceutical composition comprising about 30 mg of a solid state form of Compound 1, a pharmaceutically acceptable carrier, and from about 10 w/w % to about 35 w/w % of tartaric acid, wherein the solid state form of Compound 1 is selected from the group consisting of Amorphous Freebase, Freebase Hydrate Form B, Freebase Hydrate Form C, and Freebase Anhydrate Form D. In some such embodiments, the pharmaceutical composition is a once daily extended release dosage form (e.g., tablet or capsule).

In one embodiment, the present disclosure is directed to a pharmaceutical composition comprising about 30 mg of Freebase Hydrate Form B, a pharmaceutically acceptable carrier, and from about 10 w/w % to about 35 w/w % of tartaric acid. In some such embodiments, the pharmaceutical composition is a once daily extended release dosage form (e.g., tablet or capsule).

In one embodiment, the present disclosure is directed to a pharmaceutical composition comprising about 30 mg of Amorphous Freebase, a pharmaceutically acceptable carrier, and from about 10 w/w % to about 35 w/w % of tartaric acid. In some such embodiments, the pharmaceutical composition is a once daily extended release dosage form (e.g., tablet or capsule).

In one embodiment, the present disclosure is directed to a pharmaceutical composition comprising about 30 mg of Freebase Anhydrate Form D, a pharmaceutically acceptable carrier, and from about 10 w/w % to about 35 w/w % of tartaric acid. In some such embodiments, the pharmaceutical composition is a once daily extended release dosage form (e.g., tablet or capsule).

In one embodiment, the present disclosure is directed to a pharmaceutical composition comprising about 30 mg of Freebase Hydrate Form C, a pharmaceutically acceptable carrier, and from about 10 w/w % to about 35 w/w % of tartaric acid. In some such embodiments, the pharmaceutical composition is a once daily extended release dosage form (e.g., tablet or capsule).

In one embodiment, the present disclosure is directed to a pharmaceutical composition comprising about 30 mg of Freebase Hydrate Form C, a pharmaceutically acceptable carrier, and about 10 w/w % of tartaric acid. In some such embodiments, the pharmaceutical composition is a once daily extended release dosage form (e.g., tablet or capsule).

In one embodiment, the present disclosure is directed to a pharmaceutical composition comprising about 30 mg of Freebase Hydrate Form C, a pharmaceutically acceptable carrier, and about 20 w/w % of tartaric acid. In some such embodiments, the pharmaceutical composition is a once daily extended release dosage form (e.g., tablet or capsule).

In one embodiment, the present disclosure is directed to a pharmaceutical composition comprising about 30 mg of Freebase Hydrate Form C, a pharmaceutically acceptable carrier, and about 30 w/w % of tartaric acid. In some such embodiments, the pharmaceutical composition is a once daily extended release dosage form (e.g., tablet or capsule).

In one embodiment, the present disclosure is directed to a pharmaceutical composition comprising about 7.5 mg or about 15 mg or about 30 mg or about 45 mg of Compound 1 freebase or a pharmaceutically acceptable salt thereof or a solid state form of Compound 1, and a pharmaceutically acceptable carrier, wherein the pharmaceutical composition is a once daily extended release dosage form (e.g., tablet or capsule) that sustains release of the Compound 1 freebase or a pharmaceutically acceptable salt thereof or the solid state form of Compound 1 for from about 4 hours to about 24 hours following entry of the dosage form into a use environment, and wherein the dosage form has a release rate of not more than about 60% after passage of about 4 hours following entry of the dosage form into a use environment. In some such embodiments, the dosage form has a release rate of not more than about 60% after passage of about 4 hours following entry of the dosage form into a use environment, from about 50% to about 80% after passage of about 8 hours following entry of the dosage form into a use environment, from about 55% to about 90% after passage of about 10 hours following entry of the dosage form into a use environment, and from about 70% to 100% after passage of about 20 hours following entry of the dosage form into a use environment. In some embodiments, the solid state form of Compound 1 is selected from the group consisting of Amorphous Freebase, Freebase Hydrate Form B, Freebase Hydrate Form C, and Freebase Anhydrate Form D, In one embodiment, the present disclosure is directed to a pharmaceutical composition comprising about 15 mg of a solid state form of Compound 1, a pharmaceutically acceptable carrier, and from about 10 w/w % to about 35 w/w % of tartaric acid, wherein the solid state form of Compound 1 is selected from the group consisting of Amorphous Freebase, Freebase Hydrate Form B, Freebase Hydrate Form C, and Freebase Anhydrate Form D, and the pharmaceutical composition is a once daily extended release dosage form (e.g., tablet or capsule) that sustains release of the Compound 1 freebase or the solid state form of Compound 1 for from about 4 hours to about 24 hours following entry of the dosage form into a use environment, and wherein the dosage form has a release rate of not more than about 60% after passage of about 4 hours following entry of the dosage form into a use environment. In some such embodiments, the dosage form has a release rate of not more than about 60% after passage of about 4 hours following entry of the dosage form into a use environment, from about 50% to about 80% after passage of about 8 hours following entry of the dosage form into a use environment, from about 55% to about 90% after passage of about 10 hours following entry of the dosage form into a use environment, and from about 70% to 100% after passage of about 20 hours following entry of the dosage form into a use environment.

In one embodiment, the present disclosure is directed to a pharmaceutical composition comprising about 15 mg of Freebase Hydrate Form C, a pharmaceutically acceptable carrier, and from about 10 w/w % to about 35 w/w % of tartaric acid, wherein the pharmaceutical composition is a once daily extended release dosage form (e.g., tablet or capsule) that sustains release of the Compound 1 freebase or the solid state form of Compound 1 for from about 4 hours to about 24 hours following entry of the dosage form into a use environment, and wherein the dosage form has a release rate of not more than about 60% after passage of about 4 hours following entry of the dosage form into a use environment, from about 50% to about 80% after passage of about 8 hours following entry of the dosage form into a use environment, from about 55% to about 90% after passage of about 10 hours following entry of the dosage form into a use environment, and from about 70% to 100% after passage of about 20 hours following entry of the dosage form into a use environment.

In one embodiment, the present disclosure is directed to a pharmaceutical composition comprising about 30 mg of a solid state form of Compound 1, a pharmaceutically acceptable carrier, and from about 10 w/w % to about 35 w/w % of tartaric acid, wherein the solid state form of Compound 1 is selected from the group consisting of Amorphous Freebase, Freebase Hydrate Form B, Freebase Hydrate Form C, and Freebase Anhydrate Form D, and the pharmaceutical composition is a once daily extended release dosage form (e.g., tablet or capsule) that sustains release of the Compound 1 freebase or the solid state form of Compound 1 for from about 4 hours to about 24 hours following entry of the dosage form into a use environment, and wherein the dosage form has a release rate of not more than about 60% after passage of about 4 hours following entry of the dosage form into a use environment. In some such embodiments, the dosage form has a release rate of not more than about 60% after passage of about 4 hours following entry of the dosage form into a use environment, from about 50% to about 80% after passage of about 8 hours following entry of the dosage form into a use environment, from about 55% to about 90% after passage of about 10 hours following entry of the dosage form into a use environment, and from about 70% to 100% after passage of about 20 hours following entry of the dosage form into a use environment.

In one embodiment, the present disclosure is directed to a pharmaceutical composition comprising about 30 mg of Freebase Hydrate Form C, a pharmaceutically acceptable carrier, and from about 10 w/w % to about 35 w/w % of tartaric acid, wherein the pharmaceutical composition is a once daily extended release dosage form (e.g., tablet or capsule) that sustains release of the Compound 1 freebase or the solid state form of Compound 1 for from about 4 hours to about 24 hours following entry of the dosage form into a use environment, and wherein the dosage form has a release rate of not more than about 60% after passage of about 4 hours following entry of the dosage form into a use environment, from about 50% to about 80% after passage of about 8 hours following entry of the dosage form into a use environment, from about 55% to about 90% after passage of about 10 hours following entry of the dosage form into a use environment, and from about 70% to 100% after passage of about 20 hours following entry of the dosage form into a use environment.

In some of the foregoing embodiments, the dosage form releases the active ingredient (i.e., Compound 1 freebase or a pharmaceutically acceptable salt thereof or a solid state form of Compound 1), at a release rate of not more than about 25%, or from about 10% to about 25%, or from about 15% to about 20%, or about 20% after passage of about 1 hour following entry into the use environment. In one embodiment, the dosage form releases the active ingredient at a release rate of not more than about 40%, or from about 20% to about 40%, or from about 25% to about 35% after passage of about 2 hours following entry into the use environment. In one embodiment, the dosage form releases the active ingredient at a release rate of not more than about 60%, or from about 30% to about 60%, or from about 40% to about 60%, or from about 45% to about 55% after passage of about 4 hours following entry into the use environment. In one embodiment, the dosage form releases the active ingredient at a release rate of not more than about 70% or from about 40% to about 70%, or from about 55% to about 70% after passage of about 6 hours following entry into the use environment. In one embodiment, the dosage form releases the active ingredient at a release rate of not more than about 80% or from about 55% to about 80%, or from about 60% to about 80% after passage of about 6 hours following entry into the use environment. In one embodiment, the dosage form releases the active ingredient at a release rate of not more than about 80%, or not less than about 50%, or not less than about 60%, or not less than about 70%, or not less than about 75%, or from about 50% to about 80%, or from about 60% to about 80%, or from about 65% to about 80% after passage of about 8 hours following entry into the use environment. In one embodiment, the dosage form releases the active ingredient at a release rate of not less than about 55%, or not less than about 60% or not less than about 70%, or not less than about 80%, or not less than about 85%, or from about 55% to about 90%, or from about 70% to about 90% after passage of about 10 hours following entry into the use environment. In one embodiment, the dosage form releases the active ingredient at a release rate of not less than about 65%, or not less than about 70%, or not less than about 80%, or not less than about 90%, or from about 65% to about 99%, or from about 80% to about 99%, or from about 90% to about 99% after passage of about 16 hours following entry into the use environment. In one embodiment, the dosage form releases the active ingredient at a release rate of not less than about 70%, or not less than about 80%, or not less than about 90%, or from about 70% to 100%, or from about 80% to 100% after passage of about 20 hours following entry into the use environment. In one aspect, the dosage form has a release rate of not more than about 60% after passage of about 4 hours following entry of the dosage form into a use environment, from about 50% to about 80% after passage of about 8 hours following entry of the dosage form into a use environment, from about 55% to about 90% after passage of about 10 hours following entry of the dosage form into a use environment, and from about 70% to 100% after passage of about 20 hours following entry of the dosage form into a use environment.

In one embodiment, the present disclosure is directed to a pharmaceutical composition comprising about 7.5 mg or about 15 mg or about 30 mg or about 45 mg of Compound 1 freebase or a pharmaceutically acceptable salt thereof or a solid state form of Compound 1, and a pharmaceutically acceptable carrier, wherein the solid state form of Compound 1 is selected from the group consisting of Amorphous Freebase, Freebase Hydrate Form B, Freebase Hydrate Form C, and Freebase Anhydrate Form D, wherein the pharmaceutical composition is a once daily extended release dosage form (e.g., tablet or capsule) that, when added to a test medium comprising 900 mL of 50 mM pH 6.8 sodium phosphate buffer at 37° C.±0.5° C. in a standard USP rotating paddle apparatus when the paddles are rotated at 75 rpm±4%, dissolves not more than about 60% of Compound 1 freebase or the solid state form of Compound 1 after passage of about 4 hours, froth about 50% to about 80% of Compound 1 freebase or the solid state form of Compound 1 after passage of about 8 hours, from about 55% to about 90% of Compound 1 freebase or the solid state form of Compound 1 after passage of about 10 hours, and from about 70% to 100% of Compound 1 freebase or the solid state form of Compound 1 after passage of about 20 hours.

In one embodiment, the present disclosure is directed to a pharmaceutical composition comprising about 15 mg of a solid state form of Compound 1, a pharmaceutically acceptable carrier, and from about 10 wt % to about 30 wt % of tartaric acid, wherein the solid state form of Compound 1 is selected from the group consisting of Amorphous Freebase, Freebase Hydrate Form B, Freebase Hydrate Form C, and Freebase Anhydrate Form D, wherein the pharmaceutical composition is a once daily extended release dosage form (e.g., tablet or capsule) that, when added to a test medium comprising 900 mL of 50 mM pH 6.8 sodium phosphate buffer at 37° C.±0.5° C. in a standard USP rotating paddle apparatus when the paddles are rotated at 75 rpm±4%, dissolves not more than about 60% of Compound 1 freebase or the solid state form of Compound 1 after passage of about 4 hours, from about 50% to about 80% of Compound 1 freebase or the solid state form of Compound 1 after passage of about 8 hours, from about 55% to about 90% of Compound 1 freebase or the solid state form of Compound 1 after passage of about 10 hours, and from about 70% to 100% of Compound 1 freebase or the solid state form of Compound 1 after passage of about 20 hours.

In one embodiment, the present disclosure is directed to a pharmaceutical composition comprising about 15 mg of Freebase Hydrate Form C, a pharmaceutically acceptable carrier, and from about 10 wt % to about 30 wt % of tartaric acid, wherein the pharmaceutical composition is a once daily extended release dosage form (e.g., tablet or capsule) that, when added to a test medium comprising 900 mL of 50 mM pH 6.8 sodium phosphate buffer at 37° C.±0.5° C. in a standard USP rotating paddle apparatus when the paddles are rotated at 75 rpm±4%, dissolves not more than about 60% of Compound 1 freebase or the solid state form of Compound 1 after passage of about 4 hours, from about 50% to about 80% of Compound 1 freebase or the solid state form of Compound 1 after passage of about 8 hours, from about 55% to about 90% of Compound 1 freebase or the solid state form of Compound 1 after passage of about 10 hours, and from about 70% to 100% of Compound 1 freebase or the solid state form of Compound 1 after passage of about 20 hours.

In one embodiment, the present disclosure is directed to a pharmaceutical composition comprising about 30 mg of a solid state form of Compound 1, a pharmaceutically acceptable carrier, and from about 10 wt % to about 30 wt % of tartaric acid, wherein the solid state form of Compound 1 is selected from the group consisting of Amorphous Freebase, Freebase Hydrate Form B, Freebase Hydrate Form C, and Freebase Anhydrate Form D, wherein the pharmaceutical composition is a once daily extended release dosage form (e.g., tablet or capsule) that, when added to a test medium comprising 900 mL of 50 mM pH 6.8 sodium phosphate buffer at 37° C.±0.5° C. in a standard USP rotating paddle apparatus when the paddles are rotated at 75 rpm±4%, dissolves not more than about 60% of Compound 1 freebase or the solid state form of Compound 1 after passage of about 4 hours, from about 50% to about 80% of Compound 1 freebase or the solid state form of Compound 1 after passage of about 8 hours, from about 55% to about 90% of Compound 1 freebase or the solid state form of Compound 1 after passage of about 10 hours, and from about 70% to 100% of Compound 1 freebase or the solid state form of Compound 1 after passage of about 20 hours.

In one embodiment, the present disclosure is directed to a pharmaceutical composition comprising about 30 mg of Freebase Hydrate Form C, a pharmaceutically acceptable carrier, and from about 10 wt % to about 30 wt % of tartaric acid, wherein the pharmaceutical composition is a once daily extended release dosage form (e.g., tablet or capsule) that, when added to a test medium comprising 900 mL of 50 mM pH 6.8 sodium phosphate buffer at 37° C.±0.5° C. in a standard USP rotating paddle apparatus when the paddles are rotated at 75 rpm±4%, dissolves not more than about 60% of Compound 1 freebase or the solid state form of Compound 1 after passage of about 4 hours, from about 50% to about 80% of Compound 1 freebase or the solid state form of Compound 1 after passage of about 8 hours, from about 55% to about 90% of Compound 1 freebase or the solid state form of Compound 1 after passage of about 10 hours, and from about 70% to 100% of Compound 1 freebase or the solid state form of Compound 1 after passage of about 20 hours.

VII. PHARMACOKINETIC PARAMETERS 15 mg Dosage Formulations

In certain embodiments, the methods of the present disclosure comprise administering to an adult subject (e.g., a human subject) Compound 1 (freebase), or a pharmaceutically acceptable salt thereof, or a crystalline hydrate of Compound 1 in an amount sufficient to deliver to the subject 15 mg of Compound 1 freebase equivalent. In one embodiment, the freebase or the hydrate is in a once daily extended release formulation.

Unless otherwise indicated, the following pharmacokinetic parameters are achieved after administration of a single 15 mg dose the Compound 1 (freebase) or a pharmaceutically acceptable salt thereof or the crystalline hydrate (e.g., Freebase Hydrate Form C) to the adult subject, or after administration of a sufficient number of once-daily 15 mg doses to achieve a steady-state. By a single 15 mg dose, it is meant a single dosage unit containing an amount of freebase or pharmaceutically acceptable salt or crystalline hydrate sufficient to deliver to the subject 15 mg of Compound 1 freebase equivalent. In one embodiment, the single dosage unit is a once daily extended release formulation.

In certain embodiments, the administration of the Compound 1 (freebase) or a pharmaceutically acceptable salt thereof or the crystalline hydrate to the adult subject achieves a mean $C_{max}$ for Compound 1 of from about 25 to about 70 ng/mL, after a single 15 mg dose. In some embodiments, when administered to the adult subject, the Compound 1 (freebase) or the crystalline hydrate achieve a mean $C_{max}$ for Compound 1 of from about 25.0 to about 60.0 ng/mL, or from about 25.0 to about 40.0 ng/mL, from about 25.0 to about 30.0 ng/mL, or about 25.0 to about 28.0 ng/mL, or about 25.0 to about 27.0 ng/mL, or about 27.0 to about 40.0 ng/mL, or about 27.0 to about 35.0 ng/mL, or about 27.0 to about 30.0 ng/mL, or about 27.0 to about 29.0 ng/mL, or about 28.0 to about 30.0 ng/mL, or about 29.0 to about 31.0 ng/mL, or about 30.0 to about 32.0 ng/mL, after a single 15 mg dose. In some embodiments, when administered to the adult subject, the Compound 1 (freebase) or a pharmaceutically acceptable salt thereof or the crystalline hydrate achieve a mean $C_{max}$ for Compound 1 of from about 26.0 to about 26.4 ng/mL, or from about 26.2 to about 26.6 ng/mL, or from about 26.4 to about 26.8 ng/mL, or from about 26.6 to about 27.0 ng/mL, or from about 26.8 to about 27.2 ng/mL, or from about 27.0 to about 27.4 ng/mL, or from about 27.2 to about 27.6 ng/mL, or from about 27.4 to about 27.8 ng/mL, or from about 27.6 to about 28.0 ng/mL, or from about 27.8 to about 28.2 ng/mL, or from about 28.0 to about 28.4 ng/mL, or from about 28.2 to about 28.6 ng/mL, or from about 28.4 to about 28.8 ng/mL, or from about 28.6 to about 29.0 ng/mL, or from about 28.8 to about 29.2 ng/mL, or from about 29.0 to about 29.4 ng/mL, or from about 29.2 to about 29.6 ng/mL, or from about 29.4 to about 29.8 ng/mL, or from about 29.6 to about 30.0 ng/mL, or from about 29.8 to about 30.2 ng/mL, or from about 30.0 to about 30.4 ng/mL, or from about 30.2 to about 30.6 ng/mL, or from about 30.4 to about 30.8 ng/mL, or from about 30.6 to about 31.0 ng/mL, or from about 30.8 to about 31.2 ng/mL, or from about 31.0 to about 31.4 ng/mL, or from about 31.2 to about 31.6 ng/mL, or from about 31.4 to about 31.8 ng/mL, or from about 31.6 to about 32.0 ng/mL, after a single 15 mg dose.

In some embodiments, when administered to the adult subject under fasting conditions, the Compound 1 (freebase) or a pharmaceutically acceptable salt thereof or the crystalline hydrate achieve a mean $C_{max}$ for Compound 1 of about 26 ng/mL or about 32 ng/mL, after a single 15 mg dose. In other embodiments, when administered to the adult subject under non-fasting conditions, the Compound 1 (freebase) or a pharmaceutically acceptable salt thereof or the crystalline hydrate achieve a mean $C_{max}$ for Compound 1 of about 37 ng/mL or about 40 ng/mL after a single 15 mg dose.

In certain embodiments, when the Compound 1 (freebase) or a pharmaceutically acceptable salt thereof or the crystalline hydrate is administered to the adult subject, the difference in the $C_{max}$ for Compound 1 after a single 15 mg dose in the fed versus the fasted state is selected from about 30% or less, about 20% or less, and about 10% or less. As used herein, a subject in a "fed" state (also referred to herein as "non-fasting" state or "non-fasting conditions") is one who has consumed a standard or high-fat meal within about 30 minutes prior to administration of the drug. As used herein, a subject in a "fasted" state (also referred to herein as "fasting conditions") refers to a subject who has fasted for at least 10 hours prior to initial administration the drug, or, if the subject is being administered the drug over multiple days, refers to a subject who has fasted for at least two hours prior to each subsequent administration of the drug.

When administered to the adult subject, in certain embodiments, the Compound 1 (freebase) or a pharmaceutically acceptable salt thereof or the crystalline hydrate achieve a $T_{max}$ for Compound 1 from about 1.0 to about 6.0 hours after a single 15 mg dose. In some embodiments, when administered to the adult subject, the Compound 1 (freebase) or a pharmaceutically acceptable salt thereof or the crystalline hydrate achieve a $T_{max}$ for Compound 1 of from about 1.0 to about 5.0 hours, or from about 1.0 to about 4.0 hours, or from about 1.0 to about 3.0 hours, or from about 1.0 to about 2.0 hours, or from about 2.0 to about 6.0 hours, or from about 3.0 to about 6.0 hours, or from about 4.0 to about 6.0 hours, or from about 5.0 to about 6.0 hours, or from about 2.0 to about 5.0 hours, or from about 2.0 to about 4.0 hours, or from about 2.0 to about 3.0 hours, or from about 3.0 to about 4.0 hours, or from about 3.0 to about 5.0 hours, or from about 4.0 to about 5.0 hours, after a single 15 mg dose. In some embodiments, when administered to the adult subject, the Compound 1 (freebase) or a pharmaceutically acceptable salt thereof or the crystalline hydrate achieve a $T_{max}$ for Compound 1 of from about 2.6 to about 3.0 hours, or from about 2.8 to about 3.2 hours, or from about 3.0 to about 3.4 hours, or from about 3.2 to about 3.6 hours, or from about 3.4 to about 3.8 hours, or from about 3.6 to about 4.0 hours, or from about 3.8 to about 4.2 hours, or from about 4.0 to about 4.4 hours, after a single 15 mg dose.

In other embodiments, when administered to the adult subject under fasting conditions, the Compound 1 (freebase) or a pharmaceutically acceptable salt thereof or the crystalline hydrate achieve a $T_{max}$ for Compound 1 of from about 1.0 to about 4.0 hours after a single 15 mg dose, or achieve a $T_{max}$ for Compound 1 from about 1.5 to about 6.0 hours after a single 15 mg dose, or achieve a median $T_{max}$ for Compound 1 of about 3.0 hours after a single 15 mg dose. In other embodiments, when administered to the adult subject under non-fasting conditions, the Compound 1 (freebase) or a pharmaceutically acceptable salt thereof or the crystalline hydrate achieve a $T_{max}$ for Compound 1 from about 3.0 to about 6.0 hours after a single 15 mg dose, or achieve a median $T_{max}$ for Compound 1 of about 4.0 hours after a single 15 mg dose.

When administered to the adult subject, in certain embodiments, the Compound 1 (freebase) or a pharmaceutically acceptable salt thereof or the crystalline hydrate achieve a harmonic mean $t_{1/2}$ for Compound 1 of from about 10.0 to about 14.0 hours after a single 15 mg dose. In other embodiments, when administered to an adult subject, the Compound 1 (freebase) or a pharmaceutically acceptable salt thereof or the crystalline hydrate achieve a harmonic mean $t_{1/2}$ for Compound 1 of from about 10.0 to about 13.0 hours, or from about 10.0 to about 12.0 hours, or from about 10.0 to about 11.0 hours, or from about 11.0 to about 14.0 hours, or from about 11.0 to about 13.0 hours, or from about 11.0 to about 12.0 hours, or from about 12.0 to about 14.0 hours, or from about 12.0 to about 13.0 hours, or from about 13.0 to about 14.0 hours, after a single 15 mg dose. In other embodiments, when administered to an adult subject, the Compound 1 (freebase) or a pharmaceutically acceptable salt thereof or the crystalline hydrate achieve a harmonic mean $t_{1/2}$ for Compound 1 of from about 12.0 to about 12.4 hours, or from about 12.2 to about 12.6 hours, or from about 12.4 to about 12.8 hours, or from about 12.6 to about 13.0 hours, or from about 12.8 to about 13.2 hours, or from about 13.0 to about 13.4 hours, or from about 13.4 to about 13.8 hours, or from about 13.6 to about 14.0 hours, after a single 15 mg dose. In other embodiments, when administered to the adult subject, the Compound 1 (freebase) or a pharmaceutically acceptable salt thereof or the crystalline hydrate achieve a harmonic mean $t_{1/2}$ for Compound 1 of about 12.5 hours after a single 15 mg dose.

When administered to the adult subject, in certain embodiments, the Compound 1 (freebase) or a pharmaceutically acceptable salt thereof or the crystalline hydrate achieve a mean $AUC_{inf}$ for Compound 1 of from about 220 to about 450 ng·hours/mL after a single 15 mg dose. When administered to the adult subject, in certain embodiments, the Compound 1 (freebase) or a pharmaceutically acceptable salt thereof or the crystalline hydrate achieve a mean $AUC_{inf}$ for Compound 1 of from about 220 to about 320 ng·hours/mL, or from about 220 to about 260 ng·hours/mL, or from about 220 to about 250 ng·hours/mL, or from about 220 to about 245 ng·hours/mL, or from about 230 to about 260 ng·hours/mL, or from about 230 to about 250 ng·hours/mL, or from about 230 to about 245 ng·hours/mL, or from about 240 to about 260 ng·hours/mL, or from about 240 to about 250 ng·hours/mL, or from about 242 to about 250 ng·hours/mL, or from about 240 to about 245 ng·hours/mL after a single 15 mg dose. When administered to the adult subject, in certain embodiments, the Compound 1 (freebase) or a pharmaceutically acceptable salt thereof or the crystalline hydrate achieve a mean $AUC_{inf}$ for Compound 1 of from about 238 to about 240 ng·hours/mL, or from about 239 to about 241 ng·hours/mL, or from about 240 to about 242 ng·hours/mL, or from about 242 to about 244 ng·hours/mL, or from about 243 to about 245 ng·hours/mL, or from about 244 to about 246 ng·hours/mL, or from about 245 to about 247 ng·hours/mL, or from about 246 to about 248 ng·hours/mL, or from about 247 to about 249 ng·hours/mL after a single 15 mg dose.

When administered to the adult subject under fasting conditions, in certain embodiments, the Compound 1 (freebase) or a pharmaceutically acceptable salt thereof or the crystalline hydrate achieve a mean $AUC_{inf}$ for Compound 1 of from about 240 to about 245 ng·hours/mL, or about 242 ng·hours/mL after a single 15 mg dose.

When administered to the adult subject under fasting conditions, in certain embodiments, the Compound 1 (freebase) or a pharmaceutically acceptable salt thereof or the crystalline hydrate achieve a mean $AUC_t$ for Compound 1 of about 227 ng·hours/mL after a single 15 mg dose, or achieve a mean $AUC_{24}$ for Compound 1 of about 249 ng·hours/mL after a single 15 mg dose. When administered to the adult subject under non-fasting conditions, in certain embodiments, the Compound 1 (freebase) or a pharmaceutically acceptable salt thereof or the crystalline hydrate achieve a mean $AUC_{24}$ for Compound 1 of about 305 ng·hours/mL or about 318 ng·hours/mL after a single 15 mg dose.

In certain embodiments, when the Compound 1 (freebase) or a pharmaceutically acceptable salt thereof or the crystalline hydrate is administered to the subject, the difference in the $AUC_{inf}$ for Compound 1 after a 15 mg dose in the fed versus the fasted state is selected from about 30% or less, about 20% or less, and about 10% or less.

When administered to the adult subject, in certain embodiments, the Compound 1 (freebase) or a pharmaceutically acceptable salt thereof or the crystalline hydrate achieve a mean $C_{24}$ for Compound 1 of from about 1.4 to about 2.5 ng/mL after a single 15 mg dose. When administered to the adult subject under fasting conditions, in certain embodiments, the Compound 1 (freebase) or a pharmaceutically acceptable salt thereof or the crystalline hydrate achieve a mean $C_{24}$ for Compound 1 of about 1.5 ng/mL or about 1.9 ng/mL after a single 15 mg dose. When administered to the adult subject under non-fasting conditions, in certain embodiments, the Compound 1 (freebase) or a pharmaceutically acceptable salt thereof or the crystalline hydrate achieve a mean $C_{24}$ for Compound 1 of about 2.4 ng/mL.

When administered QD (once-daily) to the adult subject, in certain embodiments the Compound 1 (freebase) or a pharmaceutically acceptable salt thereof or the crystalline hydrate achieve a mean $C_{max,ss}$ for Compound 1 of from about 27 to about 55 ng/mL. When administered QD (once-daily) to the adult subject, in certain embodiments the Compound 1 (freebase) or a pharmaceutically acceptable salt thereof or the crystalline hydrate achieve a mean $C_{max,ss}$ for Compound 1 of from about 27 to about 38 ng/mL, or from about 27 to about 36 ng/mL, or from about 27 to about 34 ng/mL, or from about 27 to about 32 ng/mL, or from about 27 to about 30 ng/mL, or from about 29 to about 38 ng/mL, or from about 29 to about 36 ng/mL, or from about 29 to about 34 ng/mL, or from about 29 to about 32 ng/mL, or from about 30 to about 36 ng/mL, or from about 30 to about 34 ng/mL. When administered QD (once-daily) to the adult subject, in certain embodiments the Compound 1 (freebase) or a pharmaceutically acceptable salt thereof or the crystalline hydrate achieve a mean $C_{max,ss}$ for Compound 1 of from about 31.0 to about 31.4 ng/mL, or from about 31.2 to about 31.6 ng/mL, or from about 31.4 to about 31.8 ng/mL, or from about 31.6 to about 32.0 ng/mL, or from about 31.8 to about 32.2 ng/mL, or from about 32.0 to about 32.4 ng/mL, or from about 32.2 to about 32.6 ng/mL, or from about 32.4 to about 32.8 ng/mL, or from about 32.6 to about 33.0 ng/mL, or from about 32.8 to about 33.2 ng/mL, or from about 33.0 to about 33.4 ng/mL, or from about 33.2 to about 33.6 ng/mL, or from about 33.4 to about 33.8 ng/mL, or from about 33.6 to about 34.0 ng/mL, or from about 33.8 to about 34.2 ng/mL, or from about 34.0 to about 34.4 ng/mL, or from about 34.2 to about 34.6 ng/mL, or from about 34.4 to about 34.8 ng/mL, or from about 34.6 to about 35.0 ng/mL, or from about 34.8 to about 35.2 ng/mL, or from about 35.0 to about 35.4 ng/mL, or from about 35.2 to about 35.6 ng/mL, or from about 35.4 to about 35.8 ng/mL, or from about 35.6 to about 36.0 ng/mL, or from about 35.8 to about 36.2 ng/mL, or from about 36.0 to about 36.4 ng/mL, or from about 36.2 to about 36.6 ng/mL, or from about 36.4 to about 36.8 ng/mL, or from about 36.6 to about 37.0 ng/mL, or from about 36.8 to about 37.2 ng/mL, or from about 37.0 to about 37.4 ng/mL, or from about 37.2 to about 37.6 ng/mL, or from about 37.4 to about 37.8 ng/mL, or from about 37.6 to about 38.0 ng/mL.

When administered QD (once-daily) to the adult subject under fasting conditions, in certain embodiments, the Compound 1 (freebase) or a pharmaceutically acceptable salt thereof or the crystalline hydrate achieve a mean $C_{max,ss}$ for Compound 1 of about 32 ng/mL. When administered QD (once-daily) to the adult subject under non-fasting conditions; in certain embodiments, the Compound 1 (freebase) or a pharmaceutically acceptable salt thereof or the crystalline hydrate achieve a mean $C_{max,ss}$ for Compound 1 of about 36 ng/mL or about 37 ng/mL.

When administered QD (once-daily) to the adult subject, in certain embodiments, the Compound 1 (freebase) or a pharmaceutically acceptable salt thereof or the crystalline hydrate achieve a $T_{max,ss}$ for Compound 1 of from about 1.5 to about 6.0 hours. When administered QD (once-daily) to the adult subject, in certain embodiments, the Compound 1 (freebase) or a pharmaceutically acceptable salt thereof or the crystalline hydrate achieve a $T_{max,ss}$ for Compound 1 of from about 1.5 to about 5.0 hours, or from about 1.5 to about 4.0 hours, or from about 1.5 to about 3.0 hours, or from about 1.5 to about 2.0 hours, or from about 2.0 to about 6.0 hours, or from about 3.0 to about 6.0 hours, or from about 4.0 to about 6.0 hours, or from about 2.0 to about 5.0 hours, or from about 2.0 to about 4.0 hours, or from about 2.0 to about 3.0 hours, or from about 3.0 to about 5.0 hours, or from about 3.0 to about 4.0 hours, or from about 4.0 to about 5.0 hours. In some embodiments, when administered QD (once-daily) to the adult subject, the Compound 1 (freebase) or a pharmaceutically acceptable salt thereof or the crystalline hydrate achieve a $T_{max,ss}$ for Compound 1 of from about 2.6 to about 3.0 hours, or from about 2.8 to about 3.2 hours, or from about 3.0 to about 3.4 hours, or from about 3.2 to about 3.6 hours, or from about 3.4 to about 3.8 hours, or from about 3.6 to about 4.0 hours, or from about 3.8 to about 4.2 hours, or from about 4.0 to about 4.4 hours.

When administered QD (once-daily) to the adult subject under fasting conditions, in certain embodiments, the Compound 1 (freebase) or a pharmaceutically acceptable salt thereof or the crystalline hydrate achieve a $T_{max,ss}$ for Compound 1 of from about 1.5 to about 4.0 hours, or achieve a median $T_{max,ss}$ for Compound 1 of about 2.5 hours. When administered QD (once-daily) to the adult subject under non-fasting conditions, in certain embodiments, the Compound 1 (freebase) or a pharmaceutically acceptable salt thereof or the crystalline hydrate achieve a $T_{max,ss}$ for Compound 1 of from about 2.0 to about 6.0 hours, or achieve a median $T_{max,ss}$ for Compound 1 of about 4.0 hours.

When administered QD (once-daily) to the adult subject, in certain embodiments, the Compound 1 (freebase) or a pharmaceutically acceptable salt thereof or the crystalline hydrate achieve a mean $C_{trough}$ for Compound 1 of from about 2.5 to about 5.1 ng/mL. When administered QD (once-daily) to the adult subject under fasting conditions, in certain embodiments, the Compound 1 (freebase) or a pharmaceutically acceptable salt thereof or the crystalline hydrate achieve a mean $C_{trough}$ for Compound 1 of about 2.8 ng/mL. When administered QD (once-daily) to the adult subject under non-fasting conditions, in certain embodiments, the Compound 1 (freebase) or a pharmaceutically acceptable salt thereof or the crystalline hydrate achieve a mean $C_{trough}$ for Compound 1 of from about 2.5 to about 5.1 ng/mL, or from about 2.5 to about 3.6 ng/mL, or achieve a mean $C_{trough}$ for Compound 1 of about 2.6 ng/mL or about 3.2 ng/mL or about 3.6 ng/mL, or about 5.0 ng/mL.

When administered QD (once-daily) to the adult subject, in certain embodiments, the Compound 1 (freebase) or a pharmaceutically acceptable salt thereof or the crystalline hydrate achieve a mean $AUC_{24,ss}$ for Compound 1 of from about 240 to about 325 ng-hours/mL. When administered QD (once-daily) to the adult subject, in certain embodiments, the Compound 1 (freebase) or a pharmaceutically acceptable salt thereof or the crystalline hydrate achieve a mean $AUC_{24,ss}$ for Compound 1 of from about 240 to about 290 ng-hours/mL, or from about 240 to about 280 ng·hours/mL, or from about 240 to about 260 ng-hours/mL, or from about 250 to about 290 ng-hours/mL, or from about 250 to about 280 ng-hours/mL, or from about 260 to about 280 ng-hours/mL, or from about 270 to about 280 ng·hours/mL, or from about 275 to about 280 ng-hours/mL, or from about 279 to about 280 ng-hours/mL. When administered QD (once-daily) to the adult subject, in certain embodiments, the Compound 1 (freebase) or a pharmaceutically acceptable salt thereof or the crystalline hydrate achieve a mean $AUC_{24,ss}$ for Compound 1 of from about 240 to about 244 ng-hours/mL, or from about 241 to about 245 ng-hours/mL, or from about 242 to about 246 ng-hours/mL, or from about 244 to about 248 ng·hours/mL, or from about 246 to about 250 ng-hours/mL, or from about 248 to about 252 ng-hours/mL, or from about 250 to about 254 ng-hours/mL, or from about 252 to about 256 ng-hours/mL, or from about 254 to about 258 ng-hours/mL, or from about 256 to about 260 ng-hours/mL, or from about 258 to about 262 ng-hours/mL, or from about 260 to about 264 ng-hours/mL, or from about 262 to about 266 ng-hours/mL, or from about 264 to about 268 ng-hours/mL, or from about 266 to about 270 ng-hours/mL, or from about 268 to about 272 ng-hours/mL, or from about 270 to about 274 ng-hours/mL, or from about 272 to about 276 ng·hours/mL, or from about 274 to about 278 ng·hours/mL, or from about 276 to about 280 ng-hours/mL.

When administered QD (once-daily) to the adult subject under fasting conditions, in certain embodiments, the Compound 1 (freebase) or a pharmaceutically acceptable salt thereof or the crystalline hydrate achieve a mean $AUC_{24,ss}$ for Compound 1 of about 241 ng-hours/mL or about 279 ng-hours/mL. When administered QD (once-daily) to the adult subject under non-fasting conditions, in certain embodiments, the Compound 1 (freebase) or a pharmaceutically acceptable salt thereof or the crystalline hydrate achieve a mean $AUC_{24,ss}$ for Compound 1 of about 317 ng-hours/mL or about 322 ng-hours/mL.

When administered QD (once-daily) to the adult subject, in certain embodiments, the Compound 1 (freebase) or a pharmaceutically acceptable salt thereof or the crystalline hydrate achieve a mean $C_{min,ss}$ for Compound 1 of from about 2.8 to about 3.2 ng/mL. When administered QD (once-daily) to the adult subject, in certain embodiments, the Compound 1 (freebase) or a pharmaceutically acceptable salt thereof or the crystalline hydrate achieve a mean $C_{min,ss}$ for Compound 1 of from about 2.8 to about 3.1 ng/mL, or from about 2.8 to about 3.0 ng/mL, or from about 2.8 to about 2.9 ng/mL, or from about 2.9 to about 3.2 ng/mL, or from about 2.9 to about 3.0 ng/mL, or from about 3.0 to about 3.2 ng/mL, or from about 3.0 to about 3.1 ng/mL, or from about 3.1 to about 3.2 ng/mL. When administered QD (once-daily) to the adult subject, in certain embodiments, the Compound 1 (freebase) or a pharmaceutically acceptable salt thereof or the crystalline hydrate achieve a mean $C_{min,ss}$ for Compound 1 of about 2.8 ng/mL or about 3.0 ng/mL, or about 3:1 ng/mL.

When administered QD (once-daily) to the adult subject, in certain embodiments, the Compound 1 (freebase) or a pharmaceutically acceptable salt thereof or the crystalline hydrate achieve a mean $C_{24,ss}$ for Compound 1 of from about 2.9 to about 3.2 hours. When administered QD (once-daily) to the adult subject under fasting conditions, in certain embodiments, the Compound 1 (freebase) or a pharmaceutically acceptable salt thereof or the crystalline hydrate achieve a mean $C_{24,ss}$ for Compound 1 of about 3.1 ng/mL. When administered QD (once-daily) to the adult subject under non-fasting conditions, in certain embodiments, the Compound 1 (freebase) or a pharmaceutically acceptable salt thereof or the crystalline hydrate achieve a mean $C_{24,ss}$ for Compound 1 of about 3.2 ng/mL.

When administered QD (once-daily) to the adult subject, in certain embodiments, the Compound 1 (freebase) or a pharmaceutically acceptable salt thereof or the crystalline hydrate achieve a harmonic mean $t_{1/2,ss}$ for Compound 1 of from about 9.4 to about 10.5 hours. When administered QD (once-daily) to the adult subject, in certain embodiments, the Compound 1 (freebase) or a pharmaceutically acceptable salt thereof or the crystalline hydrate achieve a harmonic mean $t_{1/2,ss}$ for Compound 1 of from about 9.4 to about 10.4 hours, or from about 9.4 to about 10.3 hours, or from about 9.4 to about 10.1 hours, or from about 9.4 to about 9.9 hours, or from about 9.5 to about 10.4 hours. When administered QD (once-daily) to the adult subject, in certain embodiments, the Compound 1 (freebase) or a pharmaceutically acceptable salt thereof or the crystalline hydrate achieve a harmonic mean $t_{1/2,ss}$ for Compound 1 of from about 9.4 to about 9.8 hours, or from about 9.6 to about 10.0 hours, or from about 9.8 to about 10.2 hours, or from about 10.0 to about 10.4 hours, or from about 10.1 to about 10.5 hours. When administered QD (once-daily) to the adult subject, in certain embodiments, the Compound 1 (freebase) or a pharmaceutically acceptable salt thereof or the crystalline hydrate achieve a harmonic mean $t_{1/2,ss}$ for Compound 1 of about 10.3 hours or about 9.4 hours or about 9.5 hours.

In certain embodiments, when administered to the adult subject, the Compound 1 (freebase) or a pharmaceutically acceptable salt thereof or the crystalline hydrate provides: (a) a mean $C_{max}$ for Compound 1 of from about 25 to about 70 ng/mL; (b) a $T_{max}$ for Compound 1 of from about 1.0 hours to about 6.0 hours; (c) a harmonic mean $t_{in}$ for Compound 1 of from about 10.0 to about 14.0 hours; (d) a mean $AUC_{inf}$ for Compound 1 of from about 220 to about 450 ng·hours/mL; (e) a mean $C_{max,ss}$ for Compound 1 of from about 27 to about 55 ng/mL; (f) a mean $AUC_{24,ss}$ for Compound 1 of from about 240 to about 325 ng·hours/mL; (g) a $T_{max,ss}$ for Compound 1 of from about 1.5 to about 6.0 hours; (h) a mean $C_{min,ss}$ for Compound 1 of from about 2.8 to about 3.2 ng/mL; (i) a harmonic mean $t_{1/2,ss}$ for Compound 1 of from about 9.4 to about 10.5 hours; or combinations thereof.

In certain embodiments, when administered to the adult subject, the Compound 1 (freebase) or a pharmaceutically acceptable salt thereof or the crystalline hydrate provides: (a) a mean $C_{max}$ for Compound 1 of from about 25 to about 70 ng/mL; (b) a $T_{max}$ for Compound 1 of from about 1.0 hours to about 6.0 hours; (c) a harmonic mean $t_{in}$ for Compound 1 of from about 10.0 to about 14.0 hours; (d) a mean $AUC_{inf}$ for Compound 1 of from about 220 to about 450 ng·hours/mL; or combinations thereof, after a single 15 mg dose.

In certain embodiments, when administered QD (once daily) to the adult subject, the Compound 1 (freebase) or a pharmaceutically acceptable salt thereof or the crystalline hydrate provides: (a) a mean $C_{max,ss}$ for Compound 1 of from about 27 to about 55 ng/mL; (b) a mean $AUC_{24,ss}$ for Compound 1 of from about 240 to about 325 ng·hours/mL; (c) a $T_{max,ss}$ for Compound 1 of from about 1.5 to about 6.0 hours; (d) a mean $C_{min,ss}$ for Compound 1 of from about 2.8 to about 3.2 ng/mL; (e) a harmonic mean $t_{1/2,ss}$ for Compound 1 of from about 9.4 to about 10.5 hours; or combinations thereof.

In certain embodiments, when administered to the adult subject under fasting conditions, the Compound 1 (freebase) or a pharmaceutically acceptable salt thereof or the crystalline hydrate provides: (a) a mean $C_{max}$ for Compound 1 of about 26 ng/mL or about 32 ng/mL; (b) a $T_{max}$ for Compound 1 of from about 1.0 hours to about 4.0 hours, or from about 1.5 to about 6.0 hours, or a median $T_{max}$ for Compound 1 of about 3.0 hours; (c) a harmonic mean $t_{1/2}$ for Compound 1 of about 12.5 hours; (d) a mean $AUC_{inf}$ for Compound 1 of about 242 ng·hours/mL; or combinations thereof, after a single 15 mg dose.

In certain embodiments, when administered to the adult subject under non-fasting conditions, the Compound 1 (freebase) or a pharmaceutically acceptable salt thereof or the crystalline hydrate provides: (a) a mean $C_{max}$ for Compound 1 of about 40 ng/mL; (b) a $T_{max}$ for Compound 1 of from about 3.0 to about 6.0 hours, or a median $T_{max}$ for Compound 1 of about 4.0 hours; (c) a harmonic mean $t_{1/2}$ for Compound 1 of about 12.5 hours; or combinations thereof, after a single 15 mg dose.

In certain embodiments, when administered QD (once daily) to the adult subject under fasting conditions, the Compound 1 (freebase) or a pharmaceutically acceptable salt thereof or the crystalline hydrate alternately or additionally may provide (a) a mean $C_{max,ss}$ for Compound 1 of about 32 ng/mL; (b) a mean $AUC_{24,ss}$ for Compound 1 of about 279 ng·hours/mL; (c) a $T_{max,ss}$ for Compound 1 of about 1.5 to about 4.0 hours, or a median $T_{max,ss}$ for Compound 1 of about 2.5 hours; (d) a mean $C_{min,ss}$ for Compound 1 of about 3.0 ng/mL or about 3.1 ng/mL; (e) a harmonic mean $t_{1/2,ss}$ for Compound 1 of about 9.5 hours or about 10.3 hours; or combinations thereof.

In certain embodiments, when administered QD (once daily) to the adult subject under non-fasting conditions, the Compound 1 (freebase) or a pharmaceutically acceptable salt thereof or the crystalline hydrate alternately or additionally may provide (a) a mean $C_{max,ss}$ for Compound 1 of about 36 ng/mL or about 37 ng/mL; (b) a mean $AUC_{24,ss}$ for Compound 1 of about 317 ng·hours/mL or about 322 ng·hours/mL; (c) a $T_{max,ss}$ for Compound 1 of about 2.0 to about 6.0 hours or a median $T_{max,ss}$ for Compound 1 of about 4.0 hours; (d) a mean $C_{min,ss}$ for Compound 1 of about 2.8 ng/mL or about 3.0 ng/mL; (e) a harmonic mean $t_{1/2,ss}$ for Compound 1 of about 9.4 hours or about 9.5 hours or 10.3 hours; or combinations thereof.

In certain embodiments, the present disclosure is directed to pharmaceutical compositions comprising a crystalline hydrate of Compound 1 in an amount sufficient to deliver to the subject 15 mg of Compound 1 freebase equivalent. In certain embodiments, the crystalline hydrate is Freebase Hydrate Form C. In one embodiment, the crystalline hydrate is in a once daily extended release formulation. In one embodiment, upon oral administration of the pharmaceutical composition to an adult subject, the composition provides (a) a mean $C_{max}$ for Compound 1 of from about 25 to about 70 ng/mL; (b) a $T_{max}$ for Compound 1 of from about 1.0 hours to about 6.0 hours; (c) a harmonic mean $t_{1/2}$ for Compound 1 of from about 10.0 to about 14.0 hours; (d) a mean $AUC_{inf}$ for Compound 1 of from about 220 to about 450 ng·hours/mL; (e) a mean $C_{max,ss}$ for Compound 1 of from about 27 to about 55 ng/mL; (f) a mean $AUC_{24,ss}$ for Compound 1 of from about 240 to about 325 ng·hours/mL; (g) a $T_{max,ss}$ for Compound 1 of from about 1.5 to about 6.0 hours; (h) a mean $C_{min,ss}$ for Compound 1 of from about 2.8 to about 3.2 ng/mL; (i) a harmonic mean $t_{1/2,ss}$ for Compound 1 of from about 9.4 to about 10.5 hours; or combinations thereof.

In one embodiment, upon oral administration of the pharmaceutical composition to an adult subject, the composition provides (a) a mean $C_{max}$ for Compound 1 of from about 25 to about 70 ng/mL; (b) a $T_{max}$ for Compound 1 of from about 1.0 hours to about 6.0 hours; (c) a harmonic mean $t_{1/2}$ for Compound 1 of from about 10.0 to about 14.0 hours; (d) a mean $AUC_{inf}$ for Compound 1 of from about 220 to about 450 ng-hours/mL; or combinations thereof, after a single 15 mg dose.

In one embodiment, when administered QD (once daily) to the adult subject the pharmaceutical composition provides (a) a mean $C_{max,ss}$ for Compound 1 of from about 27 to about 55 ng/mL; (b) a mean $AUC_{24,ss}$ for Compound 1 of from about 240 to about 325 ng-hours/mL; (c) a $T_{max,ss}$ for Compound 1 of from about 1.5 to about 6.0 hours; (d) a mean $C_{min,ss}$ for Compound 1 of from about 2.8 to about 3.2 ng/mL; (e) a harmonic mean $t_{1/2,ss}$ for Compound 1 of from about 9.4 to about 10.5 hours; or combinations thereof.

In one embodiment, upon oral administration of the pharmaceutical composition to an adult subject under fasting conditions, the pharmaceutical composition provides (a) a mean $C_{max}$ for Compound 1 of about 26. ng/mL or about 32 ng/mL; (b) a $T_{max}$ for Compound 1 of from about 1.0 to about 4.0 hours, or from about 1.5 to about 6.0 hours, or a median $T_{max}$ for Compound 1 of about 3.0 hours; (c) a harmonic mean $t_{1/2}$ for Compound 1 of about 12.5 hours; (d) a mean $AUC_{inf}$ for Compound 1 of about 242 ng·hours/mL; or combinations thereof, after a single 15 mg dose. In one embodiment, upon oral administration of the pharmaceutical composition to an adult subject under non-fasting conditions, the composition provides (a) a mean $C_{max}$ for Compound 1 of about 40 ng/mL; (b) a $T_{max}$ for Compound 1 of from about 3.0 to about 6.0 hours, or a median $T_{max}$ for Compound 1 of about 4.0 hours; (c) a harmonic mean $t_{1/2}$ for Compound 1 of about 12.5 hours; or combinations thereof, after a single 15 mg dose.

In one embodiment, upon oral administration of the pharmaceutical composition to an adult subject QD (once daily) under fasting conditions, the composition alternately or additionally provides (a) a mean $C_{max,ss}$ for Compound 1 of about 32 ng/mL; (b) a mean $AUC_{24,ss}$ for Compound 1 of about 279 ng-hours/mL; (c) a $T_{max,ss}$ for Compound 1 of about 1.5 to about 4.0 hours, or a median $T_{max,ss}$ for Compound 1 of about 2.5 hours; (d) a mean $C_{min,ss}$ for Compound 1 of about 3.0 ng/mL or about 3.1 ng/mL; (e) a harmonic mean $t_{1/2,ss}$ for Compound 1 of about 9.5 hours or about 10.3 hours; or combinations thereof. In one embodiment, upon oral administration of the pharmaceutical composition to an adult subject QD (once daily) under non-fasting conditions, the composition alternately or additionally provides (a) a mean $C_{max,ss}$ for Compound 1 of about 36 ng/mL or about 37 ng/mL; (b) a mean $AUC_{24,ss}$ for Compound 1 of about 317 ng-hours/mL or about 322 ng-hours/mL; (c) a $T_{max,ss}$ for Compound 1 of about 2.0 to about 6.0 hours or a median $T_{max,ss}$ for Compound 1 of about 4.0; (d) a mean $C_{min,ss}$ for Compound 1 of about 2.8 ng/mL or about 3.0 ng/mL; (e) a harmonic mean $t_{1/2,ss}$ for Compound 1 of about 9.4 hours or about 9.5 hours or about 10.3 hours; or combinations thereof.

In one embodiment, the present disclosure is directed to pharmaceutical composition comprising about 15 mg of Freebase Hydrate Form C, a pharmaceutically acceptable carrier, and from about 10 w/w % to about 35 w/w % of tartaric acid, wherein the pharmaceutical composition is a once daily extended release dosage form (e.g., tablet or capsule) and, upon oral administration of the pharmaceutical composition to an adult subject, the composition provides (a) a mean $C_{max}$ for Compound 1 of from about 25 to about 70 ng/mL; (b) a $T_{max}$ for Compound 1 of from about 1.0 hours to about 6.0 hours; (c) a harmonic mean $t_{1/2}$ for Compound 1 of from about 10.0 to about 14.0 hours; (d) a mean $AUC_{inf}$ for Compound 1 of from about 220 to about 450 ng-hours/mL; (e) a mean $C_{max,ss}$ for Compound 1 of from about 27 to about 55 ng/mL; (f) a mean $AUC_{24,ss}$ for Compound 1 of from about 240 to about 325 ng-hours/mL; (g) a $T_{max,ss}$ for Compound 1 of from about 1.5 to about 6.0 hours; (h) a mean $C_{min,ss}$ for Compound 1 of from about 2.8 to about 3.2 ng/mL; (i) a harmonic mean $t_{1/2,ss}$ for Compound 1 of from about 9.4 to about 10.5 hours; or combinations thereof.

In one embodiment, the present disclosure is directed to pharmaceutical composition comprising about 15 mg of Freebase Hydrate Form C, a pharmaceutically acceptable carrier, and about 10 w/w % or about 20 w/w % or about 30 w/w % of tartaric acid, wherein the pharmaceutical composition is a once daily extended release dosage form (e.g., tablet or capsule) and, upon oral administration of the pharmaceutical composition to an adult subject, the composition provides (a) a mean $C_{max}$ for Compound 1 of from about 25 to about 70 ng/mL; (b) a $T_{max}$ for Compound 1 of from about 1.0 hours to about 6.0 hours; (c) a harmonic mean $t_{1/2}$ for Compound 1 of from about 10.0 to about 14.0 hours; (d) a mean $AUC_{inf}$ for Compound 1 of from about 220 to about 450 ng-hours/mL; or combinations thereof after a single 15 mg dose.

In one embodiment, the present disclosure is directed to pharmaceutical composition comprising about 15 mg of Freebase Hydrate Form C, a pharmaceutically acceptable carrier, and about 10 w/w % or about 20 w/w % or about 30 w/w % of tartaric acid, wherein the pharmaceutical composition is a once daily extended release dosage form (e.g., tablet or capsule) and, upon oral administration of the pharmaceutical composition to an adult subject QD (once daily), the composition provides (a) a mean $C_{max,ss}$ for Compound 1 of from about 27 to about 55 ng/mL; (b) a mean $AUC_{24,ss}$ for Compound 1 of from about 240 to about 325 ng-hours/mL; (c) a $T_{max,ss}$ for Compound 1 of from about 1.5 to about 6.0 hours; (d) a mean $C_{min,ss}$ for Compound 1 of from about 2.8 to about 3.2 ng/mL; (e) a harmonic mean $t_{1/2,ss}$ for Compound 1 of from about 9.4 to about 10.5 hours; or combinations thereof.

30 mg Dosage Formulations

In certain embodiments, the methods of the present disclosure comprise administering to an adult subject (e.g., a human subject) 30 mg of Compound 1 (freebase), or a pharmaceutically acceptable salt thereof or a crystalline hydrate of Compound 1 in an amount sufficient to deliver to the subject 30 mg of Compound 1 freebase equivalent. In one embodiment, the freebase or the hydrate is in a once daily extended release formulation.

Unless otherwise indicated, the following pharmacokinetic parameters are achieved after administration of a single 30 mg dose the Compound 1 (freebase) or a pharmaceutically acceptable salt thereof or the crystalline hydrate (e.g., Freebase Hydrate Form C) to the adult subject, or after administration of a sufficient number of once-daily 30 mg doses to achieve a steady-state. By a single 30 mg dose, it is meant a single dosage unit containing an amount of freebase or pharmaceutically acceptable salt or crystalline hydrate sufficient to deliver to the subject 30 mg of Compound 1 freebase equivalent. In one embodiment, the single dosage unit is a once daily extended release formulation.

In certain embodiments, when administered to the adult subject, the Compound 1 (freebase) or a pharmaceutically acceptable salt thereof or the crystalline hydrate achieve a mean $C_{max}$ for Compound 1 of from about 55 to about 85 ng/mL after a single 30 mg dose. In certain embodiments, when administered to the adult subject, the Compound 1 (freebase) or a pharmaceutically acceptable salt thereof or the crystalline hydrate achieve a mean $C_{max}$ for Compound 1 of from about 55 to about 70 ng/mL, or from about 55 to about 67 ng/mL, or from about 55 to about 66 ng/mL, or from about 70 to about 85 ng/mL, or from about 72 to about 85 ng/mL, or from about 74 to about 85 ng/mL, after a single 30 mg dose.

In certain embodiments, when administered to the subject under fasting conditions, the Compound 1 (freebase) or a pharmaceutically acceptable salt thereof or the crystalline hydrate achieve a mean $C_{max}$ for Compound 1 of from about 55 ng/mL to about 66 ng/mL, or about 55 ng/mL, or about 56 ng/mL, or about 57 ng/mL, or about 59 ng/mL, or about 61 ng/mL, or about 64 ng/mL, or about 66 ng/mL after a single 30 mg dose. In other embodiments, when administered to the subject under non-fasting conditions, the Compound 1 (freebase) or a pharmaceutically acceptable salt thereof or the crystalline hydrate achieve a mean $C_{max}$ for Compound 1 of from about 74 ng/mL to about 85 ng/mL, or about 74 ng/mL, or about 76 ng/mL, or about 77 ng/mL, or about 79 ng/mL, about 82 ng/mL, or about 84 ng/mL after a single 30 mg dose.

In certain embodiments, when the Compound 1 (freebase) or a pharmaceutically acceptable salt thereof or the crystalline hydrate is administered to the subject, the difference in the $C_{max}$ for Compound 1 after a 30 mg dose in the fed versus the fasted state is about 55% or less, or about 53% or less, or about 30% or less, or about 20% or less, or about 10% or less. In one embodiment, the difference in the $C_{max}$ for Compound 1 after a 30 mg dose in the fed versus the fasted state is from about 3% to about 40%, or from about 15% to about 55%.

When administered to the adult subject, in certain embodiments, the Compound 1 (freebase) or a pharmaceutically acceptable salt thereof or the crystalline hydrate achieve a $T_{max}$ for Compound 1 from about 1.0 to about 8.0 hours after a single 30 mg dose. When administered to the adult subject, in certain embodiments, the Compound 1 (freebase) or a pharmaceutically acceptable salt thereof or the crystalline hydrate achieve a $T_{max}$ for Compound 1 from about 2.0 to about 6.0 hours, or from about 1.0 to about 4.0 hours, or from about 1.5 to about 4.0 hours, or from about 1.5 to about 8.0 hours, or from about 2.0 to about 4.0 hours, or from about 2.0 to about 3.0 hours, after a single 30 mg dose.

In other embodiments, when administered to the adult subject under fasting conditions, the Compound 1 (freebase) or a pharmaceutically acceptable salt thereof or the crystalline hydrate achieve a $T_{max}$ for Compound 1 of from about 1.0 to about 4.0 hours, or from about 1.5 to about 4.0 hours, or a median $T_{max}$ for Compound 1 of about 2.0 hours, or about 2.5 hours, or about 3.0 hours after a single 30 mg dose. In other embodiments, when administered to the adult subject under non-fasting conditions, the Compound 1 (freebase) or a pharmaceutically acceptable salt thereof or the crystalline hydrate achieve a $T_{max}$ for Compound 1 of from about 1.5 to about 8.0 hours, or about 2.0 to about 6.0 hours, or a median $T_{max}$ for Compound 1 of about 4.0 hours after a single 30 mg dose.

When administered to the adult subject, in certain embodiments, the Compound 1 (freebase) or a pharmaceutically acceptable salt thereof or the crystalline hydrate achieve a harmonic mean $t_{1/2}$ for Compound 1 of from about 9.0 to about 12.0 hours after a single 30 mg dose. When administered to the adult subject, in certain embodiments, the Compound 1 (freebase) or a pharmaceutically acceptable salt thereof or the crystalline hydrate achieve a harmonic mean $t_{1/2}$ for Compound 1 of from about 9.0 to about 11.0 hours, or from about 9.0 to about 10.0 hours, or from about 10.0 to about 12.0 hours, or from about 10.0 to about 11.5 hours, after a single 30 mg dose.

When administered to the adult subject, in certain embodiments, the Compound 1 (freebase) or a pharmaceutically acceptable salt thereof or the crystalline hydrate achieve a harmonic mean $t_{1/2}$ for Compound 1 of about 9.0 hours, or about 9.5 hours, or about 10.0 hours, or about 10.5 hours, or about 11.0 hours, or about 11.5 hours, or about 12.0 hours, after a single 30 mg dose.

When administered to the adult subject, in certain embodiments, the Compound 1 (freebase) or a pharmaceutically acceptable salt thereof or the crystalline hydrate achieve a mean $AUC_{inf}$ for Compound 1 of from about 453 to about 660 ng·hours/mL after a single 30 mg dose. When administered to the adult subject, in certain embodiments, the Compound 1 (freebase) or a pharmaceutically acceptable salt thereof or the crystalline hydrate achieve a mean $AUC_{inf}$ for Compound 1 of from about 483 to about 660 ng·hours/mL, from about 483 to about 550 ng·hours/mL, or from about 484 to about 515 ng·hours/mL, or from about 484 to about 513 ng·hours/mL, or from about 560 to about 660 ng·hours/mL, or from about 570 to about 660 ng·hours/mL, or from about 577 to about 657 ng·hours/mL, after a single 30 mg dose.

When administered to the adult subject under fasting conditions, in certain embodiments, the Compound 1 (freebase) or a pharmaceutically acceptable salt thereof or the crystalline hydrate achieve a mean $AUC_{inf}$ for Compound 1 of from about 484 to about 550 ng·hours/mL, or about 484 ng·hours/mL, or about 491 ng·hours/mL, or about 495 ng·hours/mL, or about 499 ng·hours/mL, or about 513 ng·hours/mL after a single 30 mg dose. When administered to the adult subject under fasting conditions, in certain embodiments, the Compound 1 (freebase) or a pharmaceutically acceptable salt thereof or the crystalline hydrate achieve a mean $AUC_t$ for Compound 1 of about 473 ng·hours/mL, or about 477 ng·hours/mL, about 481 ng·hours/mL, or about 487 ng·hours/mL, or about 495 ng·hours/mL, or a mean $AUC_{24}$ of about 454 ng·hours/mL, after a single 30 mg dose. When administered to the adult subject under non-fasting conditions, in certain embodiments, the Compound 1 (freebase) or a pharmaceutically acceptable salt thereof or the crystalline hydrate achieve a mean $AUC_{inf}$ for Compound 1 of from about 560 to about 660 ng·hours/mL, or about 577 ng·hours/mL, or about 609 ng·hours/mL, or about 622 ng·hours/mL, or about 657 ng·hours/mL, after a single 30 mg dose. When administered to the adult subject under non-fasting conditions, in certain embodiments, the Compound 1 (freebase) or a pharmaceutically acceptable salt thereof or the crystalline hydrate achieve a mean $AUC_{24}$ for Compound 1 of about 517 ng·hours/mL or about 563 ng·hours/mL, or a mean $AUC_t$ of about 564 ng·hours/mL, or about 605 ng·hours/mL, or about 615 ng·hours/mL, or about 648 ng·hours/mL, after a single 30 mg dose.

In certain embodiments, when the Compound 1 (freebase) or a pharmaceutically acceptable salt thereof or the crystalline hydrate is administered to the subject, the difference in the $AUC_{inf}$ for Compound 1 after a 30 mg dose in the fed versus the fasted state is about 30% or less, or about 20% or less, or about 10% or less.

When administered to the adult subject, in certain embodiments, the Compound 1 (freebase) or a pharmaceutically acceptable salt thereof or the crystalline hydrate achieve a mean $C_{24}$ for Compound 1 of from about 2.3 to about 4.5 ng/mL after a single 30 mg dose. When administered to the adult subject under fasting conditions, in certain embodiments, the Compound 1 (freebase) or a pharmaceutically acceptable salt thereof or the crystalline hydrate achieve a mean $C_{24}$ for Compound 1 of about 2.7 ng/mL, or about 3.2 ng/mL, or about 2.8 ng/mL, or about 3.5 ng/mL, or about 3.7 ng/mL, or about 3.9 ng/mL, after a single 30 mg dose. When administered to the adult subject under non-fasting conditions, in certain embodiments, the Compound 1 (freebase) or a pharmaceutically acceptable salt thereof or the crystalline hydrate achieve a mean $C_{24}$ for Compound 1 of about 2.4 ng/mL, or about 2.6 ng/mL, or about 2.8 ng/mL, or about 2.9 ng/mL, or about 4.3 ng/mL, after a single 30 mg dose.

When administered QD (once daily) to the adult subject, in certain embodiments, the Compound 1 (freebase) or a pharmaceutically acceptable salt thereof or the crystalline hydrate achieve a mean $C_{max,ss}$ for Compound 1 of from about 65 to about 86 ng/mL. When administered QD (once daily) to the adult subject, in certain embodiments, the Compound 1 (freebase) or a pharmaceutically acceptable salt thereof or the crystalline hydrate achieve a mean $C_{max,ss}$ for Compound 1 of from about 65 to about 70 ng/mL, or from about 67 to about 68 ng/mL, or from about 78 to about 86 ng/mL, or from about 80 to about 84 ng/mL.

When administered QD (once daily) to the adult subject under fasting conditions, in certain embodiments, the Compound 1 (freebase) or a pharmaceutically acceptable salt thereof or the crystalline hydrate achieve a mean $C_{max,ss}$ for Compound 1 of about 67 ng/mL or about 68 ng/mL. When administered QD (once daily) to the adult subject under non-fasting conditions, in certain embodiments, the Compound 1 (freebase) or a pharmaceutically acceptable salt thereof or the crystalline hydrate achieve a mean $C_{max,ss}$ for Compound 1 of about 80 ng/mL or about 84 ng/mL.

When administered QD (once-daily) to the adult subject, in certain embodiments, the Compound 1 (freebase) or a pharmaceutically acceptable salt thereof or the crystalline hydrate achieve a $T_{max,ss}$ of from about 1.5 to about 6.0 hours. When administered QD (once-daily) to the adult subject, in certain embodiments, the Compound 1 (freebase) or a pharmaceutically acceptable salt thereof or the crystalline hydrate achieve a $T_{max,ss}$ of from about 1.5 to about 4.0 hours, or from about 2.0 to about 4.0 hours, or from about 3.0 to about 4.0 hours, or from about 3.5 to about 4.0 hours.

When administered QD (once-daily) to the adult subject under fasting conditions, in certain embodiments, the Compound 1 (freebase) or a pharmaceutically acceptable salt thereof or the crystalline hydrate achieve a $T_{max,ss}$ of from about 2.0 to about 4.0 hours, or a median $T_{max,ss}$ for Compound 1 of about 3.0 hours. When administered QD (once-daily) to the adult subject under non-fasting conditions, in certain embodiments, the Compound 1 (freebase) or a pharmaceutically acceptable salt thereof or the crystalline hydrate achieve a $T_{max,ss}$ of from about 1.5 to about 6.0 hours, or a median $T_{max,ss}$ for Compound 1 of about 3.5 hours or about 4.0 hours.

When administered QD (once daily) to the adult subject, in certain embodiments, the Compound 1 (freebase) or the crystalline hydrate achieve a mean $C_{trough}$ for Compound 1 of from about 2.8 to about 6.1 ng/mL. When administered QD (once daily) to the adult subject under fasting conditions, in certain embodiments, the Compound 1 (freebase) or the crystalline hydrate achieve a mean $C_{trough}$ for Compound 1 of about 4.9 ng/mL. When administered QD (once daily) to the adult subject under non-fasting conditions, in certain embodiments, the Compound 1 (freebase) or a pharmaceutically acceptable salt thereof or the crystalline hydrate achieve a mean $C_{trough}$ for Compound 1 of from about 2.8 to about 6.1 ng/mL, or from about 4.6 to about 6.1 ng/mL, or about 3.0 ng/mL, or about 4.7 ng/mL or about 5.3 ng/mL or about 6.1 ng/mL.

When administered QD (once daily) to the adult subject, in certain embodiments, the Compound 1 (freebase) or a pharmaceutically acceptable salt thereof or the crystalline hydrate achieve a mean $AUC_{24,ss}$ for Compound 1 of from about 485 to about 658 ng·hours/mL. When administered QD (once daily) to the adult subject, in certain embodiments, the Compound 1 (freebase) or a pharmaceutically acceptable salt thereof or the crystalline hydrate achieve a mean $AUC_{24,ss}$ for Compound 1 of from about 520 to about 640 ng·hours/mL, or from about 520 to about 630 ng·hours/mL, or from about 525 to about 620 ng·hours/mL, or from about 525 to about 585 ng·hours/mL, or from about 580 to about 630 ng·hours/mL, or from about 582 to about 620 ng·hours/mL.

When administered to the adult subject under fasting conditions, in certain embodiments, the Compound 1 (freebase) or a pharmaceutically acceptable salt thereof or the crystalline hydrate achieve a mean $AUC_{24,ss}$ for Compound 1 of about 525 ng·hours/mL. When administered to the adult subject under non-fasting conditions, in certain embodiments, the Compound 1 (freebase) or a pharmaceutically acceptable salt thereof or the crystalline hydrate achieve a mean $AUC_{24,ss}$ for Compound 1 of about 582 ng·hours/mL or about 620 ng·hours/mL.

When administered QD (once-daily) to the adult subject, in certain embodiments, the Compound 1 (freebase) or a pharmaceutically acceptable salt thereof or the crystalline hydrate achieve a mean $C_{min,ss}$ for Compound 1 of from about 3.5 to about 5.3 ng/mL. When administered QD (once-daily) to the adult subject, in certain embodiments, the Compound 1 (freebase) or a pharmaceutically acceptable salt thereof or the crystalline hydrate achieve a mean $C_{min,ss}$ for Compound 1 of from about 3.6 to about 5.2 ng/mL, or from about 3.8 to about 5.2 ng/mL, or from about 4.6 to about 5.2 ng/mL.

When administered QD (once-daily) to the adult subject under fasting conditions, in certain embodiments, the Compound 1 (freebase) or a pharmaceutically acceptable salt thereof or the crystalline hydrate achieve a mean $C_{min,ss}$ for Compound 1 of about 3.8 ng/mL. When administered QD (once-daily) to the adult subject under non-fasting conditions, in certain embodiments, the Compound 1 (freebase) or a pharmaceutically acceptable salt thereof or the crystalline hydrate achieve a mean $C_{min,ss}$ for Compound 1 of about 4.6 ng/mL or about 5.2 ng/mL.

When administered QD (once-daily) to the adult subject, in certain embodiments, the Compound 1 (freebase) or a pharmaceutically acceptable salt thereof or the crystalline hydrate achieve a mean $C_{24,ss}$ for Compound 1 of from about 4.0 to about 5.3 hours. When administered QD (once-daily) to the adult subject under fasting conditions, in certain embodiments, the Compound 1 (freebase) or a pharmaceutically acceptable salt thereof or the crystalline hydrate achieve a mean $C_{24,ss}$ for Compound 1 of about 4.3 ng/mL or about 4.4 ng/mL. When administered QD (once-daily) to the adult subject under non-fasting conditions, in certain embodiments, the Compound 1 (freebase) or a pharmaceutically acceptable salt thereof or the crystalline hydrate achieve a mean $C_{24,ss}$ for Compound 1 of about 5.3 ng/mL.

When administered QD (once-daily) to the adult subject, in certain embodiments, the Compound 1 (freebase) or a pharmaceutically acceptable salt thereof or the crystalline hydrate achieve a harmonic mean $t_{1/2,ss}$ for Compound 1 of from about 10.0 to about 14.5 hours. When administered QD (once-daily) to the adult subject, in certain embodiments, the Compound 1 (freebase) or the crystalline hydrate achieve a harmonic mean $t_{1/2,ss}$ for Compound 1 of from about 10.1 to about 14.4 hours, or from about 10.1 to about 10.4 hours, or from about 10.4 hours to about 14.4 hours. When administered QD (once-daily) to the adult subject, in certain embodiments, the Compound 1 (freebase) or a pharmaceutically acceptable salt thereof or the crystalline hydrate achieve a harmonic mean $t_{1/2,ss}$ for Compound 1 of about 14.4 hours or about 10.1 hours or about 10.4 hours.

In certain embodiments, when administered to the adult subject, the Compound 1 (freebase) or a pharmaceutically acceptable salt thereof or the crystalline hydrate provides: (a) a mean $C_{max}$ for Compound 1 of from about 55 to about 85 ng/mL; (b) a $T_{max}$ for Compound 1 of from about 1.0 hours to about 8.0 hours; (c) a harmonic mean $t_{1/2}$ for Compound 1 of from about 9.0 to about 12.0 hours; (d) a mean $AUC_{inf}$ for Compound 1 of from about 483 to about 660 ng·hours/mL; (e) a mean $C_{max,ss}$ for Compound 1 of from about 65 to about 85 ng/mL; (f) a mean $AUC_{24,ss}$ for Compound 1 of from about 485 to about 658 ng·hours/mL; (g) a $T_{max,ss}$ for Compound 1 of from about 1.5 to about 6.0 hours; (h) a mean $C_{min,ss}$ for Compound 1 of from about 3.5 to about 5.3 ng/mL; (i) a harmonic mean $t_{1/2,ss}$ for Compound 1 of from about 10.0 to about 14.5 hours; or combinations thereof.

In certain embodiments, when administered to the adult subject, the Compound 1 (freebase) or a pharmaceutically acceptable salt thereof or the crystalline hydrate provides: (a) a mean $C_{max}$ for Compound 1 of from about 55 to about 85 ng/mL; (b) a $T_{max}$ for Compound 1 of from about 1.0 hours to about 8.0 hours; (c) a harmonic mean $t_{1/2}$ for Compound 1 of from about 9.0 to about 12.0 hours; (d) a mean $AUC_{inf}$ for Compound 1 of from about 483 to about 660 ng·hours/mL; or combinations thereof, after a single 30 mg dose.

In certain embodiments, when administered QD (once-daily) to the adult subject, the Compound 1 (freebase) or a pharmaceutically acceptable salt thereof or the crystalline hydrate provides: (a) a mean $C_{max,ss}$ for Compound 1 of from about 65 to about 85 ng/mL; (b) a mean $AUC_{24,ss}$ for Compound 1 of from about 485 to about 658 ng·hours/mL; (c) a $T_{max,ss}$ for Compound 1 of from about 1.5 to about 6.0 hours; (d) a mean $C_{min,ss}$ for Compound 1 of from about 3.5 to about 5.3 ng/mL; (e) a harmonic mean $t_{1/2,ss}$ for Compound 1 of from about 10.0 to about 14.5 hours; or combinations thereof.

In certain embodiments, when administered to the adult subject under fasting conditions, the Compound 1 (freebase) or a pharmaceutically acceptable salt thereof or the crystalline hydrate provides: (a) a mean $C_{max}$ for Compound 1 of from about 55 ng/mL to about 66 ng/mL, or about 55 ng/mL, or about 56 ng/mL, or about 57 ng/mL, or about 59 ng/mL, or about 61 ng/mL, or about 64 ng/mL or about 66 ng/mL; (b) a $T_{max}$ for Compound 1 of from about 1.0 hours to about 4.0 hours, or about 1.5 hours to about 4.0 hours, or a median $T_{max}$ for Compound 1 of about 2.0 hours, or about 2.5 hours, or about 3.0 hours; (c) a harmonic mean $t_{1/2}$ for Compound 1 of about 9.0 hours, or about 9.5 hours, or about 10.0 hours, or about 10.5 hours, or about 11.0 hours, or about 11.5 hours, or about 12.0 hours; (d) a mean $AUC_{inf}$ for Compound 1 of about 484 to about 550 ng·hours/mL, or about 484 ng·hours/mL, or about 491 ng·hours/mL, or about 495 ng·hours/mL, or about 499 ng·hours/mL, or about 513 ng·hours/mL; or combinations thereof, after a single 30 mg dose.

In certain embodiments, when administered to the adult subject under non-fasting conditions, the Compound 1 (freebase) or a pharmaceutically acceptable salt thereof or the crystalline hydrate provides (a) a mean $C_{max}$ for Compound 1 of from about 76 ng/mL to about 85 ng/mL, or about 76 ng/mL, or about 77 ng/mL, or about 79 ng/mL, or about 82 ng/mL, or about 84 ng/mL; (b) a $T_{max}$ for Compound 1 of from about 1.5 hours to about 8.0 hours, or from about 2.0 hours to about 6.0 hours, or a median $T_{max}$ for Compound 1 of about 4.0 hours; (c) a harmonic mean $t_{1/2}$ for Compound 1 of about 9.0 hours, or about 9.5 hours, or about 10.0 hours, or about 10.5 hours, or about 11.0 hours, or about 11.5 hours, or about 12.0 hours; (d) a mean $AUC_{inf}$ for Compound 1 of about 577 ng·hours/mL, or about 609 ng·hours/mL, or about 622 ng·hours/mL, or about 657 ng·hours/mL; or combinations thereof, after a single 30 mg dose.

In one embodiment, when administered QD (once daily) to the adult subject under fasting conditions, the Compound 1 (freebase) or a pharmaceutically acceptable salt thereof or the crystalline hydrate alternately or additionally provides (a) a mean $C_{max,ss}$ for Compound 1 of about 67 ng/mL or about 68 ng/mL; (b) a mean $AUC_{24,ss}$ for Compound of about 525 ng·hours/mL; (c) a $T_{max,ss}$ for Compound 1 of from about 2.0 to about 4.0 hours, or a median $T_{max,ss}$ for Compound 1 of about 3.0 hours; (d) a mean $C_{min,ss}$ for Compound 1 of about 3.8 ng/mL; (e) a harmonic mean $t_{1/2,ss}$ for Compound 1 of about 10.1 hours or about 10.4 hours or about 14.4 hours; or combinations thereof.

In one embodiment, when administered QD (once daily) to the adult subject under non-fasting conditions, the Compound 1 (freebase) or a pharmaceutically acceptable salt thereof or the crystalline hydrate alternately or additionally provides (a) a mean $C_{max,ss}$ for Compound 1 of about 80 ng/mL or about 84 ng/mL; (b) a mean $AUC_{24,ss}$ for Compound 1 of about 582 ng·hours/mL or about 620 ng·hours/mL; (c) a $T_{max,ss}$ for Compound 1 of from about 1.5 to about 6.0 hours or a median $T_{max,ss}$ for Compound 1 of about 3.5 hours or about 4.0 hours; (d) a $C_{min,ss}$ for Compound 1 of about 4.6 ng/mL or about 5.2 ng/mL; (e) a harmonic mean $t_{1/2,ss}$ for Compound 1 of about 10.1 hours or about 10.4 hours or about 14.4 hours; or combinations thereof.

In certain embodiments, the present disclosure is directed to pharmaceutical compositions comprising a crystalline hydrate of Compound 1 in an amount sufficient to deliver to the subject 30 mg of Compound 1 freebase equivalent. In certain embodiments, the crystalline hydrate is Freebase Hydrate Form C. In one embodiment, the crystalline hydrate is in a once daily extended release formulation. In one embodiment, upon oral administration of the pharmaceutical composition to an adult subject, the composition provides (a) a mean $C_{max}$ for Compound 1 of from about 55 to about 85 ng/mL; (b) a $T_{max}$ for Compound 1 of from about 1.0 hours to about 8.0 hours; (c) a harmonic mean $t_{1/2}$ for Compound 1 of from about 9.0 to about 12.0 hours; (d) a mean $AUC_{inf}$ for Compound 1 of from about 483 to about 660 ng·hours/mL; (e) a mean $C_{max,ss}$ for Compound 1 of from about 65 to about 85 ng/mL; (f) a mean $AUC_{24,ss}$ for Compound 1 of from about 485 to about 658 ng·hours/mL; (g) a $T_{max,ss}$ for Compound 1 of from about 1.5 to about 6.0 hours; (h) a mean $C_{min,ss}$ for Compound 1 of from about 3.5 to about 5.3 ng/mL; (i) a harmonic mean $t_{1/2,ss}$ for Compound 1 of from about 10.0 to about 14.5 hours; or combinations thereof.

In one embodiment, upon oral administration of the pharmaceutical composition to an adult subject, the composition provides (a) a mean $C_{max}$ for Compound 1 of from about 55 to about 85 ng/mL; (b) a $T_{max}$ for Compound 1 of from about 1.0 hours to about 8.0 hours; (c) a harmonic mean $t_{1/2}$ for Compound 1 of from about 9.0 to about 12.0 hours; (d) a mean $AUC_{inf}$ for Compound 1 of from about 483 to about 660 ng·hours/mL; or combinations thereof, after a single 30 mg dose.

In one embodiment, upon oral administration of the pharmaceutical composition to an adult subject QD (once daily), the composition provides (a) a mean $C_{max,ss}$ for Compound 1 of from about 65 to about 85 ng/mL; (b) a mean $AUC_{24,ss}$ for Compound 1 of from about 485 to about 658 ng·hours/mL; (c) a $T_{max,ss}$ for Compound 1 of from about 1.5 to about 6.0 hours; (d) a mean $C_{min,ss}$ for Compound 1 of from about 3.5 to about 5.3 ng/mL; (e) a harmonic mean $t_{1/2,ss}$ for Compound 1 of from about 10.0 to about 14.5 hours; or combinations thereof.

In one embodiment, upon oral administration of the pharmaceutical composition to an adult subject under fasting conditions, the composition provides (a) a mean $C_{max}$ for Compound 1 of from about 55 ng/mL to about 66 ng/mL, or about 55 ng/mL, or about 56 ng/mL, or about 57 ng/mL, or about 59 ng/mL, or about 61 ng/mL, or about 64 ng/mL or about 66 ng/mL; (b) a $T_{max}$ for Compound 1 of from about 1.0 hours to about 4.0 hours, or from about 1.5 hours to about 4.0 hours, or a median $T_{max}$ for Compound 1 of about 2.0 hours, or about 2.5 hours, or about 3.0 hours; (c) a harmonic mean $t_{1/2}$ for Compound 1 of about 9.0 hours, or about 9.5 hours, or about 10.0 hours, or about 10.5 hours, or about 11.0 hours, or about 11.5 hours, or about 12.0 hours; (d) a mean $AUC_{inf}$ for Compound 1 of about 484 to about 550 ng·hours/mL, or about 484 ng·hours/mL, or about 491 ng·hours/mL, or about 495 ng·hours/mL, or about 499 ng·hours/mL, or about 513 ng·hours/mL; or combinations thereof, after a single 30 mg dose.

In one embodiment, upon oral administration of the pharmaceutical composition to an adult subject under non-fasting conditions, the composition provides (a) a mean $C_{max}$ for Compound 1 of from about 76 ng/mL to about 85 ng/mL, or about 76 ng/mL, or about 77 ng/mL, or about 79 ng/mL, about 82 ng/mL, or about 84 ng/mL; (b) a $T_{max}$ for Compound 1 of from about 1.5 hours to about 8.0 hours, or from about 2.0 hours to about 6.0 hours, or a median $T_{max}$ for Compound 1 of about 4.0 hours; (c) a harmonic mean $t_{1/2}$ for Compound 1 of about 9.0 hours, or about 9.5 hours, or about 10.0 hours, or about 10.5 hours, or about 11.0 hours, or about 11.5 hours, or about 12.0 hours; (d) a mean $AUC_{inf}$ for Compound 1 of about 577 ng·hours/mL, or about 609 ng·hours/mL, or about 622 ng·hours/mL, or about 657 ng·hours/mL; or combinations thereof, after a single 30 mg dose.

In one embodiment, upon oral administration of the pharmaceutical composition to an adult subject QD (once daily) under fasting conditions, the composition alternately or additionally provides (a) a mean $C_{max,ss}$ for Compound 1 of about 67 ng/mL or about 68 ng/mL; (b) a mean $AUC_{24,ss}$ for Compound 1 of about 525 ng·hours/mL; (c) a $T_{max,ss}$ for Compound 1 of from about 2.0 to about 4.0 hours, or a median $T_{max,ss}$ for Compound 1 of about 3.0 hours; (d) a mean $C_{min,ss}$ for Compound 1 of about 3.8 ng/mL; (e) a harmonic mean $t_{1/2,ss}$ for Compound 1 of about 10.1 hours or about 10.4 hours or about 14.4 hours; or combinations thereof.

In one embodiment, upon oral administration of the pharmaceutical composition to an adult subject QD (once daily) under non-fasting conditions, the composition alternately or additionally provides (a) a mean $C_{max,ss}$ for Compound 1 of about 80 ng/mL or about 84 ng/mL; (b) a mean $AUC_{24,ss}$ for Compound 1 of about 582 ng·hours/mL or about 620 ng·hours/mL; (c) a $T_{max,ss}$ for Compound 1 of from about 1.5 to about 6.0 hours or a median $T_{max,ss}$ for Compound 1 of about 3.5 hours or about 4.0 hours; (d) a $C_{min,ss}$ for Compound 1 of about 4.6 ng/mL or about 5.2 ng/mL; (e) a harmonic mean $t_{1/2,ss}$ for Compound 1 of about 10.1 hours or about 10.4 hours or about 14.4 hours; or combinations thereof; or combinations thereof.

In one embodiment, the present disclosure is directed to pharmaceutical compositions comprising about 30 mg of Freebase Hydrate Form C, a pharmaceutically acceptable carrier, and from about 10 w/w % to about 35 w/w % of tartaric acid, wherein the pharmaceutical composition is a once daily extended release formulation, and wherein upon oral administration of the pharmaceutical composition to an adult subject, the composition provides (a) a mean $C_{max}$ for Compound 1 of from about 55 to about 85 ng/mL; (b) a $T_{max}$ for Compound 1 of from about 1.0 hours to about 8.0 hours; (c) a harmonic mean $t_{1/2}$ for Compound 1 of from about 9.0 to about 12.0 hours; (d) a mean $AUC_{inf}$ for Compound 1 of from about 483 to about 660 ng·hours/mL; (e) a mean $C_{max,ss}$ for Compound 1 of from about 65 to about 85 ng/mL; (f) a mean $AUC_{24,ss}$ for Compound 1 of from about 485 to about 658 ng·hours/mL; (g) a $T_{max,ss}$ for Compound 1 of from about 1.5 to about 6.0 hours; (h) a mean $C_{min,ss}$ for Compound 1 of from about 3.5 to about 5.3 ng/mL; (i) a harmonic mean $t_{1/2,ss}$ for Compound 1 of from about 10.0 to about 14.5 hours; or combinations thereof.

In one embodiment, the present disclosure is directed to pharmaceutical compositions comprising about 30 mg of Freebase Hydrate Form C, a pharmaceutically acceptable carrier, and about 10 w/w % or about 20 w/w % or about 30 w/w % of tartaric acid, wherein the pharmaceutical composition is a once daily extended release formulation, and wherein upon oral administration of the pharmaceutical composition to an adult subject, the composition provides (a) a mean $C_{max}$ for Compound 1 of from about 55 to about 85 ng/mL; (b) a $T_{max}$ for Compound 1 of from about 1.0 hours to about 8.0 hours; (c) a harmonic mean $t_{1/2}$ for Compound 1 of from about 9.0 to about 12.0 hours; (d) a mean $AUC_{inf}$ for Compound 1 of from about 483 to about 660 ng·hours/mL; or combinations thereof after a single 30 mg dose.

In One embodiment, the present disclosure is directed to pharmaceutical compositions comprising about 30 mg of Freebase Hydrate Form C, a pharmaceutically acceptable carrier, and about 10 w/w % or about 20 w/w. % or about 30 w/w % of tartaric acid, wherein the pharmaceutical composition is a once daily extended release formulation, and wherein upon oral administration of the pharmaceutical composition to an adult subject QD (once daily), the composition provides (a) a mean $C_{max,ss}$ for Compound 1 of from about 65 to about 85 ng/mL; (b) a mean $AUC_{24,ss}$ for Compound 1 of from about 485 to about 658 ng·hours/mL; (c) a $T_{max,ss}$ for Compound 1 of from about 1.5 to about 6.0 hours; (d) a mean $C_{min,ss}$ for Compound 1 of from about 3.5 to about 5.3 ng/mL; (e) a harmonic mean $t_{1/2,ss}$ for Compound 1 of from about 10.0 to about 14.5 hours; or combinations thereof.

VIII. EXTENDED RELEASE TABLETS

In one embodiment, the Compound 1 (freebase) or a pharmaceutically acceptable salt thereof or the crystalline hydrate used in the methods of the present disclosure is in a once daily extended release formulation. In one embodiment, the Compound 1 (freebase) or a pharmaceutically acceptable salt thereof or the crystalline hydrate is in a once daily extended release formulation, and the formulation delivers about 7.5 mg or about 15 mg or about 30 mg or about 45 mg per unit dosage form (e.g., per tablet or capsule) of Compound 1 (freebase equivalent) orally QD (once daily). In one particular embodiment, the crystalline hydrate is Freebase Hydrate Form C.

In one embodiment, the Compound 1 (freebase) or a pharmaceutically acceptable salt thereof or the crystalline hydrate is in a once daily extended release formulation, and the formulation delivers 7.5 mg of Compound 1 (freebase equivalent) orally QD (once daily). In some such embodiments, the once daily extended release formulation will have a relative bioavailability approximately equivalent to that of an immediate release capsule comprising Compound 1 (freebase) or a pharmaceutically acceptable salt thereof or a solid state form thereof that delivers 3 mg of Compound 1 (freebase equivalent) and that is administered two times per day (BID). In one embodiment, the immediate release capsule comprises a crystalline hydrate of Compound 1. In one embodiment, the immediate release capsule comprises Freebase Hydrate Form C. In one embodiment, the immediate release capsule comprises Tartrate Hydrate.

In one embodiment, the Compound 1 (freebase) or a pharmaceutically acceptable salt thereof or the crystalline hydrate is in a once daily extended release formulation, and the formulation delivers 15 mg of Compound 1 (freebase equivalent) orally QD (once daily). In some such embodiments, the once daily extended release formulation will have a relative bioavailability approximately equivalent to that of an immediate release capsule comprising Compound 1 (freebase) or a pharmaceutically acceptable salt thereof or a solid state form thereof that delivers 6 mg of Compound 1 (freebase equivalent) and that is administered two times per day (BID). In one embodiment, the immediate release capsule comprises a crystalline hydrate of Compound 1. In one embodiment, the immediate release capsule comprises Freebase Hydrate Form C. In one embodiment, the immediate release capsule comprises Tartrate Hydrate.

In one embodiment, the Compound 1 (freebase) or a pharmaceutically acceptable salt thereof or the crystalline hydrate is in a once daily extended release formulation, and the formulation delivers 30 mg of Compound 1 (freebase equivalent) orally QD (once daily). In some such embodiments, the once daily extended release formulation will have a relative bioavailability approximately equivalent to that of an immediate release capsule comprising Compound 1 (freebase) or a pharmaceutically acceptable salt thereof or a solid state form thereof that delivers 12 mg of Compound 1 (freebase equivalent) and that is administered two times per day (BID). In one embodiment, the immediate release capsule comprises a crystalline hydrate of Compound 1. In one embodiment, the immediate release capsule comprises Freebase Hydrate Form C. In one embodiment, the immediate release capsule comprises Tartrate Hydrate.

In one embodiment, the Compound 1 (freebase) or a pharmaceutically acceptable salt thereof or the crystalline hydrate is in a once daily extended release formulation, and the formulation delivers 45 mg of Compound 1 (freebase equivalent) orally QD (once daily). In some such embodiments, the once daily extended release formulation will have a relative bioavailability approximately equivalent to that of an immediate release capsule comprising Compound 1 (freebase) or a pharmaceutically acceptable salt thereof or a solid state form thereof that delivers 18 mg of Compound 1 (freebase equivalent) and that is administered two times per day (BID). In one embodiment, the immediate release capsule comprises a crystalline hydrate of Compound 1. In one embodiment, the immediate release capsule comprises Freebase Hydrate Form C. In one embodiment, the immediate release capsule comprises Tartrate Hydrate.

In one embodiment, the present disclosure is directed to a pharmaceutical composition comprising about 15 mg of Compound 1 freebase or a pharmaceutically acceptable salt thereof or a solid state form of Compound 1, and a pharmaceutically acceptable carrier, wherein pharmaceutical composition is a once daily extended release formulation, and the solid state form of Compound 1 is selected from the group consisting of Amorphous Freebase, Freebase Hydrate Form B, Freebase Hydrate Form C, and Freebase Anhydrate Form D.

In one embodiment, the present disclosure is directed to a pharmaceutical composition comprising about 15 mg of Compound 1 freebase or a pharmaceutically acceptable salt thereof or a solid state form of Compound 1, a pharmaceutically acceptable carrier, and a pH modifier, wherein the pharmaceutical composition is a once daily extended release formulation, and the solid state form of Compound 1 is selected from the group consisting of Amorphous Freebase, Freebase Hydrate Form B, Freebase Hydrate Form C, and Freebase Anhydrate Form D. In one embodiment, the pharmaceutical composition comprises from about 10 wt % to about 30 wt. % of the pH modifier. In one embodiment, the pH modifier is tartaric acid.

In one embodiment, the present disclosure is directed to a pharmaceutical composition comprising about 15 mg of a solid state form of Compound 1, a pharmaceutically acceptable carrier, and from about 10 w/w % to about 35 w/w % of tartaric acid, wherein the pharmaceutical composition is a once daily extended release formulation, and the solid state form of Compound 1 is selected from the group consisting of Amorphous Freebase, Freebase Hydrate Form B, Freebase Hydrate Form C, and Freebase Anhydrate Form D.

In one embodiment, the present disclosure is directed to a pharmaceutical composition comprising about 15 mg of Freebase Hydrate Form B, a pharmaceutically acceptable carrier, and from about 10 w/w % to about 35 w/w % of tartaric acid wherein the pharmaceutical composition is a once daily extended release formulation.

In one embodiment, the present disclosure is directed to a pharmaceutical composition comprising about 15 mg of Amorphous Freebase, a pharmaceutically acceptable carrier, and from about 10 w/w % to about 35 w/w % of tartaric acid wherein the pharmaceutical composition is a once daily extended release formulation.

In one embodiment, the present disclosure is directed to a pharmaceutical composition comprising about 15 mg of Freebase Anhydrate Form D, a pharmaceutically acceptable carrier, and from about 10 w/w % to about 35 w/w % of tartaric acid wherein the pharmaceutical composition is a once daily extended release formulation.

In one embodiment, the present disclosure is directed to a pharmaceutical composition comprising about 15 mg of Freebase Hydrate Form C, a pharmaceutically acceptable carrier, and from about 10 w/w % to about 35 w/w % of tartaric acid wherein the pharmaceutical composition is a once daily extended release formulation.

In one embodiment, the present disclosure is directed to a pharmaceutical composition comprising about 15 mg of Freebase Hydrate Form C, a pharmaceutically acceptable carrier, and about 10 w/w % of tartaric acid, wherein the pharmaceutical composition is a once daily extended release formulation.

In one embodiment, the present disclosure is directed to a pharmaceutical composition comprising about 15 mg of Freebase Hydrate Form C, a pharmaceutically acceptable carrier, and about 20 w/w % of tartaric acid, wherein the pharmaceutical composition is a once daily extended release formulation.

In one embodiment, the present disclosure is directed to a pharmaceutical composition comprising about 15 mg of Freebase Hydrate Form C, a pharmaceutically acceptable carrier, and about 30 w/w % of tartaric acid, wherein the pharmaceutical composition is a once daily extended release formulation.

In one embodiment, the present disclosure is directed to a pharmaceutical composition comprising about 30 mg of Compound 1 freebase or a pharmaceutically acceptable salt thereof or a solid state form of Compound 1, and a pharmaceutically acceptable carrier, wherein pharmaceutical composition is a once daily extended release formulation, and the solid state form of Compound 1 is selected from the group consisting of Amorphous Freebase, Freebase Hydrate Form B, Freebase Hydrate Form C, and Freebase Anhydrate Form D.

In one embodiment, the present disclosure is directed to a pharmaceutical composition comprising about 30 mg of Compound 1 freebase or a pharmaceutically acceptable salt thereof or a solid state form of Compound 1, a pharmaceutically acceptable carrier, and a pH modifier, wherein the pharmaceutical composition is a once daily extended release formulation, and the solid state form of Compound 1 is selected from the group consisting of Amorphous Freebase, Freebase Hydrate Form B, Freebase Hydrate Form C, and Freebase Anhydrate Form D. In one embodiment, the pharmaceutical composition comprises from about 10 wt % to about 30 wt. % of the pH modifier. In one embodiment, the pH modifier is tartaric acid.

In one embodiment, the present disclosure is directed to a pharmaceutical composition comprising about 30 mg of a solid state form of Compound 1, a pharmaceutically acceptable carrier, and from about 10 w/w % to about 35 w/w % of tartaric acid, wherein the pharmaceutical composition is a once daily extended release formulation, and the solid state form of Compound 1 is selected from the group consisting of Amorphous Freebase, Freebase Hydrate Form B, Freebase Hydrate Form C, and Freebase Anhydrate Form D.

In one embodiment, the present disclosure is directed to a pharmaceutical composition comprising about 30 mg of Freebase Hydrate Form B, a pharmaceutically acceptable carrier, and from about 10 w/w % to about 35 w/w % of tartaric acid wherein the pharmaceutical composition is a once daily extended release formulation.

In one embodiment, the present disclosure is directed to a pharmaceutical composition comprising about 30 mg of Amorphous Freebase, a pharmaceutically acceptable carrier, and from about 10 w/w % to about 35 w/w % of tartaric acid wherein the pharmaceutical composition is a once daily extended release formulation.

In one embodiment, the present disclosure is directed to a pharmaceutical composition comprising about 30 mg of Freebase Anhydrate Form D, a pharmaceutically acceptable carrier, and from about 10 w/w % to about 35 w/w % of tartaric acid wherein the pharmaceutical composition is a once daily extended release formulation.

In one embodiment, the present disclosure is directed to a pharmaceutical composition comprising about 30 mg of Freebase Hydrate Form C, a pharmaceutically acceptable carrier, and from about 10 w/w % to about 35 w/w % of tartaric acid wherein the pharmaceutical composition is a once daily extended release formulation.

In one embodiment, the present disclosure is directed to a pharmaceutical composition comprising about 30 mg of Freebase Hydrate Form C, a pharmaceutically acceptable carrier, and about 10 w/w % of tartaric acid wherein the pharmaceutical composition is a once daily extended release formulation.

In one embodiment, the present disclosure is directed to a pharmaceutical composition comprising about 30 mg of Freebase Hydrate Form C, a pharmaceutically acceptable carrier, and about 20 w/w % of tartaric acid wherein the pharmaceutical composition is a once daily extended release formulation.

In one embodiment, the present disclosure is directed to a pharmaceutical composition comprising about 30 mg of Freebase Hydrate Form C, a pharmaceutically acceptable carrier, and about 30 w/w % of tartaric acid wherein the pharmaceutical composition is a once daily extended release formulation.

IX. KITS

The present disclosure also relates to kits comprising one or more solid pharmaceutical dosage units (such as tablets or capsules) comprising a solid state form of the present disclosure. The kit optionally can comprise one or more additional therapeutic agents and/or instructions, for example, instructions for using the kit. In one aspect, the kit comprises one or more solid pharmaceutical dosage units (such as tablets or capsules) comprising a solid state form of the present disclosure and instructions for administering the one or more dosage forms to a subject.

In one embodiment, the kit comprises a first dosage unit and a second dosage unit, wherein the first dosage unit is a solid pharmaceutical dosage unit comprising a solid state form of the present disclosure, and the second dosage unit comprises a second therapeutic agent. In one aspect, the second therapeutic agent is one of the therapeutic agents identified in the previous discussion relating to combination therapies. In another aspect, the second therapeutic agent is an imunosuppressant. In another aspect, the second therapeutic agent is a therapeutic agent for treating systemic lupus erythematosus. In another aspect, the second therapeutic agent is acetaminophen. In another aspect, the second therapeutic agent is methotrexate. In another aspect, the second therapeutic agent is a TNF antagonist, such as a humanized or human anti-TNF antibody (e.g., adalimumab, infliximab, golimumab, certolizumab pegol, tocilizumab, or etanercept).

X. METHODS OF PREPARATION

The present disclosure also relates to methods for preparing a solid state form of Compound 1. In one aspect, the solid state form prepared is the Amorphous Freebase. In another aspect, the solid state form prepared is the Freebase Hydrate Form B. In another aspect, the solid state form prepared is the Freebase Hydrate Form C. In another aspect, the solid state form prepared is the Tartrate Hydrate. In another aspect, the solid state form prepared is the Freebase Anhydrate Form D.

A. Preparation of Amorphous Freebase

The present disclosure relates to methods for preparing the Amorphous Freebase. In one embodiment, the method comprises dehydrating the Freebase Hydrate Form B to provide the Amorphous Freebase. In another embodiment, the method comprises desolvating the Freebase Solvate Form A to provide the Amorphous Freebase. A wide range of process conditions can be employed for the dehydration/desolvation. The dehydration can be conducted, for example, under ambient conditions or in a vacuum oven. FIG. 1A schematically illustrates one method of preparing the Amorphous Freebase by dehydration of the Freebase Hydrate Form B.

In another embodiment, the method comprises dissolving Compound 1 in a solvent or mixture of solvents; and adjusting the pH of the solvent or mixture of solvents to a pH greater than about 8 to initiate precipitation of the Amorphous Freebase. In one aspect, the solvent or mixture of solvents comprises water. In another aspect, the pH is adjusted to a pH greater than about 9. In another aspect, the pH is adjusted to a pH greater than about 10. In another aspect, the pH is adjusted to a pH greater than about 11. In another aspect, the pH is adjusted to a pH of at least about 9.

In still other embodiments, the method comprises preparing the Amorphous Freebase using a method selected from the group consisting of impinging jet, spray drying, and hot-melt extrusion.

B. Preparation of Crystalline Freebase Solvate Form A and Crystalline Freebase Hydrate Form B The present disclosure additionally relates to methods for preparing the Freebase Solvate Form A and Freebase Hydrate Form B. In one embodiment, the method comprises dissolving Compound 1 in a solvent or mixture of solvents comprising an anti-solvent; and maintaining the solvent or mixture of solvents at a temperature less than about 15° C. for an amount of time sufficient to initiate crystallization of the Freebase Solvate Form A or the Freebase Hydrate Form B. The anti-solvent can comprise, for example, water. The solvent or mixture of solvents can comprise a polar solvent such as a solvent is selected from the group consisting of methanol, ethanol, n-butylamine, acetone, acetonitrile, ethyl formate, methyl acetate, ethyl acetate, methyl ethyl ketone, methyl isobutyl ketone, methyl isobutyl ketone, methyl tert-butyl ether, and isopropyl acetate. The Freebase Solvate Form A and Freebase Hydrate Form B exhibit similar PXRD patterns, and are therefore isostructural. The method generally is conducted at sub-ambient temperatures, for example, less than about 10° C., less than about 5° C., or less than about 0° C. In certain aspects, the process further comprises seeding the solvent or mixture of solvents with crystals of the Freebase Solvate Form A or the Freebase Hydrate Form B.

C. Preparation of Crystalline Freebase Hydrate Form C

The present disclosure additionally relates to methods for preparing the Freebase Hydrate Form C. In one embodiment, the method comprises dissolving Compound 1 in a solvent or mixture of solvents; and initiating crystallization to provide the Freebase Hydrate Form C. The solvent or mixture of solvents generally will comprise an anti-solvent (such as water) which can be present in the solvent or mixture of solvents before, or added to the solvent or mixture of solvents after, the Compound 1 is dissolved in the solvent or mixture of solvents. The solvent or mixture of solvents can comprise, for example, one or more polar solvents (such as polar solvent selected from the group consisting of ethanol and ethyl acetate); one or more nonpolar solvents (such as a nonpolar solvent is selected from the group consisting of hexane and heptane); or at least one polar solvent and at least one nonpolar solvent. In one aspect, the solvent or mixture of solvents is a ternary solvent mixture comprising ethyl acetate, heptane, and water. The method generally is conducted at temperatures less than about 30° C., less than about 20° C., or less than about 10° C. In certain aspects, the initiating crystallization step comprises mixing the solvent or mixture of solvents to provide sufficient agitation to initiate crystallization. In certain aspects, the initiating crystallization step comprises seeding the solvent or mixture of solvents with crystals of the Freebase Hydrate Form C. In certain aspects, the initiating crystallization step comprises both mixing the solvent or mixture of solvents and seeding the solvent or mixture of solvents with crystals of the Freebase Hydrate Form C.

In one embodiment, Compound 1 is first prepared according to any of the methods set forth herein, a reaction mixture comprising Compound 1 is filtered, and the resulting solution is suspended in a solvent or mixture of solvents. The solvent or mixture of solvents can comprise, for example, one or more polar solvents (such as polar solvent selected from the group consisting of ethanol and ethyl acetate); one or more nonpolar solvents (such as a nonpolar solvent is selected from the group consisting of hexane and heptane); Or at least one polar solvent and at least one nonpolar solvent. In one particular embodiment, the solvent is ethyl acetate, or a mixture of ethyl acetate and water. In certain aspects, the initiating crystallization step comprises seeding the solvent or mixture of solvents with crystals of the Freebase Hydrate Form C. In one particular aspect, the crystallization occurs in a wet mill.

Figure 1B:
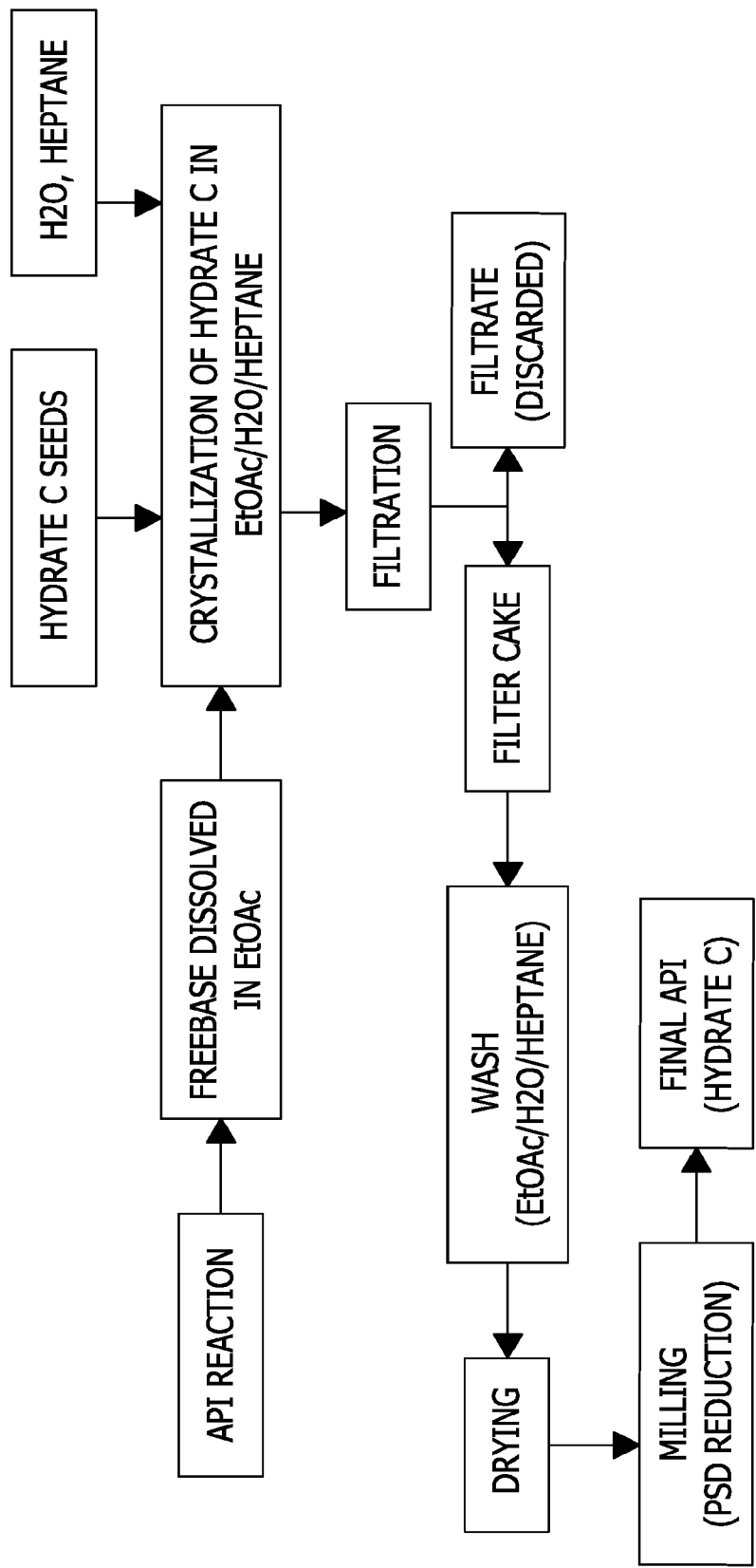
FIG. 1B schematically illustrates one method of preparing the Freebase Hydrate Form C.

FIG. 1B schematically illustrates one method of preparing the Freebase Hydrate Form C.

D. Preparation of Crystalline Freebase Anhydrate Form D

The present disclosure additionally relates to methods for preparing the Freebase Anhydrate Form D. In one embodiment, the method comprises dissolving Compound 1 in a solvent or mixture of solvents; and initiating crystallization to provide the Freebase Anhydrate Form D. The solvent or mixture of solvents will be water-free, or close to water-free. In embodiments, the solvent or mixture of solvents will have a water content of less than about 0.15 wt %, or less than about 0.10 wt. %, or less than about 0.05 wt. %, or about 0 wt. % at 23° C. In one embodiment, the solvent or mixture of solvents will have a water activity of about 2.4% or less, or about 2.2% or less, or about 2.0% or less, or about 1.5% or less. The solvent or mixture of solvents can comprise, for example, ethyl acetate (EtOAc), heptane, and combinations thereof. In one embodiment, the solvent system comprises a mixture of heptane in ethyl acetate. In some embodiments, the solvent system comprises about 10 wt. %, or about 20 wt. %, or about 30 wt. %, or about 40 wt. % heptane in ethyl acetate. The method generally is conducted at temperatures of at least about 7° C., at least about 23° C., at least about 25° C. or less, or at least about 30° C. In one embodiment, the method is conducted at about 23° C. In certain aspects, the initiating crystallization step comprises mixing the solvent or mixture of solvents to provide sufficient agitation to initiate crystallization. In certain aspects, the initiating crystallization step comprises seeding the solvent or mixture of solvents with crystals of the Freebase Anhydrate Form D. In certain aspects, the initiating crystallization step comprises both mixing the solvent or mixture of solvents and seeding the solvent or mixture of solvents with crystals of the Freebase Anhydrate Form D.

E. Preparation of Crystalline Tartrate Hydrate

The present disclosure additionally relates to methods for preparing the Tartrate Hydrate. In one embodiment, the method comprises dissolving Compound 1 and L-tartaric acid in a solvent or mixture of solvents to form a crystallization solution; and crystallizing the Tartrate Hydrate from the crystallization solution. The solvent or mixture of solvents can comprise, for example, water and/or, for example, one or more polar solvents (such as isopropyl acetate). The solvent or mixture of solvents also can comprise an antisolvent (such as isopropyl acetate). In certain aspects, the process further comprises seeding the solvent or mixture of solvents with crystals of the Tartrate Hydrate.

The crystallization generally is conducted at a temperature less than about 40° C. When an anti-solvent is used, a moderate rate of addition is employed for the anti-solvent as a faster rate of addition typically results in the precipitation of an amorphous tartrate and a slower rate of addition allows the resulting slurry to thicken. Proper control of filtration, washing, and drying may be needed to avoid potential issues associated with consolidation of the filter cake, including solvent entrapment, solid properties (e.g., hard, chunky solids) and handing, and damage to equipment. Depending upon the properties of the dried Tartrate Hydrate material, milling may require a mechanical impact-type of mills rather than a shear-based mill (such as a co-mill).

Figure 1C:
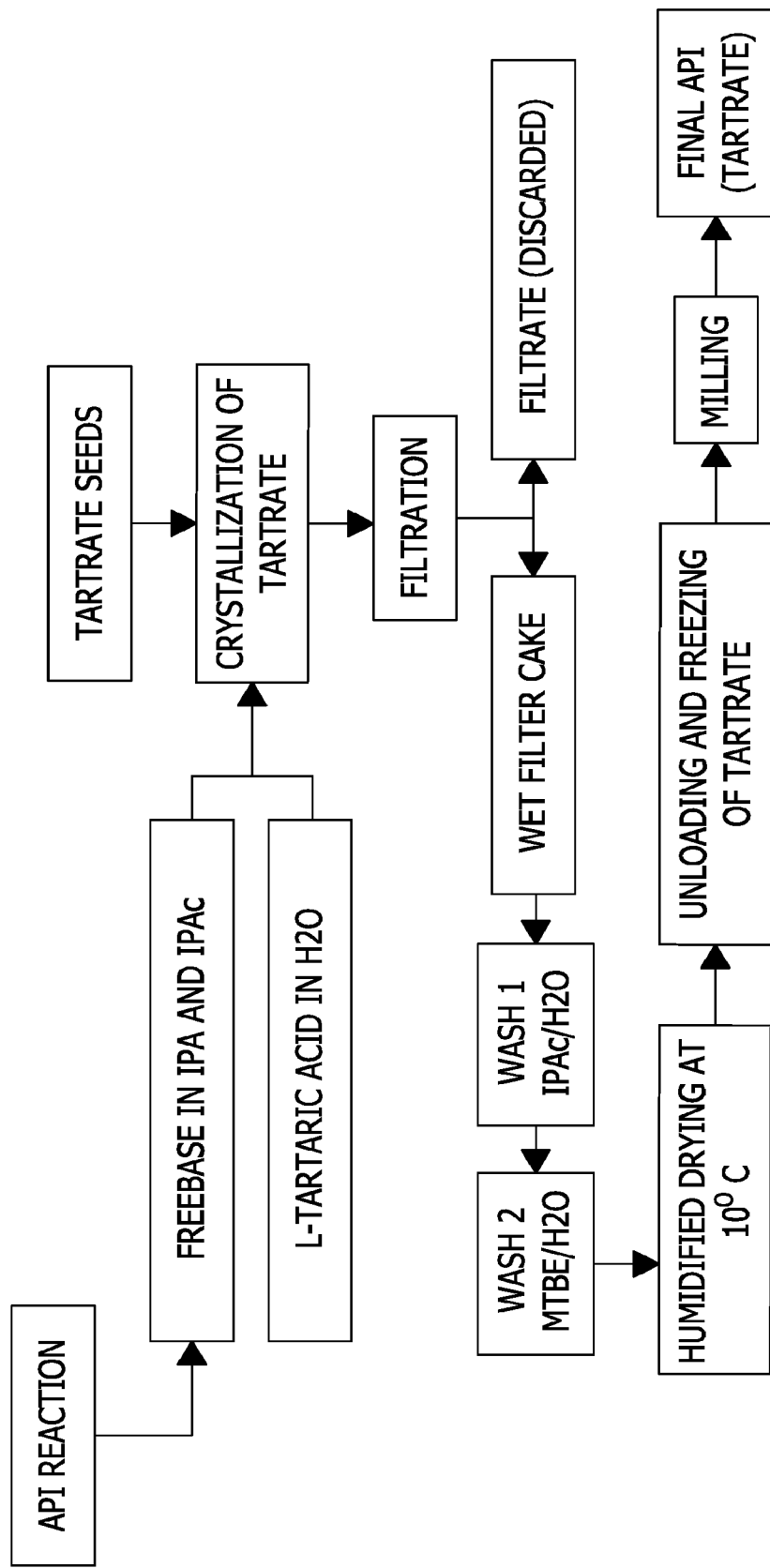
FIG. 1C schematically illustrates one method of preparing the Tartrate Hydrate.

FIG. 1C schematically illustrates one method of preparing the Tartrate Hydrate.

XI. PRODUCT-BY-PROCESS

The present disclosure also relates to a solid state form of Compound 1 prepared in accordance with any of the methods described in the disclosure.

In one embodiment, the solid state form prepared is the Amorphous Freebase.

In one embodiment, the solid state form prepared is the Freebase Hydrate Form B.

In one embodiment, the solid state form prepared is the Freebase Hydrate Form C.

In one embodiment, the solid state form prepared is the Tartrate Hydrate.

In one embodiment, the solid state form prepared is Freebase Anhydrate Form D.

XII. ADDITIONAL EMBODIMENTS

In some aspects, the disclosure is directed to the following additional embodiments:

Embodiment A: A crystalline hydrate of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide.

Embodiment A1: The crystalline hydrate of Embodiment A, wherein the hydrate is a hemihydrate.

Embodiment A2: The crystalline hydrate of Embodiment A or Embodiment A1 having an X-ray powder diffraction pattern characterized by peaks at 13.4±0.2, 15.1±0.2, and 21.7±0.2 degrees two theta when measured at about 25° C. with monochromatic Kα1 radiation.

Embodiment A3: The crystalline hydrate of Embodiment A2, wherein the X-ray powder diffraction pattern is further characterized by a peak at 15.5±0.2 degrees two theta when measured at about 25° C. with monochromatic Kα1 radiation.

Embodiment A4: The crystalline hydrate of Embodiment A3, wherein the X-ray powder diffraction pattern is further characterized by a peak at 17.0±0.2 degrees two theta when measured at about 25° C. with monochromatic Kα1 radiation.

Embodiment A5: The crystalline hydrate of Embodiment A4, wherein the X-ray powder diffraction pattern is further characterized by a peak at 20.9±0.2 degrees two theta when measured at about 25° C. with monochromatic Kα1 radiation.

Embodiment A6: The crystalline hydrate of any one of Embodiments A to A5, wherein the crystalline hydrate has an X-ray powder diffraction pattern substantially as shown in FIG. 3C.

Embodiment A7: The crystalline hydrate of any one of Embodiments A to A6, wherein the crystalline hydrate has a thermogravimetric analysis profile substantially as shown in FIG. 4E.

Embodiment A8: The crystalline hydrate of any one of Embodiments A to A7, wherein the crystalline hydrate has a differential scanning calorimetry profile substantially as shown in FIG. 5C.

Embodiment A9: The crystalline hydrate of any one of Embodiments A to A8, wherein the crystalline hydrate has a moisture sorption isotherm profile substantially as shown in FIG. 6B.

Embodiment A10: The crystalline hydrate of any one of Embodiments A to A9, wherein the crystalline hydrate has a thermogravimetric analysis profile showing a weight loss of about 2.3% to about 2.6% between about 120° C. and 160° C. when heated at a rate of 10° C./minute; and a differential scanning calorimetry profile comprising an endotherm between about 120° C. and about 170° C. when heated at a rate of 10° C./minute.

Embodiment A11: The crystalline hydrate of any one of Embodiments A to A10, wherein the crystalline hydrate has an orthorhombic lattice type.

Embodiment A12: The crystalline hydrate of Embodiment A11, wherein the crystalline hydrate has a $P2_12_12_1$ space group.

Embodiment A13: The crystalline hydrate of Embodiment A11 or A12, wherein the crystalline hydrate has unit cell a, b and c values of about 12.7 Å, about 13.1 Å, and about 22.6 Å, respectively Embodiment A14: The crystalline hydrate of Embodiment A having an X-ray powder diffraction pattern characterized by peaks at 3.1±0.2, 9.3±0.2, and 12.0±0.2 degrees two theta when measured at about 25° C. with monochromatic Kα1 radiation.

Embodiment A15: The crystalline hydrate of Embodiment A14, wherein the X-ray powder diffraction pattern is further characterized by a peak at 20.8±0.2 degrees two theta when measured at about 25° C. with monochromatic Kα1 radiation.

Embodiment A16: The crystalline hydrate of Embodiment A15, wherein the X-ray powder diffraction pattern is further characterized by a peak at 25.0±0.2 degrees two theta when measured at about 25° C. with monochromatic Kα1 radiation.

Embodiment A17: The crystalline hydrate of any one of Embodiments A or A14 to A16, wherein the crystalline hydrate has an X-ray powder diffraction pattern substantially as shown in FIG. 3B.

Embodiment A18: The crystalline hydrate of any one of Embodiments A or A14 to A17, wherein the crystalline hydrate has a thermogravimetric analysis profile substantially as shown in FIG. 4D.

Embodiment A19: The crystalline hydrate of any one of Embodiments A or A14 to A18, wherein the crystalline hydrate has a differential scanning calorimetry profile substantially as shown in FIG. 5B.

Embodiment A20: A pharmaceutical composition comprising a crystalline hydrate of any one of Embodiments A to A19, and a pharmaceutically acceptable carrier.

Embodiment A21: The pharmaceutical composition of Embodiment A20, wherein greater than about 90% by weight of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide in the composition is a crystalline hydrate of (3S,4R)-3-ethyl-4-(3H-imidazo[1,2-a]pyrrolo[2,3-e]pyrazin-8-yl)-N-(2,2,2-trifluoroethyl)-pyrrolidine-1-carboxamide having an X-ray powder diffraction pattern characterized by peaks at 13.4±0.2, 15.1±0.2, and 21.7±0.2 degrees two theta when measured at about 25° C. with monochromatic Kα1 radiation.

Embodiment A22: The pharmaceutical composition of Embodiment A20, wherein greater than about 90% by weight of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide in the composition is a crystalline hydrate of (3S,4R)-3-ethyl-4-(3H-imidazo[1,2-a]pyrrolo[2,3-e]pyrazin-8-yl)-N-(2,2,2-trifluoroethyl)-pyrrolidine-1-carboxamide having an X-ray powder diffraction pattern comprising peaks at 3.1±0.2, 9.3±0.2, and 12.0±0.2 degrees two theta when measured at about 25° C. with monochromatic Kα1 radiation.

Embodiment B: Amorphous freebase (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide.

Embodiment B1: The amorphous freebase (3S,4R)-3-ethyl-4-(3H-imidazo[1,2-a]pyrrolo[2,3-e]pyrazin-8-ye-N-(2,2,2-trifluoroethyl)pyrrolidine-1-carboxamide of Embodiment B comprising less than about 12% by weight water.

Embodiment B2: The amorphous freebase (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide of Embodiment B or B1 having a glass transition temperature onset at about 119° C.

Embodiment B3: The amorphous freebase (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide of any of Embodiments B to B2 having a glass transition temperature midpoint at about 122° C.

Embodiment B4: A pharmaceutical composition comprising the amorphous freebase (3S,4R)-3-ethyl-4-(3H-imidazo[1,2-a]pyrrolo[2,3-e]pyrazin-8-ye-N-(2,2,2-trifluoroethyl)pyrrolidine-1-carboxamide of any one of Embodiments B to B3, and a pharmaceutically acceptable carrier.

Embodiment B5: The pharmaceutical composition of Embodiment B4, wherein greater than about 90% by weight of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide in the composition is amorphous freebase (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide.

Embodiment C: A crystalline anhydrate of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide.

Embodiment C1: The crystalline anhydrate of Embodiment C having an X-ray powder diffraction pattern characterized by peaks at 8.0±0.2, 9.7±0.2, 14.2±0.2, 14.5±0.2, and 20.3±0.2 degrees two theta when measured at about 25° C. with monochromatic Kα1 radiation.

Embodiment C2: The crystalline anhydrate of Embodiment C1, wherein the X-ray powder diffraction pattern is further characterized by a peak at 4.0±0.2 degrees two theta when measured at about 25° C. with monochromatic Kα1 radiation.

Embodiment C3: The crystalline anhydrate of Embodiment C2, wherein the X-ray powder diffraction pattern is further characterized by a peak at 19.0±0.2 degrees two theta when measured at about 25° C. with monochromatic Kα1 radiation.

Embodiment C4: The crystalline anhydrate of Embodiment C3, wherein the X-ray powder diffraction pattern is further characterized by peaks at 18.4±0.2, 23.0±0.2, and 24.7±0.2 degrees two theta when measured at about 25° C. with monochromatic Kα1 radiation.

Embodiment C5: The crystalline anhydrate of any one of Embodiments C to C4, wherein the crystalline anhydrate has an X-ray powder diffraction pattern substantially as shown in FIG. 3J.

Embodiment C6: The crystalline anhydrate of any one of Embodiments C to C5, wherein the crystalline anhydrate has a thermogravimetric analysis profile substantially as shown in FIG. 4I.

Embodiment C7: The crystalline anhydrate of any one of Embodiments C to C6, wherein the crystalline anhydrate has a differential scanning calorimetry profile substantially as shown in FIG. 5E.

Embodiment C8: The crystalline anhydrate of any one of Embodiments C to C7, wherein the crystalline anhydrate has a moisture sorption isotherm profile substantially as shown in FIG. 6D.

Embodiment C9: The crystalline anhydrate of any one of Embodiments C to C8, wherein the crystalline anhydrate has an orthorhombic lattice type.

Embodiment C10: The crystalline anhydrate of any one of Embodiments C to C9, wherein the crystalline anhydrate has a P2$_1$2$_1$2 space group.

Embodiment C11: The crystalline anhydrate of any one of Embodiments C to C10, wherein the crystalline anhydrate has unit cell a, b and c values of about 43.8 Å, about 8.6 Å, and about 9.2 Å, respectively.

Embodiment C12: The crystalline anhydrate of any one of Embodiments C to C11, wherein the crystalline anhydrate has a thermogravimetric analysis profile showing a weight loss of about 0.5% to about 0.8% between about 43° C. and 188° C. when heated at a rate of 10° C./minute; and a differential scanning calorimetry profile comprising an endotherm between about 180° C. and about 220° C. when heated at a rate of 10° C./minute.

Embodiment C13: The crystalline anhydrate of any one of Embodiments C to C12, wherein the crystalline anhydrate has an onset melting point of about 199.6° C.

Embodiment C14: A pharmaceutical composition comprising a crystalline anhydrate of any one of claims C to C13, and a pharmaceutically acceptable carrier.

Embodiment C15: The pharmaceutical composition of Embodiment C14, wherein greater than about 90% by weight of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide in the composition is a crystalline anhydrate of (3S,4R)-3-ethyl-4-(3H-imidazo[1,2-a]pyrrolo[2,3-e]pyrazin-8-yl)-N-(2,2,2-trifluoroethyl)-pyrrolidine-1-carboxamide having an X-ray powder diffraction pattern characterized by peaks at 8.0±0.2, 9.7±0.2, 14.2±0.2, 14.5±0.2, and 20.3±0.2 degrees two theta when measured at about 25° C. with monochromatic Kα1 radiation.

Embodiment D: A pharmaceutical composition comprising (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide tartrate, from about 10 w/w % to about 35 w/w % of an organic acid selected from the group consisting of tartaric acid, fumaric acid, citric acid, succinic acid, malic acid, and combinations thereof, and a pharmaceutically acceptable carrier.

Embodiment D1: The pharmaceutical composition of Embodiment D, wherein the tartrate is crystalline (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide tartrate tetrahydrate.

Embodiment D2: The pharmaceutical composition of Embodiment D or Embodiment D1, wherein the tartrate has an X-ray powder diffraction pattern characterized by peaks at 3.9±0.2, 6.8±0.2, and 14.1±0.2 degrees two theta when measured at about 25° C. with monochromatic Kα1 radiation.

Embodiment D3: The pharmaceutical composition of any one of Embodiments D to D2, wherein the tartrate has an X-ray powder diffraction pattern substantially as shown in FIG. 3D.

Embodiment D4: The pharmaceutical composition of any one of Embodiments D to D3, wherein the tartrate has a thermogravimetric analysis profile substantially as shown in FIG. 4F.

Embodiment D5: The pharmaceutical composition of any one of Embodiments D to D4, wherein the tartrate has a differential scanning calorimetry profile substantially as shown in FIG. 5D.

Embodiment D6: The pharmaceutical composition of any one of Embodiments D to D5, wherein the tartrate has a moisture sorption isotherm profile substantially as shown in FIG. 6C.

Embodiment D7: The pharmaceutical composition of any one of Embodiments D to D6, wherein greater than about 90% by weight of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide in the composition is crystalline (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide tartrate tetrahydrate.

Embodiment E: The pharmaceutical composition of any one of Embodiments A20 to A22, B4, B5, C14, C15, or D to D7, wherein the composition comprises a release control polymer.

Embodiment E1: The pharmaceutical composition of Embodiment E, wherein the release control polymer is a hydrophilic polymer.

Embodiment E2: The pharmaceutical composition of Embodiment E or E1, wherein the release control polymer is a cellulose derivative with a viscosity between 1000 and 150,000 mPa·s.

Embodiment E3: The pharmaceutical composition of any one of Embodiments E to E2, wherein the release control polymer is selected from the group consisting of hydroxypropylmethyl cellulose, hydroxyethyl cellulose, and copolymers of acrylic acid crosslinked with a polyalkenyl polyether, and combinations thereof.

Embodiment E4: The pharmaceutical composition of any one of Embodiments E to E3, wherein the release control polymer is selected from the group consisting of hydroxypropylmethyl cellulose, hydroxyethyl cellulose, and combinations thereof.

Embodiment E5: The pharmaceutical composition of any one of Embodiments E to E4, wherein the release control polymer is hydroxypropylmethyl cellulose.

Embodiment E6: The pharmaceutical composition of Embodiment E5, wherein the hydroxypropylmethyl cellulose is grade E, F, or K.

Embodiment E6: The pharmaceutical composition of Embodiment E5, wherein the hydroxypropylmethyl cellulose is Hypromellose 2208.

Embodiment E7: The pharmaceutical composition of any one of Embodiments E to E6, wherein the composition comprises a filler.

Embodiment E8: The pharmaceutical composition of Embodiment E7, wherein the filler is selected from the group consisting of microcrystalline cellulose, mannitol, and combinations thereof.

Embodiment E9: The pharmaceutical composition of any one of Embodiments E to E8, wherein the composition comprises a lubricant.

Embodiment E10: The pharmaceutical composition of any one of Embodiments E to E9, wherein the composition comprises a glidant.

Embodiment E11: The pharmaceutical composition of any one of Embodiments E to E10, wherein the composition comprises a pH modifier.

Embodiment E12: The pharmaceutical composition of Embodiment E11, wherein the pH modifier is selected from the group consisting of tartaric acid, fumaric acid, citric acid, succinic acid, malic acid, and combinations thereof.

Embodiment E13: The pharmaceutical composition of Embodiments E11 or E12, wherein the pH modifier is selected from the group consisting of tartaric acid, fumaric acid, citric acid, succinic acid, and combinations thereof.

Embodiment E14: The pharmaceutical composition of any one of Embodiments E11 to E13, wherein the pH modifier is selected from the group consisting of tartaric acid, fumaric acid, and combinations thereof.

Embodiment E15: The pharmaceutical composition of any one of Embodiments E11 to E14, wherein the pH modifier is tartaric acid.

Embodiment E16: The pharmaceutical composition of any one of Embodiments E11 to E14, wherein the pH modifier is fumaric acid or citric acid.

Embodiment E17: The pharmaceutical composition of any one of Embodiments E1 to E16, wherein the pH modifier is present in an amount from about 10 to about 35 w/w %.

Embodiment E18: The pharmaceutical composition of any one of Embodiments E11 to E17, wherein the pH modifier is present in an amount from about 20 to about 35 w/w %.

Embodiment E19: The pharmaceutical composition of any one of Embodiments E11 to E18, wherein the pH modifier is present in an amount from about 20 to about 30 w/w %.

Embodiment E20: The pharmaceutical composition of any one of Embodiments E11 to E19, wherein the pH modifier is present in an amount from about 20 to about 25 w/w %.

Embodiment E21: The pharmaceutical composition of any one of Embodiments E11 to E20, wherein the pH modifier is present in an amount of about 10 w/w %.

Embodiment E22: The pharmaceutical composition of any one of Embodiments E11 to E20, wherein the pH modifier is present in an amount of about 20 w/w %.

Embodiment E23: The pharmaceutical composition of any one of Embodiments E11 to E20, wherein the pH modifier is present in an amount of about 30 w/w %.

Embodiment F: A method of treating a JAK-1 associated condition, the method comprising administering a therapeutically effective amount of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide of any one of Embodiments A to A19, B to B3, or C to C13 to a subject suffering from or susceptible to the condition.

Embodiment F1: The method of embodiment F wherein the therapeutically effective amount of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide is selected from the group consisting of 7.5 mg once daily, 15 mg once daily, 30 mg once daily, and 45 mg once daily.

Embodiment F2: A method of treating a JAK-1 associated condition, the method comprising administering the pharmaceutical composition of any one of Embodiments A20 to A22, B4, B5, C14, C15, D to D7, or E to E23 to a subject suffering from or susceptible to the condition.

Embodiment F2a: The method of any one of Embodiments F to F2, wherein the condition is selected from the group consisting of immunomodulation, inflammation, and proliferative disorders.

Embodiment F2b: The method of any one of Embodiments F to F2a, wherein the (3S,4R)-3-ethyl-4-(3H-imidazo[1,2-a]pyrrolo[2,3-e]pyrazin-8-yl)-N-(2,2,2-trifluoroethyl) pyrrolidine-1-carboxamide is the Freebase Hydrate Form C.

Embodiment F3: A (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide of any one of Embodiments A to A19, B to B3, or C to C13 for use in treating a JAK-1 associated condition. In certain aspects of Embodiment E3, the use comprising administering a therapeutically effective amount of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide of any one of Embodiments A to A19, B to B3, or C to C13 to a subject suffering from or susceptible to the condition. In one embodiment, the condition is selected from the group consisting of immunomodulation, inflammation, and proliferative disorders. In certain aspects, in Embodiment F3, the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide may be the Freebase Hydrate Form C. In some aspects, in Embodiment F3, the therapeutically effective amount of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide is selected from the group consisting of 7.5 mg once daily, 15 mg once daily, 30 mg once daily, and 45 mg once daily.

Embodiment F4: A pharmaceutical composition of any one of Embodiments A20 to A22, B4, B5, CM, C15, D to D7, or E to E23 for use in treating a JAK-1 associated condition. In certain aspects of Embodiment F4, the use comprises administering the pharmaceutical composition to a subject suffering from or susceptible to the condition. In one embodiment, the condition is selected from the group consisting of immunomodulation, inflammation, and proliferative disorders. In certain aspects, in Embodiment F4, the composition comprises the Freebase Hydrate Form C.

Embodiment G: A method of treating a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis, and systemic lupus erythematosus, the method comprising administering a therapeutically effective amount of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide of any one of Embodiments A to A19, B to B3, or C to C13 to a subject suffering from or susceptible to the condition.

Embodiment G1: The method of embodiment G, wherein the therapeutically effective amount of the (3S,4R)-3-ethyl-4-(3H-imidazo[1,2-a]pyrrolo[2,3-e]pyrazin-8-yl)-N-(2,2;2-trifluoroethyl)pyrrolidine-1-carboxamide is selected from the group consisting of 7.5 mg once daily, 15 mg once daily, 30 mg once daily, and 45 mg once daily.

Embodiment G2: A method of treating a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis, and systemic lupus erythematosus, the method comprising administering the pharmaceutical composition of any one of Embodiments A20 to A22, B4, B5, C14, C15, D to D7, or E to E23 to a subject suffering from or susceptible to the condition.

Embodiment G3: The method of any one of Embodiments G to G2, wherein the condition is rheumatoid arthritis.

Embodiment G3a: The method of any one of Embodiments G to G3, wherein the (3S,4R)-3-ethyl-4-(3H-imidazo[1,2-a]pyrrolo[2,3-e]pyrazin-8-yl)-N-(2,2,2-trifluoroethyl) pyrrolidine-1-carboxamide is the Freebase Hydrate Form C.

Embodiment G4: A (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide of any one of Embodiments A to A19, B to B3, or C to C13 for use in treating a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis, and systemic lupus erythematosus. In certain aspects of Embodiment G4, the use comprises administering a therapeutically effective amount of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide of any one of Embodiments A to A19, B to B3, or C to C13 to a subject suffering from or susceptible to the condition. In one embodiment, the condition is rheumatoid arthritis. In some instances, in Embodiment G4, the therapeutically effective amount of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide may be selected from the group consisting of 7.5 mg once daily, 15 mg once daily, 30 mg once daily, and 45 mg once daily. In certain aspects, in Embodiment G4, the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide may be the Freebase Hydrate Form C.

Embodiment G5: A pharmaceutical composition of any one of Embodiments A20 to A22, B4, B5, C14, C15, D to D7, or E to E23 for use in treating a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis, and systemic lupus erythematosus. In certain aspects of Embodiment G5, the use comprises administering the pharmaceutical composition to a subject suffering from or susceptible to the condition. In one embodiment, the condition is rheumatoid arthritis. In certain aspects, in Embodiment G5, the composition comprises Freebase Hydrate Form C.

Embodiment H: A method of treating moderate to severe active rheumatoid arthritis, the method comprising administering a therapeutically effective amount of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide of any one of Embodiments A to A19, B to B3, or C to C13 to a subject suffering from or susceptible to the condition.

Embodiment H1: The method of Embodiment H wherein the therapeutically effective amount of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide is about 7.5 mg once daily.

Embodiment H2: The method of Embodiment H wherein the therapeutically effective amount of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide is about 15 mg once daily.

Embodiment H3: The method of Embodiment H wherein the therapeutically effective amount of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide is about 30 mg once daily.

Embodiment H4: The method of Embodiment H wherein the therapeutically effective amount of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide is about 45 mg once daily.

Embodiment H5: A method of treating moderate to severe active rheumatoid arthritis, the method comprising administering the pharmaceutical composition of any one of Embodiments A20 to A22, B4, B5, C14, C15, D to D7, or E to E23 to a subject suffering from or susceptible to the condition.

Embodiment H6: The method of any one of Embodiments H to H5, wherein the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide is the Freebase Hydrate Form C.

Embodiment H7: The method of any one of Embodiments H to H6, wherein the subject has had an inadequate response to methotrexate.

Embodiment H8: The method of any one of Embodiments H to H7, wherein the subject has had an inadequate response to biologics medicines approved for rheumatoid arthritis.

Embodiment H9: The method of any one of Embodiments H to H8, wherein the subject has not previously been administered biologics medicines approved for rheumatoid arthritis.

Embodiment H10: A (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide of any one of Embodiments A to A19, B to B3, or C to C13 for use in treating moderate to severe active rheumatoid arthritis. In certain aspects of Embodiment H10, the use comprises administering a therapeutically effective amount of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide of any one of Embodiments A to A19, B to B3, or C to C13 to a subject suffering from or susceptible to the condition. In one aspect, in Embodiment H10, the therapeutically effective amount of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide is about 7.5 mg or about 15 mg or about 30 mg or about 45 mg once daily.

Embodiment H11: A pharmaceutical composition of any one of Embodiments A20 to A22, B4, B5, C14, C15, D to D7, or E to E23 for use in treating moderate to severe active rheumatoid arthritis. In certain aspects of Embodiment H11, the use comprises administering the pharmaceutical composition to a subject suffering from or susceptible to the condition.

Embodiment I: A method of treating a subject having rheumatoid arthritis, the method comprising administering to the subject about 7.5 mg, per unit dosage form of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide orally once daily.

Embodiment I1: A method of treating a subject having rheumatoid arthritis, the method comprising administering to the subject about 7.5 mg, per unit dosage form of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide of any one of Embodiments A to A19, B to B3, or C to C13 orally once daily.

Embodiment I1a: A (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide of any one of Embodiments A to A19, B to B3, or C to C13 for use in treating a subject having rheumatoid arthritis. In certain aspects of Embodiment E1a, the use comprises administering to the subject about 7.5 mg, per unit dosage form of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide of any one of Embodiments A to A19, B to B3, or C to C13 orally once daily.

Embodiment I2: A method of treating a subject having rheumatoid arthritis, the method comprising administering to the subject orally once daily the pharmaceutical composition of any one of Embodiments A20 to A22, B4, B5, C14, C15, D to D7, or E to E23, wherein the composition comprises about 7.5 mg, per unit dosage form of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide.

Embodiment I3: A pharmaceutical composition of any one of Embodiments A20 to A22, B4, B5, C14, C15, D to D7, or E to E23 for use in treating a subject having rheumatoid arthritis. In certain aspects of Embodiment 13, the use comprises administering to the subject orally once daily the pharmaceutical composition, wherein the composition comprises about 7.5 mg, per unit dosage form of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide.

Embodiment I4: A method of treating a subject having rheumatoid arthritis, the method comprising administering to the subject about 15 mg, per unit dosage form of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide orally once daily.

Embodiment I5: A method of treating a subject having rheumatoid arthritis, the method comprising administering to the subject about 15 mg, per unit dosage form of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide of any one of Embodiments A to A19, B to B3, or C to C13 orally once daily.

Embodiment I6: A (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide of any one of Embodiments A to A19, B to B3, or C to C13 for use in treating a subject having rheumatoid arthritis. In certain aspects of Embodiment 16, the use comprises administering to the subject about 15 mg, per unit dosage form of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide of any one of Embodiments A to A19, B to B3, or C to C13 orally once daily.

Embodiment I7: A method of treating a subject having rheumatoid arthritis, the method comprising administering to the subject orally once daily the pharmaceutical composition of any one of Embodiments A20 to A22, B4, B5, C14, C15, D to D7, or E to E23, wherein the composition comprises about 15 mg, per unit dosage form of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide.

Embodiment I8: A pharmaceutical composition of any one of Embodiments A20 to A22, B4, B5, C14, C15, D to D7, or E to E23 for use in treating a subject having rheumatoid arthritis. In certain aspects of Embodiment 18, the use comprises administering to the subject orally once daily the pharmaceutical composition, wherein the composition comprises about 15 mg, per unit dosage form of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide.

Embodiment I9: A method of treating a subject having rheumatoid arthritis, the method comprising administering to the subject about 30 mg, per unit dosage form of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide orally once daily.

Embodiment I10: A method of treating a subject having rheumatoid arthritis, the method comprising administering to the subject about 30 mg, per unit dosage form of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide of any one of Embodiments A to A19, B to B3, or C to C13 orally once daily.

Embodiment I11: A (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide of any one of Embodiments A to A19, B to B3, or C to C13 for use in treating a subject having rheumatoid arthritis. In certain aspects of Embodiment I11, the use comprises administering to the subject about 30 mg, per unit dosage form of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide of any one of Embodiments A to A19, B to B3, or C to C13 orally once daily.

Embodiment I12: A method of treating a subject having rheumatoid arthritis, the method comprising administering to the subject orally once daily the pharmaceutical composition of any one of Embodiments A20 to A22, B4, B5, C14, C15, D to D7, or E to E23, wherein the composition comprises about 30 mg, per unit dosage form of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide.

Embodiment I13: A pharmaceutical composition of any one of Embodiments A20 to A22, B4, B5, C14, C15, D to D7, or E to E23 for use in treating a subject having rheumatoid arthritis. In certain aspects of Embodiment I13, the use comprises administering to the subject orally once daily the pharmaceutical composition, wherein the composition comprises about 30 mg, per unit dosage form of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide.

Embodiment I14: A method of treating a subject having rheumatoid arthritis, the method comprising administering to the subject about 45 mg, per unit dosage form of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide orally once daily.

Embodiment I15: A method of treating a subject having rheumatoid arthritis, the method comprising administering to the subject about 45 mg, per unit dosage form of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide of any one of Embodiments A to A19, B to B3, or C to C13 orally once daily.

Embodiment I16: A (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide of any one of Embodiments A to A19, B to B3, or C to C13 for use in treating a subject having rheumatoid arthritis. In certain aspects of Embodiment I16, the use comprises administering to the subject about 45 mg, per unit dosage form of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide of any one of Embodiments A to A19, B to B3, or C to C13 orally once daily.

Embodiment I17: A method of treating a subject having rheumatoid arthritis, the method comprising administering to the subject orally once daily the pharmaceutical composition of any one of Embodiments A20 to A22, B4, B5, C14, C15, D to D7, or E to E23, wherein the composition comprises about 45 mg, per unit dosage form of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide.

Embodiment I18: A pharmaceutical composition of any one of Embodiments A20 to A22, B4, B5, C14, C15, D to D7, or E to E23 for use in treating a subject having rheumatoid arthritis. In certain aspects of Embodiment 118, the use comprises administering to the subject orally once daily the pharmaceutical composition, wherein the composition comprises about 45 mg, per unit dosage form of the (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide.

Embodiment J: A method for the preparation of the crystalline hydrate of Embodiment A1 or A2, the method comprising:
dissolving (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide in a solvent or mixture of solvents; and
initiating crystallization to provide the crystalline hydrate.

Embodiment J1: The method of Embodiment J, wherein the solvent or mixture of solvents comprises an anti-solvent.

Embodiment J2: The method of Embodiment J or J1, wherein the solvent or mixture of solvents comprises a polar solvent.

Embodiment J3: The method of Embodiment J or J1, wherein the solvent or mixture of solvents comprises a nonpolar solvent.

Embodiment J4: The method of any one of Embodiments J to J3, wherein the initiating crystallization step comprises mixing the solvent or mixture of solvents.

Embodiment J5: The method of any one of Embodiments J to J4, wherein the initiating crystallization step comprises seeding the solvent or mixture of solvents with crystals of the crystalline hydrate of Embodiment A1 or A2.

Embodiment J6: The method of any one of Embodiments J to J5, wherein the initiating crystallization step comprises both mixing the solvent or mixture of solvents and seeding the solvent or mixture of solvents with crystals of the crystalline hydrate of Embodiment A1 or A2.

Embodiment J7: The method of Embodiment J, wherein the method comprises adding an anti-solvent to the solvent or mixture of solvents, and the solvent or mixture of solvents comprises a polar solvent.

Embodiment J8: The method of Embodiments J, wherein the method comprises adding an anti-solvent to the solvent or mixture of solvents, and the solvent or mixture of solvents comprises a nonpolar solvent.

Embodiment J9: The method of any one of Embodiments J, J7, or J8, wherein the method comprises adding an anti-solvent to the solvent or mixture of solvents, and seeding the solvent or mixture of solvents with crystals of the crystalline hydrate of Embodiment A1 or A2.

Embodiment J10: The method of any one of Embodiments J, J7, or J8, wherein the method comprises adding an anti-solvent to the solvent or mixture of solvents, and mixing the solvent or mixture of solvents.

Embodiment J11: The method of any one of Embodiments J, J7, or J8, wherein the method comprises adding an anti-solvent to the solvent or mixture of solvents, and both seeding the solvent or mixture of solvents with crystals of the crystalline hydrate of claim 2 and mixing the solvent or mixture of solvents.

Embodiment J12: The method of any one of Embodiments J to J11, wherein the crystallization occurs in a wet mill.

Embodiment K: A method for the preparation of the crystalline hydrate of Embodiment A14, the method comprising:

dissolving (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide in a solvent or mixture of solvents comprising an anti-solvent; and maintaining the solvent or mixture of solvents at a temperature less than about 15° C. for an amount of time sufficient to initiate crystallization of the crystalline hydrate.

Embodiment K1: The method of Embodiment K, wherein the solvent or mixture of solvents comprises a polar solvent.

Embodiment K2: The method of Embodiment K or K11, wherein the temperature is less than about 10° C.

Embodiment K3: The method of any one of Embodiments K to K2, wherein the process further comprises seeding the solvent or mixture of solvents with crystals of the crystalline hydrate of Embodiment A14.

Embodiment L: A method for the preparation of the amorphous freebase (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide of Embodiment B, the method comprising dehydrating the crystalline hydrate of Embodiment A14 to provide the amorphous freebase (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide.

Embodiment L1: A method for the preparation of the amorphous freebase (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide of Embodiment B, the method comprising:

dissolving (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide in a solvent or mixture of solvents; and adjusting the pH of the solvent or mixture of solvents to a pH greater than about 8 to initiate precipitation of the amorphous freebase (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide.

Embodiment L2: The method of Embodiment LI, wherein the solvent or mixture of solvents comprises water.

Embodiment L3: The method of Embodiment L1 or L2, wherein the pH of the solvent or mixture of solvents is adjusting to a pH equal to or greater than about 12.

Embodiment M: A method for the preparation of the crystalline anhydrate of Embodiment C, the method comprising:

dissolving (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide in a solvent or mixture of solvents, wherein the solvent or mixture of solvents comprises less than about 0.15 wt. % of water; and initiating crystallization to provide the crystalline anhydrate.

Embodiment M1: The method of Embodiment M, wherein the solvent or mixture of solvents has a water activity of about 2.4% or less.

Embodiment M2: The method of Embodiment M or M1, wherein the initiating crystallization step comprises mixing the solvent or mixture of solvents.

Embodiment M3: The method of Embodiment M2, wherein the mixing occurs at a temperature of at least 23° C.

Embodiment M4: The method of any one of Embodiments M to M3, wherein the initiating crystallization step comprises seeding the solvent or mixture of solvents with crystals of the crystalline anhydrate of Embodiment C or C1.

Embodiment N: A crystalline hydrate of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide prepared by the process of any of Embodiments J to J12.

Embodiment N1: A crystalline hydrate of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide prepared by the process of any one of Embodiments K to K3.

Embodiment N2: Amorphous freebase (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide prepared by the process of any one of Embodiments L to L3.

Embodiment N3: A crystalline anhydrate of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide prepared by the process of any one of Embodiments M to M4.

Embodiment O: A process for preparing (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide, or a pharmaceutically acceptable salt thereof, the process comprising:

a) reacting a compound of formula (I)

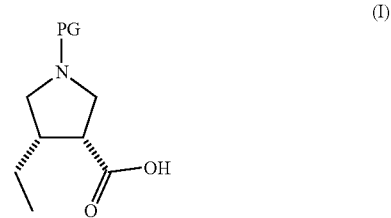

(I)

or a pharmaceutically acceptable salt thereof with trimethylsulfoxonium chloride to form a compound of formula (II)

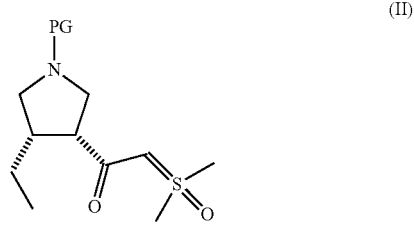

(II)

wherein PG is a protecting group;

b) contacting the compound of formula (II) with LiX and a sulfonic acid to form a compound of formula (III)

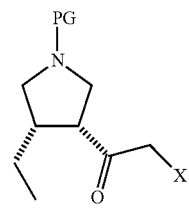

(III)

wherein X is Br or Cl;

c) reacting the compound of formula (III) with a compound of formula (IV)

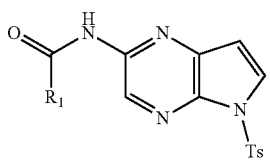

(IV)

to produce a compound of formula (V)

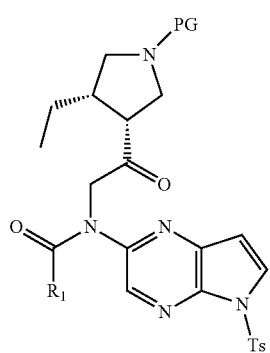

(V)

wherein $R_1$ is selected from the group consisting of alkyl, aryl, and —$OR_2$; $R_2$ is alkyl; and Ts is tosyl;

d) contacting the compound of formula (V) with a perfluoro acid anhydride and an organic base to form a compound of formula (VI)

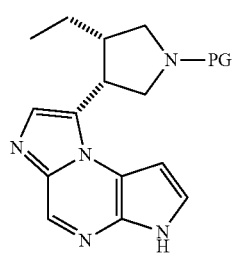

(VI)

e) deprotecting the compound of formula (VI) and forming a pharmaceutically acceptable salt of the compound of formula (VII):

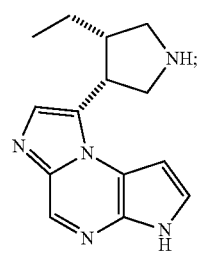

(VII)

and f) reacting the pharmaceutically acceptable salt of the compound of formula (VII) with 2,2,2-trifluoroethylamine to produce (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide.

Embodiment O1: The process of Embodiment O, wherein the pharmaceutically acceptable salt of the compound of formula (I) is selected from the group consisting of a compound of formula (Ia) and a compound of formula (Ib)

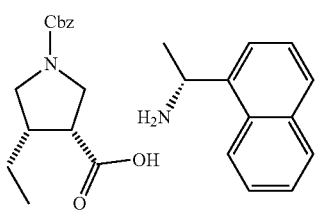

(Ia)

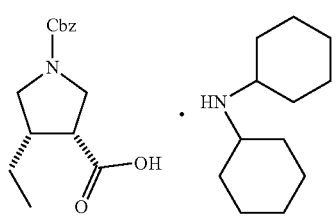

(Ib)

wherein Cbz is carboxybenzyl.

Embodiment O2: The process of Embodiment O1, further comprising contacting the compound of formula (Ia) or (Ib) with an acid prior to reacting to trimethylsulfoxonium chloride.

Embodiment O3: The process of Embodiment O2, wherein the acid is selected from the group consisting of a mineral acid or an organic acid.

Embodiment O4: The process of Embodiment O3, wherein the acid is selected from the group consisting of phosphoric acid, hydrochloric acid, acetic acid, citric acid, and combinations thereof.

Embodiment O5: The process of Embodiment O4, wherein the acid is phosphoric acid.

Embodiment O6: The process of any one of Embodiments O to O5, wherein the reaction of step a) is conducted in the presence of carbonyldiimidazole and a strong base.

Embodiment O7: The process of any one of Embodiments O to O6, wherein the reaction of step a) is conducted in a solvent selected from the group consisting of tetrahydrofuran, water, and methyl tert-butyl ether.

Embodiment O8: The process of any one of Embodiments O to O7, wherein the reaction of step b) is conducted in a solvent selected from the group consisting of tetrahydrofuran, ethyl acetate, heptanes, ethanol, and water.

Embodiment O9: The process of any one of Embodiments O to O8, wherein the reaction of step c) is conducted in the presence of a base.

Embodiment O10: The process of any one of Embodiments O to O9, wherein the reaction of step c) is conducted in a solvent selected from the group consisting of dimethylacetamide, tetrahydrofuran, dichloromethane, ethyl acetate, and heptanes, and combinations thereof.

Embodiment O11: The process of any one of Embodiments O to O10, wherein the reaction of step d) is conducted in a solvent selected from the group consisting of acetonitrile, toluene, and combinations thereof.

Embodiment O12: The process of any one of Embodiments O to O11, further comprising contacting the reaction mixture formed in step d) with a hydroxide.

Embodiment O13: The process of Embodiment O12, wherein the hydroxide is sodium hydroxide.

Embodiment O14: The process of any one of Embodiments O to O13, wherein the reaction of step e) is conducted in a solvent selected from the group consisting of ethanol, isopropyl acetate, and combinations thereof.

Embodiment O15: The process of any one of Embodiments O to O14, wherein step e) comprises contacting the compound of formula (VII) with an acid to form the pharmaceutically acceptable salt of the compound of formula (VII).

Embodiment O16: The process of any one of Embodiments O to O15, wherein the pharmaceutically acceptable salt of the compound of formula (VII) is selected from the group consisting of:

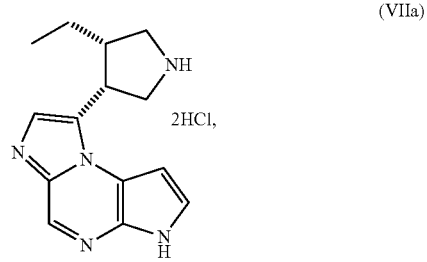

(VIIa)

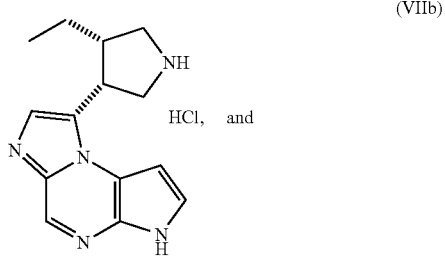

(VIIb)

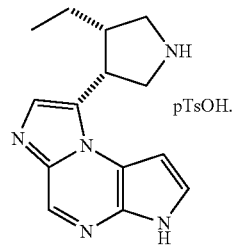

(VIIc)

Embodiment O17: The process of any one of Embodiments O to O16, wherein step e) comprises contacting the compound of formula (VI) with an acid to form the pharmaceutically acceptable salt of the compound of formula (VII).

Embodiment O18: The process of any one of Embodiments O to O17, wherein the pharmaceutically acceptable salt of the compound of formula (VII) in step f) is selected from the group consisting of a compound of formula (VIIa), a compound of formula (VIIb), and a compound of formula (VIIc).

Embodiment O19: The process of any one of Embodiments O to O18, wherein the reaction of step f) is conducted in the presence of carbonyldiimidazole, dipotassium phosphate, and potassium hydroxide.

Embodiment O20: The process of any one of Embodiments O to O19, further comprising preparing a crystalline hydrate of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide, the process comprising:
dissolving (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide in a solvent or mixture of solvents; and
initiating crystallization to provide the crystalline hydrate;
wherein the crystalline hydrate is a hemihydrate.

Embodiment O21: A crystalline hydrate of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide prepared by the process of Embodiment O20.

Embodiment O22: The process of any one of Embodiments O to O19, further comprising preparing a crystalline hydrate of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide, the process comprising:
dissolving (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide in a solvent or mixture of solvents comprising an anti-solvent; and
maintaining the solvent or mixture of solvents at a temperature less than about 15° C. for an amount of time sufficient to initiate crystallization of the crystalline hydrate;
wherein the crystalline hydrate has an X-ray powder diffraction pattern characterized by peaks at 3.1±0.2, 9.3±0.2, and 12.0±0.2 degrees two theta when measured at about 25° C. with monochromatic Kα1 radiation.

Embodiment O23: A crystalline hydrate of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide prepared by the process of Embodiment O22.

Embodiment O24: The process of any one of Embodiments O to O19, further comprising preparing an amorphous freebase (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide, the process comprising dehydrating the crystalline hydrate produced in the process of Embodiment O22 to provide the amorphous freebase (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide.

Embodiment O25: The process of any one of Embodiments O to O19, further comprising preparing an amorphous freebase (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide, the process comprising:

dissolving (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide in a solvent or mixture of solvents; and adjusting the pH of the solvent or mixture of solvents to a pH greater than about 8 to initiate precipitation of the amorphous freebase (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide.

Embodiment O26: An amorphous freebase (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide prepared by the process of Embodiment O24 or O25.

Embodiment O27: The process of any one of Embodiments O to O19, further comprising preparing a crystalline anhydrate of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide, the process comprising:

dissolving (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide in a solvent or mixture of solvents, wherein the solvent or mixture of solvents comprises less than about 0.15 wt. % of water; and initiating crystallization to provide the crystalline anhydrate.

Embodiment O28: A crystalline anhydrate of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide prepared by the process of Embodiment O27.

Embodiment O29: The process of any one of Embodiments O to O19, wherein the pharmaceutically acceptable salt of the compound of formula (I) is the compound of formula (Ib):

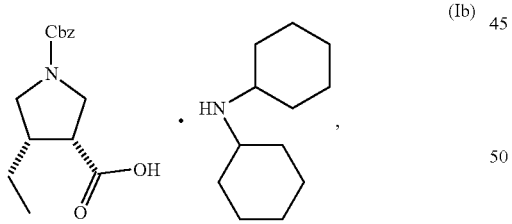

wherein the compound of formula (Ib) is prepared by:
(i) reacting carboxybenzyl-glycine ethyl ester with ethyl acrylate to form a compound of formula (VIII):

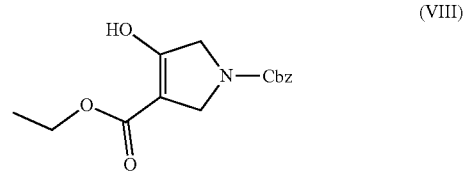 [SMILES: CCOC(=O)C1=C(O)CN(C(=O)OCc2ccccc2)C1]

(ii) protecting the compound of formula (VIII) to form a compound of formula (IX):

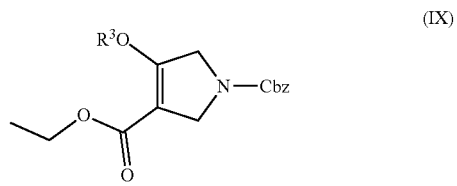

wherein $R^3$ is selected from the group consisting of $CF_3SO_2$—; $CH_3SO_2$—; and tosyl;

(iii) contacting the compound of formula (IX) with one of ethyl boronic acid, ethyl magnesium bromide, or ethyl zinc chloride in the presence of a catalyst to form a compound of formula (X):

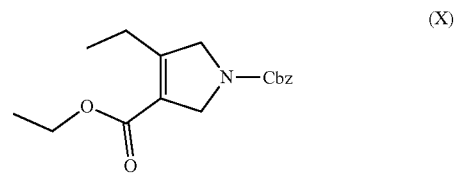 [SMILES: CCOC(=O)C1=C(CC)CN(C(=O)OCc2ccccc2)C1]

(iv) hydrolyzing the compound of formula (X) to produce the compound of formula (XI):

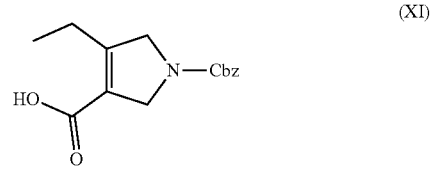 [SMILES: CCC1=C(C(=O)O)CN(C(=O)OCc2ccccc2)C1]

(v) converting the compound of formula (XI) to the compound of formula (XII):

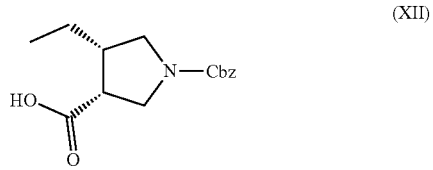 [SMILES: CC[C@@H]1CN(C(=O)OCc2ccccc2)C[C@@H]1C(=O)O]

(vi) contacting the compound of formula (XII) with dicyclohexylamine to form the compound of formula (Ib);
wherein Cbz is carboxybenzyl.

Embodiment O29a: The process of Embodiment O29, wherein the reaction of step (i) is conducted in the presence of a strong base.

Embodiment O29b: The process of Embodiment O29 or O29a, wherein the reaction of step (ii) is conducted in the presence of diisopropylethylamine.

Embodiment O29c: The process of any one of Embodiments O29 to O29b, wherein the catalyst in step (iii) is a palladium catalyst.

Embodiment O29d: The process of any one of Embodiments O29 to O29c, wherein the compound of formula (X) is contacted with an alkali metal hydroxide to form the compound of formula (XI).

Embodiment O29e: The process of any one of Embodiments O29 to O29d, wherein the compound of formula (XI) is contacted with a ruthenium catalyst to form the compound of formula (XII).

Embodiment O30: The process of any one of Embodiments O to O19, wherein the pharmaceutically acceptable salt of the compound of formula (I) is the compound of formula (Ia):

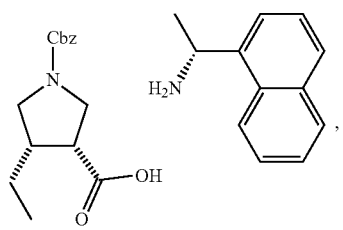

(Ia)

wherein the compound of formula (Ia) is prepared by:

(i) hydrogenating ethyl pent-2-ynoate with a Lindlar catalyst to form (Z)-ethyl pent-2-enoate;

(ii) reacting (Z)-ethyl pent-2-enoate with N-(methoxymethyl)-N-(trimethylsilyl methyl)benzylamine to form a compound of formula (XIII)

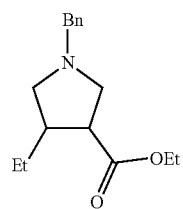

(XIII)

(iii) deprotecting the compound of formula (XIII) to form a compound of formula (XIV)

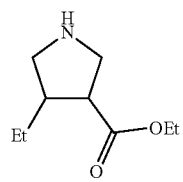

(XIV)

(iv) hydrolyzing the compound of formula (XIV) to form a compound of formula (XV)

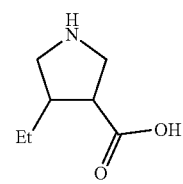

(XV)

(v) reacting the compound of formula (XV) with N-benzyloxycarbonyloxy succinimide to form a compound of formula (XVI)

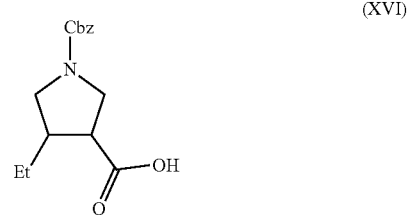 [SMILES: CCC1CN(C(=O)OCc2ccccc2)CC1C(=O)O]

(XVI)

(vi) contacting the compound of formula (XVI) with (R)-1-(naphthalene-1-yl)ethanamine to form the compound of formula (Ia);

wherein Cbz is carboxybenzyl; Bn is benzyl; and Et is ethyl.

Embodiment O30a: The process of Embodiment O30, wherein the reaction of step (i) is conducted in a solvent selected from pyridine, tetrahydrofuran, and combinations thereof.

Embodiment O30b: The process of Embodiment O30 or O30a, wherein the compound of formula (XIII) is deprotected by hydrogenating with a catalyst and hydrogen gas.

Embodiment O30c: The process of any one of Embodiments O30 to O30b, wherein the compound of formula (XIV) is contacted with hydrochloric acid to form the compound of formula (XV).

Embodiment P: A process for preparing (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide, or a pharmaceutically acceptable salt thereof, the process comprising:

a) reacting a compound of formula (Ib)

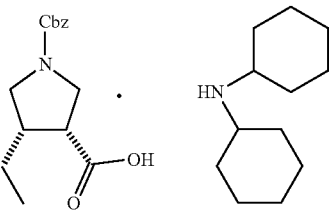

(Ib)

with trimethylsulfoxonium chloride in the presence of carbonyldiimidazole and a strong base to form a compound of formula (IIa)

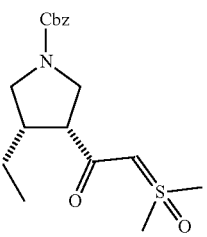

(IIa)

wherein Cbz is carboxybenzyl;

b) contacting the compound of formula (IIa) with lithium bromide and a sulfonic acid to form a compound of formula (IIIa)

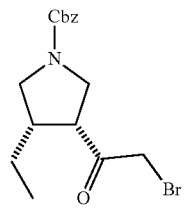
(IIIa)

c) reacting the compound of formula (IIIa) with a compound of formula (IVa)

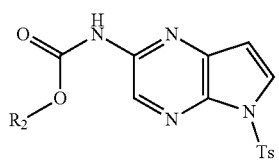
(IVa)

in the presence of lithium tert-butoxide to produce a compound of formula (Va)

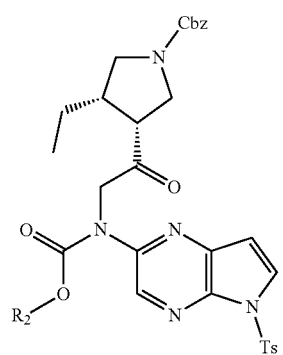
(Va)

wherein R₂ is methyl or ethyl; and Ts is tosyl;

d) contacting the compound of formula (Va) with a perfluoro acid anhydride and an organic base to form a compound of formula (VIa)

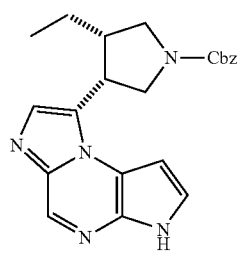
(VIa)

e) deprotecting the compound of formula (VIa) to form a compound of formula (VII)

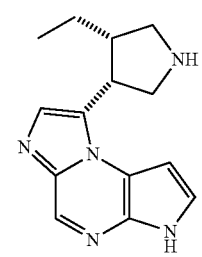
(VII)

f) contacting the compound of formula (VII) with hydrochloric acid to form a compound of formula (VIIa)

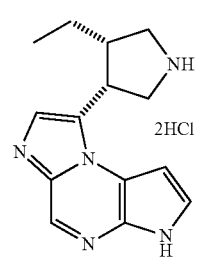
(VIIa)

g) reacting the compound of formula (VIIa) with 2,2,2-trifluoroethylamine in the presence of carbonyldiimidazole to produce (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide.

Embodiment P1: The process of Embodiment P, wherein:
the strong base of step a) is potassium tert-butoxide;
the sulfonic acid of step b) is selected from the group consisting of methanesulfonic acid and p-toluenesulfonic acid;
the perfluoro acid anhydride of step d) is trifluoroacetic anhydride;
the organic base of step d) is pyridine;
the compound of formula (VIa) is deprotected using hydrogen gas and Pd(OH)₂/C; and
the reaction of step g) is conducted in the presence of dipotassium phosphate and potassium hydroxide.

Embodiment P2: The process of Embodiment P or P1, further comprising contacting the compound of formula (Ib) with an acid prior to reacting to trimethylsulfoxonium chloride.

Embodiment P3: The process of Embodiment P2, wherein the acid is selected from the group consisting of a mineral acid or an organic acid.

Embodiment P4: The process of Embodiment P3, wherein the acid is selected from the group consisting of phosphoric acid, hydrochloric acid, acetic acid, citric acid, and combinations thereof.

Embodiment P5: The process of Embodiment P4, wherein the acid is phosphoric acid.

Embodiment P6: The process of any one of Embodiments P to P5, further comprising preparing a crystalline hydrate of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide, the process comprising:

dissolving (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide in a solvent or mixture of solvents; and initiating crystallization to provide the crystalline hydrate; wherein the crystalline hydrate is a hemihydrate.

Embodiment P7: A crystalline hydrate of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide prepared by the process of Embodiment P6.

Embodiment P8: The process of any one of Embodiments P to P5, further comprising preparing a crystalline hydrate of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide, the process comprising:

dissolving (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide in a solvent or mixture of solvents comprising an anti-solvent; and maintaining the solvent or mixture of solvents at a temperature less than about 15° C. for an amount of time sufficient to initiate crystallization of the crystalline hydrate;

wherein the crystalline hydrate has an X-ray powder diffraction pattern characterized by peaks at 3.1±0.2, 9.3±0.2, and 12.0±0.2 degrees two theta when measured at about 25° C. with monochromatic Kα1 radiation.

Embodiment P9: A crystalline hydrate of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide prepared by the process of Embodiment P8.

Embodiment P10: The process of any one of Embodiments P to P5, further comprising preparing an amorphous freebase (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide, the process comprising dehydrating the crystalline hydrate produced in the process of Embodiment P8 to provide the amorphous freebase (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide.

Embodiment P11: The process of any one of Embodiments P to P5, further comprising preparing an amorphous freebase (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide, the process comprising:

dissolving (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide in a solvent or mixture of solvents; and adjusting the pH of the solvent or mixture of solvents to a pH greater than about 8 to initiate precipitation of the amorphous freebase (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide.

Embodiment P12: An amorphous freebase (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide prepared by the process of Embodiment P10 or P11.

Embodiment P13: The process of any one of Embodiments P to P5, further comprising preparing a crystalline anhydrate of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide, the process comprising:

dissolving (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide in a solvent or mixture of solvents, wherein the solvent or mixture of solvents comprises less than about 0.15 wt. % of water; and initiating crystallization to provide the crystalline anhydrate.

Embodiment P14: A crystalline anhydrate of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide prepared by the process of Embodiment P13.

Embodiment Q: A process for preparing (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide, or a pharmaceutically acceptable salt thereof, the process comprising:

a) converting a compound of formula (XIa):

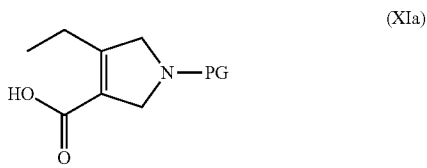

(XIa)

to a compound of formula (I):

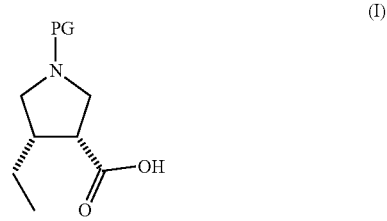

(I)

wherein PG is a protecting group;

b) reacting the compound of formula (I) with trimethylsulfoxonium chloride to form a compound of formula (II)

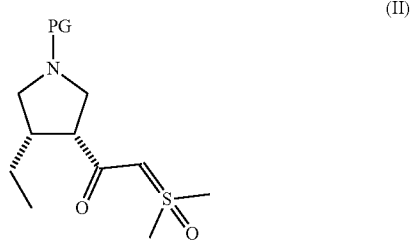

(II)

c) contacting the compound of formula (II) with an anhydrous source of HBr or HCl to form a compound of formula (III)

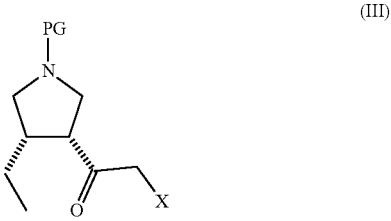

(III)

wherein X is Br or Cl;

d) reacting the compound of formula (III) with a compound of formula (IV)

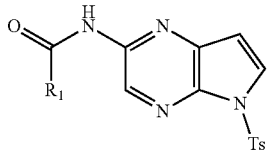
(IV)

to produce a compound of formula (V)

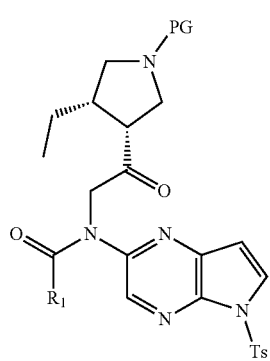
(V)

wherein $R_1$ is selected from the group consisting of alkyl, aryl, and —$OR_2$; $R_2$ is alkyl; and Ts is tosyl;

e) contacting the compound of formula (V) with a perfluoro acid anhydride and an organic base to form a compound of formula (VI)

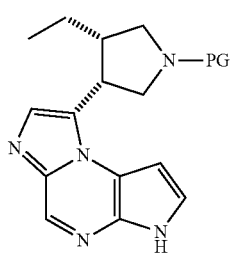
(VI)

f) deprotecting the compound of formula (VI) and forming a pharmaceutically acceptable salt of the compound of formula (VII):

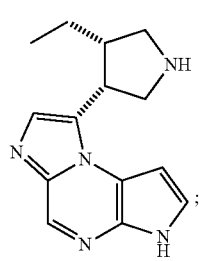
(VII)

and g) reacting the pharmaceutically acceptable salt of the compound of formula (VII) with 2,2,2-trifluoroethylamine to produce (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide.

Embodiment Q1: The process of Embodiment Q, wherein step 0 comprises contacting, the compound of formula (VII) with an acid to form the pharmaceutically acceptable salt of the compound of formula (VII).

Embodiment Q2: The process of Embodiment Q or Q1, wherein the protecting group is carboxybenzyl.

Embodiment Q3: The process of any one of Embodiments Q to Q2, wherein the anhydrous source of HBr or HCl comprises no more than 0.2% water (by volume).

Embodiment Q4: The process of any one of Embodiments Q to Q3, wherein step a) is conducted in a solvent selected from the group consisting of methanol, trimethylamine, and combinations thereof.

Embodiment Q5: The process of any one of Embodiments Q to Q4, wherein step b) comprises reacting the compound of formula (I) with trimethylsulfoxonium chloride in the presence of carbonyldiimidazole and a strong base to form the compound of formula (II).

Embodiment Q6: The process of Embodiment Q5, wherein the base is selected from the group consisting of potassium tert-butoxide, sodium tert-butoxide, and combinations thereof.

Embodiment Q7: The process of any one of Embodiments Q to Q6, wherein step b) is conducted in a solvent selected from the group consisting of tetrahydrofuran, water, methyl tert-butyl ether, and combinations thereof.

Embodiment Q8: The process of any one of Embodiments Q to Q7, wherein step c) is conducted in tetrahydrofuran, and comprises contacting the compound of formula (II) with an anhydrous source of HBr to form the compound of formula (III).

Embodiment Q9: The process of Embodiment Q8, wherein the anhydrous source of HBr is HBr/HOAc.

Embodiment Q10: The process of any one of Embodiments Q to Q9, wherein step d) comprises reacting the compound of formula (III) with the compound of formula (IV) in the presence of lithium tert-butoxide to produce the compound of formula (V).

Embodiment Q11: The process of any one of Embodiments Q to Q10, wherein the reaction of step e) is conducted in a solvent selected from the group consisting of acetonitrile, toluene, and combinations thereof.

Embodiment Q12: The process of any one of Embodiments Q to Q11, further comprising contacting the reaction mixture formed in step d) with a hydroxide.

Embodiment Q13: The process of Embodiment Q12, wherein the hydroxide is sodium hydroxide.

Embodiment Q14: The process of any one of Embodiments Q to Q13, wherein the reaction of step f) is conducted in a solvent selected from the group consisting of ethanol, isopropyl acetate, and combinations thereof.

Embodiment Q15: The process of any one of Embodiments Q to Q14, wherein step f) comprises contacting the compound of formula (VII) with an acid to form the pharmaceutically acceptable salt of the compound of formula (VII).

Embodiment Q16: The process of any one of Embodiments Q to Q14, wherein step f) comprises contacting the compound of formula (VI) with an acid to form the pharmaceutically acceptable salt of the compound of formula (VII).

Embodiment Q17: The process of any one of Embodiments Q to Q16, wherein the pharmaceutically acceptable salt of the compound of formula (VII) is selected from the group consisting of:

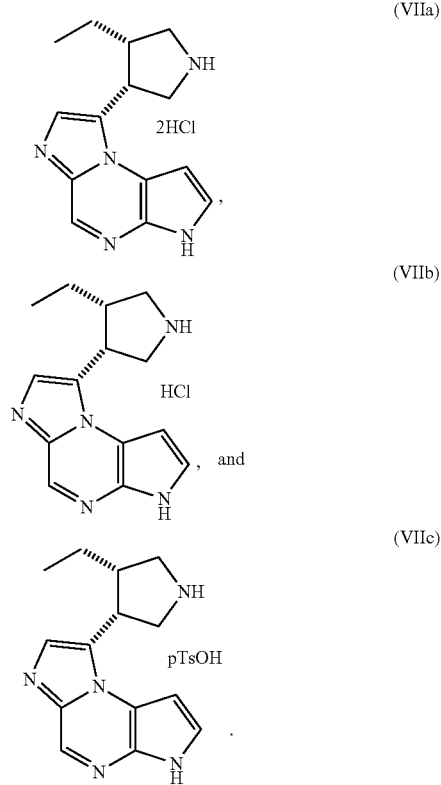

Embodiment Q18: The process of any one of Embodiments Q to Q17, further comprising preparing a crystalline hydrate of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide, the process comprising:
dissolving (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide in a solvent or mixture of solvents; and
initiating crystallization to provide the crystalline hydrate;
wherein the crystalline hydrate is a hemihydrate.

Embodiment Q19: A crystalline hydrate of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide prepared by the process of Embodiment Q18.

Embodiment Q20: The process of any one of Embodiments Q to Q17, further comprising preparing a crystalline hydrate of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide, the process comprising:
dissolving (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide in a solvent or mixture of solvents comprising an anti-solvent; and
maintaining the solvent or mixture of solvents at a temperature less than about 15° C. for an amount of time sufficient to initiate crystallization of the crystalline hydrate;
wherein the crystalline hydrate has an X-ray powder diffraction pattern characterized by peaks at 3.1±0.2, 9.3±0.2, and 12.0±0.2 degrees two theta when measured at about 25° C. with monochromatic Kα1 radiation.

Embodiment Q21: A crystalline hydrate of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide prepared by the process of Embodiment Q20.

Embodiment Q22: The process of any one of Embodiments Q to Q17, further comprising preparing an amorphous freebase (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide, the process comprising dehydrating the crystalline hydrate produced in the process of Embodiment Q20 to provide the amorphous freebase (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide.

Embodiment Q23: The process of any one of Embodiments Q to Q17, further comprising preparing an amorphous freebase (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide, the process comprising:
dissolving (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide in a solvent or mixture of solvents; and
adjusting the pH of the solvent or mixture of solvents to a pH greater than about 8 to initiate precipitation of the amorphous freebase (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide.

Embodiment Q24: An amorphous freebase (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide prepared by the process of Embodiment Q22 or Q23.

Embodiment Q25: The process of any one of Embodiments Q to Q17, further comprising preparing a crystalline anhydrate of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide, the process comprising:
dissolving (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide in a solvent or mixture of solvents, wherein the solvent or mixture of solvents comprises less than about 0.15 wt. % of water; and
initiating crystallization to provide the crystalline anhydrate.

Embodiment Q26: A crystalline anhydrate of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide prepared by the process of Embodiment Q25.

Embodiment R: A compound of formula (II):

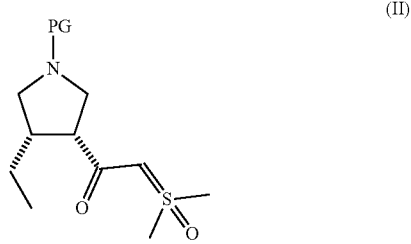

wherein PG is a protecting group.

Embodiment R1: The compound of Embodiment R, wherein the protecting group is selected from the group consisting of carboxybenzyl, p-methoxybenzyl carbonyl, benzyl, p-methoxybenzyl, and 3,4-dimethoxybenzyl.

Embodiment R2: A process for preparing a compound of formula (II):

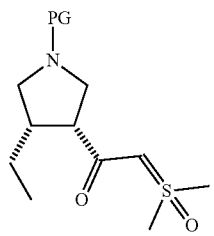
(II)

the process comprising reacting a compound of formula (I)

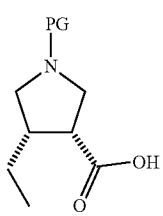
(I)

or a pharmaceutically acceptable salt thereof with trimethylsulfoxonium chloride to form the compound of formula (II), wherein PG is a protecting group.

Embodiment R2a: The process of Embodiment R2, wherein the protecting group is selected from the group consisting of carboxybenzyl, p-methoxybenzyl carbonyl, benzyl, p-methoxybenzyl, and 3,4-dimethoxybenzyl.

Embodiment R2b: The process of Embodiment R2 or R2a, wherein the pharmaceutically acceptable salt of the compound of formula (I) is selected from the group consisting of a compound of formula (Ia) and a compound of formula (Ib)

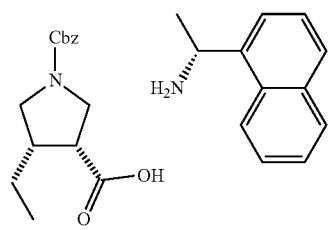
(Ia)

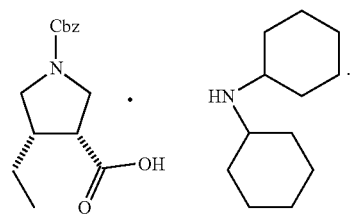
(Ib)

Embodiment R2c: The process of any one of embodiments R2 to R2b, wherein the reaction is conducted in the presence of carbonyldiimidazole and a strong base.

Embodiment R2d: The process of any one of embodiments R2 to R2c, wherein the reaction is conducted in the presence of phosphoric acid.

Embodiment R2e: The process of any one of embodiments R2 to R2d, wherein the reaction is conducted in a solvent selected from the group consisting of tetrahydrofuran, water, and methyl tert-butyl ether.

Embodiment R3: A process for preparing a compound of formula (II):

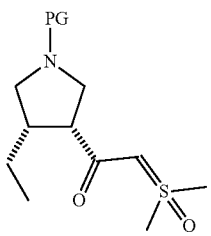
(II)

the process comprising
a) converting a compound of formula (XIa):

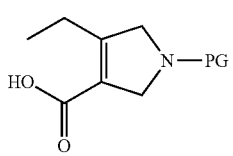
(XIa)

to a compound of formula (I):

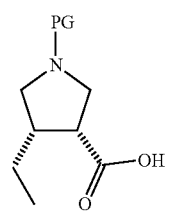
(I)

wherein PG is a protecting group; and
b) reacting the compound of formula (I) with trimethylsulfoxonium chloride to form the compound of formula (II).

Embodiment R3a: The process of Embodiment R3, wherein the reaction of step b) is conducted in the presence of carbonyldiimidazole and a strong base.

Embodiment S: A process for the preparation of a compound of formula (III):

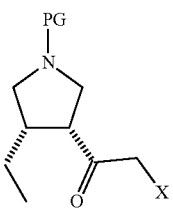
(III)

the process comprising contacting a compound of formula (II)

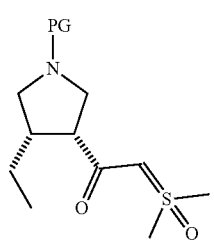
(II)

with LiX and a sulfonic acid to form the compound of formula (III);

wherein PG is a protecting group; and X is Br or Cl.

Embodiment S1: The process of Embodiment S, wherein the compound of formula (II) is formed by reacting a compound of formula (I)

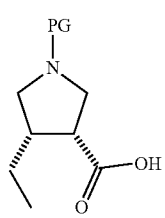
(I)

or a pharmaceutically acceptable salt thereof with trimethylsulfoxonium chloride.

Embodiment S2: The process of Embodiment S1, wherein the pharmaceutically acceptable salt of the compound of formula (I) is selected from the group consisting of a compound of formula (Ia) and a compound of formula (Ib)

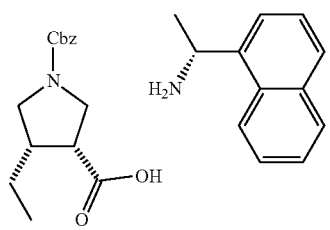
(Ia)

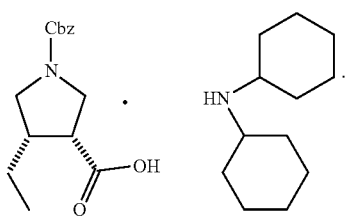
(Ib)

Embodiment S3: The process of Embodiment S1 or S2, wherein the compound or the pharmaceutically acceptable salt of formula (I) is reacted with trimethylsulfoxonium chloride in the presence of carbonyldiimidazole and a strong base.

Embodiment S4: A process for the preparation of a compound of formula (III):

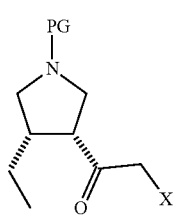
(III)

the process comprising contacting a compound of formula (II)

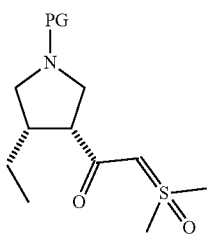
(II)

with an anhydrous source of HBr or HCl to form a compound of formula (III), wherein PG is a protecting group, and X is Br or Cl.

Embodiment S4a: The process of Embodiment S4, wherein the compound of formula (II) is formed by converting a compound of formula (XIa):

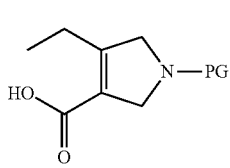
(XIa)

to a compound of formula (I):

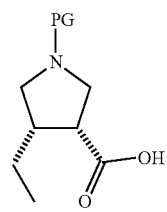
(I)

wherein PG is a protecting group; and reacting the compound of formula (I) with trimethylsulfoxonium chloride to form the compound of formula (II).

Embodiment S4b: The process of Embodiment S4 or S4a, wherein the compound of formula (II) is contacted with an anhydrous source of HBr to form the compound of formula (III).

Embodiment S4c: The process of Embodiment S4b, wherein the anhydrous source of HBr is HBr/HOAc.

Embodiment T: A compound of formula (Va)

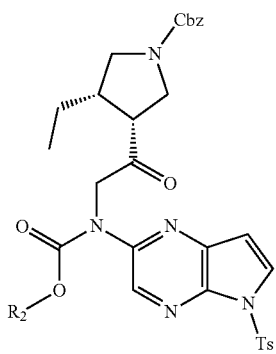
(Va)

wherein $R_2$ is methyl or ethyl; Ts is tosyl; and Cbz is carboxybenzyl.

Embodiment T1: A process for preparing a compound of formula (V)

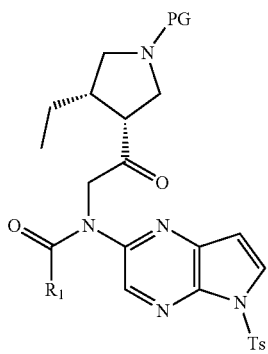
(V)

the process comprising:
a) reacting a compound of formula (I)

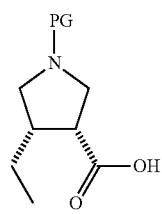
(I)

or a pharmaceutically acceptable salt thereof with trimethylsulfoxonium chloride to form a compound of formula (II)

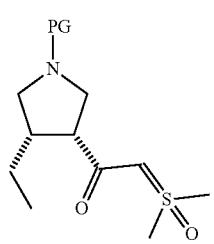
(II)

b) contacting the compound of formula (II) with LiX and a sulfonic acid to form a compound of formula (III)

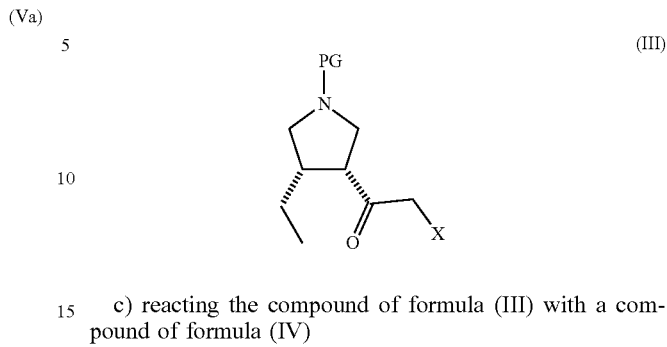
(III)

c) reacting the compound of formula (III) with a compound of formula (IV)

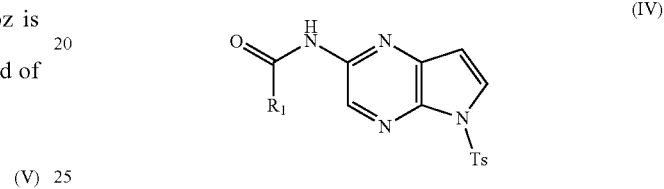
(IV)

to produce the compound of formula (V);
wherein:
PG is a protecting group;
X is Br or Cl;
$R_1$ is selected from the group consisting of alkyl, aryl, and —$OR_2$;
$R_2$ is alkyl; and
Ts is tosyl.

Embodiment T1a: The process of Embodiment T1, wherein the pharmaceutically acceptable salt of the compound of formula (I) is selected from the group consisting of a compound of formula (Ia) and a compound of formula (Ib)

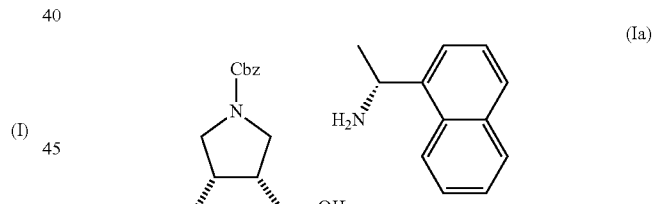
(Ia)

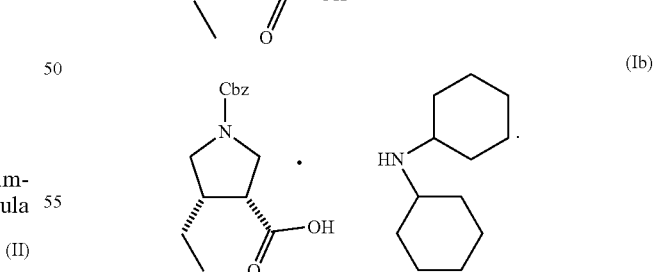
(Ib)

Embodiment T1b: The process of Embodiment T1 or T1a, wherein the reaction of step a) is conducted in the presence of carbonyldiimidazole and a strong base.

Embodiment T1c: The process of any one of Embodiments T1 to T1b, wherein the reaction of step c) is conducted in the presence of a base selected from the group consisting of lithium tert-butoxide, sodium tert-butoxide, and combinations thereof.

Embodiment T2: A process for preparing a compound of formula (V)

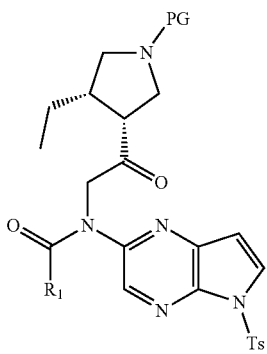 (V)

the process comprising:

a) converting a compound of formula (XIa):

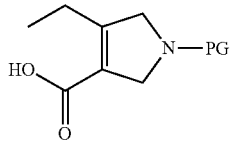 (XIa)

to a compound of formula (I):

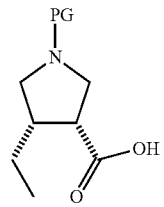 (I)

wherein PG is a protecting group;

b) reacting the compound of formula (I) with trimethylsulfoxonium chloride to form a compound of formula (II)

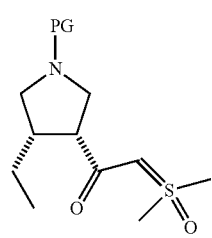 (II)

c) contacting the compound of formula (II) with an anhydrous source of HBr or HCl to form a compound of formula (III)

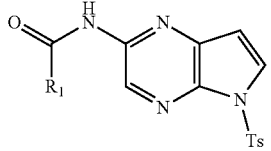 (III)

wherein X is Br or Cl;

d) reacting the compound of formula (III) with a compound of formula (IV)

 (IV)

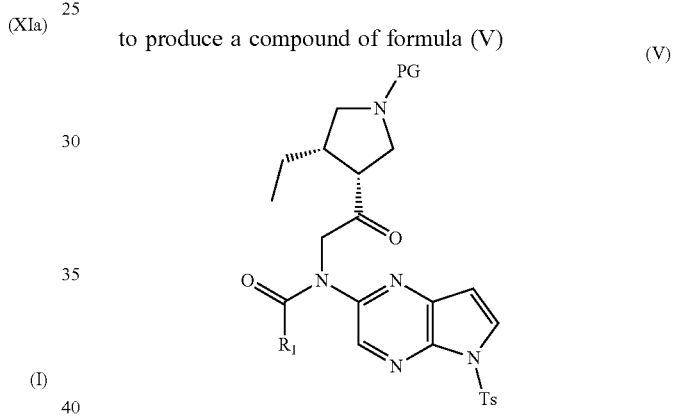

to produce a compound of formula (V)

(V)

wherein $R_1$ is selected from the group consisting of alkyl, aryl, and $-OR_2$; $R_2$ is alkyl; and Ts is tosyl.

Embodiment T2a: The process of Embodiment T2, wherein the compound of formula (II) is contacted with an anhydrous source of HBr to form the compound of formula (III).

Embodiment T2b: The process of Embodiment T2a, wherein the anhydrous source of HBr is HBr/HOAc.

Embodiment T3: A process for preparing a crystalline compound of formula (V)

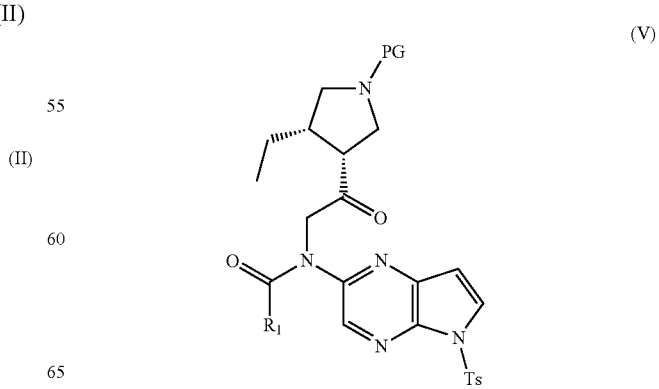 (V)

the process comprising:

a) reacting a compound of formula (III)

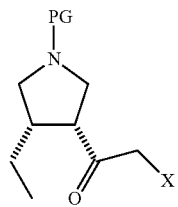
(III)

with a compound of formula (IV):

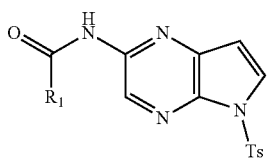
(IV)

to produce the compound of formula (V);
wherein:
PG is a protecting group;
X is Br or Cl;
R₁ is —OR₂;
R₂ is methyl or ethyl; and
Ts is tosyl.

Embodiment U: A compound of formula (IVa):

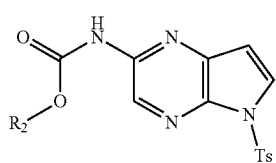
(IVa)

wherein R₂ is methyl or ethyl, and Ts is tosyl.

Embodiment V: A compound of formula (VII):

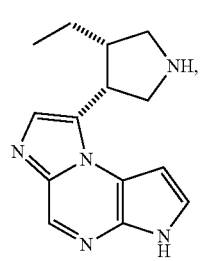
(VII)

or a pharmaceutically acceptable salt thereof.

Embodiment V1: The compound of Embodiment V, wherein the pharmaceutically acceptable salt of the compound of formula (VII) is selected from the group consisting of:

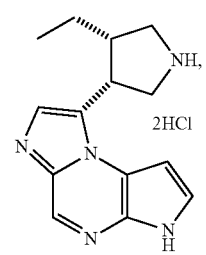
(VIIa)

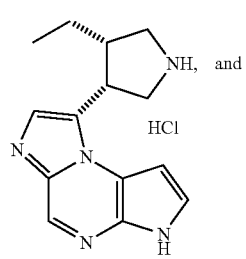
(VIIb)
and

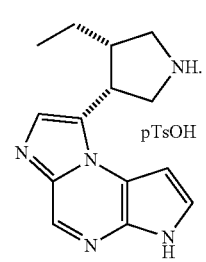
(VIIc)

Embodiment W: A process for preparing a compound of formula (Ib)

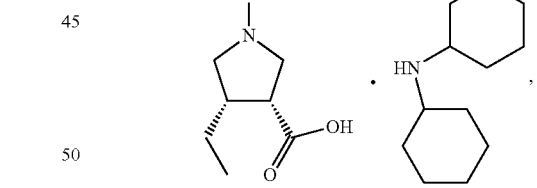
(Ib)

wherein Cbz is carboxybenzyl, the process comprising:

(i) reacting carboxybenzyl-glycine ethyl ester with ethyl acrylate to form a compound of formula (VIII):

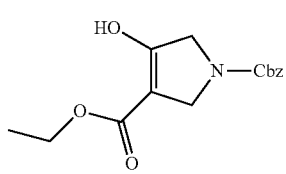
(VIII)

(ii) protecting the compound of formula (VIII) to form a compound of formula (IX):

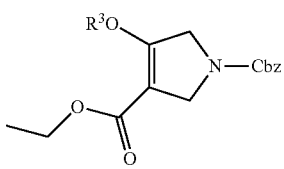

wherein R³ is selected from the group consisting of CF₃SO₂—; CH₃SO₂—; and tosyl;

(iii) contacting the compound of formula (IX) with one of ethyl boronic acid, ethyl magnesium bromide, or ethyl zinc chloride in the presence of a catalyst to form a compound of formula (X):

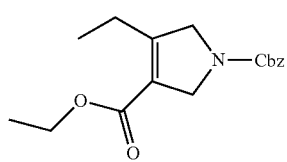

(iv) hydrolyzing the compound of formula (X) to produce the compound of formula (XI):

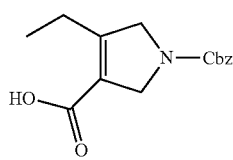

(v) converting the compound of formula (XI) to the compound of formula (XII):

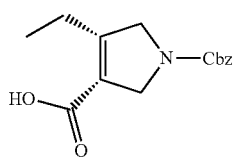

(vi) contacting the compound of formula (XII) with dicyclohexylamine to form the compound of formula (Ib).

Embodiment W1: The process of Embodiment W, wherein the reaction of step (i) is conducted in the presence of a strong base.

Embodiment W2: The process of Embodiment W or W1, wherein the reaction of step (i) is conducted in an organic solvent.

Embodiment W3: The process of any one of Embodiments W to W2, wherein the reaction of step (ii) is conducted in the presence of diisopropylethylamine.

Embodiment W4: The process of any one of Embodiments W to W3, wherein the reaction of step (ii) is conducted in a solvent selected from the group consisting of triethylamine, N-methylmorpholine, pyridine, diisopropyl ether, and combinations thereof.

Embodiment W5: The process of any one of Embodiments W to W4, wherein the reaction of step (iii) is conducted in a buffer selected from the group consisting of potassium carbonate, sodium carbonate, potassium phosphate tribasic, and combinations thereof.

Embodiment W6: The process of any one of Embodiments W to W5, wherein the reaction of step (iii) is conducted in a solvent selected from the group consisting of toluene, water, dioxane, tetrahydrofuran, and combinations thereof.

Embodiment W7: The process of any one of Embodiments W to W6, wherein the compound of formula (X) is contacted with an alkali metal hydroxide to form the compound of formula (XI).

Embodiment W8: The process of any one of Embodiments W to W7, wherein the compound of formula (XI) is contacted with a ruthenium catalyst to form the compound of formula (XII).

Embodiment W9: The process of any one of Embodiments W to W8, wherein:
the reaction of step (i) is conducted in the presence of sodium tert-butoxide;
the reaction of step (ii) is conducted in the presence of diisopropylethylamine;
the catalyst in step (iii) PdCl₂(dppf);
the reaction of step (iii) is conducted in potassium carbonate;
the compound of formula (X) is contacted with sodium hydroxide to form the compound of formula (XI); and
the compound of formula (XI) is contacted with a ruthenium catalyst to form the compound of formula (XII).

Embodiment X: The dicyclohexylamine salt of (3R,4S)-1-((benzyloxy)carbonyl)-4-ethylpyrrolidine-3-carboxylate.

Embodiment Y: A method of treating an adult subject having moderate to severely active rheumatoid arthritis, the method comprising administering to the subject:
a) about 7.5 mg of Compound 1 freebase, or a pharmaceutically acceptable salt thereof, or a crystalline hydrate or a crystalline anhydrate of Compound 1 in an amount sufficient to deliver to the subject about 7.5 mg of Compound 1 freebase equivalent; or
b) about 15 mg of Compound 1 freebase, or a pharmaceutically acceptable salt thereof, or a crystalline hydrate or a crystalline anhydrate of Compound 1 in an amount sufficient to deliver to the subject about 15 mg of Compound 1 freebase equivalent; or
c) about 30 mg of Compound 1 freebase, or a pharmaceutically acceptable salt thereof, or a crystalline hydrate or a crystalline anhydrate of Compound 1 in an amount sufficient to deliver to the subject about 30 mg of Compound 1 freebase equivalent; or
d) about 45 mg of Compound 1 freebase, or a pharmaceutically acceptable salt thereof, or a crystalline hydrate or a crystalline anhydrate of Compound 1 in an amount sufficient to deliver to the subject about 45 mg of Compound 1 freebase equivalent.

Embodiment Y1: The method of Embodiment Y, wherein the crystalline hydrate is a hemihydrate.

Embodiment Y2: The method of Embodiment Y1, wherein the crystalline hydrate is Freebase Hydrate Form C.

Embodiment Y3: The method of Embodiment Y, wherein the crystalline anhydrate is Freebase Anhydrate Form D.

Embodiment Y4: The method of any one of Embodiments Y to Y3, wherein the freebase, or the pharmaceutically acceptable salt thereof, or the hydrate, or the anhydrate is in a once daily extended release formulation.

Embodiment Y5: A pharmaceutical composition for use in treating an adult subject having moderate to severely active rheumatoid arthritis, wherein the pharmaceutical composition comprises:

a) about 7.5 mg of Compound 1 freebase, or a pharmaceutically acceptable salt thereof, or a crystalline hydrate or a crystalline anhydrate of Compound 1 in an amount sufficient to deliver to the subject about 7.5 mg of Compound 1 freebase equivalent; or b) about 15 mg of Compound 1 freebase, or a pharmaceutically acceptable salt thereof, or a crystalline hydrate or a crystalline anhydrate of Compound 1 in an amount sufficient to deliver to the subject about 15 mg of Compound 1 freebase equivalent; or c) about 30 mg of Compound 1 freebase, or a pharmaceutically acceptable salt thereof, or a crystalline hydrate or a crystalline anhydrate of Compound 1 in an amount sufficient to deliver to the subject about 30 mg of Compound 1 freebase equivalent; or d) about 45 mg of Compound 1 freebase, or a pharmaceutically acceptable salt thereof, or a crystalline hydrate or a crystalline anhydrate of Compound 1 in an amount sufficient to deliver to the subject about 45 mg of Compound 1 freebase equivalent.

In certain aspects of Embodiment Y5, the use comprises administering to the subject the pharmaceutical composition, Embodiment Y6: The method or pharmaceutical composition of any one of Embodiments Y to Y5, wherein the adult subject achieves ACR20 response at week 12 of said treating.

Embodiment Y7: The method or pharmaceutical composition of any one of Embodiments Y to Y6, wherein the adult subject achieves ACR20 response at week 8 of said treating.

Embodiment Y8: The method or pharmaceutical composition of any one of Embodiments Y to Y7, wherein the adult subject achieves ACR20 response at week 6 of said treating.

Embodiment Y9: The method or pharmaceutical composition of any one of Embodiments Y to Y8, wherein the adult subject achieves ACR20 response at week 4 of said treating.

Embodiment Y10: The method or pharmaceutical composition of any one of Embodiments Y to Y9, wherein the adult subject achieves ACR20 response at week 2 of said treating.

Embodiment Y11: The method or pharmaceutical composition of any one of Embodiments Y to Y10, wherein the adult subject achieves ACR50 response at week 12 of said treating.

Embodiment Y12: The method or pharmaceutical composition of any one of Embodiments Y to Y11, wherein the adult subject achieves ACR50 response at week 8 of said treating.

Embodiment Y13: The method or pharmaceutical composition of any one of Embodiments Y to Y12, wherein the adult subject achieves ACR50 response at week 6 of said treating.

Embodiment Y14: The method or pharmaceutical composition of any one of Embodiments Y to Y13, wherein the adult subject achieves ACR50 response at week 4 of said treating.

Embodiment Y15: The method or pharmaceutical composition of any one of Embodiments Y to Y14, wherein the adult subject achieves ACR50 response at week 2 of said treating.

Embodiment Y16: The method or pharmaceutical composition of any one of Embodiments Y to Y15, wherein the adult subject achieves ACR70 response at week 12 of said treating.

Embodiment Y17: The method or pharmaceutical composition of any one of Embodiments Y to Y16, wherein the adult subject achieves ACR70 response at week 8 of said treating.

Embodiment Y18: The method or pharmaceutical composition of any one of Embodiments Y to Y17, wherein the adult subject achieves ACR70 response at week 6 of said treating.

Embodiment Y19: The method or pharmaceutical composition of any one of Embodiments Y to Y18, wherein the adult subject achieves ACR70 response at week 4 of said treating.

Embodiment Y20: The method or pharmaceutical composition of any one of Embodiments Y to Y19, wherein the adult subject achieves a decrease in DAS28(CRP) as compared to baseline at week 12 of said treating.

Embodiment Y21: The method or pharmaceutical composition of any one of Embodiments Y to Y20, wherein the adult subject achieves a decrease in DAS28(CRP) as compared to baseline at week 8 of said treating.

Embodiment Y22: The method or pharmaceutical composition of any one of Embodiments Y to Y21, wherein the adult subject achieves a decrease in DAS28(CRP) as compared to baseline at week 6 of said treating.

Embodiment Y23: The method or pharmaceutical composition of any one of Embodiments Y to Y22, wherein the adult subject achieves a decrease in DAS28(CRP) as compared to baseline at week 4 of said treating.

Embodiment Y24: The method or pharmaceutical composition of any one of Embodiments Y to Y23, wherein the adult subject achieves a decrease in DAS28(CRP) as compared to baseline at week 2 of said treating.

Embodiment Y25: The method or pharmaceutical composition of any one of Embodiments Y to Y5, wherein the adult subject has had an inadequate response or tolerance to one or more disease-modifying antirheumatic drugs (DMARDS).

Embodiment Y26: The method or pharmaceutical composition Embodiment Y25, wherein the DMARD is a conventional synthetic DMARD or a biologic DMARD.

Embodiment Y27: The method or pharmaceutical composition Embodiment Y25, wherein the DMARD is an anti-TNF biologic DMARD.

Embodiment Y28: The method or pharmaceutical composition of Embodiment Y27, wherein the adult subject has received the anti-TNF biologic DMARD for at least three months prior to said treating.

Embodiment Y29: The method or pharmaceutical composition of any one of Embodiments Y25 to Y28, wherein the DMARD is methotrexate.

Embodiment Y30: The method or pharmaceutical composition of Embodiment Y29, wherein the adult subject has received the methotrexate for at least three months prior to said treating.

Embodiment Y31: The method or pharmaceutical composition of any one of Embodiments Y25 to Y30, wherein the adult subject is administered stable background methotrexate for at least three months prior to said treating.

Embodiment Y32: The method or pharmaceutical composition of any one of Embodiments Y25 to Y31, wherein the adult subject is administered stable background methotrexate during said treating.

Embodiment Y33: The method or pharmaceutical composition of any one of Embodiments Y25 to Y32, wherein the adult subject receives a supplement of folic acid for at least four weeks prior to said treating.

Embodiment Y34: The method or pharmaceutical composition of any one of Embodiments Y25 to Y33, wherein the adult subject is administered a supplement of folic acid during said treating.

Embodiment Y35: The method or pharmaceutical composition of any one of Embodiments Y25 to Y34, wherein the adult subject achieves ACR20 response at week 12 of said treating.

Embodiment Y36: The method or pharmaceutical composition of any one of Embodiments Y25 to Y35, wherein the adult subject achieves ACR20 response at week 8 of said treating.

Embodiment Y37: The method or pharmaceutical composition of any one of Embodiments Y25 to Y36, wherein the adult subject achieves ACR20 response at week 6 of said treating.

Embodiment Y38: The method or pharmaceutical composition of any one of Embodiments Y25 to Y37, wherein the adult subject achieves ACR20 response at week 4 of said treating.

Embodiment Y39: The method or pharmaceutical composition of any one of Embodiments Y25 to Y38, wherein the adult subject achieves ACR20 response at week 2 of said treating.

Embodiment Y40: The method or pharmaceutical composition of any one of Embodiments Y25 to Y39, wherein the adult subject achieves ACR50 response at week 12 of said treating.

Embodiment Y41: The method or pharmaceutical composition of any one of Embodiments Y25 to Y40, wherein the adult subject achieves ACR50 response at week 8 of said treating.

Embodiment Y42: The method or pharmaceutical composition of any one of Embodiments Y25 to Y41, wherein the adult subject achieves ACR50 response at week 6 of said treating.

Embodiment Y43: The method or pharmaceutical composition of any one of Embodiments Y25 to Y42, wherein the adult subject achieves ACR50 response at week 4 of said treating.

Embodiment Y44: The method or pharmaceutical composition of any one of Embodiments Y25 to Y43, wherein the adult subject achieves ACR50 response at week 2 of said treating.

Embodiment Y45: The method or pharmaceutical composition of any one of Embodiments Y25 to Y44, wherein the adult subject achieves ACR70 response at week 12 of said treating.

Embodiment Y46: The method or pharmaceutical composition of any one of Embodiments Y25 to Y45, wherein the adult subject achieves ACR70 response at week 8 of said treating.

Embodiment Y47: The method or pharmaceutical composition of any one of Embodiments Y25 to Y46, wherein the adult subject achieves ACR70 response at week 6 of said treating.

Embodiment Y48: The method or pharmaceutical composition of any one of Embodiments Y25 to Y47, wherein the adult subject achieves ACR70 response at week 4 of said treating.

Embodiment Y49: The method or pharmaceutical composition of any one of Embodiments Y25 to Y48, wherein the adult subject achieves a decrease in DAS28(CRP) as compared to baseline at week 12 of said treating.

Embodiment Y50: The method or pharmaceutical composition of any one of Embodiments Y25 to Y49, wherein the adult subject achieves a decrease in DAS28(CRP) as compared to baseline at week 8 of said treating.

Embodiment Y51: The method or pharmaceutical composition of any one of Embodiments Y25 to Y50, wherein the adult subject achieves a decrease in DAS28(CRP) as compared to baseline at week 6 of said treating.

Embodiment Y52: The method or pharmaceutical composition of any one of Embodiments Y25 to Y51, wherein the adult subject achieves a decrease in DAS28(CRP) as compared to baseline at week 4 of said treating.

Embodiment Y53: The method or pharmaceutical composition of any one of Embodiments Y25 to Y52, wherein the adult subject achieves a decrease in DAS28(CRP) as compared to baseline at week 2 of said treating.

Embodiment Y54: The method or pharmaceutical composition of any one of Embodiments Y25 to Y53, wherein the adult subject is also administered a conventional synthetic or a biologic DMARD.

Embodiment Y55: The method or pharmaceutical composition Embodiment Y54, wherein the DMARD is methotrexate.

Embodiment Y56: The method or pharmaceutical composition of Embodiment Y54 or Y55, wherein the adult subject achieves ACR20 response at week 12 of said treating.

Embodiment Y57: The method or pharmaceutical composition of any one of Embodiments Y54 to Y56, wherein the adult subject achieves ACR20 response at week 8 of said treating.

Embodiment Y58: The method or pharmaceutical composition of any one of Embodiments Y54 to Y57, wherein the adult subject achieves ACR20 response at week 6 of said treating.

Embodiment Y59: The method or pharmaceutical composition of any one of Embodiments Y54 to Y58, wherein the adult subject achieves ACR20 response at week 4 of said treating.

Embodiment Y60: The method or pharmaceutical composition of any one of Embodiments Y54 to Y59, wherein the adult subject achieves ACR20 response at week 2 of said treating.

Embodiment Y61: The method or pharmaceutical composition of any one of Embodiments Y54 to Y60, wherein the adult subject achieves ACR50 response following said treating.

Embodiment Y62: The method or pharmaceutical composition of any one of Embodiments Y54 to Y61, wherein the adult subject achieves ACR50 response at week 12 of said treating.

Embodiment Y63: The method or pharmaceutical composition of any one of Embodiments Y54 to Y62, wherein the adult subject achieves ACR50 response at week 8 of said treating.

Embodiment Y64: The method or pharmaceutical composition of any one of Embodiments Y54 to Y63, wherein the adult subject achieves ACR50 response at week 6 of said treating.

Embodiment Y65: The method or pharmaceutical composition of any one of Embodiments Y54 to Y64, wherein the adult subject achieves ACR50 response at week 4 of said treating.

Embodiment Y66: The method or pharmaceutical composition of any one of Embodiments Y54 to Y65, wherein the adult subject achieves ACR50 response at week 2 of said treating.

Embodiment Y67: The method or pharmaceutical composition of any one of Embodiments Y54 to Y66, wherein the adult subject achieves ACR70 response following said treating.

Embodiment Y68: The method or pharmaceutical composition of any one of Embodiments Y54 to Y67, wherein the adult subject achieves ACR70 response at week 12 of said treating.

Embodiment Y69: The method or pharmaceutical composition of any one of Embodiments Y54 to Y68, wherein the adult subject achieves ACR70 response at week 8 of said treating.

Embodiment Y70: The method or pharmaceutical composition of any one of Embodiments Y54 to Y69, wherein the adult subject achieves ACR70 response at week 6 of said treating.

Embodiment Y71: The method or pharmaceutical composition of any one of Embodiments Y54 to Y70, wherein the adult subject achieves ACR70 response at week 4 of said treating.

Embodiment Y72: The method or pharmaceutical composition of any one of Embodiments Y54 to Y71, wherein the adult subject achieves ACR70 response at week 2 of said treating.

Embodiment Y73: The method or pharmaceutical composition of any one of Embodiments Y to Y72, wherein the arthritis is further treated by alleviating at least one symptom selected from the group consisting of bone erosion, cartilage erosion, inflammation and vascularity.

Embodiment Y74: The method or pharmaceutical composition of Embodiment Y73, wherein the arthritis is further treated by alleviating at least one symptom selected from the group consisting of joint distortion, swelling, joint deformation, ankyloses on flexion and severely impaired movement.

Embodiment Y75: The method or pharmaceutical composition of any one of Embodiments Y to Y74, wherein the crystalline hydrate or crystalline anhydrate of Compound 1 is administered in an amount sufficient to deliver to the subject 7.5 mg of Compound 1 freebase equivalent.

Embodiment Y76: The method or pharmaceutical composition of any one of Embodiments Y to Y74, wherein the crystalline hydrate or the crystalline anhydrate of Compound 1 is administered in an amount sufficient to deliver to the subject 15 mg of Compound 1 freebase equivalent.

Embodiment Y77: The method or pharmaceutical composition of any one of Embodiments Y to Y74, wherein the crystalline hydrate or the crystalline anhydrate of Compound 1 is administered in an amount sufficient to deliver to the subject 30 mg of Compound 1 freebase equivalent.

Embodiment Y78: The method or pharmaceutical composition of any one of Embodiments Y to Y74, wherein the crystalline hydrate or the crystalline anhydrate of Compound 1 is administered in an amount sufficient to deliver to the subject 45 mg of Compound 1 freebase equivalent.

Embodiment Z: A method of treating structural damage associated with rheumatoid arthritis in an adult subject, the method comprising administering to the subject:

a) about 7.5 mg per day of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide (Compound 1) freebase or a pharmaceutically acceptable salt thereof, or a crystalline hydrate or crystalline anhydrate of Compound 1 in an amount sufficient to deliver to the subject about 7.5 mg per day of Compound 1 freebase equivalent; or b) about 15 mg per day of Compound 1 freebase or a pharmaceutically acceptable salt thereof, or a crystalline hydrate or crystalline anhydrate of Compound 1 in an amount sufficient to deliver to the subject about 15 mg per day of Compound 1 freebase equivalent; or c) about 30 mg per day of Compound 1 freebase or a pharmaceutically acceptable salt thereof, or a crystalline hydrate or crystalline anhydrate of Compound 1 in an amount sufficient to deliver to the subject about 30 mg per day of Compound 1 freebase equivalent; or d) about 45 mg per day of Compound 1 freebase or a pharmaceutically acceptable salt thereof, or a crystalline hydrate or crystalline anhydrate of Compound 1 in an amount sufficient to deliver to the subject about 45 mg per day of Compound 1 freebase equivalent;

such that the structural damage in the adult subject is inhibited or lessened.

Embodiment Z1: A pharmaceutical composition for use in treating structural damage associated with rheumatoid arthritis in an adult subject, wherein the pharmaceutical composition comprises:

a) about 7.5 mg per day of Compound 1 freebase or a pharmaceutically acceptable salt thereof, or a crystalline hydrate or crystalline anhydrate of Compound 1 in an amount sufficient to deliver to the subject about 7.5 mg per day of Compound 1 freebase equivalent; or b) about 15 mg per day of Compound 1 freebase or a pharmaceutically acceptable salt thereof, or a crystalline hydrate or crystalline anhydrate of Compound 1 in an amount sufficient to deliver to the subject about 15 mg per day of Compound 1 freebase equivalent; or c) about 30 mg per day of Compound 1 freebase or a pharmaceutically acceptable salt thereof, or a crystalline hydrate or crystalline anhydrate of Compound 1 in an amount sufficient to deliver to the subject about 30 mg per day of Compound 1 freebase equivalent; or d) about 45 mg per day of Compound 1 freebase or a pharmaceutically acceptable salt thereof, or a crystalline hydrate or crystalline anhydrate of Compound 1 in an amount sufficient to deliver to the subject about 45 mg per day of Compound 1 freebase equivalent;

such that the structural damage in the adult subject is inhibited or lessened. In certain aspects of Embodiment Z1, the use comprising administering the pharmaceutical composition to the subject, Embodiment Z2: A method of treating structural damage associated with rheumatoid arthritis in an adult subject, the method comprising administering to the subject about 7.5 mg per day of Compound 1 freebase or a pharmaceutically acceptable salt thereof, or a crystalline hydrate or crystalline anhydrate of Compound 1 in an amount sufficient to deliver to the subject about 15 mg per day of Compound 1 freebase equivalent, such that the structural damage in the adult subject is inhibited or lessened Embodiment Z3: The method of Embodiment Z2, comprising administering the crystalline hydrate or crystalline anhydrate of Compound 1 in an amount sufficient to deliver to the subject 7.5 mg of Compound 1 freebase equivalent.

Embodiment Z4: A method of treating structural damage associated with rheumatoid arthritis in an adult subject, the method comprising administering to the subject about 15 mg per day of Compound 1 freebase or a pharmaceutically acceptable salt thereof, or a crystalline hydrate or crystalline anhydrate of Compound 1 in an amount sufficient to deliver to the subject about 15 mg per day of Compound 1 freebase equivalent, such that the structural damage in the adult subject is inhibited or lessened.

Embodiment Z5: The method of Embodiment Z4, comprising administering the crystalline hydrate or crystalline anhydrate of Compound 1 in an amount sufficient to deliver to the subject 15 mg of Compound 1 freebase equivalent.

Embodiment Z6: A method of treating structural damage associated with rheumatoid arthritis in an adult subject, the method comprising administering to the subject about 30 mg per day of Compound 1 freebase or a pharmaceutically acceptable salt thereof, or a crystalline hydrate or crystalline anhydrate of Compound 1 in an amount sufficient to deliver to the subject about 30 mg per day of Compound 1 freebase equivalent, such that the structural damage in the adult subject is inhibited or lessened.

Embodiment Z7: The method of Embodiment Z6, comprising administering the crystalline hydrate or crystalline anhydrate of Compound 1 in an amount sufficient to deliver to the subject 30 mg of Compound 1 freebase equivalent.

Embodiment Z8: A method of treating structural damage associated with rheumatoid arthritis in an adult subject, the method comprising administering to the subject about 45 mg per day of Compound 1 freebase or a pharmaceutically acceptable salt thereof, or a crystalline hydrate or crystalline anhydrate of Compound 1 in an amount sufficient to deliver to the subject about 45 mg per day of Compound 1 freebase equivalent, such that the structural damage in the adult subject is inhibited or lessened.

Embodiment Z9: The method of Embodiment Z8, comprising administering the crystalline hydrate or crystalline anhydrate of Compound 1 in an amount sufficient to deliver to the subject 45 mg of Compound 1 freebase equivalent.

Embodiment Z10: The method or composition of any one of Embodiments Z to Z9, wherein the hydrate is a hemihydrate.

Embodiment Z11: The method or composition of Embodiment Z10, wherein the hydrate is Freebase Hydrate Form C.

Embodiment Z12: The method or composition of any one of Embodiments Z to Z9, wherein the anhydrate is Freebase Anhydrate Form D.

Embodiment Z13: The method or composition of any one of Embodiments Z to Z12, wherein the freebase or the hydrate or the anhydrate is in a once daily extended release formulation.

Embodiment AA: A method of treating moderate to severely active rheumatoid arthritis in an adult subject, the method comprising administering to the subject:
  a) about 7.5 mg per day of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide (Compound 1) freebase or a pharmaceutically acceptable salt thereof, or a crystalline hydrate or crystalline anhydrate of Compound 1 in an amount sufficient to deliver to the subject about 7.5 mg per day of Compound 1 freebase equivalent; or
  b) about 15 mg per day of Compound 1 freebase or a pharmaceutically acceptable salt thereof, or a crystalline hydrate or crystalline anhydrate of Compound 1 in an amount sufficient to deliver to the subject about 15 mg per day of Compound 1 freebase equivalent; or
  c) about 30 mg per day of Compound 1 freebase or a pharmaceutically acceptable salt thereof, or a crystalline hydrate or crystalline anhydrate of Compound 1 in an amount sufficient to deliver to the subject about 30 mg per day of Compound 1 freebase equivalent; or
  d) about 45 mg per day of Compound 1 freebase or a pharmaceutically acceptable salt thereof, or a crystalline hydrate or crystalline anhydrate of Compound 1 in an amount sufficient to deliver to the subject about 45 mg per day of Compound 1 freebase equivalent; and
  wherein the subject has symptoms selected from the group consisting of at least 6 swollen joints, at least 6 tender joints, and combinations thereof prior to treating.

Embodiment AA1: A pharmaceutical composition for use in treating moderate to severely active rheumatoid arthritis in an adult subject, wherein the pharmaceutical composition comprises:
  a) about 7.5 mg per day of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide (Compound 1) freebase or a pharmaceutically acceptable salt thereof, or a crystalline hydrate or crystalline anhydrate of Compound 1 in an amount sufficient to deliver to the subject about 7.5 mg per day of Compound 1 freebase equivalent; or
  b) about 15 mg per day of Compound 1 freebase or a pharmaceutically acceptable salt thereof, or a crystalline hydrate or crystalline anhydrate of Compound 1 in an amount sufficient to deliver to the subject about 15 mg per day of Compound 1 freebase equivalent; or
  c) about 30 mg per day of Compound 1 freebase or a pharmaceutically acceptable salt thereof, or a crystalline hydrate or crystalline anhydrate of Compound 1 in an amount sufficient to deliver to the subject about 30 mg per day of Compound 1 freebase equivalent; or
  d) about 45 mg per day of Compound 1 freebase or a pharmaceutically acceptable salt thereof, or a crystalline hydrate or crystalline anhydrate of Compound 1 in an amount sufficient to deliver to the subject about 45 mg per day of Compound 1 freebase equivalent; and
  wherein the subject has symptoms selected from the group consisting of at least 6 swollen joints, at least 6 tender joints, and combinations thereof prior to treating. In certain aspects of Embodiment AA1, the use comprising administering the pharmaceutical composition to the subject.

Embodiment AA2: A method of treating moderate to severely active rheumatoid arthritis in an adult subject, the method comprising administering to the subject about 7.5 mg per day of Compound 1 freebase or a pharmaceutically acceptable salt thereof, or a crystalline hydrate or crystalline anhydrate of Compound 1 in an amount sufficient to deliver to the subject about 7.5 mg per day of Compound 1 freebase equivalent, wherein the subject has symptoms selected from the group consisting of at least 6 swollen joints, at least 6 tender joints, and combinations thereof prior to treating.

Embodiment AA3: The method of Embodiment AA2, comprising administering the crystalline hydrate or crystalline anhydrate of Compound 1 in an amount sufficient to deliver to the subject 7.5 mg of Compound 1 freebase equivalent.

Embodiment AA4: A method of treating moderate to severely active rheumatoid arthritis in an adult subject, the method comprising administering to the subject about 15 mg per day of Compound 1 freebase or a pharmaceutically acceptable salt thereof, or a crystalline hydrate or crystalline anhydrate of Compound 1 in an amount sufficient to deliver to the subject about 15 mg per day of Compound 1 freebase equivalent, wherein the subject has symptoms selected from the group consisting of at least 6 swollen joints, at least 6 tender joints, and combinations thereof prior to treating.

Embodiment AA5: The method of Embodiment AA4, comprising administering the crystalline hydrate or crystalline anhydrate of Compound 1 in an amount sufficient to deliver to the subject 15 mg of Compound 1 freebase equivalent.

Embodiment AA6: A method of treating moderate to severely active rheumatoid arthritis in an adult subject, the method comprising administering to the subject about 30 mg per day of Compound 1 freebase or a pharmaceutically acceptable salt thereof, or a crystalline hydrate or crystalline anhydrate of Compound 1 in an amount sufficient to deliver to the subject about 30 mg per day of Compound 1 freebase equivalent, wherein the subject has symptoms selected from the group consisting of at least 6 swollen joints, at least 6 tender joints, and combinations thereof prior to treating.

Embodiment AA7: The method of Embodiment AA6, comprising administering the crystalline hydrate or crystalline anhydrate of Compound 1 in an amount sufficient to deliver to the subject 30 mg of Compound 1 freebase equivalent.

Embodiment AA8: A method of treating moderate to severely active rheumatoid arthritis in an adult subject, the method comprising administering to the subject about 45 mg per day of Compound 1 freebase or a pharmaceutically acceptable salt thereof, or a crystalline hydrate or crystalline anhydrate of Compound 1 in an amount sufficient to deliver to the subject about 45 mg per day of Compound 1 freebase equivalent, wherein the subject has symptoms selected from the group consisting of at least 6 swollen joints, at least 6 tender joints, and combinations thereof prior to treating.

Embodiment AA9: The method of Embodiment AA8, comprising administering the crystalline hydrate or crystalline anhydrate of Compound 1 in an amount sufficient to deliver to the subject 45 mg of Compound 1 freebase equivalent.

Embodiment AA10: The method or composition of any one of Embodiments AA to AA9, wherein said symptoms result from the progression of structural damage assessed by radiograph.

Embodiment BB: A method of reducing signs and symptoms of rheumatoid arthritis in an adult subject with moderately to severely active rheumatoid arthritis, the method comprising administering to the subject:
a) about 7.5 mg per day of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide (Compound 1) freebase or a pharmaceutically acceptable salt thereof, or a crystalline hydrate or crystalline anhydrate of Compound 1 in an amount sufficient to deliver to the subject about 7.5 mg of Compound 1 freebase equivalent; or
b) about 15 mg per day of Compound 1 freebase or a pharmaceutically acceptable salt thereof, or a crystalline hydrate or crystalline anhydrate of Compound 1 in an amount sufficient to deliver to the subject about 15 mg of Compound 1 freebase equivalent; or
c) about 30 mg per day of Compound 1 freebase or a pharmaceutically acceptable salt thereof, or a crystalline hydrate or crystalline anhydrate of Compound 1 in an amount sufficient to deliver to the subject about 30 mg of Compound 1 freebase equivalent; or
d) about 45 mg per day of Compound 1 freebase or a pharmaceutically acceptable salt thereof, or a crystalline hydrate or crystalline anhydrate of Compound 1 in an amount sufficient to deliver to the subject about 45 mg of Compound 1 freebase equivalent.

Embodiment BB1: A pharmaceutical composition for reducing signs and symptoms of rheumatoid arthritis in an adult subject with moderately to severely active rheumatoid arthritis, wherein the pharmaceutical composition comprises:
a) about 7.5 mg per day of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide (Compound 1) freebase or a pharmaceutically acceptable salt thereof, or a crystalline hydrate or crystalline anhydrate of Compound 1 in an amount sufficient to deliver to the subject about 7.5 mg of Compound 1 freebase equivalent; or
b) about 15 mg per day of Compound 1 freebase or a pharmaceutically acceptable salt thereof, or a crystalline hydrate or crystalline anhydrate of Compound 1 in an amount sufficient to deliver to the subject about 15 mg of Compound 1 freebase equivalent; or
c) about 30 mg per day of Compound 1 freebase or a pharmaceutically acceptable salt thereof, or a crystalline hydrate or crystalline anhydrate of Compound 1 in an amount sufficient to deliver to the subject about 30 mg of Compound 1 freebase equivalent; or
d) about 45 mg per day of Compound 1 freebase or a pharmaceutically acceptable salt thereof, or a crystalline hydrate or crystalline anhydrate of Compound 1 in an amount sufficient to deliver to the subject about 45 mg of Compound 1 freebase equivalent.

In certain aspects of Embodiment BB1, the use comprising administering the pharmaceutical composition to the subject.

Embodiment BB2: A method of reducing signs and symptoms of rheumatoid arthritis in an adult subject with moderately to severely active rheumatoid arthritis, the method comprising administering to the subject about 7.5 mg per day of Compound 1 freebase or a pharmaceutically acceptable salt thereof, or a crystalline hydrate or crystalline anhydrate of Compound 1 in an amount sufficient to deliver to the subject about 7.5 mg of Compound 1 freebase equivalent.

Embodiment BB3: The method of Embodiment BB2 wherein the freebase or hydrate or anhydrate is in a once daily extended release formulation.

Embodiment BB4: The method of Embodiment BB2 or BB3, wherein the hydrate is a hemihydrate.

Embodiment BB5: The method of Embodiment BB4, wherein the hemihydrate is Freebase Hydrate Form C.

Embodiment BB6: The method of Embodiment BB2 or BB3, wherein the anhydrate is Freebase Anhydrate Form D.

Embodiment BB7: The method of any one of Embodiments BB2 to BB6, wherein the crystalline hydrate or the crystalline anhydrate of Compound 1 is administered in an amount sufficient to deliver to the subject 7.5 mg of Compound 1 freebase equivalent.

Embodiment BB8: A method of reducing signs and symptoms of rheumatoid arthritis in an adult subject with moderately to severely active rheumatoid arthritis, the method comprising administering to the subject about 15 mg per day of Compound 1 freebase or a pharmaceutically acceptable salt thereof, or a crystalline hydrate or crystalline anhydrate of Compound 1 in an amount sufficient to deliver to the subject about 15 mg of Compound 1 freebase equivalent.

Embodiment BB9: The method of Embodiment BB8, wherein the freebase or hydrate or anhydrate is in a once daily extended release formulation.

Embodiment BB10: The method of Embodiment BB8 or BB9 wherein the hydrate is a hemihydrate.

Embodiment BB11: The method of Embodiment BB10, wherein the hemihydrate is Freebase Hydrate Form C.

Embodiment BB12: The method of Embodiment BB8 or BB9, wherein the anhydrate is Freebase Anhydrate Form D.

Embodiment BB13: The method of any one of Embodiments BB8 to BB12, wherein the crystalline hydrate or crystalline anhydrate of Compound 1 is administered in an amount sufficient to deliver to the subject 15 mg of Compound 1 freebase equivalent.

Embodiment BB14: A method of reducing signs and symptoms of rheumatoid arthritis in an adult subject with moderately to severely active rheumatoid arthritis, the method comprising administering to the subject about 30 mg per day of Compound 1 freebase or a pharmaceutically acceptable salt thereof, or a crystalline hydrate or crystalline anhydrate of Compound 1 in an amount sufficient to deliver to the subject about 30 mg of Compound 1 freebase equivalent.

Embodiment BB15: The method of Embodiment BB14, wherein the freebase or hydrate or anhydrate is in a once daily extended release formulation.

Embodiment BB16: The method of Embodiment BB14 or BB15, wherein the hydrate is a hemihydrate.

Embodiment BB17: The method of Embodiment BB16 wherein the hemihydrate is Freebase Hydrate Form C.

Embodiment BB18: The method of Embodiment BB14 or BB15, wherein the anhydrate is Freebase Anhydrate Form D.

Embodiment BB19: The method of any one of Embodiments BB14 to BB17, wherein the crystalline hydrate or crystalline anhydrate of Compound 1 is administered in an amount sufficient to deliver to the subject 30 mg of Compound 1 freebase equivalent.

Embodiment BB20: A method of reducing signs and symptoms of rheumatoid arthritis in an adult subject with moderately to severely active rheumatoid arthritis, the method comprising administering to the subject about 45 mg per day of Compound 1 freebase or a pharmaceutically acceptable salt thereof, or a crystalline hydrate or crystalline anhydrate of Compound 1 in an amount sufficient to deliver to the subject about 45 mg of Compound 1 freebase equivalent.

Embodiment BB21: The method of Embodiment BB20, wherein the freebase or hydrate or anhydrate is in a once daily extended release formulation.

Embodiment BB22: The method of Embodiment BB20 or BB21, wherein the hydrate is a hemihydrate.

Embodiment BB23: The method of Embodiment BB22, wherein the hemihydrate is Freebase Hydrate Form C.

Embodiment BB24: The method of Embodiment BB20 or BB21, wherein the anhydrate is Freebase Anhydrate Form C.

Embodiment BB25: The method of any one of Embodiments BB20 to BB24 wherein the crystalline hydrate or crystalline anhydrate of Compound 1 is administered in an amount sufficient to deliver to the subject 45 mg of Compound 1 freebase equivalent.

Embodiment BB26: The method or composition of any one of Embodiments BB to BB25, wherein the method or use further comprises alleviating at least one symptom of arthritis selected from the group consisting of bone erosion, cartilage erosion, inflammation and vascularity.

Embodiment BB27: The method or composition of Embodiment B26, wherein the method or use further comprises alleviating at least one symptom of arthritis selected from the group consisting of joint distortion, swelling, joint deformation, ankyloses on flexion and severely impaired movement.

Embodiment BB28: The method or composition of any one of Embodiments Y to Y78, Z to Z13, AA to AA10, or BB to BB27, wherein the freebase or hydrate or anhydrate is administered for at least 8 weeks.

Embodiment BB29: The method or composition of Embodiment BB28, wherein the freebase or hydrate is administered for at least 12 weeks.

Embodiment CC: The method or pharmaceutical composition of any one of Embodiments Y to Y78, Z to Z13, AA to AA10, or BB to BB29, comprising administering to the subject about 7.5 mg, or about 15 mg, or about 30 mg, or about 45 mg per day of a crystalline hydrate or a crystalline anhydrate of Compound 1.

Embodiment CC1: The method or pharmaceutical composition of any one of Embodiments Y to Y78, Z to Z13, AA to AA10, or BB to BB29, wherein the crystalline anhydrate is Freebase Anhydrate Form D.

Embodiment CC2: The method or pharmaceutical composition of any one of Embodiments Y to Y78, Z to Z13, AA to AA10, or BB to BB29, wherein the crystalline hydrate of Compound 1 is administered in an amount sufficient to deliver to the subject about 7.5 mg of Compound 1 freebase equivalent.

Embodiment CC2a: The method or pharmaceutical composition of Embodiment CC2, wherein the hydrate is a hemihydrate.

Embodiment CC2b: The method or pharmaceutical composition of Embodiment CC2a, wherein the hydrate is Freebase Hydrate Form C.

Embodiment CC2c: The method or pharmaceutical composition of any one of Embodiments CC2 to CC2b, wherein the crystalline hydrate is in a once daily extended release formulation.

Embodiment CC3: The method or pharmaceutical composition of any one of Embodiments Y to Y78, Z to Z13, AA to AA10, or BB to BB29, wherein the crystalline hydrate of Compound 1 is administered in an amount sufficient to deliver to the subject about 45 mg of Compound 1 freebase equivalent.

Embodiment CC3a: The method or pharmaceutical composition of Embodiment CC3, wherein the hydrate is a hemihydrate.

Embodiment CC3b: The method or pharmaceutical composition of Embodiment CC3a, wherein the hydrate is Freebase Hydrate Form C.

Embodiment CC3c: The method or pharmaceutical composition of any one of Embodiments CC3 to CC3b, wherein the crystalline hydrate is in a once daily extended release formulation.

Embodiment CC4: The method or pharmaceutical composition of any one of Embodiments Y to Y78, Z to Z13, AA to AA10, or BB to BB29, wherein the crystalline hydrate of Compound 1 is administered in an amount sufficient to deliver to the subject about 15 mg of Compound 1 freebase equivalent.

Embodiment CC4a: The method or pharmaceutical composition of Embodiment CC4, wherein the hydrate is a hemihydrate.

Embodiment CC4b: The method or pharmaceutical composition of Embodiment CC4a, wherein the hydrate is Freebase Hydrate Form C.

Embodiment CC4c: The method or pharmaceutical composition of any one of Embodiments CC4 to CC4b, wherein the crystalline hydrate is in a once daily extended release formulation.

Embodiment CC4d: The method or pharmaceutical composition of any one of Embodiments CC4 to CC4c, wherein administration of the crystalline hydrate achieves a mean peak plasma concentration ($C_{max}$) for Compound 1 of from about 25 to about 70 ng/mL.

Embodiment CC4e: The method or pharmaceutical composition of any one of Embodiments CC4 to CC4d, wherein administration of the crystalline hydrate achieves a mean peak plasma concentration ($C_{max}$) for Compound 1 of from about 25 to about 40 ng/mL.

Embodiment CC4f: The method or pharmaceutical composition of any one of Embodiments CC4 to CC4e, wherein administration of the hydrate under fasting conditions achieves a mean $C_{max}$ for Compound 1 of about 26.0 ng/mL.

Embodiment CC4g: The method or pharmaceutical composition of any one of Embodiments CC4 to CC4e, wherein administration of the hydrate under fasting conditions achieves a mean $C_{max}$ for Compound 1 of about 32 ng/mL.

Embodiment CC4h: The method or pharmaceutical composition of any one of Embodiments CC4 to CC4g, wherein administration of the hydrate under non-fasting conditions achieves a mean $C_{max}$ for Compound 1 of about 37 ng/mL.

Embodiment CC4i: The method or pharmaceutical composition of any one of Embodiments CC4 to CC4g, wherein administration of the hydrate under non-fasting conditions achieves a mean $C_{max}$ for Compound 1 of about 40 ng/mL.

Embodiment CC4j: The method or pharmaceutical composition of any one of Embodiments CC4 to CC4i, wherein the difference in the $C_{max}$ for Compound 1 when the hydrate is administered in the fed versus the fasted state is selected from the group consisting of about 30% or less, about 20% or less, and about 10% or less.

Embodiment CC4k: The method or pharmaceutical composition of any one of Embodiments CC4 to CC4j, wherein administration of the crystalline hydrate achieves a time to peak plasma concentration ($T_{max}$) for Compound 1 of from about 1.0 to about 6.0 hours.

Embodiment CC4l: The method or pharmaceutical composition of any one of Embodiments CC4 to CC4k, wherein administration of the hydrate under fasting conditions achieves a $T_{max}$ for Compound 1 of from about 1.0 to about 4.0 hours.

Embodiment CC4m: The method or pharmaceutical composition of any one of Embodiments CC4 to CC4k, wherein administration of the hydrate under fasting conditions achieves a $T_{max}$ for Compound 1 of from about 1.5 to about 6.0 hours.

Embodiment CC4n: The method or pharmaceutical composition of any one of Embodiments CC4 to CC4m, wherein administration of the hydrate under fasting conditions achieves a median $T_{max}$ for Compound 1 of about 3.0 hours.

Embodiment CC4o: The method or pharmaceutical composition of any one of Embodiments CC4 to CC4n, wherein administration of the hydrate under non-fasting conditions achieves a $T_{max}$ for Compound 1 of from about 3.0 to about 6.0 hours.

Embodiment CC4p: The method or pharmaceutical composition of any one of Embodiments CC4 to CC4o, wherein administration of the hydrate under non-fasting conditions achieves a median $T_{max}$ for Compound 1 of about 4.0 hours.

Embodiment CC4q: The method or pharmaceutical composition of any one of Embodiments CC4 to CC4p, wherein administration of the crystalline hydrate achieves a mean area under the plasma concentration time curve from time 0 to infinity ($AUC_{inf}$) for Compound 1 of from about 220 to about 450 ng·hours/mL.

Embodiment CC4r: The method or pharmaceutical composition of any one of Embodiments CC4 to CC4q, wherein administration of the hydrate under fasting conditions achieves a mean $AUC_{inf}$ for Compound 1 of about 242 ng·hours/mL.

Embodiment CC4s: The method or pharmaceutical composition of any one of Embodiments CC4 to CC4r, wherein administration of the crystalline hydrate achieves a harmonic mean terminal half-life ($t_{1/2}$) for Compound 1 of from about 10.0 to about 14.0 hours.

Embodiment CC4t: The method or pharmaceutical composition of any one of Embodiments CC4 to CC4s, wherein administration of the crystalline hydrate achieves a harmonic mean $t_{1/2}$ for Compound 1 of about 12.5 hours.

Embodiment CC4u: The method or pharmaceutical composition of any one of Embodiments CC4 to CC4t, wherein administration of the crystalline hydrate achieves a mean peak steady-state plasma concentration ($C_{max,ss}$) for Compound 1 of from about 27 to about 55 ng/mL.

Embodiment CC4v: The method or pharmaceutical composition of any one of Embodiments CC4 to CC4u, wherein administration of the hydrate under fasting conditions achieves a mean $C_{max,ss}$ for Compound 1 of about 32 ng/mL.

Embodiment CC4w: The method or pharmaceutical composition of any one of Embodiments CC4 to CC4v, wherein administration of the hydrate under non-fasting conditions achieves a mean $C_{max,ss}$ for Compound 1 of about 37 or about 37 ng/mL.

Embodiment CC4x: The method or pharmaceutical composition of any one of Embodiments CC4 to CC4w, wherein administration of the crystalline hydrate achieves a time to peak plasma concentration at steady-state ($T_{max,ss}$) of from about 1.5 to about 6.0 hours.

Embodiment CC4y: The method or pharmaceutical composition of any one of Embodiments CC4 to CC4x, wherein administration of the hydrate under fasting conditions achieves a $T_{max,ss}$ of from about 1.5 to about 4.0 hours.

Embodiment CC4z: The method or pharmaceutical composition of any one of Embodiments CC4 to CC4y, wherein administration of the hydrate under fasting conditions achieves a median $T_{max,ss}$ of about 2.5 hours.

Embodiment CC4aa: The method or pharmaceutical composition of any one of Embodiments CC4 to CC4z, wherein administration of the hydrate under non-fasting conditions achieves a $T_{max,ss}$ of from about 2.0 to about 6.0 hours.

Embodiment CC4bb: The method or pharmaceutical composition of any one of Embodiments CC4 to CC4aa, wherein administration of the hydrate under non-fasting conditions achieves a median $T_{max,ss}$ of about 4.0 hours.

Embodiment CC4cc: The method or pharmaceutical composition of any one of Embodiments CC4 to CC4bb, wherein administration of the crystalline hydrate achieves a mean steady-state area under the plasma concentration time curve from time 0 to 24 hours ($AUC_{24,ss}$) for Compound 1 of from about 240 to about 325 ng·hours/mL.

Embodiment CC4dd: The method or pharmaceutical composition of any one of Embodiments CC4 to CC4cc, wherein administration of the hydrate under fasting conditions achieves a mean $AUC_{24,ss}$ for Compound 1 of about 241 ng·hours/mL.

Embodiment CC4ee: The method or pharmaceutical composition of any one of Embodiments CC4 to CC4cc, wherein administration of the hydrate under fasting conditions achieves a mean $AUC_{24,ss}$ for Compound 1 of about 279 ng·hours/mL.

Embodiment CC4ff: The method or pharmaceutical composition of any one of Embodiments CC4 to CC4ee, wherein administration of the hydrate under non-fasting conditions achieves a mean $AUC_{24,ss}$ for Compound 1 of about 317 ng·hours/mL.

Embodiment CC4gg: The method or pharmaceutical composition of any one of Embodiments CC4 to CC4ee, wherein administration of the hydrate under non-fasting conditions achieves a mean $AUC_{24,ss}$ for Compound 1 of about 322 ng·hours/mL.

Embodiment CC4hh: The method or pharmaceutical composition of any one of Embodiments CC4 to CC4gg, wherein administration of the crystalline hydrate achieves a harmonic mean steady-state terminal half-life ($t_{1/2,ss}$) for Compound 1 of from about 9.4 to about 10.5 hours.

Embodiment CC4ii: The method or pharmaceutical composition of any one of Embodiments CC4 to CC4hh, wherein administration of the crystalline hydrate achieves a harmonic mean $t_{1/2,ss}$ for Compound 1 of about 9.4 hours or about 9.5 hours or about 10.3 hours.

Embodiment CC4jj: The method or pharmaceutical composition of any one of Embodiments CC4 to CC4ii, wherein administration of the crystalline hydrate achieves a mean minimum steady-state plasma concentration ($C_{min,ss}$) for Compound 1 of from about 2.8 to about 3.2 ng/mL.

Embodiment CC4kk: The method or pharmaceutical composition of any one of Embodiments CC4 to CC4jj, wherein administration of the crystalline hydrate achieves a mean minimum steady-state plasma concentration ($C_{min,ss}$) for Compound 1 of about 2.8 or about 3.0 ng/mL.

Embodiment CC5: The method or pharmaceutical composition of any one of Embodiments Y to Y78, Z to Z13, AA to AA10, or BB to BB29, wherein the crystalline hydrate of Compound 1 is administered in an amount sufficient to deliver to the subject about 30 mg of Compound 1 freebase equivalent.

Embodiment CC5a: The method or pharmaceutical composition of Embodiment CC5, wherein the hydrate is a hemihydrate.

Embodiment CC5b: The method or pharmaceutical composition of Embodiment CC5a, wherein the hydrate is Freebase Hydrate Form C.

Embodiment CC5c: The method or pharmaceutical composition of any one of Embodiments CC5 to CC5b, wherein the crystalline hydrate is in a once daily extended release formulation.

Embodiment CC5d: The method or pharmaceutical composition of any one of Embodiments CC5 to CC5c, wherein administration of the crystalline hydrate achieves a mean $C_{max}$ for Compound 1 of from about 55 to about 85 ng/mL.

Embodiment CC5e: The method or pharmaceutical composition of any one of Embodiments CC5 to CC5d, wherein administration of the hydrate under fasting conditions achieves a mean $C_{max}$ for Compound 1 of from about 55 ng/mL to about 66 ng/mL.

Embodiment CC5f: The method or pharmaceutical composition of any one of Embodiments CC5 to CC5e, wherein administration of the hydrate under fasting conditions achieves a mean $C_{max}$ for Compound 1 of about 55 ng/mL, or about 56 ng/mL, or about 57 ng/mL, or about 59 ng/mL, or about 61 ng/mL, or about 64 ng/mL, or about 66 ng/mL.

Embodiment CC5g: The method or pharmaceutical composition of any one of Embodiments CC5 to CC5f, wherein administration of the hydrate under non-fasting conditions achieves a mean $C_{max}$ for Compound 1 of from about 74 ng/mL to about 85 ng/mL.

Embodiment CC5h: The method or pharmaceutical composition of any one of Embodiments CC5 to CC5g, wherein administration of the hydrate under non-fasting conditions achieves a mean $C_{max}$ for Compound 1 of about 74 ng/mL, or about 76 ng/mL, or about 77 ng/mL, or about 79 ng/mL, about 82 ng/mL, or about 84 ng/mL.

Embodiment CC5i: The method or pharmaceutical composition of any one of Embodiments CC5 to CC5h, wherein the difference in the $C_{max}$ for Compound 1 when the hydrate is administered in the fed versus the fasted state is selected from the group consisting of about 55% or less, about 53% or less, about 20% or less, about 10% or less, from about 3% to about 40%, and from about 15% to about 55%.

Embodiment CC5j: The method or pharmaceutical composition of any one of Embodiments CC5 to CC5i, wherein administration of the crystalline hydrate achieves a $T_{max}$ for Compound 1 of from about 1.0 to about 8.0 hours.

Embodiment CC5k: The method or pharmaceutical composition of any one of Embodiments CC5 to CC5j, wherein administration of the hydrate under fasting conditions achieves a $T_{max}$ for Compound 1 of from about 1.0 to about 4.0 hours.

Embodiment CC5l: The method or pharmaceutical composition of any one of Embodiments CC5 to CC5k, wherein administration of the hydrate under fasting conditions achieves a median $T_{max}$ for Compound 1 of about 2.0 hours or about 2.5 hours, or about 3.0 hours.

Embodiment CC5m: The method or pharmaceutical composition of any one of Embodiments CC5 to CC5l, wherein administration of the hydrate under non-fasting conditions achieves a $T_{max}$ for Compound 1 of from about 1.5 to about 8.0 hours.

Embodiment CC5n: The method or pharmaceutical composition of any one of Embodiments CC5 to CC5m, wherein administration of the hydrate under non-fasting conditions achieves a median $T_{max}$ for Compound 1 of about 4.0 hours.

Embodiment CC5o: The method or pharmaceutical composition of any one of Embodiments CC5 to CC5n, wherein administration of the crystalline hydrate achieves a mean $AUC_{inf}$ for Compound 1 of from about 483 to about 660 ng-hours/mL.

Embodiment CC5p: The method or pharmaceutical composition of any one of Embodiments CC5 to CC5o, wherein administration of the hydrate under fasting conditions achieves a mean $AUC_{24,inf}$ for Compound 1 of from about 484 to about 550 ng·hours/mL.

Embodiment CC5q: The method or pharmaceutical composition of any one of Embodiments CC5 to CC5p, wherein administration of the hydrate under fasting conditions achieves a mean $AUC_{inf}$ for Compound 1 of about 484 ng·hours/mL, or about 491 ng·hours/mL, or about 495 ng·hours/mL, or about 499 ng·hours/mL, or about 513 ng·hours/mL.

Embodiment CC5r: The method or pharmaceutical composition of any one of Embodiments CC5 to CC5q, wherein administration of the hydrate under non-fasting conditions achieves a mean $AUC_{inf}$ for Compound 1 of from about 560 to about 660 ng·hours/mL.

Embodiment CC5s: The method or pharmaceutical composition of any one of Embodiments CC5 to CC5r, wherein administration of the hydrate under non-fasting conditions achieves a mean $AUC_{inf}$ for Compound 1 of about 577 ng·hours/mL, or about 609 ng·hours/mL, or about 622 ng·hours/mL, or about 657 ng·hours/mL.

Embodiment CC5t: The method or pharmaceutical composition of any one of Embodiments CC5 to CC5s, wherein administration of the crystalline hydrate achieves a harmonic mean $t_{1/2}$ for Compound 1 of from about 9.0 to about 12.0 hours.

Embodiment CC5u: The method or pharmaceutical composition of any one of Embodiments CC5 to CC5t, wherein administration of the crystalline hydrate achieves a mean $C_{max,ss}$ for Compound 1 of from about 65 to about 86 ng/mL.

Embodiment CC5v: The method or pharmaceutical composition of any one of Embodiments CC5 to CC5u, wherein administration of the hydrate under fasting conditions achieves a mean $C_{max,ss}$ for Compound 1 of about 67 ng/mL.

Embodiment CC5w: The method or pharmaceutical composition of any one of Embodiments CC5 to CC5u, wherein administration of the hydrate under fasting conditions achieves a mean $C_{max,ss}$ for Compound 1 of about 68 ng/mL.

Embodiment CC5x: The method or pharmaceutical composition of any one of Embodiments CC5 to CC5w, wherein administration of the hydrate under non-fasting conditions achieves a mean $C_{max,ss}$ for Compound 1 of about 80 ng/mL.

Embodiment CC5y: The method or pharmaceutical composition of any one of Embodiments CC5 to CC5w, wherein administration of the hydrate under non-fasting conditions achieves a mean $C_{max,ss}$ for Compound 1 of about 84 ng/mL.

Embodiment CC5z: The method or pharmaceutical composition of any one of Embodiments CC5 to CC5y, wherein administration of the crystalline hydrate achieves a mean $AUC_{24,ss}$ for Compound 1 of from about 485 to about 658 ng-hours/mL.

Embodiment CC5aa: The method or pharmaceutical composition of any one of Embodiments CC5 to CC5z, wherein administration of the hydrate under fasting conditions achieves a mean $AUC_{24,ss}$ for Compound 1 of about 525 ng-hours/mL.

Embodiment CC5bb: The method or pharmaceutical composition of any one of Embodiments CC5 to CC5aa, wherein administration of the hydrate under non-fasting conditions achieves a mean $AUC_{24,ss}$ for Compound 1 of about 582 ng-hours/mL.

Embodiment CC5cc: The method or pharmaceutical composition of any one of Embodiments CC5 to CC5aa, wherein administration of the hydrate under non-fasting conditions achieves a mean $AUC_{24,ss}$ for Compound 1 of about 620 ng-hours/mL.

Embodiment CC5dd: The method or pharmaceutical composition of any one of Embodiments CC5 to CC5cc, wherein administration of the crystalline hydrate achieves a $T_{max,ss}$ of from about 1.5 to about 6.0 hours.

Embodiment CC5ee: The method or pharmaceutical composition of any one of Embodiments CC5 to CC5dd, wherein administration of the hydrate under fasting conditions achieves a $T_{max,ss}$ of from about 2.0 to about 4.0 hours.

Embodiment CC5ff: The method or pharmaceutical composition of any one of Embodiments CC5 to CC5ee, wherein administration of the hydrate under fasting conditions achieves a median $T_{max,ss}$ of about 3.0 hours.

Embodiment CC5gg: The method or pharmaceutical composition of any one of Embodiments CC5 to CC5ff, wherein administration of the hydrate under non-fasting conditions achieves a median $T_{max,ss}$ of about 3.5 hours or about 4.0 hours.

Embodiment CC5hh: The method or pharmaceutical composition of any one of Embodiments CC5 to CC5gg, wherein administration of the crystalline hydrate achieves a harmonic mean $t_{1/2,ss}$ for Compound 1 of from about 10.0 to about 14.5 hours.

Embodiment CC5ii: The method or pharmaceutical composition of any one of Embodiments CC5 to CC5hh, wherein administration of the crystalline hydrate achieves a harmonic mean $t_{1/2,ss}$ for Compound 1 of about 10.1 hours or about 10.4 hours, or about 14.4 hours.

Embodiment CC5jj: The method or pharmaceutical composition of any one of Embodiments CC5 to CC5ii, wherein administration of the crystalline hydrate achieves a mean $C_{min,ss}$ for Compound 1 of from about 3.5 to about 5.3 ng/mL.

Embodiment CC5kk: The method or pharmaceutical composition of any one of Embodiments CC5 to CC5jj, wherein administration of the crystalline hydrate under fasting conditions achieves a mean $C_{min,ss}$ for Compound 1 of about 3.8 ng/mL.

Embodiment CC5ll: The method or pharmaceutical composition of any one of Embodiments CC5 to CC5jj, wherein administration of the crystalline hydrate under non-fasting conditions achieves a mean $C_{min,ss}$ for Compound 1 of about 4.6 ng/mL or about 5.2 ng/mL.

Embodiment DD: A pharmaceutical composition comprising a crystalline hydrate or a crystalline anhydrate of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide (Compound 1) and a pharmaceutically acceptable carrier, wherein the composition comprises the crystalline hydrate or the crystalline anhydrate in an amount sufficient to deliver about 7.5 mg of Compound 1 freebase equivalent or about 15 mg of Compound 1 freebase equivalent or about 30 mg of Compound 1 freebase equivalent or about 45 mg of Compound 1 freebase equivalent.

Embodiment DD1: A pharmaceutical composition comprising about 7.5 mg, or about 15 mg, or about 30 mg, or about 45 mg of a crystalline hydrate or a crystalline anhydrate of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide (Compound 1), and a pharmaceutically acceptable carrier.

Embodiment DD2: A pharmaceutical composition comprising a crystalline hydrate of Compound 1 and a pharmaceutically acceptable carrier, wherein the composition comprises the crystalline hydrate in an amount sufficient to deliver about 15 mg of Compound 1 freebase equivalent.

Embodiment DD3: A pharmaceutical composition comprising a crystalline hydrate of Compound 1 and a pharmaceutically acceptable carrier, wherein the composition comprises the crystalline hydrate in an amount sufficient to deliver about 30 mg of Compound 1 freebase equivalent.

Embodiment DD4: The composition of any one of Embodiments DD to DD3, wherein the hydrate is Freebase Hydrate Form C.

Embodiment DD5: The composition of any one of Embodiments DD to DD4, wherein the hydrate or the anhydrate is in a once daily extended release formulation.

Embodiment DD6: The composition of Embodiment DD4 or DD5, wherein the composition comprises about 15 mg of Freebase Hydrate Form C, and administration of the composition to a subject provides:

(a) a mean $C_{max}$ for Compound 1 of from about 25 to about 70 ng/mL;

(b) a $T_{max}$ for Compound 1 of from about 1.0 hours to about 6.0 hours;

(c) a harmonic mean $t_{1/2}$ for Compound 1 of from about 10.0 to about 14.0 hours;

(d) a mean $AUC_{inf}$ for Compound 1 of from about 220 to about 450 ng-hours/mL;

(e) a mean $C_{max,ss}$ for Compound 1 of from about 27 to about 55 ng/mL;

(f) a mean $AUC_{24,ss}$ for Compound 1 of from about 240 to about 325 ng-hours/mL;

(g) a $T_{max,ss}$ for Compound 1 of from about 1.5 to about 6.0 hours;

(h) a mean $C_{min,ss}$ for Compound 1 of from about 2.8 to about 3.2 ng/mL;

(i) a harmonic mean $t_{1/2,ss}$ for Compound 1 of from about 9.4 to about 10.5 hours;

or any combination thereof.

Embodiment DD7: The composition of Embodiment DD4 or DD5, wherein the composition comprises about 30 mg of Freebase Hydrate Form C, and administration of the composition to a subject provides:

(a) a mean $C_{max}$ for Compound 1 of from about 55 to about 85 ng/mL;

(b) a $T_{max}$ for Compound 1 of from about 1.0 hours to about 8.0 hours;

(c) a harmonic mean $t_{1/2}$ for Compound 1 of from about 9.0 to about 12.0 hours;

(d) a mean $AUC_{inf}$ for Compound 1 of from about 483 to about 660 ng-hours/mL;

(e) a mean $C_{max,ss}$ for Compound 1 of from about 65 to about 85 ng/mL;

(f) a mean $AUC_{24,ss}$ for Compound 1 of from about 485 to about 658 ng-hours/mL;

(g) a $T_{max,ss}$ for Compound 1 of from about 1.5 to about 6.0 hours;

(h) a mean $C_{min,ss}$ for Compound 1 of from about 3.5 to about 5.3 ng/mL;

(i) a harmonic mean $t_{1/2,ss}$ for Compound 1 of from about 10.0 to about 14.5 hours;

or any combination thereof.

Embodiment DD8: A pharmaceutical composition comprising a crystalline hydrate of Compound 1 and a pharmaceutically acceptable carrier, wherein the composition comprises the crystalline hydrate in an amount sufficient to deliver about 7.5 mg of Compound 1 freebase equivalent.

Embodiment DD9: The composition of Embodiment DD8, wherein the hydrate is Freebase Hydrate Form C.

Embodiment DD10: The composition of Embodiment DD8 or DD9, wherein the hydrate is in a once daily extended release formulation.

Embodiment DD11: The composition of any one of Embodiments DD8 to DD10, wherein the composition comprises the hydrate in an amount sufficient to deliver 7.5 mg of Compound 1 freebase equivalent.

Embodiment DD12: A pharmaceutical composition comprising a crystalline hydrate of Compound 1 and a pharmaceutically acceptable carrier, wherein the composition comprises the crystalline hydrate in an amount sufficient to deliver about 45 mg of Compound 1 freebase equivalent.

Embodiment DD13: The composition of Embodiment DD12, wherein the hydrate is Freebase Hydrate Form C.

Embodiment DD14: The composition of Embodiment DD12 or DD13, wherein the hydrate is in a once daily extended release formulation.

Embodiment DD15: The composition of any one of Embodiments DD12 to DD14, wherein the composition comprises the hydrate in an amount sufficient to deliver 45 mg of Compound 1 freebase equivalent.

Embodiment EE: A method of treating an adult subject having moderate to severely active rheumatoid arthritis, the method comprising administering to the subject about 7.5 mg, or about 15 mg, or about 30 mg, or about 45 mg of a crystalline hydrate of Compound 1.

Embodiment EE1: A method of treating structural damage associated with rheumatoid arthritis in an adult subject, the method comprising administering to the subject about 7.5 mg, or about 15 mg, or about 30 mg, or about 45 mg per day of a crystalline hydrate of Compound 1, such that the structural damage in the adult subject is inhibited or lessened.

Embodiment EE2: A method of treating moderate to severely active rheumatoid arthritis in an adult subject, the method comprising administering to the subject about 7.5 mg, or about 15 mg, or about 30 mg, or about 45 mg per day of a crystalline hydrate of Compound 1, wherein the subject has symptoms selected from the group consisting of at least 6 swollen joints, at least 6 tender joints, and combinations thereof prior to treating.

Embodiment EE3: A method of reducing signs and symptoms of rheumatoid arthritis in an adult subject with moderately to severely active rheumatoid arthritis, the method comprising administering to the subject about 7.5 mg, or about 15 mg, or about 30 mg, or about 45 mg per day of a crystalline hydrate of Compound 1.

Embodiment EE4: The method of any one of Embodiments EE to EE3, wherein the hydrate is a hemihydrate.

Embodiment EE5: The method of Embodiment EE4, wherein the hydrate is Freebase Hydrate Form C.

Embodiment EE6: The method of any one of Embodiments EE to EE5, wherein the hydrate is in a once daily extended release formulation.

Embodiment FF: A pharmaceutical composition comprising about 7.5 mg, or about 15 mg, or about 30 mg, or about 45 mg of a crystalline hydrate of Compound 1, and a pharmaceutically acceptable carrier.

Embodiment FF1: The composition of Embodiment FF, wherein the hydrate is a hemihydrate.

Embodiment FF2: The composition of Embodiment FF1, wherein the hydrate is Freebase Hydrate Form C.

Embodiment FF3: The composition of any one of Embodiments FF to FF2 wherein the freebase or the hydrate is in a once daily extended release formulation.

Embodiment GG: An extended release formulation for oral administration comprising Compound 1 or a pharmaceutically acceptable salt thereof, a hydrophilic polymer, and a pH modifier, wherein the hydrophilic polymer, in contact with water, forms a gel layer that provides an environment suitable for Compound 1 and the pH modifier to dissolve.

Embodiment GG1: An extended release formulation for oral administration comprising a solid state form of Compound 1, a hydrophilic polymer, and a pH modifier, wherein the hydrophilic polymer, in contact with water, forms a gel layer that provides an environment suitable for the solid state form of Compound 1 and the pH modifier to dissolve.

Embodiment GG1a: The extended release formulation of Embodiment GG1, wherein the solid state form is a crystalline hydrate.

Embodiment GG1b: The extended release formulation of Embodiment GG1a, wherein the crystalline hydrate is a hemihydrate.

Embodiment GG1c: The extended release formulation of Embodiment GG1b, wherein the hemihydrate is Freebase Hydrate Form C.

Embodiment GG1d: The extended release formulation of Embodiment GG1a, wherein the crystalline hydrate is Freebase Hydrate Form B.

Embodiment GG1e: The extended release formulation of Embodiment GG1, wherein the solid state form is a crystalline anhydrate.

Embodiment GG1f: The extended release formulation of Embodiment GG1e, wherein the crystalline anhydrate is Freebase Anhydrate Form D.

Embodiment GG2: The extended release formulation of any one of Embodiments GG to GG1f, wherein the environment suitable for Compound 1 or the solid state form to dissolve has a pH equal to or less than 3.8 at 37° C.

Embodiment GG2a: The extended release formulation of any one of Embodiments GG to GG2, wherein the environment suitable for Compound 1 or the solid state form to dissolve has a pH of 1.5 to 3.7.

Embodiment GG3: The extended release formulation of any one of Embodiments GG to GG2a, wherein the environment suitable for Compound 1 or the solid state form to dissolve has a pH of 2.0 to 3.7.

Embodiment GG4: The extended release formulation of any one of Embodiments GG to GG3, wherein the environment suitable for Compound 1 or the solid state form to dissolve has a pH of 2.5 to 3.6.

Embodiment GG5: The extended release formulation of any one of Embodiments GG to GG4, wherein the environment suitable for Compound 1 or the solid state form to dissolve has a pH of 3.0 to 3.6.

Embodiment GG6: The extended release formulation of any one of Embodiments GG to GG5, wherein the environment suitable for Compound 1 or the solid state form to dissolve has a pH of 3.0 to 3.5.

Embodiment GG7: The extended release formulation of any one of Embodiments GG to GG6, wherein the pH modifier is selected from the group consisting of tartaric acid, fumaric acid, citric acid, succinic acid, malic acid, and combinations thereof.

Embodiment GG8: The extended release formulation of any one of Embodiments GG to GG7, wherein the pH modifier is selected from the group consisting of tartaric acid, fumaric acid, citric acid, succinic acid and combinations thereof.

Embodiment GG9: The extended release formulation of any one of Embodiments GG to GG8, wherein the pH modifier is selected from the group consisting of tartaric acid, fumaric acid, and combinations thereof.

Embodiment GG10: The extended release formulation of any one of Embodiments GG to GG9, wherein the pH modifier is tartaric acid.

Embodiment GG11: The extended release formulation of any one of Embodiments GG to GG10, wherein the pH modifier is fumaric acid or citric acid.

Embodiment GG12: The extended release formulation of any one of Embodiments GG to GG11, wherein the pH modifier is present in an amount of from about 10 to about 35 w/w %.

Embodiment GG13: The extended release formulation of any one of Embodiments GG to GG12, wherein the pH modifier is present in an amount of from about 20 to about 35% w/w.

Embodiment GG14: The extended release formulation of any one of Embodiments GG to GG13, wherein the pH modifier is present in an amount of from about 20 to about 30% w/w.

Embodiment GG15: The extended release formulation of any one of Embodiments GG to GG14, wherein the pH modifier is present in an amount of from about 20 to about 25% w/w.

Embodiment GG16: The extended release formulation of any one of Embodiments GG to GG15, wherein the pH modifier is present in an amount of about 30% w/w.

Embodiment GG17: The extended release formulation of any one of Embodiments GG to GG16, wherein the pH modifier is present in an amount of about 20% w/w.

Embodiment GG18: The extended release formulation of any one of Embodiments GG to GG17, wherein the pH modifier is present in an amount of about 10% w/w Embodiment GG19: The extended release formulation of any one of Embodiments GG to GG18, wherein the hydrophilic polymer is a cellulose derivative with a viscosity between 1000 and 150000 mPa-s.

Embodiment GG20: The extended release formulation of any one of Embodiments GG to GG19, wherein the hydrophilic polymer is selected from the group consisting of hydroxypropyl methylcellulose, hydroxyethyl cellulose, and mixtures thereof.

Embodiment GG21: The extended release formulation of any one of Embodiments GG to GG20, wherein the hydrophilic polymer is hydroxypropyl methylcellulose.

Embodiment GG22: The extended release formulation of Embodiment GG21, wherein the hydroxypropyl methylcellulose is grade E, F or K.

Embodiment GG22: The extended release formulation of Embodiment GG21, wherein the hydroxypropyl methylcellulose is Hypromellose 2208.

Embodiment HH: A process for preparing a pharmaceutical composition, the process comprising:

(a) combining (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide (Compound 1) or a pharmaceutically acceptable salt thereof, or a solid state form of Compound 1, and at least a portion of one additional composition component to form a dry granulation mixture;

(b) contacting the dry granulation mixture with a granulation fluid to form a wet granulation mixture;

(c) drying the wet granulation mixture to form a granulated material;

(d) milling the granulated material to form a milled granulated material;

(e) combining the milled granulation material with any remaining composition components; and (f) compressing the composition to form the pharmaceutical composition

EXAMPLES

Example 1

Preparation of (3R,4S)-1-((benzyloxy)carbonyl)-4-ethylpyrrolidine-3-carboxylate dicyclohexylamine salt (3R,4S)-1-((benzyloxy)carbonyl)-4-ethylpyrrolidine-3-carboxylate dicyclohexylamine salt was prepared according to the following reaction scheme:

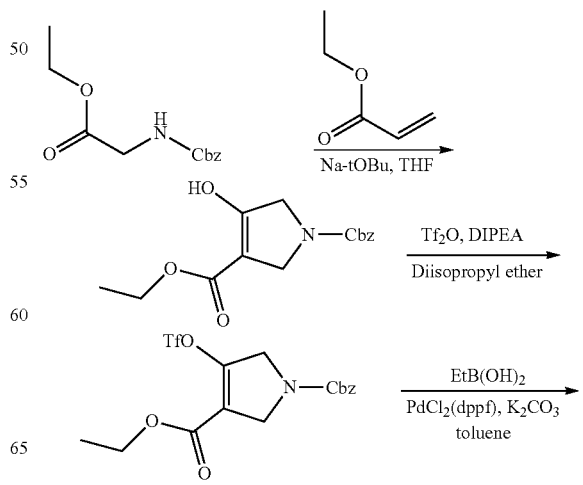

251

-continued

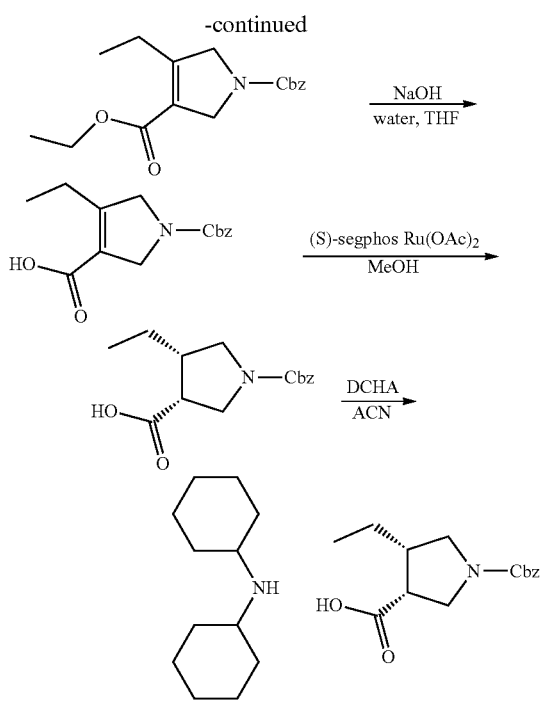

A. Step A: Preparation of 1-benzyl 3-ethyl 4-hydroxy-1H-pyrrole-1,3(2H,5H)-dicarboxylate

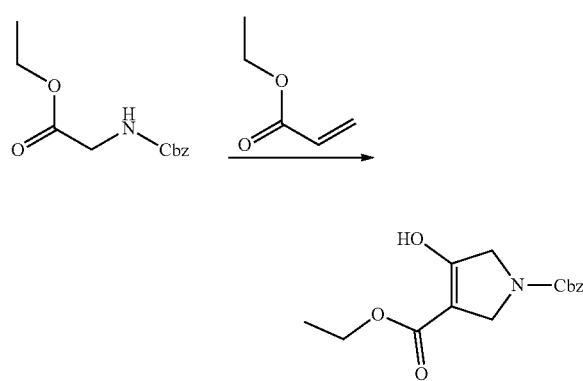

To a mixture of carboxybenzyl-glycine ethyl ester (5.5 g, 23.2 mmol) and ethyl acrylate (2.3 g, 23.2 mmol) in THF (55 mL) at 0° C. was added NatOBu (2.2 g, 23.2 mmol) portionwise over 1 hour. The resulting mixture was warmed to room temperature and stirred overnight. Upon completion, the reaction was quenched with water (30 mL), the pH adjusted to 4.0 with concentrated HCl, and the THF removed by distillation. The product was extracted into DCM (40 mL) and the organic layer washed with water (15 mL). After removal of the DCM the product was crystallized from diisopropyl ether/heptane (30 mL/60 mL). The solids were collected by filtration and washed with heptane (6 mL). The wet material (5.5 g potency adjusted, 82%) is used directly in the next step.

252

B. Step B: Preparation of 1-benzyl 3-ethyl 4-(((trifluoromethyl)sulfonyl)oxy)-1H-pyrrole-1,3(2H,5H)-dicarboxylate

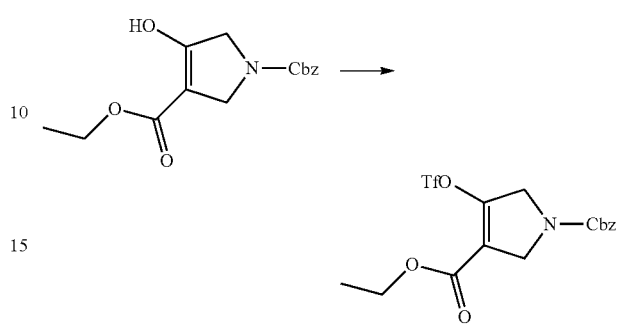

To a mixture of 1-benzyl 3-ethyl 4-hydroxy-1H-pyrrole-1,3(2H,5H)-dicarboxylate (16.2 g dry weight, 55.6 mmol) in diisopropyl ether (150 mL) was added at 0° C. trifluoromethanesulfonic anhydride (17.3 g, 61.2 mmol) followed by a slow addition of DIPEA (8.6 g, 66.7 mmol) over 30 min. The resulting mixture was warmed to room temperature and stirred 1 hour. Upon completion, the reaction was carefully quenched with 0.5 M HCl (200 mL), additional diisopropyl ether (50 mL) was added and the layers separated. The organic layer was washed twice with water (30 mL) and concentrated. The residue was chased with toluene, taken up in toluene to provide a 30 wt % solution (21.7 g potency adjusted, 92%) and used directly in the next step.
$^1$H NMR (400 MHz, CDCl$_3$) δ 7.48-7.28 (m, 5H), 5.20 (s, 2H), 4.60-4.42 (m, 4H), 4.42-4.23 (m, 2H), 1.40-1.31 (m, 3H) on a purified sample.

C. Step C: Preparation of 1-benzyl 3-ethyl 4-ethyl-1H-pyrrole-1,3(2H,5H)-dicarboxylate

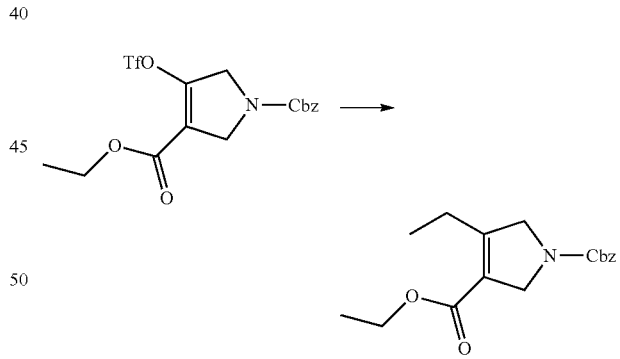

To the toluene solution of triflate from above (21.3 g triflate, 50.3 mmol) was added additional toluene (170 mL), water (20 mL), ethyl boronic acid (EtB(OH)$_2$) (5.6 g, 75.4 mmol), potassium carbonate (10.4 g, 75.4 mmol) and the resulting mixture was purged with nitrogen. PdCl$_2$(dppf) (735 mg, 1.0 mmol) was added, the resulting mixture warmed to 85° C. and stirred for 6 hours. Upon completion, the mixture was cooled to room temperature, filtered and the layers separated. The organic layer was washed with water, concentrated to approximately 15% of the volume (30 mL) and diluted with heptane (120 mL). The solution of product was treated with activated charcoal, filtered and concentrated to dryness to afford the desired product (13.9 g, 91%)

$^1$H NMR (400 MHz, CDCl$_3$) δ 7.50-7.31 (m, 5H), 5.20 (s, 2H), 4.54-4.30 (m, 4H), 4.24 (q, J=7.2 Hz, 2H), 2.68 (p, J=7.8 Hz, 2H), 1.36-1.30 (m, 3H), 1.22-1.00 (m, 3H).

D. Step D: Preparation of 1-((benzyloxy)carbonyl)-4-ethyl-2,5-dihydro-1H-pyrrole-3-carboxylic Acid

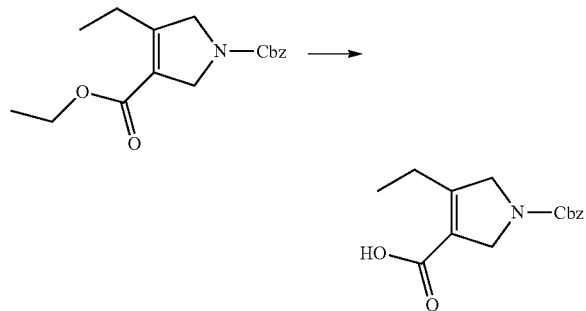

To a THF (90 mL) solution of 1-benzyl 3-ethyl 4-ethyl-1H-pyrrole-1,3(2H,5H)-dicarboxylate (13.9 g, 46.0 mmol) was added 30% aqueous NaOH (61.3 g, 460 mmol). The resulting mixture was warmed to 50° C. and stirred 7 h. Upon completion, the mixture was cooled to room temperature, additional water (50 mL) was added and the pH adjusted to 9 with concentrated HCl. The THF was removed by distillation and the aqueous layer washed at 50° C. twice with toluene (2×50 mL). The aqueous layer was cooled to room temperature and the pH adjusted to 4 with concentrated HCl. The resulting slurry of product was stirred for 2 hours before collecting the solids by filtration. The cake was washed with water (50 mL) and dried in a vacuum oven. The product was then dissolved in EtOAc (275 mL) at 75° C., treated with active charcoal, and filtered. The product crystallized upon cooling to 0° C., was collected by filtration, washed with EtOAc (2×10 mL), and dried in a vacuum oven to afford the desired compound (10.3 g, 83%)

$^1$H NMR (400 MHz, CDCl$_3$) δ 7.63-7.33 (m, 5H), 5.20 (s, 2H), 4.51-4.37 (m, 4H), 2.78-2.58 (m, 2H), 1.17-1.08 (m, 3H).

E. Step E: Preparation of (3R,4S)-1-((benzyloxy)carbonyl)-4-ethylpyrrolidine-3-carboxylate dicyclohexylamine Salt

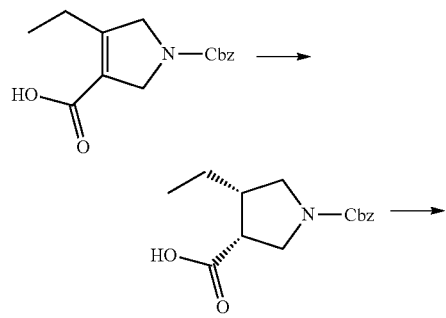

-continued

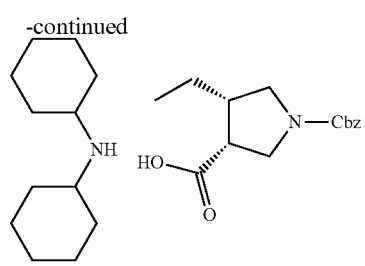

A MeOH (100 mL) solution of 1-((benzyloxy)carbonyl)-4-ethyl-2,5-dihydro-1H-pyrrole-3-carboxylic acid (9.9 g, 36 mmol), TEA (4.2 g, 41.4 mmol) and (S)-segphos Ru(OAc)$_2$ (29.8 mg, 0.04 mmol) was hydrogenated at 580 psi and 80° C. for 2 hours. Upon completion, the reaction mixture was cooled to room temperature, filtered and concentrated by distillation. The residue was taken up in EtOAc (50 mL) and water (50 mL) and the pH of the aqueous layer adjusted to 11 with 30% aqueous NaOH. The layers were separated, the pH of the aqueous layer was adjusted to 3 with concentrated HCl, and the product extracted with EtOAc (50 mL). The EtOAc was removed by distillation, the residue taken up in ACN (75 mL) and filtered. Additional ACN (100 mL) and dicyclohexylamine (6.3 g, 34.6 mmol) was added and the mixture heated to 80° C. The resulting solution was cooled slowly to room temperature and stirred 1 hour. The resulting solids were collected by filtration, washed with ACN (50 mL) and dried in a vacuum oven to provide the desired product (14.9 g, 90%, >99% ee).

$^1$H NMR (400 MHz, CDCl$_3$) δ 7.47-7.18 (m, 5H), 5.14 (ddd, J=15.5, 12.6, 3.7 Hz, 2H), 3.67 (td, J=10.5, 4.8 Hz, 1H), 3.61-3.47 (m, 2H), 3.34 (ddd, J=13.4, 10.1, 7.5 Hz, 1H), 3.02-2.77 (m, 3H), 2.33-2.14 (m, 1H), 1.96 (t, J=8.0 Hz, 4H), 1.77 (d, J=10.0 Hz, 4H), 1.69-1.53 (m, 3H), 1.49-1.30 (m, 5H), 1.29-1.05 (m, 6H), 0.98 (td, J=7.3, 2.5 Hz, 3H).

Example 2

Preparation of ethyl (5-tosyl-5H-pyrrolo[2,3-b]pyrazin-2-yl)carbamate

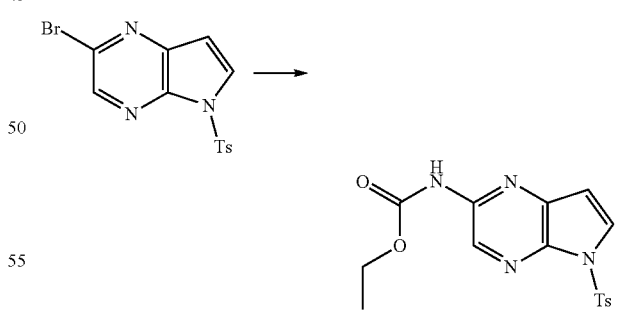

A degassed mixture of 2-bromo-5-tosyl-5H-pyrrolo[2,3-b]pyrazine (100 g, 284 mmol), K$_2$CO$_3$ (118 g, 852 mmol), ethyl carbamate (50.6 g, 568 mmol), Palladium (II) acetate (Pd(OAc)$_2$) (640 mg, 2.8 mmol) and Xantphos (3.3 g, 5.7 mmol) in toluene (1 L) was heated to 95° C. and stirred overnight. The resulting mixture was cooled to 50° C. and THF (1 L) was added and the solids filtered off rinsing the cake with THF (2 L). The resulting solution was mixed with a solution of cysteine (50 g) in saturated aqueous sodium bicarbonate (1 L) for two hours. After separating the layers the organic layer was washed with saturated aqueous sodium bicarbonate (1 L) and brine (500 mL), treated with active charcoal, filtered and concentrated. The resulting solid was triturated with EtOAc (500 mL), the solid collected, washed with EtOAc (100 mL) and dried in a vacuum oven at 50° C. to afford 85 g (83%).

$^1$H NMR (400 MHz, DMSO-$d_6$) δ 10.45 (s, 1H), 8.86 (s, 1H), 8.22 (d, J=4.0 Hz, 1H), 7.99 (d, J=8.5 Hz, 2H), 7.55-7.29 (m, 2H), 6.88 (d, J=4.0 Hz, 1H), 4.18 (q, J=7.1 Hz, 2H), 2.35 (s, 3H), 1.26 (t, J=7.1 Hz, 3H).

Example 3

Preparation of (3S,4R)-3-ethyl-4-(3H-imidazo[1,2-a]pyrrolo[2,3-e]pyrazin-8-yl)-N-(2,2,2-trifluoro-ethyl)pyrrolidine-1-carboxamide (Compound 1)

Compound 1 was prepared according to the following reaction scheme:

A. Step A: Preparation of dimethylsulfoxonium 2-((3R,4S)-1-benzyloxycarbonyl-4-ethylpyrrolidin-3-yl)-2-oxo-ethylide

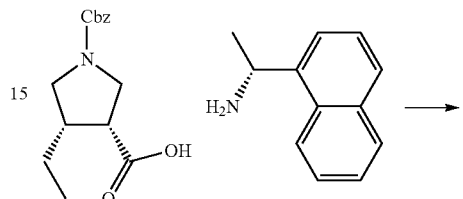

Scheme XV

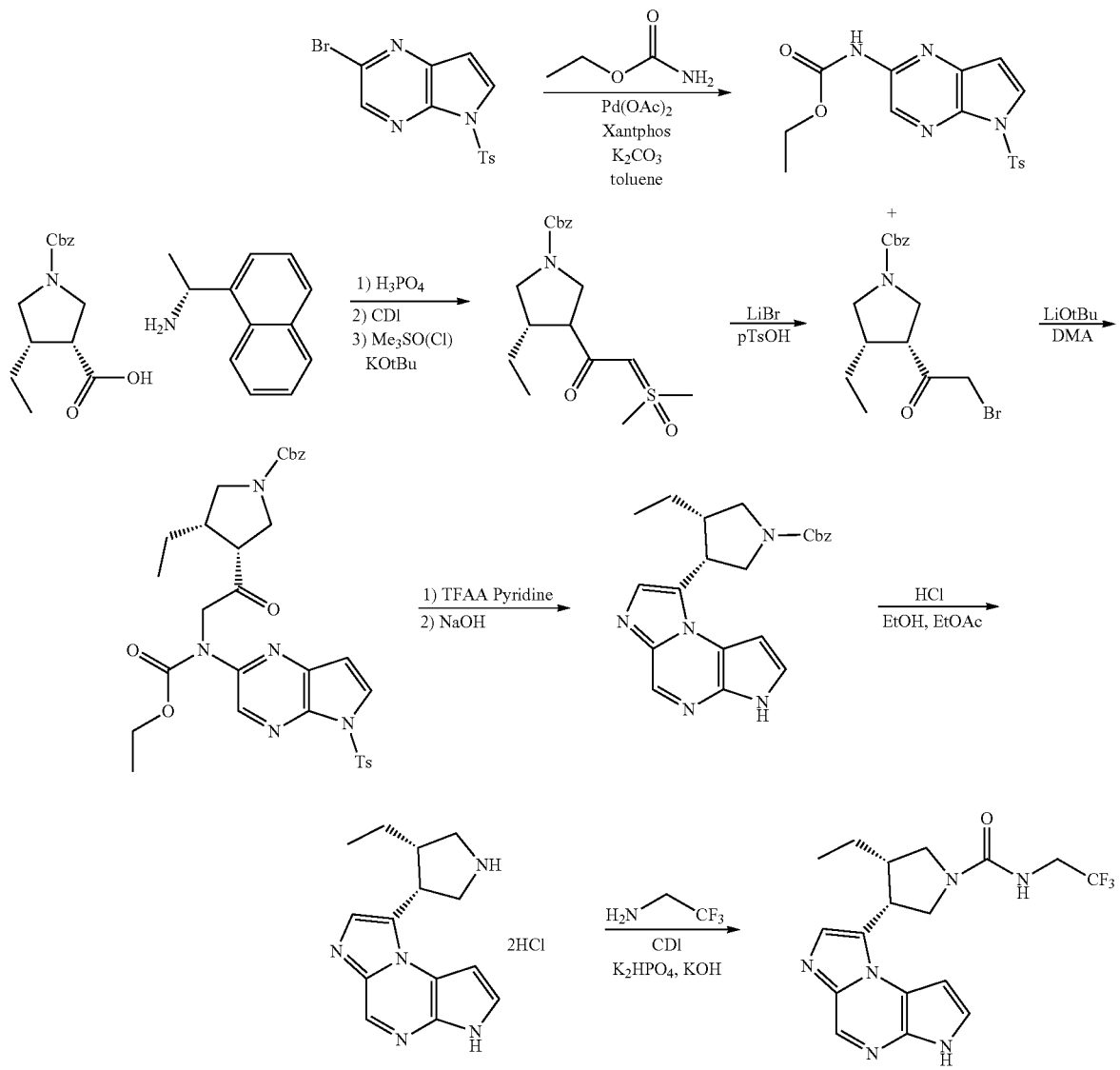

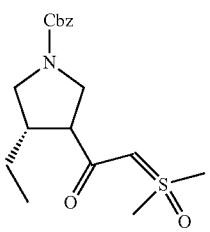

(3R,4S)-1-((benzyloxy)carbonyl)-4-ethylpyrrolidine-3-carboxylate, (R)-1-(naphthalen-1-yl)ethanamine salt (150 g, 334 mmol) was partitioned between MTBE (1.5 L) and 0.5 M $H_3PO_4$ (750 mL) and stirred 30 min. After separating the layers the organic layer was washed with 0.25 $H_3PO_4$ (750 mL) and saturated aqueous NaCl (500 mL). After concentrating to an oil the free acid is taken up in THF (250 mL) and stored for later.

To a slurry of CDI (81 g, 501 mmol) in THF (400 mL) was added the THF solution of (3R,4S)-1-(benzyloxycarbonyl)-4-ethylpyrrolidine-3-carboxylic acid from above (93 g, 334 mmol) over 30 minutes. The resulting mixture was stirred at room temperature for 1 hour. A suspension of trimethylsulfoxonium chloride (86 g, 668 mmol) and KOtBu (77 g, 685 mmol) in THF (1 L) was heated to reflux for 2 hours and then cooled −5° C. The (3S,4R)-benzyl 3-ethyl-4-(1H-imidazole-1-carbonyl)pyrrolidine-1-carboxylate solution (109 g, 334 mmol) prepared above was added dropwise over 15 minutes while maintaining the internal temperature below −1° C. After the addition was complete, the solution was quenched with 5% NaCl (1.2 L). The layers were separated and the aqueous layer was extracted with EtOAc (1 L). The combined organic layers were washed with 12% NaCl (600 mL) and concentrated to near dryness. The crude yellow oil was chased with water (3×400 mL), concentrating to dryness each time, during which solids formed. The residue was taken up in water (1.5 L) and heated to 70° C. The suspension was allowed to cool to room temperature. The solids were collected by filtration, washed with water (2×200 mL), and dried in a vacuum oven. The product was isolated (96.1 g) (82%) as a white solid.

$^1$H NMR (400 MHz, DMSO) δ 7.41-7.25 (m, 5H), 5.11-4.93 (m, 2H), 4.76 (s, 1H), 3.54-3.23 (m, 9H), 3.15 (dd, J=18.0, 9.6 Hz, 1H), 2.91-2.72 (m, 1H), 2.26-2.02 (m, 1H), 1.57-1.39 (m, 1H), 1.20 (tq, J=14.1, 7.3 Hz, 1H), 0.88 (td, J=7.4, 2.7 Hz, 3H). MS (ESI+): 352.0 m/e (M+H).

B. Step B: Preparation of (3R,4S)-benzyl 3-(2-bromoacetyl)-4-ethylpyrrolidine-1-carboxylate

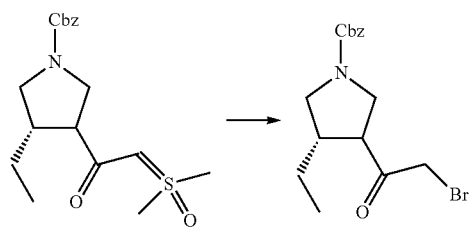 [SMILES: CC[C@@H]1CN(C(=O)OCc2ccccc2)CC1C(=O)C=S(C)(C)=O ; CC[C@@H]1CN(C(=O)OCc2ccccc2)CC1C(=O)CBr]

To a THF (100 mL) solution of dimethylsulfoxonium 2-((3R,4S)-1-benzyloxycarbonyl-4-ethylpyrrolidin-3-yl)-2-oxo-ethylide (10.0 g, 28.5 mmol) and lithium bromide (LiBr) (2.97 g, 34.1 was added p-toluene sulfonic acid monohydrate (5.95 g, 31.3 mmol). The resulting mixture was warmed to 40° C. and stirred overnight. After cooling to room temperature, the reaction mixture was diluted with EtOAc (100 mL), washed with water (100 mL), saturated aqueous sodium bicarbonate (100 mL) and brine (50 mL). The organic layer was concentrated and used without purification.

$^1$H NMR (400 MHz, CDCL3) δ 7.41-7.27 (m, 5H), 5.22-5.03 (m, 2H), 3.98-3.83 (m, 2H), 3.76-3.65 (m, 1H), 3.65-3.49 (m, 3H), 3.46-3.27 (m, 1H), 2.47-2.32 (m, 1H), 1.48-1.21 (m, 2H), 0.99-0.89 (m, 3H). MS (ESI+): 353.9 m/e (M+H).

C. Step C: Preparation of (3S,4R)-benzyl 3-ethyl-4-(2-((ethoxycarbonyl)(5-tosyl-5H-pyrrolo[2,3-b]pyrazin-2-yl)amino)acetyl)pyrrolidine-1-carboxylate

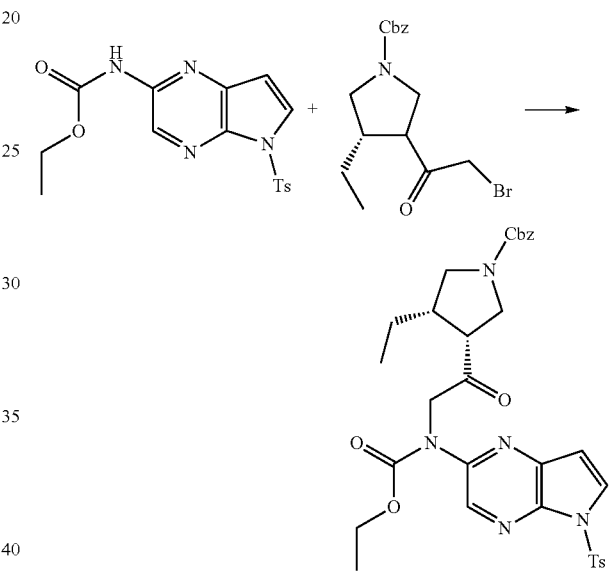

To a DMA (40 mL) suspension of ethyl (5-tosyl-5H-pyrrolo[2,3-b]pyrazin-2-yl)carbamate (8.25 g, 22.9 mmol) (prepared as described in Example 2) cooled to 5° C. was added a N,N-dimethylacetamide (DMA) (20 mL) solution of LiOtBu (1.75 g, 21.9 mmol). The resulting solution was stirred 30 minutes and cooled to −10° C. A DMA (20 mL) solution of (3R,4S)-benzyl 3-(2-bromoacetyl)-4-ethylpyrrolidine-1-carboxylate from above (approximately 7.1 g, 19.9 mmol) was added over 30 min and stirred at −10° C. for 30 minutes. The resulting mixture was quenched with HOAc (2.3 mL, 40 mmol) and warmed to 25° C. EtOH (40 mL) was added and the mixture seeded with the desired product (500 mg). After stirring an additional 2 hours, a mixture of EtOH (40 mL) and water (20 mL) was added over 8 hours. The product was then collected, washed with ethanol (2×40 mL) and dried to afford 10.7 g (88 wt % pure with 12% of the starting carbamate). A purified sample was prepared by recrystallizing from EtOAc.

$^1$H NMR (400 MHz, DMSO-d$_6$) δ 8.75 (s, 1H), 8.20 (dd, J=9.0, 4.1 Hz, 1H), 8.06-7.86 (m, 2H), 7.51-7.35 (m, 2H), 7.33-7.23 (m, 5H), 6.74 (dd, J=36.1, 4.1 Hz, 1H), 5.02 (d, J=4.1 Hz, 2H), 4.80 (s, 2H), 4.14 (qd, J=7.1, 4.5 Hz, 2H), 3.64-3.34 (m, 4H), 3.21-3.08 (m, 1H), 2.46-2.34 (m, 1H), 2.32 (s, 3H), 1.41 (d, J=13.3 Hz, 1H), 1.29-1.08 (m, 4H), 0.86 (td, J=7.3, 4.8 Hz, 3H).

D. Step D: Preparation of (3S,4R)-benzyl 3-ethyl-4-(3H-imidazo[1,2-a]pyrrolo[2,3-e]pyrazin-8-yl)pyrrolidine-1-carboxylate

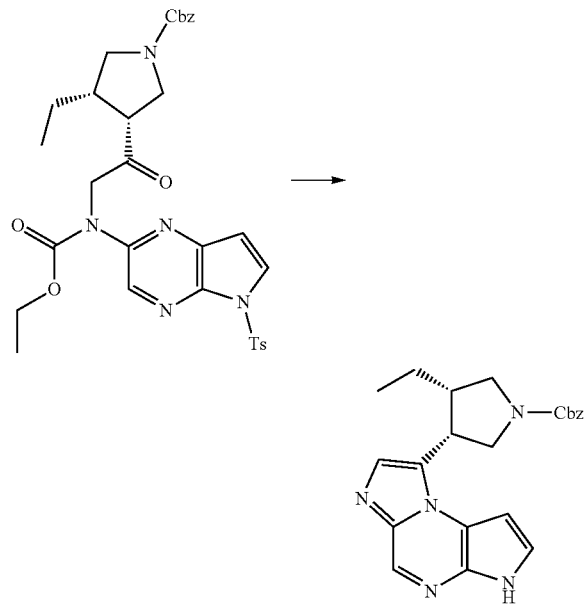

To a solution of (3S,4R)-benzyl 3-ethyl-4-(2-(ethoxycarbonyl(5-tosyl-5H-pyrrolo[2,3-b]pyrazin-2-yl)amino)acetyl)pyrrolidine-1-carboxylate (27.0 g, 42.6 mmol) in ACN (140 mL) was charged pyridine (9.3 mL, 115 mmol) and trifluoroacetic anhydride (24.1 mL, 170 mmol) and the mixture was warmed to 75° C. and stirred for 2 hours. Upon completion, the reaction mixture was cooled to room temperature and concentrated on the rotary evaporator. The residue was taken up in 2-methyl tetrahydrofuran (2-MeTHF) (200 mL) and poured into a 20% NaOH solution (200 g) and the mixture stirred at 55° C. for 1 hour. Upon completion, the reaction mixture was cooled to room temperature and the layers separated. The organic layer was washed with 20% NaOH (100 g) and brine (100 g) and the solvent switched to EtOH. The EtOH solution was assayed for product (15.2 g, 92%) and carried into the Cbz removal step as a solution.

E. Step E: Preparation of 8-((3R,4S)-4-ethylpyrrolidin-3-yl)-3H-imidazo[1,2-a]pyrrolo[2,3-e]pyrazine bis hydrochloride

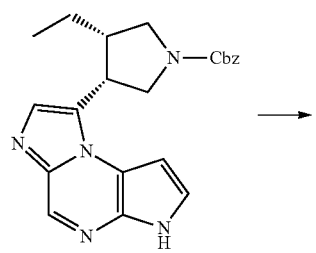

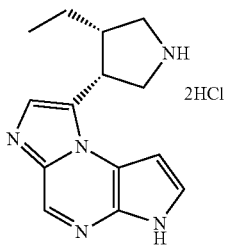

A mixture of 10% Pd(OH)$_2$/C (1 g) and (3S,4R)-benzyl 3-ethyl-4-(3H-imidazo[1,2-a]pyrrolo[2,3-e]pyrazin-8-yl)pyrrolidine-1-carboxylate (5.13 g, 13.2 mmol) in EtOH (70 mL) were mixed under hydrogen pressure at 20 psig. The mixture was agitated for 16 hours at 50° C. Upon completion, the reaction was cooled to room temperature and filtered through a short plug of diatomaceous earth. To this solution was added 35% aqueous HCl (2.6 mL, 31.1 mmol) and the mixture concentrated. The resulting residue was suspended in EtOH (17 mL) and EtOAc (34 mL), and stirred for 1 hour. The crystalline solids were collected, washed with EtOAc/ethanol (2/1, 15 mL) and EtOAc (15 mL) and dried in a vacuum oven to obtain the product (3.63 g, 83%).

$^1$H NMR (400 MHz, DMSO-d$_6$) δ 13.13 (s, 1H), 10.32-9.91 (m, 2H), 8.91 (s, 1H), 8.60 (s, 1H), 7.89 (t, J=3.3 Hz, 1H), 7.29 (dd, J=3.5, 1.9 Hz, 1H), 4.58 (q, J=7.4 Hz, 1H), 3.80-3.67 (m, 1H), 3.67-3.55 (m, 2H), 3.20-3.02 (m, 1H), 2.75-2.59 (m, 1H), 1.16-1.01 (m, 1H), 1.01-0.87 (m, 1H), 0.65 (t, J=7.3 Hz, 3H).

F1. Step F1: Preparation of Compound 1

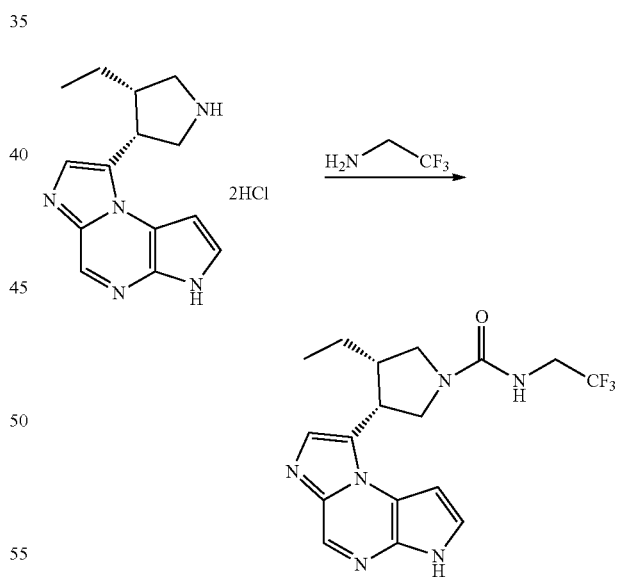

To a THF (60 mL) slurry of CDI (8.7 g, 53.7 mmol) was added dropwise 2,2,2-trifluoroethyl amine (4.52 mL, 57.5 mmol) over 20 minutes while maintaining an internal temperature less than 30° C. The resulting solution was stirred for 1 hour.

To a biphasic mixture of 8-((3R,4S)-4-ethylpyrrolidin-3-yl)-3H-imidazo[1,2-a]pyrrolo[2,3-e]pyrazine bis hydrochloride (12.7 g, 38.7 mmol) and potassium phosphate dibasic (K$_2$HPO$_4$) (7.4 g, 42.6 mmol) in THF (60 mL) and water (30 mL) was added 10% KOH to adjust the pH to 9. The imidazolide from above was added and the resulting mixture was mixed at 25° C. while maintaining a pH of 9 by the portionwise addition of 10% KOH for 1 hour. Upon completion, the reaction was quenched with 20% aqueous citric acid (50 mL), stirred for 1 hour and the product extracted with EtOAc (2×50 mL). The combined organic layers were washed with 15% aqueous $KH_2PO_4$ (50 mL), saturated aqueous sodium bicarbonate (50 mL) and brine (25 mL). The solution of product was treated with active charcoal and concentrated by distillation. The residue was taken up in 2% water in EtOAc (70 mL), seeded and stirred 1 hour. Heptane (35 mL) was added, stirred for 1 hour and the solids collected by filtration. The wet cake was washed with 1% water in EtOAc/heptane (2/1, 2×25 mL) and dried in a vacuum oven to yield the desired product (12.8 g, 87%).

$^1$H NMR (400 MHz, DMSO-$d_6$) δ 12.24 (s, 1H), 8.54 (s, 1H), 7.47-7.35 (m, 2H), 7.02-6.85 (m, 2H), 4.31 (q, J=6.4 Hz, 1H), 3.91-3.68 (m, 4H), 3.65 (dd, J=10.2, 6.9 Hz, 1H), 3.23 (dd, J=10.3, 6.1 Hz, 1H), 2.59-2.48 (m, 1H), 1.06 (dtd, J=14.7, 7.4, 4.7 Hz, 1H), 0.84-0.70 (m, 1H), 0.60 (t, J=7.4 Hz, 3H).

F2. Step F2: Alternate Preparation of Compound 1

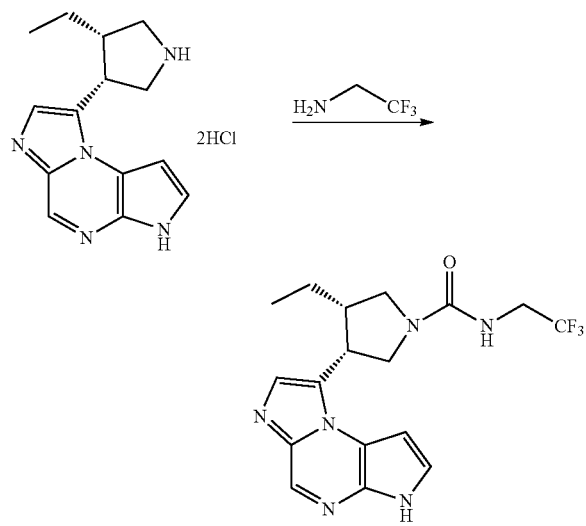

As an alternative to the Step F1 procedure, Compound 1 was prepared according to Step F2.

To a THF (500 mL) slurry of CDI (67.1 g, 414 mmol) was added dropwise 2,2,2-trifluoroethylamine (34.6 mL, 441 mmol) over 20 minutes while maintaining an internal temperature less than 30° C. The resulting solution was stirred for 1 hour.

To a biphasic mixture of 8-((3R,4S)-4-ethylpyrrolidin-3-yl)-3H-imidazo[1,2-a]pyrrolo[2,3-e]pyrazine bis hydrochloride (91.0 g, 276 mmol) and potassium phosphate dibasic ($K_2HPO_4$) (48.0 g, 276 mmol) in THF (500 mL) and water (500 mL) was added 20% KOH to adjust the pH to 9. The imidazolide from above was added and the resulting mixture was mixed at 25° C. while maintaining a pH of 9 by the portionwise addition of 20% KOH for 1 hour. Upon completion, the reaction was quenched with 50% aqueous citric acid (200 g), stirred for 1 hour and the product extracted with 2-MeTHF (2×500 mL). The combined organic layers were treated with 20% KOH at 50° C. for 30 min and after cooling to 25° C., the layers were separated, the organic layer was washed with 15% aqueous $KH_2PO_4$ (2×500 mL), and brine (250 mL). The solution of product was treated with active charcoal.

G. Alternate Process for Crystallization and Isolation of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide (Compound 1)

Following the carbon filtration of the solution containing 50 g of dissolved Compound 1 in Step F2 of Example 3, the solution was distilled to dryness. Two consecutive 250 mL portions of EtOAc were added and distilled to approximately 100 mL to bring the water content of the solution to below 1% w/w (as determined by coulometric Karl Fischer titration). This solution was adjusted to a total weight by adding 25% w/w EtOH 200 proof (75 g) and EtOAc (to give 500 g of solution). This solution was then treated with a 20 µm Teflon polish filter to remove residual salts from the reaction work-up. After filtration, the solution was again distilled to approximately 100 mL, followed by addition of 2 consecutive portions of 250 mL of EtOAc which were each distilled to a minimum volume (achieving a water content of not more than 0.05% w/w water and not more than 1% w/w EtOH after the final distillation). The final solution was adjusted to approximately 250 mL, and a sample was analyzed by HPLC to assay the concentration of Compound 1 (with a target concentration of not less than 18% w/w Compound 1).

Crystallization

The distillation product solution (250 g of total solution) was separated into two portions: 15% (37.5 g) and 85% (212.5 g) of the total volume. The 15% portion was added to the crystallization vessel and diluted with a premixed solution of EtOAc (353 g) and water (3.95 g) to achieve a final solution of approximately 1.9% w/w of Compound 1 and 1% w/w of water. This solution was allowed to recirculate from the crystallization vessel via a pump through an IKA wet mill (medium-fine-fine rotor-stator configuration) and returning into the top of the crystallization vessel. The wet mill was set to a rotor tip speed of 9 meters/sec and the crystallization solution was seeded with the desired crystal form, Freebase Hydrate Form C, of Compound 1. This crystal slurry was allowed to wet mill continuously for not less than 2 hours at a recirculation rate giving least 10 turnovers of the crystallization solution through the wet mill setup. Upon completion, the wet mill tip speed was reduced to 4 meters/sec, and the remaining 85% of the Compound 1 product solution was slowly added into the crystallization vessel over not less than 4 hours. After addition of the entire product solution, the antisolvent, n-heptane, was added slowly over not less than 4 hours to achieve approximately 30% w/w (260 g) of n-heptane in the final crystallization liquor (while maintaining a wet mill tip speed of 4 meters/second). Upon completion, wet milling was discontinued, the crystal slurry contents were recirculated into the crystallization vessel, and the crystal slurry was allowed to mix for not less than 1 hour.

Isolation and Drying

The crystal slurry was filtered under low pressure (approximately 10 psig of nitrogen) while collecting the mother liquor and continued until the resulting crystal cake was completely deliquored. A wash solution (69.4% w/w EtOAc, 30% w/w n-heptane, and 0.4% w/w water; 5 volumes of wash in total, 250 mL) was applied to the wet cake in two portions by deliquoring the cake completely after each portion. The wet cake was purged with a stream of nitrogen for not less than 3 hours, and then heated slowly (~10° C./hour) to a target temperature of 50° C., not more than 55° C. and allowed to dry for not less than 12 hours. After 12 hours, a sample was taken to analyze the cake for residual ethyl acetate by gas chromatography and water content by Karl Fischer titration. The final dry product was analyzed further for product identity, impurity profiling, water content and Compound 1 potency.

Example 4

Alternate Process for Preparation of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide (Compound 1)

In this example, Steps A-C of the Example 3 process were modified to eliminate certain work up steps and the isolation of the salt, and to improve purity of the bromomethyl ketone. Specifically, Compound 1 was prepared according to the following reaction scheme:

A. Step A: Preparation of dimethylsulfoxonium 2-((3R,4S)-1-benzyloxycarbonyl-4-ethylpyrrolidin-3-yl)-2-oxo-ethylide

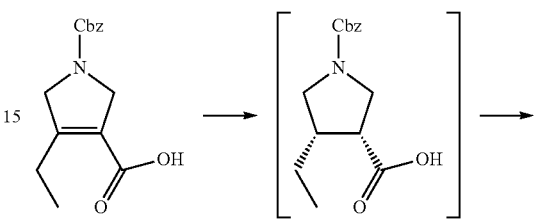

Scheme XVI

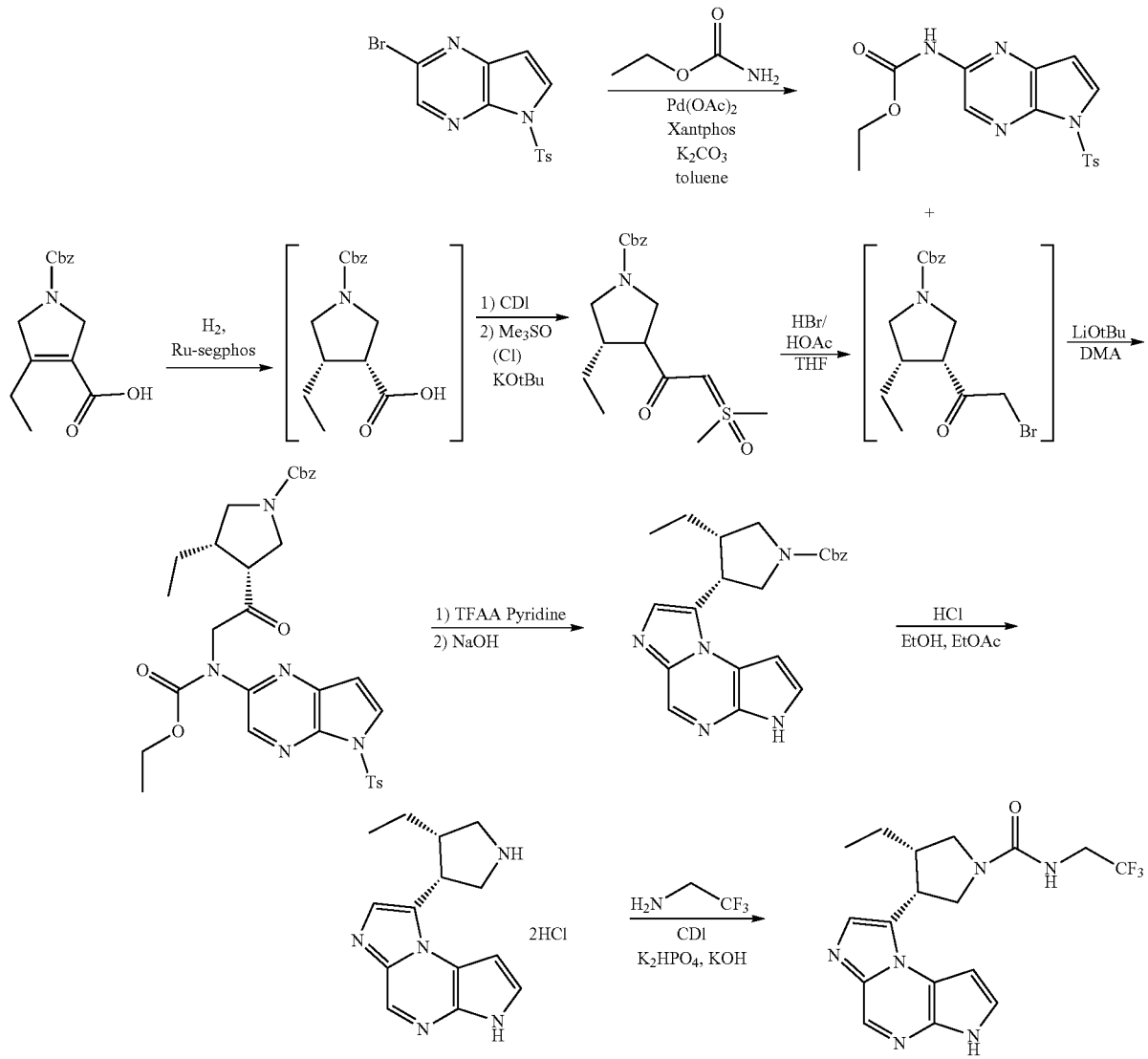

-continued

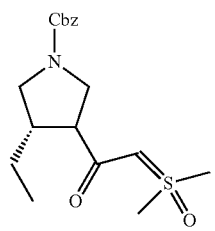

1-((benzyloxy)carbonyl)-4-ethyl-2,5-dihydro-1H-pyrrole-3-carboxylic acid (prepared as described in Example 1) (10 g, 36.3 mmol) and Ru(OAc)$_2$-Segphos (0.030 g, 0.036 mmol) were charged to a 300 mL stirred SS Parr reactor, and were transferred to the controlled atmosphere glovebox. A solution of TEA (5.82 mL, 41.8 mmol) in MeOH (60 mL) was added, and then the reactor was closed and was removed from the glove box. The reactor was placed in a reactor station, and was purged first with inert gas and then pressurized with hydrogen (200 psig). The mixture was agitated and heated at 80° C. for 4 hours. The reaction was monitored by HPLC for conversion.

The reaction mixture was filtered through a polypropylene filter funnel with diatomaceous earth/polyethylene fritted disc (Chemglass part #OP-6603-12) to remove the catalyst, and MeOH (10 mL) was used as a rinse. The combined filtrate obtained was a light amber solution.

The combined filtrate from step 1 was concentrated in vacuo to approximately 20 mL. The concentrate was diluted with THF (10 g) and was concentrated in vacuo to approximately 20 mL. This was repeated four additional times. The concentrate was then diluted with THF (40 mL). To this solution was added CDI (8.62 g, 53.2 mmol) in portions over 30 minutes. The reaction was stirred at room temperature for 1 hour. The reaction was monitored by HPLC (derivatized with MeOH and DBU) for conversion.

A suspension of trimethylsulfoxonium chloride (9.29 g, 72.2 mmol) and KOtBu (7.18 g, 64.0 mmol) in THF (70 mL) was heated to 45° C. for 1 hour and then cooled −5° C. The (3S,4R)-benzyl 3-ethyl-4-(1H-imidazole-1-carbonyl)pyrrolidine-1-carboxylate solution (prepared above) was added dropwise over 1 hour while maintaining the internal temperature below −1° C. After the addition was complete, the reaction stirred for 1 hour at −5° C. The reaction was monitored by HPLC for conversion.

The slurry was adjusted to 0° C. and was quenched with water (16 mL). Then the mixture was concentrated in vacuo to approximately 170 mL. The concentrate was diluted with water (22 mL) and was concentrated in vacuo to approximately 170 mL. This was repeated five additional times. By the last concentration, the internal temperature was approximately 45° C. The solution was reduced to 5° C. over 6 hours. During this time the product precipitated. The slurry was held at 5° C. for 1 hour, and then the product was collected by vacuum filtration. The solid was washed with water (100 mL) and was dried in a vacuum oven at 45° C. for 24 hours. The dimethylsulfoxonium 2-((3R,4S)-1-benzyloxycarbonyl-4-ethylpyrrolidin-3-yl)-2-oxo-ethylide (9.62 g, 27.4 mmol) was isolated in 77% yield.

$^1$H NMR (400 MHz, DMSO) δ 7.41-7.25 (m, 5H), 5.11-4.93 (m, 2H), 4.76 (s, 1H), 3.54-3.23 (m, 9H), 3.15 (dd, J=18.0, 9.6 Hz, 1H), 2.91-2.72 (m, 1H), 2.26-2.02 (m, 1H), 1.57-1.39 (m, 1H), 1.20 (tq, J=14.1, 7.3 Hz, 1H), 0.88 (td, J=7.4, 2.7 Hz, 3H). MS (ESI+): 352.0 m/e (M+H).

B. Step B: Preparation of (3R,4S)-benzyl 3-(2-bromoacetyl)-4-ethylpyrrolidine-1-carboxylate

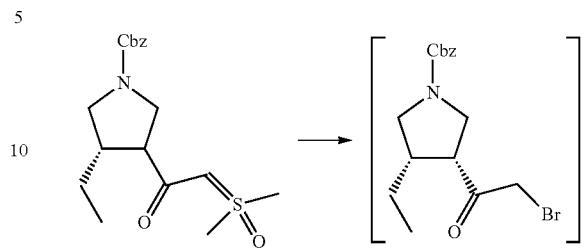

Dimethylsulfoxonium 2-((3R,4S)-1-benzyloxycarbonyl-4-ethylpyrrolidin-3-yl)-2-oxo-ethylide (10.0 g, 28.5 mmol, 1.0 equivalents), THF (100 mL), and 33% HBr in AcOH (8.37 g, 34.1 mmol, 1.2 equivalents) were charged sequentially and heated to 40° C. The reaction mixture was agitated for 5 hours, cooled to 20° C., and then distilled under vacuum to approximately 65 mL. EtOAc (20 mL) and heptane (50 mL) were charged, and the reaction mixture was washed with water (5×50 mL). The organic layer was concentrated under vacuum and chased with EtOAc (2×50 mL) concentrating to dryness each time. N,N-dimethylacetamide (20 mL) was then charged to provide 30.8 g of a 24.0 wt/wt % solution of (3R,4S)-benzyl 3-(2-bromoacetyl)-4-ethylpyrrolidine-1-carboxylate (73% yield). The solution was carried forward to the next step.

C. Step C: Preparation of (3S,4R)-benzyl 3-ethyl-4-(2-((ethoxycarbonyl)(5-tosyl-5H-pyrrolo[2,3-b]pyrazin-2-yl)amino)acetyl)pyrrolidine-1-carboxylate

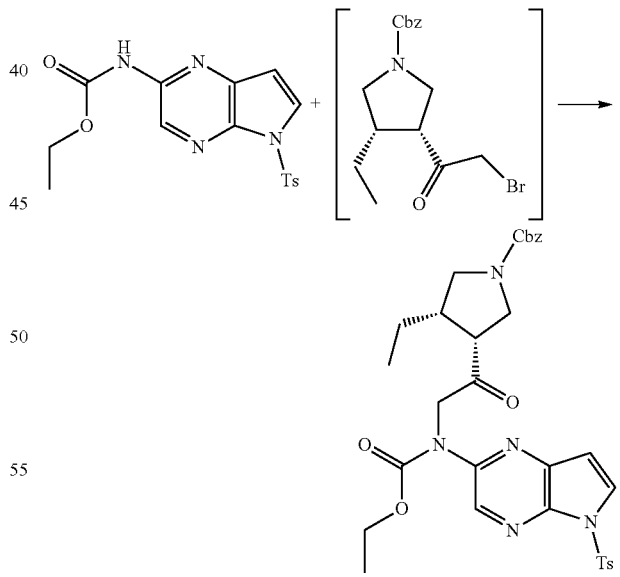

To a suspension of ethyl 5-tosyl-5H-pyrrolo[2,3-b]pyrazin-2-ylcarbamate (5.0 g, 13.9 mmol, 1.0 equivalents) and N,N-dimethylacetamide (20 mL) at 0° C. was charged a solution of LiOtBu (1.3 g, 16.0 mmol, 1.15 equivalents) and N,N-dimethylacetamide (10 mL) over 30 minutes. After agitating for 30 minutes, the reaction mixture was cooled to −10° C. A portion of the bromomethyl ketone solution (23.6 g, 24 wt/wt % in DMA, 16.0 mmol, 1.15 equivalents) from Step B above was then added over 1 hour. After the addition, the reaction mixture was agitated at −10° C. for 30 minutes, quenched with acetic acid (0.4 mL, 6.9 mmol, 0.5 equivalents), and warmed to 20° C. EtOH (40 mL) was then charged followed by seed (25 mg). The resulting slurry was aged at 20° C. for 1 hour, heated to 50° C. over 1 hour, and cooled to 20° C. over 3 hours. The heat cycling was performed 5 times total. After the heat cycling was complete, water (10 mL) was charged at 50° C. over 2 hours, and the slurry was cooled to 20° C. over 3 hours. The slurry was aged at 20° C. for 2 hours, filtered, and then washed with EtOH (2×25 mL). The isolated solids were dried under vacuum at 45° C. to deliver 7.4 g of (3S,4R)-benzyl 3-ethyl-4-(2-((ethoxycarbonyl)(5-tosyl-5H-pyrrolo[2,3-b]pyrazin-2-yl)amino)acetyl)pyrrolidine-1-carboxylate in 84% yield (99.6% purity).

$^1$H NMR (400 MHz, DMSO-$d_6$) δ 8.75 (s, 1H), 8.20 (dd, J=9.0, 4.1 Hz, 1H), 8.06-7.86 (m, 2H), 7.51-7.35 (m, 2H), 7.33-7.23 (m, 5H), 6.74 (dd, J=36.1, 4.1 Hz, 1H), 5.02 (d, J=4.1 Hz, 2H), 4.80 (s, 2H), 4.14 (qd, J=7.1, 4.5 Hz, 2H), 3.64-3.34 (m, 4H), 3.21-3.08 (m, 1H), 2.46-2.34 (m, 1H), 2.32 (s, 3H), 1.41 (d, J=13.3 Hz, 1H), 1.29-1.08 (m, 4H), 0.86 (td, J=7.3, 4.8 Hz, 3H).

Compound 1 may be prepared from the (3S,4R)-benzyl 3-ethyl-4-(2-((ethoxycarbonyl)(5-tosyl-5H-pyrrolo[2,3-b]pyrazin-2-yl)amino)acetyl)pyrrolidine-1-carboxylate according to the procedure described in Steps D-F of Example 3, and Compound 1 may be isolated and crystallized according to the procedure described in Example 3G.

Example 5

Preparation of Amorphous Freebase

A. Method A: Precipitation From Water

Compound 1 (approximately 300 g) was dissolved in water (10 L) and 50% sodium hydroxide (160 g) was added drop-wise over a two hour period to adjust the pH to greater than 12. Solids formed immediately. The solids were filtered, washed with two 500 mL aliquots of water, and then dried in a vacuum oven. The solids were equilibrated for a short period of time at ambient temperature prior to characterization. Conversion to Amorphous Freebase of Compound 1 was confirmed by PXRD analysis.

B. Method B: Dehydration of Freebase Hydrate Form B

A sample of the Freebase Hydrate Form B form of Compound 1 (crystallized from ethanol/water at sub-ambient temperatures as described in Example 5, Method C below) was placed in a vacuum oven at 40° C. overnight. The solids removed from the vacuum oven were equilibrated for a short time at 23° C. prior to characterization. Conversion to Amorphous Freebase of Compound 1 was confirmed by PXRD analysis.

Example 6

Preparation of Freebase Solvate Form A and Freebase Hydrate Form B

A. Method A: Freebase Solvate Form A (Isopropyl Acetate/Water Solvate)

A sample of the Amorphous Freebase of Compound 1 (25 mg) was added to a vial followed by isopropyl acetate (125 µL) and water (10 µL). All solids dissolved at ambient temperature. The solution was placed in a freezer at −16° C. for 4 days. The liquor was decanted and the crystallized solids were isolated. The isolated crystals were analyzed by PXRD while still wet. Conversion to Freebase Solvate Form A (isopropyl acetate/water solvate) of Compound 1 was confirmed by PXRD analysis.

B. Method B: Freebase Hydrate Form B from Methanol/Water

A sample of the Amorphous Freebase of Compound 1 (164 mg) and MeOH (621 mg) were added to a vial. The components were mixed at ambient temperature until the solids dissolved. Water (approximately 680 µL) was added to the vial and the vial was placed in an ice/sodium chloride bath at approximately −3° C. Crystal seeds comprising Freebase Hydrate Form B were added to the vial and the vial was placed in a freezer at −16° C. A sample was pulled from the crystallized suspension and the solids were immediately analyzed with PXRD and TGA-MS. Conversion to Freebase Hydrate Form B of Compound 1 was confirmed by PXRD and TGA-MS analysis.

C. Method C: Freebase Hydrate Form B from Ethanol/Water

A sample of the Amorphous Freebase of Compound 1 (4.2 g) was dissolved in EtOH (15.3g) in a jacketed reactor. Water (23.3 g) was slowly added to the reactor. The reactor solution was cooled to approximately 2° C. A small portion of a seed solution comprising the Freebase Hydrate Form B was charged to the reactor. The suspension was mixed at approximately 2° C. for 3 hours and water (36 g) in was charged to the reactor in small aliquots over several hours while maintaining the suspension at a temperature of approximately 2° C. The crystallized suspension was mixed at approximately 2° C. and the solids were isolated via filtration. Conversion to Freebase Hydrate Form B of Compound 1 was confirmed by PXRD analysis.

The Freebase Solvate Form A and Freebase Hydrate Form B do not readily crystallize from solution. In general, sub-ambient temperatures and sufficient water activity are needed to crystallize Freebase Solvate Form A and Freebase Hydrate Form B from solution.

Crystalline freebase hydrates and solvates have been isolated from several solvent systems either through primary nucleation (without seeding) or through seeding. In addition to crystallization from isopropyl acetate/water (as described in Method A above), crystalline freebase hydrates or solvates also have been isolated through primary nucleation (without seeding) from, e.g., n-butylamine/water and ethanol/water solvent systems. In addition to crystallization from methanol/water (as described in Method B above) and ethanol/water (as described in Method C above), crystalline freebase hydrates or solvates also have been isolated through seeding from, e.g., acetone/water; acetonitrile/water; ethyl formate/water; methyl acetate/water; ethyl acetate/water; methyl ethyl ketone/water; methyl isobutyl ketone/water, methyl isobutyl ketone/methyl tert-butyl ether/water; and isopropyl acetate/methyl tert-butyl ether/water solvent systems. The Freebase Solvate Form A (isopropyl acetate/water solvate) prepared in Method A above, the Freebase Hydrate Form B prepared in Methods B and C above, and these other crystalline freebase solvates or hydrates that have been prepared are isostructural and exhibit similar PXRD patterns. Notably, these crystalline freebase solvates and hydrates are distinguishable from and exhibit a different PXRD pattern than Freebase Hydrate Form C (a hemihydrate), which is described below.

The Freebase Solvate Form A and Freebase Hydrate Form B that were prepared were not stable after isolation at ambient conditions and readily dehydrated to the Amorphous Freebase.

Example 7

Preparation of Freebase Hydrate Form C

A. Method A: Freebase Hydrate Form C from Ethanol/Water

A sample of the Amorphous Freebase of Compound 1 (2 g) was transferred to a 500 mL beaker equipped with a stirring bar. EtOH (50 g) was added to the beaker and stirred until all solids dissolved. The solution was transferred to a 250 mL jacketed flask equipped with a dispersing device. The solution was cooled to 6° C. Water (150 g) was added to the solution and the solution was subjected to high shear for two hours using the dispersing device. After solid formation was observed, an additional amount of water (50 g) was added to the resulting suspension. The suspension was held overnight at ambient temperature. Solids were isolated and examined on the following day. Conversion to Compound 1 Freebase Hydrate Form C was confirmed by PXRD analysis.

B. Method B: Freebase Hydrate Form C From Ethyl Acetate/Heptane/Water

A crude reaction mixture assaying for 11.1 g of Compound 1 was taken up in 2% water in EtOAc (70 g) and seeded with Freebase Hydrate Form C (100 mg). The suspension was stirred overnight and heptane (70 g) was added. The solids were collected by filtration, washed with water saturated EtOAc/heptane (1/1, 100 mL), and dried under vacuum at 50° C. Conversion to Compound 1 Freebase Hydrate Form C was confirmed by PXRD analysis.

As was observed with the Freebase Solvate Form A and the Freebase Hydrate Form B, the Freebase Hydrate Form C also does not readily crystallize from solution.

Example 8

Preparation of Tartrate Hydrate

Three methods for the preparation of Compound 1 tartrate tetrahydrate (the "Tartrate Hydrate") are described below. Method A describes an initial procedure that was used to prepare the tartrate tetrahydrate. Method B describes a modified procedure used to prepare the tartrate tetrahydrate at a larger scale. Method C describes a further modified procedure used to prepare the tartrate tetrahydrate. The modified procedure of Method C relative to the procedure of Method B further reduces solidification of the filter cake, a potential problem that potentially can impact manufacturability and downstream processing.

A. Method A

A sample of the Amorphous Freebase of Compound 1 (28.2 mg) was transferred to an amber vial. Water (200 µL) and L-tartaric acid (34.5 mg (approximately 3 equivalents)) were added to the vial. The suspension was vortexed under ambient conditions until all the solids dissolved. The solution in the vial was magnetically stirred at 0° C. The following day, the solids were isolated from the solution and left at ambient temperature for a short period of time prior to characterization. Conversion to the Compound 1 Tartrate Hydrate (tetrahydrate) was confirmed by PXRD analysis.

B. Method B

Compound 1 (4.6 g) was added to a jacketed reactor followed by the addition of isopropanol (6.5 mL) and IPAc (7.8 mL). The slurry was mixed at ambient condition until the solids dissolved. In a separate vial, L-tartaric acid (1.96 g) was dissolved in deionized water (3.92 mL). The L-tartaric acid solution was added to the reactor followed by the addition of tartrate tetrahydrate seed crystals (28 mg). The suspension was mixed for 30 minutes under ambient conditions. IPAc (71 mL) was added in small aliquots over 2 hours. The crystallized suspension was cooled to 5° C. and equilibrated at 5° C. overnight. The suspension was discharged onto a filter and the filter cake rinsed with 20 mL of water saturated IPAc. The filtered solids were air-dried for two days. Conversion to the Compound 1 Tartrate Hydrate (tetrahydrate) was confirmed by PXRD analysis.

C. Method C

Crystallization: Compound 1 (104 g) was added to a flask together with isopropanol (222.7 g) and IPAc (375.8 g). The components were mixed under ambient conditions until the solids dissolved. In a separate flask, L-tartaric acid (61.6 g) was dissolved in water (98.3 g). The contents of the two flasks were then added to a jacketed reactor. Tartrate tetrahydrate seed crystals (1.55 g) were added to the reactor solution. The resulting suspension was mixed overnight under ambient conditions. IPAc (2542 g) was charged to the reactor suspension over an 8 hour period.

Filtration, Washing and Drying Approximately half of the crystallized tartrate suspension was charged to a jacketed agitated filter dryer. The suspension was cooled inside the filter dryer to approximately 11° C. The suspension was filtered using positive pressure until a wet cake was obtained. Water saturated IPAc (438 g) was charged to the filter dryer and the suspension was mixed overnight at approximately 11° C. The suspension was filtered using positive pressure until a wet cake was obtained. Water saturated MTBE (110 g) was charged to the filter dryer. After 10 minutes, the suspension was filtered with positive pressure until a wet cake was obtained. Water saturated MTBE (261 g) was charged to the filter dryer and the suspension was mixed at approximately 11° C. for 3.5 hours. The suspension was filtered with agitation using positive pressure until a wet cake was obtained. The wet cake was dried with constant agitation at a temperature of approximately 11° C. under humidified nitrogen and positive pressure for two days. Conversion to the Compound 1 Tartrate Hydrate (tetrahydrate) was confirmed by PXRD analysis.

Example 9

Preparation of Hydrochloride Solvate Form AA

Initial Preparation: A sample of the Amorphous Freebase of Compound 1 (23.8 mg), EtOAc (200 µL), and concentrated HCl (5 µL) were added to a vial. The viscous solution was warmed on a hot plate at 50° C. MeOH (20 µL) was added to the solution and stirring continued. EtOH (10 µL) was added and stirring continued at 50° C. The resulting solution was bi-phasic. The vial was placed in a bath at 0° C. while mixing with a magnetic stirrer continued. A white solid was obtained after approximately 1.5 hours.

Larger-Scale Preparation: The above-described procedure was repeated at larger scale to generate additional solids for characterization. A sample of the Amorphous Freebase of Compound 1 (50.3 mg), EtOAc (500 µL), and concentrated HCl (11 µL) were added to a vial. The solution was warmed on a hot plate and the same viscous phase as observed in the above-described procedure was obtained. EtOH (40 µL) was added to the solution and stirring continued. MeOH (40 µL) was added and the vial was placed in a bath at 0° C. while mixing with a magnetic stirrer continued. Once the solution was cooled, a drop of the seed slurry from the initial preparation was added. The suspension was mixed for 30 minutes in the cooling bath. The vial was placed in a freezer at −16° C. overnight. The solids in the vial were isolated via vacuum filtration. The filtered solids were equilibrated for a short period of time prior to characterization. Conversion to Compound 1 hydrochloride (Hydrochloride Solvate Form AA) was confirmed by PXRD analysis.

Example 10

Preparation of Hydrochloride Solvate Form BB

A sample of the Amorphous Freebase of Compound 1 (76 mg) and THF (approximately 228 µL) were added to a vial. The slurry was sonicated until a clear solution was obtained. Concentrated HCl (12 µL) was added to the clear solution. Some precipitation occurred immediately. The vial was placed in a freezer at −16° C. for 4 hours. More precipitation occurred. The solids were isolated from the vial after a few days and equilibrated for a short time at ambient prior to characterization. Conversion to Compound 1 hydrochloride (Hydrochloride Solvate Form BB) was confirmed by PXRD analysis.

Example 11

Preparation of Hydrochloride Solvate Form CC

A sample of the Amorphous Freebase of Compound 1 (50 mg) was dissolved in 0.2 mL of 50/50 v/v EtOAc/EtOH. Concentrated HCl (404) and 0.8 mL of 50/50 v/v EtOAc/EtOH were added to the solution. EtOAc was slowly diffused via the gas phase into the product solution (i.e., vapor diffusion procedure). Solids were obtained after approximately three weeks. The solids were isolated via centrifugation filtration and equilibrated for a short time prior to characterization. Conversion to Compound 1 hydrochloride (Hydrochloride Solvate Form CC) was confirmed by PXRD analysis.

Example 12

Preparation of L-Maleate Form AAA

Compound 1 (78.5 mg), L-maleic acid (32 mg), and water saturated methyl isobutyl ketone (630 µL) were add to a vial. A thick slurry formed quickly after the addition of the solvents. Additional methyl isobutyl ketone was added and the suspension mixed over three days. The isolated wet solids were equilibrated for a short time prior to characterization. Conversion to the Compound 1 L-Maleate Form AAA was confirmed by PXRD analysis.

Example 13

Preparation of L-Maleate Form BBB

The L-Maleate Form BBB can be obtained by drying the L-Maleate Form AAA under vacuum. The L-Maleate Form BBB also can be obtained as described below.

Compound 1 (500 mg), L-maleic acid (150 mg), and water saturated methyl isobutyl ketone (4 mL) were add to a vial. The contents of the vial were mixed overnight. Approximately 10 mg of L-Maleate Form BBB crystal seeds were added to the vial. An additional 2 mL of water saturated methyl isobutyl ketone was added to the vial. The solids were isolated after crystallization and dried at 50° C./75% relative humidity. Conversion to the Compound 1 L-Maleate Form BBB was confirmed by PXRD analysis.

Example 14

Preparation of Freebase Anhydrate Form D

A sample of the Amorphous Freebase of Compound 1 was dissolved in water-free EtOAc at a concentration of 19.6% (w/w). An aliquot comprising approximately 1 mL was transferred to a 4 mL vial equipped with a magnetic stirrer. The vial was sealed with parafilm and mixed at 400 rpm on a magnetic stir plate at around 23° C. for almost 8 weeks. The resulting slurry was filtered and left at ambient conditions for a short period of time prior to characterization. Conversion to Freebase Anhydrate Form D was confirmed by PXRD analysis.

Example 15

Microscopy/Crystal Morphology

The solid state forms of Compound 1 were evaluated by microscopy. Samples were examined by microscopic visual examination using a polarizing microscope (model Eclipse E-600 POL, Nikon Corp., Garden City, N.Y.). A color video camera was used to record digital images (model DXC 390, Fryer Co., Inc., Huntley, Ill.). Images were captured using MetaMorph Imaging System (version 4.6R8, Universal Imaging Corporation, Downingtown, Pa.). Observations regarding the crystal morphology of the samples are reported in Table 15-A below. Those of skill in the art will recognize that variation in crystal shape and size may be observed depending upon the specific crystallization conditions employed. The solvation states and PXRD profiles reported in Table 15-A correspond to the information presented in the figures and subsequent examples of this application.

TABLE 15-A

| Solid Form Nomenclature | Species | Solvation/Hydration State | Morphology |
| --- | --- | --- | --- |
| Amorphous Freebase | Freebase | Anhydrous | Blades (when prepared via precipitation or dehydration of Freebase Hydrate Form B) |
| Freebase Solvate Form A | Freebase | Isopropyl Acetate/Water Solvate | Irregular |
| Freebase Hydrate Form B | Freebase | Labile Hydrate | Blades |
| Freebase Hydrate Form C | Freebase | Hemihydrate | Prisms |

TABLE 15-A-continued

| Solid Form Nomenclature | Species | Solvation/Hydration State | Morphology |
|---|---|---|---|
| Tartrate Hydrate | Tartrate | Tetrahydrate | Needles |
| Hydrochloride Solvate Form AA | Hydrochloride | Solvated, but converts to amorphous upon isolation | Not Determined |
| Hydrochloride Solvate Form BB | Hydrochloride | Solvated, but converts to amorphous upon isolation | Not Determined |
| Hydrochloride Solvate Form CC | Hydrochloride | Solvated, but converts to amorphous upon isolation | Irregular |
| L-Maleate Form AAA | L-Maleate | Appears to be either a hydrate or a methyl isobutyl ketone/water solvate | Needles |
| L-Maleate Form BBB | L-Maleate | Not Determined | Not Determined |
| Freebase Anhydrate Form D | Freebase | Anhydrous | Not Determined |

Example 16

PXRD Analysis

The solid state forms of Compound 1 listed in Table 15-A were analyzed by X-ray powder diffraction ("PXRD"). The PXRD data were collected with a G3000 diffractometer (Inel Corp., Artenay, France) equipped with a curved position sensitive detector and parallel beam optics. The diffractometer was operated with a copper anode tube (1.5 kW fine focus) at 40 kV and 30 mA. An incident beam germanium monochromator provided monochromatic Kα1 radiation $\lambda$, =1.540562 Å). The diffractometer was calibrated using the attenuated direct beam at one-degree intervals. Calibration was checked using a silicon powder line position reference standard (NIST 640c). Samples were prepared by spreading the sample powder in a thin layer on an aluminum sample holder and gently leveling with a glass microscope slide. The instrument was computer controlled using the Symphonix software (Inel Corp., Artenay, France) and the data was analyzed using the Jade software (version 6.5, Materials Data, Inc., Livermore, Calif.). The aluminum sample holder was mounted on the rotating sample holder of the G3000 diffractometer and the diffraction data collected at ambient conditions.

Tables 16-A through 16-J set out the significant parameters of the main peaks in terms of 2Θ values and intensities for the crystalline forms analyzed. It is known in the art that an X-ray powder diffraction pattern may be obtained which has one or more measurement errors depending on measurement conditions (such as equipment, sample preparation or machine used). In particular, it is generally known that intensities in an X-ray powder diffraction pattern may fluctuate depending on measurement conditions and sample preparation. For example, persons skilled in the art of X-ray powder diffraction will realize that the relative intensities of peaks may vary according to the orientation of the sample under testing and on the type and setting of the instrument used. The skilled person also will realize that the position of reflections can be affected by the precise height at which the sample sits in the diffractometer and the zero calibration of the diffractometer. The surface planarity of the sample also may have an effect on the results. A person skilled in the art will appreciate that the diffraction pattern data presented below is not to be construed as absolute and any crystalline form that provides a power diffraction pattern substantially identical to those disclosed below fall within the scope of the present disclosure (for further information see Jenkins, R & Snyder, R. L. 'Introduction to X-Ray Powder Diffractometry', John Wiley & Sons, 1996).

Figure 2A:
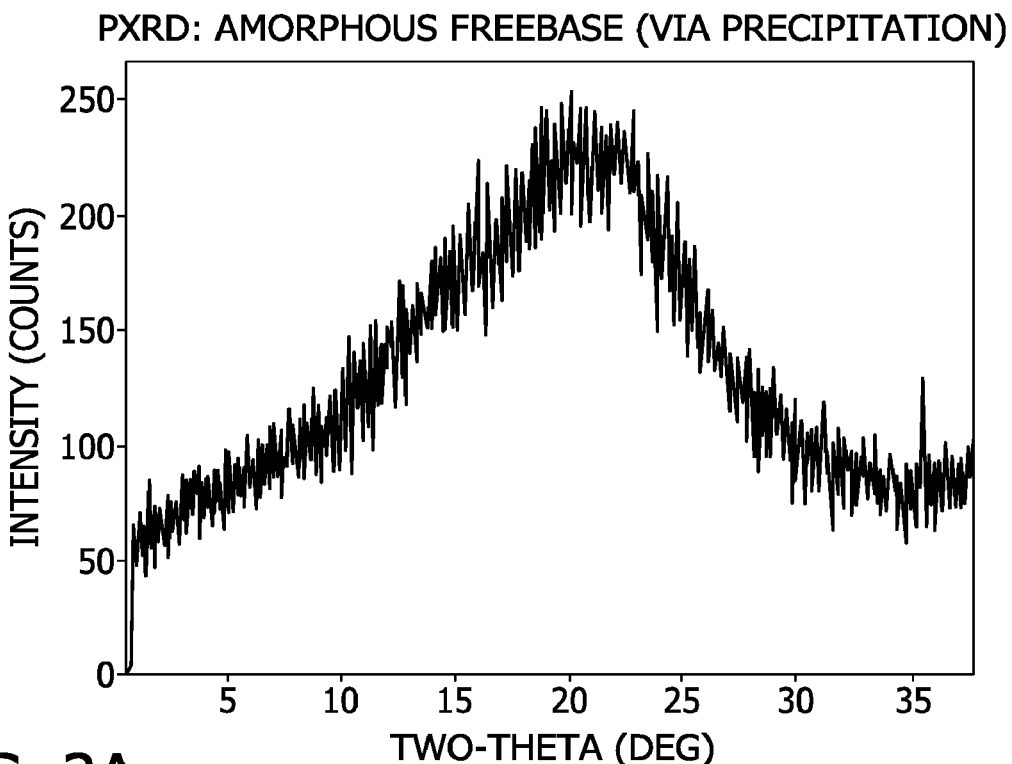
FIGS. 2A and 2B are powder X-ray diffraction patterns corresponding to the Amorphous Freebase (via precipitation) and the Amorphous Freebase (via dehydration), respectively.
Figure 2B:
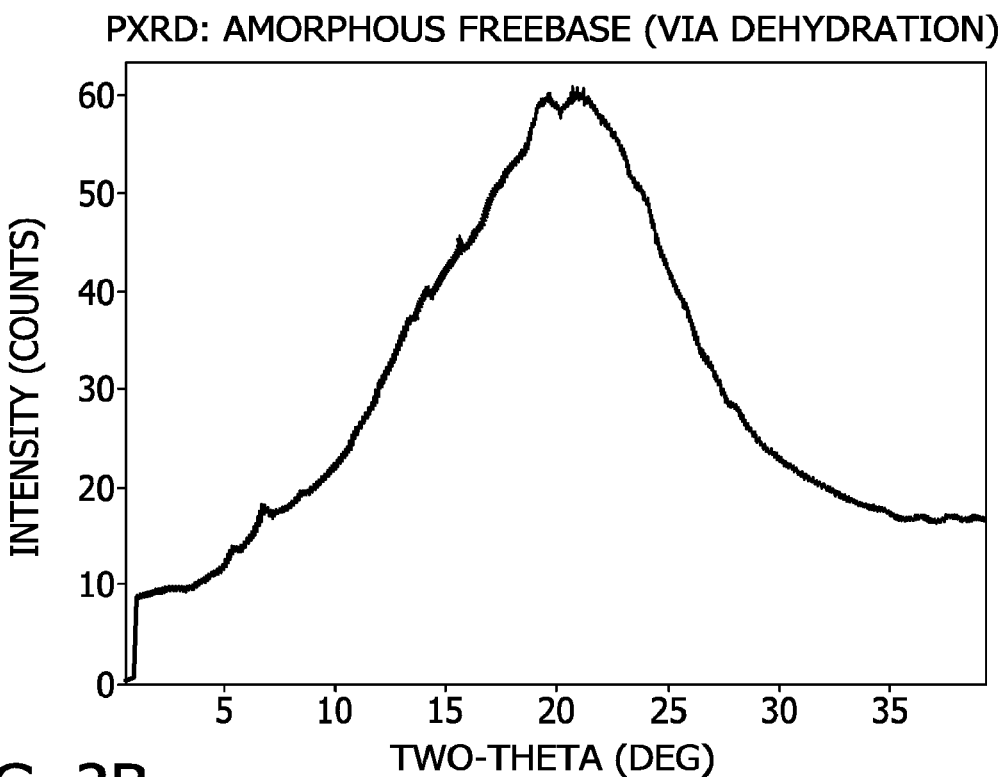

The PXRD pattern corresponding to the Amorphous Freebase (via precipitation) and the Amorphous Freebase (via dehydration) are shown in FIGS. 2A and 2B, respectively.

The PXRD pattern corresponding to the Freebase Solvate Form A is shown in FIG. 3A. Peak listing of the experimental PXRD pattern with relative intensities is given in Table 16-A below.

TABLE 16-A

PXRD Peak Listing
Freebase Solvate Form A (Isopropyl Acetate/Water Solvate)

| PEAK POSITION (°2Θ) | RELATIVE INTENSITY |
|---|---|
| 3.1 | 100.0 |
| 5.4 | 15.4 |
| 6.6 | 10.7 |
| 8.2 | 8.7 |
| 9.4 | 74.7 |
| 10.8 | 9.2 |
| 11.1 | 6.7 |
| 12.1 | 33.5 |
| 13.1 | 7.4 |
| 15.1 | 6.4 |
| 16.2 | 11.6 |
| 17.0 | 7.1 |
| 19.1 | 13.3 |
| 21.1 | 20.7 |
| 22.3 | 7.2 |
| 22.9 | 11.9 |
| 26.2 | 5.8 |
| 29.6 | 4.4 |

The PXRD pattern corresponding to the Freebase Hydrate Form B is shown in FIG. 3B. Peak listing of the experimental PXRD pattern with relative intensities is given in Table 16-B below.

TABLE 16-B

PXRD Peak Listing
Freebase Hydrate Form B

| PEAK POSITION (°2Θ) | RELATIVE INTENSITY |
|---|---|
| 3.1 | 100.0 |
| 6.1 | 3.4 |

TABLE 16-B-continued

PXRD Peak Listing
Freebase Hydrate Form B

| PEAK POSITION (°2Θ) | RELATIVE INTENSITY |
|---|---|
| 7.9 | 4.6 |
| 9.3 | 54.8 |
| 10.7 | 3.1 |
| 12.0 | 27.1 |
| 12.4 | 6.3 |
| 13.0 | 3.3 |
| 13.7 | 4.3 |
| 14.9 | 7.5 |
| 15.6 | 4.2 |
| 16.0 | 3.5 |
| 17.1 | 3.7 |
| 18.8 | 7.0 |
| 20.8 | 13.4 |
| 22.9 | 6.6 |
| 23.3 | 4.5 |
| 24.0 | 6.6 |
| 24.6 | 4.2 |
| 25.0 | 12.4 |
| 26.0 | 4.7 |
| 26.9 | 5.1 |
| 28.1 | 3.3 |
| 28.9 | 2.5 |
| 29.8 | 4.1 |

The PXRD pattern corresponding to the Freebase Hydrate Form C is shown in FIG. 3C. Peak listing of the experimental PXRD pattern with relative intensities is given in Table 16-C below.

TABLE 16-C

PXRD Peak Listing
Freebase Hydrate Form C

| PEAK POSITION (°2Θ) | RELATIVE INTENSITY |
|---|---|
| 7.7 | 28.8 |
| 7.9 | 41.1 |
| 9.6 | 10.2 |
| 10.3 | 35.0 |
| 12.4 | 9.8 |
| 13.4 | 72.5 |
| 13.9 | 16.9 |
| 15.1 | 74.6 |
| 15.5 | 93.7 |
| 15.9 | 11.7 |
| 17.0 | 76.1 |
| 17.2 | 46.8 |
| 17.8 | 21.6 |
| 18.1 | 10.0 |
| 18.3 | 37.2 |
| 19.3 | 33.0 |
| 19.7 | 24.7 |
| 20.5 | 52.4 |
| 20.9 | 54.9 |
| 21.2 | 7.9 |
| 21.7 | 100.0 |
| 21.9 | 34.6 |
| 22.2 | 21.7 |
| 22.6 | 6.2 |
| 23.5 | 27.2 |
| 24.0 | 5.0 |
| 24.4 | 18 |
| 24.9 | 35.1 |
| 27.4 | 9.8 |
| 28.2 | 19.8 |
| 29.2 | 8.2 |
| 29.5 | 13.7 |
| 31.5 | 6.9 |

The PXRD pattern corresponding to the Tartrate Hydrate is shown in FIG. 3D. Peak listing of the experimental PXRD pattern with relative intensities is given in Table 16-D below.

The experimental PXRD pattern is shown at the bottom of FIG. 3D and the calculated PXRD pattern is shown at the top of FIG. 3D.

TABLE 16-D

PXRD Peak Listing
Tartrate Hydrate

| PEAK POSITION (°2Θ) | RELATIVE INTENSITY |
|---|---|
| 3.9 | 80.3 |
| 6.8 | 24.6 |
| 10.4 | 12.8 |
| 11.8 | 21.6 |
| 14.1 | 100.0 |
| 15.7 | 63.3 |
| 16.1 | 10.4 |
| 17.1 | 4.5 |
| 18.0 | 22.1 |
| 18.4 | 11.6 |
| 18.8 | 12.4 |
| 19.7 | 5.2 |
| 20.0 | 3.1 |
| 21.2 | 15.2 |
| 21.9 | 55.9 |
| 24.0 | 11.9 |
| 24.8 | 3.0 |
| 25.2 | 3.6 |
| 25.9 | 32.6 |
| 26.7 | 9.2 |
| 27.0 | 6.8 |
| 27.6 | 11.5 |
| 28.7 | 6.3 |
| 30.4 | 4.9 |
| 30.9 | 4.9 |
| 32.4 | 4.3 |
| 33.4 | 3.0 |

The PXRD pattern corresponding to the Hydrochloride Solvate Form AA is shown in FIG. 3E. Peak listing of the experimental PXRD pattern with relative intensities is given in Table 16-E below.

TABLE 16-E

PXRD Peak Listing
Hydrochloride Solvate Form AA

| PEAK POSITION (°2Θ) | RELATIVE INTENSITY |
|---|---|
| 4.6 | 29.3 |
| 8.0 | 31.7 |
| 8.4 | 100.0 |
| 11.2 | 52.1 |
| 11.7 | 16.3 |
| 12.4 | 62.5 |
| 15.6 | 17.8 |
| 16.8 | 30.1 |
| 17.1 | 44.8 |
| 17.7 | 32.5 |
| 18.2 | 18.7 |
| 19.8 | 63.5 |
| 22.5 | 30.2 |
| 23.0 | 28.0 |
| 24.0 | 55.8 |
| 24.8 | 39.2 |
| 25.3 | 51.6 |
| 27.2 | 26.8 |
| 30.8 | 10.7 |
| 32.6 | 15.5 |

The PXRD pattern corresponding to the Hydrochloride Solvate Form BB is shown in FIG. 3F. Peak listing of the experimental PXRD pattern with relative intensities is given in Table 16-F below.

TABLE 16-F

PXRD Peak Listing
Hydrochloride Solvate Form BB

| PEAK POSITION (°2Θ) | RELATIVE INTENSITY |
|---|---|
| 2.48 | 100.0 |
| 2.9 | 6.4 |
| 4.9 | 60.1 |
| 7.2 | 83.8 |
| 7.8 | 16.4 |
| 8.4 | 19.8 |
| 9.1 | 15.7 |
| 9.5 | 7.2 |
| 10.2 | 11.6 |
| 10.5 | 26.0 |
| 11.0 | 24.8 |
| 12.0 | 13.7 |
| 12.7 | 27.6 |
| 13.4 | 11.5 |
| 13.7 | 8.0 |
| 14.7 | 23.6 |
| 16.4 | 13.3 |
| 16.9 | 18.2 |
| 17.4 | 15.1 |
| 18.2 | 25.4 |
| 18.4 | 17.2 |
| 19.2 | 14.9 |
| 19.4 | 16.2 |
| 19.7 | 15.3 |
| 20.3 | 16.1 |
| 20.5 | 36.1 |
| 20.7 | 29.4 |
| 21.6 | 9.7 |
| 21.8 | 14.1 |
| 22.1 | 17.8 |
| 22.4 | 11.2 |
| 22.8 | 36.7 |
| 23.2 | 17.1 |
| 23.9 | 43.0 |
| 25.1 | 12.1 |
| 25.7 | 9.3 |
| 26.6 | 8.8 |
| 28.1 | 8.1 |
| 29.9 | 9.3 |
| 30.5 | 9.7 |

The PXRD pattern corresponding to the Hydrochloride Solvate Form CC is shown in FIG. 3G. Peak listing of the experimental PXRD pattern with relative intensities is given in Table 16-G below.

TABLE 16-G

PXRD Peak Listing
Hydrochloride Solvate Form CC

| PEAK POSITION (°2Θ) | RELATIVE INTENSITY |
|---|---|
| 8.3 | 100.0 |
| 10.8 | 19.2 |
| 11.1 | 8.4 |
| 16.7 | 19.6 |
| 20.2 | 7.0 |
| 22.9 | 7.5 |
| 23.8 | 18.4 |
| 24.6 | 11.7 |
| 25.1 | 32.2 |
| 27.1 | 13.7 |
| 28.1 | 5.3 |
| 30.6 | 6.9 |
| 32.3 | 7.8 |

The PXRD pattern corresponding to the L-Maleate Form AAA is shown in FIG. 3H. Peak listing of the experimental PXRD pattern with relative intensities is given in Table 16-H below.

TABLE 16-H

PXRD Peak Listing
L-Maleate Form AAA

| PEAK POSITION (°2Θ) | RELATIVE INTENSITY |
|---|---|
| 3.2 | 100.0 |
| 9.7 | 21.6 |
| 12.9 | 78.2 |
| 14.1 | 3.9 |
| 14.3 | 7.6 |
| 16.2 | 12.8 |
| 18.8 | 13.8 |
| 19.1 | 4.2 |
| 19.9 | 11.4 |
| 25.2 | 5.9 |
| 25.7 | 4.3 |
| 26.6 | 4.8 |

The PXRD pattern corresponding to the L-Maleate Form BBB is shown in FIG. 3I. Peak listing of the experimental PXRD pattern with relative intensities is given in Table 16-I below.

TABLE 16-I

PXRD Peak Listing
L-Maleate Form BBB

| PEAK POSITION (°2Θ) | RELATIVE INTENSITY |
|---|---|
| 3.6 | 100.0 |
| 9.6 | 14.2 |
| 10.8 | 62.2 |
| 12.4 | 18.4 |
| 14.1 | 14.4 |
| 14.5 | 8.5 |
| 15.7 | 15.5 |
| 16.9 | 4.1 |
| 17.9 | 14.8 |
| 19.0 | 22.2 |
| 20.1 | 14.9 |
| 21.3 | 2.7 |
| 22.5 | 9.8 |
| 22.9 | 9.2 |
| 25.2 | 14.1 |
| 25.5 | 9.6 |
| 26.0 | 7.1 |
| 26.3 | 12.4 |
| 27.1 | 3.5 |
| 27.7 | 4.8 |
| 28.4 | 5.6 |
| 28.9 | 2.9 |
| 29.3 | 4.3 |
| 29.6 | 7.8 |
| 32.3 | 2.2 |
| 33.9 | 3.9 |

The PXRD pattern corresponding to the Freebase Anhydrate Form D is shown in FIG. 3J. Peak listing of the experimental PXRD pattern with relative intensities is given in Table 16-J below.

TABLE 16-J

PXRD Peak Listing
Freebase Anhydrate Form D

| PEAK POSITION (°2Θ) | RELATIVE INTENSITY |
|---|---|
| 4.0 | 20.6 |
| 8.0 | 29.3 |
| 9.7 | 52.1 |
| 11.2 | 7.5 |
| 12.0 | 9.8 |
| 13.0 | 1.4 |
| 14.2 | 100.0 |

TABLE 16-J-continued

PXRD Peak Listing
Freebase Anhydrate Form D

| PEAK POSITION (°2Θ) | RELATIVE INTENSITY |
|---|---|
| 14.5 | 65.7 |
| 16.1 | 3.1 |
| 17.2 | 7.5 |
| 18.4 | 24.3 |
| 19.0 | 23.5 |
| 20.3 | 43.1 |
| 21.4 | 18.5 |
| 23.0 | 35.7 |
| 23.8 | 18.3 |
| 24.7 | 35.8 |
| 25.6 | 6.0 |
| 26.1 | 14.5 |
| 27.4 | 11.7 |
| 28.2 | 9.3 |
| 28.7 | 5.2 |
| 30.3 | 6.6 |
| 31.1 | 1.3 |
| 31.9 | 3.8 |
| 32.7 | 1.0 |
| 33.3 | 5.1 |
| 34.8 | 0.7 |

Example 17

Unit Cell Parameters

Unit cell parameters were determined for the Freebase Hydrate Form C based on a single crystal X-ray diffraction study and are reported below in Table 17-A. The single crystal X-ray diffraction data were collected using a Bruker Apex II diffractometer (Bruker AXS, Madison, Wis.) equipped with an Apex II CCD area detector. The diffractometer was operated with a molybdenum anode tube (2.0 kW fine focus) at 50 kV and 40 mA. An incident beam silicon monochrometer provided Mo-Kα1 monochromatic radiation. The data were collected under a stream of cold nitrogen gas at 100 K using a Kryoflex low temperature device (Bruker AXS, Madison, Wis.). The beam diameter for data collection was 5 mm and the detector distance was 6 cm. The alignment of the goniometer was checked using a spherical 2-Dimethylsufuranylidene-1,3-indanedione (YLID) crystal. The instrument was computer controlled using the BIS and Apex 2 software programs (Bruker AXS, Madison, Wis.). The data were analyzed using Apex 2 software (Version 2011.2-0, Bruker AXS, Madison, Wis.).

TABLE 17-A

Unit Cell Parameters
Freebase Hydrate Form C

| Lattice Type | Orthorhombic |
|---|---|
| Space Group | $P2_12_12_1$ |
| a (Å) | 12.7373 |
| b (Å) | 13.0763 |
| c (Å) | 22.5650 |
| α (°) | 90.0 |
| β (°) | 90.0 |
| γ (°) | 90.0 |
| Volume (Å$^3$) | 3758.4 |
| Z | 8 |
| Density (g/cm$^3$) | 1.376 |
| R-Factor (%) | 2.4 |

Unit cell parameters also were determined for the Tartrate Hydrate based on data from a PXRD study and are reported below in Table 17-B. The unit cell parameters for the Tartrate Hydrate, however, have not been confirmed in a single crystal X-ray diffraction study. The asymmetric unit contains one molecule of Compound 1, one molecule of L-tartaric acid, and 4 molecules of water.

TABLE 17-B

Unit Cell Parameters
Tartrate Hydrate

| Lattice Type | Hexagonal |
|---|---|
| Space Group | $P6_3$ |
| a (Å) | 26.0506 |
| b (Å) | 26.0506 |
| c (Å) | 7.1652 |
| α (°) | 90.0 |
| β (°) | 90.0 |
| γ (°) | 120.0 |
| Volume (Å$^3$) | 4211.09 |
| Z | 0 |

Unit cell parameters also were determined for the Freebase Anhydrate Form D based on a single crystal X-ray diffraction study, performed using the method as described above for Freebase Hydrate Form C, and are reported below in Table 17-C.

TABLE 17-C

Unit Cell Parameters
Freebase Anhydrate Form D

| Lattice Type | Orthorhombic |
|---|---|
| Space Group | $P2_12_12$ |
| a (Å) | 43.819(8) |
| b (Å) | 8.6147(16) |
| c (Å) | 9.1957(17) |
| α (°) | 90.00 |
| β (°) | 90.00 |
| γ (°) | 90.00 |
| Volume (Å$^3$) | 3471.26(11) |
| Z | 8 |
| Density (g/cm$^3$) | 1.456 |
| R-Factor (%) | 4.94 |

Example 18

Thermogravimetric Analysis

The solid state forms of Compound 1 listed in Table 15-A were analyzed in a thermogravimetric analysis ("TGA") study. TGA thermograms were collected with a Mettler TGA/sDTA 851e (Mettler-Toledo International Incorporated, Scwezenbach, Switzerland) equipped with a TSO801RO robotic autosampler. The instrument was operated and data evaluated with the Stare software (V9.01, Mettler-Toledo International Incorporated, Scwezenbach, Switzerland). The temperature axis was calibrated with indium and aluminum standards. The sample powders were encapsulated in an appropriate pan and scanned at certain rate as specified in TGA thermogram plots. A 50 mL/minute nitrogen purge to the sample chamber was used. In cases where TGA was run with TA instruments, data were collected on a thermal balance (Q-500 or Q-5000, TA Instruments, New Castle, Del.) equipped with a data analyzer (Universal Analysis 2000, version 4.5A, TA Instruments, New Castle, Del.). During experiments, the furnace was purged with nitrogen at 60 mL/minute, while the balance chamber was purged at 40 mL/minute. Temperature of the TGA furnace was calibrated using curie points of aluminum and nickel. Sample size ranged from 2 mg to 20 mg, and a heating rate of 10° C./minute was used.

For TGA-MS, the thermogravimetric analysis part was the same as above. The mass of evolved gas was analyzed with PFEIFFER GSD 301 T3 ThermoStar (PFEIFFER Vacuum, Asslar, Germany). The instrument was operated and data evaluated with Software Quadstar 32-bit (V7.01, Inficon, LI-9496 Balzers, Liechtenstein).

For thermogravimetric analyses that were performed on Mettler TGA/sDTA 851e (Mettler-Toledo International Incorporated, Scwezenbach, Switzerland), simultaneous Differential Thermal Analysis (sDTA) signals were also recorded and the data were analyzed with the Stare software (V9.01, Mettler-Toledo International Incorporated, Scwezenbach, Switzerland).

The TGA thermograms corresponding to the Amorphous Freebase (via precipitation) and the Amorphous Freebase (via dehydration of Freebase Hydrate Form B) are shown in FIGS. 4A and 4B, respectively.

The TGA thermogram corresponding to the Freebase Solvate Form A is shown in FIG. 4C.

The TGA thermogram corresponding to the Freebase Hydrate Form B is shown in FIG. 4D.

The TGA thermogram corresponding to the Freebase Hydrate Form C is shown in FIG. 4E.

The TGA thermogram corresponding to the Tartrate Hydrate is shown in FIG. 4F.

The TGA thermogram corresponding to the Hydrochloride Solvate Form AA is shown in FIG. 4G.

The TGA thermogram corresponding to the L-Maleate Form BBB is shown in FIG. 4H.

The TGA thermogram corresponding to the Freebase Anhydrate Form D is shown in FIG. 4I.

Amorphous Freebase: TGA indicates that the Amorphous Freebase loses most of its water at or before 100° C. at a heating rate of 10° C./minute.

Freebase Hydrate Form B: TGA indicates that Freebase Hydrate Form B is a labile hydrate. The exact stoichiometry has not been confirmed. The available data suggest a higher hydrate, possibly 4 to 5 molecules of water per molecule of Freebase.

Freebase Hydrate Form C: TGA indicates that Freebase Hydrate Form C is a hemihydrate which is consistent with the single-crystal X-ray diffraction data. In general, TGA at a heating rate of 10° C./minute (ambient relative humidity) shows dehydration of Freebase Hydrate Form C between approximately 120° C. and 160° C. with a weight loss of approximately 2.3% to 2.6% between these temperatures.

Tartrate Hydrate: TGA indicates that the Tartrate Hydrate is a tetrahydrate. In general, TGA at a heating rate of 10° C./minute (ambient relative humidity) shows dehydration of Tartrate Hydrate between approximately 25° C. and 160° C. with a weight loss of approximately 12% between these temperatures.

Freebase Anhydrate Form D: In general, TGA at a heating rate of 10° C./minute (ambient relative humidity) shows dehydration of Freebase Anhydrate Form D between about 43° C. and 188° C., with a weight loss of approximately 0.5% between these temperatures.

Example 19

Differential Scanning Calorimetry

The solid state forms of Compound 1 listed in Table 15-A were analyzed by differential scanning calorimetry ("DSC"). DSC data were collected with a Mettler DSC 823e (Mettler-Toledo International Incorporated, Schwerzenbach, Switzerland) equipped with a TSO801RO robotic autosampler. The instrument was operated and data evaluated with the Stare software (V9.01, Mettler-Toledo International Incorporated, Schwerzenbach, Switzerland). The temperature axis was calibrated with indium and aluminum standards. Unless otherwise stated, the sample (2 mg to 5 mg) was encapsulated in a ventilated aluminum pan, pricked just prior to loading into the measurement cell, and heated at a rate of 10° C./minute under a nitrogen gas flow of 50 mL/minute during the study.

The DSC thermogram corresponding to the Amorphous Freebase (via dehydration) is shown in FIG. 5A.

The DSC thermogram corresponding to the Freebase Hydrate Form B is shown in FIG. 5B.

The DSC thermogram corresponding to the Freebase Hydrate Form C is shown in FIG. 5C.

The DSC thermogram corresponding to the Tartrate Hydrate is shown in FIG. 5D.

The DSC thermogram corresponding to the Freebase Anhydrate Form D is shown in FIG. 5E.

Amorphous Freebase: DSC indicates that Amorphous Freebase has a glass transition onset temperature of about 119° C. with a midpoint of about 122° C.

Freebase Hydrate Form B: The DSC thermogram for Freebase Hydrate Form B, at a heating rate of 10° C./minute (ambient relative humidity), shows two endotherms. The first endotherm relates to loss of water (12.3%) and the second endotherm relates to both loss of water (5.5%) and incongruent melting.

Freebase Hydrate Form C: The DSC thermogram for Freebase Hydrate Form C, at a heating rate of 10° C./minute (ambient relative humidity), shows an endotherm between approximately 120 and 170° C., with an onset temperature of 134.7° C. and a peak temperature of 149.9° C.

Tartrate Hydrate: The DSC thermogram for Tartrate Hydrate, at a heating rate of 10° C./minute (ambient relative humidity), shows an endotherm corresponding to dehydration at approximately 60° C. to 100° C.

Freebase Anhydrate Form D: The DSC thermogram for Freebase Anhydrate Form D, at a heating rate of 10° C./minute (ambient relative humidity), shows an endotherm between about 180° C. and about 220° C., with an onset melting point of about 199.55° C., and a melting enthalpy of 85.4 J/g.

As with all thermal analysis, one of skill in the art will appreciate that the DSC thermogram may change to some extent depending on factors such as heating rate, sample particle size, sample purity, sample moisture content, ambient relative humidity, etc.

Example 20

Moisture Sorption Isotherm

The solid state forms of Compound 1 listed in Table 15-A were analyzed in a moisture vapor isotherm study. Moisture vapor isotherm data were collected with a DVS Advantage (Surface Measurement Systems Ltd, Alperton, United Kingdom). The sample powder (5 mg to 20 mg) was loaded on a tared pan of the DVS Advantage. The moisture sorption isotherm data were collected from 30-0-90-0-30% relative humidity in 10% relative humidity intervals. For each step, the dm/dt criteria was 0.001% over 5 minutes, a minimum dm/dt time of 30 minutes, and a maximum dm/dt of 120 minutes. Data was collected isothermally at 25° C. with a nitrogen flow rate of 200 cm³/minute. The post DVS sample was kept at approximately 30% relative humidity before PXRD analysis.

The moisture sorption isotherm corresponding to the Amorphous Freebase (via dehydration) is shown in FIG. 6A.

The moisture sorption isotherm corresponding to the Freebase Hydrate Form C (Hemihydrate) is shown in FIG. 6B.

The moisture sorption isotherm corresponding to the Tartrate Hydrate is shown in FIG. 6C.

The moisture sorption isotherm corresponding to the Freebase Anhydrate Form D is shown in FIG. 6D.

Amorphous Freebase: Moisture sorption isotherm analysis indicates that the Amorphous Freebase obtained through dehydration of Freebase Hydrate Form B reversibly sorbs up to 13% at 90% relative humidity at 25° C.

Freebase Hydrate Form B: No moisture sorption isotherm could be obtained for Freebase Hydrate Form B. The Freebase Hydrate Form B is not stable at ambient conditions and readily dehydrates to the Amorphous Freebase.

Freebase Hydrate Form C: Moisture sorption isotherm analysis indicates that the Freebase Hydrate Form C is not hygroscopic.

Tartrate Hydrate: Moisture sorption isotherm analysis indicates that the Tartrate Hydrate dehydrates to an amorphous tartrate below 10% relative humidity at 25° C. If the moisture sorption isotherm analysis is restricted to a relative humidity range of 10% to 90%, the appearance of the moisture sorption isotherm generally will correspond to the moisture sorption shown in FIG. 6C for the Tartrate Hydrate.

Freebase Anhydrate Form D: Moisture sorption isotherm analysis indicates that Freebase Anhydrate Form D reversibly sorbs up to 1.8% water at 90% relative humidity at 25° C.

Example 21

Solid State Accelerated Stability Study

The solid state forms of Compound 1 listed in Table 15-A were analyzed in a solid state accelerated stability study. Samples (approximately 1 mg to 2 mg) of the solid state form were weighed into glass vials and tested as described below. Chemical stability was acceptable for the Amorphous Freebase, the Freebase Hydrate Form C, and the Tartrate Hydrate. The L-maleate salt, however, was prone to chemical degradation.

Amorphous Freebase: The Amorphous Freebase exhibited no growth of degradation products after storage at 50° C./75% relative humidity (open and closed glass vials) for up to six weeks and after storage at 40° C./75% relative humidity (open and closed glass vials) for up to 24 weeks. No material change was observed for any of the attributes evaluated (description, crystal form, assay, impurities and water content).

Freebase Hydrate Form C: The Freebase Hydrate Form C surprisingly exhibited no growth of degradation products under the conditions listed in Table 16-A below (open and closed glass vials):

TABLE 21-A

| Testing Conditions | | | |
|---|---|---|---|
| Storage Condition (Temp ° C./% RH) | Packaging | Duration | Tests |
| 80/75 | Open and closed vials | 10 Days | Description |
| 50/75 | Open and closed vials | 6 Weeks | Crystal Form |
| 40/75 | Open and closed vials | 24 Weeks | Assay |
| 30/65 | Open and closed vials | 24 Weeks | Impurities |
| 25/60 | Double polyethylene bags, twist tie, in HDPE drum | 12 Months | Water Content |

No material change was observed for any of the attributes evaluated (description, crystal form, assay, impurities and water content).

Tartrate Hydrate: The Tartrate Hydrate exhibited no growth of degradation products after storage at 25° C./60% relative humidity (open and closed glass vials) for up to 24 months, after storage at 40° C./75% relative humidity (open and closed glass vials) for least one month, and after storage at 50° C./75% relative humidity (open and closed glass vials) for up to six weeks. No material change was observed for any of the attributes evaluated (description, crystal form, assay, impurities and water content).

L-Maleate Form BBB: When stored at 50° C./75% relative humidity (open and closed glass vials), the L-maleate salt degraded to products that were not observed for the Freebase Hydrate Form C or the Tartrate Hydrate.

Example 22

Thermal Degradation Study

The solid state forms of Compound 1 listed in Table 15-A were analyzed in a thermal degradation study. The following pH solutions were prepared: 0.1N hydrochloric acid (HCl); 50 mM sodium phosphate buffer (pH 7.4, adjusted to 0.155 M ionic strength with sodium chloride) and FasSIF (pH 6.5). For each buffer, a target concentration of about 100 µg/mL was prepared by accurately weighing about 1 mg of the solid state form using a microanalytical balance into a scintillation vial. Water (1 mL) was added to dissolve the solid as a stock solution. The stock solution was diluted 10 times in the various buffers to prepare reaction solutions. The peak area of the compound in these reaction solutions was monitored at 37° C. by HPLC every two hours up to 32 hours total.

Example 23

Solubility Stability

For equilibrium solubility, sufficient solid was added to 3-4 mL liquid medium in triplicate, such that excess solid remained undissolved. The mixtures were equilibrated for 24-48 hr at 25 rpm on an end-over-end tumbler model 30-1200 (Vankel, Cary, N.C.) in a constant temperature water bath. After equilibration, the mixtures were inspected to assure that the amount of excess solid was sufficient to permit re-characterization. If not, additional solid was added and the mixtures were again equilibrated for 24-48 hr. The pH of aqueous suspensions was determined after equilibration. The solid phase was separated from the liquid phase by centrifugation at 3300 rpm at equilibration temperatures (i.e., 25° C. or 37° C.). The supernatant was then filtered (13 mm Acrodisc® syringe filter with 0.45µ GHP membrane, Pall® Life Sciences, Ann Arbor, Mich.) to discard the initial 2 mL (to saturate filter) and capture the last 1 mL for analysis. The filtrate was diluted as needed for quantification of the material studied by HPLC method (as detailed elsewhere herein). The physical form of the recovered solid was characterized by powder X-ray diffraction to examine whether or not phase change had occurred The results are set forth in Table 23-A.

TABLE 23-A

| Medium | Amorphous Freebase (mg/mL) | Freebase Hydrate Form C (mg/mL) |
|---|---|---|
| pH 1 at 25° C. | >3.5 | 55.3 |
| pH 7.4 at 25° C. | 0.68 | 0.19 |
| FasSIF (pH 6.5 at 37° C.) | 1.14 | 0.22 |
| FedSIF (pH 5.0 at 37° C.) | 2.13 | 0.47 |

Examples 24-27

Extended Release Tablets

The Freebase Hydrate Form C and Amorphous Freebase solid state form of Compound 1 listed in Table 15-A were formulated into 24 mg extended release tablets according to the formulations set forth in Table 24-A.

TABLE 24-A

Extended Release Tablets (no pH modifier)

| Component | Function | Ex. 24 (ER1) (mg) | Ex. 25 (ER2) (mg) | Ex. 26 (ER3) (mg) | Ex. 27 (mg) |
|---|---|---|---|---|---|
| Freebase Hydrate Form C | Active | 24.0 | 24.0 | 24.0 | — |
| Amorphous Freebase | Active | — | — | — | 24.0 |
| Microcrystalline cellulose (Avicel ® PH 102) | Filler | 351.4 | 303.4 | 303.4 | 303.4 |
| HPMC (Methocel ® K100 Premium LVCRLH) | Release control polymer | 96.0 | 96.0 | — | — |
| HPMC (Methocel ® K4M Premium CR) | Release control polymer | — | 48.0 | 144.0 | 144.0 |
| Colloidal silicon dioxide | Glidant | 3.8 | 3.8 | 3.8 | 3.8 |
| Magnesium stearate impalpable powder | Lubricant | 4.8 | 4.8 | 4.8 | 4.8 |
| Uncoated weight of tablet | | 480.0 | 480.0 | 480.0 | 480.0 |

The formulations were prepared by combining and blending the active, microcrystalline cellulose, hydroxypropyl methyl cellulose (HPMC), and colloidal silicone dioxide. The blend was milled using a Mobil Mill fitted with a 610 micron screen. The magnesium stearate was screened through mesh #30 and was added to the bin and blended.

The lubricated granulation was compressed into 480 mg weight tablets using a rotary tablet press. The tablets may optionally be coated with any suitable film coating.

The effect of solid state form on the dissolution profile of the tablets was evaluated. In particular, the dissolution profile of the Example 26 (containing Freebase Hydrate Form C as active) and Example 27 (containing Amorphous Freebase as active) tablets was evaluated at pH 6.8 (representative of the pH in the lower intestine). The dissolution test was carried out using the following dissolution parameters and conditions:

Apparatus: USP Dissolution Apparatus 2 and fraction collector
Medium: 900 mL of 50 mM sodium phosphate buffer solution, pH 6.8.
Temperature: 37° C.±0.5° C.
RPM: 75 RPM±4%
Filter: 35 μm PE filter, or equivalent, for automatic sampling
Sampling Times: 1, 2, 4, 6, 8, 10, 12, 16, and 20 Hours.
Other samples may be taken at other times, as appropriate.
Sample Volume: 1.5 mL obtained automatically, without media replacement.

The medium used for the study was a 0.05 M sodium phosphate buffer solution, pH 6.8±0.05. The medium was prepared using an acid stage medium (0.1 N hydrochloric acid solution) and a buffer stage concentrate (0.05 M sodium phosphate buffer concentrate solution, prepared by dissolving about 41.4 g of sodium phosphate, monobasic, monohydrate and about 14.4 g of sodium hydroxide pellets in about 4 L of water, dilute to 6 L with water and mixing well). The medium was prepared by mixing 500 mL of the acid stage medium and 400 mL of buffer stage concentrate in an appropriate size container or directly in the dissolution vessel and adjusting the pH with 1 N phosphoric acid or 1 N sodium hydroxide, if the pH was not within 6.8±0.05.

For the dissolution test, one tablet each was added to a dissolution vessel containing 900 mL of the 0.05 M sodium phosphate buffer solution maintained at 37° C. The paddles of the dissolution apparatus were operated at 75 RPM, with 1.5 mL samples from the dissolution vessel automatically obtained at the designated time periods. The sample filtrate was the sample preparation.

For the analysis of the sample, conventional liquid chromatography methods were utilized, wherein the % of the labelled amount of active released (% LA Released) was calculated. The results are set forth in FIG. 7.

Figure 7:
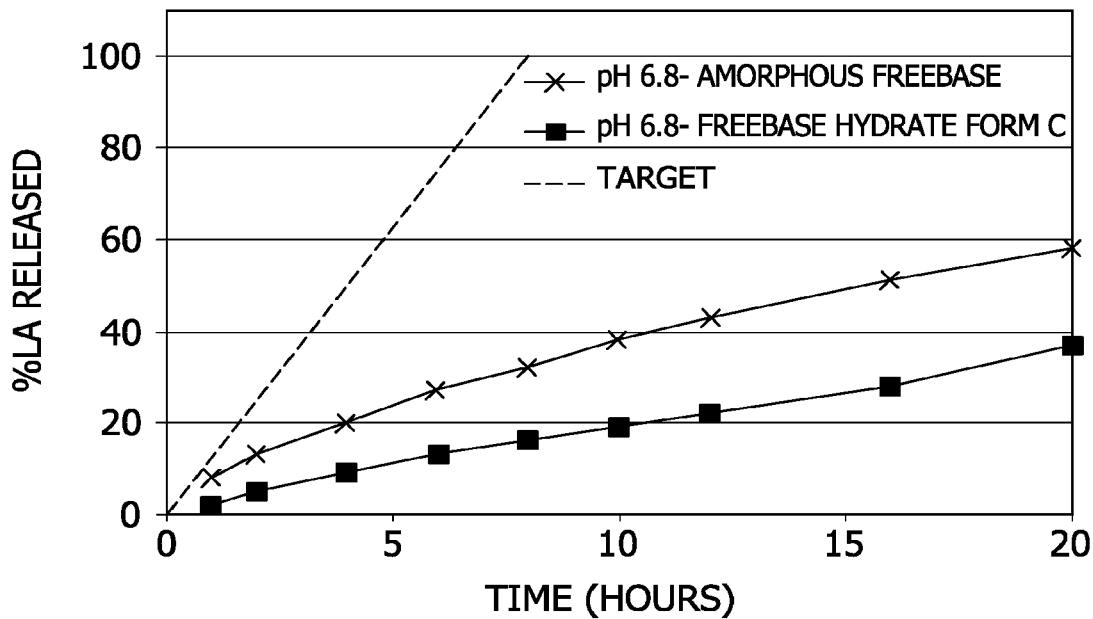
FIG. 7 is a comparison of the dissolution profile of the extended release tablets from Example 26 (Freebase Hydrate Form C) and Example 27 (Amorphous Freebase) at pH 6.8.

As can be seen from FIG. 7, the formulation containing Freebase Hydrate Form C (Example 26) as the active showed a slower rate of dissolution than the formulation containing Amorphous Freebase (Example 27) as the active at pH 6.8.

The dissolution profile of formulations comprising Freebase Hydrate Form C as an active was further evaluated at pH 6.8 and in a dual pH system. In particular, the dissolution profile of the Example 24 (ER1), Example 25 (ER2), and Example 26 (ER3) tablets at pH 6.8 was carried out as described above. The dissolution profile of the Examples 24-26 tablets was also carried out in a dual pH system using the following dissolution parameters and conditions:

Apparatus: USP Dissolution Apparatus 2 and fraction collector
Medium: Acid Stage: 500 mL of Acid Stage Medium (0.1 N hydrochloric acid solution)
Buffer Stage: 900 mL of 50 mM sodium phosphate buffer solution, pH 6.8.
Temperature: 37° C.±0.5° C.
RPM: 75 RPM±4%
Filter: 35 μm PE filter, or equivalent, for automatic sampling
Sampling Times: Acid Stage: 1 Hour
Buffer Stage: 2, 4, 6, 8, 10, 12, 16, and 20 Hours.
Other samples may be taken at other times, as appropriate.
Sample Volume: Acid: 1.5 mL obtained automatically, without media replacement.

The acid stage medium is a 0.1 N hydrochloric acid solution. A buffer stage medium for the study was prepared using a buffer stage concentrate (0.05 M sodium phosphate buffer concentrate solution, prepared by dissolving about 41.4 g of sodium phosphate, monobasic, monohydrate and about 14.4 g of sodium hydroxide pellets in about 4 L of water, dilute to 6 L with water and mixing well). The buffer stage medium of a 0.05 M sodium phosphate buffer solution, pH 6.8±0.05, was prepared by mixing 500 mL of the acid stage medium and 400 mL of buffer stage medium concentrate in an appropriate size container or directly in the dissolution vessel and adjusting the pH of the buffer stage medium concentrate with 1 N phosphoric acid or 1 N sodium hydroxide, if the pH was not within 6.8±0.05.

For the dissolution test, one tablet each was added to a dissolution vessel containing 500 mL of a 0.1 N hydrochloric acid solution maintained at 37° C. The paddles of the dissolution apparatus were operated at 75 RPM for 1 hour, and then a 1.5 mL sample from the dissolution vessel was automatically obtained. After the acid stage sample was obtained, 400 mL of buffer stage medium concentrate was added, maintained at 37° C. The dissolution test was continued, with the paddles remaining at a speed of 75 RPM. The sample filtrate was the sample preparation.

For the analysis of the sample, conventional liquid chromatography methods were utilized, wherein the % relative standard deviation (RSD) of peak areas was calculated for each set of six standard injections. The results are set forth in FIG. 8.

Figure 8:
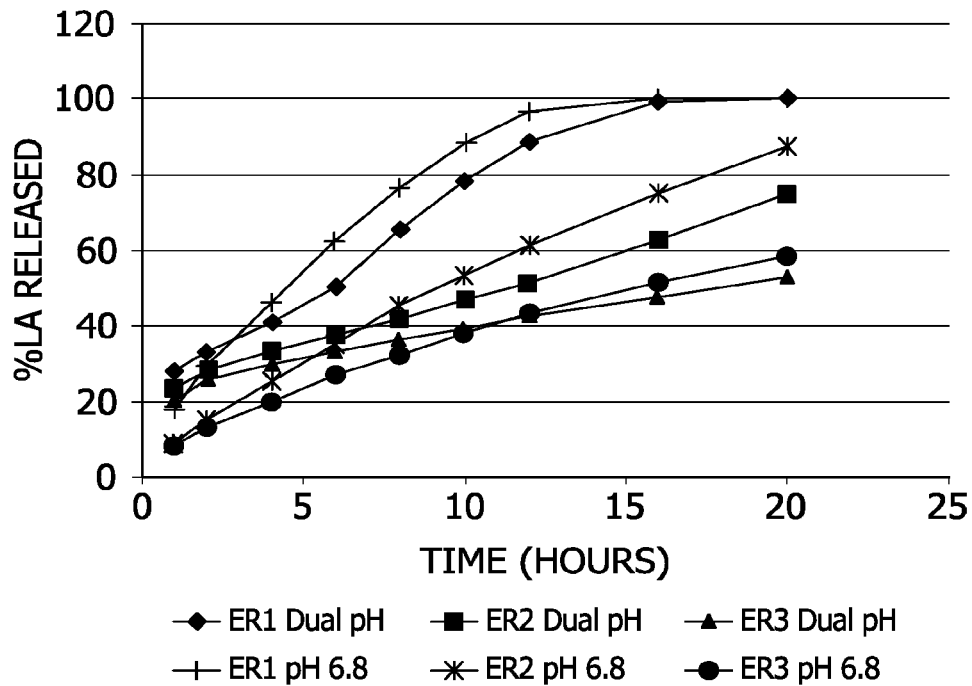
FIG. 8 is a comparison of the dissolution profile of the extended release tablets from Example 24 (ER1), Example 25 (ER2), and Example 26 (ER3) in a dual pH system and at pH 6.8.

As can be seen from FIG. 8, after the initial release at the low pH (representative of the pH in the stomach), release of the drug is slowed at the higher pH (representative of the pH in the lower intestine). Therefore, in order to achieve the desired bioavailability, a formulation which allowed pH independent release was required.

Examples 28-35

Extended Release Tablets

The Freebase Hydrate Form C solid state form of Compound 1 listed in Table 15-A was formulated into 15 mg, 24 mg, or 30 mg extended release tablets according to the formulations set forth in Table 28-A using direct compression.

TABLE 28-A

| | | Extended Release Tablets (tartaric acid pH modifier) | | | | | | | |
|---|---|---|---|---|---|---|---|---|---|
| Component | Function | Ex. 28 (mg) (ER7) | Ex. 29 (mg) | Ex. 30 (mg) | Ex. 31 (mg) (ER8) | Ex. 32 (mg) (ER4) | Ex. 33 (mg) (ER4, no mannitol) | Ex. 34 (mg) (ER5) | Ex. 35 (mg) (ER6) |
| Freebase Hydrate Form C | Active | 15.4$^a$ | 15.4$^a$ | 15.4$^a$ | 30.7$^b$ | 24.6$^c$ | 24.6$^c$ | 24.6$^c$ | 24.6$^c$ |
| Microcrystalline cellulose (Avicel ® PH 102) | Filler | 162.4 | 162.4 | 162.4 | 147.1 | 158.0 | 210.6 | 282.6 | 258.6 |
| Mannitol (Pearlitol ® 100 SD) | Filler | 52.6 | 52.4 | — | 52.6 | 52.7 | — | — | — |
| Mannitol (Pearlitol ® 200 SD) | Filler | — | — | 52.4 | — | — | — | — | — |
| Tartaric acid | pH modifier | 144.0 | 144.0 | 144.0 | 144.0 | 144.0 | 144.0 | 96.0 | 96.0 |
| HPMC (Hypromellose 2208) | Release control polymer | 96.0 | — | — | 96.0 | — | — | — | — |
| HPMC (Methocel ® K4M Premium CR) | Release control polymer | — | 96.0 | 96.0 | — | 96.0 | 96.0 | — | — |
| Carbopol ® 71G | Release control polymer | — | — | — | — | — | — | 48.0 | 72.1 |
| Carbopol ® 971P | Release control polymer | — | — | — | — | — | — | 24.0 | 24.0 |
| Colloidal silicon dioxide | Glidant | 2.4 | 2.4 | 2.4 | 2.4 | — | — | — | — |
| Magnesium stearate impalpable powder | Lubricant | 7.2 | 7.2 | 7.2 | 7.2 | 4.8 | 4.8 | 4.8 | 4.8 |
| Uncoated weight of tablet | | 480.0 | 479.8 | 479.8 | 480.0 | 480.1 | 480.0 | 480.0 | 480.1 |
| Opadry ® II Yellow (PVA based) | Film coat | 14.40 | — | — | 14.40 | — | — | — | — |
| Total weight of tablet | | 494.39 | | | 494.43 | — | — | — | — |

$^a$Provides 15 mg of Compound 1 freebase equivalent.
$^b$Provides 30 mg of Compound 1 freebase equivalent.
$^c$Provides 24 mg of Compound 1 freebase equivalent.

The formulations were prepared by first milling the tartaric acid through a Fitz mill Model M5A, fitted with a 1512-0027 screen. The Freebase Hydrate Form C, microcrystalline cellulose, mannitol (when present), milled tartaric acid, release control polymer, and colloidal silicone dioxide (when present) were combined and blended. The blend was milled using a Mobil Mill fitted with a 610 or 1397 micron screen. The magnesium stearate was screened through mesh #30 and was then added to the bin and blended. The lubricated granulation was compressed into about 480 mg weight tablets using a rotary tablet press.

The Example 28 and 31 tablets were coated using a film coater, which sprayed a solution containing the Opadry® II Yellow film coat and purified water until 14.40 mg of coating had been applied to the tablets.

The dissolution profile of the Example 32 (ER4, 24 mg active), Example 33 (ER4, no mannitol, 24 mg active), Example 34 (ER5, 24 mg active), and Example 35 (ER6, 24 mg active) tablets was evaluated at pH 1.2, at pH 6.8, and in a dual pH system. The pH 6.8 study was performed as described above for Examples 26 and 27. For the dual pH study, an acid stage medium of 0.05 M sodium phosphate solution, pH 3.5±0.05, was prepared by dissolving about 41.4 g of sodium phosphate, monobasic, monohydrate in about 4 L of water, measuring the pH and adding phosphoric acid, 85%, dropwise as needed to adjust to the target pH. The mixture was diluted to 6 L with water and mixed. A buffer stage medium for the study was prepared using a buffer stage concentrate (0.05 M sodium phosphate buffer concentrate solution, prepared by dissolving about 41.4 g of sodium phosphate, monobasic, monohydrate and about 14.4 g of sodium hydroxide pellets in about 4 L of water, dilute to 6 L with water and mixing well). The buffer stage medium of a 0.05 M sodium phosphate buffer solution, pH 6.8±0.05, was prepared by mixing 500 mL of the acid stage medium and 400 mL of buffer stage medium concentrate in an appropriate size container or directly in the dissolution vessel and adjusting the pH of the buffer stage medium concentrate with 1 N phosphoric acid or 1 N sodium hydroxide, if the pH was not within 6.8±0.05.

The dissolution test was carried out using the following dissolution parameters and conditions:
Apparatus: USP Dissolution Apparatus 2 and fraction collector
Medium: Acid Stage: 500 mL of Acid Stage Medium
  Buffer Stage: 900 mL of 50 mM sodium phosphate buffer solution, pH 6.8
Temperature: 37° C.±0.5° C.
RPM: 75 RPM±4%
Filter: 35 µm PE filter, or equivalent, for automatic sampling
Sampling Times: Acid Stage: 1 Hour
  Buffer Stage: 2, 4, 6, 8, 10, 12, 16, and 20 Hours.
  Other samples may be taken at other times, as appropriate.
Sample Volume: Acid and Buffer Stage: 1.5 mL obtained automatically, without media replacement.

For the dissolution test, one tablet each was added to a dissolution vessel containing 500 mL of the acid stage medium, maintained at 37° C. The paddles of the dissolution apparatus were operated at 75 RPM for 1 hour, and then a 1.5 mL sample from the dissolution vessel was automatically obtained. After the acid stage sample was obtained, 400 mL of buffer stage medium concentrate was added, and then the mixture was maintained at 37° C. The dissolution test was continued, with the paddles remaining at a speed of 75 RPM. The sample filtrate was the sample preparation.

For the pH 1.2 study, the dissolution test was carried out using the following dissolution parameters and conditions:
Apparatus: USP Dissolution Apparatus 2 and fraction collector
Medium: 500 mL of Acidic Medium, pH 1.2
Temperature: 37° C.±0.5° C.
RPM: 75 RPM±4%
Filter: 35 µm PE filter, or equivalent, for automatic sampling
Sampling Times: 1, 2, 4, 6, 8, 10, 12, 16, and 20 Hours.
  Other samples may be taken at other times, as appropriate.
Sample Volume: 1.5 mL obtained automatically, without media replacement.

For this study, an acidic medium of 0.05 M sodium phosphate solution, pH 3.5±0.05, was prepared by dissolving about 41.4 g of sodium phosphate, monobasic, monohydrate in about 4 L of water, measuring the pH and adding phosphoric acid, 85%, dropwise as needed to adjust to the target pH of 1.2. The mixture was diluted to 6 L with water and mixed.

For the dissolution test, one tablet each was added to a dissolution vessel containing 500 mL of the acidic medium, maintained at 37° C. The paddles of the dissolution apparatus were operated at 75 RPM, with 1.5 mL samples from the dissolution vessel automatically obtained at the designated time periods. The sample filtrate was the sample preparation.

Figure 9:
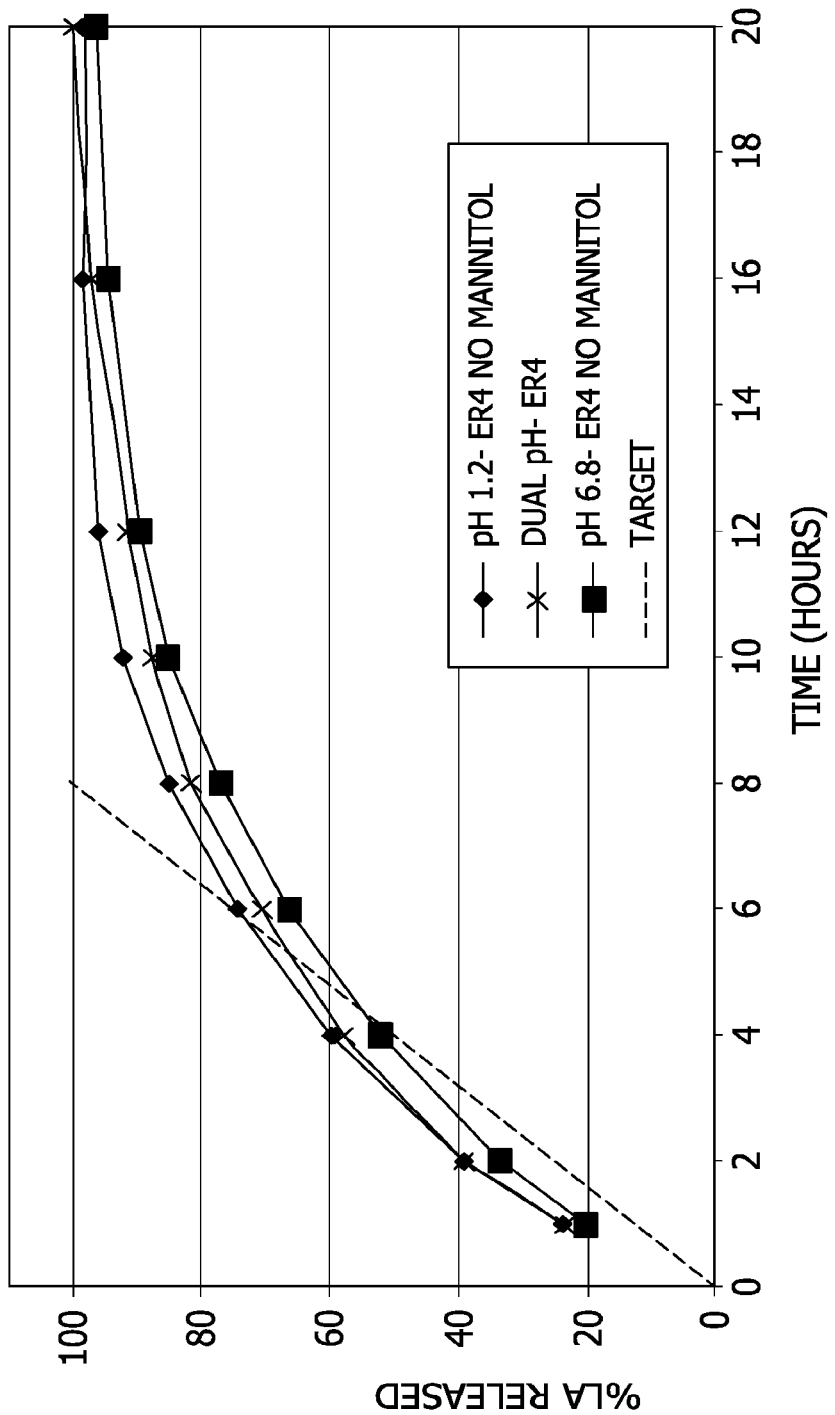
FIG. 9 is a comparison of the dissolution profile of the extended release tablet from Example 32 (ER4) and Example 33 (ER4, no mannitol) at pH 1.2, pH 6.8, or a dual pH system.
Figure 10:
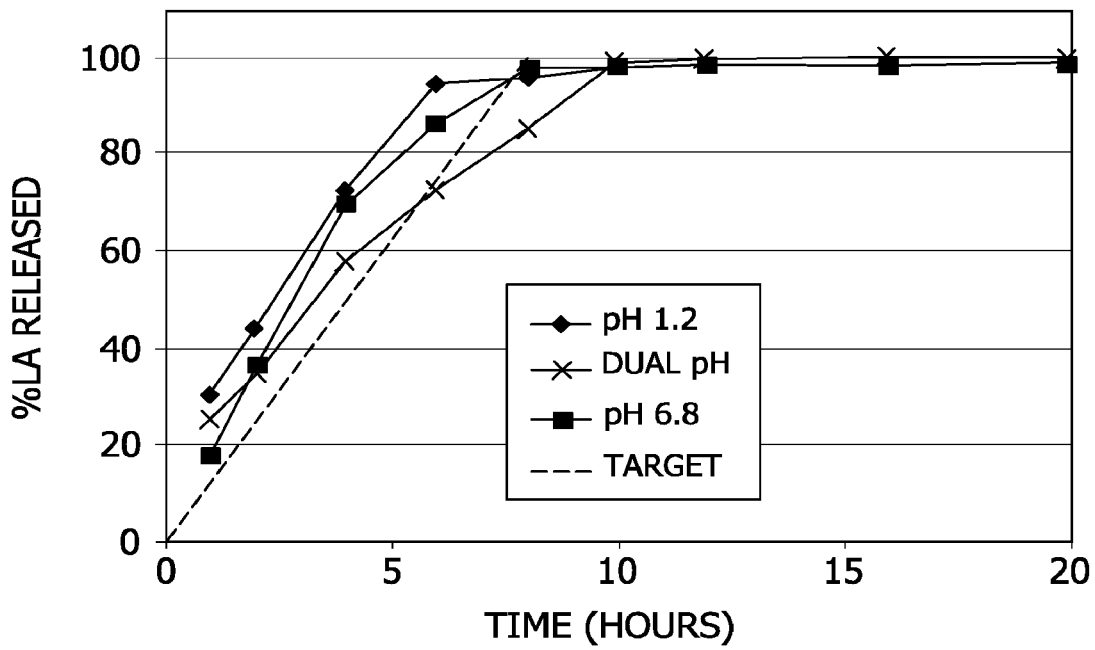
FIG. 10 is a comparison of the dissolution profile of the extended release tablet from Example 34 (ER5) at pH 1.2, pH 6.8, and a dual pH system.
Figure 11:
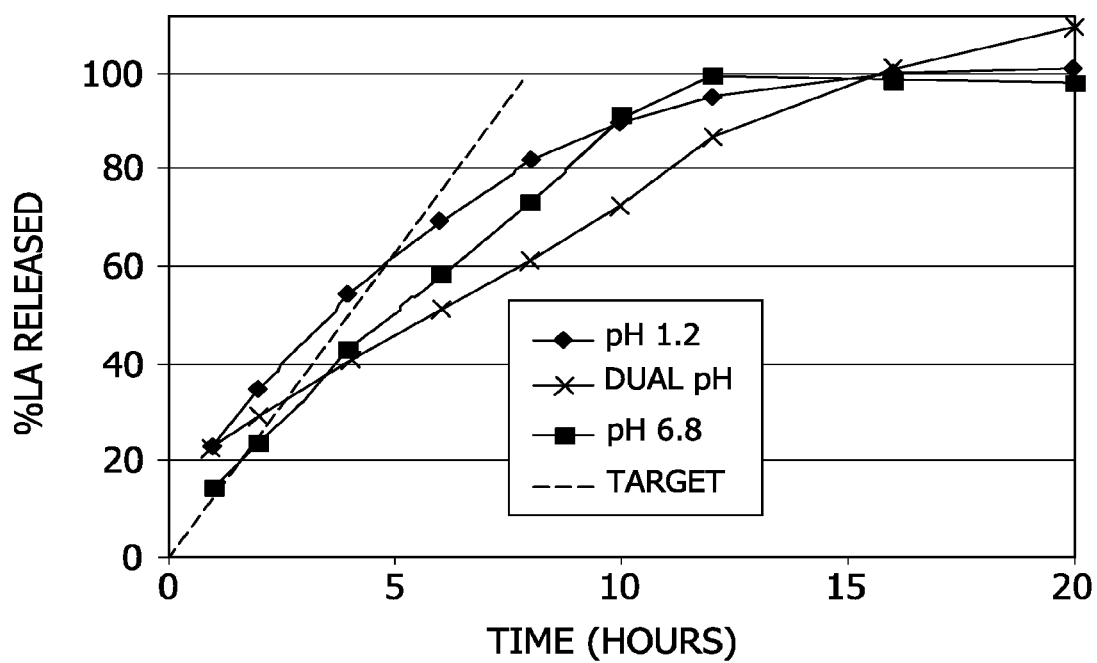
FIG. 11 is a comparison of the dissolution profile of the extended release tablet from Example 35 (ER6) at pH 1.2, pH 6.8, and a dual pH system.

For the analysis of the sample, conventional liquid chromatography methods were utilized, wherein the % relative standard deviation (RSD) of peak areas was calculated for each set of six standard injections. The results are set forth in FIG. 9 (Example 32 and 33 tablets), FIG. 10 (Example 34 tablet) and FIG. 11 (Example 35 tablet). As can be seen from FIGS. 9-11, pH independence is achieved in the once daily formulations.

Figure 12:
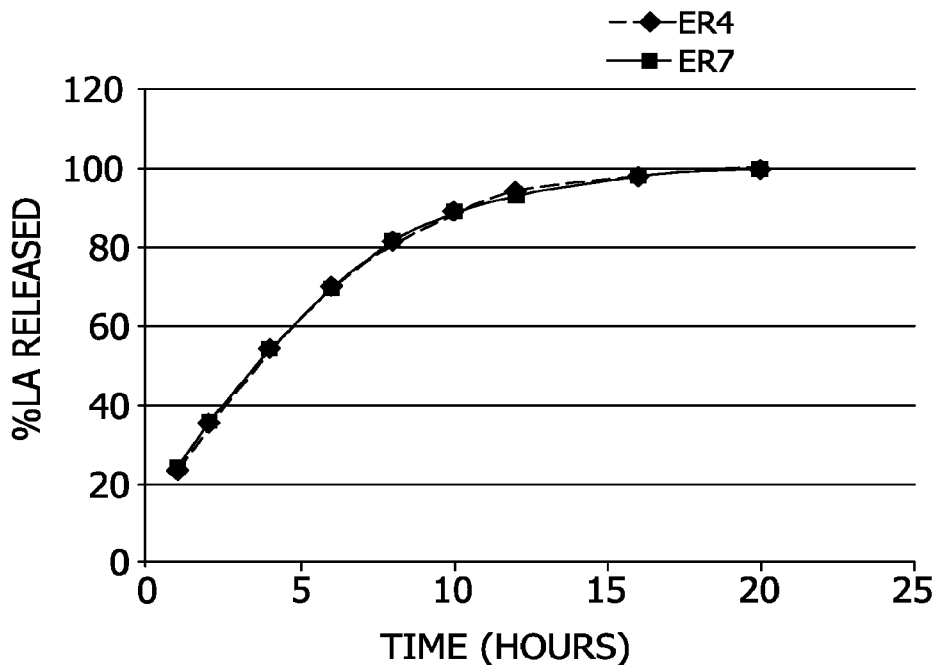
FIG. 12 is a comparison of the dissolution profile of the extended release tablet from Example 28 (ER7) and Example 32 (ER4) in a dual pH system.
Figure 13:
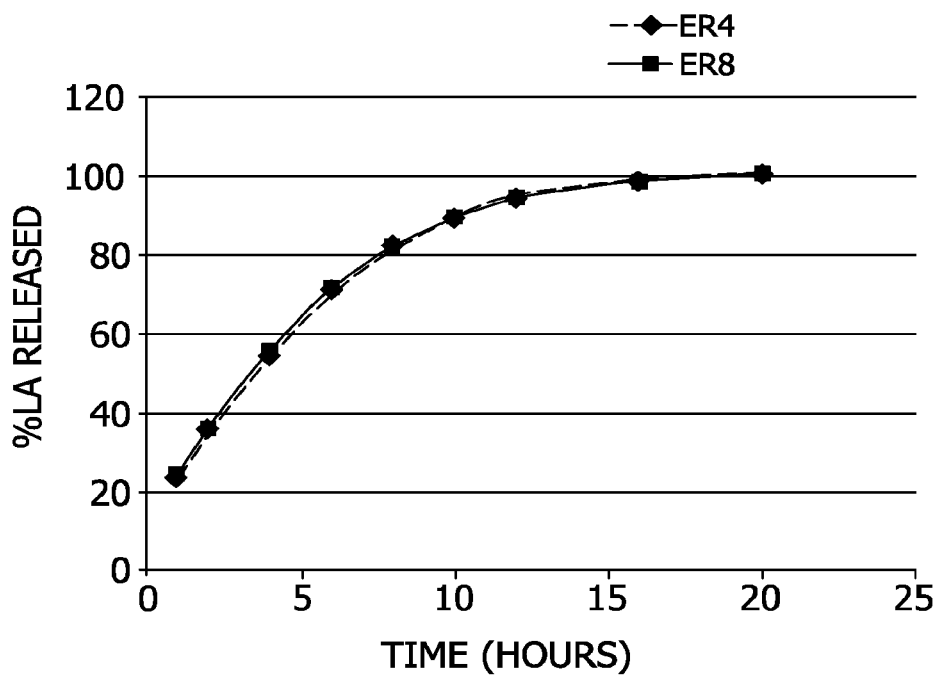
FIG. 13 is a comparison of the dissolution profile of the extended release tablet from Example 31 (ER8) and Example 32 (ER4) in a dual pH system.

The dissolution profile of the Example 28 (ER7), Example 31 (ER8), and Example 32 (ER4) tablets were evaluated in a dual pH system, as described above. The results are set forth in FIGS. 12 and 13. As can be seen from FIGS. 12 and 13, the formulations provide an extended release profile of 80-100% over a period of about 8-10 hours.

Figure 14:
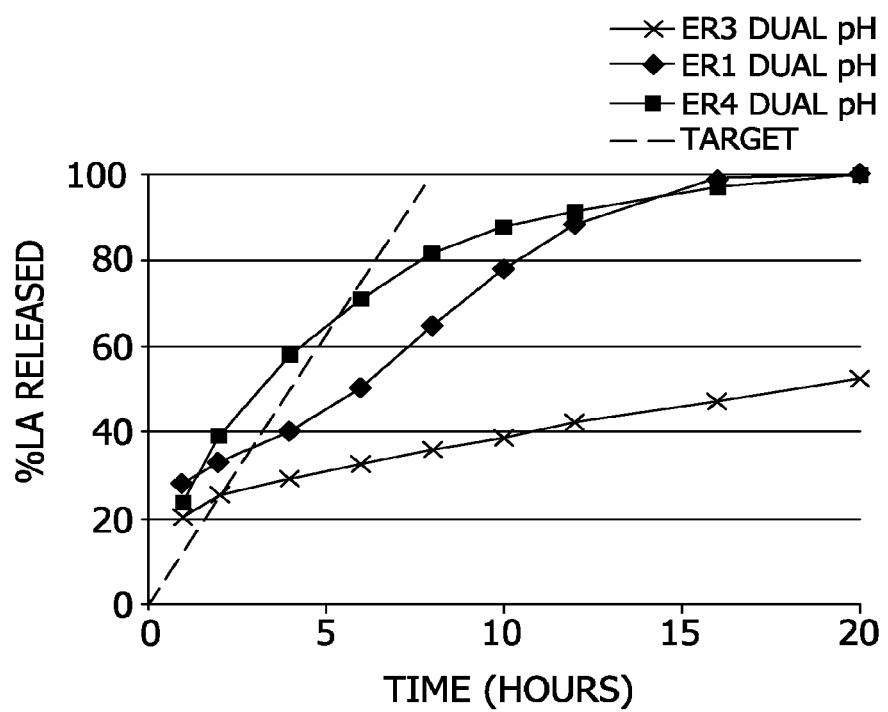
FIG. 14 is comparison of the dissolution profile of the extended release tablets from Example 24 (ER1), Example 26 (ER3), and Example 32 (ER4) in a dual pH system.
Figure 15A:
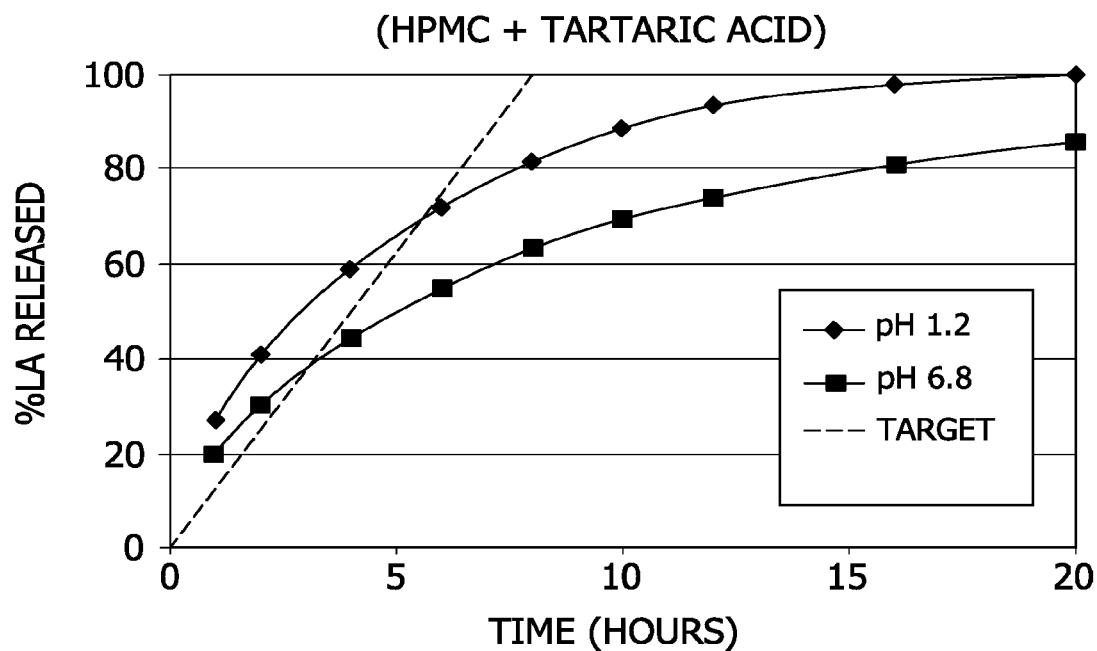
FIGS. 15A-15H are comparisons of the dissolution profile at pH 1.2 and 6.8 for the extended release tablets from Example 43, which contain either HPMC (FIGS. 15A-15D) or Carbopol® (FIGS. 15E-15H) as release control polymers, and tartaric acid (FIGS. 15A and 15E), citric acid (FIGS. 15B and 15F), succinic acid (FIGS. 15C and 15G), or fumaric acid (FIGS. 15D and 15H) as a pH modifier.
Figure 15B:
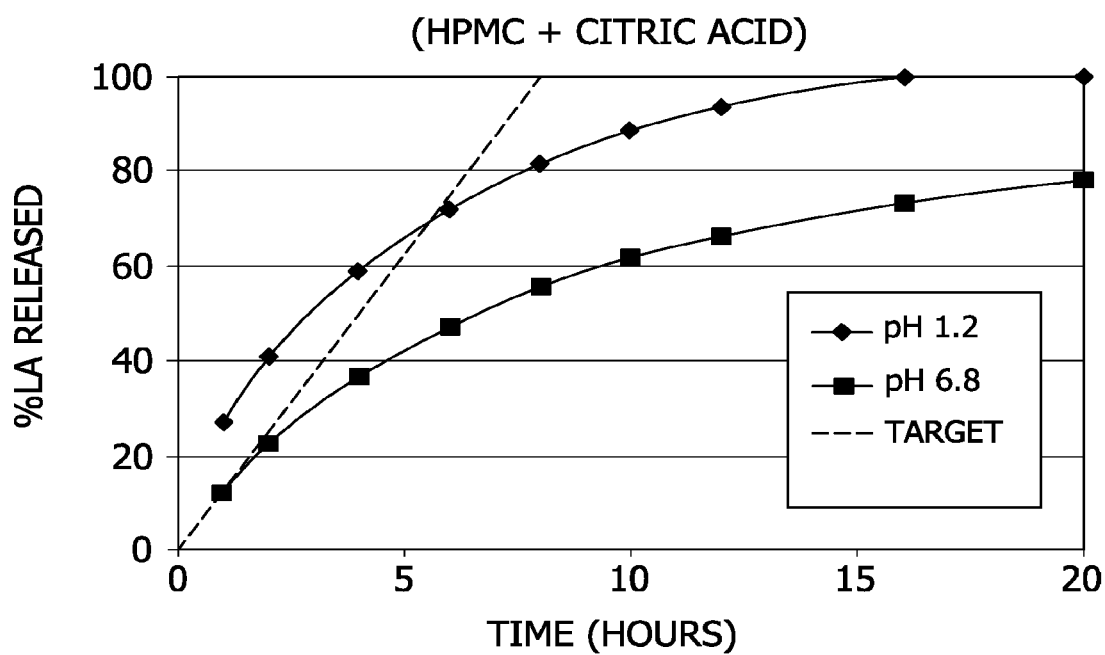
Figure 15C:
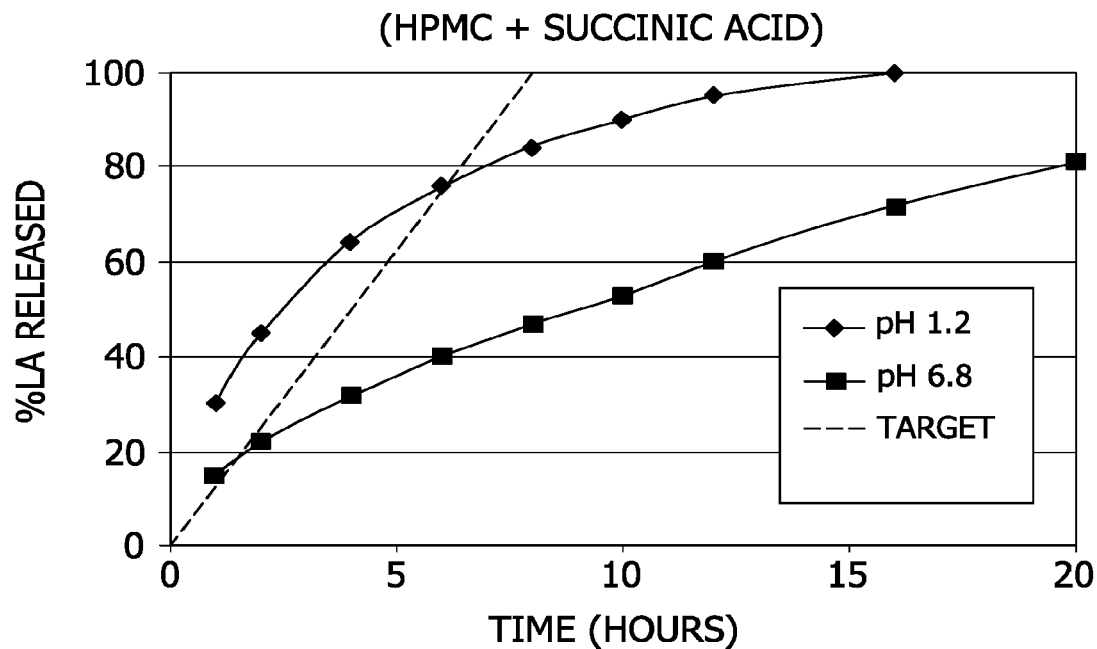
Figure 15D:
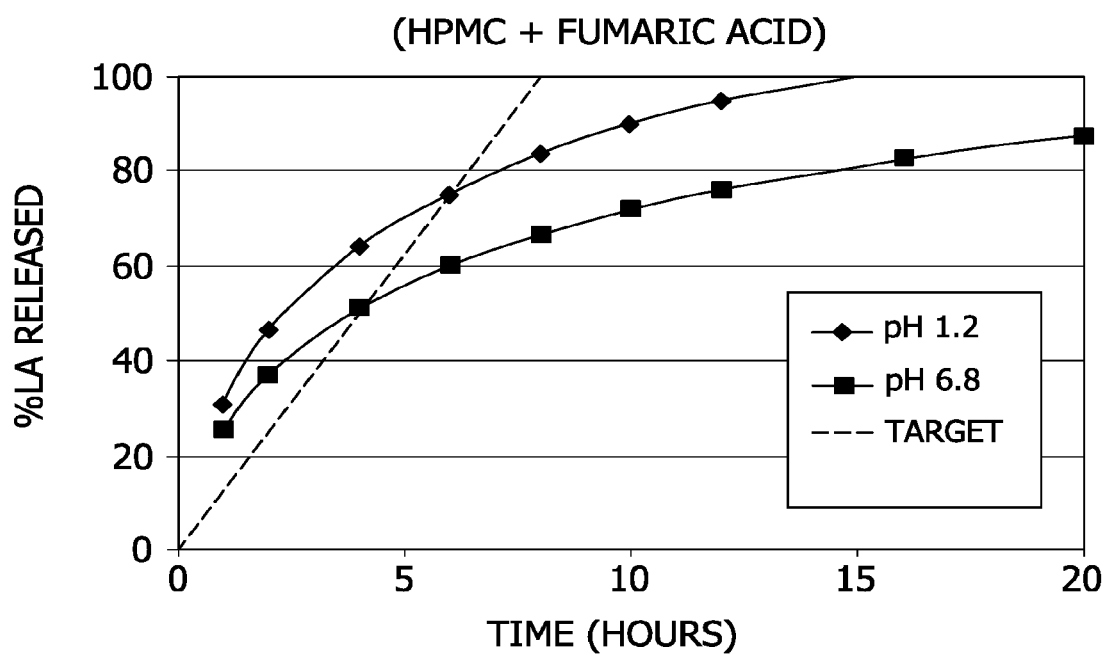
Figure 15E:
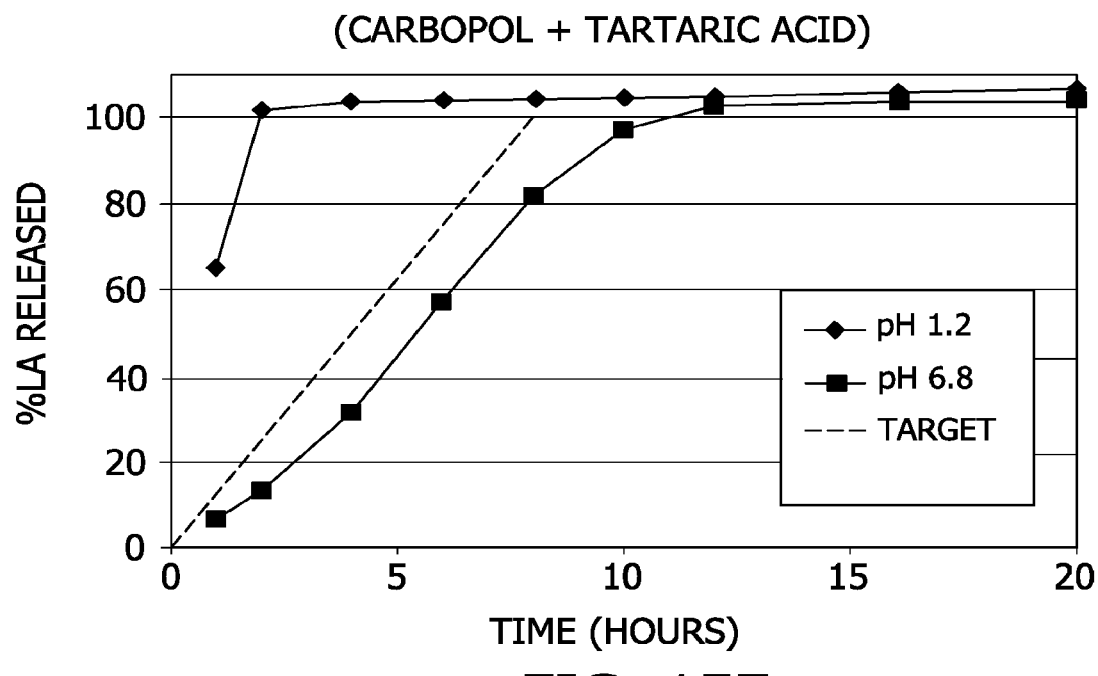
Figure 15F:
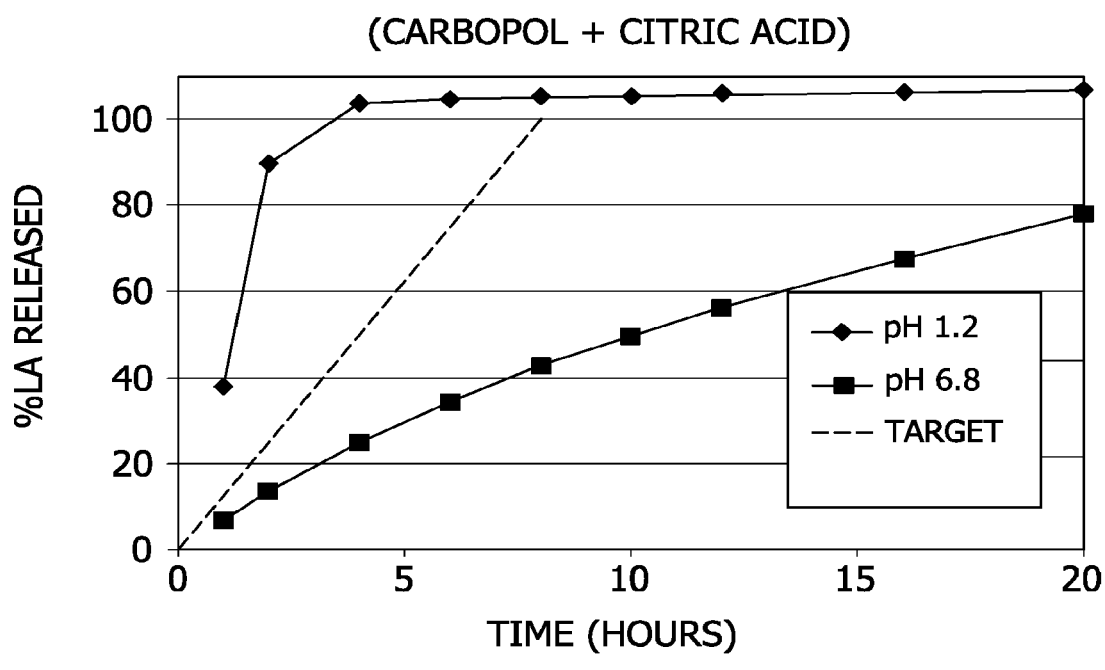
Figure 15G:
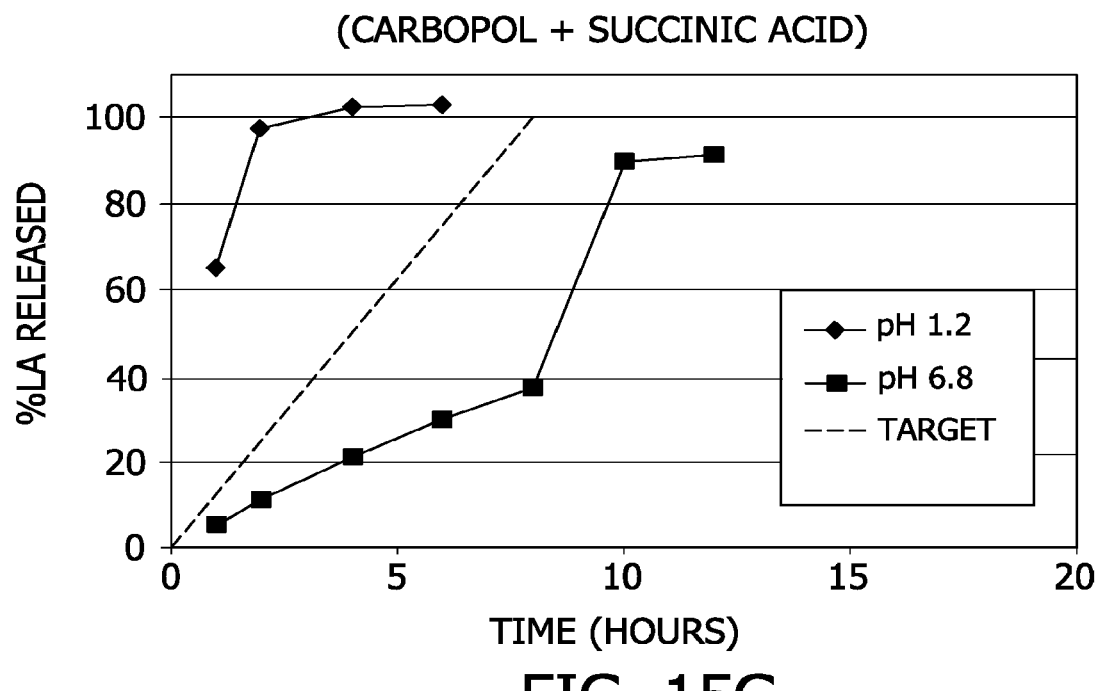
Figure 15H:
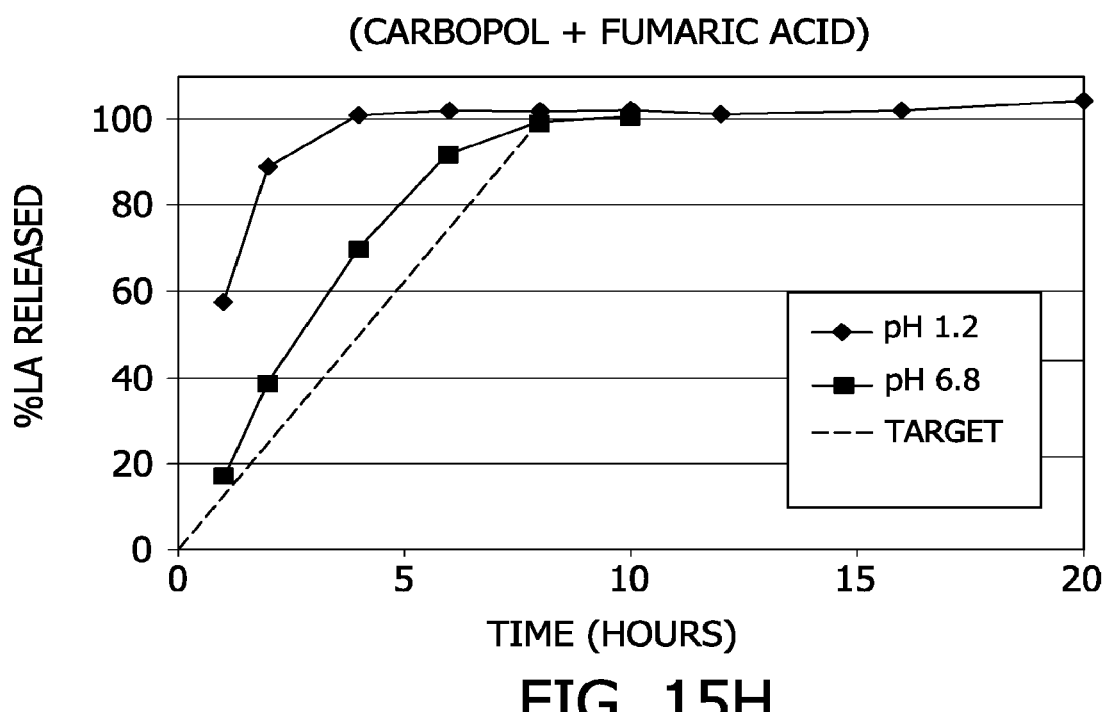

The formulations of Examples 28 and 31-35 all exhibited pH independent release of the active ingredient. In contrast, as can be seen from FIG. 8, after the initial release at the low pH, release of the active is slowed at the higher pH for the formulations of Examples 24-26. Without wishing to be bound by any particular theory, it is believed that the inclusion of tartaric acid as a pH modifier in the Example 28 and 31-35 formulations contributed to the pH independent release observed for these tablets. A comparison of the dissolution profile of the Example 24 (no pH modifier), Example 26 (no pH modifier), and Example 32 (tartaric acid pH modifier) tablets in a dual pH system is depicted in FIG. 14.

Example 36

Extended Release Tablet

The Freebase Hydrate Form C solid state form of Compound 1 listed in Table 15-A was formulated into a 7.5 mg extended release tablet according to the formulation set forth in Table 36-A.

TABLE 36-A

Extended Release Tablets (tartaric acid pH modifier)

| Component | Function | Ex. 34 (mg) (ER9) |
|---|---|---|
| Freebase Hydrate Form C* | Active | 7.678$^a$ |
| Microcrystalline cellulose (Avicel ® PH 102) | Filler | 170.1 |
| Mannitol (Pearlitol ® 100 SD) | Filler | 52.62 |
| Tartaric acid (crystalline) | pH modifier | 144.0 |
| HPMC (Hypromellose 2208) | Release control polymer | 96.0 |
| Colloidal silicon dioxide | Glidant | 2.4 |
| Magnesium stearate | Lubricant | 7.2 |
| Uncoated weight of tablet | | 479.998 |

TABLE 36-A-continued

Extended Release Tablets (tartaric acid pH modifier)

| Component | Function | Ex. 34 (mg) (ER9) |
|---|---|---|
| Opadry ® II Yellow | Film coat | 14.40 |
| Purified water | Processing aid | n/a |
| Total weight of tablet | | 494.398 |

[a]Provides 7.5 mg of Compound 1 freebase equivalent.

The formulation was prepared by first milling the tartaric acid through a Fitz mill Model M5A, fitted with a 1512-0027 screen. The Freebase Hydrate Form C, microcrystalline cellulose, mannitol, milled tartaric acid, release control polymer, and colloidal silicone dioxide were combined and blended. The blend was milled using a Mobil Mill fitted with a 610 micron screen. The magnesium stearate was screened through mesh #30 and was then added to the bin and blended. The lubricated granulation was compressed into about 480 mg weight tablets using a rotary tablet press.

The tablets were coated using a film coater, which sprayed a solution containing the Opadry® II Yellow film coat and purified water until 14.4 mg of coating had been applied to the tablets.

Examples 37-42

Extended Release Tablets

The Freebase Hydrate Form C solid state form of Compound 1 listed in Table 15-A was formulated into 15 mg or 30 mg extended release tablets according to the formulations set forth in Table 37-A. The tablets were prepared using a wet granulation process, and were compressed into tablets having a core weight of about 480 mg.

The formulation was prepared by first milling the tartaric acid through a Fitz mill Model M5A, fitted with a 1512-0027 screen. The intragranular portion of the hydroxypropylmethyl cellulose release control polymer, the Freebase Hydrate Form C, and intragranular portion of the microcrystalline cellulose filler were added to a granulator, and mixed. Water was sprayed to granulate. The granulated material was then dried and milled using a comill fitted with a 610 micron screen. The milled granulation was then added to the extragranular tablet components other than magnesium stearate, and sieved using a comill fitted with a 1397 micron screen, followed by blending. The magnesium stearate was then added to the bin and blended. The lubricated granulation was compressed into about 480 mg weight tablets using a rotary tablet press.

The tablets were coated using a film coater, which sprayed a solution containing the Opadry® II Yellow film coat and purified water until 14.4 mg of coating had been applied to the tablets.

Example 43

Evaluation of the Effect of Organic Acids on Dissolution Profile of Extended Release Tablets In this example, the effect of various organic acid pH modifiers (e.g., tartaric acid, citric acid, succinic acid, and fumaric acid) on the release rate of Freebase Hydrate Form C from 24 mg once-daily extended release (ER) tablets was evaluated. Freebase Hydrate Form C was formulated into 24 mg extended release tablets according to the formulations set forth in Table 43-A.

TABLE 37-A

Extended Release Tablets (tartaric acid pH modifier)

| Component | Function | Ex. 37 (mg) (ER10) | Ex. 38 (mg) (ER11) | Ex. 39 (mg) (ER12) | Ex. 40 (mg) (ER13) | Ex. 41 (mg) (ER14) | Ex. 42 (mg) (ER15) |
|---|---|---|---|---|---|---|---|
| Tablet Core (Intragranular) | | | | | | | |
| Freebase Hydrate Form C | Active | 30.7[a] | 30.7[a] | 30.7[a] | 15.4[b] | 15.4[b] | 15.4[b] |
| Microcrystalline cellulose (Avicel ® PH 101) | Filler | 79.9 | 79.9 | 79.9 | 40.0 | 40.0 | 40.0 |
| HPMC (Hypromellose 2208) | Release control polymer | 9.5 | 9.5 | 9.5 | 4.8 | 4.8 | 4.8 |
| Tablet Core (Extragranular) | | | | | | | |
| Microcrystalline cellulose (Avicel ® PH 102) | Filler | 67.2 | 67.2 | 67.2 | 122.5 | 122.5 | 122.5 |
| Mannitol | Filler | 52.6 | 100.6 | 148.6 | 52.6 | 100.6 | 148.6 |
| Tartaric acid (crystalline) | pH modifier | 144.0 | 96.0 | 48.0 | 144.0 | 96.0 | 48.0 |
| HPMC (Hypromellose 2208) | Release control polymer | 86.5 | 86.5 | 86.5 | 91.2 | 91.2 | 91.2 |
| Colloidal silicon dioxide/silica | Glidant | 2.4 | 2.4 | 2.4 | 2.4 | 2.4 | 2.4 |
| Magnesium stearate | Lubricant | 7.2 | 7.2 | 7.2 | 7.2 | 7.2 | 7.2 |
| Uncoated weight of tablet | | 480.0 | 480.0 | 480.0 | 480.1 | 480.1 | 480.1 |
| Opadry ® II Yellow[c] | Film coat | 14.4 | 14.4 | 14.4 | 14.4 | 14.4 | 14.4 |
| Total weight of tablet | | 494.4 | 494.4 | 494.4 | 494.5 | 494.5 | 494.5 |

[a]Provides 30 mg of Compound 1 freebase equivalent.
[b]Provides 15 mg of Compound 1 freebase equivalent.
[c]Film coat weight is approximate.

TABLE 43-A

Extended Release Tablets

| Component | Function | Tartaric acid | | Citric acid | | Succinic acid | | Fumaric acid | |
| --- | --- | --- | --- | --- | --- | --- | --- | --- | --- |
| | | A | B | C | D | E | F | G | H |
| Freebase Hydrate Form C | Active | 24.6 | 24.6 | 24.6 | 24.6 | 24.6 | 24.6 | 24.6 | 24.6 |
| Microcrystalline cellulose (Avicel ® PH 102) | Filler | 306.6 | 306.6 | 306.6 | 306.6 | 306.6 | 306.6 | 306.6 | 306.6 |
| HPMC (Methocel ® K4M) | Release control polymer | 96.0 | — | 96.0 | — | 96.0 | — | 96.0 | — |
| Carbopol ® 71G | Release control polymer | — | 96.0 | — | 96.0 | — | 96.0 | — | 96.0 |
| Organic acid | pH modifier | 48.0 | 48.0 | 48.0 | 48.0 | 48.0 | 48.0 | 48.0 | 48.0 |
| Magnesium stearate | Lubricant | 4.8 | 4.8 | 4.8 | 4.8 | 4.8 | 4.8 | 4.8 | 4.8 |
| Total | | 480.0 | 480.0 | 480.0 | 480.0 | 480.0 | 480.0 | 480.0 | 480.0 |

The formulations were prepared by first milling the organic acid through a Fitz mill Model M5A, fitted with a 1512-0027 screen. The active, microcrystalline cellulose, milled organic acid, and release control polymer, were combined and blended. The blend was milled using a Mobil Mill fitted with a 610 micron screen. The magnesium stearate was screened through mesh #30 and was added to the bin and blended. The lubricated granulation was compressed into 480 mg weight tablets using a rotary tablet press.

The effect of the organic acids on the dissolution profile of the tablets was evaluated at pH 1.2 and pH 6.8. The dissolution tests were carried out using the dissolution parameters and conditions as described above in Examples 26 and 27 and 32-35. For analysis of the sample, conventional liquid chromatography methods were utilized, wherein the % of the labelled amount of active released (% LA Released) was calculated. The results are set forth in FIGS. 15A-15H.

As can be seen from these results, organic acids improved dissolution rate at high pH, with tartaric acid showing the best improvement. The formulations comprising the control release polymer Carbopol® with tartaric acid provided near linear release at pH 6.8.

Example 44

Gel pH Measurements for Tablets with Different Amounts of Tartaric Acid

To measure the pH of the environment created when Compound 1 reacts with HPMC, the following experiment was performed.

The Freebase Hydrate Form C solid state form of Compound 1 was formulated into 30 mg extended release tablets according to the formulations set forth in Table 44-A. The tablets were prepared using a wet granulation process, as described in Examples 37-42.

Figure 31:
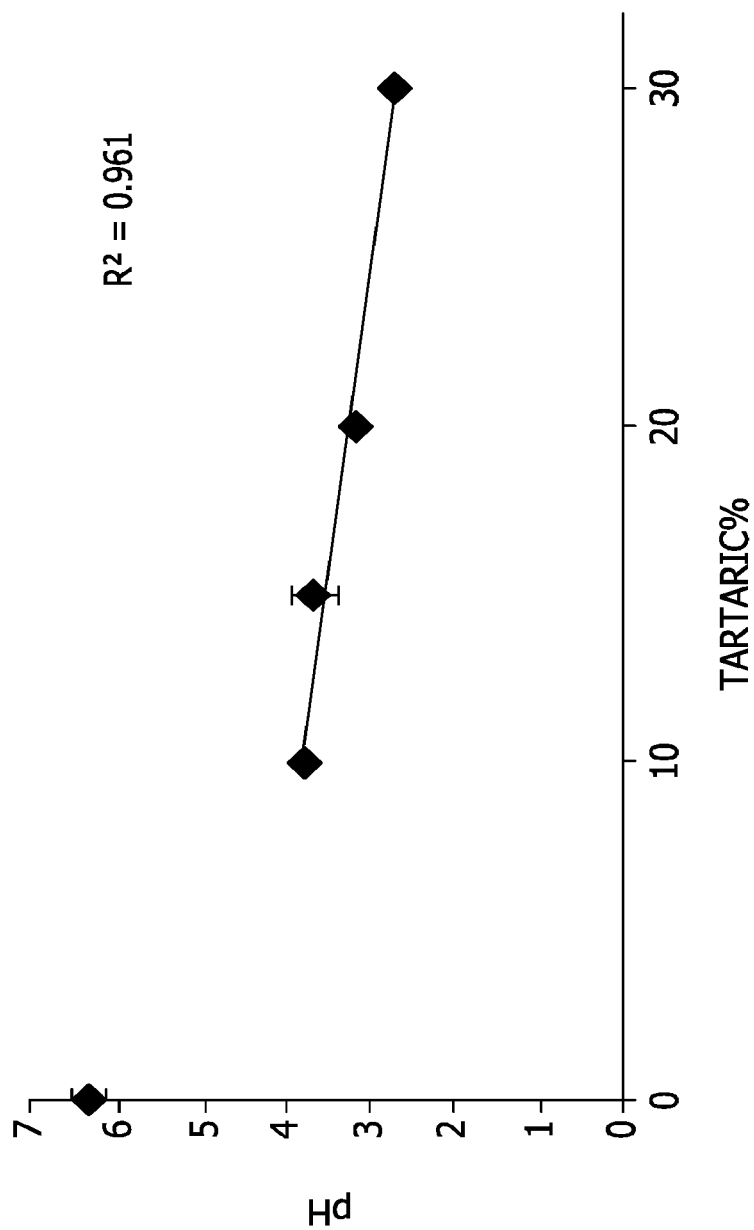
FIG. 31 shows a plot of the pH of the gel formed on tablets comprising varying amounts of tartaric acid.

Dissolution media of 0.01 N HCl (pH 2) and 113 mM sodium phosphate buffer (pH 6.8) was prepared at 37° C. One tablet was added to 500 mL of 0.01 N HCl media and stirred at 75 rpm at 37° C. for one hour in a Vankel VK 7010 dissolution bath. Then 400 mL of sodium phosphate buffer was added. The solution was stirred an additional three hours. The tablet was removed, rinsed with water and dried using laboratory tissues. The gel that formed on the tablet was separated from the dry core for pH measurement. This procedure was repeated three times for each formulation. The pH of the gel formed on the tablets is set forth in Table 44-B. The pH results are plotted in FIG. 31.

TABLE 44-A

Formulations

| Component | Formulation 1 mg/tab | Formulation 2 mg/tab | Formulation 3 mg/tab | Formulation 4 mg/tab | Formulation 5 mg/tab |
| --- | --- | --- | --- | --- | --- |
| Intragranular | | | | | |
| Freebase Hydrate Form C | 30.71 | 30.71 | 30.71 | 30.71 | 30.71 |
| HPMC (Methocel ® K4M) | 3.920 | 3.920 | 3.920 | 3.920 | 3.920 |
| Microcrystalline cellulose (Avicel ® PH102) | 30.71 | 30.71 | 30.71 | 30.71 | 30.71 |
| extragranular | | | | | |
| Microcrystalline cellulose (Avicel ® PH102) | 116.4 | 164.4 | 188.4 | 212.4 | 260.4 |
| Tartaric Acid (milled) | 144.0 | 96.00 | 72.00 | 48.00 | 0.00 |
| Mannitol (Pearlitol ® 100SD) | 52.62 | 52.62 | 52.62 | 52.62 | 52.62 |
| HPMC (Methocel ® K4M) | 92.08 | 92.08 | 92.08 | 92.08 | 92.08 |
| Colloidal silicon dioxide | 2.400 | 2.400 | 2.400 | 2.400 | 2.400 |
| Magnesium Stearate | 7.200 | 7.200 | 7.200 | 7.200 | 7.200 |
| Total | 480.04 | 480.04 | 480.04 | 480.04 | 480.04 |

TABLE 44-B pH Results

| Formulation | % Tartaric Acid | 1st tablet | 2nd tablet | 3rd tablet | Average |
|---|---|---|---|---|---|
| 1 | 30 | 2.63 | 2.68 | 2.81 | 2.71 |
| 2 | 20 | 3.17 | 3.09 | 3.23 | 3.16 |
| 3 | 15 | 3.42 | 3.94 | 3.65 | 3.67 |
| 4 | 10 | 3.88 | 3.67 | 3.77 | 3.77 |
| 5 | 0 | 6.26 | 6.21 | 6.55 | 6.34 |

Example 45

Evaluation of the In Vivo Pharmacokinetic Profile of 15 mg Extended Release Tablets (Fasting)

The pharmacokinetic profile of the 15 mg once-daily extended release (ER) tablets prepared in Example 28 was evaluated, and compared to that of a 12 mg immediate-release (IR) capsule comprising Tartrate Hydrate as the active.

Healthy human subjects (n=11) were administered a single dose of the 12 mg IR capsule (Regimen A) and the 15 mg ER (once-daily) tablet from Example 28 (Regimen B) under fasting conditions in a randomized, two-period, cross-over study design. Subjects were administered Regimen A in the first study period and Regimen B in the second study period, or administered Regimen B in the first study period and Regimen A in the second study period. Serial blood samples were collected from each subject prior to dosing and for 72 hours after dosing in each study period. Upon collection, the samples were promptly placed in an ice bath, and within 2 hours after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter by regimen.

Figure 16A:
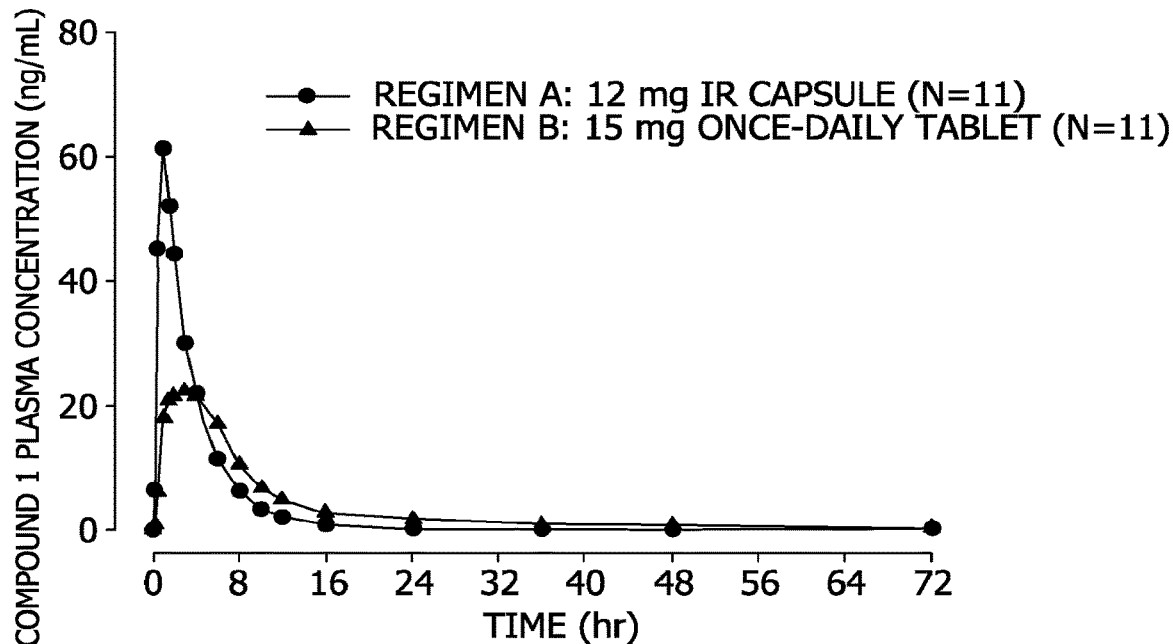
FIGS. 16A and 16B show the Compound 1 mean plasma concentration versus time following administration of a 12 mg immediate release capsule (Regimen A) or a 15 mg once-daily extended release tablet (Regimen B) under fasting conditions using a linear (FIG. 16A) or semi-log (FIG. 16B) scale.
Figure 16B:
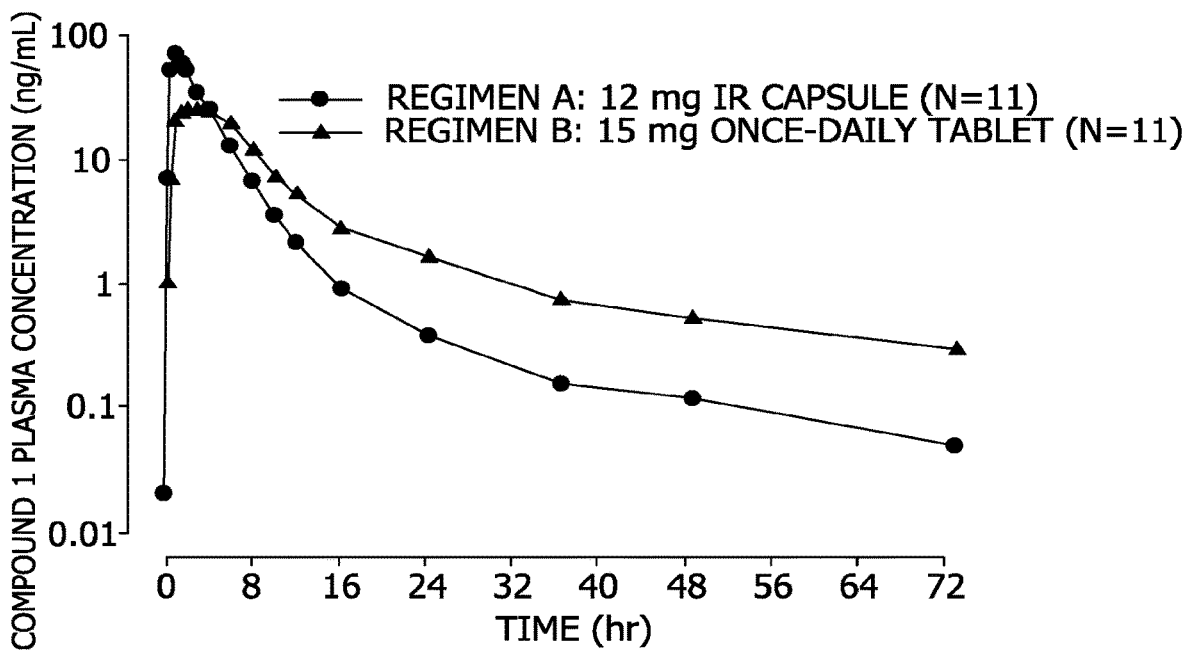

The results are summarized in Table 45-A. The mean concentration of Compound 1 at each time point using linear (FIG. 16A) and semi-log (FIG. 16B) scales for each of the two regimens is set forth in FIGS. 16A and 16B.

TABLE 45-A

Mean (% CV)[c] Pharmacokinetic Parameters for Compound 1 Following Administration of 15 mg ER Tablet and 12 mg IR Capsule Formulations Under Fasting Conditions

| PK Parameter | Units | Regimen A (IR Capsule, 12 mg) | Regimen B (ER Tablet, 15 mg) |
|---|---|---|---|
| $C_{max}$ | ng/mL | 64.6 (16) | 26.0 (37) |
| $T_{max}$[a] | hours | 1.0 (0.5-1.5) | 3.0 (1.0-4.0) |
| $t_{1/2}$[b] | hours | 9.2 (119) | 12.5 (90) |
| $AUC_t$ | ng·h/mL | 231 (15) | 227 (26) |
| $AUC_{inf}$ | ng·h/mL | 234 (15) | 242 (26) |

[a]Median (minimum, maximum)
[b]Harmonic mean (pseudo-% CV)
[c]Data in parentheses is coefficient of variance of the PK parameter (% CV), unless otherwise indicated.

As can be seen from this data, the 15 mg ER tablet provided a lower $C_{max}$ and comparable AUC to the 12 mg IR capsule under fasting conditions.

The relative bioavailability for a single dose of the once-daily (ER) tablet formulation (Regimen B) relative to the IR capsule formulation (Regimen A) was also determined based on analysis of the natural logarithms of $C_{max}$ and AUC. The results are summarized in Table 45-B below.

TABLE 45-B

Relative Bioavailability and 90% Confidence Intervals for Bioequivalence Assessment

| | Relative Bioavailability | |
|---|---|---|
| PK Parameter | Point Estimate | 90% Confidence Interval |
| $C_{max}$ | 0.373 | 0.312-0.446 |
| $AUC_t$ | 0.939 | 0.869-1.013 |
| $AUC_{inf}$ | 0.992 | 0.909-1.082 |

For Regimen B versus Regimen A, the point estimates for the ratios of $AUC_t$ and $AUC_{inf}$ were near unity, and the 90% confidence intervals were within the 0.86-1.09 range.

Example 46

Evaluation of the In Vivo Pharmacokinetic Profile of 30 mg Extended Release Tablets (Fasting)

The pharmacokinetic profile of the 30 mg once daily extended release (ER) tablets prepared in Example 31 was evaluated, and compared to that of a 24 mg dose of an immediate release (IR) capsule comprising Tartrate Hydrate as the active.

Healthy human subjects (n=12) were administered a single 24 mg dose (two 12 mg IR capsules) (Regimen C) and the 30 mg ER (once daily) tablet from Example 31 (Regimen D) under fasting conditions in a randomized, two-period, cross-over study design. Half the subjects were administered Regimen C in the first study period and Regimen D in the second study period, while the other half were administered Regimen D in the first study period and Regimen C in the second study period. Serial blood samples were collected from each subject prior to dosing and for 72 hours after dosing in each study period. Upon collection, the samples were promptly placed in an ice bath, and within 2 hours after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter by regimen.

Figure 17A:
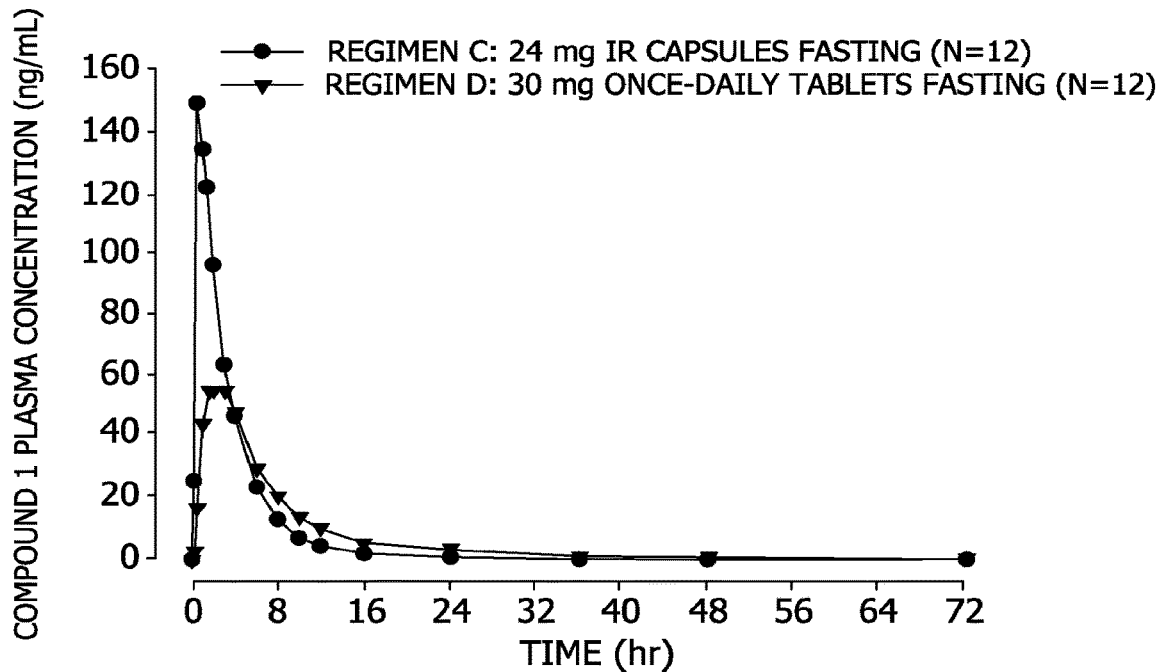
FIGS. 17A and 17B show the Compound 1 mean plasma concentration versus time following administration of a 24 mg dose (2×12 mg) of immediate release capsule (Regimen C) or a 30 mg once-daily extended release tablet (Regimen D) under fasting conditions using a linear (FIG. 17A) or semi-log (FIG. 17B) scale.
Figure 17B:
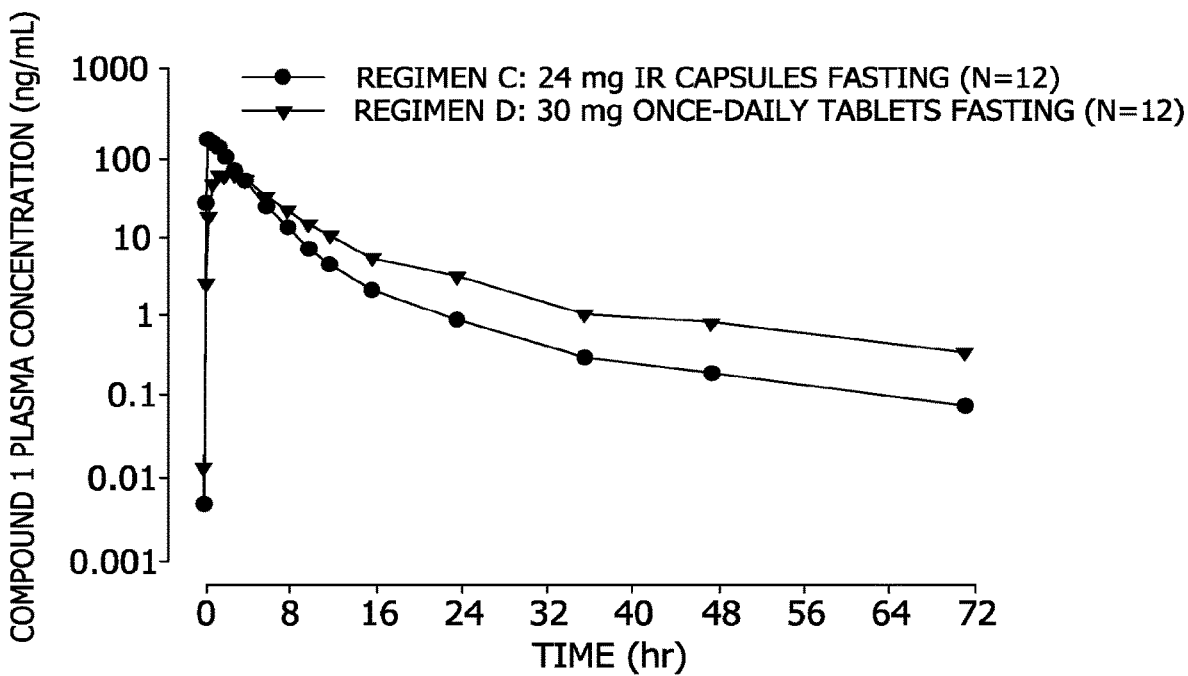

The results are summarized in Table 46-A. The mean concentration of Compound 1 at each time point using linear (FIG. 17A) and semi-log (FIG. 17B) scales for each of the two regimens is set forth in FIGS. 17A and 17B.

TABLE 46-A

Mean (% CV)c Pharmacokinetic Parameters for Compound 1 Following Administration of 30 mg ER Tablet and 24 mg Dose (2 × 12 mg) IR Capsule Formulations Under Fasting Conditions

| PK Parameter | Units | Regimen C (IR Capsules, 24 mg) | Regimen D (ER Tablet, 30 mg) |
|---|---|---|---|
| $C_{max}$ | ng/mL | 176 (37) | 63.7 (33) |
| $T_{max}$[a] | hours | 0.5 (0.5-1.5) | 2.0 (1.5-4.0) |

TABLE 46-A-continued

Mean (% CV)c Pharmacokinetic Parameters for Compound 1 Following Administration of 30 mg ER Tablet and 24 mg Dose (2 × 12 mg) IR Capsule Formulations Under Fasting Conditions

| PK Parameter | Units | Regimen C (IR Capsules, 24 mg) | Regimen D (ER Tablet, 30 mg) |
|---|---|---|---|
| $t_{1/2}^{b}$ | hours | 9.9 (52) | 10.8 (67) |
| $AUC_t$ | ng · h/mL | 520 (25) | 477 (27) |
| $AUC_{inf}$ | ng · h/mL | 524 (25) | 491 (27) |

[a]Median (minimum-maximum)
[b]Harmonic mean (pseudo % CV)
cData in parentheses is the coefficient of variance of the PK parameter (% CV), unless otherwise indicated.

As can be seen from this data, the 30 mg ER tablet provided a lower C. and comparable AUC to the 24 mg dose IR capsule (2×12 mg) under fasting conditions.

The relative bioavailability for a single dose of the once-daily (ER) tablet formulation (Regimen D) relative to the IR capsule formulations (Regimen C) was also determined based on analysis of the natural logarithms of $C_{max}$ and AUC. The results are summarized in Table 46-B below.

TABLE 46-B

Relative Bioavailability and 90% Confidence Intervals for Bioequivalence Assessment

| | PK Value | | Relative Bioavailability | |
|---|---|---|---|---|
| PK Parameter | Regimen D | Regimen C (reference) | Point Estimate | 90% Confidence Interval |
| $C_{max}$ | 63.7 | 176 | 0.368 | 0.326-0.415 |
| $AUC_t$ | 477 | 520 | 0.912 | 0.828-1.004 |
| $AUC_{inf}$ | 491 | 524 | 0.933 | 0.845-1.029 |

For Regimen D versus Regimen C, the point estimates for the ratios of $AUC_t$ and $AUC_{inf}$ were near unity, and the 90% confidence intervals were within the 0.82-1.03 range.

Example 47

Comparison of the In Vivo Pharmacokinetic Profile of 30 mg Extended Release Tablets Under Fasting Versus Fed Conditions The pharmacokinetic profile of the 30 mg extended release tablets prepared in Example 31 after a high-fat meal was evaluated, and compared to the pharmacokinetic profile of the 30 mg extended release tablets under fasting conditions (see Example 46).

Following completion of the Example 46 study, the healthy human subjects (n=12) were administered single doses of the 30 mg ER (once daily) tablet from Example 31 after a high-fat meal (Regimen E). Serial blood samples were collected from each subject prior to dosing and for 72 hours after dosing. Upon collection, the samples were promptly placed in an ice bath, and within 2 hours after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures.

Figure 18A:
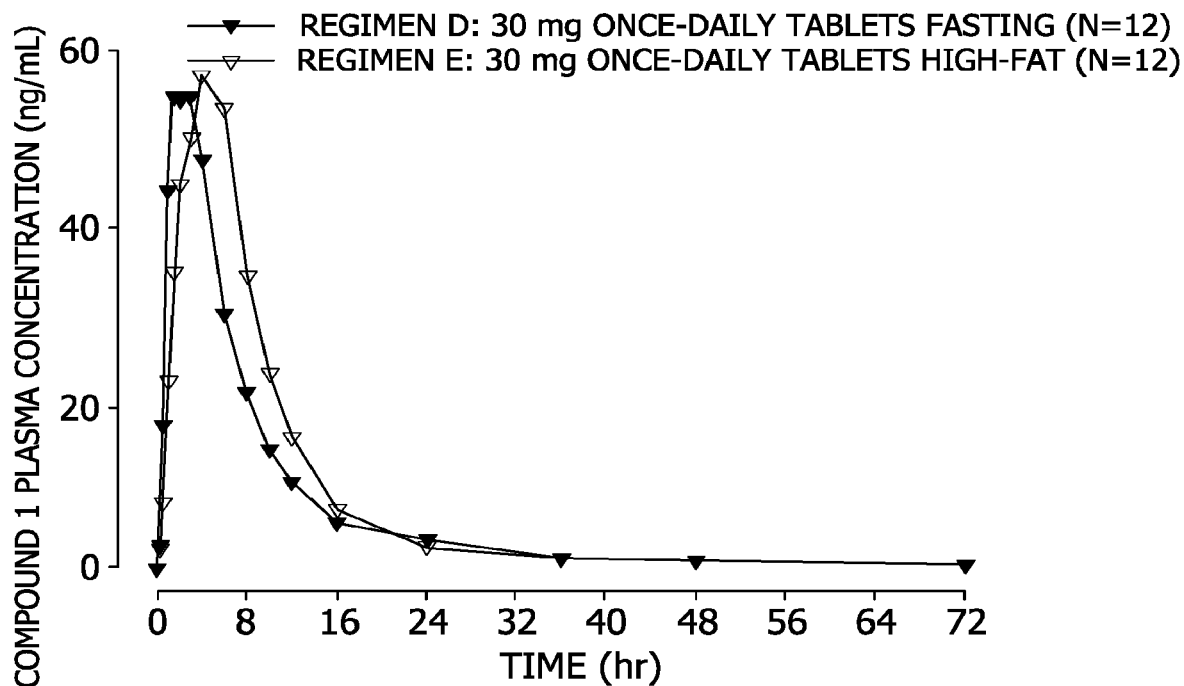
FIGS. 18A and 18B show the Compound 1 mean plasma concentration versus time following administration of a 30 mg once-daily extended release tablet under fasting conditions (Regimen D) or a 30 mg once-daily extended release tablet after consumption of a high-fat meal (Regimen E) using a linear (FIG. 18A) or semi-log (FIG. 18B) scale.
Figure 18B:
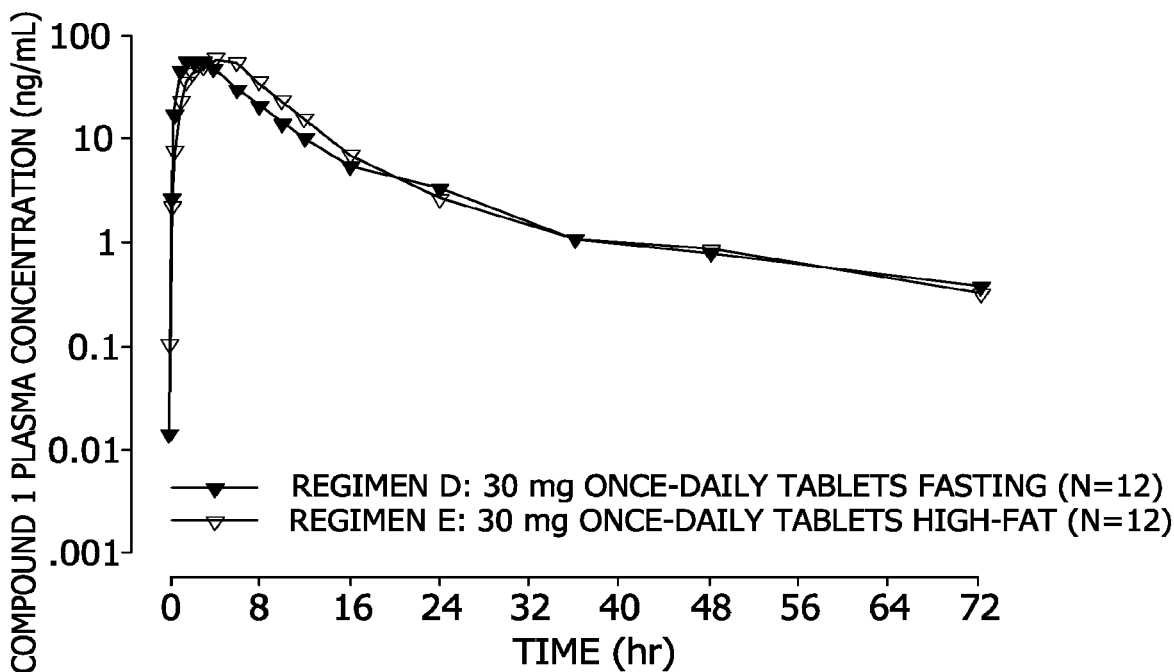

Pharmacokinetic parameters were estimated using non-compartmental methods, and summary statistics were computed for each parameter, and compared to the pharmacokinetic parameters for the 30 mg tablets administered under fasting conditions (see Example 46, Regimen D). The results are summarized in Table 47-A. The mean concentration of Compound 1 at each time point using linear (FIG. 18A) and semi-log (FIG. 18B) scales for each of the two regimens is set forth in FIGS. 18A and 18B.

TABLE 47-A

Mean (% CV)c Pharmacokinetic Parameters for Compound 1 Following Administration of 30 mg ER Tablet Under Fasting Conditions or After a High-Fat Meal

| PK Parameter | Units | Regimen D (Fasting) | Regimen E (After High-Fat Meal) |
|---|---|---|---|
| $C_{max}$ | ng/mL | 63.7 (33) | 76.8 (39) |
| $T_{max}^{a}$ | hours | 2.0 (1.5-4.0) | 4.0 (1.5-8.0) |
| $t_{1/2}^{b}$ | hours | 10.8 (67) | 11.9 (51) |
| $AUC_t$ | ng · h/mL | 477 (27) | 564 (26) |
| $AUC_{inf}$ | ng · h/mL | 491 (27) | 577 (27) |

[a]Median (minimum-maximum)
[b]Harmonic mean (pseudo-CV %)
cData in parentheses is coefficient of variance of the PK parameter (% CV), unless otherwise indicated.

The relative bioavailability for a single dose of the once-daily (ER) 30 mg tablet formulation after a high-fat meal (Regimen E) relative to the bioavailability of the ER 30 mg tablet under fasting conditions (Regimen D) was also determined based on analysis of the natural logarithms of $C_{max}$ and AUC. The results are summarized in Table 47-B below.

TABLE 47-B

Relative Bioavailability and 90% Confidence Intervals for Bioequivalence Assessment

| | PK Value | | Relative Bioavailability | |
|---|---|---|---|---|
| PK Parameter | Regimen E (after high-fat meal) | Regimen D (fasting) | Point Estimate | 90% Confidence Interval |
| $C_{max}$ | 76.8 | 63.7 | 1.197 | 1.027-1.395 |
| $AUC_t$ | 564 | 477 | 1.184 | 1.042-1.344 |
| $AUC_{inf}$ | 577 | 491 | 1.171 | 1.035-1.326 |

As can be seen from Tables 47-A and 47-B, there is no clinically meaningful food effect for the 30 mg ER tablets. Administration following a high-fat meal increased the Compound 1 mean AUC and $C_{max}$ by 17% and 20%, respectively.

Example 48

Observed Steady State Exposures for 15 mg and 30 mg Extended Release Tablets Under Non-Fasting Conditions The steady state pharmacokinetic profile of the 15 mg once daily extended release (ER) tablets (prepared in Example 28) and the 30 mg once daily ER tablets (prepared in Example 31) was evaluated.

Healthy human subjects (n=24) were assigned to one of two regimens. Subjects in Regimen F (n=12) were administered the 15 mg ER tablet from Example 28 once daily for seven days under non-fasting conditions. Subjects in Regimen G (n=12) were administered the 30 mg ER tablet from Example 31 once daily for seven days under non-fasting conditions. On days one and seven, serial blood samples were collected from each subject prior to the daily dosing and up to 24 hours after dosing. Upon collection, the samples were promptly placed in an ice bath, and within 2 hours after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter by regimen.

Figure 19:
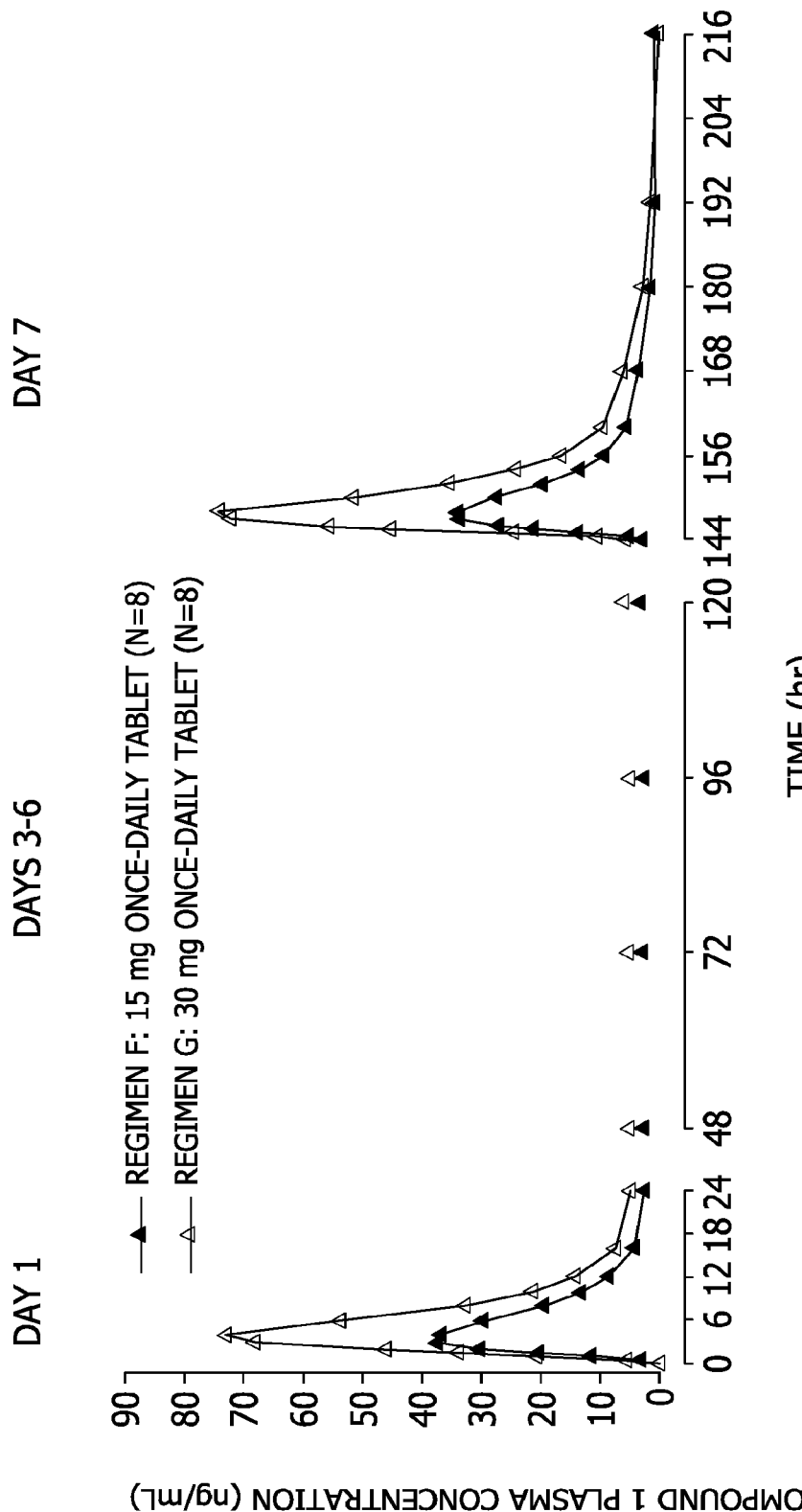
FIG. 19 shows the Compound 1 mean plasma concentration versus time following administration of a 15 mg once-daily extended release tablet (Regimen F) or a 30 mg once-daily extended release tablet (Regimen G) for seven days under non-fasting conditions.

The results are summarized in Table 48-A. The mean plasma concentration of Compound 1 at each time point measured for each of the two regimens is set forth in FIG. 19.

compared to that of a 6 mg immediate release (IR) twice daily (BID) capsule comprising Tartrate Hydrate as the active.

Healthy human subjects were assigned to one of two regimens under fasting conditions in a randomized, two-period, cross-over study design. Subjects in Regimen K (n=12 at onset; n=11 on Day 7) were administered the 6 mg IR capsule twice daily for seven days under fasting conditions. Subjects in Regimen L (n=12) were administered the 15 mg ER tablet from Example 28 once daily for seven days under fasting conditions. On days one and seven, serial blood samples were collected from each subject prior to the

TABLE 48-A

Mean (% CV)e Pharmacokinetic Parameters for Compound 1 Following Administration of 15 mg ER Tablet or 30 mg ER Tablet QD for Seven Days (Non-Fasting)

| PK Parameter | Units | Regimen F (15 mg ER Tablet) | | Regimen G (30 mg ER Tablet) | |
|---|---|---|---|---|---|
| | | Day 1 | Day 7 | Day 1 | Day 7 |
| $C_{max}$ | ng/mL | 36.8 (26) | 36.0 (24) | 74.3 (32) | 79.5 (40) |
| $T_{max}^a$ | hours | 4.0 (3.0-6.0) | 4.0 (2.0-6.0) | 4.0 (2.0-6.0) | 4.0 (1.5-6.0) |
| $AUC_{24}$ | ng · h/mL | 305 (24) | 317 (21) | 517 (30) | 582 (30) |
| $C_{24}$ | ng/mL | 2.42 (45) | 3.22 (46) | 4.27 (48) | 5.25 (44) |
| $C_{trough}$ | ng/mL | — | 2.96 (35) | — | 5.02 (42) |
| $C_{min, ss}$ | ng/mL | — | 2.80 (41) | — | 4.62 (38) |
| Fluctuation Index | % | 291 (14) | 251 (14) | 345 (14) | 306 (17) |
| $t_{1/2}^b$ | hours | — | 9.43 (76) | — | 10.4 (44) |
| $C_{max}$ to $C_{24}$ ratio | | 17 (7.8-44) | 13 (5.6-35) | 17 (9.9-38) | 14 (7.0-30) |
| $C_{max}$/Dose | (ng/mL)/mg | 2.46 (26) | 2.40 (24) | 2.48 (32) | 2.65 (40) |
| $C_{trough}$/Dose | (ng/mL)/mg | 0.16 (45) | 0.21 (46) | 0.14 (48) | 0.18 (44) |
| $AUC_{24}$/Dose | (ng · h/mL)/mg | 20.3 (24) | 21.2 (21) | 17.2 (30) | 19.4 (30) |
| $R_{AUC}^c$ | | — | 1.02 (0.91-1.40) | — | 1.16 (0.92-1.31) |
| $R_{Cmax}^d$ | | — | 1.00 (0.84-1.26) | — | 1.02 (0.82-1.40) |

[a]Median (minimum-maximum)
[b]Harmonic mean (pseudo-% CV)
[c]$R_{AUC}$ = $AUC_{24}$Day 7/$AUC_{24}$Day 1; median (range)
[d]$R_{Cmax}$ = $C_{max}$Day 7/$C_{max}$Day 1; median (range)
[e]Data in parentheses is the coefficient of variance of the PK parameter (% CV), unless otherwise indicated As can be seen from this data, the observed steady state $C_{max}$ and $AUC_{24}$ following 15 mg QD and 30 mg QD administration are generally consistent with the single dose and food-effect results obtained in Examples 45-47. The bioavailability of the 15 mg and 30 mg ER tablets is 70% to 80% relative to the same dose of IR capsules.

Example 49

Observed Steady State Exposures for 15 mg Extended Release Tablets and 6 mg Immediate Release Capsules Under Fasting Conditions The steady state pharmacokinetic profile of the 15 mg once daily extended release (ER) tablets (prepared in Example 28) under fasting conditions was evaluated, and daily dosing and up to 24 hours after dosing. Blood samples were also collected at 48, 72, 96 and 120 hours after initial dosing. Upon collection, the samples were promptly placed in an ice bath, and within 2 hours after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter by regimen.

Figure 20:
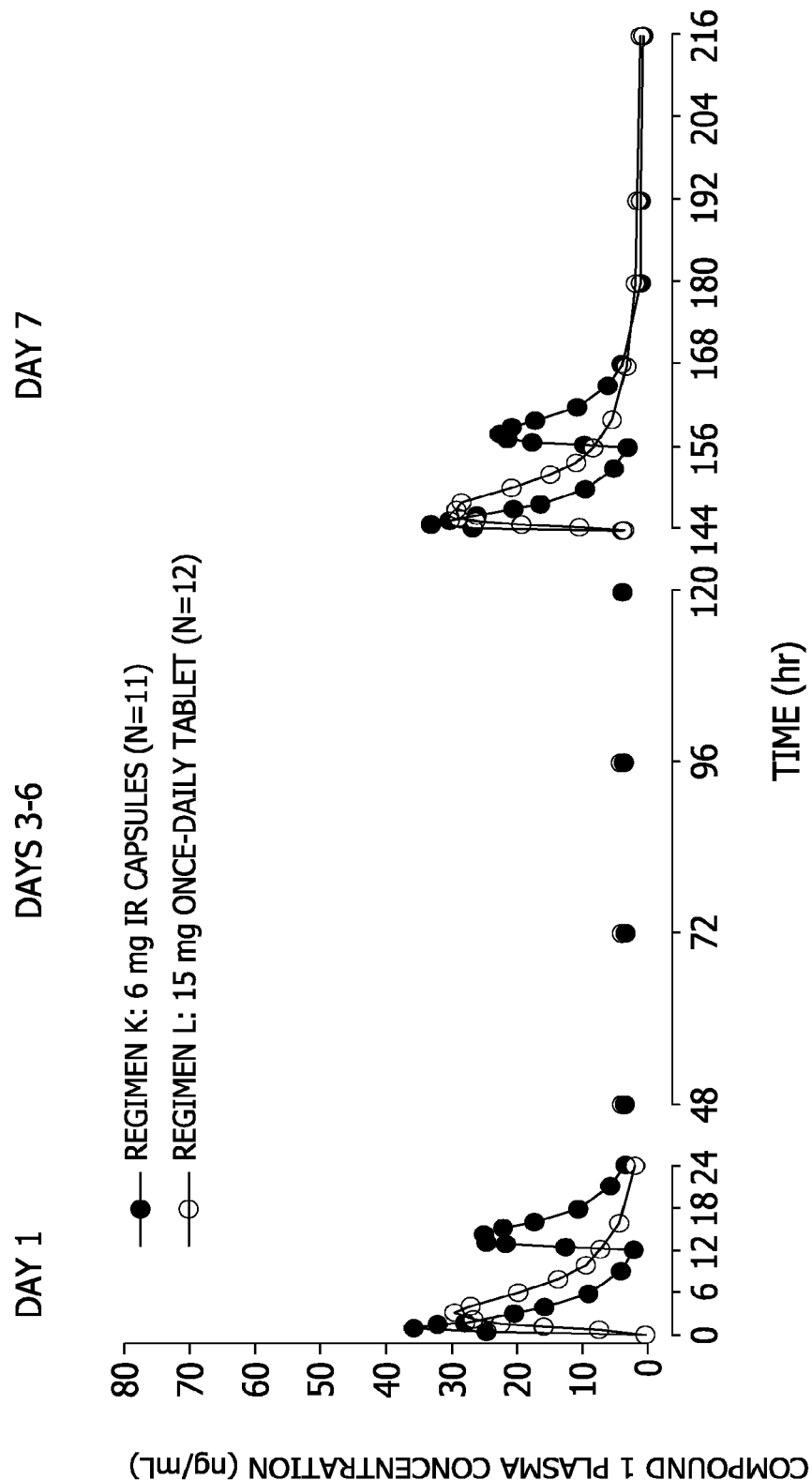
FIG. 20 shows the Compound 1 mean plasma concentration versus time following administration of 6 mg twice daily immediate release capsules (Regimen K) or a 15 mg once-daily extended release tablet (Regimen L) for seven days under fasting conditions.

The results are summarized in Table 49-A. The mean plasma concentration of Compound 1 at each time point measured for each of the two regimens is set forth in FIG. 20.

TABLE 49-A

Mean (% CV)e Pharmacokinetic Parameters for Compound 1 Following Administration of 6 mg BID (IR) Capsules and 15 mg QD (ER) Tablets for Seven Days (Fasting Conditions)

| PK Parameter | Units | Regimen K (6 mg IR Capsules (BID)) | | Regimen L (15 mg ER Tablet (QD)) | |
|---|---|---|---|---|---|
| | | Day 1 | Day 7 | Day 1 | Day 7 |
| $C_{max}$ | ng/mL | 36.5 (25) | 33.9 (26) | 31.7 (40) | 31.9 (35) |
| $T_{max}^a$ | hours | 1.0 (1.0-13) | 1.0 (0.5-14) | 3.0 (1.5-6.0) | 2.5 (1.5-4.0) |

TABLE 49-A-continued

Mean (% CV)e Pharmacokinetic Parameters for Compound 1 Following Administration of 6 mg BID (IR) Capsules and 15 mg QD (ER) Tablets for Seven Days (Fasting Conditions)

| PK Parameter | Units | Regimen K (6 mg IR Capsules (BID)) | | Regimen L (15 mg ER Tablet (QD)) | |
|---|---|---|---|---|---|
| | | Day 1 | Day 7 | Day 1 | Day 7 |
| $AUC_{24}$ | ng · h/mL | 289 (21) | 288 (22) | 249 (29) | 279 (26) |
| $C_{12}$ | ng/mL | 2.0 (30) | 2.8 (24) | — | — |
| $C_{24}$ | ng/mL | 3.2 (36) | 3.6 (23) | 1.9 (42) | 3.1 (37) |
| $C_{min}$ | ng/mL | — | 2.7 (26) | — | 3.1 (37) |
| Fluctuation Index | % | 303 (13) | 259 (13) | 299 (22) | 246 (21) |
| $t_{1/2}{}^b$ | hours | — | 14.7 (77) | — | 10.3 (76) |
| $C_{max}$ to $C_{24}$ ratio$^a$ | — | 12 (7.7-19) | 8.8 (7.4-13) | 22 (5.8-43) | 12 (4.2-20) |
| $C_{max}$ to $C_{min}$ ratio$^a$ | — | — | 13 (8.3-18) | — | 12 (4.2-20) |
| $AUC_{24}$/Dose | (ng · h/mL)/mg | 24.8 (23) | 24.0 (22) | 16.6 (29) | 18.6 (26) |
| $R_{AUC}{}^c$ | — | — | 1.02 (0.88-1.09) | — | 1.11 (0.87-1.99) |
| $R_{Cmax}{}^d$ | — | — | 0.97 (0.68-1.17) | — | 1.01 (0.65-3.01) |

$^a$Median (minimum-maximum)
$^b$Harmonic mean (pseudo-% CV)
$^c R_{AUC} = AUC_{24}$Day 7/$AUC_{24}$Day 1; median (range)
$^d R_{Cmax} = C_{max}$Day 7/$C_{max}$Day 1; median (range)
eData in parentheses is the coefficient of variance of the PK parameter (% CV), unless otherwise indicated The relative bioavailability for the once-daily (ER) tablet formulation (Regimen L) relative to the twice daily (IR) capsule formulation (Regimen K) at steady state was also determined based on analysis of the natural logarithms of $C_{max}$, $AUC_{24}$, $C_{min}$, and $C_{-24}$. The results are summarized in Table 49-B below.

TABLE 49-B

Relative Bioavailability Estimates and 90% Confidence Intervals for 15 mg QD Tablets Relative to 6 mg BID Capsules at Steady State under Fasting Conditions

| PK Parameter | Relative Bioavailability | |
|---|---|---|
| | Point Estimate | 90% Confidence Interval |
| $C_{max}$ | 0.909 | 0.736-1.122 |
| $AUC_{24}$ | 0.939 | 0.837-1.053 |
| $C_{min}$ | 1.090 | 0.852-1.395 |

The ratio of steady-state AUC for the 15 mg QD tablets relative to the 6 mg BID capsules was approximately 1, with the 90% confidence intervals within the equivalence boundaries. The ratio of the steady-state $C_{min}$ was approximately 1 for the 15 mg QD tablet relative to the 6 mg BID capsules.

Figure 21:
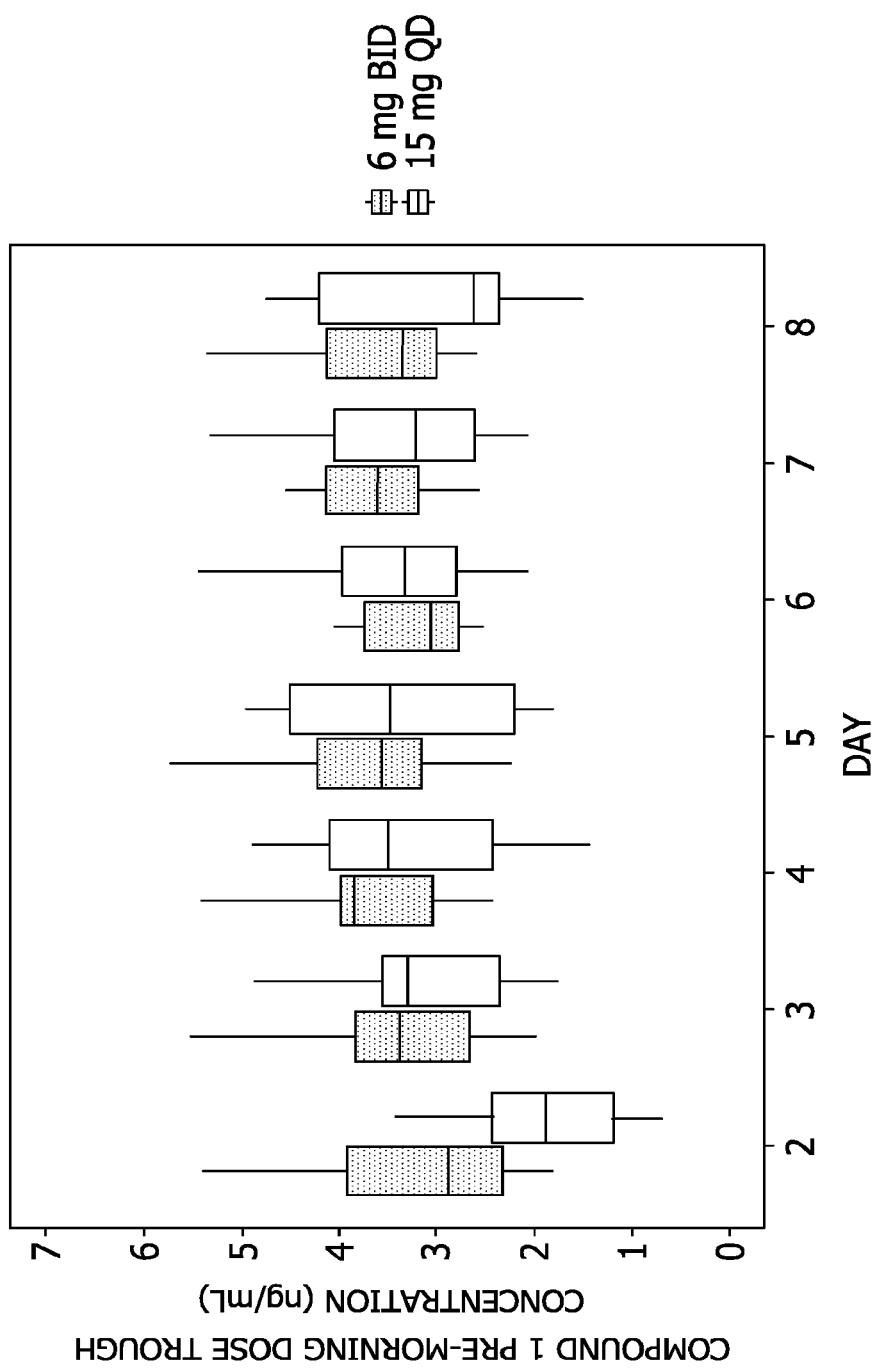
FIG. 21 shows the Compound 1 pre-morning dose trough concentration ($C_{trough}$) following administration of 6 mg twice daily immediate release capsules or a 15 mg once-daily extended release tablet over seven days under fasting conditions.

The pre-morning dose trough concentration ($C_{trough}$) for the 6 mg BID capsules and 15 mg QD tablets was determined prior to the morning dose on Days 2-8. The results are set forth in FIG. 21.

As can be seen from this data, at steady state under fasting conditions, the 15 mg QD tablets provided equivalent $AUC_{24}$ and comparable $C_{max}$ and $C_{min}$ relative to the 6 mg BID capsules. The steady state $C_{max}$ was 10% lower for the 15 mg QD tablet compared to the 6 mg BID capsule.

Example 50

Observed Steady State Exposures for 30 mg Extended Release Tablets and 12 mg Immediate Release Capsules Under Fasting Conditions The steady state pharmacokinetic profile of the 30 mg once daily extended release (ER) tablets (prepared in Example 31) under fasting conditions was evaluated, and compared to that of a 12 mg immediate release (IR) twice daily (BID) capsule comprising Tartrate Hydrate as the active.

Healthy human subjects were assigned to one of two regimens under fasting conditions in a randomized, two-period, cross-over study design. Subjects in Regimen M (n=11) were administered the 12 mg IR capsule twice daily for seven days under fasting conditions. Subjects in Regimen N (n=12 at onset; n=11 at Day 7) were administered the 30 mg ER tablet from Example 31 once daily for seven days under fasting conditions. On days one and seven, serial blood samples were collected from each subject prior to the daily dosing and up to 24 hours after dosing. Blood samples were also collected at 48, 72, 96 and 120 hours after initial dosing. Upon collection, the samples were promptly placed in an ice bath, and within 2 hours after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter by regimen.

Figure 22:
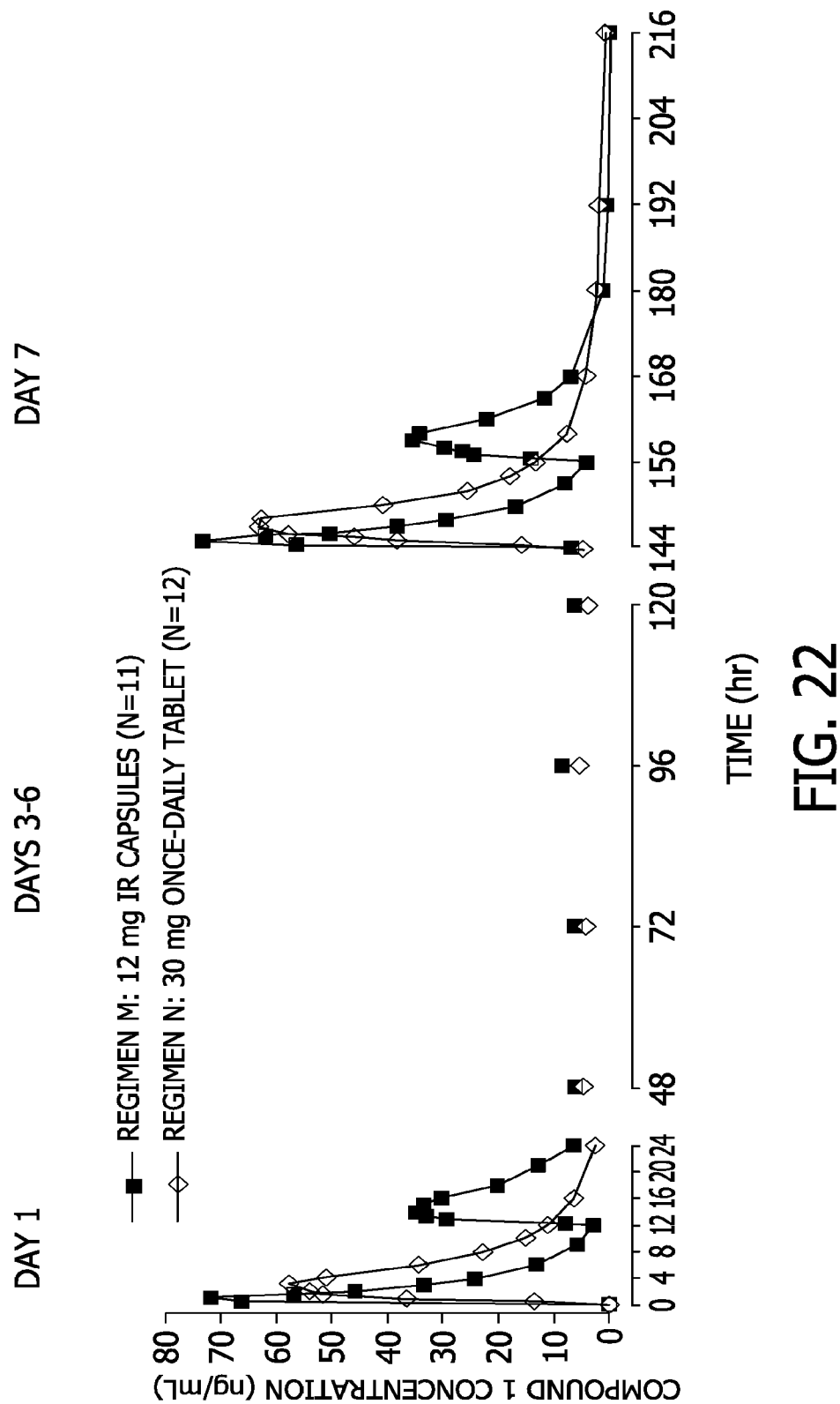
FIG. 22 shows the Compound 1 mean plasma concentration versus time following administration of 12 mg twice daily immediate release capsules (Regimen M) or a 30 mg once-daily extended release tablet (Regimen N) for seven days under fasting conditions.

The results are summarized in Table 50-A. The mean plasma concentration of Compound 1 at each time point measured for each of the two regimens is set forth in FIG. 22.

TABLE 50-A

Mean (% CV)e Pharmacokinetic Parameters for Compound 1 Following Administration of 12 mg BID (IR) Capsules and 30 mg QD (ER) Tablets for Seven Days (Fasting Conditions)

| PK Parameter | Units | Regimen M (12 mg IR Capsules (BID)) | | Regimen N (30 mg ER Tablet (QD)) | |
|---|---|---|---|---|---|
| | | Day 1 | Day 7 | Day 1 | Day 7 |
| $C_{max}$ | ng/mL | 80.8 (23) | 73.9 (19) | 65.7 (22) | 68.2 (30) |
| $T_{max}^a$ | hours | 1.0 (0.5-13) | 1.0 (0.5-1.5) | 2.5 (1.5-4.0) | 3.0 (2.0-4.0) |
| $AUC_{24}$ | ng · h/mL | 497 (15) | 534 (18) | 454 (23) | 525 (23) |
| $C_{12}$ | ng/mL | 3.0 (46) | 4.1 (55) | — | — |
| $C_{24}$ | ng/mL | 6.5 (54) | 6.9 (37) | 2.8 (37) | 4.4 (39) |
| $C_{min}$ | ng/mL | — | 3.8 (58) | — | 3.8 (43) |
| Fluctuation Index | % | 388 (15) | 317 (14) | 349 (12) | 291 (17) |
| $t_{1/2}^b$ | hours | — | 7.3 (60) | — | 14.4 (64) |
| $C_{max}$ to $C_{24}$ ratio$^a$ | — | — | 15 (5.4-20) | 12 (5.9-16) | 29 (13-38) | 17 (4.1-33) |
| $C_{max}$ to $C_{min}$ ratio$^a$ | — | — | 19 (8.4-31) | — | 17 (11-37) |
| $AUC_{24}$/Dose | (ng · h/mL)/mg | 21.1 (15) | 22.3 (18) | 15.1 (22) | 17.5 (23) |
| $R_{AUC}^c$ | — | — | 1.08 (0.97-1.18) | — | 1.11 (0.79-1.67) |
| $R_{Cmax}^d$ | — | — | 0.98 (0.65-1.18) | — | 1.03 (0.40-1.82) |

$^a$Median (minimum-maximum)
$^b$Harmonic mean (pseudo-% CV)
$^c R_{AUC} = AUC_{24}$Day 7/$AUC_{24}$Day 1; median (range)
$^d R_{Cmax} = C_{max}$Day 7/$C_{max}$Day 1; median (range)
eData in parentheses is the coefficient of variance of the PK parameter (% CV), unless otherwise indicated The relative bioavailability for a single dose of the once-daily (ER) tablet formulation (Regimen N) relative to the twice daily (IR) capsule formulation (Regimen M) was also determined based on analysis of the natural logarithms of $C_{max}$, $AUC_{24}$, $C_{min}$, and $C_{24}$. The results are summarized in Table 50-B below.

TABLE 50-B

Relative Bioavailability Estimates and 90% Confidence Intervals for 30 mg QD Tablets Relative to 12 mg BID Capsules at Steady State under Fasting Conditions

| PK Parameter | Relative Bioavailability | |
|---|---|---|
| | Point Estimate | 90% Confidence Interval |
| $C_{max}$ | 0.900 | 0.732-1.107 |
| $AUC_{24}$ | 0.974 | 0.869-1.092 |
| $C_{min}$ | 0.874 | 0.747-1.022 |

The ratio of steady-state AUC for the 30 mg QD tablets relative to the 12 mg BID capsules was approximately 1, with the 90% confidence intervals within the equivalence boundaries. The steady-state $C_{min}$ for the 30 mg QD tablet was approximately 13% lower than for the 12 mg BID capsules. Outliers with high $C_{min}$ in the 12 mg BID dose may have contributed to this difference.

Figure 23:
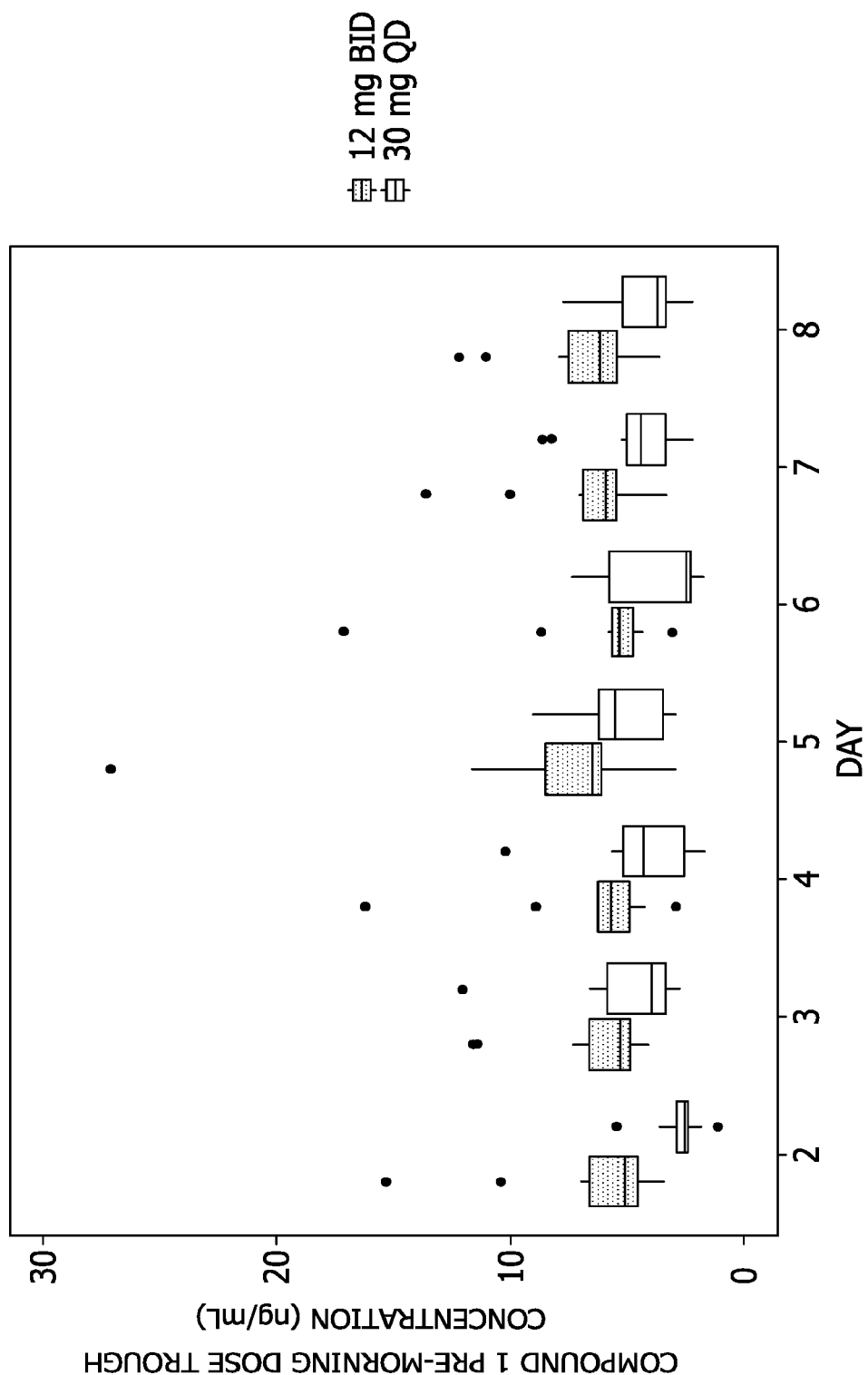
FIG. 23 shows the Compound 1 pre-morning dose trough concentration ($C_{trough}$) following administration of 12 mg twice daily immediate release capsules or a 30 mg once-daily extended release tablet over seven days under fasting conditions.

The pre-morning dose trough concentration ($C_{trough}$) for the 12 mg BID capsules and 30 mg QD tablets was determined prior to the morning dose on Days 2-8. The results are set forth in FIG. 23. As can be seen from this data, at steady state under fasting conditions, the 30 mg QD tablets provided equivalent $AUC_{24}$ and comparable $C_{max}$ and $C_{min}$ relative to the 12 mg BID capsules. The steady state $C_{max}$ was 10% lower for the 30 mg QD tablet compared to the 12 mg BID capsules.

Example 51

Comparison of AM vs. PM Pharmacokinetic Profile Following Administration of 6 mg or 12 mg Immediate Release Capsules Under Fasting Conditions The pharmacokinetic profile of the 6 mg immediate release (IR) twice daily (BID) capsules and the 12 mg IR twice daily capsules was determined on Day 7 of Regimen K (Example 49) and Regimen M (Example 50), respectively, after administration of the morning (AM dose) and evening (PM dose). The results are summarized in Table 51-A.

TABLE 51-A

Mean (% CV)$^b$ Pharmacokinetic Parameters for Compound 1 Following Administration of AM and PM Doses of 6 mg and 12 mg Immediate Release Capsules on Day 7 (Fasting Conditions)

| PK Parameter | Units | Regimen K (6 mg IR Capsules) | | Regimen M (12 mg IR Capsules) | |
|---|---|---|---|---|---|
| | | AM Dose | PM Dose$^c$ | AM Dose | PM Dose$^c$ |
| $C_{max}$ | ng/mL | 33.6 (28) | 24.4 (22) | 73.9 (19) | 46.0 (26) |
| $T_{max}^a$ | hours | 1 (0.5-1.5) | 2 (1.0-3.0) | 1 (0.5-1.5) | 3 (1.0-4.0) |
| $AUC_{12}$ | ng · h/mL | 152 (26) | 153 (19) | 290 (19) | 244 (19) |
| $C_{12}$ | ng/mL | 2.76 (24) | 3.63 (23) | 4.1 (55) | 6.94 (37) |
| $C_{max}/C_{12}$ | — | 12.3 (23) | 6.9 (22) | 18.0 (30) | 7.4 (39) |

$^a$Median (Minimum-Maximum)
$^b$Data in parentheses is the coefficient of variance of the PK parameter (% CV), unless otherwise indicated
$^c$The PM dose was administered 3 hours after starting dinner and 4 hours before a snack.

Example 52

Evaluation of the In Vivo Pharmacokinetic Profile of 30 mg Extended Release Tablets The pharmacokinetic profiles of the 30 mg once-daily extended release (ER) tablets that were prepared in Examples 37 (ER10, 30% tartaric acid), 38 (ER11, 20% tartaric acid), and 39 (ER12, 10% tartaric acid) using wet granulation were evaluated, and compared to that of the 30 mg ER tablet that was prepared in Example 31 (ER8, 30% tartaric acid) using direct compression (no wet granulation). The effect of a high-fat meal on the Example 37, 38, and 39 formulations was also evaluated.

Healthy human subjects (n=36) were administered a single dose of the 30 mg ER (once daily) tablet from Example 31 (ER8), Example 37 (ER10), Example 38 (ER11), and Example 39 (ER12) under fasting conditions or after a high-fat meal (non-fasting), in an open-label, randomized, four-period, incomplete crossover study. Doses in the four periods were separated by at least four days. Dosing regimens were as set forth below in Table 52-A.

TABLE 52-A

Dosing Regimens

| Regimen | Dose | Formulation | Fasting/Non-Fasting |
|---|---|---|---|
| A | Single 30 mg | Example 31 (ER8) | Fasting |
| B | Single 30 mg | Example 37 (ER10) | Fasting |
| C | Single 30 mg | Example 37 (ER10) | Non-Fasting |
| D | Single 30 mg | Example 38 (ER11) | Fasting |
| E | Single 30 mg | Example 38 (ER11) | Non-Fasting |
| F | Single 30 mg | Example 39 (ER12) | Fasting |
| G | Single 30 mg | Example 39 (ER12) | Non-Fasting |

Serial blood samples were collected from each subject prior to dosing and for 72 hours after dosing in each study period. Upon collection, the samples were promptly placed in an ice bath, and within 1 hour after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter by regimen.

Bioavailability Under Fasting Conditions

Figure 24A:
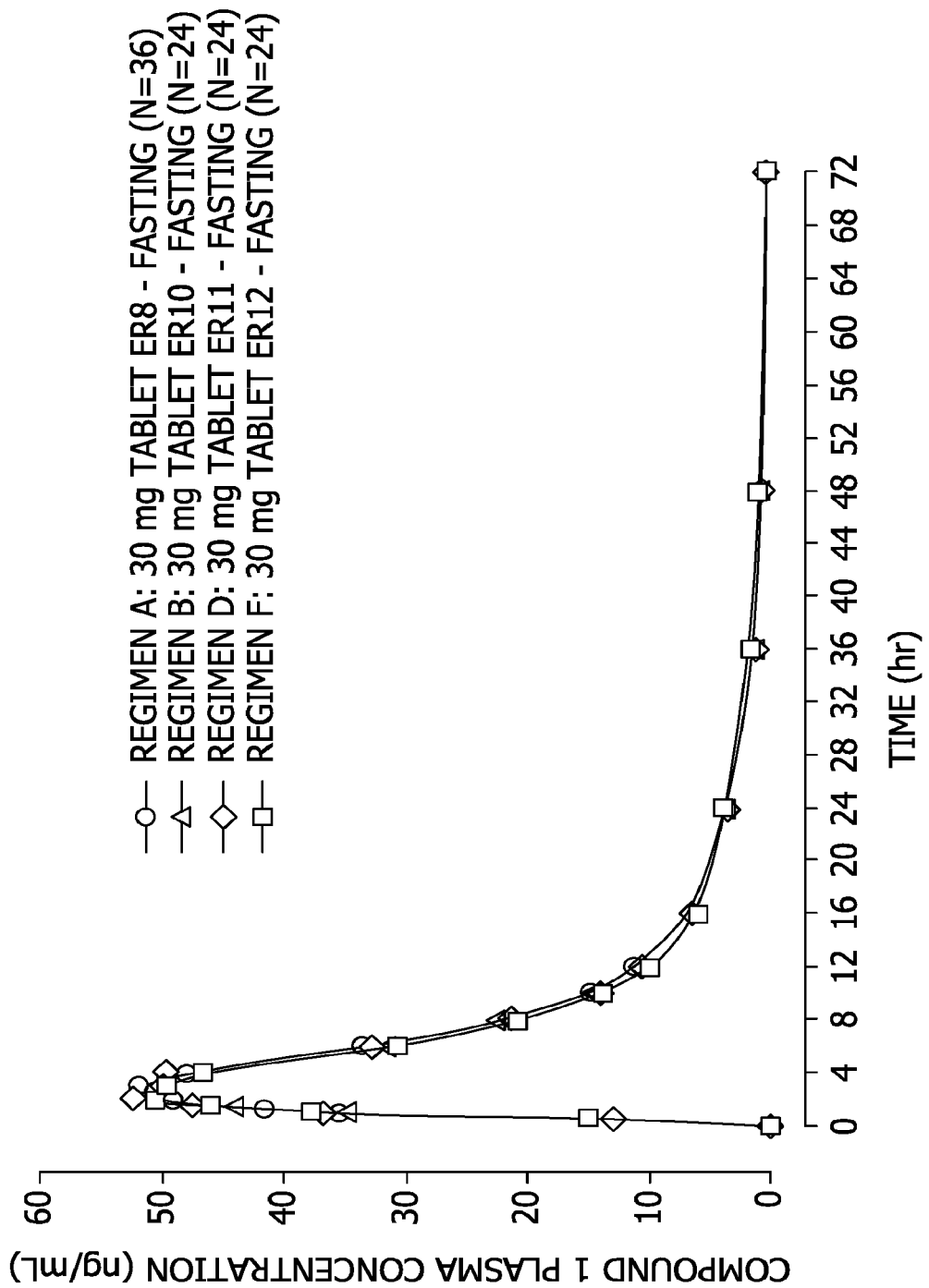
FIGS. 24A and 24B show the Compound 1 mean plasma concentration versus time following administration under fasting conditions of various 30 mg once-daily extended release tablets having varying concentrations of tartaric acid, using a linear (FIG. 24A) or log-linear (FIG. 24B) scale.
Figure 24B:
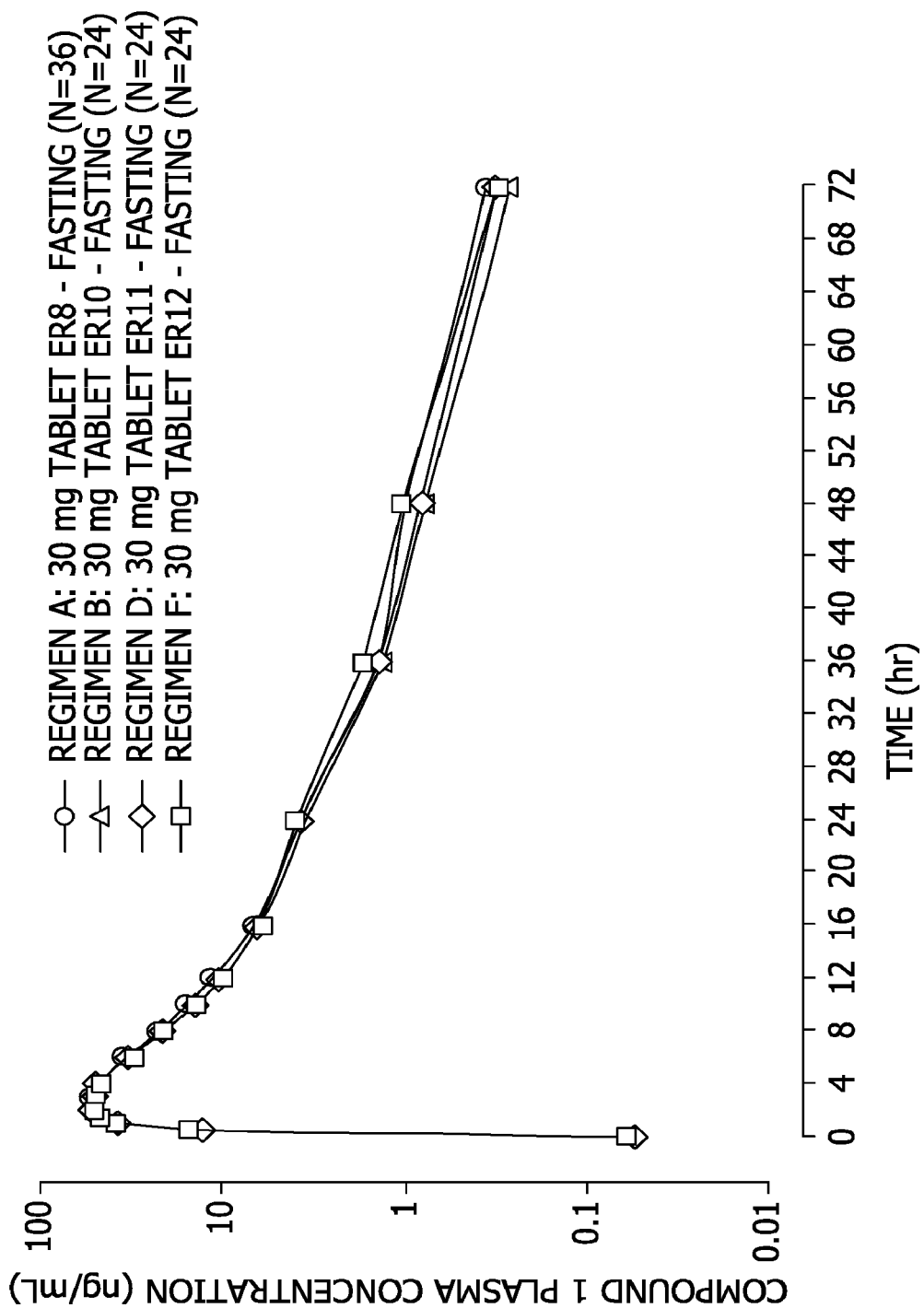

The results for administration under fasting conditions are summarized in Table 52-B. The mean plasma concentration of Compound 1 at each time point using linear (FIG. 24A) and log-linear (FIG. 24B) scales for each of the four fasting regimens is set forth in FIGS. 24A and 24B.

TABLE 52-B

Mean (% CV)[c] Pharmacokinetic Parameters for Compound 1 Following Administration of a Single 30 mg Dose of Various Compound 1 Once-Daily Formulations Prepared Using Wet Granulation Compared to Administration of a Single 30 mg Dose of a Compound 1 Once-Daily Formulation Prepared Via Direct Compression Under Fasting Conditions

| PK Parameter | Units | Regimen A (ER8) (n = 36) | Regimen B (ER10) (n = 24) | Regimen D (ER11) (n = 24) | Regimen F (ER12) (n = 24) |
|---|---|---|---|---|---|
| $C_{max}$[a] | ng/mL | 57.0 (33) | 55.8 (27) | 61.0 (25) | 58.6 (34) |
| $T_{max}$[a] | hours | 2.5 (1.0-4.0) | 3.0 (1.0-4.0) | 2.0 (1.0-4.0) | 2.0 (1.0-4.0) |
| $AUC_t$ | ng · h/mL | 495 (24) | 473 (24) | 487 (22) | 481 (23) |
| $AUC_{inf}$ | ng · h/mL | 513 (26) | 484 (24) | 499 (22) | 495 (23) |
| $t_{1/2}$[b] | hours | 9.2 (61) | 10.1 (50) | 9.0 (61) | 9.3 (63) |

[a]Median (minimum-maximum)
[b]Harmonic mean (pseudo-% CV)
[c]Data in parentheses is coefficient of variance of the PK parameter (% CV), unless otherwise indicated.

The relative bioavailability for a single dose of the three once-daily (ER) tablet formulations prepared using wet granulation (Regimens B, D, and F) relative to the ER tablet prepared via direct compression (no wet granulation) (Regimen A) was also determined based on analysis of the natural logarithms of $C_{max}$, $AUC_t$, and $AUC_{Inf}$. The results are summarized in Table 52-C below.

TABLE 52-C

Bioavailability for Three Compound 1 Once-Daily Formulations Prepared Using Wet Granulation (30 mg; ER10, ER11, ER12) Relative to a Formulation Prepared Via Direct Compression (30 mg, ER8) under Fasting Conditions

| | | Relative Bioavailability | |
|---|---|---|---|
| Regimens | PK Parameter | Point Estimate | 90% Confidence Interval |
| Regimen B (ER10) vs. Regimen A (ER8) | $C_{max}$ | 1.024 | 0.917-1.143 |
| | $AUC_t$ | 0.990 | 0.933-1.049 |
| | $AUC_{inf}$ | 0.976 | 0.918-1.037 |
| Regimen D (ER11) vs. Regimen A (ER8) | $C_{max}$ | 1.063 | 0.952-1.187 |
| | $AUC_t$ | 0.985 | 0.929-1.044 |
| | $AUC_{inf}$ | 0.977 | 0.919-1.038 |
| Regimen F (ER12) vs. Regimen A (ER8) | $C_{max}$ | 1.034 | 0.926-1.154 |
| | $AUC_t$ | 0.958 | 0.904-1.016 |
| | $AUC_{inf}$ | 0.958 | 0.901-1.018 |

As can be seen from this data, all three of the 30 mg tablets prepared using wet granulation (ER10, ER11, and ER12) were bioequivalent under fasting conditions to the tablet prepared via direct compression (no wet granulation).

Effect of a High-Fat Meal on Example 37 Formulation (ER10)

Figure 25A:
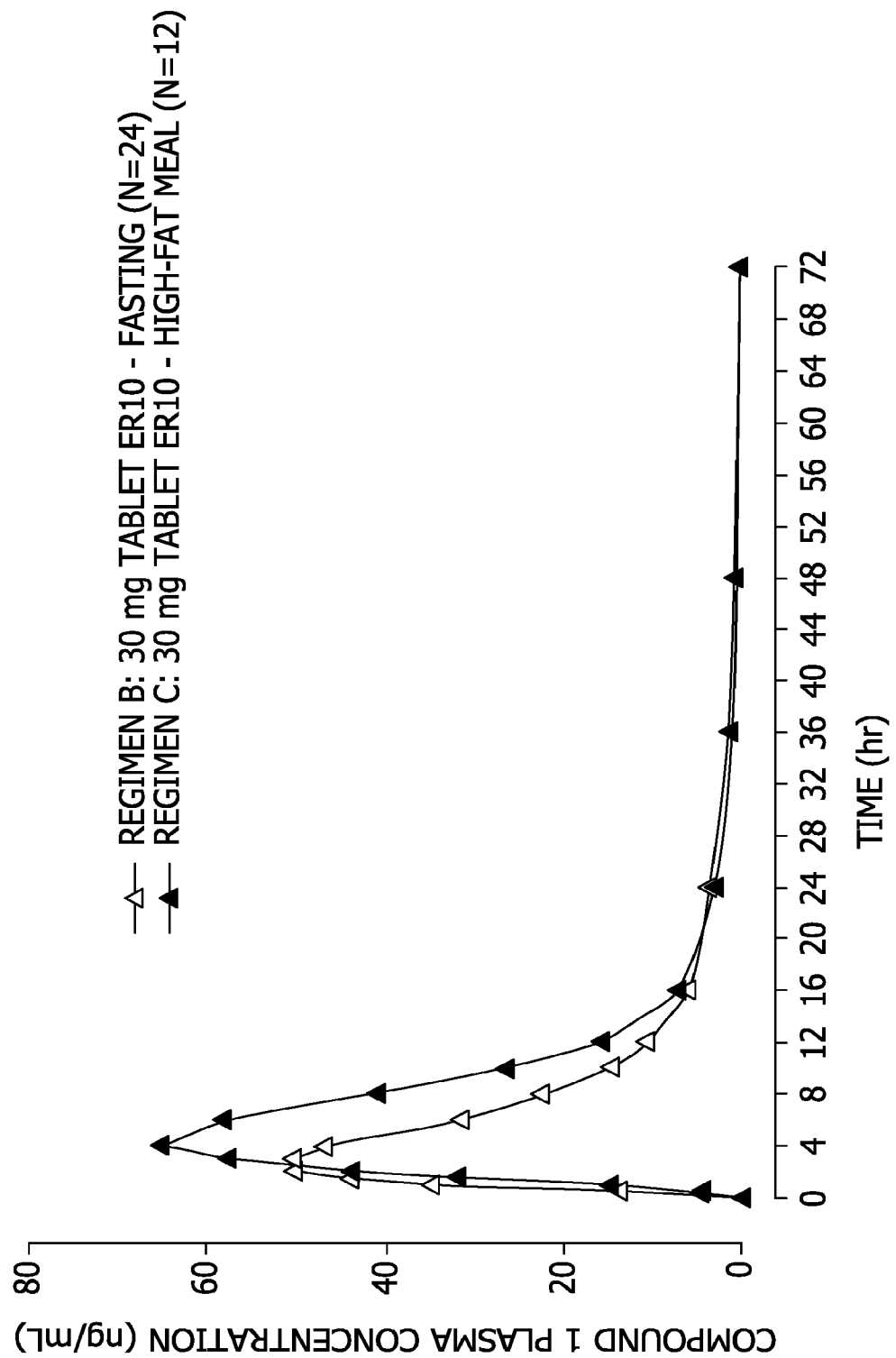
FIGS. 25A and 25B show the Compound 1 mean plasma concentration versus time following administration under fasting conditions or after a high-fat meal (non-fasting) of a 30 mg once-daily extended release tablet (ER10) using a linear (FIG. 25A) or log-linear (FIG. 25B) scale.
Figure 25B:
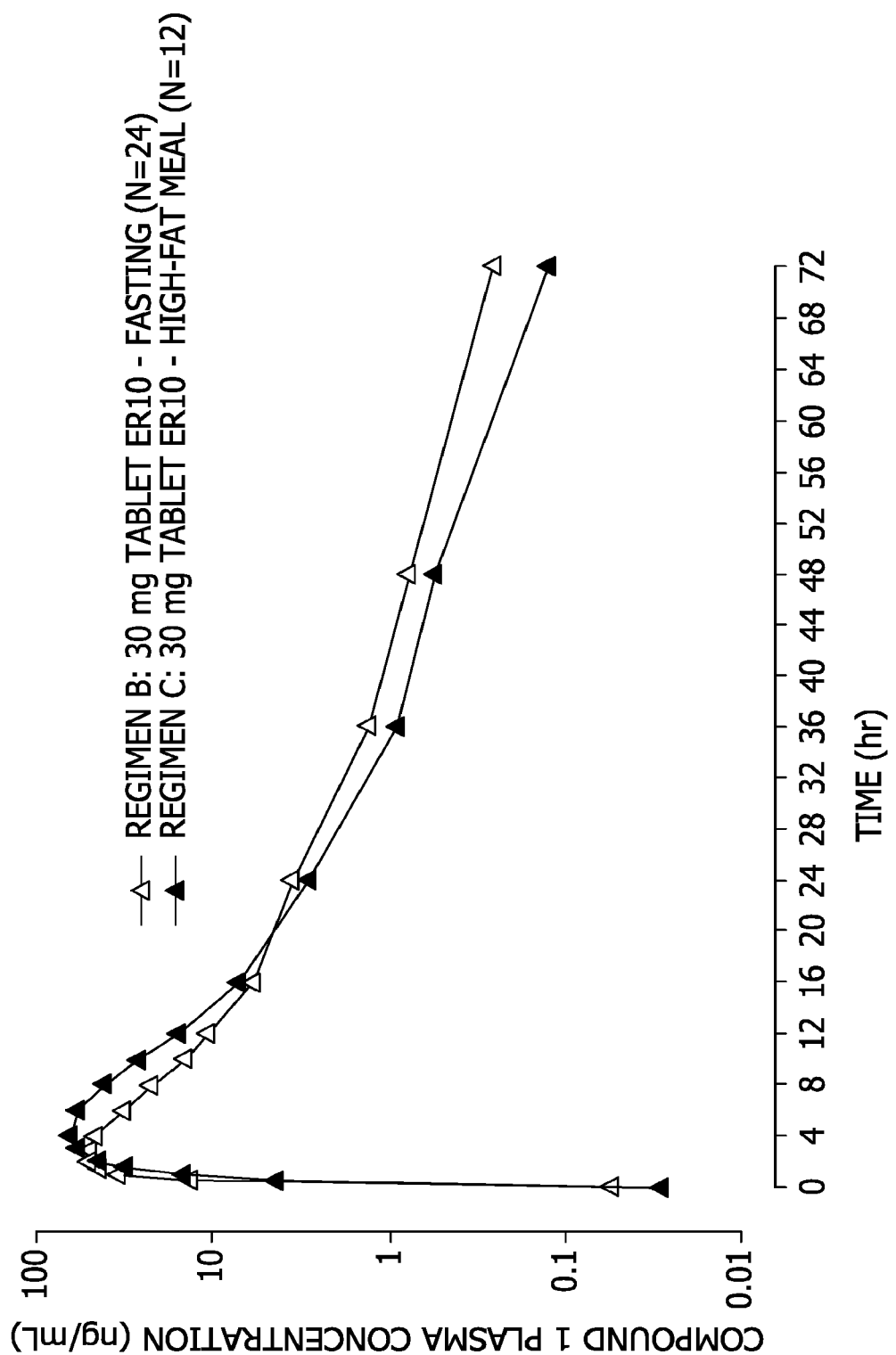
Figure 26A:
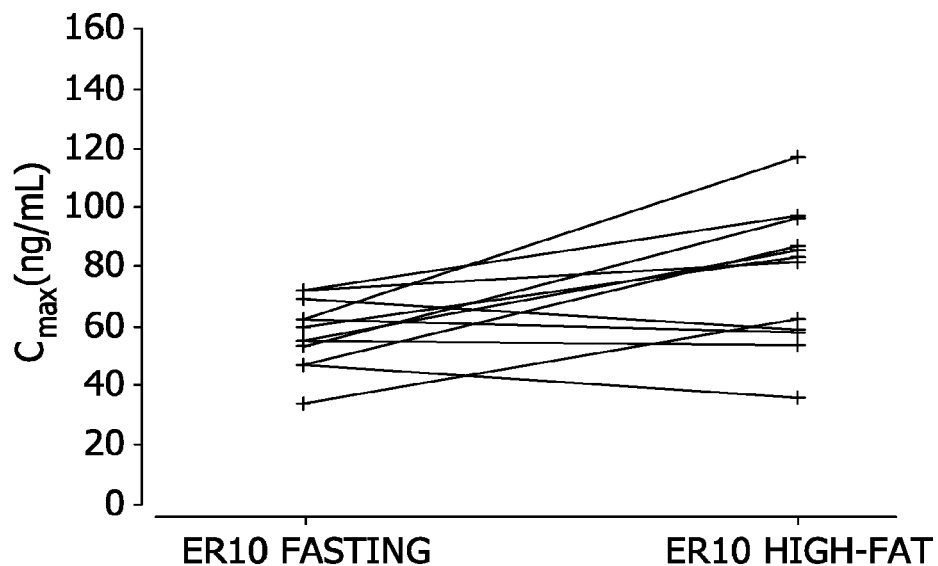
FIGS. 26A and 26B show the individual change in Compound 1 $C_{max}$ (FIG. 26A) and $AUC_{inf}$ (FIG. 26B) following administration under fasting conditions or after a high-fat meal (non-fasting) of a 30 mg once-daily extended release tablet (ER10).
Figure 26B:
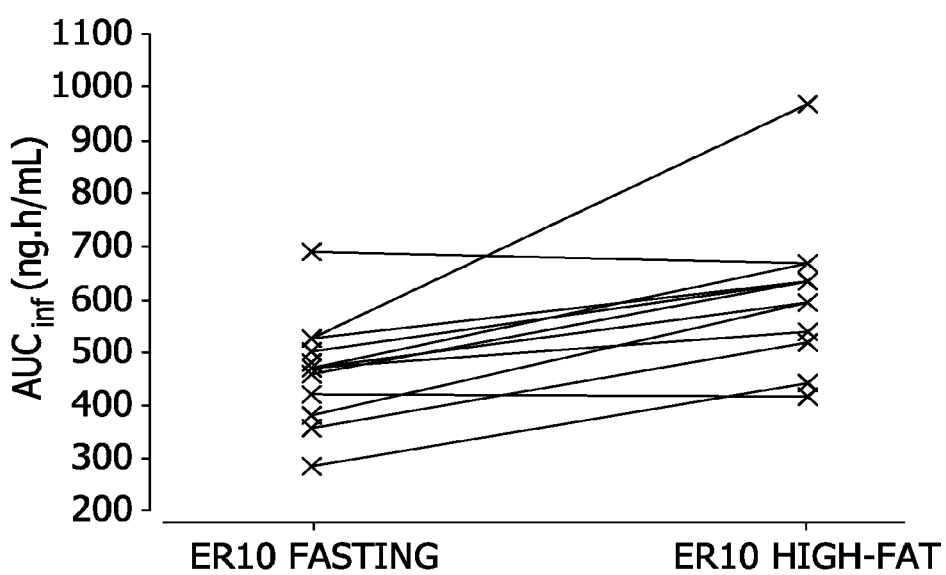

The effect of a high-fat meal on the pharmacokinetic parameters of the Example 37 (ER10, 30 mg active, 30% tartaric acid) formulation is summarized in Table 52-D. The mean plasma concentration of Compound 1 at each time point using linear (FIG. 25A) and log-linear (FIG. 25B) scales for each of Regimen B (ER10, fasting) and Regimen C (ER10, high-fat meal) is set forth in FIGS. 25A and 25B. The change in Compound 1 $C_{max}$ and $AUC_{inf}$ following administration of a single 30 mg dose of the ER10 tablet under fasting conditions and after a high-fat meal are shown in FIGS. 26A ($C_{max}$) and 26B ($AUC_{inf}$).

TABLE 52-D

Mean (% CV)[c] Pharmacokinetic Parameters for Compound 1 Following Administration of Single 30 mg Dose of the Once-Daily Tablet Formulation ER10 under Fasting Conditions and After High-Fat Meal

| PK Parameter | Units | Regimen B (ER10, fasting) (n = 24) | Regimen C (ER10, high fat meal) (n = 12) |
|---|---|---|---|
| $C_{max}$ | ng/mL | 55.8 (27) | 76.3 (30) |
| $T_{max}$[a] | hours | 3.0 (1.0-4.0) | 4.0 (1.5-8.0) |
| $AUC_t$ | ng · h/mL | 473 (24) | 605 (23) |
| $AUC_{inf}$ | ng · h/mL | 484 (24) | 609 (23) |
| $t_{1/2}$[b] | hours | 10.1 (50) | 9.1 (35) |

[a]Median (minimum-maximum)
[b]Harmonic mean (pseudo-% CV)
[c]Data in parentheses is coefficient of variance of the PK parameter (% CV), unless otherwise indicated.

The relative bioavailability for a single dose of the Example 37 formulation (ER10) administered after a high-fat meal relative to administration under fasting conditions was also determined based on analysis of the natural logarithms of $C_{max}$, $AUC_t$, and $AUC_{inf}$. The results are summarized in Table 52-E below.

TABLE 52-E

Bioavailability of Single Dose of the 30 mg Once-Daily Tablet ER10 Administered after High-Fat Meal Relative to under Fasting Conditions

| | PK Parameter | Relative Bioavailability | |
|---|---|---|---|
| | | Point Estimate | 90% Confidence Interval |
| Regimen C (ER10, high-fat meal) vs. Regimen B (ER10, fasting) | $C_{max}$ | 1.322 | 1.134-1.541 |
| | $AUC_t$ | 1.296 | 1.194-1.405 |
| | $AUC_{inf}$ | 1.278 | 1.174-1.392 |

As can be seen from this data, a high-fat meal increased the $C_{max}$ and $AUC_{inf}$ for the ER10 formulation (30 mg active, 30% tartaric acid) by about 32% and 28%, respectively.

Effect of a High-Fat Meal on Example 38 Formulation (ER11)

Figure 27A:
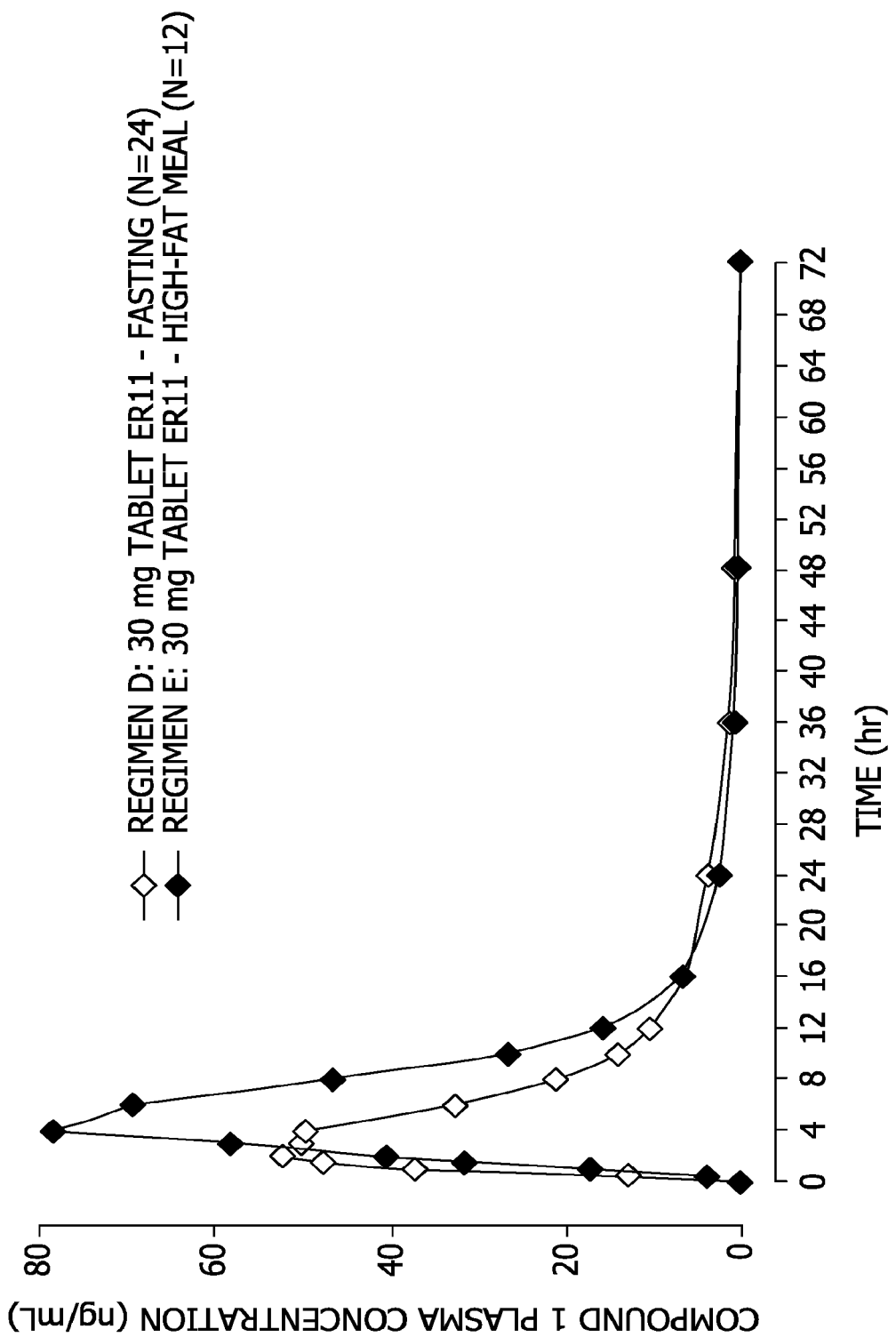
FIGS. 27A and 27B show the Compound 1 mean plasma concentration versus time following administration under fasting conditions or after a high-fat meal (non-fasting) of a 30 mg once-daily extended release tablet (ER11) using a linear (FIG. 27A) or log-linear (FIG. 27B) scale.
Figure 27B:
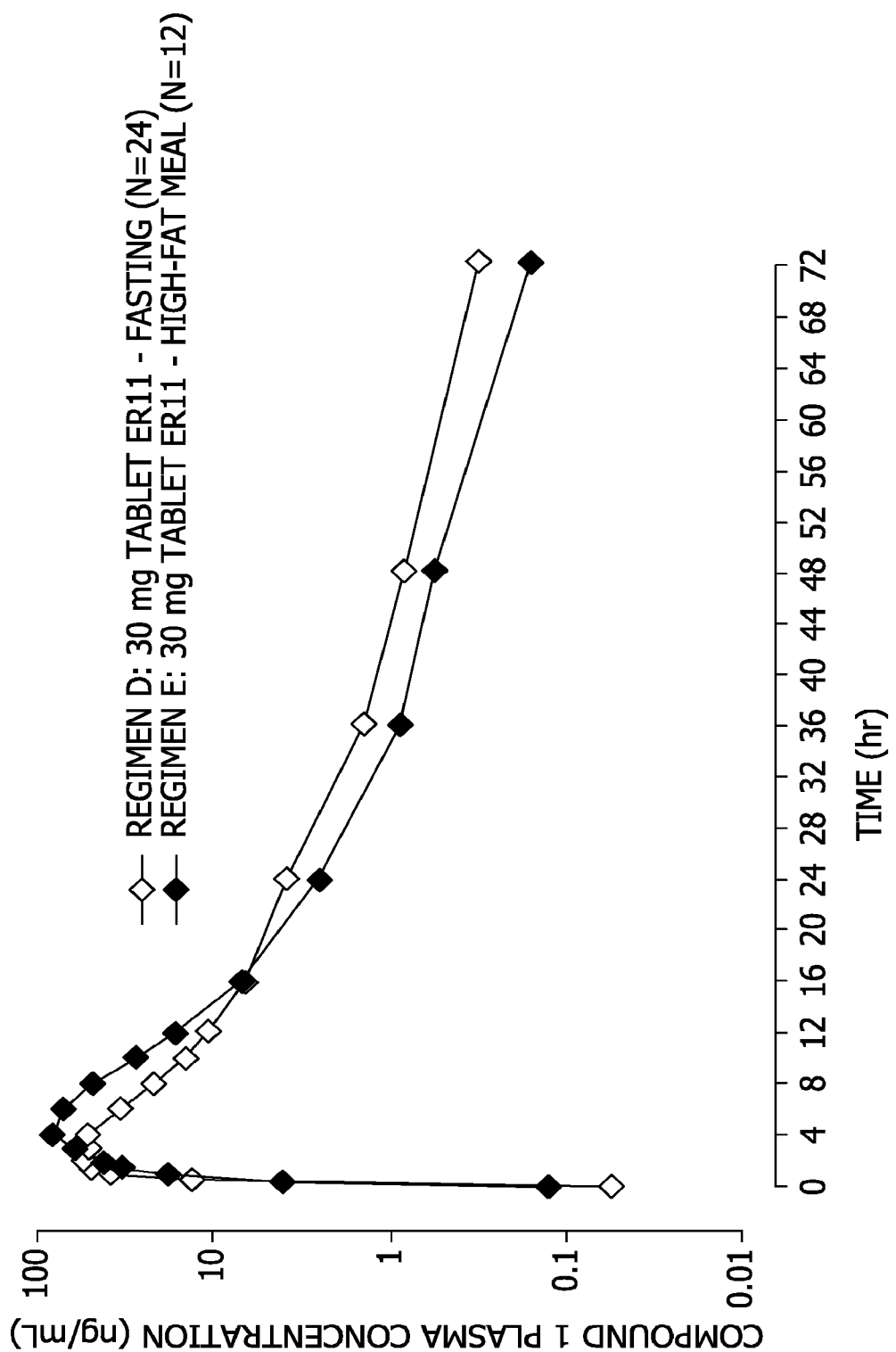
Figure 28A:
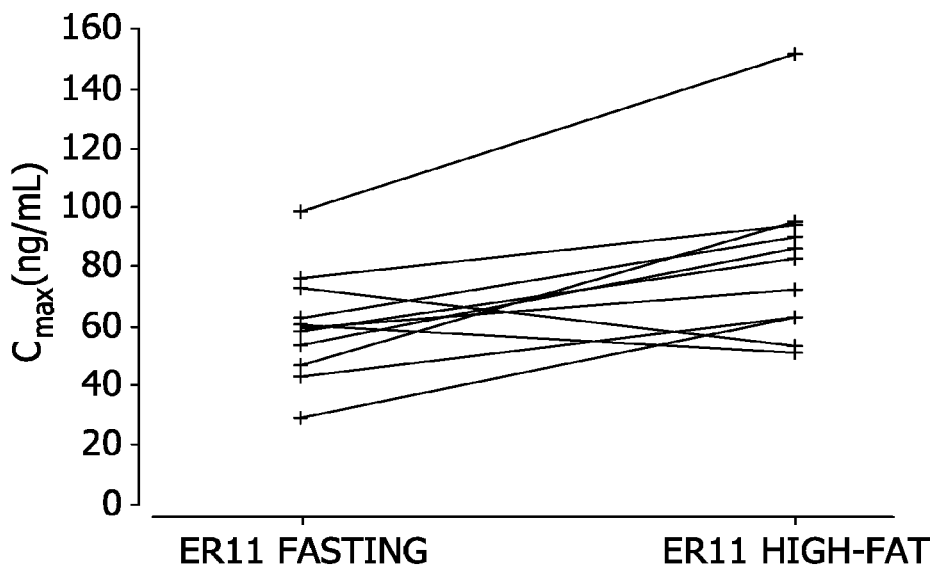
FIGS. 28A and 28B show the individual change in Compound 1 $C_{max}$ (FIG. 28A) and $AUC_{inf}$ (FIG. 28B) following administration under fasting conditions or after a high-fat meal (non-fasting) of a 30 mg once-daily extended release tablet (ER11).
Figure 28B:
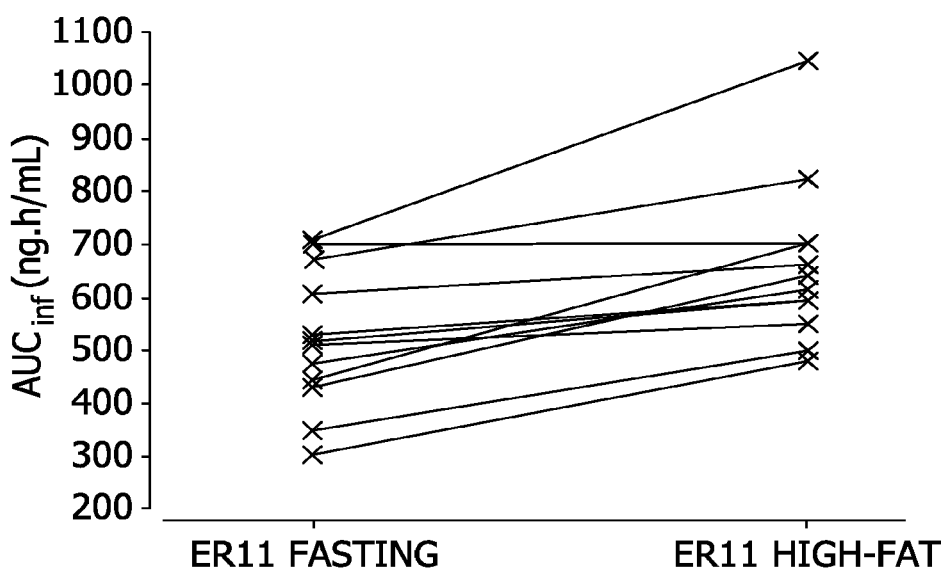

The effect of a high-fat meal on the pharmacokinetic parameters of the Example 38 (ER11, 30 mg, 20% tartaric acid) formulation is summarized in Table 52-F. The mean plasma concentration of Compound 1 at each time point using linear (FIG. 27A) and log-linear (FIG. 27B) scales for each of Regimen D (ER11, fasting) and Regimen E (ER11, high-fat meal) is set forth in FIGS. 27A and 27B. The change in Compound 1 $C_{max}$ and $AUC_{inf}$ following administration of a single 30 mg dose of the ER11 tablet under fasting conditions and after a high-fat meal are shown in FIGS. 28A ($C_{max}$) and 28B ($AUC_{inf}$).

TABLE 52-F

Mean (% CV)c Pharmacokinetic Parameters for Compound 1 Following Administration of Single 30 mg Dose of the Once-Daily Tablet Formulation ER11 under Fasting Conditions and After High-Fat Meal

| PK Parameter | Units | Regimen D (ER11, fasting) (n = 24) | Regimen E (ER11, high fat meal) (n = 12) |
|---|---|---|---|
| $C_{max}$ | ng/mL | 61.0 (25) | 82.2 (33) |
| $T_{max}$[a] | hours | 2.0 (1.0-4.0) | 4.0 (3.0-8.0) |
| $AUC_t$ | ng · h/mL | 487 (22) | 648 (24) |
| $AUC_{inf}$ | ng · h/mL | 499 (22) | 657 (24) |
| $t_{1/2}$[b] | hours | 9.0 (61) | 9.7 (53) |

[a]Median (minimum-maximum)
[b]Harmonic mean (pseudo-% CV)
cData in parentheses is coefficient of variance of the PK parameter (% CV), unless otherwise indicated.

The relative bioavailability for a single dose of the Example 38 formulation (ER11) administered after a high-fat meal relative to administration under fasting conditions was also determined based on analysis of the natural logarithms of $C_{max}$, $AUC_t$, and $AUC_{inf}$. The results are summarized in Table 52-G below.

TABLE 52-G

Bioavailability of Single Dose of the 30 mg Once-Daily Tablet ER11 Administered after High-Fat Meal Relative to under Fasting Conditions

| | PK Paramenter | Relative Bioavailability | |
|---|---|---|---|
| | | Point Estimate | 90% Confidence Interval |
| Regimen E (ER11, high-fat meal) vs. Regimen D (ER11, fasting) | $C_{max}$ | 1.343 | 1.153-1.563 |
| | $AUC_t$ | 1.305 | 1.204-1.415 |
| | $AUC_{inf}$ | 1.285 | 1.181-1.398 |

As can be seen from this data, a high-fat meal increased the $C_{max}$ and $AUC_{inf}$ for the ER11 formulation (30 mg active, 20% tartaric acid) by about 34% and 29%, respectively, which was a similar food effect as that observed for the Example 37 (ER10) tablet.

Effect of a High-Fat Meal on Example 39 Formulation (ER12)

Figure 29A:
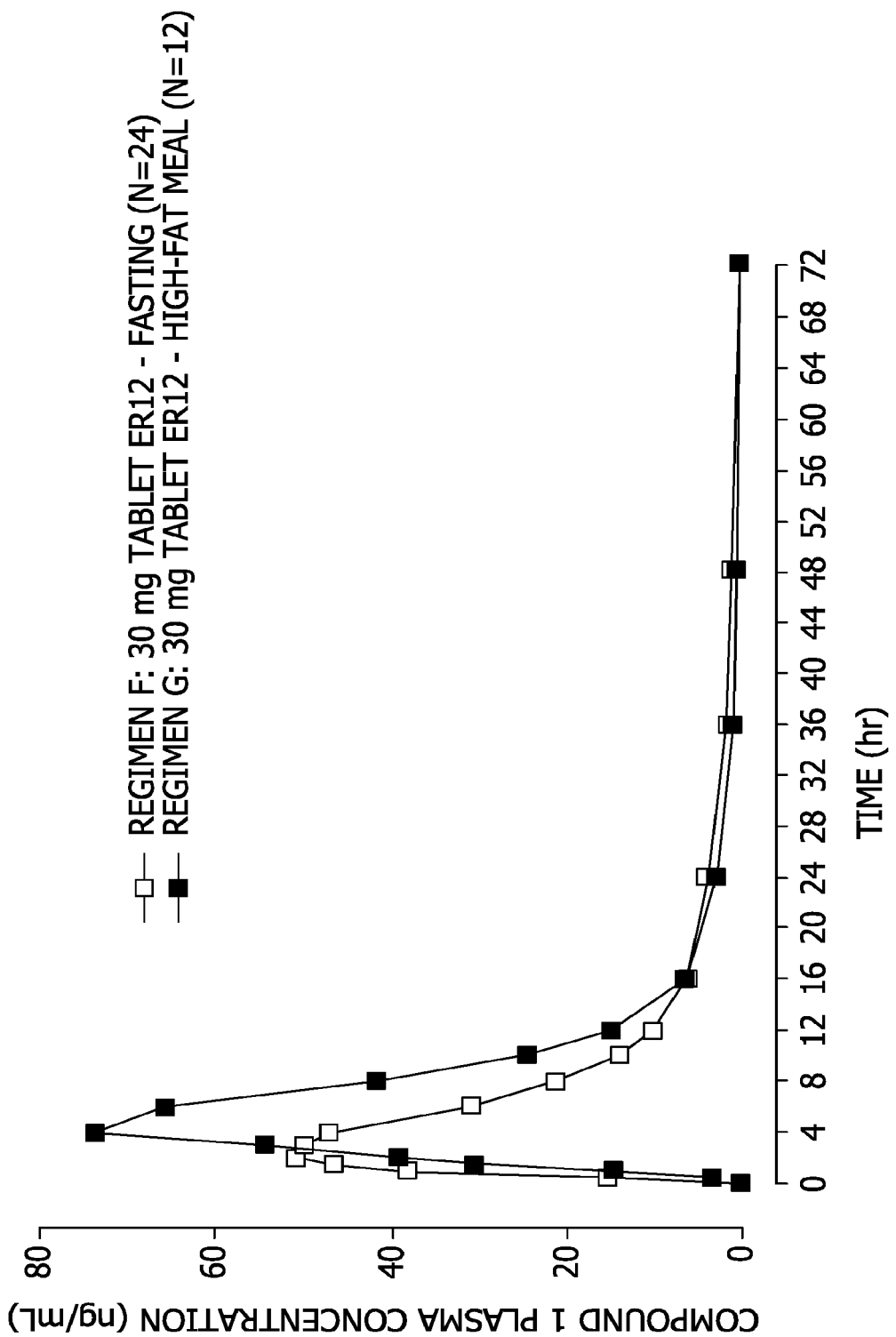
FIGS. 29A and 29B show the Compound 1 mean plasma concentration versus time following administration under fasting conditions or after a high-fat meal (non-fasting) of a 30 mg once-daily extended release tablet (ER12) using a linear (FIG. 29A) or log-linear (FIG. 29B) scale.
Figure 29B:
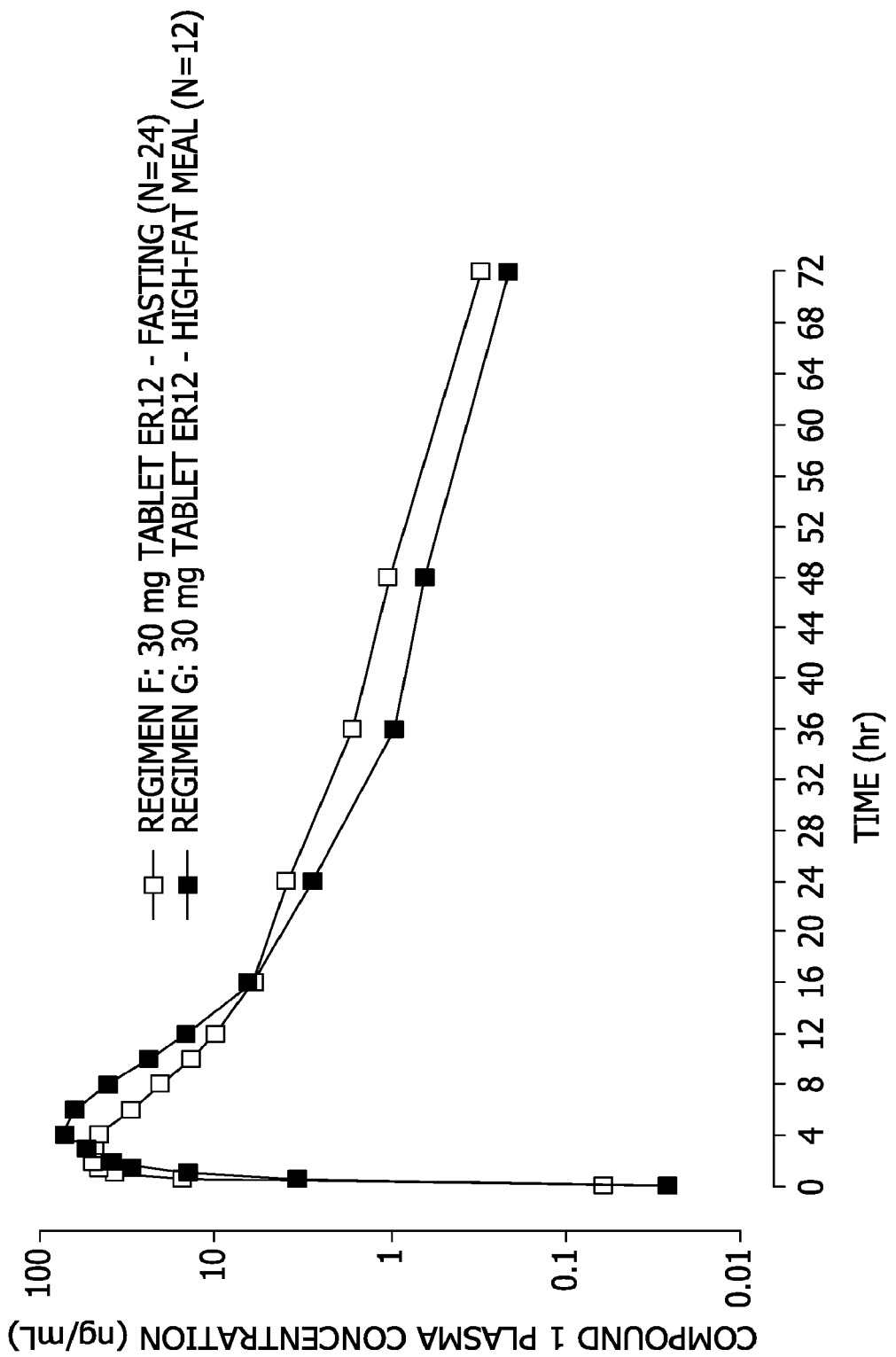
Figure 30A:
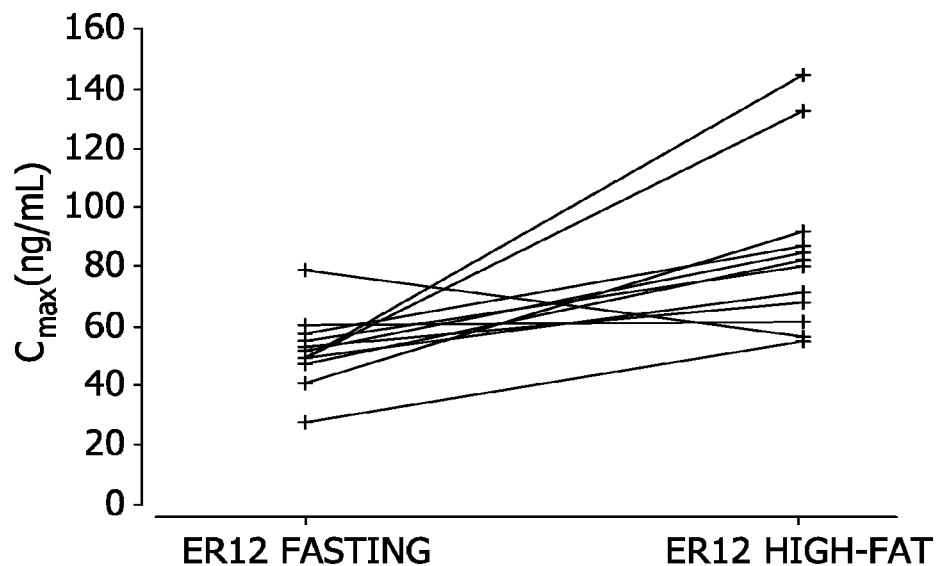
FIGS. 30A and 30B show the individual change in Compound 1 $C_{max}$ (FIG. 30A) and $AUC_{inf}$ (FIG. 30B) following administration under fasting conditions or after a high-fat meal (non-fasting) of a 30 mg once-daily extended release tablet (ER12).
Figure 30B:
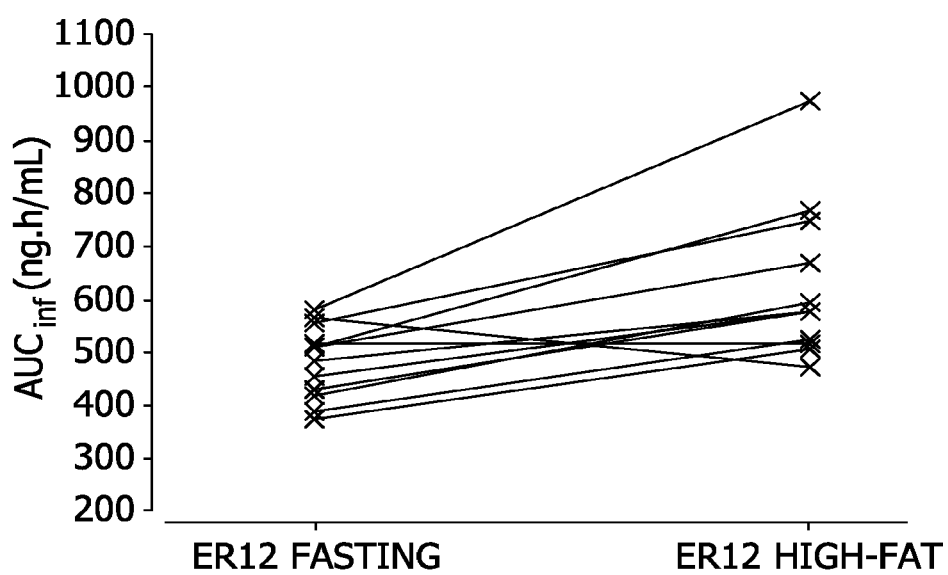

The effect of a high-fat meal on the pharmacokinetic parameters of the Example 39 (ER12, 30 mg active, 10% tartaric acid) formulation is summarized in Table 52-H. The mean plasma concentration of Compound 1 at each time point using linear (FIG. 29A) and log-linear (FIG. 29B) scales for each of Regimen F (ER12, fasting) and Regimen G (ER12, high-fat meal) is set forth in FIGS. 29A and 29B. The change in Compound 1 $C_{max}$ and $AUC_{inf}$ following administration of a single 30 mg dose of the ER12 tablet under fasting conditions and after a high-fat meal are shown in FIGS. 30A ($C_{max}$) and 30B ($AUC_{inf}$).

TABLE 52-H

Mean (% CV)c Pharmacokinetic Parameters for Compound 1 Following Administration of Single 30 mg Dose of the Once-Daily Tablet Formulation ER12 under Fasting Conditions and After High-Fat Meal

| PK Parameter | Units | Regimen E (ER12, fasting) (n = 24) | Regimen G (ER12, high fat meal) (n = 12) |
|---|---|---|---|
| $C_{max}$ | ng/mL | 58.6 (34) | 84.2 (33) |
| $T_{max}$[a] | hours | 2.0 (1.0-4.0) | 4.0 (4.0-6.0) |

TABLE 52-H-continued

Mean (% CV)c Pharmacokinetic Parameters for Compound
1 Following Administration of Single 30 mg Dose
of the Once-Daily Tablet Formulation ER12 under
Fasting Conditions and After High-Fat Meal

| PK Parameter | Units | Regimen E (ER12, fasting) (n = 24) | Regimen G (ER12, high fat meal) (n = 12) |
|---|---|---|---|
| $AUC_t$ | ng · h/mL | 481 (23) | 615 (24) |
| $AUC_{inf}$ | ng · h/mL | 495 (23) | 622 (23) |
| $t_{1/2}{}^b$ | hours | 9.3 (63) | 11.7 (91) |

[a]Median (minimum-maximum)
[b]Harmonic mean (pseudo-% CV)
[c]Data in parentheses is coefficient of variance of the PK parameter (% CV), unless otherwise indicated.

The relative bioavailability for a single dose of the Example 39 formulation (ER12) administered after a high-fat meal relative to administration under fasting conditions was also determined based on analysis of the natural logarithms of $C_{max}$, $AUC_t$, and $AUC_{inf}$. The results are summarized in Table 52-I below.

TABLE 52-I

Bioavailability of Single Dose of the 30 mg Once-
Daily Tablet ER12 Administered after High-Fat
Meal Relative to under Fasting Conditions

| | PK Parameter | Relative Bioavailability Point Estimate | 90% Confidence Interval |
|---|---|---|---|
| Regimen G (ER12, high-fat meal) vs. Regimen F (ER12, fasting) | $C_{max}$ | 1.527 | 1.314-1.774 |
| | $AUC_t$ | 1.295 | 1.196-1.402 |
| | $AUC_{inf}$ | 1.272 | 1.171-1.381 |

As can be seen from this data, a high-fat meal increased the $C_{max}$ and $AUC_{inf}$ for the ER12 formulation (30 mg active, 10% tartaric acid) by about 53% and 27%, respectively.

Example 53

Predicted Pharmacokinetic Parameters for 15 mg Extended Release Tablets

The mean pharmacokinetic parameters under fasting conditions for the once daily (QD) 15 mg extended release tablets prepared in Examples 40 (ER13), 41 (ER14), and 42 (ER15) using wet granulation were extrapolated from the single dose data obtained in Example 52 for the Examples 37 (ER10), 38 (ER11), and 39 (ER12) formulations, respectively, under fasting conditions. The results are set forth in Table 53-A.

TABLE 53-A

Predicted Mean Pharmacokinetic Parameters under Fasting
Conditions for Compound 1 Following Administration of
Single 15 mg Once-Daily Formulations (Extrapolated from
Single-Dose Profiles in Example 52 for 30 mg Doses)

| PK Parameters | Units | Single 15 mg Dose (ER 13) | Single 15 mg dose (ER14) | Single 15 mg dose (ER15) |
|---|---|---|---|---|
| $C_{max}$ | ng/mL | 27.9 | 30.5 | 29.3 |
| $T_{max}{}^a$ | h | 3.0 | 2.0 | 2.0 |
| $AUC_{inf}$ | ng · h/mL | 242 | 250 | 248 |

[a]Median (minimum-maximum)

Example 54

Preliminary Data from Phase 1 Study in Healthy Volunteers and Patients with Rheumatoid Arthritis Compound 1 has been studied in 2 Phase 1 studies, first in human single ascending dose study (Study M13-401, described in WO 2015/061665, and referred to herein as Study 1), and then in a multiple ascending dose study (Study M13-845, also generally referred to in WO 2015/061665, and referred to herein as Study 2).

In Study 1, a total of 42 healthy volunteers received a single dose of Compound 1. In Study 2; a total of 32 healthy volunteers received multiple doses of Compound 1 for 14 days (Study 2, Part 1). In addition, 14 patients with RA were enrolled and completed the double-blind Part 2 of Study 2. The study was designed as a multiple-dose, randomized, multicenter trial, with the primary objective as assessing the safety, tolerability, and PK of multiple ascending doses of Compound 1 in healthy adult volunteers and to assess the safety, tolerability, and PK of multiple doses of Compound 1 in patients with RA who are on a stable methotrexate regimen.

Details of Study 1 and Study 2 and results obtained therefrom are provided below.

Study 1—Single-Dose Escalation in Healthy Subjects

Study 1 was a single-dose escalation evaluation of Compound 1. Study 1 was designed as a single-site, randomized, double-blind, placebo-controlled study. Fifty-six subjects in general good health were randomized to receive single doses of Compound 1 immediate release capsules comprising Tartrate Hydrate (1, 3, 6, 12, 24, 36, and 48 mg) or placebo in a 3:1 ratio with 8 subjects in each dose level. Study drug was administered following at least 10 hours of fasting. The study was conducted at PPD Development (Austin, Tex.). Subjects were confined to the study site and supervised for approximately 8 consecutive days. Study protocol and informed consent were approved by RCRC institutional review board (IRB) (Austin, Tex.).

Study 2—Multiple-Dose Escalation

In Study 2, multiple twice-daily (BID) doses of immediate release capsules comprising Tartrate Hydrate were administered to healthy subjects (Part 1) or to subjects with rheumatoid arthritis (RA) receiving stable doses of methotrexate (Part 2). Both evaluations followed randomized, double-blind, placebo-controlled designs. Part 1 was conducted at PPD Development (Austin, Tex.) and Part 2 was conducted at two sites: Aspen Clinical Research (Orem, Utah) and Altoona Center for Clinical Research (Duncansville, Pa.). Study protocol and informed consents were approved by RCRC IRB (Austin, Tex.) and Quorum Review IRB (Seattle, Wash.).

Study 2—Part 1—Multiple-Dose Escalation in Healthy Subjects

The objective of Part 1 of the multiple-dose study was to characterize the pharmacokinetics, safety, and tolerability of multiple oral doses of Compound 1 immediate release capsules comprising Tartrate Hydrate in healthy subjects. Four escalating dosing regimens (3, 6, 12, and 24 mg Compound 1 or matching placebo twice daily for 13 consecutive days and once in the morning on Day 14) were evaluated. Study drug was administered approximately 30 minutes after a standard breakfast (in the morning) or a snack (in the evening). Forty-four healthy subjects participated in this part of the study with 11 subjects per dose group (8:3 Compound 1:placebo ratio). Subjects were confined to the study site and supervised for approximately 18 days.

Study 2—Part 2—Multiple-Dose Evaluation in Subjects with RA

The objective of Part 2 of the multiple dose study was to assess the pharmacokinetics, safety, and tolerability of multiple oral doses of Compound 1 immediate release capsules comprising Tartrate Hydrate in subjects with mild to moderate RA who were on stable methotrexate treatment. This evaluation was designed to enroll approximately 32 subjects randomized in a 1:1:1:1 ratio to one of four parallel twice-daily regimens (6, 12, and 24 mg Compound 1 and placebo). Subjects received study drug for 26 consecutive days (Study Days 3 through 28) and a single morning dose of study drug on Study Day 29. Compound 1 was administered following breakfast for the morning dose and dinner or snack for the evening dose. Subjects were on methotrexate therapy for at least 3 months and on a stable dose of 10 to 25 mg/week of methotrexate for at least 4 weeks prior to the first dose of study drug administered on Study Day 3 and continued their weekly stable dose of methotrexate on Study Days 1, 8, 15, 22 and 29. Subjects were confined to the study site for a total of 10 days—from Day 1 to Day 4 and from Day 27 to Day 31.

Study Participants

Subjects underwent screening procedures within 30 days prior to the initial administration of study drug. Subjects signed a written informed consent prior to the initiation of any screening or study-specific procedures. Subjects were eligible for study participation if they were men or women between 18 and 55 years of age (Study 1 and Study 2—Part 1) or 18 to 75 years of age (Study 2—Part 2); judged to be in good general health based upon the results of medical history, laboratory profile, physical examination, chest x-ray, and 12-lead electrocardiogram (ECG); and their body mass index (BMI) was within 19 to 29 kg/m$^2$ (Study 1 and Study 2—Part 1) or within 19 to 39 kg/m$^2$ (Study 2-Part 2) at screening. Subjects were considered eligible to participate in Study 2—Part 2 if they had diagnosis of RA based on the 2010 American College of Rheumatology/European League against Rheumatism criteria ≥6 months, have been on methotrexate therapy ≥3 months (and folate or equivalent for at least 2 weeks prior to Study Day 1), on a stable methotrexate dose of 10 to 25 mg/week for at least 4 weeks prior to the first dose of study drug administered on Study Day 3.

In both studies, subjects were excluded if they had any clinically significant abnormalities, infection, major febrile illness, hospitalization, or had any clinically relevant surgical procedure within 30 days prior to the first dose of study drug; had positive test result for hepatitis A virus immunoglobulin M, hepatitis B surface antigen, or hepatitis C virus antibody, or HIV antibodies at Screening; had history or evidence of active or latent tuberculosis; had history of diabetes or lymphoproliferative disease or evidence of immunosuppression (except for use of methotrexate in Study 2—Part 2); or had clinically significant findings at Screening as determined by the principal investigator. Additionally, subjects in Study 2—Part 2 were excluded if they had a history of acute inflammatory joint disease of different origin other than RA or had current or expected need for oral intake of >10 mg prednisone/day or equivalent corticosteroid therapy.

Pharmacokinetic Sampling

In healthy subjects, serial blood samples were collected over 72 hours after single dosing (Study 1) or over 12 hours after the first dose (Study Day 1) and over 72 hours after the last dose (Study Day 14) of study drug (Study 2—Part 1). In subjects with RA, serial blood samples were collected over 48 hours on Study Day 1 for methotrexate assay, over 12 hours following the first Study drug dose on Study Day 3 for Compound 1 assay, over 12 hours following the morning Study drug dose on Study Day 28 for Compound 1 assay, and over 48 hours following the last Study drug dose on Study Day 29 for Compound 1 and methotrexate assays. Pre-dose trough samples were collected prior to the morning dose on Study Days 5, 6, 7, 13, and 14 in Study 2—Part 1 to assess attainment of steady state.

Urine for Compound 1 assay was collected over a 12-hour interval after the last dose was administered on Study Day 14 in Study 2—Part 1 and on Study Days 28 and 29 in Study 2—Part 2. Urine for methotrexate assay was collected for 48 hours on Study Day 1 and Study Day 29.

Plasma and urine concentrations of Compound 1 and methotrexate were determined using validated liquid chromatography method with mass spectrometric detection methods. The lower limits of quantitation (LLOQ) for Compound 1 and methotrexate in plasma were established at 0.0503 ng/mL and 1.00 ng/mL, respectively. The LLOQ for Compound 1 and methotrexate in urine were established at 1.01 ng/mL and 0.0500 µg/mL, respectively. Samples quantified below the LLOQ were reported as zero. For Compound 1 assays, inter-run variability (measured as % coefficient of variation [% CV]) was ≤9.5% for plasma ≤8.4% for urine and the mean absolute bias was ≤6.7% for plasma and ≤5.9% for urine. For methotrexate assay, inter-run variability (% CV) was ≤3.9% for plasma and ≤5.2% for urine and the mean absolute bias was ≤5.4% in plasma and ≤13.1% in urine.

Pharmacokinetic Analyses

Compound 1 and methotrexate pharmacokinetic parameters were determined using non-compartmental analyses with Phoenix software (Version 6.3, Certara, Princeton, N.J., USA). Calculated pharmacokinetic parameters included the maximum observed plasma concentration ($C_{max}$), time to $C_{max}$ ($T_{max}$), trough plasma concentration ($C_{trough}$), the apparent terminal phase elimination rate constant ($\beta$), the terminal phase elimination half-life ($t_{1/2}$), the area under the plasma concentration-time curve (AUC) [from time 0 to time of the last measurable concentration ($AUC_t$), from time 0 to infinity ($AUC_\infty$) for single dosing, and over a 12-hour dosing interval ($AUC_{0-12}$, or $AUC_{12,ss}$) for multiple dosing and the apparent oral clearance (CL/F). Compound 1 functional half-life ($t_{1/2}F$) following multiple dosing was calculated as $\ln(2)/(\ln[C_{max}/C_{trough}]/\tau)$ at steady state, where $\tau$ is the 12 hour dosing interval (Dutta et al., Clin. Drug Investig., 2006, Vol. 26(12), pp. 681-690). The accumulation ratio ($R_{ac}$) was calculated as the ratio of Compound 1 $AUC_{0-12}$ on Day 14 to Day 1 (Study 2—Part 1) or Day 28 to Day 3 (Study 2—Part 2). The percentage of Compound 1 dose recovered unchanged in urine ($f_e\%$) at steady state was calculated as the amount of Compound 1 recovered in urine over the 0 to 12 hour interval ($Au_{,0-12}$), divided by the administered dose and multiplied by 100. Renal clearance (CLr) was calculated as $Au_{,0-12}/AUC_{0-12}$ at steady state. Methotrexate $f_e\%$ was calculated as the amount of methotrexate recovered in urine over the 0 to 48 hour interval ($Au_{,0-48}$), divided by the administered dose and multiplied by 100. CLr of methotrexate was calculated as $Au_{,0-48}/AUC_{0-48}$. The effect of co-administration of methotrexate on Compound 1 exposure was assessed from the ratios of Compound 1 $AUC_{0-12}$ and $C_{max}$ on Study Day 29 to Study Day 28. The effect of Compound 1 on methotrexate exposure was assessed from the ratios of methotrexate $AUC_\infty$ and $C_{max}$ on Study Day 29 to Study Day 1.

Safety and Tolerability Assessment

Safety was evaluated based on assessments of adverse events, vital signs, physical examination, laboratory metrics, and 12-lead electrocardiogram (ECG). All subjects who received at least one dose of study drug were included in the safety analyses. Subjects who were administered placebo multiple-dose evaluation in subjects with RA (Study 2—Part 2) was discontinued early due to slow recruitment rate and 14 subjects with RA were actually enrolled and completed this evaluation. No early withdrawals occurred in any of the three evaluations. A summary of demographic data is presented in Table 54-A.

TABLE 54-A

Baseline Demographics of Study Participants

|  | Study 1 | | Study 2 - Part 1 | | Study 2 - Part 2 | |
| --- | --- | --- | --- | --- | --- | --- |
|  | Compound 1 N = 42 | Placebo N = 14 | Compound 1 N = 32 | Placebo N = 12 | Compound 1 N = 11 | Placebo N = 3 |
| Mean Age, years ± SD | 31.0 ± 9.8 | 32.4 ± 8.6 | 33.3 ± 9.9 | 30.7 ± 5.0 | 59.3 ± 8.3 | 58.7 ± 14.3 |
| Mean Weight, kg ± SD | 74.7 ± 10.1 | 74.3 ± 8.8 | 74.1 ± 9.9 | 78.4 ± 13.6 | 78.5 ± 14.9 | 62.5 ± 6.9 |
| Mean Height, cm ± SD | 171 ± 8.9 | 171 ± 10.2 | 172 ± 7.9 | 177 ± 6.2 | 171 ± 7.3 | 165 ± 9.9 |
| Sex, number (%) | 35 males (83.3%), 7 females (16.7%) | 11 males (79%), 3 females (21%) | 29 males (91%), 3 females (9%) | 12 males (100%) | 6 males (54.5%), 5 females (45.5%) | 3 females (100%) |
| Race, number (%) | 30 White (71%), 10 Black (24%), 1 Asian (2%), 1 Other (2%) | 11 White (79%), 3 Black (21%) | 23 White (72%), 9 Black (28%) | 9 White (75%), 2 Black (17%), 1 Asian (8%) | 10 White (91%), 1 Black (9%) | 2 White (67%), 1 Asian (33%) | were pooled into a single group within each study or study part. Laboratory test values and vital signs measurements that were above or below the reference range were identified. Subjects were followed-up for a total of 7 days in Study 1, 35 days in Study 2—Part 1, and 57 days in Study 2—Part 2. In healthy subjects, clinical adverse events were graded as described in the Guidance for Industry Toxicity Grading Scale for Healthy Adult and Adolescent Volunteers Enrolled in Preventive Vaccine Clinical Trials (September 2007). In subjects with RA, the severity of adverse events were rated by the investigator as mild (transient and easily tolerated by the subject), moderate (causes subject discomfort and interrupts the subject's usual activities), or severe (causes considerable interference with the subject's usual activities and may be incapacitating or life-threatening). One subject in Study 2—Part 2 was randomized to the placebo arm, but received Compound 1 in error on Study Days 10 to 16. Therefore, this subject was included with the Compound 1 cohort for safety assessments Statistical Analyses Dose proportionality for Compound 1 in healthy subjects was tested using the natural logarithms of dose-normalized $C_{max}$ and AUC following single dosing (Study 1) or for steady-state dose-normalized $C_{max}$, $C_{trough}$, and AUC following multiple dosing (Study 2—Part 1) assessments. Attainment of steady-state following multiple doses in healthy volunteers was assessed by testing the logarithmic transformation of Compound 1 morning pre-dose concentrations for Study Days 5, 6, 7, 13, and 14 by repeated measures analysis. Statistical analyses were performed using SAS software (Version 9.3; SAS institute Inc., Cary, N.C., USA).

Results

Demographics and Subject Disposition

Figure 32A:
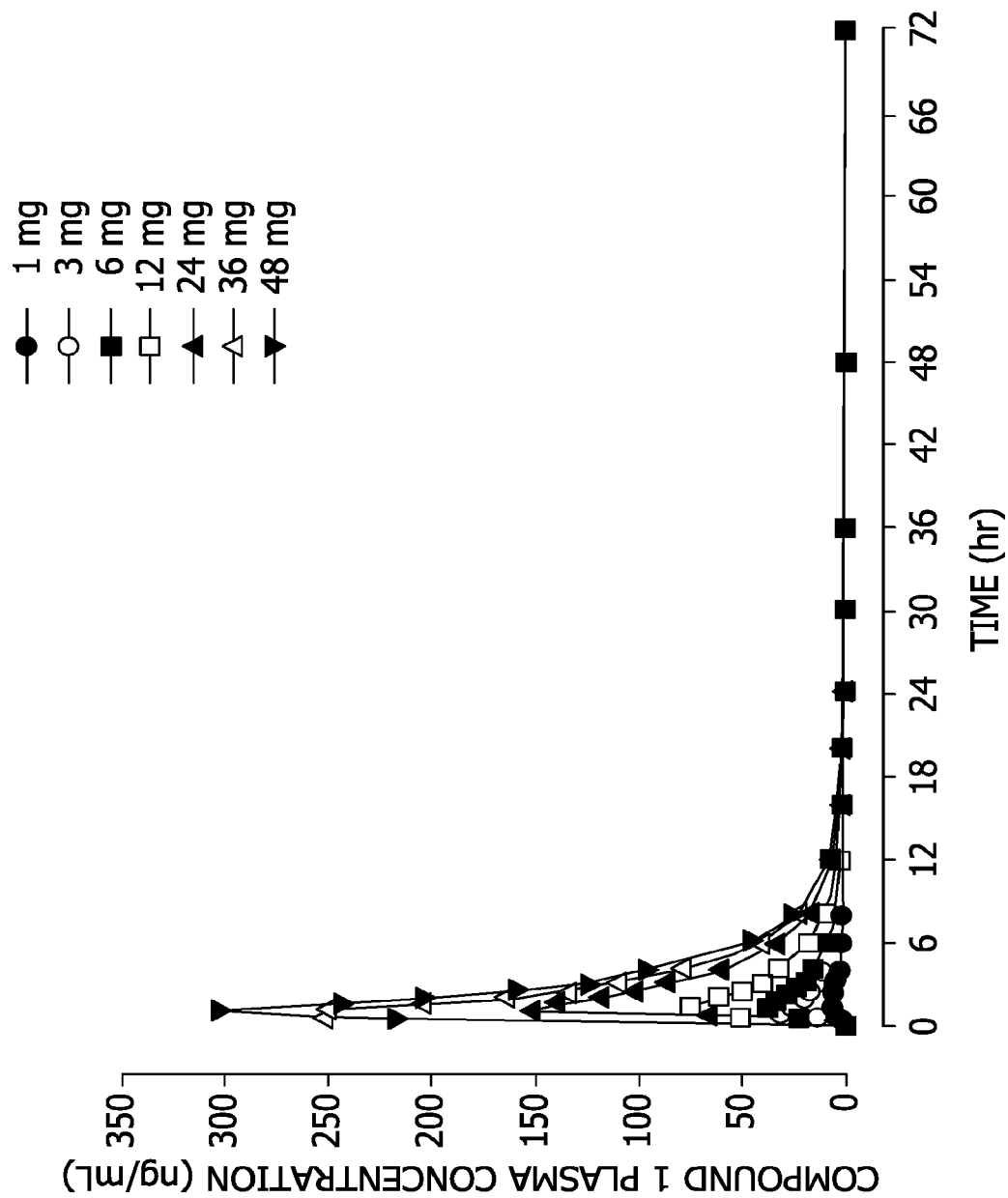
FIGS. 32A and 32B show the Compound 1 mean plasma concentrations versus time profiles following administration of single oral doses of Compound 1 immediate release capsules to healthy subjects using a linear (FIG. 32A) or log-linear (FIG. 32B) scales.
Figure 32B:
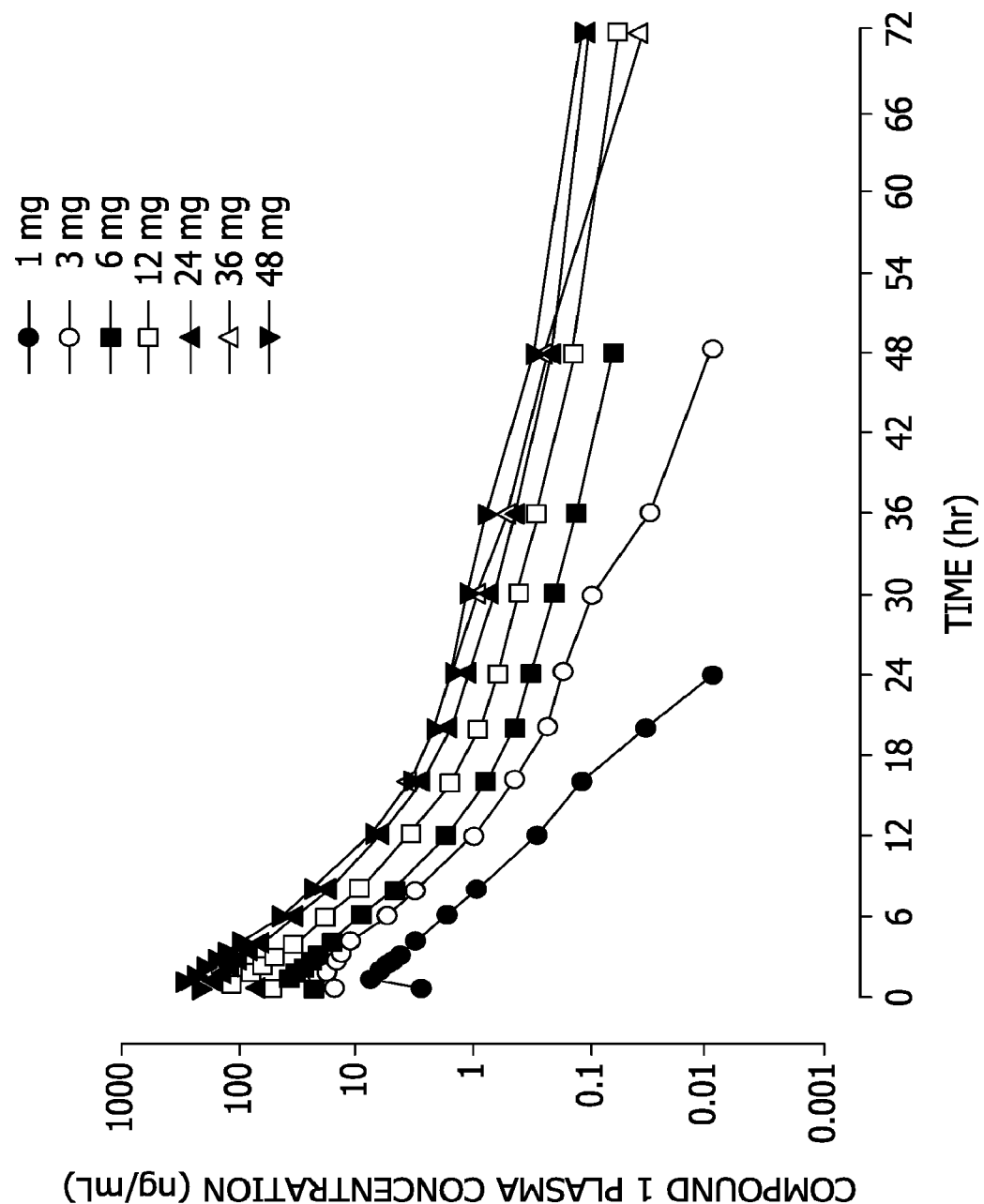
Figure 33:
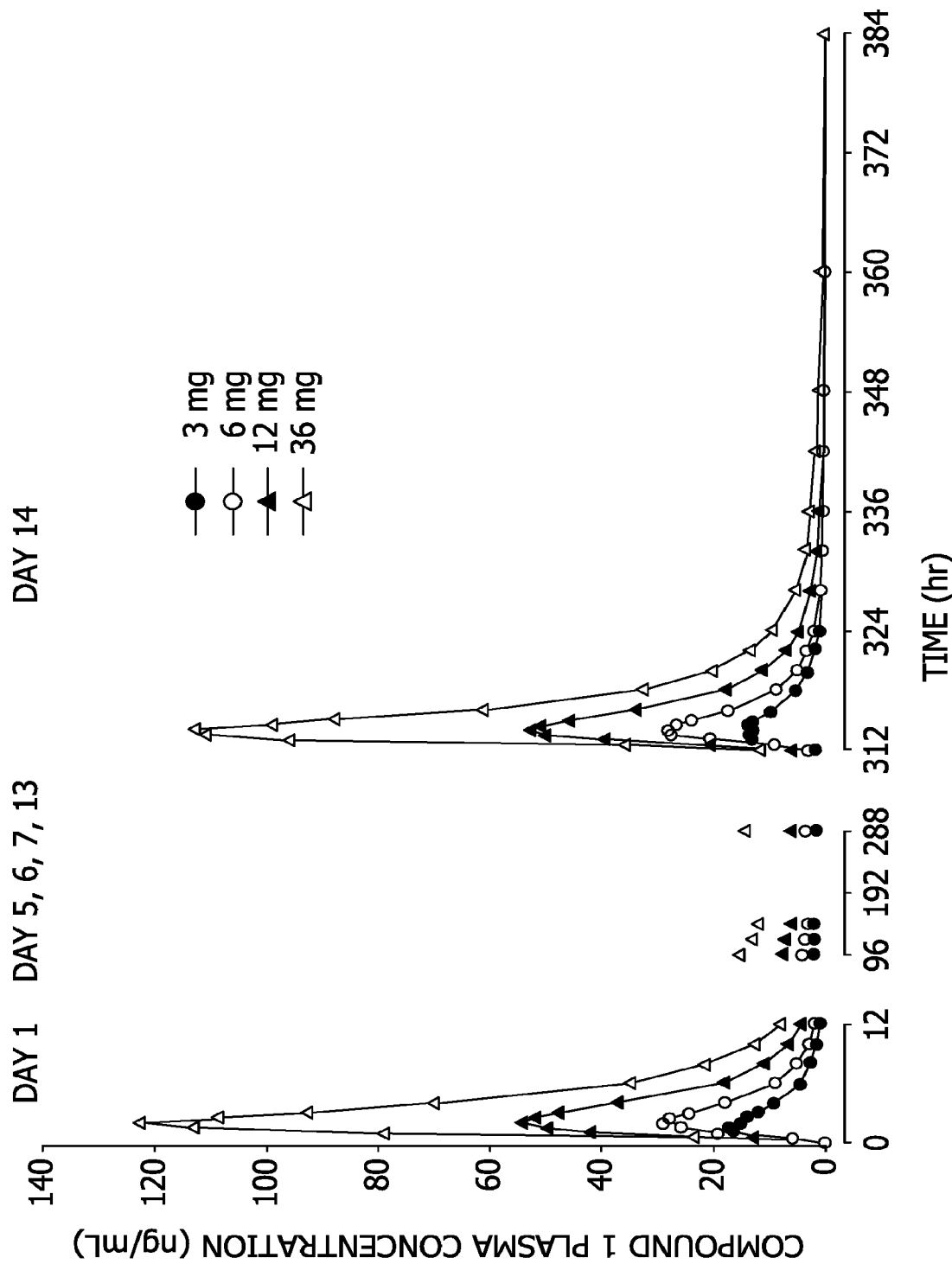
FIG. 33 shows the Compound 1 mean plasma concentration versus time profiles following administration of multiple twice-daily oral doses of Compound 1 immediate release capsules to healthy subjects.

A total of 56 healthy subjects were enrolled in and completed the single-dose evaluation (Study 1) and 44 healthy subjects were enrolled in and completed the multiple-dose evaluation (Study 2—Part 1). Enrollment in the Compound 1 Single- and Multiple-Dose Pharmacokinetics in Healthy Volunteers Compound 1 plasma concentrations reached peak levels at approximately 1 to 2 hours after oral dosing of the immediate release capsule formulation. Compound 1 plasma concentrations declined bi-exponentially afterwards with a terminal elimination $t_{1/2}$ of approximately 6 to 15 hours after single dosing (FIGS. 32A and 32B, Table 54-B) and of 8 to 16 hours after multiple twice-daily dosing (FIG. 33, Table 54-C). Compound 1 functional half-life, estimated from $C_{max}$ to $C_{trough}$ ratio at steady-state, was approximately 3 hours. After multiple dosing, there was a small but statistically significant (p<0.05) difference between Compound 1 pre-dose concentrations on Study Day 13 (13% lower) compared with Study Day 5. There was no statistically significant difference in Compound 1 pre-dose concentration on Study Day 13 and Study Day 14, indicating that steady-state was achieved by Study Day 13. At steady-state, the median accumulation ratios for Compound 1 $AUC_{0-12}$ were approximately 1.0 over the evaluated dose range (Table 54-C).

The relationships of dose-normalized $C_{max}$ and AUC values versus dose following single and multiple dosing are presented in FIGS. 34A-34D. In the single dose evaluation, 1 mg dose group was excluded from the statistical analyses for $AUC_\infty$ as the majority of samples collected at the terminal phase were below the limit of quantitation for all subjects. There was no statistically significant difference in dose-normalized $C_{max}$ between the highest (48 mg) and the lowest (1 mg) dose of Compound 1, and there was no statistically significant trend for change in the dose-normalized $C_{max}$ values with dose. There was no trend for change in Compound 1 dose-normalized $AUC_\infty$ with doses over the 3 to 36 mg dose range (P>0.05); however the dose-normalized $AUC_\infty$ following single 48 mg dose was 40% lower than that following 3 mg dose (p<0.05).

Following multiple dosing in healthy subjects, there was no statistically significant difference (p>0.05) in Compound 1 dose-normalized steady-state $C_{max}$, $C_{trough}$, or AUC for the 24 mg twice-daily regimen compared to the 3, 6, or 12 mg twice-daily regimens.

Overall, Compound 1 exposures appeared to be dose proportional particularly over the single dose range of 3 to 36 mg and the multiple dose range of 3 mg to 24 mg BID.

TABLE 54-B

Pharmacokinetic parameters (mean ± standard deviation) of Compound 1 after administration of single doses of the immediate release formulation to healthy subjects

| Pharmacokinetic Parameters (Units) | 1 mg Cpd. 1 (N = 6) | 3 mg Cpd. 1 (N = 6) | 6 mg Cpd. 1 (N = 6) | 12 mg Cpd. 1 (N = 6) | 24 mg Cpd. 1 (N = 6) | 36 mg Cpd. 1 (N = 6) | 48 mg Cpd. 1 (N = 6) |
|---|---|---|---|---|---|---|---|
| $C_{max}$ (ng/mL) | 7.72 ± 2.36 | 25.0 ± 6.88 | 38.9 ± 9.96 | 82.9 ± 12.1 | 158 ± 18.4 | 277 ± 44.5 | 314 ± 81.9 |
| $T_{max}$ (h) [a] | 1.3 (1.0-2.0) | 1.0 (1.0-1.5) | 1.0 (1.0-1.5) | 1.3 (0.5-1.5) | 1.3 (1.0-1.5) | 0.8 (0.5-1.0) | 1.0 (0.5-1.0) |
| $t_{1/2}$ (h) [b] | — | 5.9 ± 2.4 | 11.0 ± 3.4 | 12.1 ± 7.4 | 14.5 ± 9.0 | 6.4 ± 4.0 | 12.2 ± 3.5 |
| $AUC_t$ (ng · h/mL) | 29.8 ± 5.78 | 102 ± 27.5 | 159 ± 37.5 | 329 ± 48.9 | 612 ± 78.6 | 909 ± 201 | 1030 ± 174 |
| $AUC_\infty$ (ng · h/mL) | — | 103 ± 27.6 | 160 ± 37.6 | 331 ± 49.8 | 615 ± 78.1 | 911 ± 202 | 1040 ± 174 |
| CL/F(L/h) | — | 31.3 ± 10.4 | 39.1 ± 9.06 | 37.0 ± 6.32 | 39.5 ± 4.92 | 41.1 ± 8.35 | 47.6 ± 8.97 |

[a] Median (range)
[b] Terminal elimination half-life, presented as harmonic mean ± pseudo-standard deviation

TABLE 54-C

Steady-State (Day 14) Pharmacokinetic parameters (mean ± standard deviation) of Compound 1 following administration of multiple twice-daily oral doses of the immediate release formulation to healthy subjects

| PK Parameters (Units) | 3 mg BID (N = 8) | 6 mg BID (N = 8) | 12 mg BID (N = 8) | 24 mg BID (N = 8) |
|---|---|---|---|---|
| $C_{max}$ (ng/mL) | 18.5 ± 5.41 | 28.8 ± 3.67 | 57.6 ± 11.0 | 119 ± 16.9 |
| $T_{max}$ (h) | 1.5 (0.5-3.0) | 2.0 (1.5-3.0) | 2.3 (1.5-3.0) | 1.8 (1.5-2.0) |
| $AUC_{0-12}$ (ng · h/mL) | 78.3 ± 20.3 | 138 ± 16.7 | 271 ± 52.7 | 529 ± 62.6 |
| $C_{trough}$ (ng/mL) | 1.46 ± 0.50 | 2.29 ± 0.41 | 4.54 ± 1.55 | 9.50 ± 2.57 |
| $t_{1/2}$ (h) [a] | 15.7 ± 10.6 | 13.6 ± 8.5 | 7.6 ± 4.8 | 8.0 ± 4.2 |
| $t_{1/2}F$ (h) [b] | 3.2 ± 0.4 | 3.3 ± 0.3 | 3.2 ± 0.5 | 3.3 ± 0.4 |
| CL/F (L/h) | 40.7 ± 10.6 | 43.9 ± 5.4 | 45.5 ± 8.04 | 46.1 ± 6.44 |
| $CL_r$ (L/h) | 7.5 ± 2.34 | 8.1 ± 1.8 | 9.7 ± 2.3 | 8.6 ± 2.8 |
| $f_e$ (%) | 19 ± 5 | 19 ± 6 | 21 ± 4 | 19 ± 6 |
| $R_{ac}$ $AUC_{0-12}$ [c] | 1.1 (0.9-1.2) | 1.0 (0.9-1.2) | 1.0 (0.9-1.1) | 1.0 (0.8-1.3) |

[a] Terminal elimination half-life.
[b] Functional half-life calculated from $C_{max}$ to $C_{trough}$ ratio at steady state.
[c] Accumulation ratio for $AUC_{0-12}$.
Harmonic mean ± pseudo-standard deviation are presented for $t_{1/2}$ and $t_{1/2}F$. Median and range (minimum to maximum) are presented for $T_{max}$ and $R_{ac}$ $AUC_{0-12}$. BID: twice-daily.

Compound 1 Multiple-Dose Pharmacokinetics in Subjects with RA

Figure 35A:
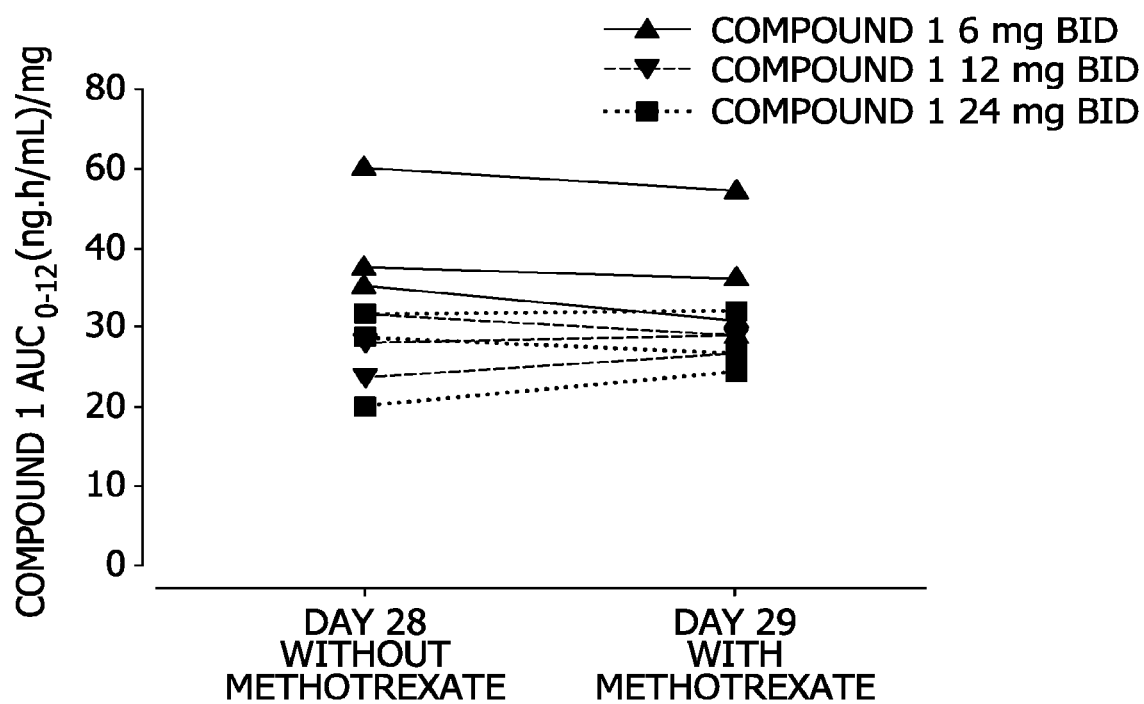
FIGS. 35A and 35B show the lack of effect of concomitant methotrexate administration on Compound 1 dose-normalized AUC (FIG. 35A) and lack of effect of concomitant Compound 1 administration on methotrexate dose-normalized AUC (FIG. 35B).

In subjects with RA who were on stable doses of methotrexate, Compound 1 plasma concentrations reached peak levels at 1 to 2 hours after dosing (Table 54-D). The mean terminal elimination half-life of Compound 1 ranged from approximately 10 to 14 hours, and the functional half-life was approximately 4 hours. The median accumulation ratio of Compound 1 after 26 days of twice-daily dosing ranged from 0.8 to 1.4. The median ratio of Compound 1 $C_{max}$ and $AUC_{0-12}$ when administered with methotrexate (on Study Day 29) to those when administered without methotrexate (Study Day 28) ranged from 0.9 to 1.2, indicating a lack of significant effect of methotrexate co-administration on Compound 1 pharmacokinetics (FIG. 35A). The steady-state dose-normalized $C_{max}$ and $AUC_{0-12}$ of Compound 1 in subjects with RA compared to healthy subjects are presented in FIGS. 34B and 34D. The ratio of Compound 1 exposure in subjects with rheumatoid arthritis to Compound 1 exposure in healthy subjects ranged from 1.1 (24 mg twice-daily dose) to 1.6 (6 mg twice-daily dose) for $AUC_{0-12}$ and from 1.2 (24 mg twice-daily dose) to 1.7 (6 mg twice-daily dose) for $C_{max}$.

TABLE 54-D

Pharmacokinetic parameters (mean ± standard deviation) of Compound 1 following administration of multiple twice-daily oral doses to subjects with mild to moderate rheumatoid arthritis on stable doses of methotrexate

| PK Parameters (Units) | Compound 1 6 mg BID (N = 4) Study Day | | Compound 1 12 mg BID (N = 3) Study Day | | Compound 1 24 mg BID (N = 3) Study Day | |
|---|---|---|---|---|---|---|
| | Day 28 | Day 29 | Day 28 | Day 29 | Day 28 | Day 29 |
| $C_{max}$ (ng/mL) | 47.1 ± 7.47 | 42.4 ± 8.85 | 71.1 ± 14.8 | 60.8 ± 4.01 | 129 ± 39.0 | 154 ± 39.5 |
| $T_{max}$ (h) | 1.5 (1.0-2.0) | 2.0 (1.5-3.0) | 2.0 (1.5-2.0) | 2.0 (1.5-3.0) | 1.5 (1.5-4.0) | 1.0 (0.5-1.5) |
| $AUC_{0-12}$ (ng · h/mL) | 231 ± 48.5 | 215 ± 49.2 | 334 ± 49.4 | 338 ± 14.5 | 637 ± 143 | 665 ± 89.8 |
| $C_{trough}$ (ng/mL) | 5.81 ± 3.06 | 4.63 ± 3.48 | 5.41 ± 0.98 | 6.44 ± 1.09 | 15.3 ± 1.86 | 14.9 ± 4.37 |
| $t_{1/2}$ (h) [a] | — | 9.5 ± 3.6 | — | 14.4 ± 5.3 | — | 11.5 ± 7.6 |
| $t_{1/2}F$ (h) [b] | — | 3.5 ± 0.9 | — | 3.7 ± 0.2 | — | 3.6 ± 0.1 |
| CL/F (L/h) | 26.7 ± 4.96 | 29.0 ± 5.92 | 36.4 ± 5.44 | 35.6 ± 1.56 | 39.1 ± 9.79 | 36.5 ± 4.70 |
| $CL_r$ (L/h) | 6.94 ± 4.04 | 4.93 ± 2.41 | 6.27 ± 2.79 | 4.96 ± 3.34 | 6.31 ± 0.96 | 8.60 ± 1.30 |
| $f_e$ (%) | 25 ± 14 | 16 ± 5 | 17 ± 8 | 14 ± 10 | 17 ± 5 | 24 ± 2 |

TABLE 54-D-continued

Pharmacokinetic parameters (mean ± standard deviation) of Compound 1 following administration of multiple twice-daily oral doses to subjects with mild to moderate rheumatoid arthritis on stable doses of methotrexate

| PK Parameters (Units) | Compound 1 6 mg BID (N = 4) | | Compound 1 12 mg BID (N = 3) Study Day | | Compound 1 24 mg BID (N = 3) | |
|---|---|---|---|---|---|---|
| | Day 28 | Day 29 | Day 28 | Day 29 | Day 28 | Day 29 |
| Rac $AUC_{0-12}{}^d$ | 14 (1.0-1.8) | — | 1.2 (0.9-1.4) | — | 1.3 (1.2-1.4) | — |
| Day 29/Day 28 $AUC_{0-12}$ Ratio$^e$ | | 0.9 (0.9-1.0) | | 1.0 (0.9-11) | | 1.0 (0.9-1.2) |

Figure 35B:
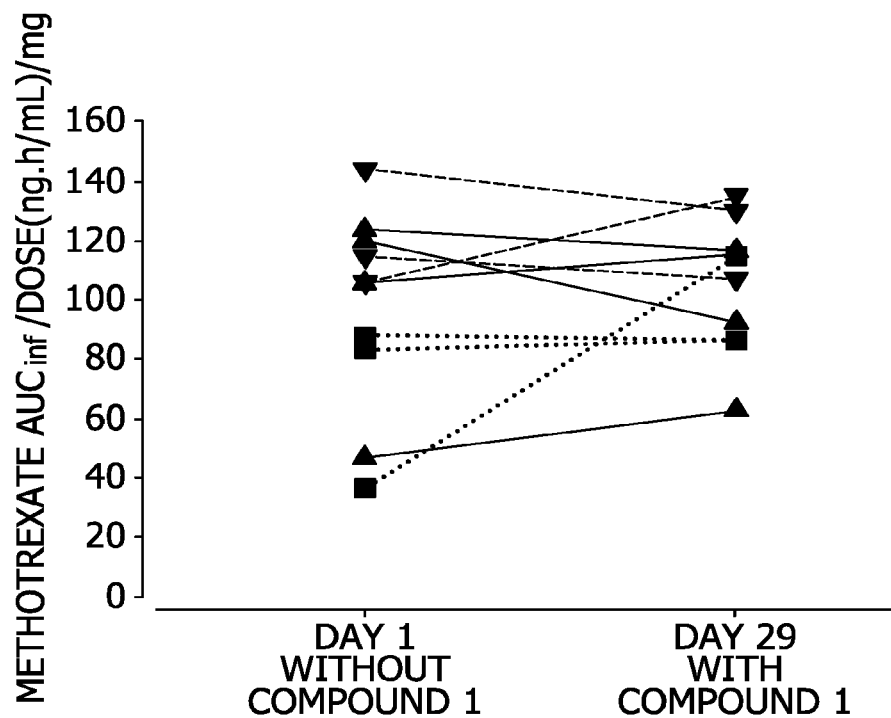

$^a$Terminal elimination half-life.
$^b$Functional half-life calculated from Cmax to Ctrough ratio at steady state.
$^c$Accumulation ratio for $AUC_{0-12}$.
Harmonic mean ± pseudo-standard deviation are presented for $t_{1/2}$ and $t_{1/2}F$.
Median and range (minimum to maximum) are presented for $T_{max}$, accumulation ratios, and Day 29/Day 28 ratios.
BID: twice-daily Effect of Compound 1 Co-Administration on Methotrexate Exposure Pharmacokinetic parameters of methotrexate when administered before (Study Day 1) and after administration of multiple doses of Compound 1 (Day 29) are summarized in Table 54-E. Since methotrexate was administered weekly and has a short plasma half-life, no plasma accumulation was expected with repeated dosing and $AUC_\infty$ was calculated for both Days 1 and 29. The median ratio for methotrexate $AUC_\infty$ and $C_{max}$ when administered after multiple doses of Compound 1 (on Study Day 29) to that when administered without Compound 1 (on Study Day 1) ranged from 0.9 to 1.1 and from 0.8 to 1.2, respectively. There was no observed change in methotrexate dose-normalized $AUC_\infty$ when administered with or without Compound 1 (FIG. 35B).

placebo. There were no dose-limiting toxicities or safety concerns with Compound 1 from the single doses up to 48 mg or multiple doses up to 24 mg twice daily. Notably, the safety and tolerability profile of Compound 1 was comparable between subjects who received Compound 1 or placebo, and between healthy subjects and subjects with RA on background treatment of methotrexate, though the number of subjects with RA was limited. There was no evidence of a dose or time dependency for the incidence of adverse events in either healthy subjects or subjects with RA. There were no study discontinuations due to adverse events, no serious adverse events and no clinically significant changes in ECG parameters, or laboratory metrics in any of the subjects or treatment groups. The maximum tolerated dose

TABLE 54-E

Pharmacokinetic parameters (mean ± standard deviation) of methotrexate following administration to subjects with RA alone (Day 1) or concomitant with Compound 1 (Day 29)

| PK Parameters (Units) | Compound 1 6 mg BID Group (N = 4) | | Compound 1 12 mg BID Group (N = 3) | | Compound 1 24 mg BID Group (N = 3) | | Placebo (N = 4) | |
|---|---|---|---|---|---|---|---|---|
| | Methotrexate Dose (mg) | | | | | | | |
| | 16.3 ± 6.6 | | 14.2 ± 5.2 | | 14.2 ± 1.4 | | 17.5 ± 5.0 | |
| | Day 1 | Day 29 | Day 1 | Day 29 | Day 1 | Day 29 | Day 1 | Day 29 |
| $C_{max}$ (ng/mL) | 245 ± 63.6 | 228 ± 23.0 | 278 ± 44.0 | 255 ± 99.9 | 196 ± 58.6 | 256 ± 29.3 | 318 ± 138 | 354 ± 182 |
| $T_{max}$ (h) | 2.5 (1.5-6.0) | 1.8 (1.0-2.0) | 3.0 (2.0-3.0) | 2.5 (2.5-3.0) | 3.0 (0-3.0) | 2.5 (2.0-3.0) | 1.8 (1.5-3.0) | 1.8 (1.0-4.0) |
| $AUC_\infty$ (ng·h/mL) | 1470 ± 494 | 1490 ± 424 | 1670 ± 393 | 1780 ± 791 | 966 ± 365 | 1370 ± 324 | 1640 ± 470 | 1590 ± 458 |
| $t_{1/2}$ (h)$^a$ | 4.0 ± 2.6 | 4.7 ± 1.3 | 4.0 ± 0.3 | 4.2 ± 0.6 | 3.0 ± 1.1 | 3.1 ± 1.3 | 3.9 ± 0.5 | 3.8 ± 0.3 |
| CL/F (L/h) | 11.8 ± 6.43 | 10.9 ± 3.43 | 8.36 ± 1.28 | 8.14 ± 1.03 | 16.9 ± 8.89 | 10.6 ± 1.61 | 11.2 ± 3.81 | 11.3 ± 2.66 |
| $CL_r$ (L/h) | 6.63 ± 3.79 | 5.43 ± 2.02 | 6.13 ± 1.93 | 4.78 ± 2.28 | 7.46 ± 0.70 | 6.43 ± 0.75 | 4.32 ± 1.12 | 5.80 ± 1.08 |
| $f_e$ (%) | 58 ± 29 | 51 ± 20 | 74 ± 19 | 59 ± 26 | 54 ± 25 | 63 ± 4 | 45 ± 25 | 57 ± 26 |
| $AUC_\infty$ Ratio$^b$ | — | 1.0 (0.8-1.4) | — | 0.9 (0.9-1.3) | — | 1.1 (1.0-3.1) | — | 0.9 (0.8-1.2) |

$^a$Terminal elimination half-life presented as harmonic mean ± pseudo-standard deviation.
$^b$Ratio of methotrexate exposure ($AUC_\infty$) on Study Day 29 to that on Study Day 1; median and range (minimum to maximum) are presented.

Safety and Tolerability

Across all three evaluations, a total of 74 healthy subjects and 11 subjects with RA received Compound 1 and a total of 26 healthy subjects and 3 subjects with RA received of Compound 1 was not reached in the single or multiple dose studies. Adverse events that were reported by at least two subjects in Compound 1 or placebo groups in Study 1 or Study 2—Part 1 are presented in Table 54-F.

TABLE 54-F

Treatment-emergent adverse events reported by two or more healthy subjects administered Compound 1 or placebo in the single and multiple ascending dose evaluations

| | Single doses (Study 1) | | | | | | | | |
|---|---|---|---|---|---|---|---|---|---|
| System Organ Class MedDRA Preferred Term | Placebo (N = 14) | 1 mg Compound 1 (N = 6) | 3 mg Compound 1 (N = 6) | 6 mg Compound 1 (N = 6) | 12 mg Compound 1 (N = 6) | 24 mg Compound 1 (N = 6) | 36 mg Compound 1 (N = 6) | 48 ng Compound 1 (N = 6) | Total Compound 1 (N = 42) |
| Any Adverse Event | 3 (21.4%) | 0 | 0 | 1 (16.7%) | 0 | 1 (16.7%) | 2 (33.3%) | 2 (33.3%) | 6 (14.3%) |
| Nervous System Disorders | | | | | | | | 0 | |
| Headache | 0 | 0 | 0 | 0 | 0 | 0 | 0 | 2 (33.3%) | 2 (4.8%) |
| Presyncope* | 0 | 0 | 0 | 1 (16.7%) | 0 | 1 (16.7%) | 0 | 0 | 2 (4.8%) |

| | Multiple twice-daily doses (Study 2 - Part 1) | | | | | |
|---|---|---|---|---|---|---|
| System Organ Class MedDRA Preferred Term | Placebo (N = 12) | 3 mg Compound 1 (N = 8) | 6 mg Compound 1 (N = 8) | 12 mg Compound 1 (N = 8) | 24 mg Compound 1 (N = 8) | Total Compound 1 (n = 32) |
| Any Adverse Event | 7 (58.3%) | 2 (25.0%) | 2 (25.0%) | 3 (37.5%) | 4 (50.0%) | 11 (34.4%) |
| Gastrointestinal Disorders | | | | | | |
| Abdominal Discomfort | 3 (25.0%) | 0 | 0 | 0 | 0 | 0 |
| Abdominal Pain | 0 | 0 | 1 (12.5%) | 0 | 1 (12.5%) | 2 (6.3%) |
| Diarrhoea | 1 (8.3%) | 0 | 1 (12.5%) | 1 (12.5%) | 0 | 2 (6.3%) |
| Infections and Infestations | | | | | | |
| Nasopharyngitis | 2 (16.7%) | 1 (12.5%) | 1 (12.5%) | 0 | 0 | 2 (6.3%) |
| Nervous System Disorders | | | | | | |
| Headache | 2 (16.7%) | 0 | 2 (25.0%) | 2 (25.0%) | 1 (12.5%) | 5 (15.6%) |

*The two cases of presyncope were associated with venipuncture.

In healthy subjects who were administered single doses of either Compound 1 (1, 3, 6, 12, 24, 36, and 48 mg) or placebo in Study 1, 14.3% (6/42) and 21.4% (3/14) of subjects, respectively, reported to have one or more treatment-emergent adverse events (TEAEs). All TEAEs were assessed as mild in severity. The adverse events reported by more than one subject who received Compound 1 were headache and presyncope (1 subject in 6 mg and 1 subject in 24 mg dose group) in association with venipuncture (see Table 54-F).

In healthy subjects who were administered multiple doses of Compound 1 (3, 6, 12, and 24 mg BID) or placebo for 14 consecutive days in Study 2—Part 1, 34% (11/32) and 58% (7/12) of subjects, respectively, reported one or more TEAEs. The overall incidences of TEAEs were numerically higher at higher doses of Compound 1; 2 (25.0%), 2 (25.0%), 3(37.5%) and 4 (50%) subjects in the 3 mg, 6 mg, 12 mg and 24 mg dose groups, respectively; however, these rates were lower than that was observed in the placebo group (58%). All TEAEs were reported as mild in severity. Four events occurred in at least two subjects who received Compound 1: headache, abdominal pain, diarrhea, and nasopharyngitis; three of these events also occurred in subjects who received placebo: headache, diarrhea and nasopharyngitis (Table 54-F).

There were no clinically significant changes in any hematologic parameters after multiple-dose administration in healthy subjects for 14 days. With increasing doses of Compound 1, there were statistically significant downward trends in mean levels of hemoglobin, RBCs, WBCs and neutrophils; however, even at the 24 mg dose, the mean levels were within the normal reference range. The mean changes in reticulocyte counts with increasing dose of Compound 1 compared to placebo were not statistically significant, suggesting no evidence of a dose related effect on reticulocyte counts after 14 days of Compound 1 treatment. Total cholesterol, HDL-cholesterol, and LDL-cholesterol showed a statistically significant upward trend with increasing Compound 1 dose compared with placebo; however, the final mean values for these lipid parameters in the Compound 1 dose groups remained within the normal reference range.

Subjects with mild to moderate RA on stable background doses of methotrexate, in Study 2—Part 2, were administered multiple doses of Compound 1 (a total of 11 subjects) or placebo (a total of 3 subjects). Five subjects in the Compound 1 dose groups and two subjects in the placebo group experienced at least one TEAE. In the Compound 1 dose groups, 7 TEAEs were reported: nausea, vomiting, viral gastroenteritis, upper respiratory tract infection, post-traumatic neck syndrome, back pain, and insomnia. All TEAEs were reported by the investigators as mild or moderate in severity, and no adverse event was reported in more than one subject in any treatment group. There was no evidence of a dose relationship with any of these events. Notably, as these subjects with RA received a stable background dose of methotrexate, there were no changes in hepatobiliary metrics for those receiving Compound 1. There was also no evidence of a Compound 1 dose-related effect on renal function in these subjects with RA, as evaluated by serum creatinine and blood urea nitrogen values.

Discussion

Compound 1 was well-tolerated after single doses up to 48 mg and multiple twice daily doses up to 24 mg of Compound 1 immediate-release formulation. All adverse events occurred after single- or multiple-dose administrations were mild to moderate in nature with comparable frequency between subjects who received Compound 1 or placebo. No anemia, serious infections, or clinically significant changes in hematology, hepatobiliary or renal laboratory metrics was observed with 14 days of repeated Compound 1 dosing in healthy volunteers or 27 days of dosing in RA patients.

Compound 1 displayed multi-exponential plasma disposition with a functional half-life of 3 to 4 hours across the dose range of 3 to 24 mg twice daily of the immediate-release formulation in healthy volunteers and subjects with RA. The terminal elimination half-life of Compound 1 ranged from 6 to 16 hours across the different dose levels. However, given the multi-exponential disposition of Compound 1, the longer terminal half-life is less relevant clinically than the functional half-life (Dutta et al., Clin. Drug Investig., 2006, Vol. 26(12), pp. 681-690; Sahin, Pharm. Res., 2008, Vol. 25(12), pp. 2869-77). Consistent with a shorter functional half-life, there was no accumulation across the evaluated 3 to 24 mg twice-daily dose range. While there are no solid clinical data to suggest that extended exposure is needed for efficacy of JAK inhibitor (i.e. to determine whether efficacy is concentration driven or AUC driven), the pharmacokinetic profile of the immediate-release formulation of Compound 1 appears to be generally more suited for twice-daily dosing than for once-daily dosing.

Compound 1 displayed dose-proportional pharmacokinetics particularly over the 3 to 36 mg dose range (FIG. 34), which encompasses the dose ranges evaluated in Phase 2b clinical trials in RA (3 to 18 mg BID and 24 mg QD), or that is currently being evaluated in Crohn's disease (3 to 24 mg BID).

It has been reported previously that the JAK inhibitors tofacitinib and filgotinib have higher exposures in subjects with RA than those in healthy volunteers (see FDA, "Clinical Pharmacology and Biopharmaceutics Review(s)—Tofacitinib", Application Number 203214Orig1s000, Center for Drug Evaluation and Research, 2011; Namour et al., Clin. Pharmacokinet., 2015, Vol. 54, pp. 859-874). Compound 1's apparent oral clearance was 23% lower in subjects with RA (leading to approximately 30% higher exposure), on average across all dose groups, compared to healthy subjects. In general, older subjects are expected to have lower renal and metabolic capacity compared to younger subjects (Mangoni, Br. J Clin. Pharmacol., 2004, Vol. 57(1), pp. 6-14). RA subjects who received multiple-doses of Compound 1 were 26 years older, on average, than the healthy subjects evaluated in Study 2 (Table 54-A); therefore, age cannot be excluded as potential contributor to the apparently 30% higher exposure of Compound 1 in RA subjects than in healthy subjects.

Methotrexate remains the first line therapy for treatment of RA and is often used with biologic DMARDs or in combination with other csDMARDs (see Ma, et al., Rheumatology (Oxford), 2010, Vol. 49(1), pp. 91-8; Singh, et al., Arthritis Care Res. (Hoboken), 2012, Vol. 64(5), pp. 625-39; Smolen, et al., Ann. Rheum. Dis., 2014, Vol. 73(3), pp. 492-509). Therefore, at least in a subset of the RA patients, it is expected that Compound 1 will be added to the first line therapy, methotrexate; thus, it was important to confirm a lack of any potential interaction between Compound 1 and methotrexate. The ratios of Compound 1 AUC and $C_{max}$ values when administered with methotrexate to those when administered alone indicate lack of significant effect of methotrexate on Compound 1 (Table 54-D; FIG. 35A). Similarly, Compound 1 did not have any significant effect on methotrexate exposures (Table 54-E; FIG. 35B). This was consistent with the observed safety and tolerability profiles in these two populations.

In summary, Compound 1 displayed favorable safety and tolerability profiles over single doses up to 48 mg and multiple doses up to 24 mg twice daily for 14 days in healthy subjects and for 27 days in subjects with RA. Compound 1 demonstrated a pharmacokinetic profile suitable for twice-daily dosing with the immediate release formulation. There was no pharmacokinetic interaction between methotrexate and Compound 1 and there was no accumulation of Compound 1 with repeated administration.

Example 55

Treatment of Moderately to Severely Active Rheumatoid Arthritis in Patients Who have Inadequately Responded to or are Intolerant to Anti-TNF Therapy The following example briefly describes the results of a Phase 2b, 12-week, randomized, double-blind, parallel-group, placebo-controlled study in which adult subjects with moderately to severely active rheumatoid arthritis (RA) who have inadequately responded to or who are intolerant to an anti-tumor necrosis factor (TNF) therapy were treated with Compound 1.

The study was conducted in accordance with the International Conference on Harmonisation guidelines, applicable regulations, and the principles of the Declaration of Helsinki. The study protocol was approved by an independent ethics committee or institutional review board. All patients provided written informed consent before participating in any study-related procedures.

Participants

Adult men and women aged 18 years or older, who had been diagnosed with RA and fulfilled either the 1987 revised American College of Rheumatology (ACR) classification criteria (Arnett et al, Arthritis Rheum., 1988, Vol. 31(3), pp. 315-324) or the 2010 ACR/European League Against Rheumatism (EULAR) criteria (Smolen et al, Ann. Rheum. Dis., 2010, Vol. 69(6), pp. 964-975) were enrolled in the study. Active RA was defined as subjects having ≥6 swollen joints (based on a 66-joint count); ≥6 tender joints (based on a 68-joint count); and high-sensitivity C-reactive protein (hsCRP) >upper limit of normal (ULN=5 mg/L) or sero-positivity for both rheumatoid factor (RF) and anti-cyclic citrullinated peptide (CCP). Eligible subjects must have been treated with ≥1 anti-TNF biologic agent for ≥3 months but continued to experience active RA, or discontinued anti-TNF biologic therapy because of intolerance or toxicity. In addition, subjects with prior exposure to non-anti-TNF biologic therapy were allowed to enroll, as long as they had failed ≥1 anti-TNF biologic. All biologic therapies had to be washed out prior to randomization: ≥4 weeks for etanercept, ≥8 weeks for adalimumab, infliximab, certolizumab, and golimumab, >8 weeks for abatacept, >12 weeks for tocilizumab, and >1 year for rituximab. A stable dose of methotrexate (7.5-25 mg/week) was required throughout the study. Key exclusion criteria were prior exposure to a JAK inhibitor, or a need for any immunosuppressant other than methotrexate. Subjects with serum aspartate transaminase (AST) or alanine transaminase (ALT) >1.5×ULN or absolute neutrophil count (ANC)<1,200/µL or absolute lymphocytes count <750/µL at screening were excluded.

Study Design and Treatment

The study was a phase 2b, 12-week, randomized, double-blind, parallel-group, placebo-controlled study conducted at 123 sites, enrolling patients in the United States (176 patients, 64%) and Puerto Rico (11 patients, 4%); Australia and New Zealand (6 patients, 2%); Western Europe including Belgium, Spain and Great Britain (29 patients, 11%); Eastern Europe including Czech Republic, Hungary, Poland (54 patients, 20%).

Subjects were equally randomized to receive oral immediate-release doses of Compound 1 (immediate release capsules comprising Tartrate Hydrate) at 3 mg BID, 6 mg BID, 12 mg BID or 18 mg BID, or matching placebo BID, for 12 weeks. Randomization was performed centrally, according to a blocked randomization schedule, by investigators enrolling via an interactive voice response system. Subjects, caregivers, investigators, joint assessors, and the study team were blinded to the treatment administered. Placebo and Compound 1 capsules were identical in appearance. Subjects should have been taking an oral supplement of folic acid (or equivalent) from four weeks prior to baseline and throughout the study. Subjects were allowed to continue stable doses of methotrexate and non-steroidal anti-inflammatory drugs (NSAIDS), acetaminophen, or oral corticosteroids (equivalent to prednisone <10 mg).

Assessments

The primary efficacy endpoint was the proportion of subjects achieving an

ACR20 response at Week 12. Secondary endpoints included the proportions of subjects achieving an ACR50/ACR70 response and the proportion of subjects achieving 28-joint count disease activity score based on C-reactive protein (DAS28(CRP))≤3.2, or <2.6, at Week 12. Among the other endpoints were the proportion of subjects achieving low disease activity (LDA) or clinical remission (CR) based on Clinical Disease Activity Index (CDAI) criteria (LDA, CDAI <10; CR, ≤2.8); change in DAS28(CRP), and change in the Health Assessment Questionnaire-Disability Index (HAQ-DI) (Anderson et al, *Arthritis Care Res.* (Hoboken), 2012, Vol. 64(5), pp. 640-647), including the proportion of subjects achieving minimal clinically important difference (MCID) of −0.22 (Strand et al, *Rheumatology* (Oxford), 2006, Vol. 45(12), pp. 1505-1513). A post hoc analysis was performed to determine the proportion of subjects who had a sustained ACR20 response, defined as achievement of the ACR20 criteria at every visit (at Weeks 2, 4, 6, 8 and 12).

Safety was evaluated at each scheduled visit during treatment and for 30 days after the last dose of study drug on the basis of AEs, serious AEs, vital signs, and laboratory tests (hematology, blood chemistry, and urinalysis). Adverse events were coded according to the Medical Dictionary for Regulatory Activities (MedDRA, version 17.1). Descriptions of AE severity and post-baseline laboratory changes were based on the Rheumatology Common Toxicity Criteria v.2.0, developed by the OMERACT Drug Safety Working Group (Woodworth et al., 2007, *J. Rheumatol.*, Vol. 34(6), ppl. 1401-14).

Statistical Methods

All efficacy analyses were conducted in modified intent-to-treat population, which consisted of all randomized patients who received >1 dose of study drug. For ACR response rates, the last observation carried forward (LOCF) was the primary missing data imputation method and non-responder imputation (NRI) was also used to assess the robustness of the results. For continuous endpoints including DAS28 (CRP), LOCF missing data imputation was implemented; NRI is reported for binary endpoints. Binary endpoints including ACR response rates were analyzed using chi-square test with normal approximation when comparing each Compound 1 treatment group to placebo group. Continuous endpoints were analyzed using an Analysis of Covariance (ANCOVA) model with treatment group as a factor and baseline measurement as the covariate. The Multiple Comparison Procedure and Modeling (MCPMod) method was implemented to detect any non-flat dose-response relationship by evaluating several non-linear dose-response models at the same time. P-values were not corrected for multiple comparisons.

Assuming ACR20 response rates of 25% in the placebo group and 55% in any Compound 1 group, a sample size of 50 subjects per group (250 patients total) was estimated to provide at least 80% power to detect a 30% difference in response rates between the placebo group and an Compound 1 group when using a 1-sided test with an alpha level of 0.05.

Results

Subject Disposition and Baseline Characteristics

In total, 276 subjects were randomized; all received their intended treatment.

Figure 39:
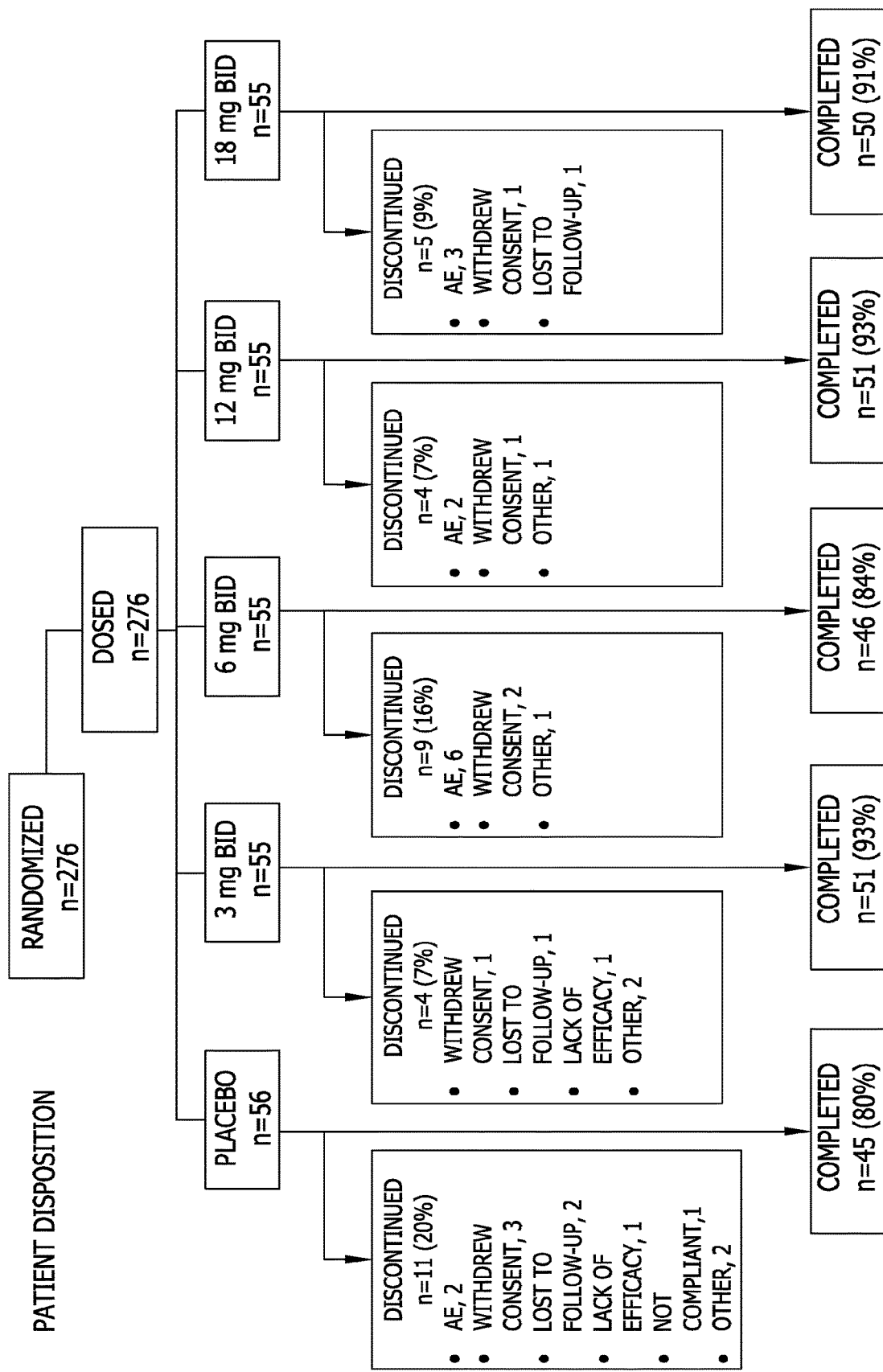
FIG. 39 shows the subject disposition for the study described in Example 55.

The overall study completion rate was 88% (FIG. 39). Baseline subject characteristics and disease activity were generally similar among treatment groups (see Table 55-A). The mean duration since RA diagnosis was 12 years. Seventy-two percent of subjects had prior exposure to only one anti-TNF, 28% to ≥2 anti-TNFs, and 20% of subjects were also exposed to non-anti-TNF biologics. At baseline, subjects had mean swollen and tender joint counts of 18 (out of 66 joints) and 28 (out of 68 joints), respectively; 60% subjects had an elevated hsCRP and mean DAS28(CRP) was 5.8.

TABLE 55-A

Baseline Patient Characteristics and Disease Activity

| | Placebo (n = 56) | Compound 1 | | | |
| --- | --- | --- | --- | --- | --- |
| | | 3 mg BID (n = 55) | 6 mg BID (n = 55) | 12 mg BID (n = 55) | 18 mg BID (n = 55) |
| Characteristic | | | | | |
| Female, number (%) | 48 (86) | 43 (78) | 43 (78) | 44 (80) | 42 (76) |
| Age, years, mean (SD) | 58 (12) | 57 (13) | 56 (12) | 59 (11) | 57 (12) |
| Duration since RA diagnosis, years, mean (SD) | 12.1 (9.0) | 11.8 (9.4) | 12.3 (10.6) | 12.2 (10.2) | 10.9 (7.7) |
| RF positive, number (%) | 49 (88) | 43 (78) | 45 (82) | 45 (82) | 48 (87) |
| Anti-CCP positive, number (%) | 48 (86) | 45 (82) | 45 (82) | 45 (82) | 47 (86) |
| Used ≥1 prior anti-TNF agent, number (%) | 42 (76) | 39 (71) | 38 (70) | 38 (72) | 38 (69) |

TABLE 55-A-continued

Baseline Patient Characteristics and Disease Activity

|  | Placebo (n = 56) | Compound 1 | | | |
|---|---|---|---|---|---|
|  |  | 3 mg BID (n = 55) | 6 mg BID (n = 55) | 12 mg BID (n = 55) | 18 mg BID (n = 55) |
| Used ≥2 prior anti-TNF agents, number (%) | 13 (24) | 16 (29) | 16 (30) | 15 (28) | 17 (31) |
| Used prior non-anti-TNF agents, number (%)* | 9 (16) | 10 (18) | 14 (26) | 14 (26) | 7 (13) |
| Disease activity |  |  |  |  |  |
| TJC68, mean (SD) | 28 (15) | 28 (15) | 30 (16) | 26 (16) | 26 (15) |
| SJC66, mean (SD) | 19 (12) | 17 (10) | 17 (10) | 17 (10) | 18 (10) |
| HAQ-DI, mean (SD) | 1.6 (0.7) | 1.5 (0.7) | 1.6 (0.7) | 1.6 (0.6) | 1.5 (0.6) |
| DAS28(CRP), mean (SD) | 5.8 (0.9) | 5.7 (0.9) | 5.9 (0.9) | 5.7 (0.9) | 5.8 (1.0) |
| CDAI, mean (SD) | 41 (12) | 40 (13) | 42 (12) | 40 (12) | 41 (14) |
| hsCRP, mg/L, mean (SD)‡ | 10.1 (13.2) | 11.4 (11.8) | 18.6 (27.4) | 14.4 (23.0) | 14.0 (15.1) |
| hsCRP > ULN,† n (%)‡ | 28 (50) | 35 (64) | 34 (62) | 33 (60) | 35 (64) |

Figure 36B:
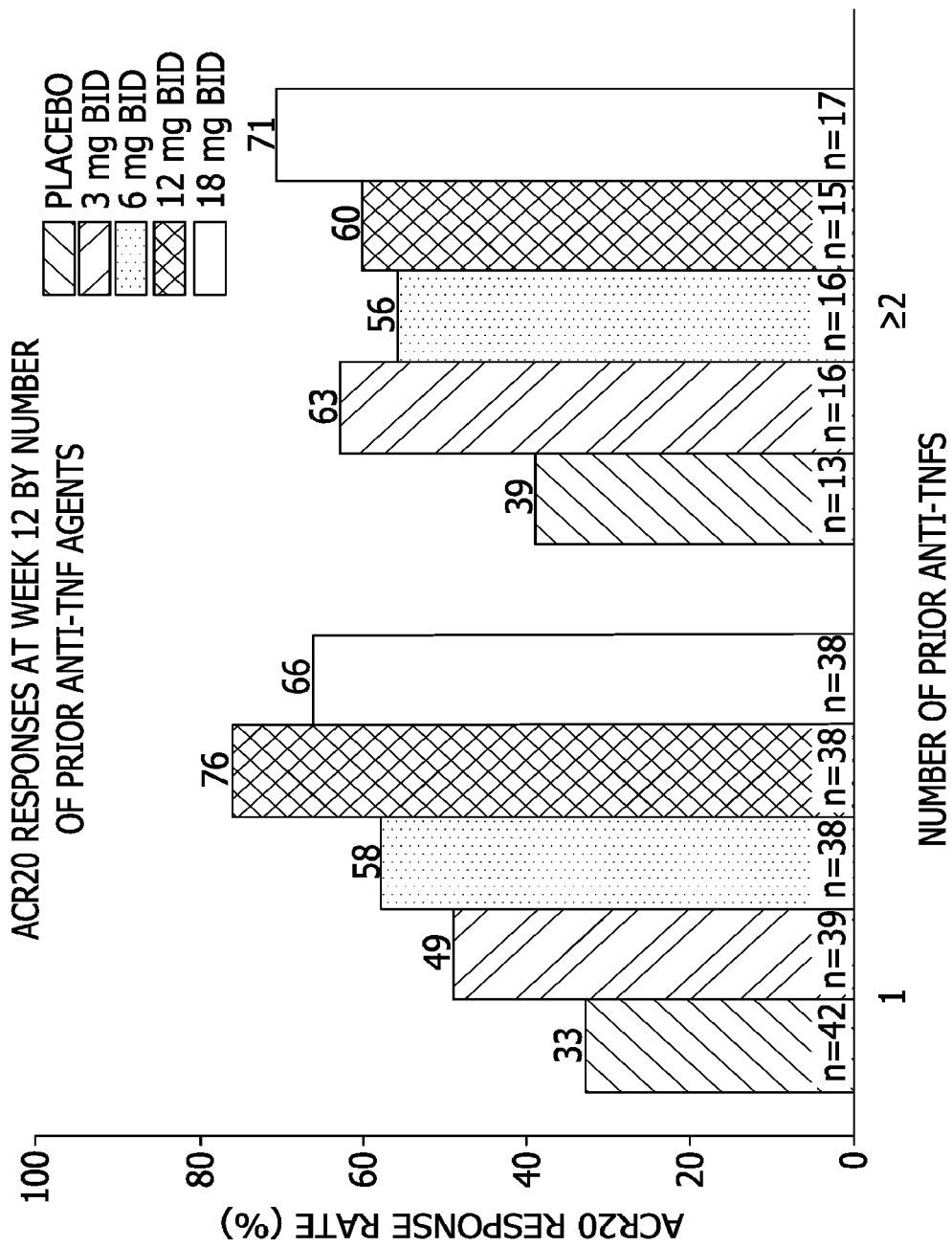
FIG. 36B shows the ACR20 response rate at week 12 in the same population, broken down by number of prior anti-TNF biologic agents.

Abbreviations: BID—twice daily; CDAI—Clinical Disease Activity Index; DAS28(CRP)—Disease Activity Score-28 joints using C-reactive protein; HAQ-DI—Health Assessment Questionnaire-Disability Index; hsCRP—high-sensitivity C-reactive protein; RA—rheumatoid arthritis; SJC66—swollen joint count using 66 joints; TJC68—tender joint count using 68 joints; TNF—tumor necrosis factor; ULN—upper limit of normal.
*Non-TNF biologic agents.
†ULN = 5 mg/L.
‡Subjects with normal hsCRP could be enrolled as long as they were positive for rheumatoid factor and anti-cyclic citrullinated peptide.
Modified intent-to-treat population.
Percentages were calculated using non-missing values Efficacy The primary analysis based on LOCF revealed that an ACR20 response was achieved by 55.6% (P=0.033), 63.5% (P=0.004), 72.7% (P<0.001), and 70.9% (P<0.001) in subjects treated with Compound 1 at 3, 6, 12, and 18 mg BID, respectively, compared with 35.2% in subjects who received placebo. Analysis based on NRI also demonstrated a statistically significant improvement in ACR20 response rate in subjects who received any dose of Compound 1 compared with those who received placebo (FIG. 36A). A significant dose-response relationship was observed for all doses of Compound 1 (P<0.01). The ACR20 response rates (NRI) at Week 12 were similar among patients who had received 1 versus >2 prior anti-TNFs (FIG. 36B). ACR50 and ACR70 response rates were significantly higher at Compound 1 doses of ≥6 mg BID versus placebo (FIG. 36A).

Figure 37A:
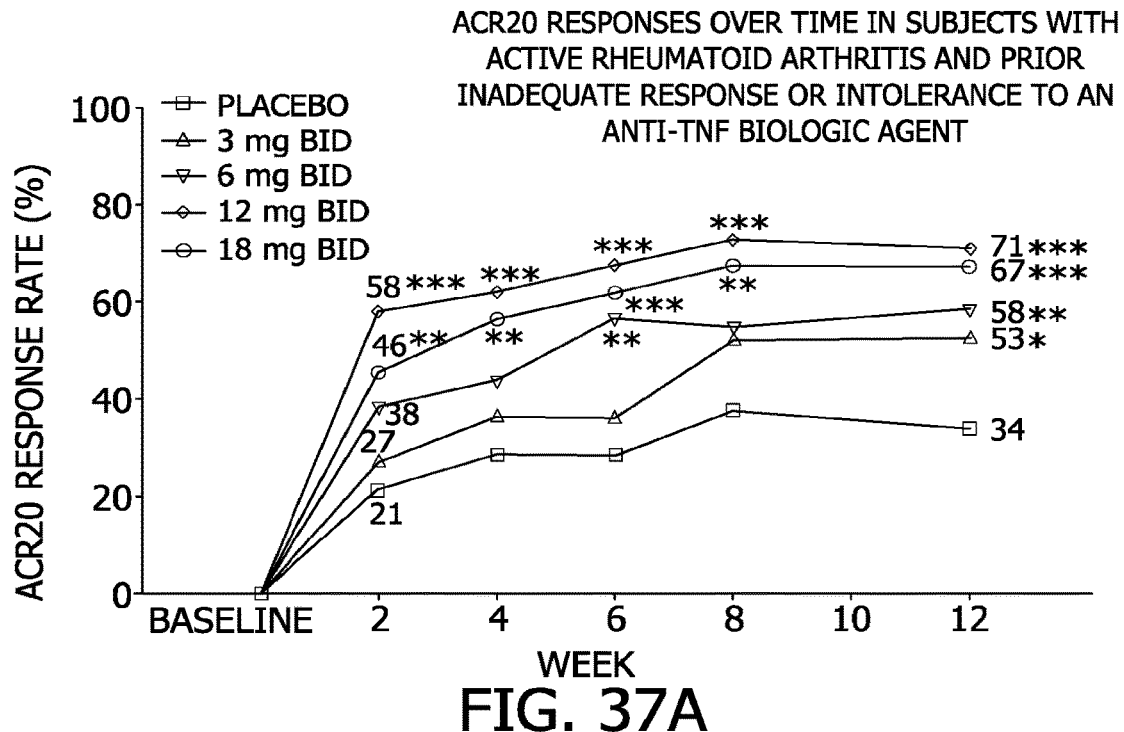
FIGS. 37A-37D show the ACR20 (FIG. 37A), ACR50 (FIG. 37B), and ACR70 (FIG. 37C) responses or DAS28 (CRP) mean change from baseline (FIG. 37D) over time following administration of placebo or various doses of Compound 1 to subjects with active rheumatoid arthritis and prior inadequate response or intolerance to an anti-TNF biologic agent (*P<0.05; P<0.01; *P<0.001 relative to placebo; modified intent-to-treat population (NRI)).
Figure 37B:
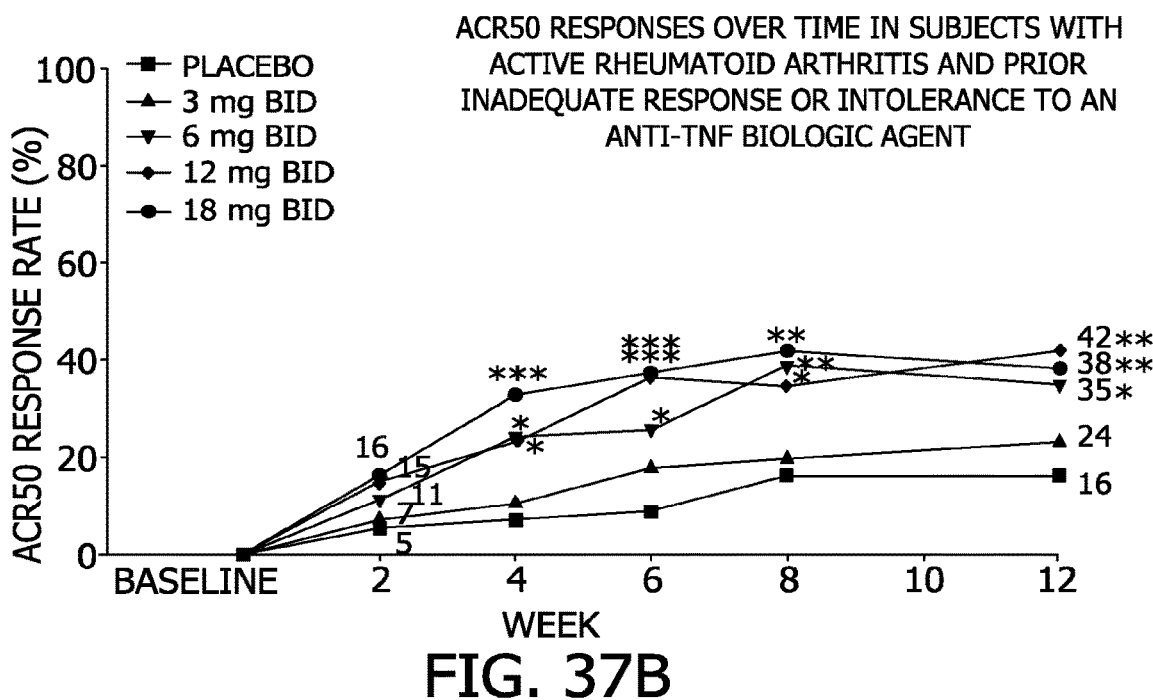
Figure 37C:
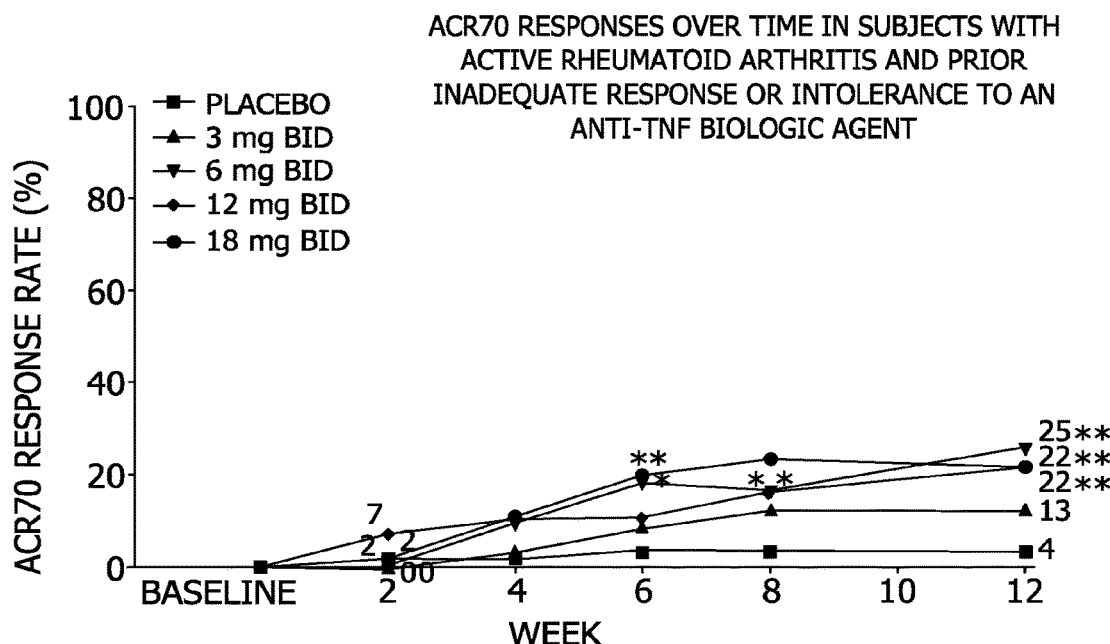
Figure 37D:
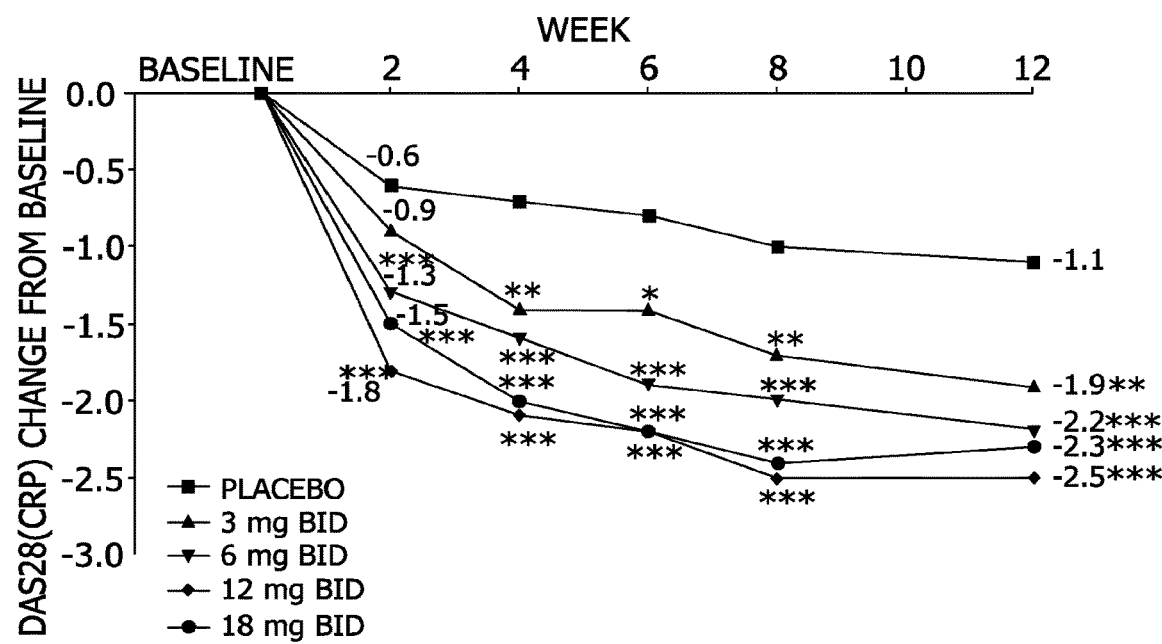

Significant differences in ACR20 response rates (NRI) were observed at the first post-baseline assessment (Week 2) in subjects treated with Compound 1 12 mg BID and 18 mg BID versus placebo (P≤0.007; FIG. 37A); the maximum response rate (71%) was observed with the 12 mg BID dose by Week 8 and plateaued thereafter. Starting at Week 4, there were significantly greater ACR50 response rates with Compound 1 doses ≥6 mg BID versus placebo; the maximum response rate (42%) was observed with the 18 mg BID dose by week 8 and plateaued thereafter (FIG. 37B). Improvements in ACR70 response rates better than placebo were observed starting at Week 6, with peak response of up to 25% at Week 12 (FIG. 37C). A sustained ACR20 response (at every visit between Week 2 through 12, NRI) was achieved by 13%, 22%, 40% and 27% of subjects in the Compound 1 3 mg, 6 mg, 12 mg and 18 mg BID groups respectively, versus 4% in the placebo group. Significant improvements in DAS28(CRP) (LOCF) occurred at the Week 2 assessment with Compound 1 at ≥6 mg BID versus placebo (P<0.001; FIG. 37D).

Figure 37E:
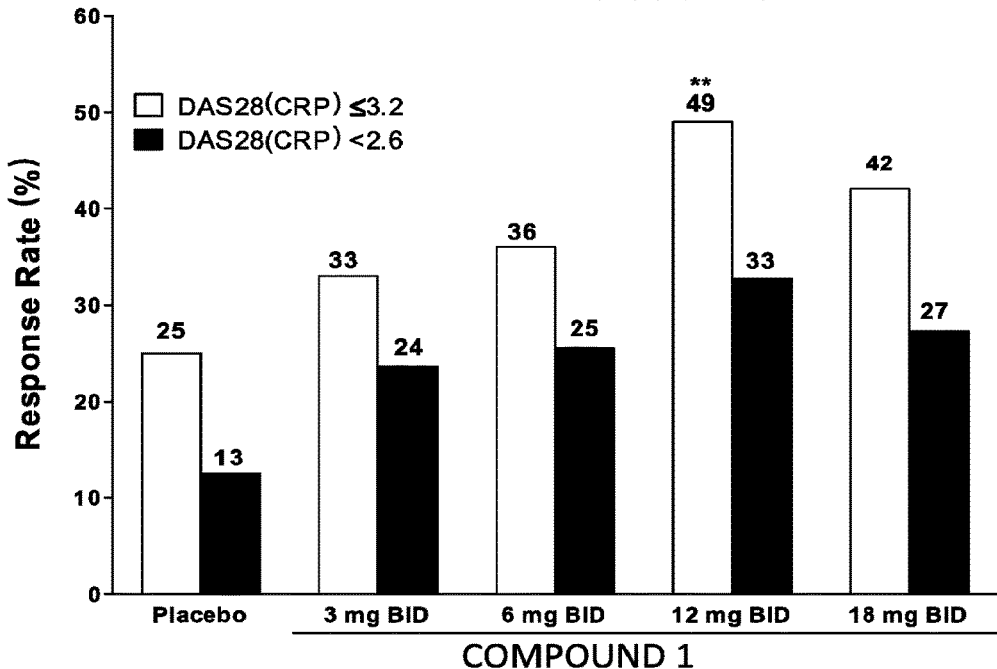
FIG. 37E shows the subjects achieving a DAS28(CRP) score of ≤3.2 or <2.6 at week 12 in the same population.
Figure 37F:
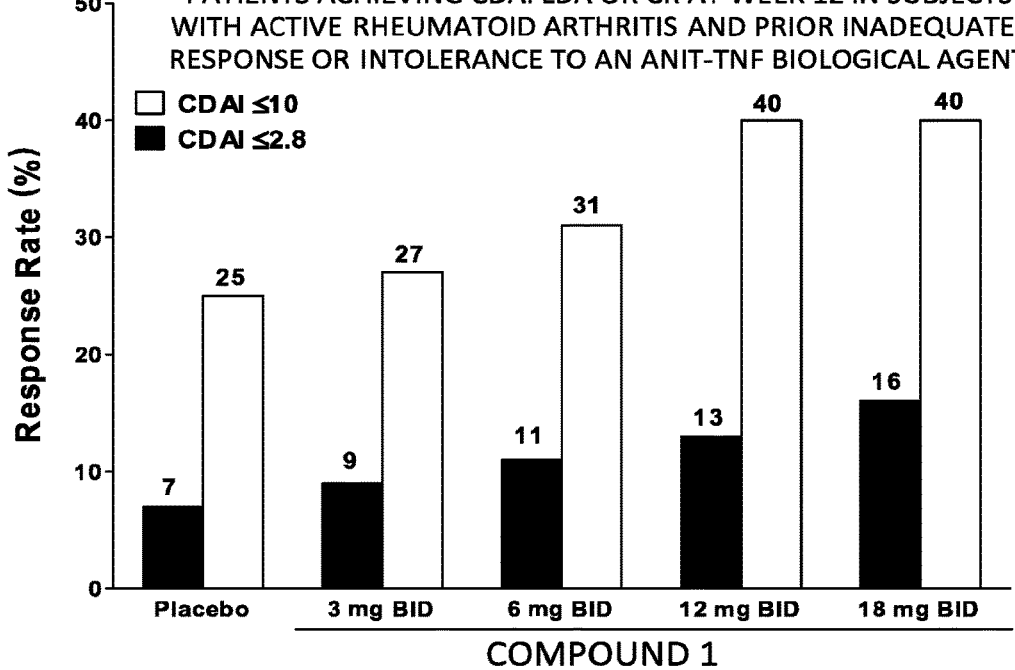
FIG. 37F shows the subjects achieving low disease activity (LDA) or clinical remission (CR) based on clinical disease activity index (CDAI) criteria (LDA is CDAI ≤10; CR is CDAI ≤2.8) at week 12 in the same population.

A higher percentage of subjects receiving Compound 1 (any dose) achieved DAS28(CRP)≤3.2 or <2.6, versus placebo at Week 12 (NRI, FIGS. 37E and 37F with the difference being statistically significantly for the Compound 1 12 mg BID group (DAS28(CRP)≤3.2, 49%; DAS28(CRP) <2.6, 33%, P<0.01) compared with placebo (25% and 13%, respectively). Similarly, a higher percentage of patients treated with any dose of Compound 1 achieved CDAI LDA or CR criteria versus placebo at Week 12 (NRI, FIG. 37F). At Week 12, treatment with Compound 1 at 12 mg BID also resulted in statistically significant mean changes from baseline in individual components of the ACR score compared with placebo (Table 55-B). In addition, a significantly greater proportion of patients achieved the MCID for HAQ-DI with Compound 1 ≥6 mg BID (58%-64%) as compared with placebo (44%).

TABLE 55-B

Mean Changes From Baseline in ACR Components at Week 12

| ACR Component | Placebo (n = 55) | Compound 1 | | | |
|---|---|---|---|---|---|
|  |  | 3 mg BID (n = 54) | 6 mg BID (n = 53) | 12 mg BID (n = 55) | 18 mg BID (n = 55) |
| TJC68 | −9.3 | −13.4 | −15.7** | −16.8** | −15.1* |
|  | (−12.5, −6.1) | (−16.6, −10.1) | (−19.0, −12.5) | (−20.1, −13.6) | (−18.3, −11.9) |
| SJC66 | −6.4 | −9.5 | −9.2 | −10.0* | −9.2 |
|  | (−8.7, −4.2) | (−11.8, −7.2) | (−11.4, −6.9) | (−12.3, −7.8) | (−11.5, −7.0) |

TABLE 55-B-continued

Mean Changes From Baseline in ACR Components at Week 12

| ACR Component | Placebo (n = 55) | Compound 1 | | | |
|---|---|---|---|---|---|
| | | 3 mg BID (n = 54) | 6 mg BID (n = 53) | 12 mg BID (n = 55) | 18 mg BID (n = 55) |
| Patient's assessment of pain | −16.5 (−23.5, −9.5) | −24.7 (−31.8, −17.6) | −31.4**,† (−38.6, −24.2) | −36.3*** (−43.3, −29.3) | −35.0*** (−42.0, −27.9) |
| PhGA | −29.6‡ (−35.3, −23.8) | −33.8 (−39.4, −28.1) | −37.5 (−43.2, −31.7) | −43.5*** (−49.1, −37.9) | −42.4** (−48.0, −36.8) |
| PtGA | −20.0 (−27.0, −13.0) | −24.2 (−31.3, −17.1) | −29.9† (−37.1, −22.6) | −37.4*** (−44.4, −30.4) | −33.5**,† (−40.6, −26.5) |
| HAQ-DI | −0.2 (−0.4, −0.1) | −0.3 (−0.4, −0.1) | −0.5**,† (−0.6, −0.3) | −0.5* (−0.6, −0.3) | −0.5**,† (−0.7, −0.4) |
| HAQ-DI ≤ MCID, § n (%), 95% CI | 24 (44), 31-57 | 27 (50), 37-63 | 30 (58), 44-71† | 35 (64), 51-76 | 34 (63), 50-76† |
| hsCRP, mg/L | −0.4 (−4.6, 3.9) | −7.9* (−12.2, −3.6) | −9.7** (−14.1, −5.4) | −6.8* (−11.1, −2.6) | −6.9* (−11.1, −2.6) |

Data are mean (95% CI), unless otherwise noted.
Abbreviations: ACR—American College of Rheumatology; BID—twice daily; HAQ-DI—Health Assessment Questionnaire-Disability Index; hsCRP—high-sensitivity C-reactive protein; LOCF—last observation carried forward; MCID—minimal clinically important difference; PhGA—physician's global assessment of disease activity; PtGA—patient global assessment of disease activity; RA—rheumatoid arthritis; SJC66—swollen joint count using 66 joints; TJC68—tender joint count using 68 joints.
*P < 0.05;
**P < 0.01;
***P < 0.001 relative to placebo.
†1 patient with missing data.
‡2 patients with missing data.
§ MCID = −0.22.
Modified intent-to-treat population (LOCF).

Safety

The percentage of subjects with any treatment-emergent AEs was numerically higher in a dose-dependent manner for the Compound 1 6, 12 and 18 mg BID treatment groups compared with placebo (Table 55-C). Most reported AEs were considered mild to moderate in severity. The most commonly observed AEs were headache, nausea, upper respiratory tract infection, and urinary tract infection. The incidences of serious AEs and severe AEs were low, without an apparent dose-response relationship (Table 55-C). Five subjects in the Compound 1 dose groups reported seven serious AEs (3 mg BID; one subject each with pancreatitis and pulmonary embolism, 6 mg BID; one subject with pulmonary embolism and deep vein thrombosis, one patient with TIA and benign prostate hyperplasia, 18 mg BID dose; one subject acute respiratory failure). One subject on placebo experienced a serious AE of bronchiectasis. The overall infection rates were similar for the Compound 1 3- and 6 mg BID dose groups and placebo (20%, 22%, and 23%, respectively), but were higher in the Compound 1 12- and 18 mg BID dose groups (40% and 38%). No serious infections were reported in any of the Compound 1 treatment groups. Herpes zoster occurred in two subjects in the placebo group (4%) and three subjects who received Compound 1 (1%, one case each in the 3-, 12- and 18 mg BID groups; all were isolated to a single dermatome). The two reported events of hepatic disorders in the 18 mg BID dose group and one event in the placebo group were attributed to increased transaminases; none were serious. There was an adjudicated case of transient ischemic attack (left ventricular hypertrophy, classified as mild) in one subject in the Compound 1 6 mg BID group. One patient in the 6 mg BID group had one event each of basal cell carcinoma and squamous cell carcinoma. There were no opportunistic infections or deaths during the study period.

Dose-dependent increases in low-density lipoprotein cholesterol (LDL-C) and high-density lipoprotein cholesterol (HDL-C) were observed; however, the ratios of LDL-C/HDL-C remained the same through Week 12. Of the subjects with normal AST or ALT at baseline, 6-18% of patients on Compound 1 had elevated AST at least twice, and 4-11% had elevated ALT at least twice, versus 2% and 6% on placebo, respectively. The number of these subjects was higher in the higher dose groups. Most of the elevations were Grade 1 (for AST and ALT, ≥1.2-<1.6×ULN) and Grade 2 (1.6-3.0×ULN). One subject each (2%) in the Compound 1 3 mg BID and placebo group (2%) had a Grade 3 ALT elevation (3.0-8.0×ULN). Of the subjects with normal creatinine at baseline, 4-14% subjects on Compound 1 had elevated creatinine at least twice versus none in the placebo group. One subject in the 18 mg BID group had a Grade 3 elevation (≥1.9-<3.0×ULN). The elevations did not result in discontinuation of any subject from the study.

Figure 38A:
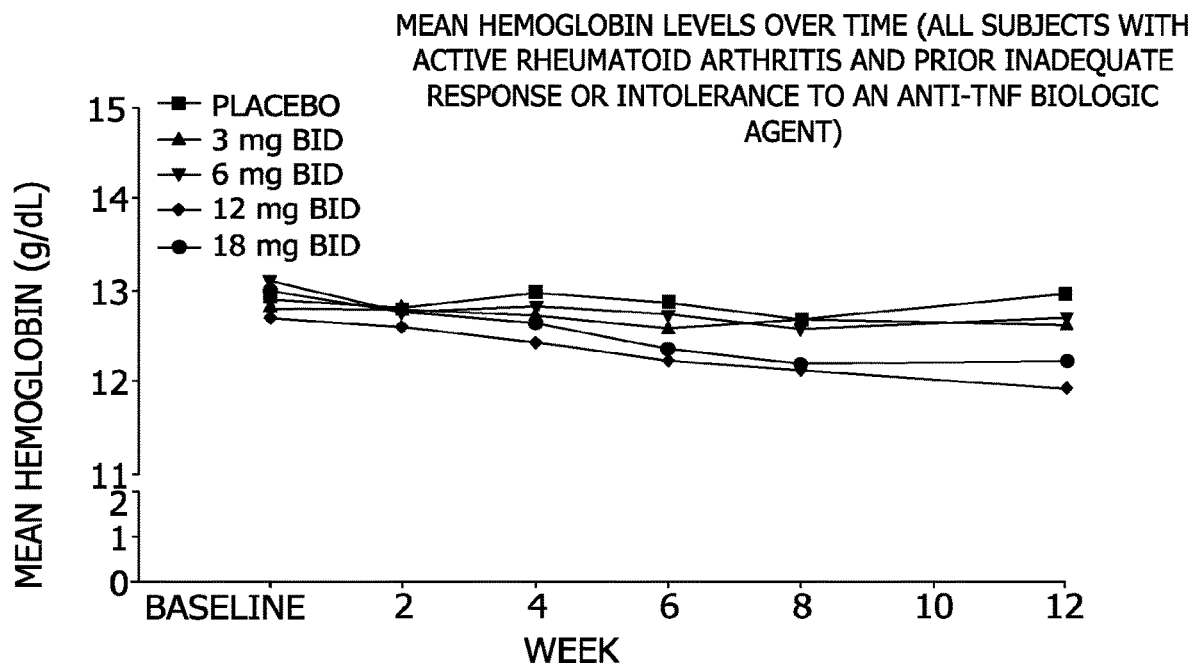
FIG. 38A shows the mean hemoglobin levels over time for all subjects following administration of placebo or various doses of Compound 1 to subjects with active rheumatoid arthritis and prior inadequate response or intolerance to an anti-TNF biologic agent (safety population with observed data (no imputation of missing values)).
Figure 38B:
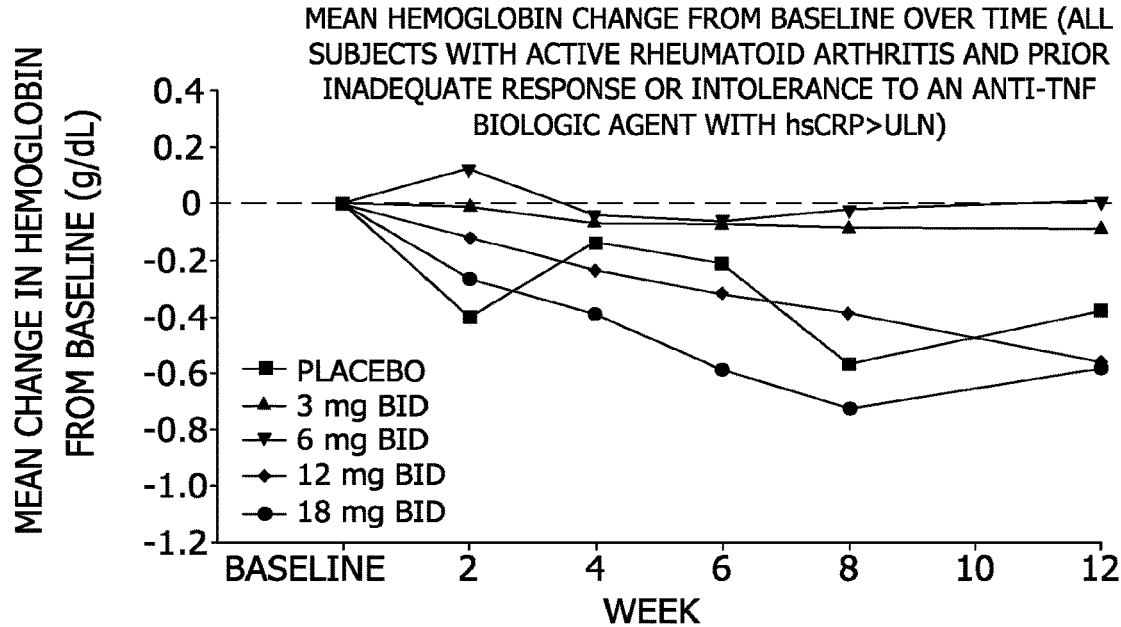
FIG. 38B shows the mean hemoglobin change from baseline over time in subjects with high-sensitivity C-reactive protein (hsCRP) greater than the upper limit of normal (ULN) (normal ranges for hemoglobin: 11.5-15.5 g/dL in females and 13.2-17.0 g/dL in males; ULN for hsCRP=5 mg/L).

Decreases from baseline in mean hemoglobin levels were observed in a dose-dependent manner with Compound 1, although mean hemoglobin levels remained within the normal range across all dose groups during the study (FIG. 38A). Twenty-six out of 219 subjects (11.9%) in the Compound 1 groups had a Grade 2 decrease in hemoglobin (from 15-20 g/L); 14/219 subjects (6.4%) had a Grade 3 decrease (from 21-29 g/L); 8/219 subjects (3.7%) had a Grade 4 decrease (≥30 g/L). The majority (79%) of these decreases were transient (only one occurrence) and one subject discontinued the study due to reported AE of low hemoglobin. However, in subjects with underlying systemic inflammation, as measured by elevated baseline hsCRP, treatment with Compound 1 at 3- or 6 mg BID resulted in mean increases from baseline in hemoglobin levels compared with placebo (FIG. 38B).

Decreases in mean circulating leukocytes, neutrophils (Table 55-D) and natural killer (NK) cells were also observed, and one subject discontinued study drug due to leukopenia. Only NK cell reductions appeared to be dose-related. The mean percentage change in NK cells was +16.5±46.6 in the placebo group; a dose-dependent decrease was seen in subjects treated with Compound 1 (−15.8±25.3 in the 3 mg BID group, −18.3±47.4 in the 6 mg BID group, −28.0±37.3 in the 12 mg BID group, and −42.6±31.7 in the 18 mg BID group). At all doses of Compound 1, there was a transient mean increase in total lymphocytes, which returned to baseline level by Week 12, except in the 18 mg dose group. There were two subjects in the 18 mg dose group with Grade 4 lymphocyte reduction; one subject was reported to have vaginal and urinary tract infection, and the other herpes zoster. One subject had a Grade 4 neutrophil reduction, which was not associated with a serious infection.

achieving an ACR20 response as early as 2 weeks after treatment. The proportion of ACR20 responders reached a maximum at 8 weeks and plateaued at 71% through Week 12. Improvements in ACR50 (up to 42%) and ACR70 (up to 25%) response rates in the Compound 1 groups also reached a maximum before Week 12. The speed of the response is in contrast to the 3-6 months observed for many biologic therapies (Bathon, et al., *The New England Journal of Medicine,* 2000, Vol. 343(22), pp. 1586-93; Keystone, et al., *Arthritis and Rheumatism,* 2008, Vol. 58(11), pp. 3319-29;

TABLE 55-C

Adverse Events Summary

| | | Compound 1 | | | |
|---|---|---|---|---|---|
| | Placebo (n = 56) | 3 mg BID (n = 55) | 6 mg BID (n = 55) | 12 mg BID (n = 55) | 18 mg BID (n = 55) |
| AE, n (%) | | | | | |
| Any AE | 25 (45) | 26 (47) | 31 (56) | 37 (67) | 39 (71) |
| Any serious AE | 1 (2) | 2 (4) | 2 (4) | 0 | 1 (2) |
| Any severe AE | 2 (4) | 1 (2) | 2 (4) | 2 (4) | 1 (2) |
| Any AE leading to discontinuation | 2 (4) | 0 | 6 (11) | 2 (4) | 3 (5) |
| Any death | 0 | 0 | 0 | 0 | 0 |
| AEs of special interest | | | | | |
| Infection | 13 (23) | 11 (20) | 12 (22) | 22 (40) | 21 (38) |
| Serious infection | 1 (2) | 0 | 0 | 0 | 0 |
| Cardiovascular event | 0 | 0 | 1 (2)† | 0 | 0 |
| Herpes zoster | 2 (4) | 1 (2) | 0 | 1 (2) | 1 (2) |
| Hepatic disorder* | 1 (2) | 0 | 0 | 0 | 2 (4) |
| Malignancy | 0 | 0 | 1 (2)‡ | 0 | 0 |

Abbreviations: AE—adverse event; BID—twice daily.
*AEs as reported by the investigator.
†The cardiovascular event was adjudicated as a transient ischemic attack.
‡One patient with basal cell and squamous cell carcinoma.

TABLE 55-D

Mean Change Over Time in Select Hematology Parameters and Incidence of Patients With Abnormalities

| | | Compound 1 | | | |
|---|---|---|---|---|---|
| Abnormality, number (%) | Placebo (n = 56)* | 3 mg BID (n = 55)* | 6 mg BID (n = 55)* | 12 mg BID (n = 55) | 18 mg BID (n = 55) |
| Neutrophils × $10^9$/L | | | | | |
| Grade 2 (1.0-1.4) | 1 (2) | 0 | 3 (6) | 4 (7) | 7 (13) |
| Grade 3 (0.5-0.9) | 0 | 0 | 0 | 2 (4) | 1 (2) |
| Grade 4 (<0.5) | 0 | 0 | 0 | 1 (2) | 0 |
| Lymphocytes × $10^9$/L | | | | | |
| Grade 2 (1.0-1.4) | 18 (33) | 14 (26) | 19 (35) | 14 (25) | 26 (47) |
| Grade 3 (0.5-0.9) | 9 (16) | 8 (15) | 8 (15) | 11 (20) | 9 (16) |
| Grade 4 (<0.5) | 0 | 1 (2) | 1 (2) | 0 | 2 (4) |

BID—twice daily.
*1 subject with missing data.
Safety population.
Grading based on OMERACT Rheumatology Common Toxicity Criteria v.2.0

Discussion

In this study, a broad dose range of Compound 1 (dosed up to 18 mg BID) was tested to assess efficacy and safety in subjects with an inadequate response or intolerance to anti-TNF biologic therapies. At all doses, Compound 1 demonstrated rapid and robust efficacy as shown by significantly greater improvements in clinical and functional outcomes compared to placebo. The onset of improvement with Compound 1 treatment was rapid with up to 58% of subjects achieving an ACR20 response as early as 2 weeks after treatment. Keystone, et al., *Arthritis and Rheumatism,* 2004, Vol. 50(5), pp. 1400-11) and comparable with that observed for other JAK inhibitors, baricitinib and tofacitinib in TNF-IR patients. (Burmester, et al., *Lancet* (London, England), 2013, Vol. 381(9865), pp. 451-60; Genovese, et al., *European League Against Rheumatism,* 2015; 2015). In addition, the ACR20 response rate was comparable between subjects with two or more prior anti TNF therapies and those with only one prior anti-TNF. In general, the maximum efficacy was observed at the 12 mg BID dose.

Despite producing significant clinical improvement in different spectra of RA patients, there are safety concerns with JAK inhibitors, predominantly around impairing the body's ability to fight infections, viral reactivation, as well as altering hematopoietic homeostasis that could link to anemia. The most commonly reported adverse events with JAK inhibitors are infections, herpes zoster, pulmonary tuberculosis, cryptococcal pneumonia and pneumocystis pneumonitis (Fleischmann, et al., *Arthritis Rheumatol.*, 2015, Vol. 67(2), pp. 334-43; Genovese, et al., *Arthritis Rheumatol.*, 2016, Vol. 68(1), pp. 46-55). In addition, increases in total cholesterol, elevation of transaminase and serum creatinine, decreases in neutrophil counts and anemia are also observed. (Burmester, et al., *Lancet* (London, England), 2013, Vol. 381(9865), pp. 451-60; Genovese, et al., *Arthritis Rheumatol.*, 2016, Vol. 68(1), pp. 46-55; Keystone, et al., *Annals of the Rheumatic Diseases*, 2015, Vol. 1 74(2), pp. 333-40).

In the current study, a broad range of doses of Compound 1 were tested to assess the selectivity of Compound 1 in vivo. Overall, Compound 1 demonstrated an acceptable safety and tolerability profile at all doses in this refractory RA population. There was no serious infection, although the proportion of overall infection rates was higher at the two highest doses of Compound 1 (12 mg and 18 mg BID). The most commonly observed infections with Compound 1 were bronchitis, upper respiratory, and urinary tract infections. The incidence of herpes zoster was similar in the placebo group (two subjects, 4%) and the Compound 1 treatment groups (three subjects, 1%), and all were non-disseminated.

At the 12 mg BID and 18 mg BID doses, there was a modest decrease in mean hemoglobin levels by Week 12, although the mean hemoglobin levels remained within the normal range. Notably, in subjects with elevated hsCRP at baseline, who were receiving 3 or 6 mg BID Compound 1, mean hemoglobin levels increased compared to placebo treatment, possibly due to a reduction of systemic inflammation while minimizing inhibitory effects on JAK2.

Circulating NK cells, which function as the critical mediator of host immunity against malignancy and infections, were measured as a pharmacodynamic readout of IL-15 inhibition. With increasing doses of Compound 1 there was a greater decrease in mean circulating NK cell counts. At the maximally efficacious dose, 12 mg BID, NK cells decreased by 28% from baseline, with proportionally smaller decreases in NK cells observed at lower doses. Given the fact that IL-15 signaling involves a heterodimer of JAK1 and JAK3, this was to be expected at higher doses of Compound 1. It is unclear how much each of the heterodimeric components (JAK1 and JAK3) contributes to the overall IL-15 signaling. However, it is possible that at higher exposure of Compound 1, the threshold for in-vivo selectivity for JAK1 compared to JAK3 is lowered in the context of the JAK1/JAK3 heterodimer. Of note, for tofacitinib at 5 mg BID, the reported median decrease in NK cells at week 24 was ~35%, with greater reduction at 10 mg BID or higher doses of tofacitinib (van Vollenhoven, et al., *Annals of the Rheumatic Diseases*, 2015, pp. 258-9; Addendum to Primary Clinical Review, NDA 203,214, Center for Drug Evaluation and Research). However, it is important to note that the significance of NK cell reduction, especially what is considered clinically meaningful reduction in NK cells in terms of predicting clinical events (i.e. onset of viral reactivation) is lacking. A significant association with the changes in nadir NK cells and treated infection rates with tofacitinib treatment was observed (van Vollenhoven, et al., *Annals of the Rheumatic Diseases*, 2015, pp. 258-9). No association of the reduced NK cells with clinical events was observed in the current study.

As reported with other JAK inhibitors, a dose-dependent elevation of low density lipoprotein cholesterol and high density lipoprotein cholesterol levels was observed with Compound 1, however, the ratio of LDL-C/HDL-C remained unchanged. For the other laboratory parameters of interest, i.e, serum transaminases, WBC, neutrophil, or lymphocytes, the mean changes were unremarkable and lacked apparent dose relationship, with only one subject discontinuing the study early due to leukopenia.

In summary, the results of the current study demonstrated safety and efficacy of a selective JAK1 inhibitor, Compound 1, in a difficult-to-treat population of RA patients who had an inadequate response or intolerance to anti-TNF biologic therapies.

Example 56

Treatment of Moderately to Severely Active Rheumatoid Arthritis in Patients Who have Inadequately Responded to Methotrexate The following example briefly describes the results of a Phase 2b, 12-week, randomized, double-blind, parallel-group, placebo-controlled study in which adult subjects with moderately to severely active rheumatoid arthritis (RA) who have inadequately responded to stable methotrexate therapy were treated with Compound 1.

Patients

Men and women aged ≥18 years with active RA and inadequate response to methotrexate were included in the study. Diagnosis of RA was based on the 1987 revised American College of Rheumatology (ACR) classification criteria (Arnett et al, *Arthritis Rheum.*, 1988, Vol. 31(3), pp. 315-324) or the 2010 ACR/European League Against Rheumatism (EULAR) criteria (Smolen et al, *Ann. Rheum. Dis.*, 2010, Vol. 69(6), pp. 964-975). Active RA was defined by minimum disease activity criteria of ≥6 swollen joints (based on 66 joint counts) at screening and baseline; ≥6 tender joints (based on 68 joint counts) at screening and baseline; and high-sensitivity C-reactive protein (hsCRP) greater than the upper limit of normal (ULN) or positive test results for both rheumatoid factor and anti-cyclic citrullinated peptide (CCP) at screening. Eligible patients had been receiving methotrexate for ≥3 months, with a stable prescription (7.5-25 mg/week) for ≥4 weeks before baseline. Stable doses of methotrexate were continued throughout the study. In addition, all patients were requested to take a dietary supplement of oral folic acid (or equivalent) from 4 weeks prior to baseline and throughout study participation. All other oral disease-modifying antirheumatic drugs (DMARDs) were discontinued before baseline for ≥5 times the mean terminal elimination half-life of the specific DMARD to ensure washout. High-potency opiates (e.g., oxycodone, methadone, morphine) were discontinued ≥4 weeks before baseline. All patients had a negative tuberculosis screening assessment or, if there was evidence of a latent tuberculosis infection, completed ≥2 weeks of tuberculosis prophylaxis or had documented completion of a full course of tuberculosis prophylaxis before baseline. Patients were allowed to receive nonsteroidal anti-inflammatory drugs, acetaminophen, oral/inhaled corticosteroids, and low-potency opiates. Patients were excluded if they had received JAK inhibitor therapy or any other investigational or approved biologic RA therapy.

Treatment

Patients were randomized in a 1:1:1:1:1:1 ratio in a double-blind manner to oral doses of Compound 1 (immediate release capsules comprising Tartrate Hydrate) 3 mg BID, 6 mg BID, 12 mg BID, 18 mg BID, or 24 mg QD (two 12 mg tablets administered at the same time), or placebo BID for 12 weeks. Patients were randomized using an interactive voice/web response system according to a blocked randomization schedule. Investigators, patients, and other study personnel were blinded to the treatment assignments throughout the study. To maintain blinding, the placebo and active treatments had an identical appearance. Patients were instructed to take their doses (6 capsules total, split into 2 batches of 3) at approximately the same times each day.

Assessments

The primary efficacy endpoint was a ≥20% improvement in ACR criteria (ACR20) at week 12. Other endpoints included ACR50 and ACR70 response rates; change in 28-joint Disease Activity Score using C-reactive protein (DAS28(CRP)); change in Clinical Disease Activity Index (CDAI); the proportion of patients achieving low disease activity (LDA) or clinical remission based on DAS28(CRP) and CDAI criteria; and change in the Health Assessment Questionnaire Disability Index (HAQ-DI). The minimal clinically important difference (MCID) on the HAQ-DI, which is a decrease of >0.22, (Strand et al, 2006) was also evaluated.

Safety was evaluated during treatment and for 30 days after the last dose of study drug on the basis of adverse events (AEs), vital signs, physical examinations, and laboratory tests. AEs were coded using the Medical Dictionary for Regulatory Activities (MeDRA), version 17.1.

Statistical Analyses

The per-protocol primary efficacy analysis was conducted in a modified intent-to-treat population, including all randomized patients who take at least 1 dose of study drug, with last observation carried forward (LOCF) imputation; data were also analyzed with nonresponder imputation (NRI). Statistical tests were 1-sided with a significance level of 0.05 for efficacy analyses and 2-sided with a significance level of 0.05 for all other analyses. A sample of 270 patients (45 per randomized treatment group) was targeted give 80% power to establish a real difference of 30% in the primary efficacy endpoint (ACR20 response rate at week 12), assuming the response rate would be 30% in the placebo group and 60% in at least 1 of the Compound 1 dose groups.

Results

Patients

Figure 40A:
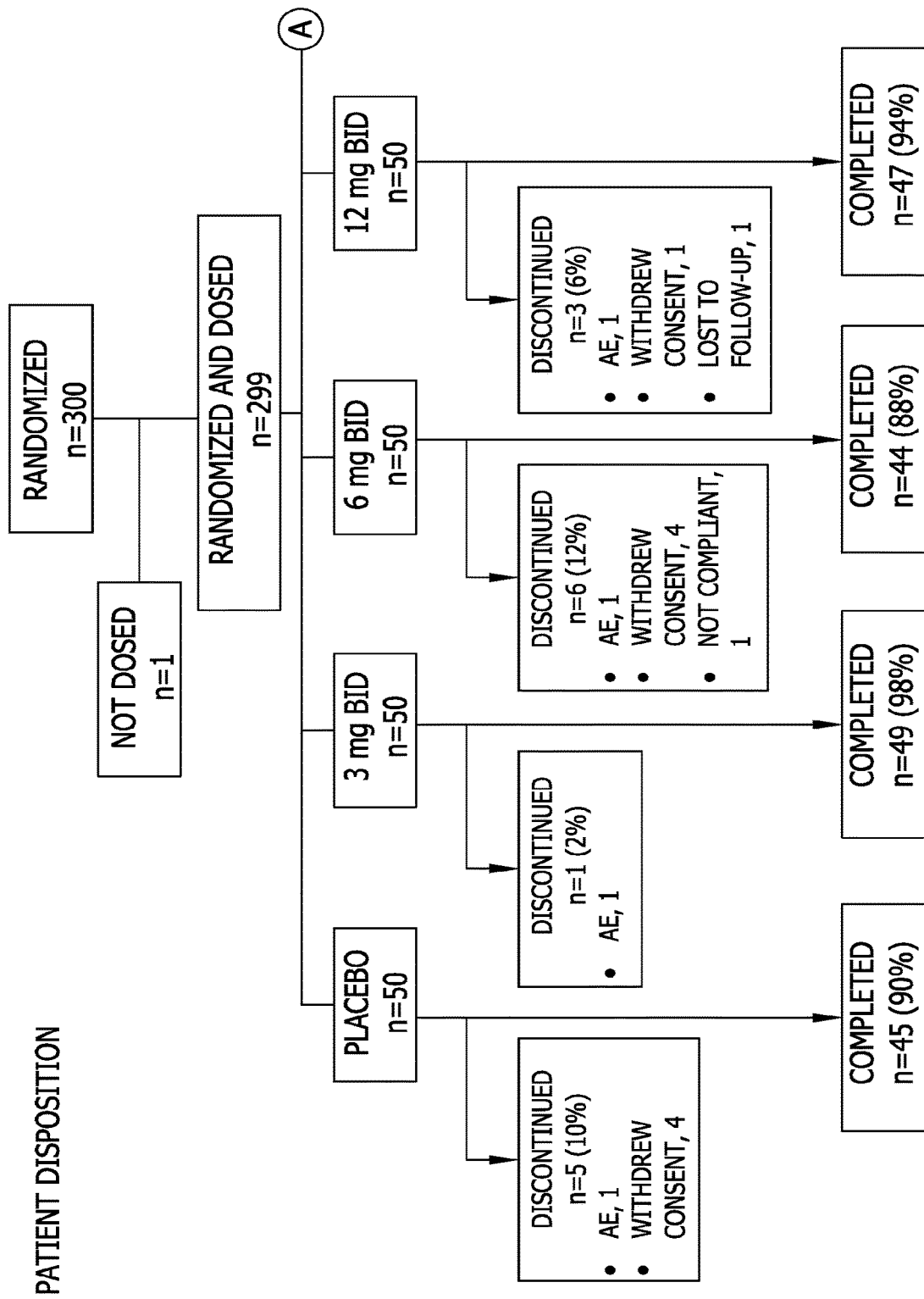
FIGS. 40A and 40B show the subject disposition for the study described in Example 56.
Figure 40B:
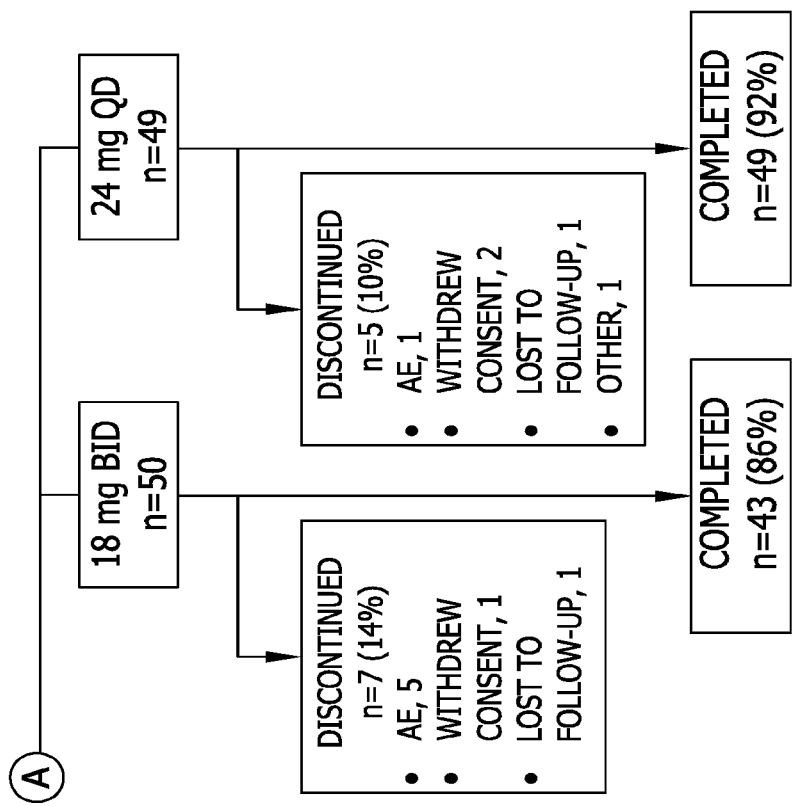

A total of 300 patients were randomized, and 299 received placebo (n=50) or Compound 1 3 mg BID (n=50), 6 mg BID (n=50), 12 mg BID (n=50), 18 mg BID (n=50), or 24 mg QD (n=49). Overall, 91% of patients completed the study, with similar discontinuation rates across treatment groups and no apparent relationship between Compound 1 dose and discontinuation (FIGS. 40A and 40B). Demographic and clinical characteristics at baseline were balanced among treatment groups (Table 56-A). Patients were from Eastern Europe (61%), Central/South America (18%), the United States (10%), Western Europe (8%), or other regions (4%). Patients had a mean disease duration of 6.9 years and 17.7% had used ≥1 prior non-methotrexate DMARD. Of note, patients with normal hsCRP could be enrolled if they were positive for rheumatoid factor and anti-CCP antibody. Approximately 43% of patients had hsCRP values ≤ULN at baseline.

TABLE 56-A

Baseline Characteristics and Disease Activity in
Patients With Inadequate Response to Methotrexate

| Characteristic | Placebo (n = 50) | Compound 1 | | | | |
| --- | --- | --- | --- | --- | --- | --- |
| | | 3 mg BID (n = 50) | 6 mg BID (n = 50) | 12 mg BID (n = 50) | 18 mg BID (n = 50) | 24 mg QD (n = 49) |
| Female, number (%) | 38 (76) | 40 (80) | 34 (68) | 41 (82) | 42 (84) | 42 (86) |
| Age, years, mean (SD) | 55 (12) | 53 (12) | 55 (12) | 56 (12) | 55 (14) | 56 (12) |
| Years since RA diagnosis, mean (SD) | 5.9 (5.3) | 3.9 (3.8) | 7.0 (5.5) | 9.3 (8.6) | 7.3 (7.9) | 8.3 (7.1) |
| RF positive, number (%) | 41 (82) | 45 (90) | 46 (92) | 44 (88) | 41 (82) | 44 (90) |
| Anti-CCP positive, number (%) | 39 (78) | 40 (80) | 45 (90) | 43 (86) | 40 (80) | 45 (92) |
| Methotrexate dose, mg, mean (SD) | 16 (4) | 16 (4) | 16 (4) | 14 (4) | 15 (5) | 15 (4) |
| Prednisolone dose, mg, mean (SD) | 0 | | | 0 | 0 | 0 |
| ≥1 prior non-MTX DMARD, number (%) | 7 (14) | 6 (12) | 12 (24) | 11 (22) | 5 (10) | 12 (24) |
| 1 | 6 (12) | 4 (8) | 10 (20) | 9 (18) | 2 (4) | 8 (16) |
| 2 | 1 (2) | 2 (4) | 1 (2) | 1 (2) | 1 (2) | 3 (6) |
| ≥3 | 0 | 0 | 1 (2) | 1 (2) | 2 (4) | 1 (2) |
| Disease Activity | | | | | | |
| TJC68, mean (SD) | 29 (16) | 27 (15) | 28 (16) | 28 (13) | 27 (15) | 28 (16) |
| SJC66, mean (SD) | 19 (12) | 15 (8) | 19 (12) | 17 (11) | 17 (12) | 18 (13) |
| HAQ-DI, mean (SD) | 1.4 (0.7) | 1.3 (0.7) | 1.6 (0.7) | 1.5 (0.6) | 1.6 (0.6) | 1.5 (0.7) |
| DAS28(CRP), mean (SD) | 5.6 (1.1) | 5.5 (1.1) | 5.8 (1.0) | 5.6 (0.9) | 5.7 (0.8) | 5.7 (1.0) |
| CDAI, mean (SD) | 40 (14) | 38 (13) | 43 (14) | 39 (12) | 40 (13) | 41 (13) |
| hsCRP, mg/L, mean (SD) | 15 (26) | 11 (15) | 17 (20) | 11 (15) | 13 (15) | 14 (16) |

TABLE 56-A-continued

Baseline Characteristics and Disease Activity in
Patients With Inadequate Response to Methotrexate

| | | Compound 1 | | | | |
|---|---|---|---|---|---|---|
| Characteristic | Placebo (n = 50) | 3 mg BID (n = 50) | 6 mg BID (n = 50) | 12 mg BID (n = 50) | 18 mg BID (n = 50) | 24 mg QD (n = 49) |
| hsCRP > ULN, * number (%) | 27 (54) | 25 (50) | 31 (62) | 26 (52) | 28 (56) | 33 (67) |

Efficacy

Figure 42A:
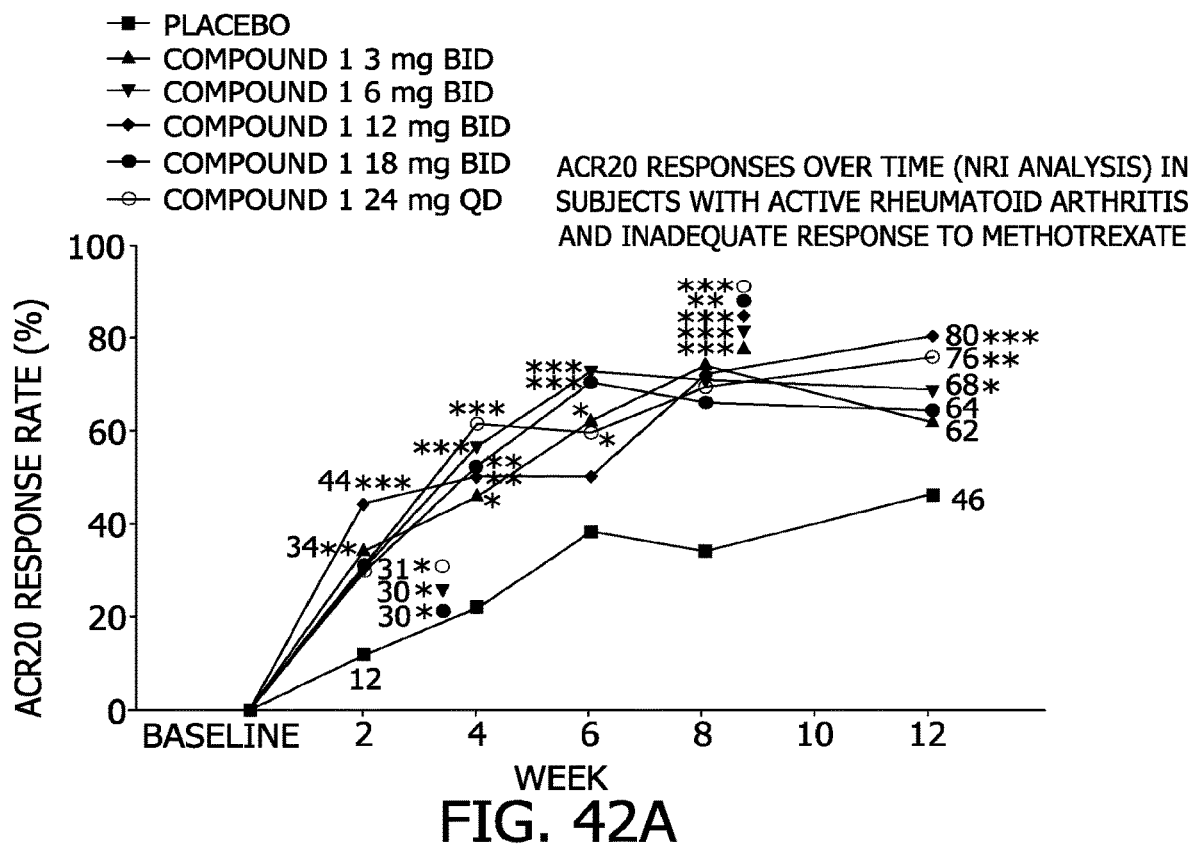
FIGS. 42A-42D show the ACR20 (FIG. 42A, NRI analysis), ACR50 (FIG. 42B, NRI analysis), and ACR70 (FIG. 42C, NRI analysis) responses or DAS28(CRP) mean change from baseline (FIG. 42D, observed cases) over time following administration of placebo or various doses of Compound 1 to subjects with active rheumatoid arthritis and inadequate response to methotrexate (*P<0.05; P<0.01; *P<0.001 relative to placebo; modified intent-to-treat population).
Figure 42B:
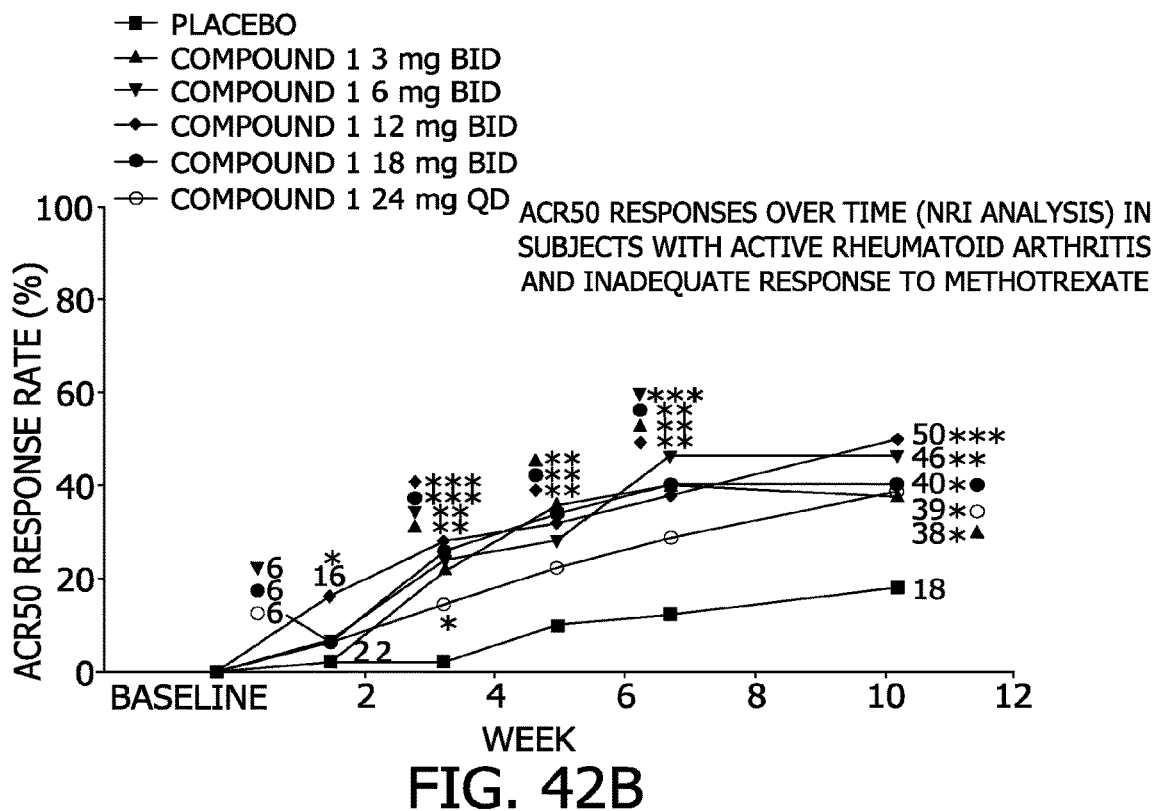
Figure 42C:
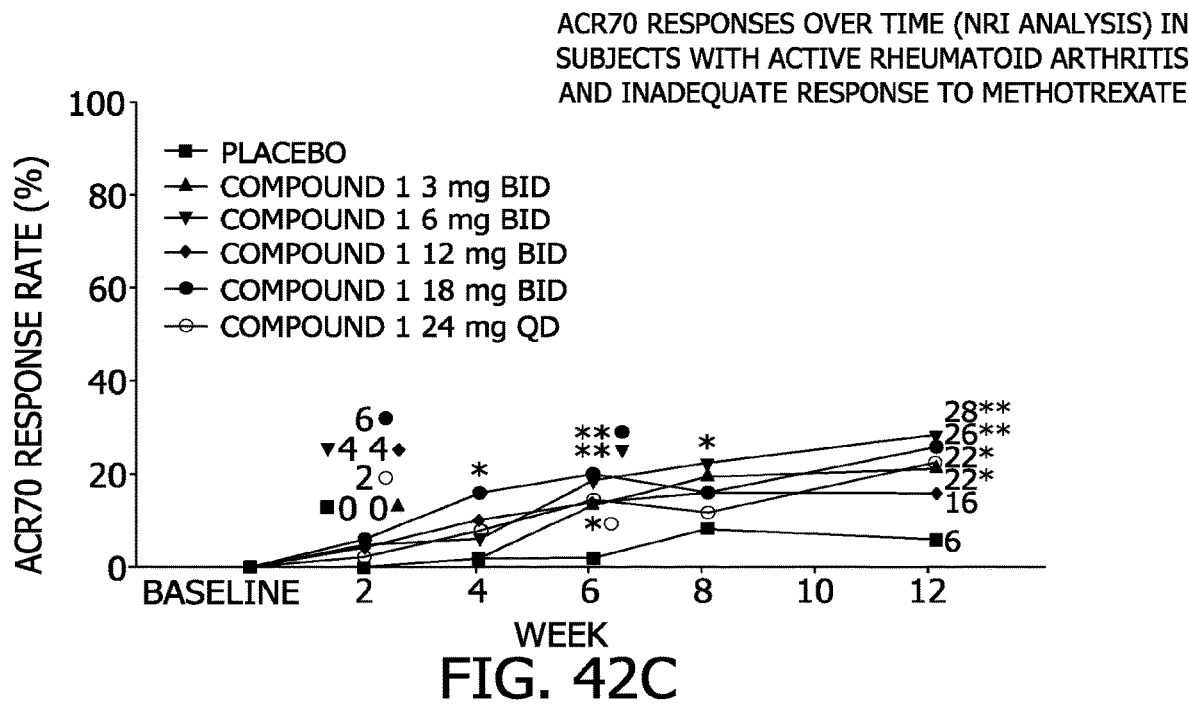
Figure 42D:
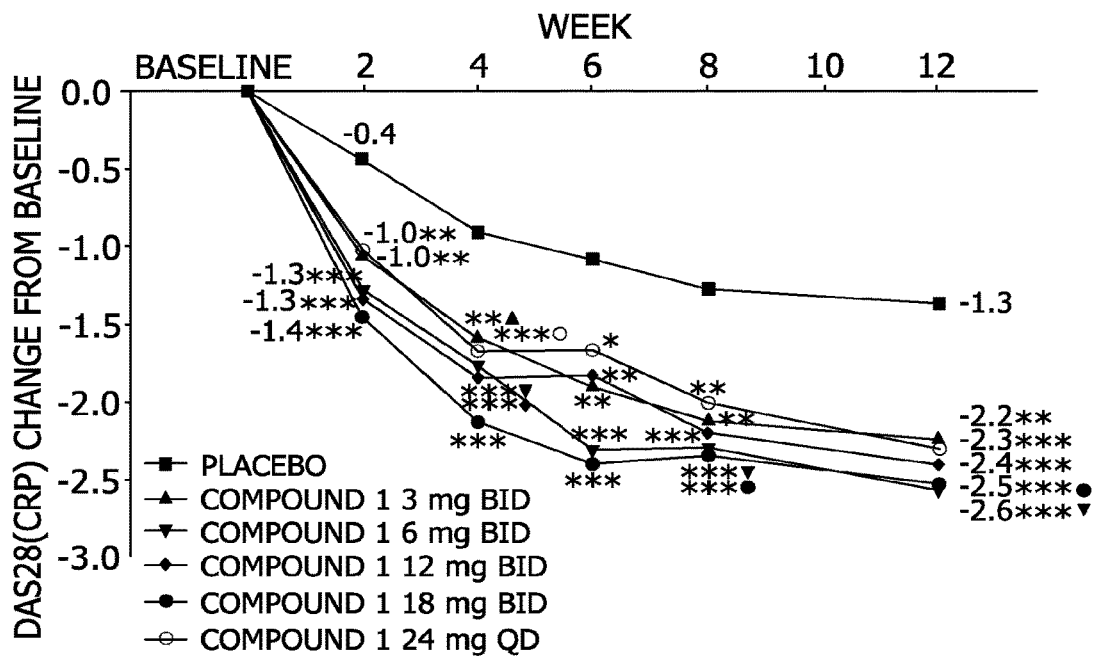

The primary per-protocol endpoint, ACR20 at week 12 (LOCF imputation), was met at every dose of Compound 1 except the lowest dose of 3 mg BID. The proportions of patients with ACR20 were 65% (P=0.153), 73% (P=0.18), 82% (P=0.001), 77% (P=0.008), and 82% (P=0.001) at 3 mg BID, 6 mg BID, 12 mg BID, 18 mg BID, and 24 mg QD, respectively, versus the placebo response rate (50%). ACR20 responses (NRI) were significantly higher with Compound 1 at 6 mg BID (68%), 12 mg BID (80%), and 24 mg QD (76%) versus placebo (46%; FIG. 41). Responses with more stringent criteria, i.e., ACR50 and ACR70, were achieved at week 12 by significantly higher percentages of patients who received Compound 1 versus placebo at all doses except 12 mg BID for ACR70 response (NRI; FIG. 41). ACR20 response rates increased over time with Compound 1 to reach mean maximum values at weeks 6 to 12 (FIG. 42A). ACR50 responses were significant from week 4 onward and plateaued at week 8 (FIG. 42B); ACR70 responses also appeared to plateau by week 8, with some further improvements up to week 12 (FIG. 42C). At the first assessment (week 2), ACR20 responses with Compound 1 ranged from 30% to 44% and were significantly higher at all doses in patients who received Compound 1 versus placebo (12%). Mean decreases in DAS28(CRP) improved over time from baseline, ranging from −2.2 to −2.6 with Compound 1 at week 12, and were significantly lower compared with placebo (−1.3) at all Compound 1 doses and every time point (FIG. 42D).

Figure 43A:
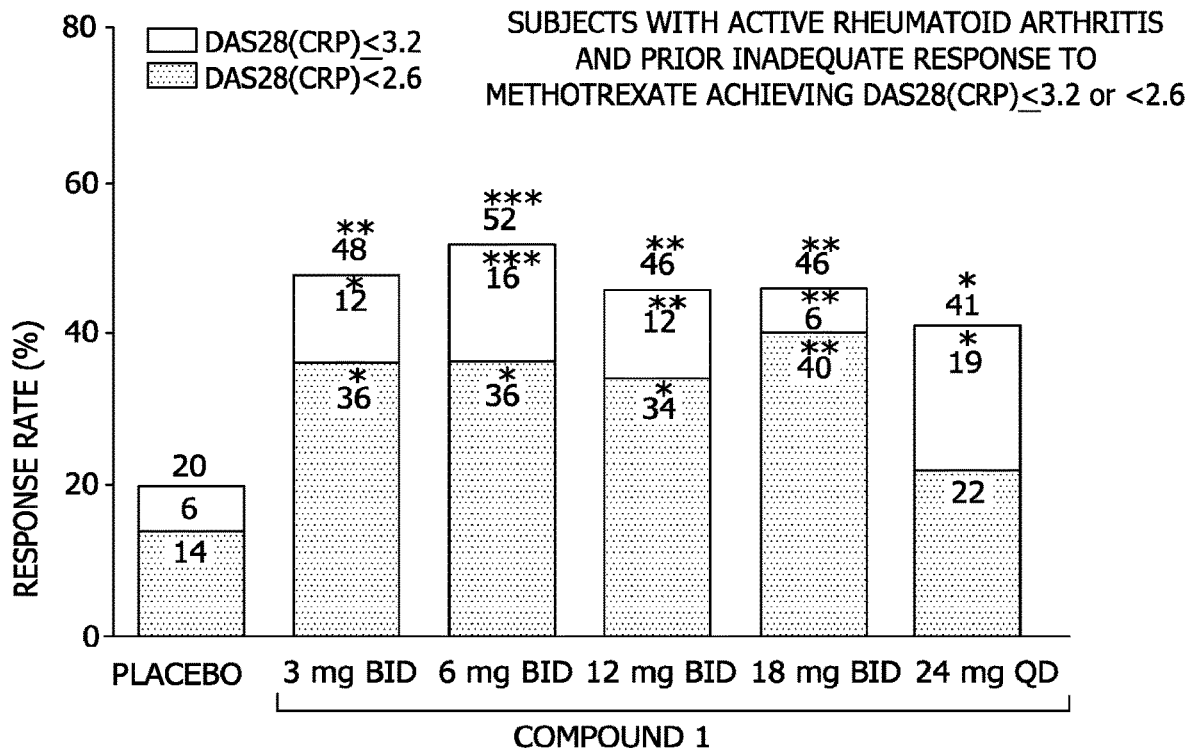
FIGS. 43A and 43B show subjects achieving a DAS28 (CRP) score of ≤3.2 or <2.6 (FIG. 44A) or CDAI of <10 or <2.8) at week 12 following administration of placebo or various doses of Compound 1 to subjects with active rheumatoid arthritis and inadequate response to methotrexate (*P<0.05; P<0.01; *P<0.001 relative to placebo; modified intent-to-treat population (NRI)). For FIGS. 43A and 43B, the bottom number indicates the percentage of subjects who achieved both cutoff values, the middle number indicates the percentage of subjects who achieved the less stringent cutoff but not the more stringent cutoff value, and the top number indicates the percentage of patients who achieved either cutoff value.
Figure 43B:
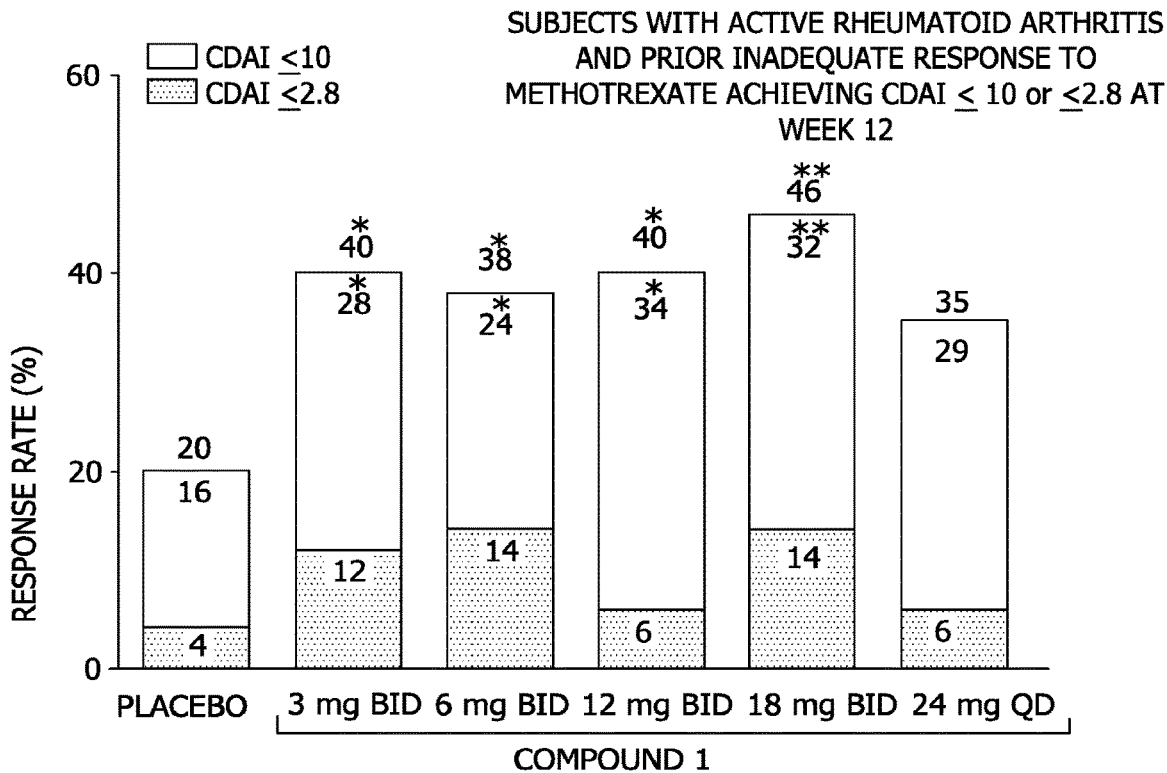

Higher percentages of patients who received Compound 1 achieved DAS28(CRP)≤3.2 or <2.6 compared with placebo. The DAS28(CRP)≤3.2 cutoff was achieved by a significantly higher percentage of patients (41%-52%) at all doses of Compound 1 compared with placebo (20%); the <2.6 cutoff was achieved by significantly higher proportions (34%-40%) with Compound 1 compared with placebo (14%) at all doses except 24 mg QD (22%; FIG. 43A). Similarly, CDAI ≤10 was achieved by a significantly higher percentage of patients (40%-46%) compared with placebo (20%) with Compound 1 at all doses except 24 mg QD (35%; FIG. 43B).

Improvements from baseline in ACR component scores were larger with Compound 1 compared with placebo, reaching statistical significance for most comparisons at doses of 6 mg BID and greater (Table 56-B). Changes from baseline on the HAQ-DI at week 12 with Compound 1 ranged from −0.6 to −0.8 and were significantly greater than that seen with placebo (−0.4) for all but the Compound 1 24 mg QD dose (−0.6). Numerically, more patients in the Compound 1 dose groups ≥6 mg BID (69%-88%) met the MCID at week 12 compared with placebo (67%); the study was not powered for this analysis, and the comparisons versus placebo mostly were not statistically significant.

TABLE 56-B

Mean Changes From Baseline in ACR Components at Week 12

| | | Compound 1 | | | | |
|---|---|---|---|---|---|---|
| ACR Component | Placebo (n = 50) | 3 mg BID (n = 50) | 6 mg BID (n = 50) | 12 mg BID (n = 50) | 18 mg BID (n = 50) | 24 mg QD (n = 49) |
| TJC68 | −14.4 | −15.9 | −19.2* | −19.2* | −17.4 | −18.9* |
| SJC66 | −9.9 | −12.1 | −11.9 | −12.7* | −13.2* | −13.1* |
| Patient's assessment of pain | −19.9 | −25.3 | −33.8** | −33.4** | −34.9** | −29.8* |
| Physician's global assessment of disease activity | −28.0 | −34.7 | −43.0*** | −45.6*** | −36.6* | −37.6* |
| Patient's global assessment of disease activity | −17.5 | −26.9 | −31.4** | −23.8 | −29.1* | −24.1 |
| HAQ-DI | −0.4 | −0.6* | −0.7** | −0.8*** | −0.6* | −0.6 |
| HAQ-DI ≤ MCID,§ | 30 (67), | 33 (67), | 34 (69), | 44 (88), | 35 (74), | 38 (78), |

TABLE 56-B-continued

Mean Changes From Baseline in ACR Components at Week 12

| | | Compound 1 | | | | |
|---|---|---|---|---|---|---|
| ACR Component | Placebo (n = 50) | 3 mg BID (n = 50) | 6 mg BID (n = 50) | 12 mg BID (n = 50) | 18 mg BID (n = 50) | 24 mg QD (n = 49) |
| number (%), 95% CI | 53-80 | 54-81 | 57-82 | 79-97 | 62-87 | 66-89 |
| hsCRP | −0.4 | −10.5*** | −8.8*** | −8.9*** | −7.5** | −8.4*** |

Abbreviations: ACR—American College of Rheumatology; BID—twice daily; HAQ-DI—Health Assessment Questionnaire Disability Index; hsCRP—high-sensitivity C-reactive protein; LOCF—last observation carried forward; MCID—minimal clinically important difference; QD—once daily; RA—rheumatoid arthritis; SJC66—swollen joint count using 66 joints; TJC68—tender joint count using 68 joints.
*$P < 0.05$;
**$P < 0.01$;
***$P < 0.001$ relative to placebo.
§MCID = −0.22.
Modified intent-to-treat population with LOCF imputation of missing values.
95% CIs were calculated based on a normal approximation to the binomial distribution.

As can be seen from these results, Compound 1 had an early onset of action in subjects who have demonstrated a prior inadequate response to methotrexate. In particular, ACR20 response rates improved starting at week 2, with a maximum effect achieved as early as week 6, with continued improvement in some dose groups through week 12. ACR50 (maximum efficacy up to 50%) and ACR70 (maximum efficacy up to 28%) response rates also quickly plateaued by about week 8. Compound 1 showed a dose-dependent efficacy that seemed to reach a maximum at 12 mg BID.

Safety

The safety and tolerability profile of Compound 1 across doses was acceptable (Table 56-C). Incidence of any AE was statistically significantly higher with Compound 1 overall versus placebo (45% vs 26%; P=0.012), with a trend of dose dependence. Among common AEs, those that occurred in ≥3% patients in any group were abdominal pain, abdominal pain upper, back pain, blood creatine phosphokinase increased, cough, diarrhea, dyslipidemia, dyspepsia, gastroenteritis, headache, herpes zoster, influenza, leukopenia, nasopharyngitis, upper respiratory tract infection, urinary tract infection, white blood cell count decreased, and wound. Most AEs in the Compound 1 treatment groups were mild or moderate in severity. Severe AEs occurred in 1 patient each with Compound 1 at 6 mg BID (lung cancer at posttreatment day 10 in a 79-year-old male patient with family and smoking histories; the patient died 3 months later), 12 mg BID (pyrexia), 18 mg BID (hyperbilirubinemia), and 24 mg QD (head injury). There were 2 serious AEs with Compound 1 that were considered possibly related to study drug: community-acquired pneumonia at 12 mg BID and syncope at 24 mg QD. Infections overall occurred in 20% of patients who received Compound 1 and 14% who received placebo, with no tendency towards higher rates at higher doses. Three herpes zoster infections, 1 with Compound 1 at 3 mg BID and 2 at 24 mg QD, involved 1 dermatome per patient. A patient in the Compound 1 6 mg BID group, aged 79 years and with a history of smoking, was diagnosed with lung cancer 10 days after stopping study treatment and died 3 months later.

At week 12, mean values for alanine aminotransferase (ALT) were significantly higher with Compound 1 18 mg BID than with placebo; mean values for aspartate aminotransferase (AST) were significantly higher than placebo with all Compound 1 doses >3 mg BID (Table 56-D). However, grade 3/4 ALT or AST abnormalities during the study were sporadic, with no clear dose dependence (Table 56-E). Creatinine and creatine phosphokinase levels were significantly higher in all Compound 1 dose groups compared with placebo. Compound 1 was associated with elevations in high-density and low-density lipoprotein cholesterol (HDL-C; LDL-C); HDL-C elevation was statistically significant at 6 mg BID, whereas LDL-C values were significantly higher than placebo for all Compound 1 doses; however, the ratios of LDL-C/HDL-C remained the same through week 12. There were no significant decreases in lymphocyte or neutrophil levels between placebo and Compound 1 dose groups by week 12. Grade 3 lymphocyte values occurred with placebo and all doses of Compound 1; grade 4 values occurred in 1 patient each with Compound 1 at 3 mg BID and 18 mg BID (Table 56-E). Grade 3 neutrophil values occurred with Compound 1 at 12 mg BID (1 patient), 18 mg BID (3 patients), and 24 mg QD (1 patient). Natural killer (NK) cell percentages were significantly lower than placebo with Compound 1 doses ≥6 mg BID (Table 56-D).

Figure 44A:
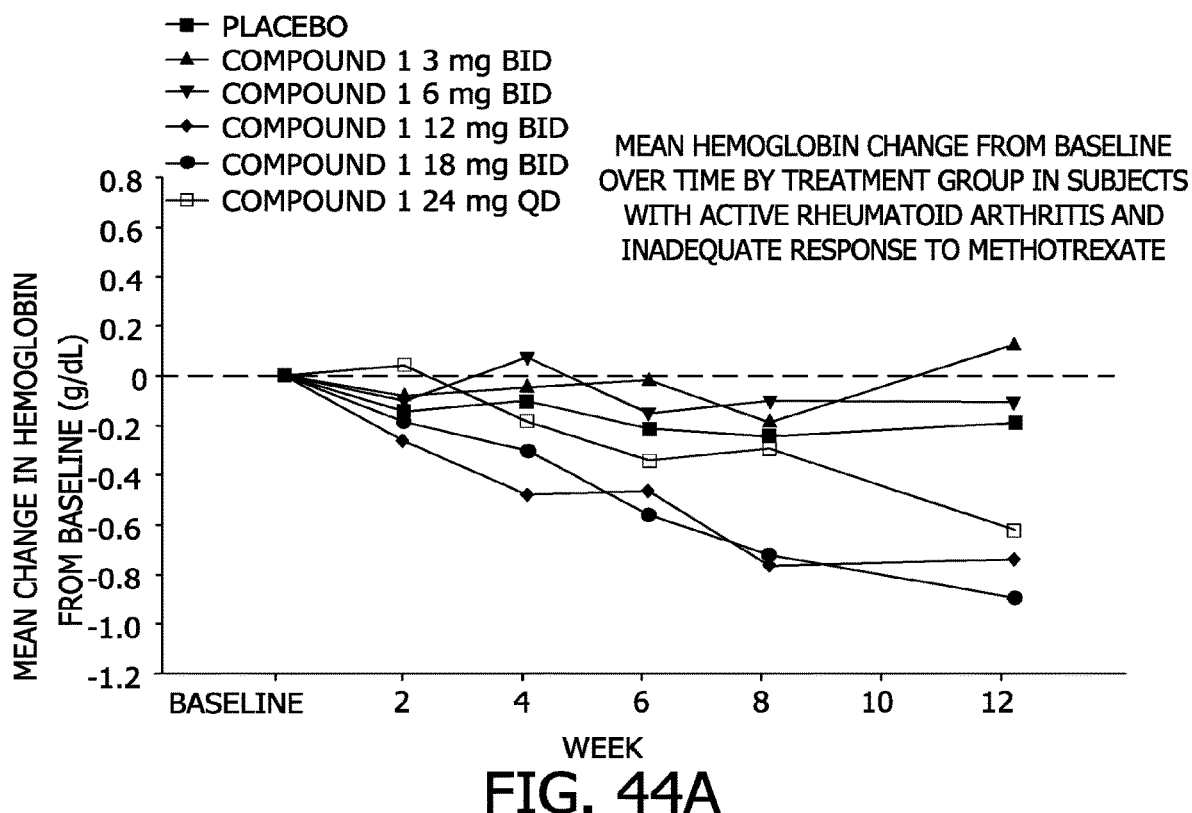
FIGS. 44A-44C show the mean change in hemoglobin from baseline over time by treatment group in all subjects (FIG. 44A), subjects with hsCRP ≤5 mg/mL at baseline (FIG. 44B), and subjects with hsCRP >5 mg/mL at baseline (FIG. 44C) following administration of placebo or various doses of Compound 1 to subjects with active rheumatoid arthritis and inadequate response to methotrexate (safety population with observed data (no imputation of missing values)).
Figure 44B:
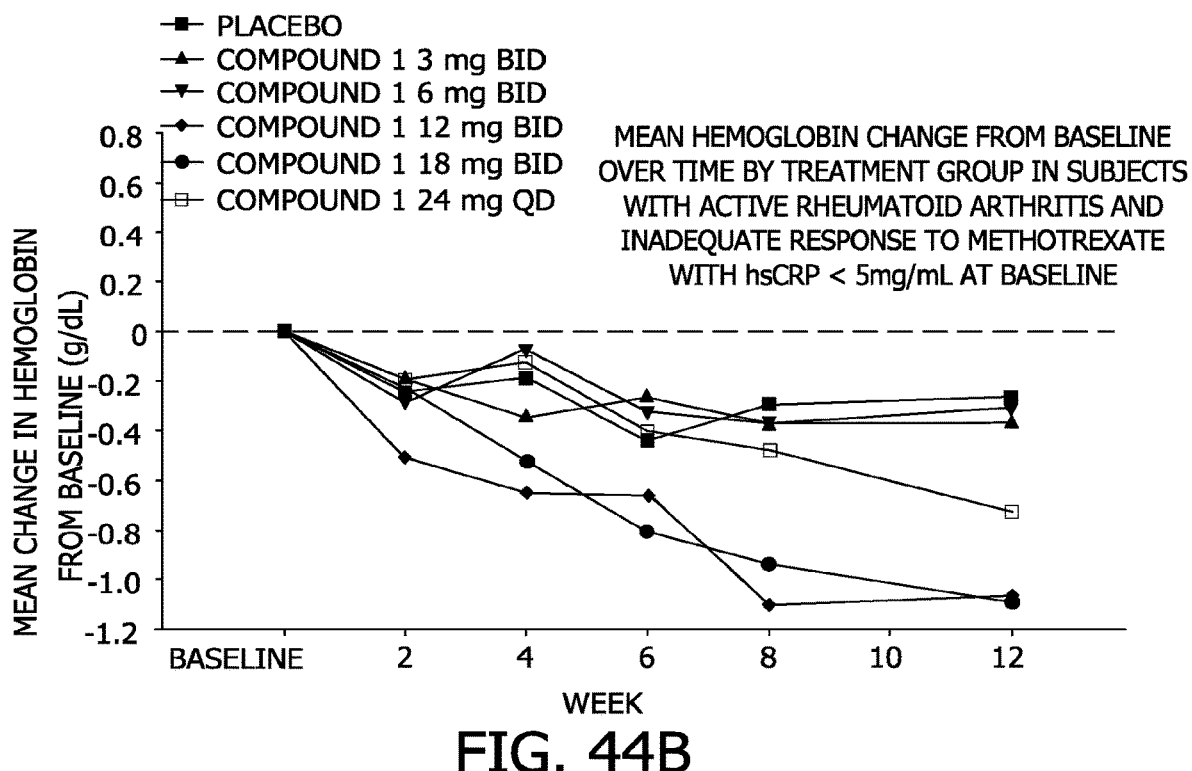
Figure 44C:
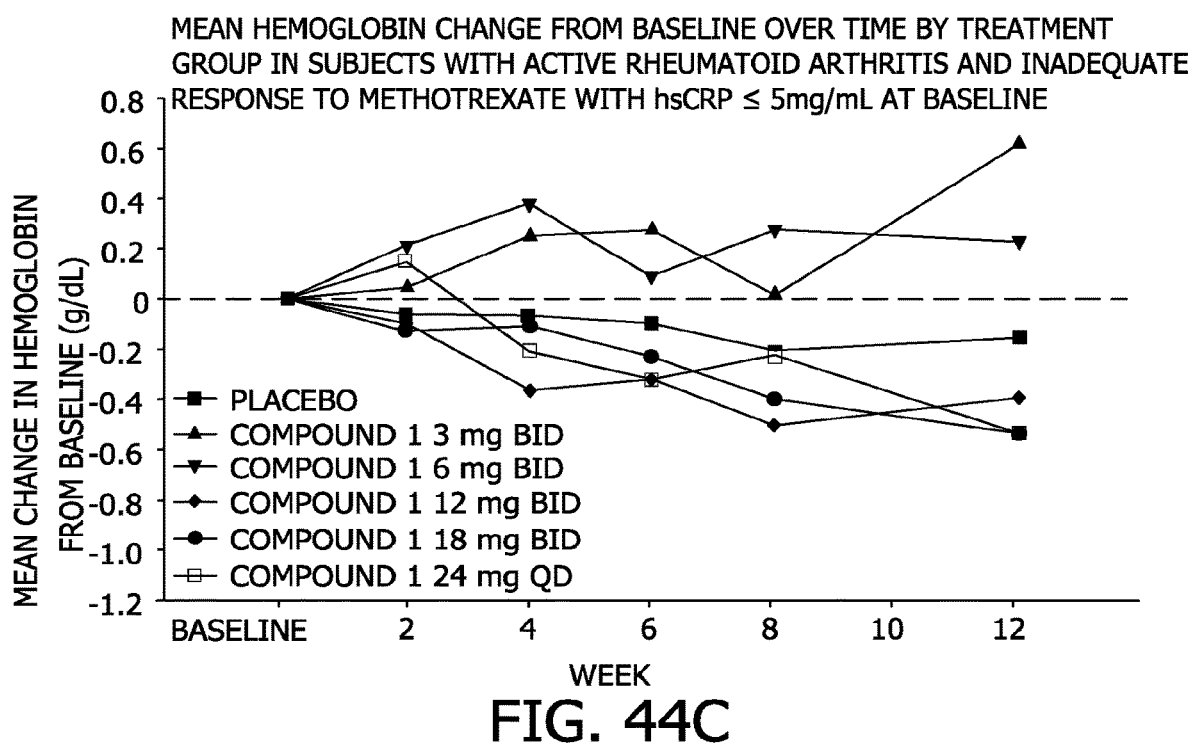

Mean changes in hemoglobin over time in all patients, patients with hsCRP values ≤5 mg/mL, and patients with hsCRP values >5 mg/mL are shown in FIGS. 44A-44C. Mean hemoglobin values remained stable or increased at lower doses, most notably in patients with elevated CRP at baseline. Dose-dependent decreases in hemoglobin were seen at higher doses without clinical impact.

TABLE 56-C

Adverse Events Summary

| | | Compound 1 | | | | |
|---|---|---|---|---|---|---|
| AE, number (%) | Placebo (n = 50) | 3 mg BID (n = 50) | 6 mg BID (n = 50) | 12 mg BID (n = 50) | 18 mg BID (n = 50) | 24 mg QD (n = 49) |
| | Overall AEs | | | | | |
| Any AE | 13 (26) | 19 (38) | 23 (46) | 29 (58) | 25 (50) | 17 (35) |
| Any AE possibly drug related* | 6 (12) | 5 (10) | 6 (12) | 17 (34) | 11 (22) | 5 (10) |

TABLE 56-C-continued

Adverse Events Summary

| | | Compound 1 | | | | |
|---|---|---|---|---|---|---|
| AE, number (%) | Placebo (n = 50) | 3 mg BID (n = 50) | 6 mg BID (n = 50) | 12 mg BID (n = 50) | 18 mg BID (n = 50) | 24 mg QD (n = 49) |
| Any serious AE | 0 | 0 | 2 (4) | 1 (2) | 3 (6) | 2 (4) |
| Any serious AE possibly drug related* | 0 | 0 | 0 | 1 (2) | 0 | 1 (2) |
| Any severe AE | 0 | 0 | 1 (2) | 1 (2) | 1 (2) | 1 (2) |
| Any AE leading to discontinuation | 1 (2) | 1 (2) | 1 (2) | 1 (2) | 5 (10) | 1 (2) |
| Any AE leading to death | 0 | 0 | 0 | 0 | 0 | 0 |
| AEs ≥3% in any group | | | | | | |
| Abdominal pain | 0 | 1 (2) | 1 (2) | 2 (4) | 0 | 1 (2) |
| Abdominal pain upper | 0 | 0 | 0 | 2 (4) | 1 (2) | 1 (2) |
| Back pain | 0 | 1 (2) | 3 (6) | 1 (2) | 0 | 1 (2) |
| Blood creatine phosphokinase increased | 0 | 0 | 0 | 3 (6) | 2 (4) | 1 (2) |
| Cough | 0 | 1 (2) | 1 (2) | 3 (6) | 1 (2) | 0 |
| Diarrhea | 0 | 0 | 1 (2) | 3 (6) | 1 (2) | 1 (2) |
| Dyslipidemia | 0 | 1 (2) | 0 | 3 (6) | 0 | 0 |
| Dyspepsia | 1 (2) | 0 | 0 | 0 | 2 (4) | 0 |
| Gastroenteritis | 0 | 2 (4) | 0 | 0 | 0 | 1 (2) |
| Headache | 1 (2) | 2 (4) | 1 (2) | 3 (6) | 0 | 1 (2) |
| Herpes zoster | 0 | 1 (2) | 0 | 0 | 0 | 2 (4) |
| Influenza | 0 | 0 | 0 | 4 (8) | 1 (2) | 0 |
| Leukopenia | 0 | 0 | 0 | 3 (6) | 1 (2) | 0 |
| Nasopharyngitis | 1 (2) | 1 (2) | 2 (4) | 4 (8) | 2 (4) | 3 (6) |
| Upper respiratory tract infection | 0 | 0 | 1 (2) | 1 (2) | 2 (4) | 0 |
| Urinary tract infection | 2 (4) | 2 (4) | 2 (4) | 2 (4) | 0 | 2 (4) |
| White blood cell count decreased | 0 | 0 | 1 (2) | 0 | 2 (4) | 0 |
| Wound | 0 | 0 | 2 (4) | 0 | 0 | 0 |
| AEs of special interest | | | | | | |
| Infection | 7 (14) | 10 (20) | 7 (14) | 12 (24) | 11 (22) | 9 (18) |
| Serious infection | 0 | 0 | 0 | 1 (2) | 0 | 0 |
| Cardiovascular event | 0 | 0 | 0 | 0 | 0 | 1 (2)* |
| Herpes zoster† | 0 | 1 (2) | 0 | 0 | 0 | 2 (4) |
| Hepatic disorder | 0 | 0 | 0 | 0 | 2 (4) | 0 |
| Malignancy | 0 | 0 | 1 (2)‡ | 0 | 0 | 0 |

Abbreviations: AE—adverse event; BID—twice daily; QD—once daily.
*The cardiovascular event was a cerebrovascular accident and was adjudicated as an ischemic stroke.
†The events of herpes zoster involved 1 dermatome per patient.
‡Lung cancer at posttreatment day 10 in a 79-year-old male patient with family and smoking histories. The patient died 3 months later.
Safety analysis population.

TABLE 56-D

Mean Changes in Laboratory Values of Interest at Week 12

| | | Compound 1 | | | | |
|---|---|---|---|---|---|---|
| Mean (SD) Value | Placebo (n = 50) | 3 mg BID (n = 50) | 6 mg BID (n = 50) | 12 mg BID (n = 50) | 18 mg BID (n = 50) | 24 mg QD (n = 49) |
| ALT, U/L | −1.3 (15.4) | −1.1 (20.7) | 6.5 (10.0) | 7.0 (31.8) | 8.5 (18.5)* | 5.3 (20.7) |
| AST, U/L | −0.1 (8.4) | 1.9 (11.9) | 6.6 (5.5)** | 7.6 (14.3)** | 7.7 (11.3)** | 4.8 (10.9)* |
| HDL-C, mmol/L | 0.01 (0.21) | 0.12 (0.32) | 0.17 (0.26)* | 0.13 (0.30) | 0.13 (0.43) | 0.13 (0.33) |
| LDL-C, mmol/L | −0.05 (0.43) | 0.28 (0.82)* | 0.34 (0.71)* | 0.49 (0.93)** | 0.27 (0.83)* | 0.32 (0.62)** |
| Creatinine, μmol/L | −0.9 (7.9) | 2.0 (8.2)** | 4.9 (9.1)** | 4.3 (7.1)** | 4.6 (10.2)** | 5.4 (8.5)** |
| Creatine phosphokinase, U/L | −7.7 (90.1) | 40.2 (46.5)* | 82.5 (80.6)** | 100.4 (126.5)** | 108.7 (140.2)** | 59.4 (94.0)** |
| Lymphocytes, ×10$^9$/L | −0.09 (0.50) | 0.12 (0.58) | 0.01 (0.79) | −0.08 (0.67) | −0.12 (0.53) | −0.13 (0.49) |

TABLE 56-D-continued

Mean Changes in Laboratory Values of Interest at Week 12

| Mean (SD) Value | Placebo (n = 50) | Compound 1 | | | | |
|---|---|---|---|---|---|---|
| | | 3 mg BID (n = 50) | 6 mg BID (n = 50) | 12 mg BID (n = 50) | 18 mg BID (n = 50) | 24 mg QD (n = 49) |
| Neutrophils, ×10$^9$/L | −0.5 (2.20) | −1.1 (2.13) | −0.9 (1.60) | −0.9 (1.90) | −0.9 (2.16) | −0.4 (1.99) |
| NK cells, CD3−/16−/56+, %† | −0.1 (4.46) | −1.3 (4.54) | −3.1 (4.09)** | −3.3 (4.67)** | −5.3 (4.24)** | −4.9 (5.12)** |

Abbreviations: ALT—alanine aminotransferase; AST—aspartate aminotransferase; BID—twice daily; HDL-C—high-density lipoprotein cholesterol; LDL-C—low-density lipoprotein cholesterol; NK—natural killer; QD—once daily.
*P < 0.05;
**P < 0.01 relative to placebo; P value for difference between treatment groups in baseline and mean change from baseline using a contrast within the one-way analysis of variance.
†Mean percentage change from baseline at week 12.
Safety analysis population.

TABLE 56-E

Incidence of Patients With Laboratory Abnormalities at Week 12

| | Placebo (n = 50) | Compound 1 | | | | |
|---|---|---|---|---|---|---|
| | | 3 mg BID (n = 50) | 6 mg BID (n = 50) | 12 mg BID (n = 50) | 18 mg BID (n = 50) | 24 mg QD (n = 49) |
| ALT, U/L | | | | | | |
| Grade 3 (3.0-8.0 × ULN) | 0 | 0 | 1 | 2 | 1 | 0 |
| Grade 4 (>8.0 × ULN) | 0 | 0 | 0 | 0 | 1 | 0 |
| AST, U/L | | | | | | |
| Grade 3 (3.0-8.0 × ULN) | 0 | 1 | 1 | 0 | 1 | 0 |
| Grade 4 (>8.0 × ULN) | 0 | 0 | 0 | 0 | 0 | 0 |
| Neutrophils, ×10$^9$/L | | | | | | |
| Grade 3 (0.5-0.9) | 0 | 0 | 0 | 1 | 3 | 1 |
| Grade 4 (<0.5) | 0 | 0 | 0 | 0 | 0 | 0 |
| Lymphocytes, ×10$^9$/L | | | | | | |
| Grade 3 (0.5-0.9) | 7 | 8 | 13 | 16 | 17 | 15 |
| Grade 4 (0.5) | 0 | 1 | 0 | 0 | 1 | 0 |

Abbreviations: ALT—alanine aminotransferase; AST—aspartate aminotransferase; BID—twice daily; QD—once daily; ULN—upper limit of normal.

As can be seen from these results, the safety and tolerability profile of Compound 1 was acceptable across doses.

Example 57

Treatment of Moderate to Severe Atopic Dermatitis

The following example briefly describes the interim results at 16 weeks of a Phase 2b, 88-week, randomized, double-blind, parallel-group, placebo-controlled study in which adult subjects with moderately to atopic dermatitis were treated with Compound 1 (upadacitinib).

The trials consists of a screening period of up to 35 days, a 16-week double-blind treatment period (Period 1) and a 72-week double-blind treatment period (Period 2) and a 30-day follow up period.

Statistical significance is manifested by a p value of less than 0.05, or less than 0.01.

Patients

Adult males or females between 18 and 75 years old at screening, having atopic dermatitis with a diagnosis confirmed by a dermatologist (according to the Hanifin and Rajka criteria); and also onset of symptoms at least 1 year prior to baseline; moderate to severe AD defined by an EASI≥16, BSA≥10 and an IGA score ≥3 at the Baseline visit; documented history (within 1 year prior to the screening visit) of inadequate response to treatment with topical corticosteroids (TCS), or topical calcineurin inhibitors (TCI), or for whom topical treatments are otherwise medically inadvisable. Patients cannot have been treated with TCSs, TCIs or prescription moisturizers with additives within 10 days before baseline. Patients with prior exposure to dupilumab or systemic JAK inhibitors were excluded.

TABLE 57A

| Demographics and Baseline Characteristics | | | | |
|---|---|---|---|---|
| | | Upadacitinb (UPA), QD | | |
| | Placebo N = 41 | 7.5 mg, N = 42 | 15 mg, N = 42 | 30 mg, N = 42 |
| Female, n (%) | 17 (41) | 14 (33) | 12 (29) | 20 (48) |
| FTPY | 40 (18) | 42 (15) | 39 (15) | 40 (15) |
| Age (yrs), mean (SD) | | | | |
| White, n (%) | 28 (68) | 24 (57) | 21 (50) | 23 (55) |
| BMI, mean (SD) | 26 (7) | 28 (6) | 27 (7) | 27 (6) |
| Region, n (%) | 29 (71) | 29 (69) | 29 (69) | 29 (69) |
| US/PR/Canada | 10 (24) | 11 (26) | 10 (23) | 10 (23) |
| EU/AUS JP | 2 (5) | 2 (5) | 3 (7) | 3 (7) |
| Years since AD diagnosis, mean (SD) | 27 (19) | 30 (18) | 23 (16) | 24 (14) |
| Years since AD symptom onset, mean (SD) | 31 (19) | 34 (18) | 24 (15) | 27 (16) |
| EASI, mean (SD) | 32.6 (14.5) | 31.4 (15.8) | 31.4 (12.3) | 28 (11.6) |
| BSA, mean (SD) | 45.7 (22.8) | 46.9 (24.9) | 50.6 (21.5) | 42.1 (20.40) |
| IGA of 4 (severe), n (%) | 23 (56) | 13 (31) | 23 (55) | 11 (26) |
| Pruritus NRS, mean (SD) | N = 39 6.5 (1.9) | N = 40 6.8 (1.8) | N = 37 6.4 (1.7) | N = 42 6.3 (2.1) |

Treatment

Approximately 160 patients with moderate to severe atopic dermatitis were randomized in a 1:1:1:1 ratio to one of four treatment groups:
Group 1: Compound 1 7.5 mg QD for 16 weeks
Group 2: Compound 1 15 mg QD for 16 weeks
Group 1: Compound 1 30 mg QD for 16 weeks
Group 1: Placebo QD for 16 weeks The analysis of the double-blind 16-week period of the study (Period 1) was conducted after all subjects have either completed Period 1 or discontinued from the study. An interim analysis after all subjects have either reached Week 32 or discontinued form the study will be performed.

Figure 45:
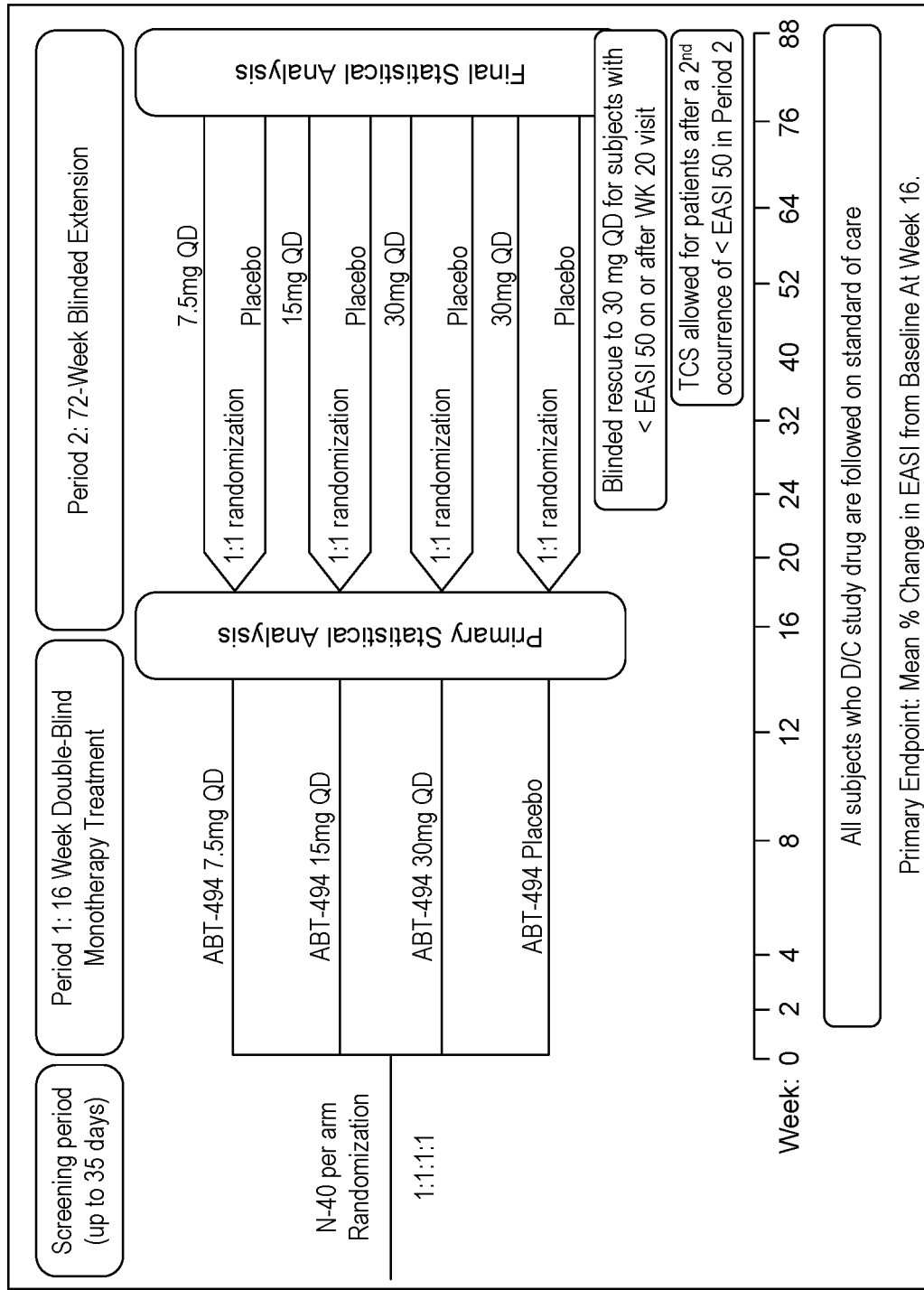
FIG. 45 is a schematic representation of the study design for the clinical study described in Example 57.

Subjects who complete Period 1 will be re-randomized at Week 16 within their original treatment group assignment to either compound 1 or placebo into a 72-week double-blind, placebo controlled treatment period (Period 2) in a 1:1 ratio as shown in FIG. 45. At the Week 16 visit, all subjects were re-randomized as follows into Period 2:
Subjects from Group 1 in Period 1: Compound 1, 7.5 mg QD or matching placebo for 24 weeks
Subjects from Group 2 in Period 1: Compound 1, 15 mg QD or matching placebo for 24 weeks
Subjects from Group 3 in Period 1: Compound 1, 30 mg QD or matching placebo for 24 weeks
Subjects from Group 4 in Period 1: Compound 1, 30 mg QD or matching placebo for 24 weeks During Period 2, concomitant Class III-IV medium potency topical corticosteroid treatment (up to twice daily triamcinolone acetonide 0.1% cream or p to once daily mometsone furoate 0.1% cream) will be permitted at the Week 24 visit and thereafter in subjects after a second instance of <EASI 50 response in any two Period 2 visits beginning from Week 20.

Results

The study's primary endpoint, percent improvement in EASI score at Week 16, was met by the 7.5/15/30 mg upadacitinib groups (39.4%/61.7%/74.4%; $p<0.05/<0.001/<0.001$) versus placebo (23.0%).

Eczema Area and Severity Index (EASI) score is a tool used to measure the extent (area) and severity of atopic eczema; EASI 75 is defined as at least a 75 percent reduction in EASI score relative to the baseline (day 1); EASI 90 is defined as at least a 90 percent reduction in EASI score relative to the baseline (day 1). The EASI score does not include a grade for dryness or scaling. Below is an example of the Eczema Area and Severity Index (EASI) Scoring:

---

Assignments for the following body regions are as follows:
Head and Neck
Trunk: include with the lower extremities
Upper limbs
Lower limbs
Area Score Area score is recorded for each of the four regions of the body. The area score is the percentage of skin affected by eczema.
Area score Percentage of skin affected by eczema in each region:
0 = no eczema in this region
1 = 1%-9%
2 = 10%-29%
3 = 30%-49%
4 = 50%-69%
5 = 70%-89%
6 = 90%-100%: the entire region is affected by eczema
Severity Score The severity score is recorded for each of the four regions of the body. The severity score
is the sum of the intensity scores for four signs. The four signs are:
Redness (erythema, inflammation)

-continued

Thickness (induration, papulation, swelling - acute eczema)
Scratching (excoriation)
Lichenification (lined skin, prurigo nodules - chronic eczema)
The average intensity of each sign in each body region is assessed as: none (0), mild (1), moderate (2) and severe (3).
Score intensity of redness, thickness/swelling, scratching, lichenification:
0 = none, absent
1 = mild
2 = moderate
3 = severe
For each region, record the intensity for each of the four signs and calculate the severity score.
Severity score = redness intensity + thickness intensity + scratching intensity + lichenification intensity
For each region, multiply the severity score by the area score and by a multiplier.
Head and neck: severity score × area score × 0.1
Trunk: severity score × are score × 0.3
Upper limbs; severity score × area score × 0.2
Lower limbs: severity score × area score × 0.4
Add up the total scores for each region to determine the final EAI score. The minimum EASI score is 0 and the maximum EASI score is 72.

Another endpoint of the study is the Investigator's Global Assessment (IGA). IGA is a 5-point scale used to measure the severity of disease at the time of the investigator's evaluation of the participant ranging from 0 (clear, no inflammatory signs of AD) to 4 (severe erythema and severe papulation/infiltration with or without oozing/crusting.

Body Surface Area Involvement of Atopic Dermatitis (BSA, %)

A qualified investigator or designee should select the subject's right or left hand as the measuring device. For purposes of clinical estimation, the total surface of the palm plus five digits will be assumed to be approximately equivalent to 1%. Measurement of the total area of involvement by the physician is aided by imagining if scattered plaques were moved so that they were next to each other and then estimating the total area involved. The site should make every attempt to have the same qualified Investigator or designee perform all BSA assessments on a given subject throughout the study Below is an example of an Investigator's Global Assessment:

| Score | Short Description | Detailed Description |
|---|---|---|
| 0 | Clear | No inflammatory signs of atopic dermatitis |
| 1 | Almost Clear | Just perceptible erythema and just perceptible papulation/infiltration |
| 2 | Mild | Mild erythema and mild papulation/infiltration |
| 3 | Moderate | Moderate erythema and moderate papulation/infiltration |
| 4 | Severe | Sever erythema and severe papulation/infiltration with or without oozing/crusting |

Another secondary endpoint of the study is the percent change in SCORAD score from Baseline at Weeks 8 and 16. The SCORAD is a tool used in clinical research and clinical practice that was developed to standardize the evaluation of the extent and severity of AD. The SCORAD is a validated tool used in clinical research and clinical practice that was developed to standardize the evaluation of the extent and severity of AD. There are 3 components to the assessment: A=extent or affected body surface area, B=severity, and C=subjective symptoms. The extent of AD is assessed as a percentage of each defined body area and reported as the sum of all areas, with a maximum score of 100% (assigned as "A" in the overall SCORAD calculation). The severity of 6 specific symptoms of AD (redness, swelling, oozing/crusting, excoriation, skin thickening/lichenification, dryness) is assessed using the following scale: none (0), mild (1), moderate (2), or severe (3) (for a maximum of 18 total points, assigned as "B" in the overall SCORAD calculation). Subjective assessment of itch and sleeplessness is recorded for each symptom by the subject or relative on a VAS, where 0 is no itch (or sleeplessness) and 10 is the worst imaginable itch (or sleeplessness), with a maximum possible score of 20. This parameter is assigned as "C" in the overall SCORAD calculation. The SCORAD is calculated as: A/5+7B/2+C where the maximum is 103.

Below is an example of the SCORAD tool:

Body Area Affected:

The extent of AD is assessed as a percentage of each defined body area. To help in determining this extent, the sites affected by eczema are shaded on a drawing of a body.
The rule of 9 is used to calculate the affected area (A) as a percentage of the whole body:
Head and neck 9%
Upper limbs 9% each
Lower limbs 18% each
Anterior trunk 18%
Back 18%
Genitals 1%
The score for each area is added up. The total area is "A" which has a possible maximums core of 100%.

Symptom Severity:

A representative area of eczema is selected. In this area, the intensity of each of the following 6 specific symptoms is assessed as none (0), mild (1), moderate (2) or severe (3).
Redness
Swelling/Oozing/crusting
Scratch marks
Skin thickening (lichenification)
Dryness (this is assess in an area where there is no inflammation)
The scores for these 6 specific symptoms should be added, for a maximum of 818 total points, assigned as "B" in the overall SCORAD calculation.

Figure 46:
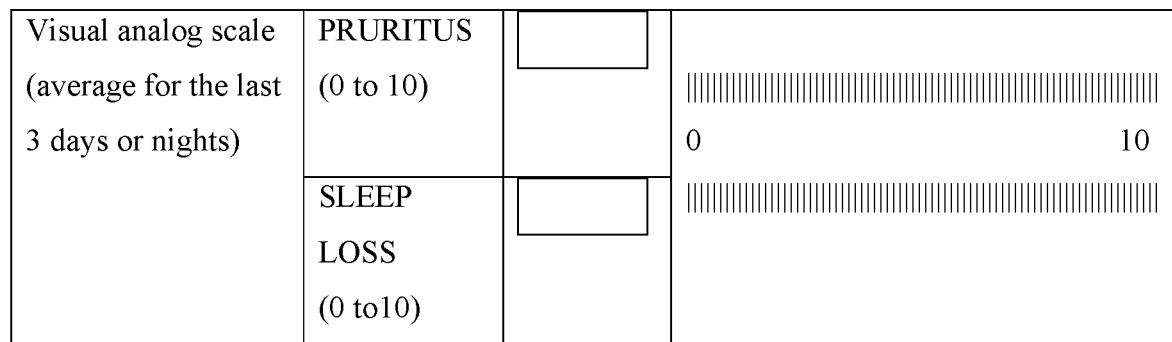
FIG. 46 illustrates a visual analogue scale (VAS) for subjective assessment of itch and sleeplessness.

Subjective Symptoms:

Subjective assessment of itch and sleeplessness is recorded for each symptom by the subject on a visual analogue scale (VAS) (FIG. 46) where 0 is no itch (or sleeplessness) and 10 is the worst imaginable itch (or sleeplessness), with a maximum possible score of 20. This parameter is assigned as "C" in the overall SCORAD calculation..

SCORAD Calculation:

The SCORAD is calculated as A/5 + 77B/2 + C

Mean percent improvement in SCORAD from baseline at week 16 (LOCF) was 32.5%/46.9%/60.4% upadacitinib groups ($p<0.01/<0.001/<0.001$; N=39/36/40) vs 12.4% placebo (N=33). SCORAD response at week 16 (NRI) for upadacitinib groups (N=42/42/42) versus placebo (N=41) was 28.6%/42.9%/61.9% versus 7.3% for SCORAD 50 ($p<0.01/<0.001/<0.001$), 4.8%/21.4%/40.5% versus 2.4% for SCORAD 75 ($p>0.05/<0.01/<0.001$), and 2.4%/9.5%/23.8% versus 0% for SCORAD 90 ($p>0.05/<0.05/<0.001$). Mean improvement [SE] from baseline to week 16 in POEM (LOCF), was 5.5 [1.43]/8.6 [1.41]/12.3 [1.40] (N=42/40/42) for upadacitinib groups ($p<0.05/<0.001/<0.001$) versus 1.6 [1.49] for placebo (N=37).

Another endpoint in the study is change from Baseline to Week 16 in Patient Oriented Eczema Measure (POEM). An example of the Patient Oriented Eczema Measure is provided in FIG. 47.

Another secondary endpoint was the percentage change from Baseline to weeks 2, 8 and 16 in pruritus numerical rating scale (NRS) to measure itch. An example of the Pruritus (Itch) Numerical Rate Scale is provided in FIG. 48.

For patients with baseline pruritus NRS of ≥4 (non-responder imputation), improvement in pruritus NRS ≥4 points from baseline to week 16, was observed in 24.3%/59.4%/528% on upadacitinib ($p<0.05/<0.001/<0.001$, N=37/32/36) versus 5.7% on placebo (N=35).

The most common treatment-emergent adverse events (AEs), upadacitinib groups vs placebo, were upper respiratory tract infection (16.7%/11.9%/11.9% versus 10.0%) and AD exacerbation (16.7%/7.1%/11.9% versus 7.5%). 4.8%/2.4%/0% of upadacitinib patients (7.5/15/30 mg groups) had serious AEs versus 2.5% placebo.

Efficacy

The primary endpoint of mean percentage change from baseline in the EASI score, a measure of the extent and severity of atopic dermatitis, was achieved by 74/62/39 percent of patients receiving the 30/15/7.5 mg doses of Compound 1, respectively, compared to 23 percent for patients receiving placebo ($p<0.001/0.001/0.05$, respectively). A 75% improvement in disease (EASI 75) was achieved by 69/52/29 percent of patients receiving the 30/15/7.5 mg doses of Compound 1, respectively, compared to 10 percent for patients receiving placebo ($p<0.001/0.001/0.05$, respectively). Disease improvement of 90 percent or more (EASI 90) was achieved by 50/26/14 percent of patients receiving the 30/15/7.5 mg doses of Compound 1, respectively, compared to 2 percent for patients receiving placebo ($p<0.001/0.01/0.05$, respectively). Correspondingly, clear or almost clear skin was achieved by 50/31/14 percent of patients receiving the 30/15/7.5 mg doses of Compound 1, as measured by the Investigator's Global Assessment scale (IGA 0 or 1), compared to 2 percent of patients receiving placebo ($p<0.001/0.001/0.05$, respectively).

In addition, significant improvement was observed with respect to pruritus (itch). Patients treated with Compound 1 experience 69/48/40 percent improvement in itch across the 30/15/7.5 mg Compound 1 doses, as measured by the pruritus numerical rating scale (NRS), compared to 10 percent for patients receiving placebo ($p<0.001/0.001/0.01$, respectively).

TABLE 57-A

| | Efficacy | | | | |
|---|---|---|---|---|---|
| Dose | Mean percentage change in EASI score**** | EASI 75 | EASI 90 | Investigator Global Assessment (IGA) or "0" or "i"**** | Percent change in pruritus/itch numerical rating scale |
| 30 mg (n = 42) | 74%*** | 69%*** | 50%*** | 50%*** | 69%*** (n = 42) |
| 15 mg (n = 42) | 62%*** | 52%*** | 26%** | 31%*** | 48%*** (n = 37) |

TABLE 57-A-continued

| | Efficacy | | | | |
|---|---|---|---|---|---|
| Dose | Mean percentage change in EASI score**** | EASI 75 | EASI 90 | Investigator Global Assessment (IGA) or "0" or "i"**** | Percent change in pruritus/itch numerical rating scale |
| 7.5 mg (n = 42) | 39%* | 29%* | 14%* | 14%* | 40%** (n = 40) |
| Placebo (n = 41) | 23% (n = 39) | 10% | 2% | 2% | 10% (n = 37) |

*p < 0.05,
**p < 0.01,
***p < 0.001
****Eczema Area and Severity Index (EASI) score is a tool used to measure the extent (area) and severity of atopic eczema; EASI 75 is defined as at least a 75 percent reduction in EASI score relative to the baseline (day 1); EASI 90 is defined as at least a 90 percent reduction in EASI score relative to the baseline (day 1).

All references (patent and non-patent) cited above are incorporated by reference into this patent application. The discussion of those references is intended merely to summarize the assertions made by their authors. No admission is made that any reference (or a portion of any reference) is relevant prior art (or prior art at all). Applicants reserve the right to challenge the accuracy and pertinence of the cited references.

We claim:

1. A method for reducing the extent and severity of atopic eczema by at least 90% in a human patient having moderate to severe atopic dermatitis, comprising orally administering once daily to the patient in need thereof a solid dosage form comprising (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide (Compound 1) in an amount sufficient to deliver to the patient 15 mg of Compound 1 free base equivalent, wherein the patient has achieved at least an Eczema Area and Severity Index (EAST) 90 at week 16 of said once daily administration.

2. The method of claim 1, wherein the patient is an adult.

3. The method of claim 2, wherein the adult patient had inadequately responded to treatment with topical corticosteroids or topical calcineurin inhibitors.

4. The method of claim 1, wherein the method further comprises administering a topical corticosteroid to the patient.

5. The method of claim 1, wherein the patient has achieved clear or almost clear skin, as measured by an Investigator's Global Assessment score of 0 or 1 at week 16 of said once daily administration.

6. A method of achieving clear or almost clear skin in a human patient having moderate to severe atopic dermatitis, comprising orally administering once daily to the patient in need thereof a solid dosage form comprising (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide (Compound 1) in an amount sufficient to deliver to the patient 15 mg of "Compound 1" free base equivalent, wherein the patient has achieved an Investigator's Global Assessment score of 0 or 1 at week 16 of said once daily administration.

7. The method of claim 6, wherein the patient is an adult.

8. The method of claim 7, wherein the adult patient had inadequately responded to treatment with topical corticosteroids or topical calcineurin inhibitors.

9. The method of claim 6, wherein the method further comprises administering a topical corticosteroid to the patient.

\* \* \* \* \*

UNITED STATES PATENT AND TRADEMARK OFFICE
CERTIFICATE OF CORRECTION

PATENT NO. : 10,995,095 B2
APPLICATION NO. : 16/721076
DATED : May 4, 2021
INVENTOR(S) : Pangan et al.

Page 1 of 1

It is certified that error appears in the above-identified patent and that said Letters Patent is hereby corrected as shown below:

In the Claims

In Claim 1, Column 349, Lines 37-38, please replace the phrase "Eczema Area and Severity Index (EAST)" with "Eczema Area and Severity Index (EASI)".

In Claim 6, Column 350, Line 32, please delete the """" around the phrase "Compound 1" for consistency with Line 30.

Signed and Sealed this
Tenth Day of August, 2021

Drew Hirshfeld
*Performing the Functions and Duties of the*
*Under Secretary of Commerce for Intellectual Property and*
*Director of the United States Patent and Trademark Office*